United States Patent
Kovtun et al.

(10) Patent No.: US 11,897,961 B2
(45) Date of Patent: Feb. 13, 2024

(54) ANTI-CD123 ANTIBODIES AND CONJUGATES AND DERIVATIVES THEREOF

(71) Applicant: IMMUNOGEN, INC., Waltham, MA (US)

(72) Inventors: Yelena Kovtun, Stow, MA (US); Daniel J. Tavares, Natick, MA (US); Lingyun Rui, Weston, MA (US); Thomas Chittenden, Sudbury, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

(21) Appl. No.: 17/711,518

(22) Filed: Apr. 1, 2022

(65) Prior Publication Data
US 2022/0372152 A1 Nov. 24, 2022

Related U.S. Application Data

(60) Continuation of application No. 17/077,877, filed on Oct. 22, 2020, now Pat. No. 11,332,535, which is a continuation of application No. 16/778,988, filed on Jan. 31, 2020, now Pat. No. 10,875,925, which is a division of application No. 15/667,697, filed on Aug. 3, 2017, now Pat. No. 10,919,969, which is a division of application No. 15/195,401, filed on Jun. 28, 2016, now Pat. No. 10,077,313.

(60) Provisional application No. 62/346,730, filed on Jun. 7, 2016, provisional application No. 62/338,203, filed on May 18, 2016, provisional application No. 62/186,161, filed on Jun. 29, 2015.

(51) Int. Cl.
| | |
|---|---|
| *A61K 39/00* | (2006.01) |
| *C07K 16/28* | (2006.01) |
| *A61K 47/68* | (2017.01) |
| *A61K 39/395* | (2006.01) |

(52) U.S. Cl.
CPC ...... *C07K 16/2866* (2013.01); *A61K 47/6801* (2017.08); *A61K 47/6803* (2017.08); *A61K 47/6849* (2017.08); *A61K 47/6883* (2017.08); *A61K 39/3955* (2013.01); *A61K 2039/505* (2013.01); *C07K 2317/24* (2013.01); *C07K 2317/33* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,868,791 B2 | 1/2018 | Fishkin et al. | |
| 10,077,313 B2 | 9/2018 | Kovtun et al. | |
| 10,287,256 B2 | 5/2019 | Hilderbrand et al. | |
| 10,442,865 B2 | 10/2019 | Kovtun et al. | |
| 10,875,925 B2 | 12/2020 | Kovtun et al. | |
| 10,898,579 B2 | 1/2021 | Yoder et al. | |
| 10,919,969 B2 | 2/2021 | Kovtun et al. | |
| 11,332,535 B2 | 5/2022 | Kovtun et al. | |
| 2010/0209341 A1 | 8/2010 | Vairo et al. | |
| 2011/0301334 A1 | 12/2011 | Bhakta et al. | |
| 2017/0014522 A1 | 1/2017 | Yoder et al. | |
| 2017/0080102 A1 | 3/2017 | Whiteman et al. | |
| 2017/0189548 A1 | 7/2017 | Bartlett | |
| 2018/0208562 A1 | 7/2018 | Hilderbrand et al. | |
| 2018/0355047 A1 | 12/2018 | Kovtun et al. | |
| 2019/0111147 A1 | 4/2019 | Fleming et al. | |
| 2019/0112359 A1 | 4/2019 | Liu et al. | |
| 2019/0270769 A1 | 9/2019 | Milano et al. | |
| 2020/0222552 A1 | 7/2020 | Bartlett | |

FOREIGN PATENT DOCUMENTS

| | | |
|---|---|---|
| EP | 2426148 A1 | 3/2012 |
| JP | 2013-519689 A | 5/2013 |
| JP | 2014-076062 A | 5/2014 |
| WO | 2008/127735 A1 | 10/2008 |
| WO | 2010/094068 A1 | 8/2010 |
| WO | 2010/126066 A1 | 11/2010 |
| WO | 2011/106528 A1 | 9/2011 |
| WO | 2011/156328 A1 | 12/2011 |
| WO | 2012/021934 A1 | 2/2012 |
| WO | 2012/112687 A1 | 8/2012 |
| WO | 2012/128868 A1 | 9/2012 |
| WO | 2014/138805 A1 | 9/2014 |
| WO | 2015/026892 A1 | 2/2015 |
| WO | 2015/044386 A1 | 4/2015 |
| WO | 2016/036794 A1 | 3/2016 |
| WO | 2016/036801 A1 | 3/2016 |
| WO | 2016/036937 A1 | 3/2016 |

OTHER PUBLICATIONS

U.S. Appl. No. 15/195,269, filed Jun. 28, 2016, U.S. Pat. No. 10,898,579, Issued.
U.S. Appl. No. 17/014,404, filed Sep. 8, 2020, N/A, Pending.
U.S. Appl. No. 15/195,401, filed Jun. 28, 2016, U.S. Pat. No. 10,077,313, Issued.
U.S. Appl. No. 15/667,697, filed Aug. 3, 2017, U.S. Pat. No. 10,919,969, Issued.
U.S. Appl. No. 15/957,757, filed Apr. 19, 2018, U.S. Pat. No. 10,442,865, Issued.

(Continued)

*Primary Examiner* — Thomas S Heard
(74) *Attorney, Agent, or Firm* — McCarter & English, LLP; Xin Zhang

(57) ABSTRACT

The present invention generally relates to antibodies, antigen-binding fragments thereof, polypeptides, and immunoconjugates that bind to CD123 antigen (the α chain of the interleukine 3 receptor, or IL-3Rα). The present invention also relates to methods of using such CD123-binding molecules for diagnosing and treating diseases, such as B-cell malignancies.

11 Claims, 54 Drawing Sheets

Specification includes a Sequence Listing.

(56) References Cited

OTHER PUBLICATIONS

U.S. Appl. No. 16/778,988, filed Jan. 31, 2020, U.S. Pat. No. 10,875,925, Issued.
U.S. Appl. No. 17/711,518, filed Apr. 1, 2022, U.S. Pat. No. 11,332,535, Issued.
Abbexa, IL3RA Antibody. ArtNr abx103027-10. Polyclonal Antibody to Interleukin 3 Receptor Alpha (IL3Ra). Retrieved online at: https://www.hoelzel-biotech.com/en/abbexa-antibody-hu-abx103027-10-il3ra-antibody.html. 1 page.
Abbexa, IL3RA Antibody. Catalogue No. abx430549. datasheet. 1 page.
antibodies-online.com, IL3RA antibody (Interleukin 3 Receptor, alpha (Low Affinity) (AA 200-305). Catalog No. ABIN1845738. 5 pages. Aug. 16, 2017.
Broughton et al., Dual mechanism of interleukin-3 receptor blockade by an anti-cancer antibody. Cell Rep. Jul. 24, 2014;8(2):410-9.
Brummell et al., Probing the combining site of an anti-carbohydrate antibody by saturation-mutagenesis: role of the heavy-chain CDR3 residues. Biochemistry. Feb. 2, 1993;32(4):1180-7.
Colman, Effects of amino acid sequence changes on antibody-antigen interactions. Res Immunol. Jan. 1994;145 (1):33-6.
Du et al., New immunotoxins targeting CD123, a stem cell antigen on acute myeloid leukemia cells. J Immunother. Sep. 2007;30(6):607-13.
Huang et al., 5A2, A new IL-3Ra (CD123) monoclonal antibody for the treatment of AML. Molecular Cancer Therapeutics. Nov. 2011;10(11 Suppl): Abstract C62.
Huang, Generation and Functional Assays of Acute Myeloid Leukemic Stem Cells Targeted Anti-CD123 Monoclonal Antibody. Huazhong University of Science and Technology. A dissertation submitted to Huazhong University of Science for the Degree of Doctor of Medicine. 110 pages, May 2011.
Rozan et al., Single-domain antibody-based and linker-free bispecific antibodies targeting FcγRIII induce potent antitumor activity without recruiting regulatory T cells. Mol Cancer Ther. 2013;12(8):1481-1491.
Kobayashi et al., Tryptophan H33 plays an important role in pyrimidine (6-4) pyrimidone photoproduct binding by a high-affinity antibody. Protein Eng. Oct. 1999;12(10):879-84.
Sun et al., Monoclonal antibody 7G3 recognizes the N-terminal domain of the human interleukin-3 (IL-3) receptor alpha-chain and functions as a specific IL-3 receptor antagonist. Blood. Jan. 1, 1996;87(1):83-92.
Testa et al., CD 123 is a membrane biomarker and a therapeutic target in hematologic malignancies. Biomark Res. Feb. 10, 2014;2(1):4, 11 pages.
International Search Report and Written Opinion for Application No. PCT/US2016/039797, dated Oct. 4, 2016.

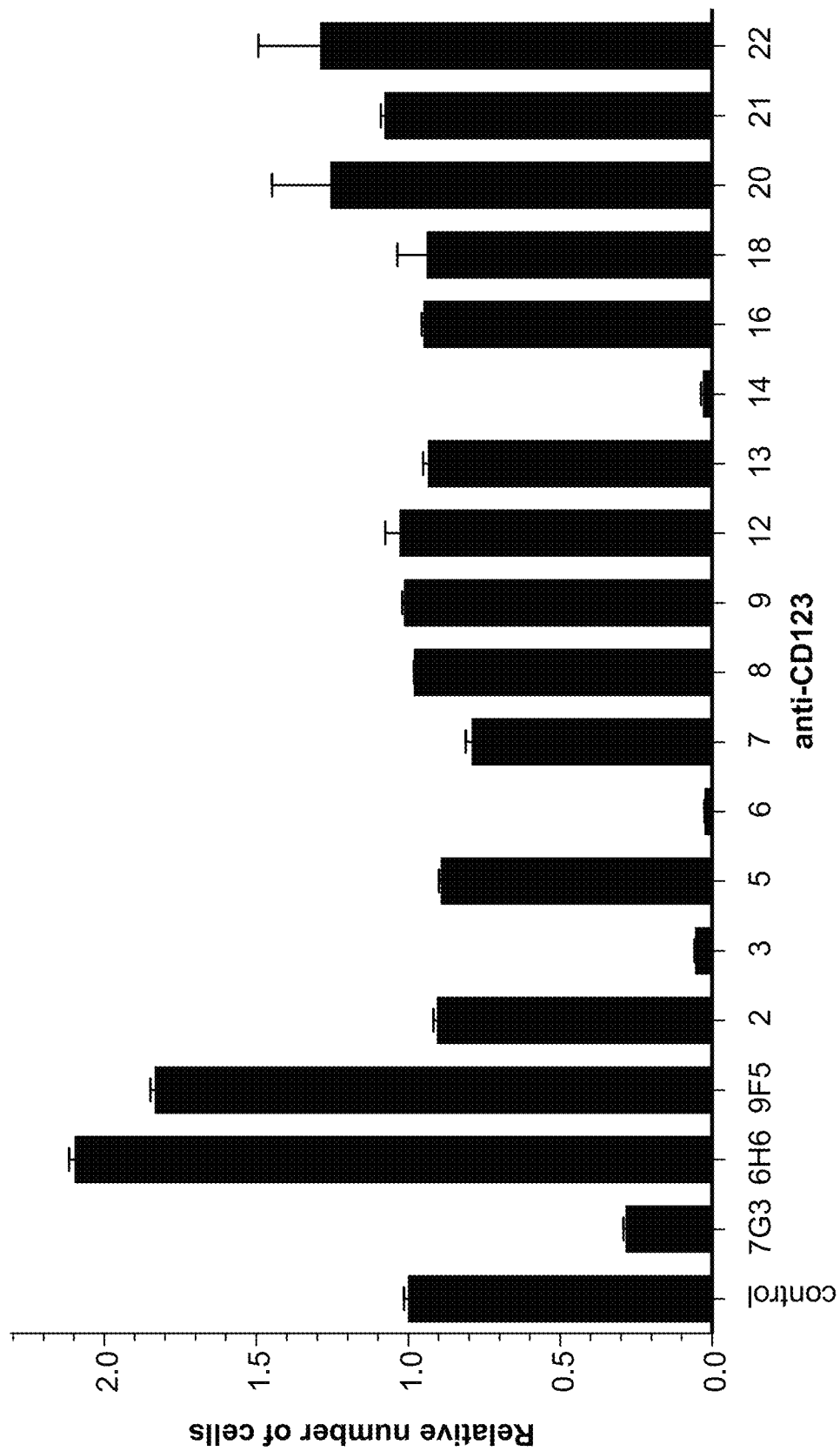

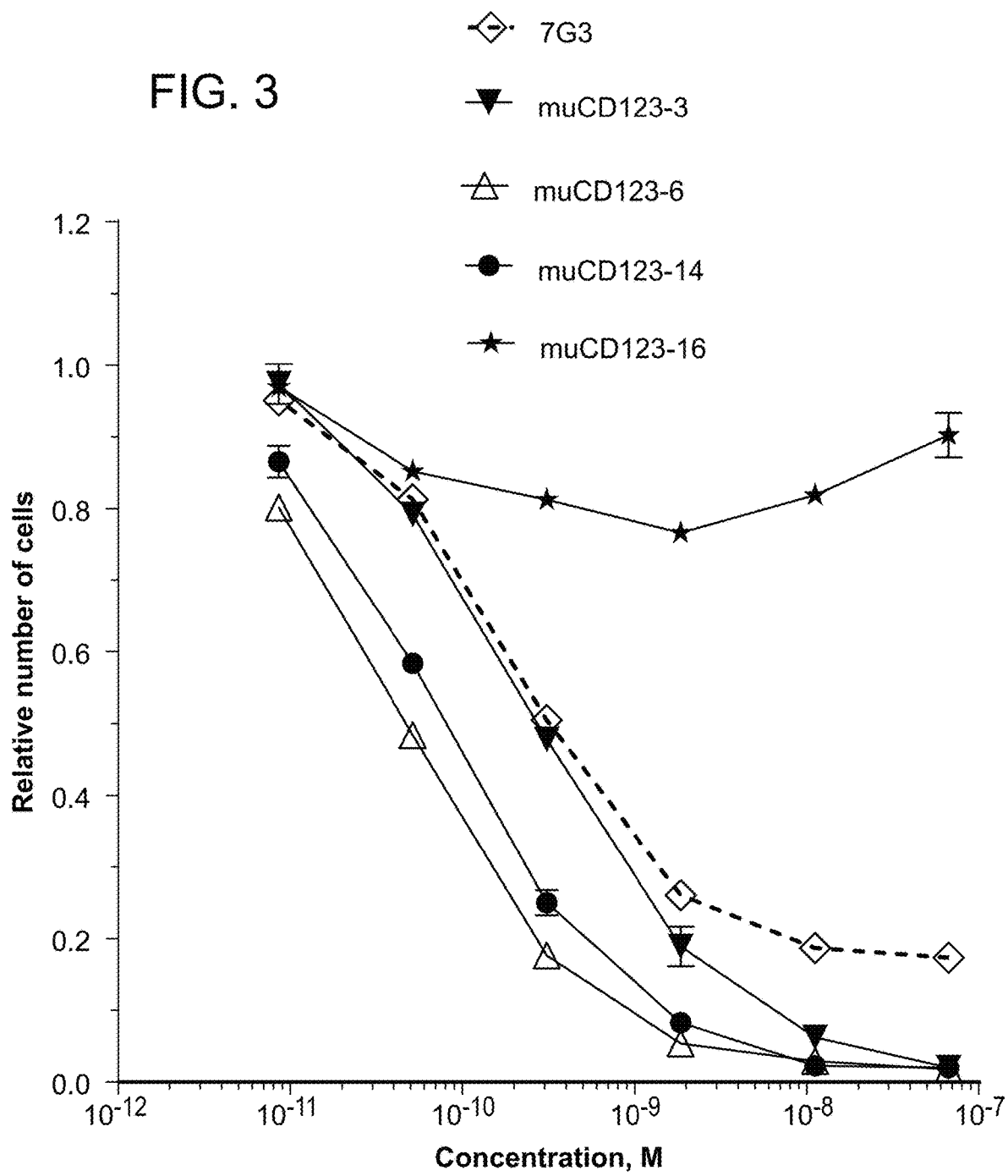

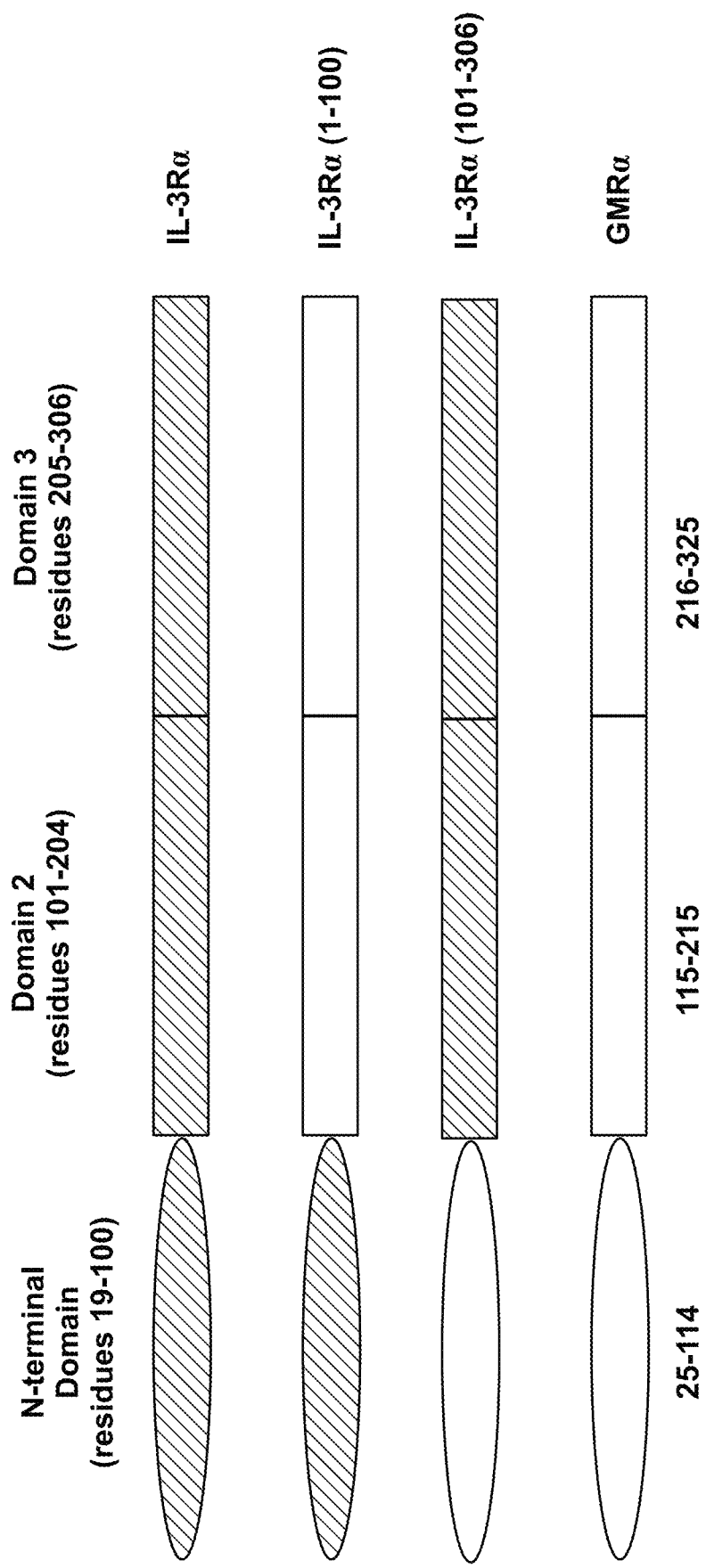

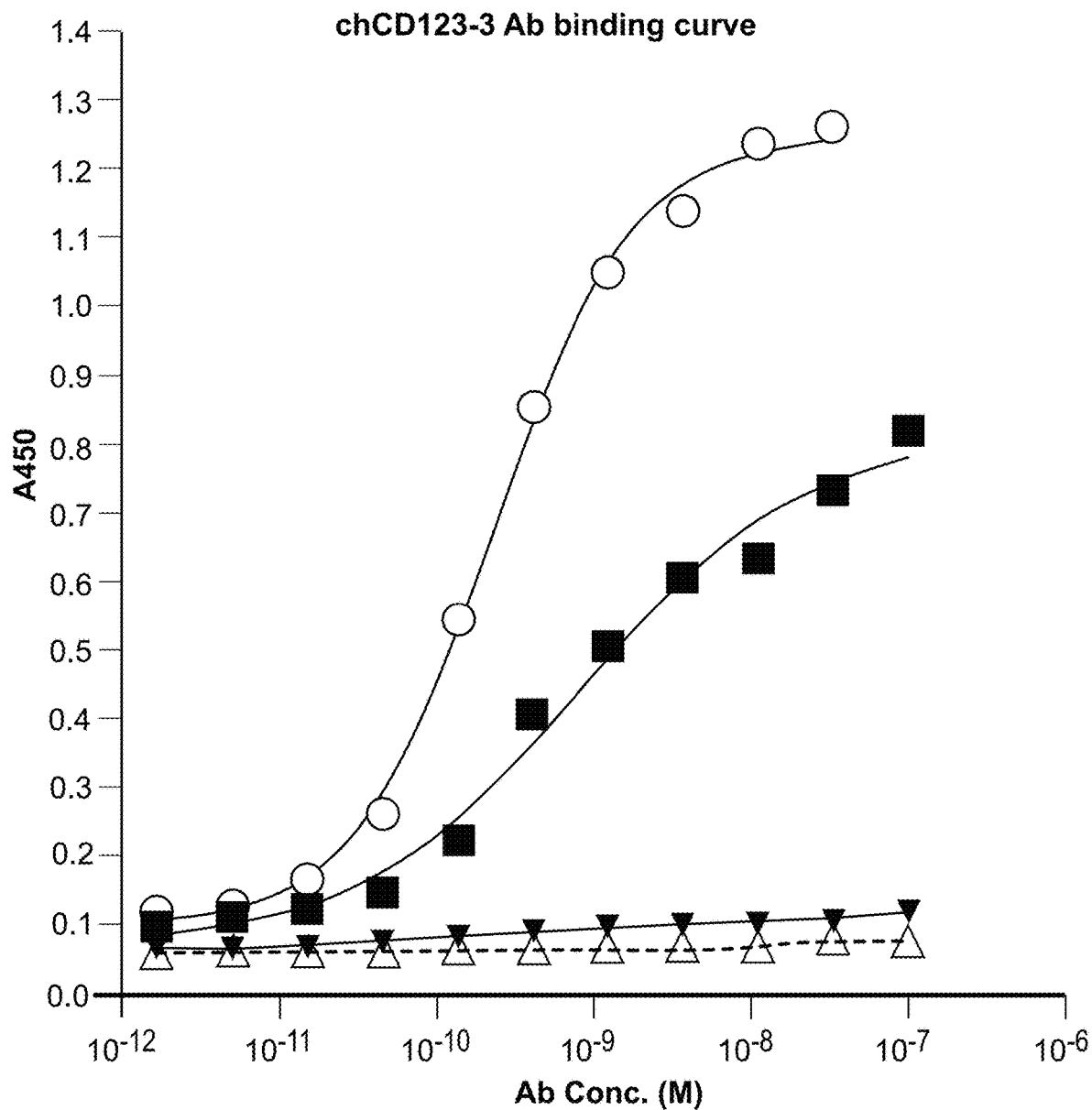

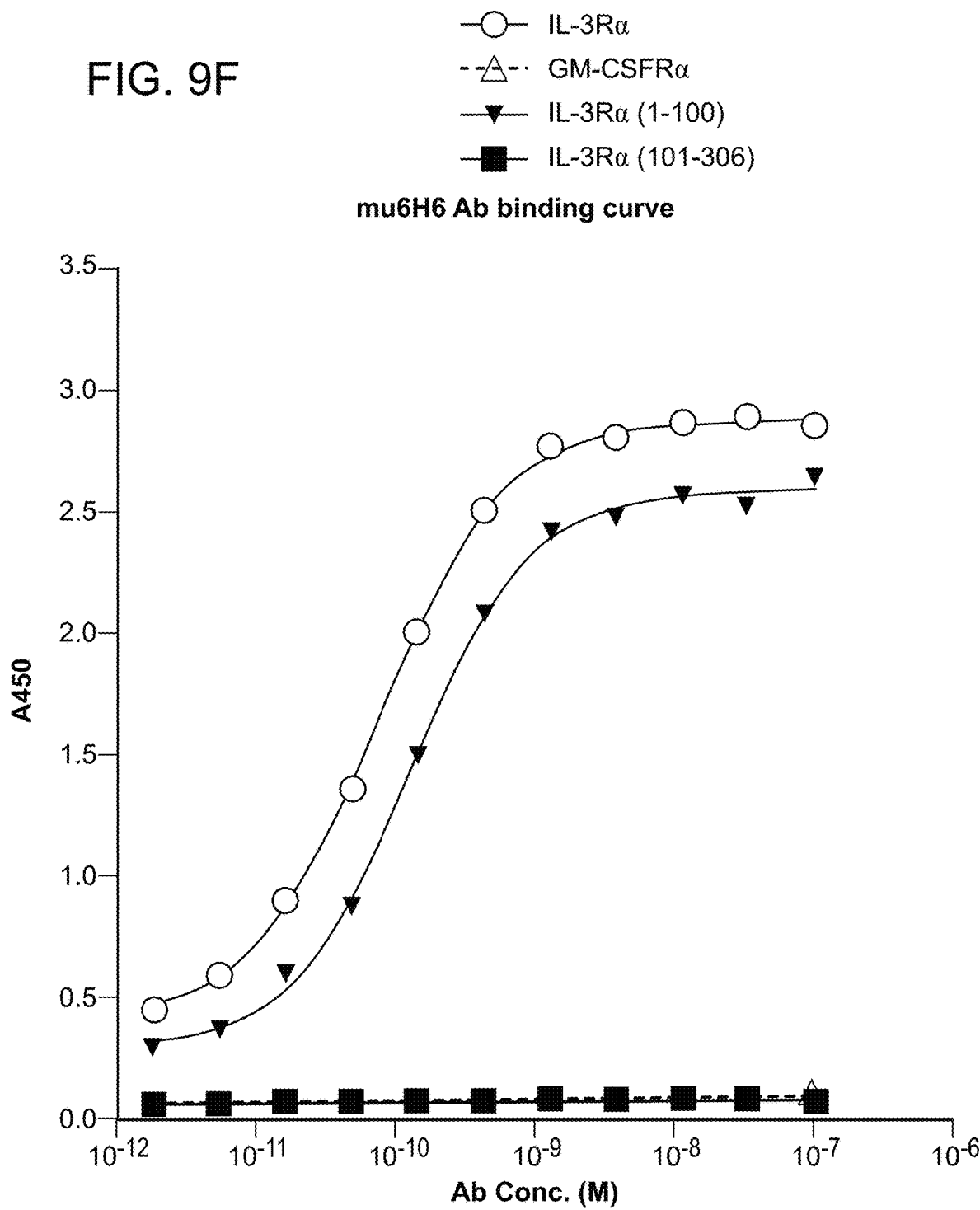

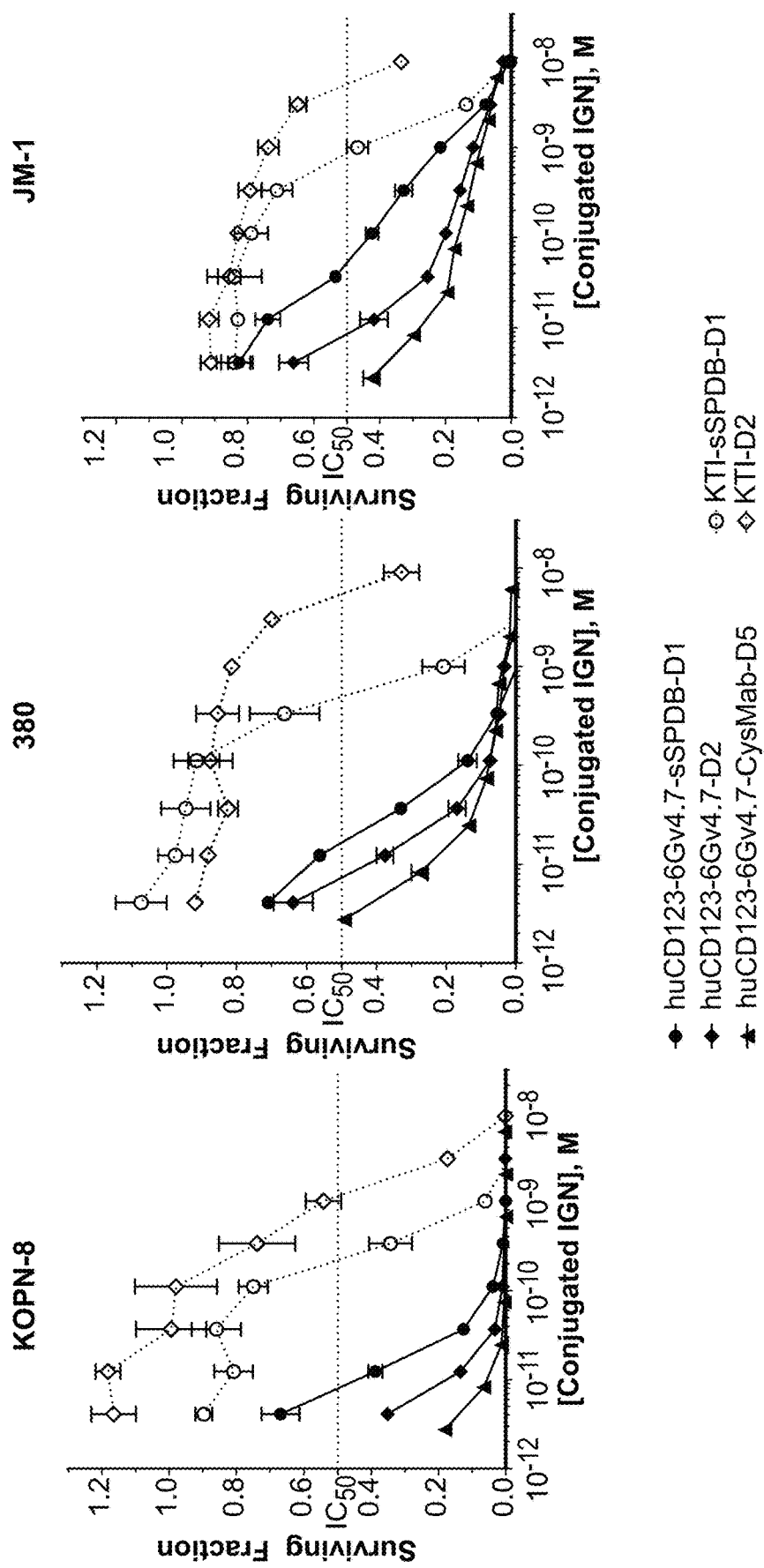

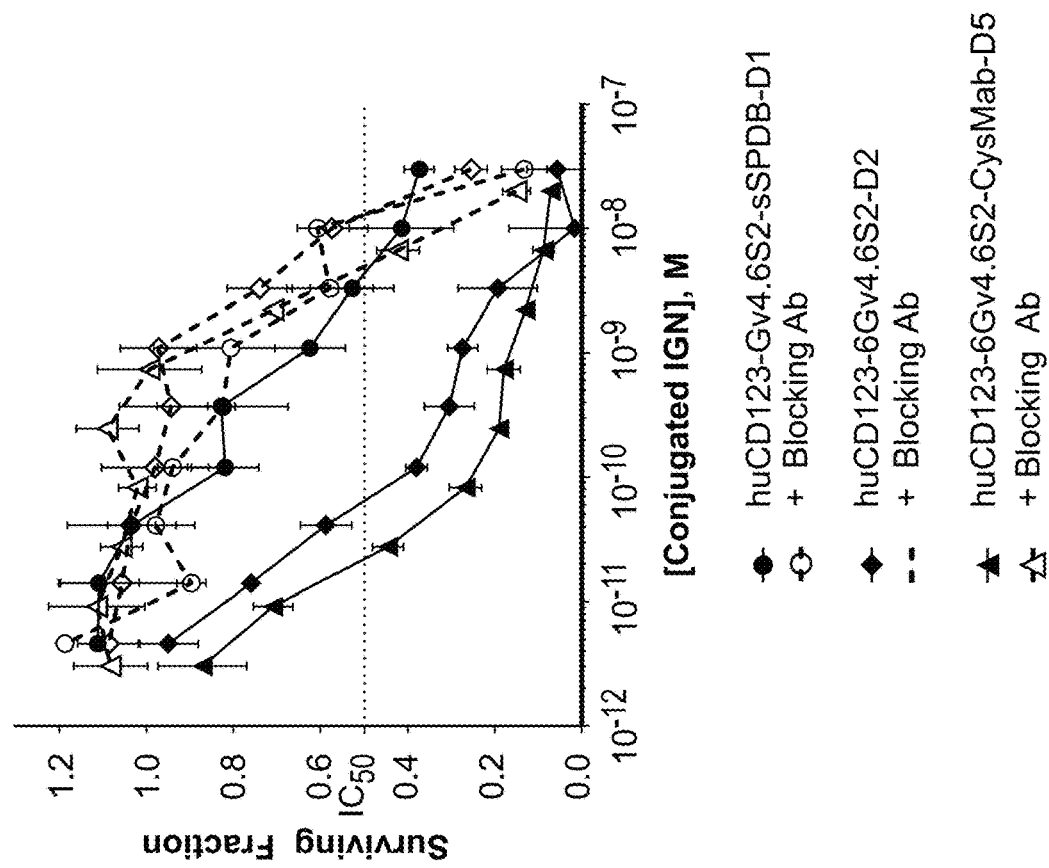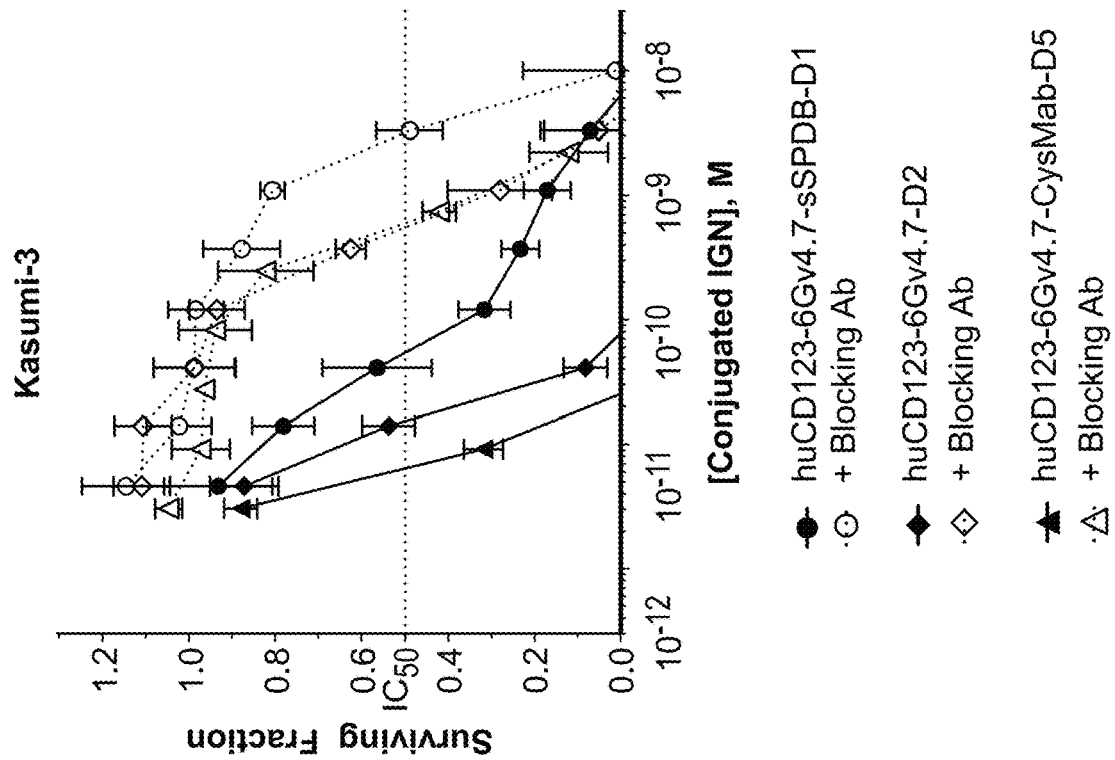
FIG. 11C

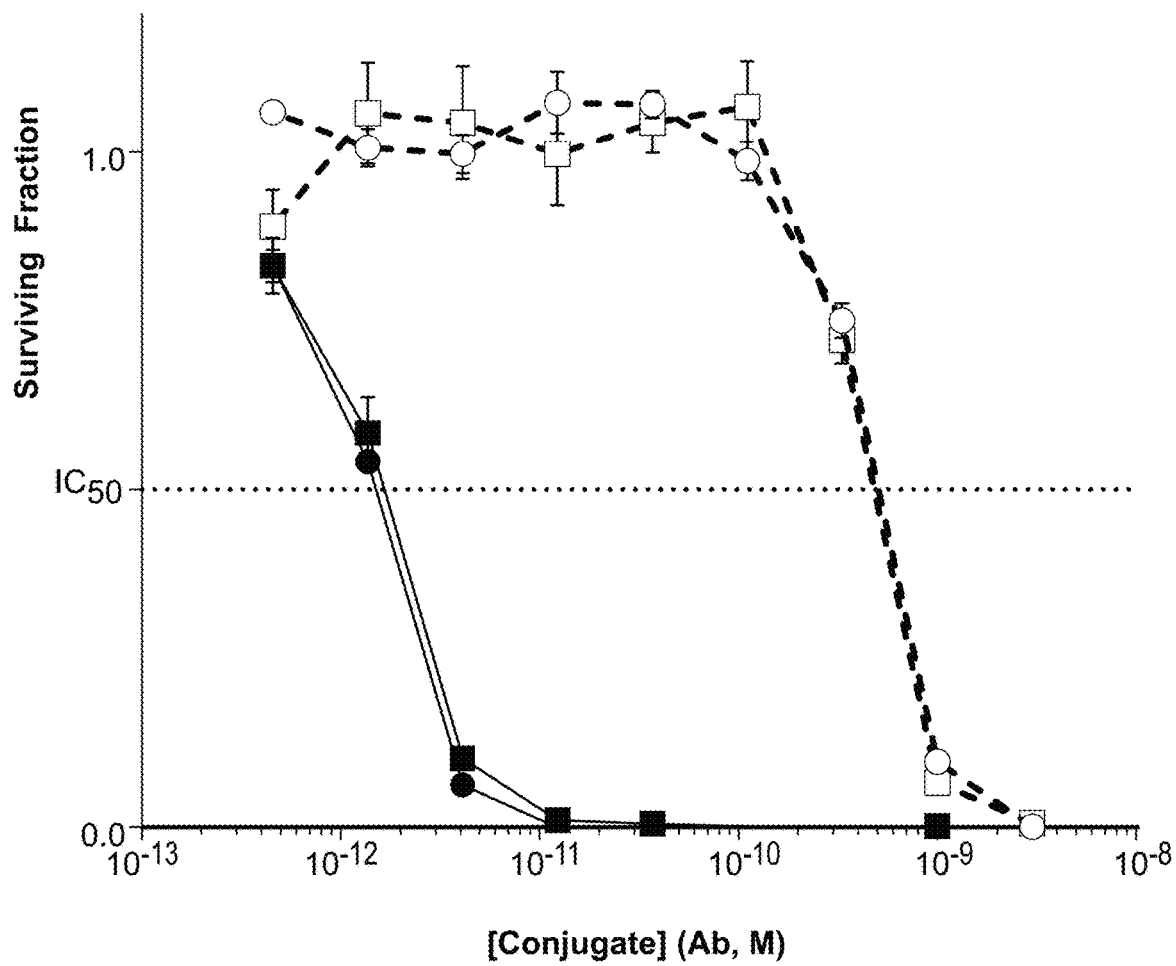

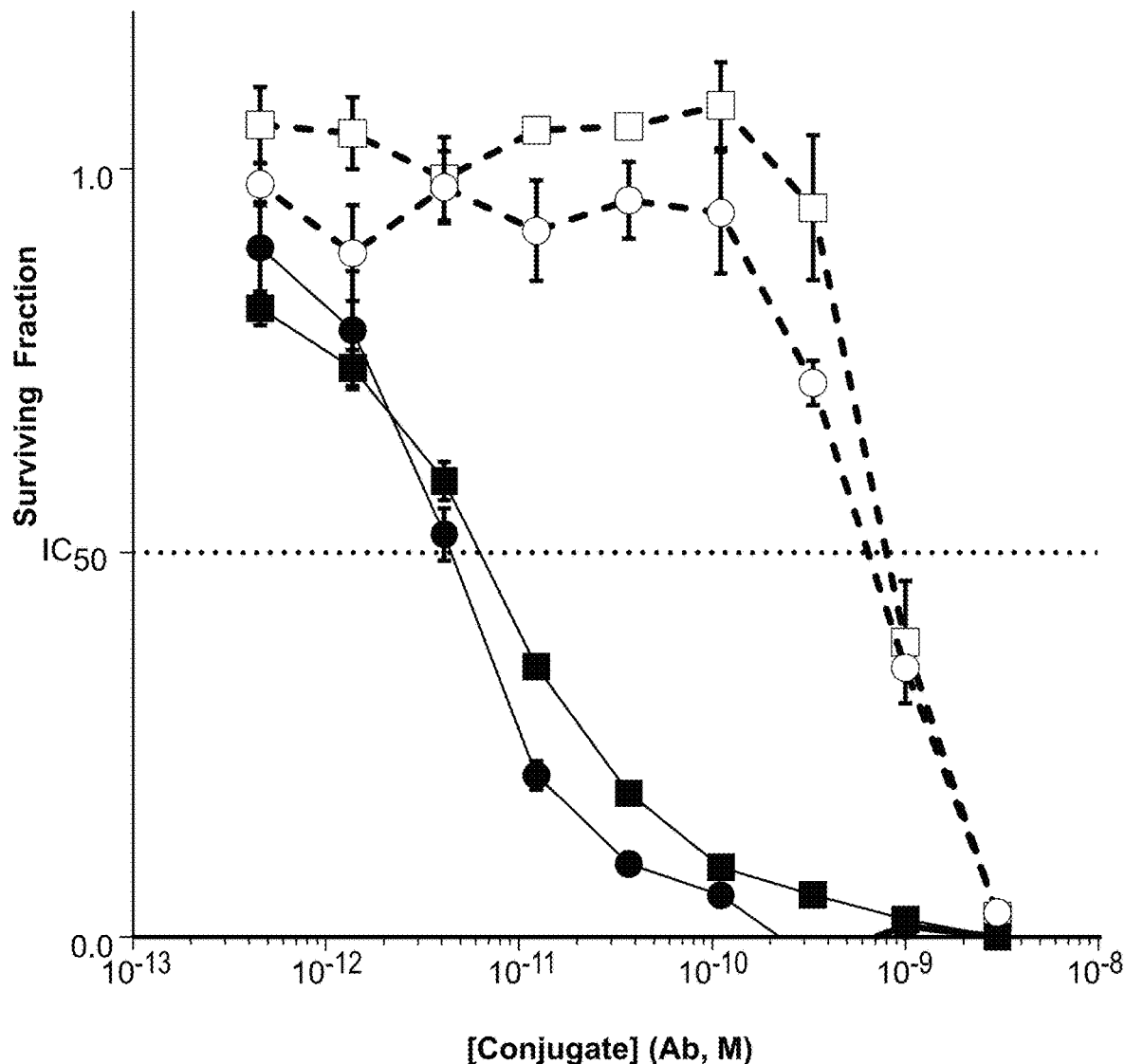

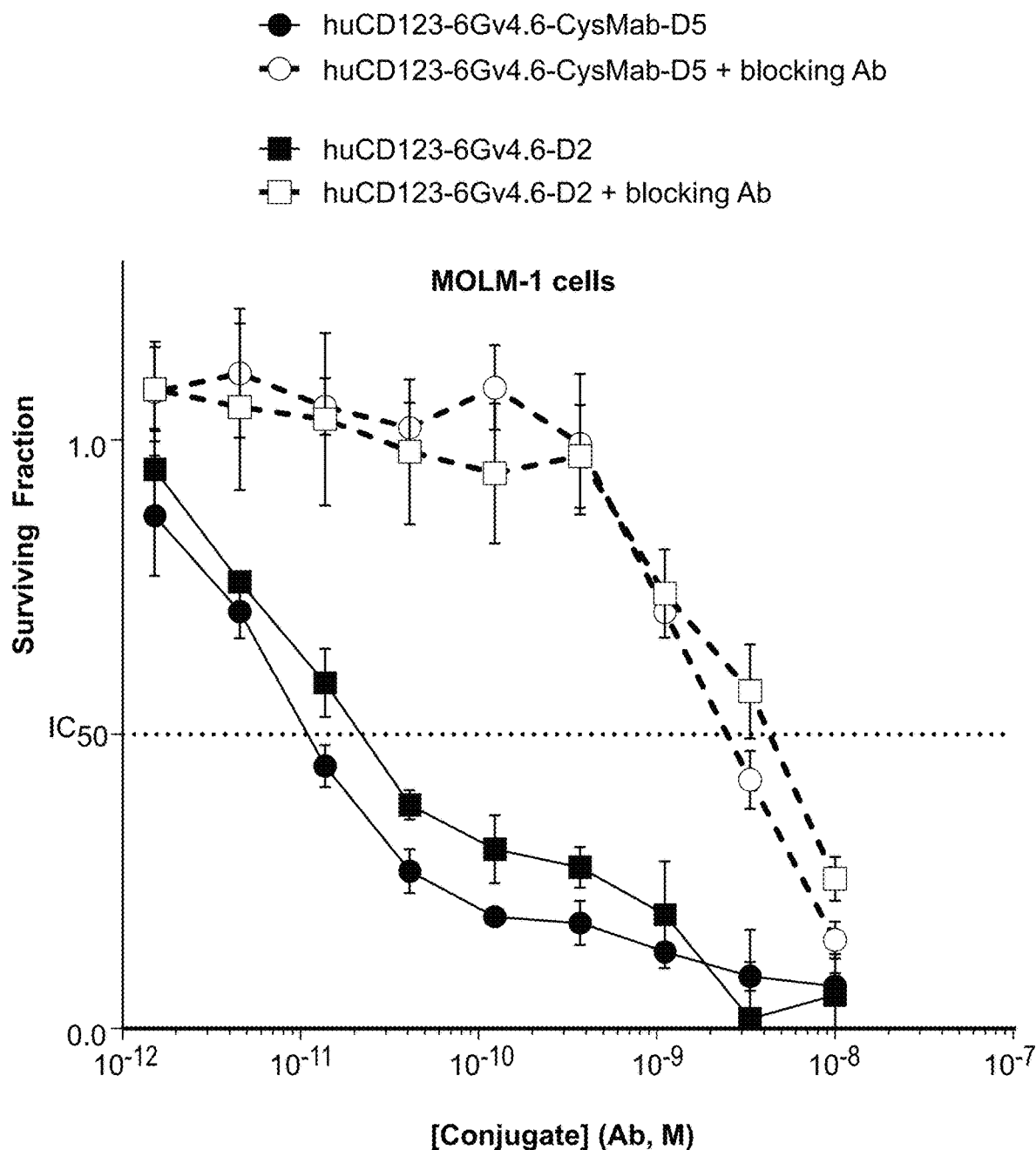

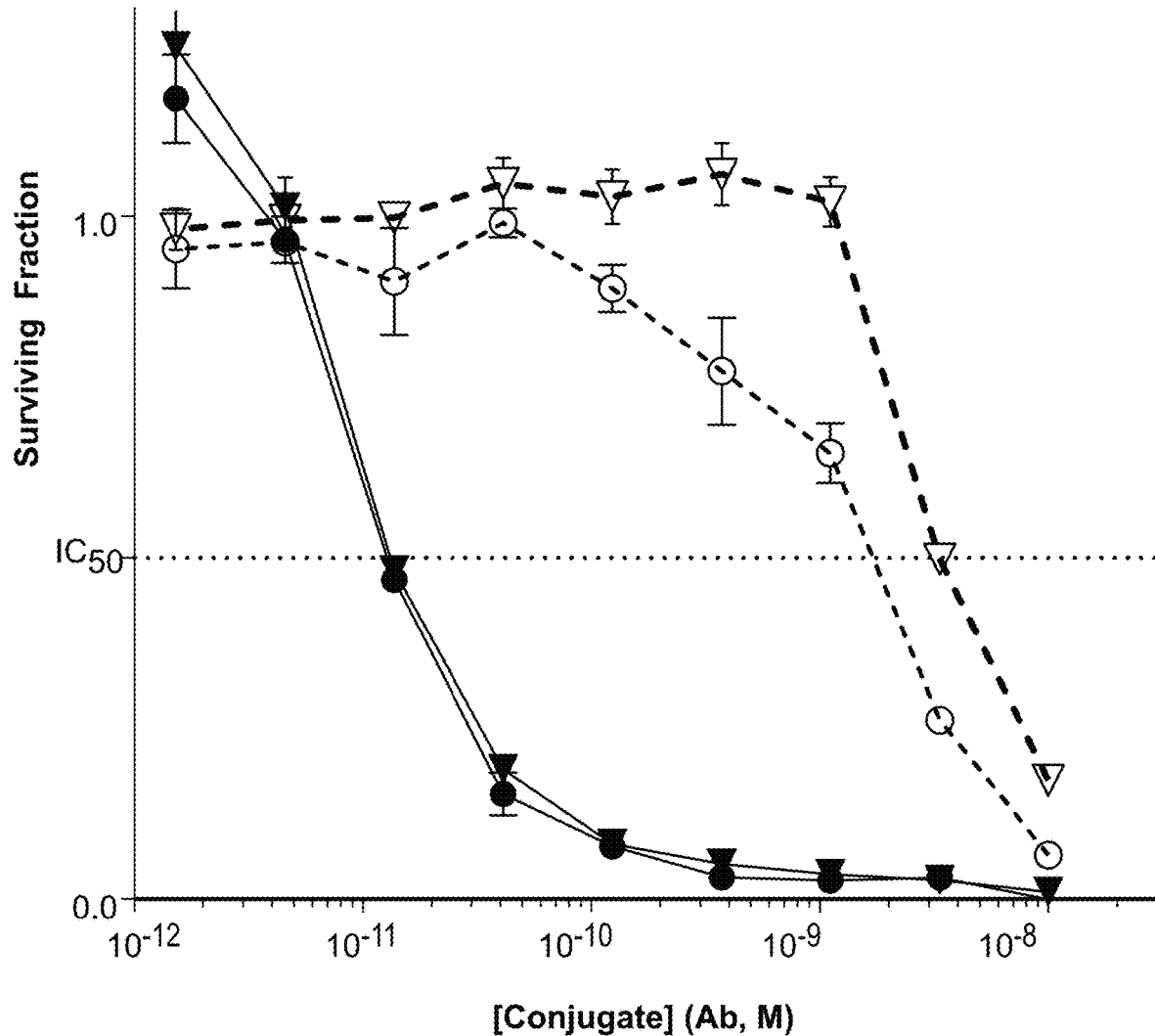

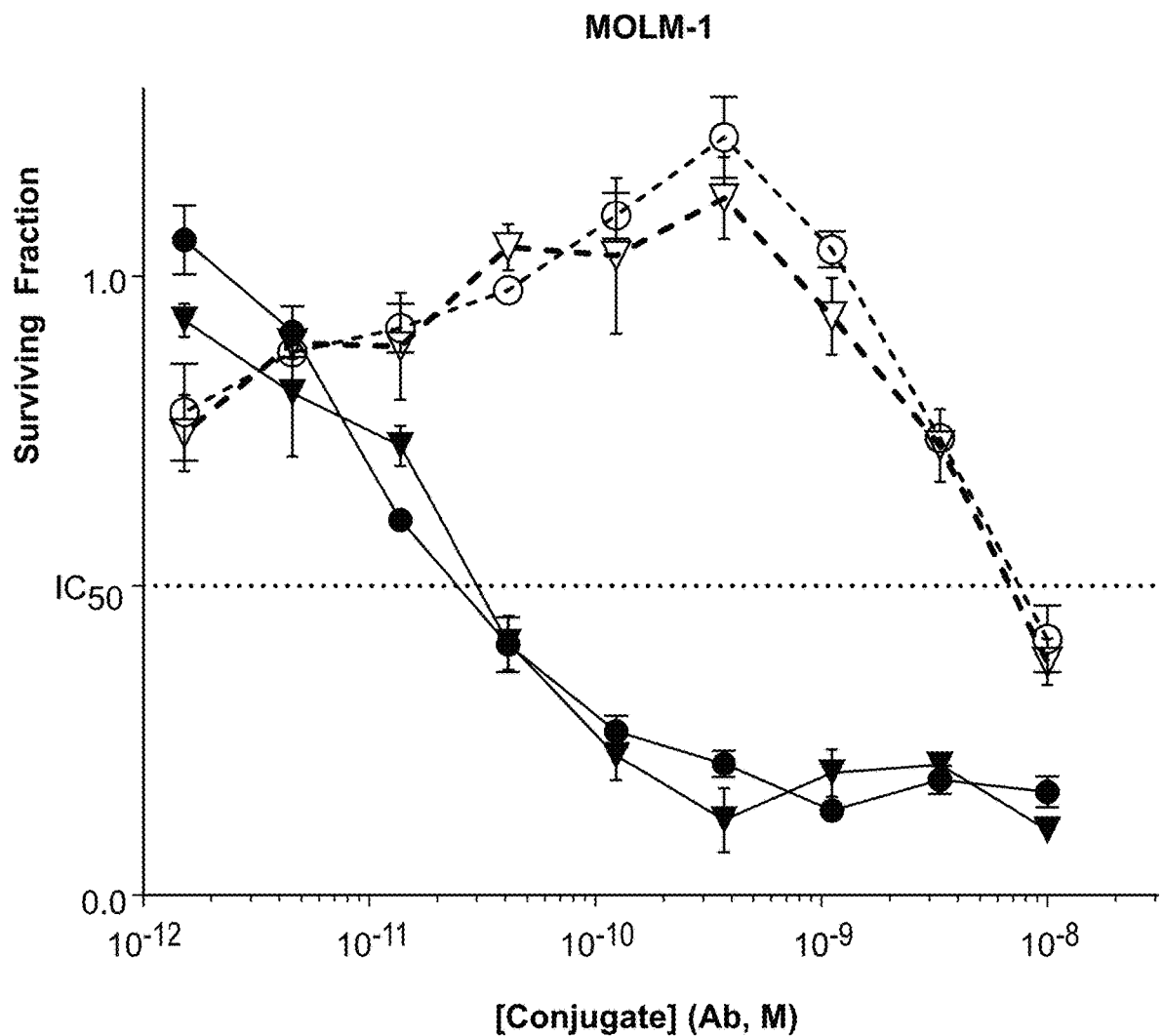

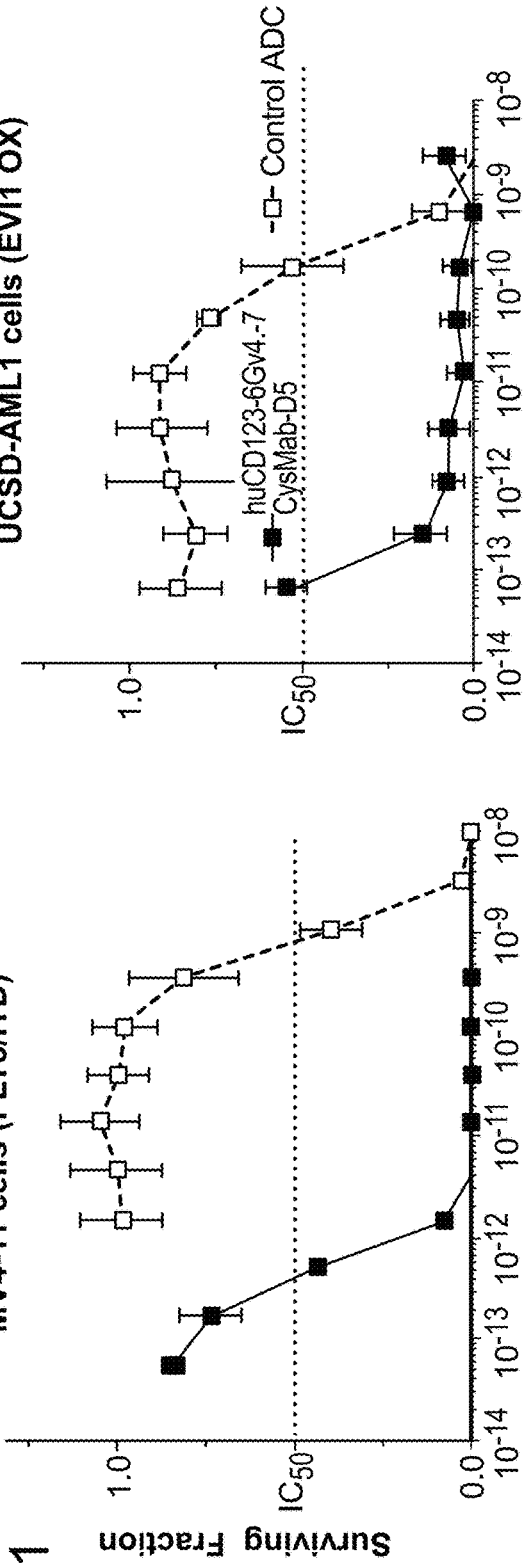
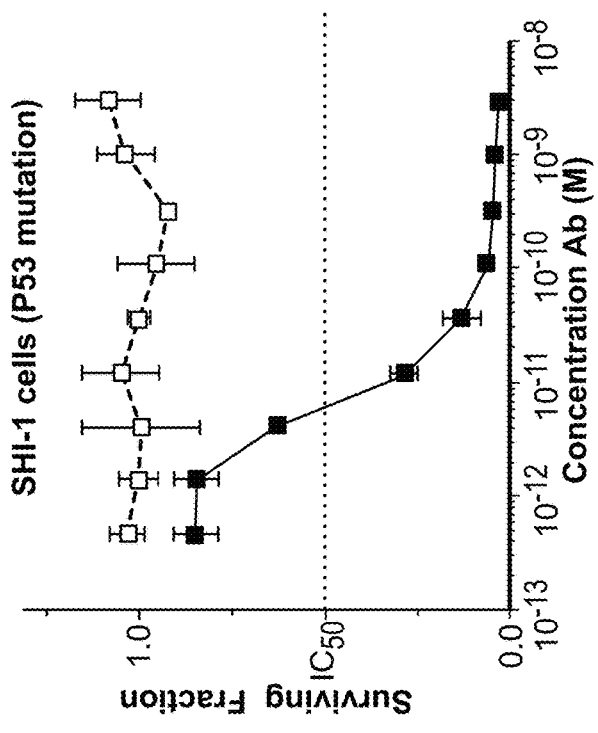
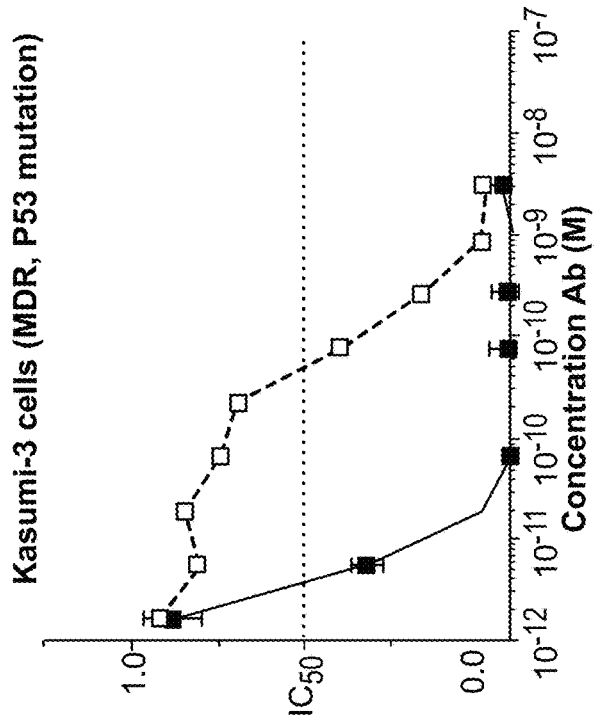
FIG. 21

ANTI-CD123 ANTIBODIES AND CONJUGATES AND DERIVATIVES THEREOF

REFERENCE TO RELATED APPLICATIONS

This application is a continuation application of U.S. patent application Ser. No. 17/077,877, filed on Oct. 22, 2020, which is a continuation application of U.S. patent application Ser. No. 16/778,988, filed on Jan. 31, 2020, now U.S. Pat. No. 10,875,925, which is a divisional application of U.S. patent application Ser. No. 15/667,697, filed Aug. 3, 2017, now U.S. Pat. No. 10,919,969, which is a divisional application of U.S. patent application Ser. No. 15/195,401, filed Jun. 28, 2016, now U.S. Pat. No. 10,077,313, which claims the benefit of the filing date, under 35 U.S.C. § 119(e), of U.S. Provisional Application No. 62/186,161, filed Jun. 29, 2015, U.S. Provisional Application No. 62/338,203, filed May 18, 2016, and U.S. Provisional Application No. 62/346,730, filed Jun. 7, 2016. The entire contents of each of the above-referenced applications are incorporated herein by reference.

FIELD OF THE INVENTION

The present invention generally relates to antibodies, antigen-binding fragments thereof, polypeptides, and immunoconjugates that bind to CD123 antigen (the α chain of the interleukin-3 receptor, or IL-3Rα). The present invention also relates to methods of using such CD123-binding molecules for diagnosing and treating diseases, such as B-cell malignancies.

BACKGROUND OF THE INVENTION

CD123 (interleukin 3 receptor alpha, IL-3Rα) is a 40 kDa molecule that is part of the interleukin 3 receptor (IL-3R) complex. The cytokine Interleukin 3 (IL-3) drives early differentiation of multipotent stem cells into cells of the erythroid, myeloid and lymphoid progenitors. CD123 is expressed on $CD34^+$-committed progenitors, but not by $CD34^+/CD38^-$ normal hematopoietic stem cells (HSCs). CD123 is expressed by basophils, mast cells, plasmacytoid dendritic cells, some expression by monocytes, macrophages and eosinophils, and low or no expression by neutrophils and megakaryocytes. Some non-hematopoietic tissues, such as placenta, Leydig cells of the testis, certain brain cell elements and some endothelial cells, also express CD123. However, expression there is mostly cytoplasmic.

CD123 is reported to be expressed by leukemic blast cells ("leukemia blasts") and leukemia stem cells (LSC) (Jordan et al., *Leukemia* 14:1777-1784, 2000; Jin et al., *Blood* 113:6603-6610, 2009). In human normal precursor populations, CD123 is expressed by a subset of hematopoietic progenitor cells (HPC), but not by normal HSCs. CD123 is also reportedly expressed by plasmacytoid dendritic cells (pDC) and basophils, and, to a lesser extent, monocytes and eosinophils.

CD123 has been reported to be overexpressed on malignant cells in a wide range of hematologic malignancies including acute myeloid leukemia (AML) and myelodysplastic syndrome (MDS) (Munoz et al., *Haematologica* 86(12):1261-1269, 2001). Overexpression of CD123 is associated with poorer prognosis in AML (Tettamanti et al., *Br. J. Haematol.* 161:389 401, 2013). AML and MDS are thought to arise in and be perpetuated by a small population of leukemic stem cells (LSCs), which are generally dormant (i.e., not rapidly dividing cells) and therefore resist cell death (apoptosis) and conventional chemotherapeutic agents. LSCs are characterized by over-expression of CD123, while CD123 is not present in the corresponding normal hematopoietic stem cell population in normal human bone marrow (Jin et al., *Blood* 113:6603-6610, 2009; Jordan et al., *Leukemia* 14:1777-1784, 2000). CD123 expression is also associated with multiple other malignancies/pre-malignancies: chronic myeloid leukemia (CML) progenitor cells (including blast crisis CML); Hodgkin's Reed Sternberg (RS) cells; transformed non-Hodgkin's lymphoma (NHL); some chronic lymphocytic leukemia (CLL) ($CD11c^+$); a subset of acute T lymphoblastic leukemia (T-ALL) (16%, most immature, mostly adult), plasmacytoid dendritic cell (pDC) (DC2) malignancies and $CD34^+/CD38^-$ myelodysplastic syndrome (MDS) marrow cell malignancies.

AML is a clonal disease characterized by the proliferation and accumulation of transformed myeloid progenitor cells in the bone marrow, which ultimately leads to hematopoietic failure. The incidence of AML increases with age, and older patients typically have worse treatment outcomes than do younger patients (Robak et al., *Clin. Ther.* 2:2349-2370, 2009). Unfortunately, at present, most adults with AML die from their disease.

Treatment for AML initially focuses in the induction of remission (induction therapy). Once remission is achieved, treatment shifts to focus on securing such remission (post-remission or consolidation therapy) and, in some instances, maintenance therapy. The standard remission induction paradigm for AML is chemotherapy with an anthracycline/cytarabine combination, followed by either consolidation chemotherapy, usually with higher doses of the same drugs as were used during the induction period, or human stem cell transplantation, depending on the patient's ability to tolerate intensive treatment and the likelihood of cure with chemotherapy alone (see Roboz, *Curr. Opin. Oncol.* 24:711-719, 2012).

Agents frequently used in induction therapy include cytarabine and the anthracyclines. Cytarabine, also known as AraC, kills cancer cells and other rapidly dividing normal cells by interfering with DNA synthesis. Side effects associated with AraC treatment include decreased resistance to infection, a result of decreased white blood cell production; bleeding, as a result of decreased platelet production; and anemia, due to a potential reduction in red blood cells. Other side effects include nausea and vomiting. Anthracyclines (e.g., daunorubicin, doxorubicin, and idarubicin) have several modes of action including inhibition of DNA and RNA synthesis, disruption of higher order structures of DNA, and production of cell damaging free oxygen radicals. The most consequential adverse effect of anthracyclines is cardiotoxicity, which considerably limits administered life-time dose and to some extent their usefulness.

Thus, unfortunately, despite substantial progress in the treatment of newly diagnosed AML, 20% to 40% of patients do not achieve remission with the standard induction chemotherapy, and 50% to 70% of patients entering a first complete remission are expected to relapse within 3 years. The optimum strategy at the time of relapse, or for patients with the resistant disease, remains uncertain. Stem cell transplantation has been established as the most effective form of antileukemic therapy in patients with AML in first or subsequent remission (Roboz, 2012).

Antibody-drug conjugates (ADC) and other cell binding agent-drug conjugates are emerging as a powerful class of anti-tumor agents with efficacy across a range of cancers. Cell binding agent-drug conjugates (such as ADCs) are commonly composed of three distinct elements: a cell-binding agent (e.g., an antibody); a linker; and a cytotoxic moiety. Conventionally, the cytotoxic drug moiety is covalently attached to lysine residues on the antibody, or to cysteine residues, obtained through reduction of interchain disulfide bonds, resulting in ADCs that are heterogeneous mixtures bearing varying numbers of drugs attached at different positions on the antibody molecule.

SUMMARY OF THE INVENTION

The present invention is based on the surprising findings that the conjugates of the present invention are highly potent against various CD123-expressing cancer cells, particularly leukemia with at least one negative prognostic factors.

One aspect of the invention provides an antibody or antigen-binding fragment thereof that: (a) binds an epitope within amino acids 101 to 346 of human CD123/IL3-Rα antigen, and (b) inhibits IL3-dependent proliferation in antigen-positive TF-1 cells.

In certain embodiments, the antibody or antigen-binding fragment thereof binds an epitope within amino acids 101 to 204 of human CD123 antigen. In another embodiment, the antibody or antigen-binding fragment thereof binds an epitope within amino acids 205 to 346 of human CD123 antigen.

A related aspect of the invention provides an antibody or antigen-binding fragment thereof that: (a) binds an epitope within amino acids 1 to 100 of human CD123 antigen, and (b) inhibits IL3-dependent proliferation in antigen-positive TF-1 cells, with an IC$_{50}$ value of 0.1 nM or less (e.g., 0.08 nM, 0.05 nM, 0.03 nM).

In certain embodiments, the antibody or antigen-binding fragment thereof inhibits the proliferation of leukemic stem cells or leukemic blast cells but not hematopoietic stem cells.

In certain embodiments, the antibody or antigen-binding fragment thereof binds to human CD123 antigen-positive cells with a dissociation constant ($K_d$) of 0.3 nM or lower, such as between 0.01 nM and 0.3 nM, between 0.01 nM and 0.2 nM, between 0.01 nM and 0.19 nM, between 0.01 nM and 0.18 nM, between 0.01 nM and 0.15 nM, or between 0.01 nM and 0.1 nM.

In certain embodiments, the antibody or antigen-binding fragment thereof binds to cynomolgus monkey CD123. For example, the antibody or antigen-binding fragment thereof may bind to cynomolgus monkey CD123 with a $K_d$ of between 0.05 and 0.3 nM, between 0.05 and 0.2 nM, between 0.05 nM and 0.19 nM, between 0.05 nM and 0.18 nM, between 0.05 nM and 0.15 nM, or between 0.05 and 0.1 nM. In certain embodiments, the antibody or antigen-binding fragment thereof binds both human and cynomolgus monkey CD123 with a substantially similar binding affinity. For example, the antibody or antigen-binding fragment thereof may bind to human and cynomolgus monkey CD123 with a $K_d$ of between 0.05 and 0.3 nM, between 0.05 and 0.2 nM, or between 0.05 and 0.1 nM. The $K_d$ may be measured by flow cytometry, surface plasmon resonance, or radioimmunoassay.

In certain embodiments, the antibody or antigen-binding fragment thereof inhibits at least 50% of IL3-dependent proliferation in antigen-positive TF-1 cells at a concentration of 0.5 nM or lower.

In certain embodiments, the antibody or antigen-binding fragment thereof may comprise: a) at least one heavy chain variable region or fragment thereof comprising three sequential complementarity-determining regions (CDR) CDR1, CDR2, and CDR3, respectively, wherein, with the exception of 1, 2, or 3 conservative amino acid substitutions, CDR1 is selected from the group consisting of: SEQ ID NOs: 1, 5, and 12, CDR2 is selected from the group consisting of: SEQ ID NOs: 2, 3, 6-10, 13, and 14, and, optionally, CDR3 is selected from the group consisting of: SEQ ID NOs: 4, 11, 15 and 70; and b) at least one light chain variable region or fragment thereof comprising three sequential complementarity-determining regions (CDR) CDR1, CDR2, and CDR3, respectively, wherein, with the exception of 1, 2, or 3 conservative amino acid substitutions, CDR1 is selected from the group consisting of: SEQ ID NOs: 16, 19, 20, 23 and 72, CDR2 is selected from the group consisting of: SEQ ID NOs: 17, 21, 24 and 71, and, optionally, CDR3 is selected from the group consisting of: SEQ ID NOs: 18, 22, and 25.

In certain embodiments, the antibody or antigen-binding fragment thereof may comprise: a) at least one heavy chain variable region or fragment thereof comprising three sequential complementarity-determining regions (CDR) CDR1, CDR2, and CDR3, respectively, wherein, with the exception of 1, 2, or 3 conservative amino acid substitutions, CDR1 is selected from the group consisting of: SEQ ID NOs: 1, 5, and 12, CDR2 is selected from the group consisting of: SEQ ID NOs: 2, 3, 6-10, 13, and 14, and, optionally, CDR3 is selected from the group consisting of: SEQ ID NOs: 4, 11 and 15; and b) at least one light chain variable region or fragment thereof comprising three sequential complementarity-determining regions (CDR) CDR1, CDR2, and CDR3, respectively, wherein, with the exception of 1, 2, or 3 conservative amino acid substitutions, CDR1 is selected from the group consisting of: SEQ ID NOs: 16, 19, 20 and 23, CDR2 is selected from the group consisting of: SEQ ID NOs: 17, 21, and 24, and, optionally, CDR3 is selected from the group consisting of: SEQ ID NOs: 18, 22, and 25.

In certain embodiments, the conservative amino acid substitutions comprise a substitution of at least one Lys in a CDR by an Arg.

In certain embodiments, the antibody is a CDR-grafted humanized antibody comprising mouse CDR regions, and wherein one or more (e.g., 1, 2, 3, 4, 5, 6, 7, or 8) heavy chain and/or light chain framework region vernier zone residues of said antibody is of mouse origin.

In certain embodiments, the antibody or antigen-binding fragment thereof may comprise: a) an immunoglobulin heavy chain variable region having the amino acid sequence set forth in SEQ ID NO: 39 or 40; and b) an immunoglobulin light chain variable region having the amino acid sequence set forth in SEQ ID NO: 41.

In certain embodiments, the antibody or antigen-binding fragment thereof may comprise: a) an immunoglobulin heavy chain variable region having the amino acid sequence set forth in SEQ ID NO: 34; and b) an immunoglobulin light chain variable region having the amino acid sequence set forth in SEQ ID NO: 35. In certain embodiments, Xaa, the second residue from the N-terminus of SEQ ID NO: 34, is Phe. In other embodiments, Xaa is Val.

In certain embodiments, the antibody or antigen-binding fragment thereof may comprise: a) an immunoglobulin heavy chain variable region having the amino acid sequence set forth in SEQ ID NO: 39 or 40, except that the N-terminal residue is Ser; and b) an immunoglobulin light chain variable region having the amino acid sequence set forth in SEQ ID NO: 41.

In certain embodiments, the antibody or antigen-binding fragment thereof may comprise: a) an immunoglobulin heavy chain variable region having the amino acid sequence set forth in SEQ ID NO: 39 or 40; and b) an immunoglobulin light chain variable region having the amino acid sequence set forth in SEQ ID NO: 41, except that the N-terminal residue is Ser.

In certain embodiments, the antibody or antigen-binding fragment thereof may comprise: a) an immunoglobulin heavy chain region having the amino acid sequence set forth in SEQ ID NO: 59 or 60, except that the N-terminal residue is Ser, and except that the residue corresponding to the 5$^{th}$ to the last residue of SEQ ID NO: 54 is Cys (i.e., Cys at EU/OU numbering position 442); and b) an immunoglobulin light chain variable region having the amino acid sequence set forth in SEQ ID NO: 41.

In certain embodiments, the antibody or antigen-binding fragment thereof may comprise: a) an immunoglobulin heavy chain region having the amino acid sequence set forth in SEQ ID NO: 59 or 60, except that the residue corresponding to the 5$^{th}$ to the last residue of SEQ ID NO: 54 is Cys; and b) an immunoglobulin light chain variable region having the amino acid sequence set forth in SEQ ID NO: 41, except that the N-terminal residue is Ser.

In certain embodiments, the antibody or antigen-binding fragment thereof may comprise: a) an immunoglobulin heavy chain variable region having the amino acid sequence set forth in SEQ ID NO: 38; and b) an immunoglobulin light chain variable region having the amino acid sequence set forth in SEQ ID NO: 35.

In certain embodiments, the antibody or antigen-binding fragment thereof may comprise: a) an immunoglobulin heavy chain variable region having the amino acid sequence set forth in SEQ ID NO: 34; and b) an immunoglobulin light chain variable region having the amino acid sequence set forth in SEQ ID NO: 37.

In certain embodiments, the antibody or antigen-binding fragment thereof may comprise: a) an immunoglobulin heavy chain region having the amino acid sequence set forth in SEQ ID NO: 56; and b) an immunoglobulin light chain variable region having the amino acid sequence set forth in SEQ ID NO: 35.

In certain embodiments, the antibody or antigen-binding fragment thereof may comprise: a) an immunoglobulin heavy chain region having the amino acid sequence set forth in SEQ ID NO: 54; and b) an immunoglobulin light chain variable region having the amino acid sequence set forth in SEQ ID NO: 37.

In certain embodiments, Xaa, the second residue from the N-terminus of SEQ ID NOS: 38, 34, 56, and 54, is Phe. In other embodiments, Xaa is Val.

In certain embodiments, the antibody or antigen-binding fragment thereof may comprise: a) an immunoglobulin heavy chain region having the amino acid sequence set forth in SEQ ID NO: 59 or 60, except that the residue corresponding to the 5$^{th}$ to the last residue of SEQ ID NO: 54 is Cys; and b) an immunoglobulin light chain variable region having the amino acid sequence set forth in SEQ ID NO: 41.

In certain embodiments, the antibody or antigen-binding fragment thereof may comprise: a) an immunoglobulin heavy chain region having the amino acid sequence set forth in SEQ ID NO: 54; and b) an immunoglobulin light chain variable region having the amino acid sequence set forth in SEQ ID NO: 35.

In certain embodiments, Xaa, the second residue from the N-terminus of SEQ ID NO: 54 or 56, is Phe. In other embodiments, Xaa is Val.

In certain embodiments, the antibody or antigen-binding fragment thereof may comprise: a) an immunoglobulin heavy chain variable region comprising a CDR1 having an amino acid sequence set forth in SEQ ID NO: 1, a CDR2 having an amino acid sequence set forth in SEQ ID NO: 2 or 3, and a CDR3 having an amino acid sequence set forth in SEQ ID NO: 4; and b) an immunoglobulin light chain variable region comprising a CDR1 having an amino acid sequence set forth in SEQ ID NO: 16, a CDR2 having an amino acid sequence set forth in SEQ ID NO: 17, and a CDR3 having an amino acid sequence set forth in SEQ ID NO: 18.

In certain embodiments, the antibody or antigen-binding fragment thereof may comprise: a) an immunoglobulin heavy chain variable region comprising a CDR1 having an amino acid sequence set forth in SEQ ID NO: 5, a CDR2 having an amino acid sequence set forth in SEQ ID NO: 6, 7, 8, 9, or 10, and a CDR3 having an amino acid sequence set forth in SEQ ID NO: 11; and, b) an immunoglobulin light chain variable region comprising a CDR1 having an amino acid sequence set forth in SEQ ID NO: 19 or 20, a CDR2 having an amino acid sequence set forth in SEQ ID NO: 21, and a CDR3 having an amino acid sequence set forth in SEQ ID NO: 22.

In certain embodiments, the antibody or antigen-binding fragment thereof may comprise: a) an immunoglobulin heavy chain variable region comprising a CDR1 having an amino acid sequence set forth in SEQ ID NO: 12, a CDR2 having an amino acid sequence set forth in SEQ ID NO: 13 or 14, and a CDR3 having an amino acid sequence set forth in SEQ ID NO: 15; and b) an immunoglobulin light chain variable region comprising a CDR1 having an amino acid sequence set forth in SEQ ID NO: 23, a CDR2 having an amino acid sequence set forth in SEQ ID NO: 24, and a CDR3 having an amino acid sequence set forth in SEQ ID NO: 25.

In certain embodiments, the antibody or antigen-binding fragment thereof may comprise: a) a $V_H$ sequence at least 95% identical to a reference $V_H$ sequence selected from the group consisting of: SEQ ID NOs: 26, 28, 30, 32, 34, 38, 39, and 40 (preferably 26, 28, 30, 32, 34, and 38); and/or, b) a $V_L$ sequence at least 95% identical to a reference $V_L$ sequence selected from the group consisting of: SEQ ID NOs: 27, 29, 31, 33, 35, 37, and 41 (preferably 27, 29, 31, 35, and 37). In certain embodiments, the $V_H$ sequence is at least 99% identical to one of SEQ ID NOs: 26, 28, 30, 32, 34, 38, 39, and 40 (preferably 26, 28, 30, 32, 34, and 38), and/or wherein the $V_L$ sequence is at least 99% identical to one of SEQ ID NOs: 27, 29, 31, 33, 35, 37, and 41 (preferably 27, 29, 31, 35, and 37). In certain embodiments, the antibody or antigen-binding fragment thereof may comprise: a) a $V_H$ sequence selected from the group consisting of SEQ ID NOs: 26, 28, 30, 32, 34, 38, 39, and 40 (preferably 26, 28, 30, 32, 34, and 38); and/or, b) a $V_L$ sequence selected from the group consisting of SEQ ID NOs: 27, 29, 31, 33, 35, 37, and 41 (preferably 27, 29, 31, 35, and 37). In certain embodiments, the antibody or antigen-binding fragment thereof may comprise a $V_H$ sequence of SEQ ID NO: 26 and a $V_L$ sequence of SEQ ID NO: 27, or a $V_H$ sequence of SEQ ID NO: 28 and a $V_L$ sequence of SEQ ID NO: 29, or a $V_H$ sequence of SEQ ID NO: 30 and a $V_L$ sequence of SEQ ID NO: 31, or a $V_H$ sequence of SEQ ID NO: 34 and a $V_L$ sequence of SEQ ID NO: 35.

In certain embodiments, the antibody is a murine, non-human mammal, chimeric, humanized, or human antibody. For example, the humanized antibody may be a CDR-grafted antibody or resurfaced antibody. In certain embodiments, the antibody is a full-length antibody. In certain embodiments, the antigen-binding fragment thereof is an Fab, Fab', F(ab')$_2$, F$_d$, single chain Fv or scFv, disulfide linked F$_v$, V-NAR domain, IgNar, intrabody, IgG$\Delta$CH$_2$, minibody, F(ab')$_3$, tetrabody, triabody, diabody, single-domain antibody, DVD-Ig, Fcab, mAb$_2$, (scFv)$_2$, or scFv-Fc.

Another aspect of the invention provides a polypeptide comprising the V$_H$ and V$_L$ sequences of any of the subject antibody or antigen-binding fragment thereof. The polypeptide may be a fusion with a protein that is not a *pseudomonas* toxin.

Another aspect of the invention provides a cell producing the antibody or antigen-binding fragment thereof of the invention, or the polypeptide of the invention.

Another aspect of the invention provides a method of producing the antibody or antigen-binding fragment thereof of the invention, or the polypeptide of the invention, comprising: (a) culturing the cell of the invention; and, (b) isolating the antibody, antigen-binding fragment thereof, or polypeptide from the cultured cell. In certain embodiments, the cell is eukaryotic cell.

Another aspect of the invention provides an immunoconjugate having the following formula:

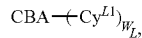

wherein:
  CBA is an antibody or antigen-binding fragment thereof of the invention, or the polypeptide thereof of the invention, that is covalently linked through a lysine residue to Cy$^{L1}$;
  W$_L$ is an integer from 1 to 20; and
  Cy$^{L1}$ is represented by the following formula:

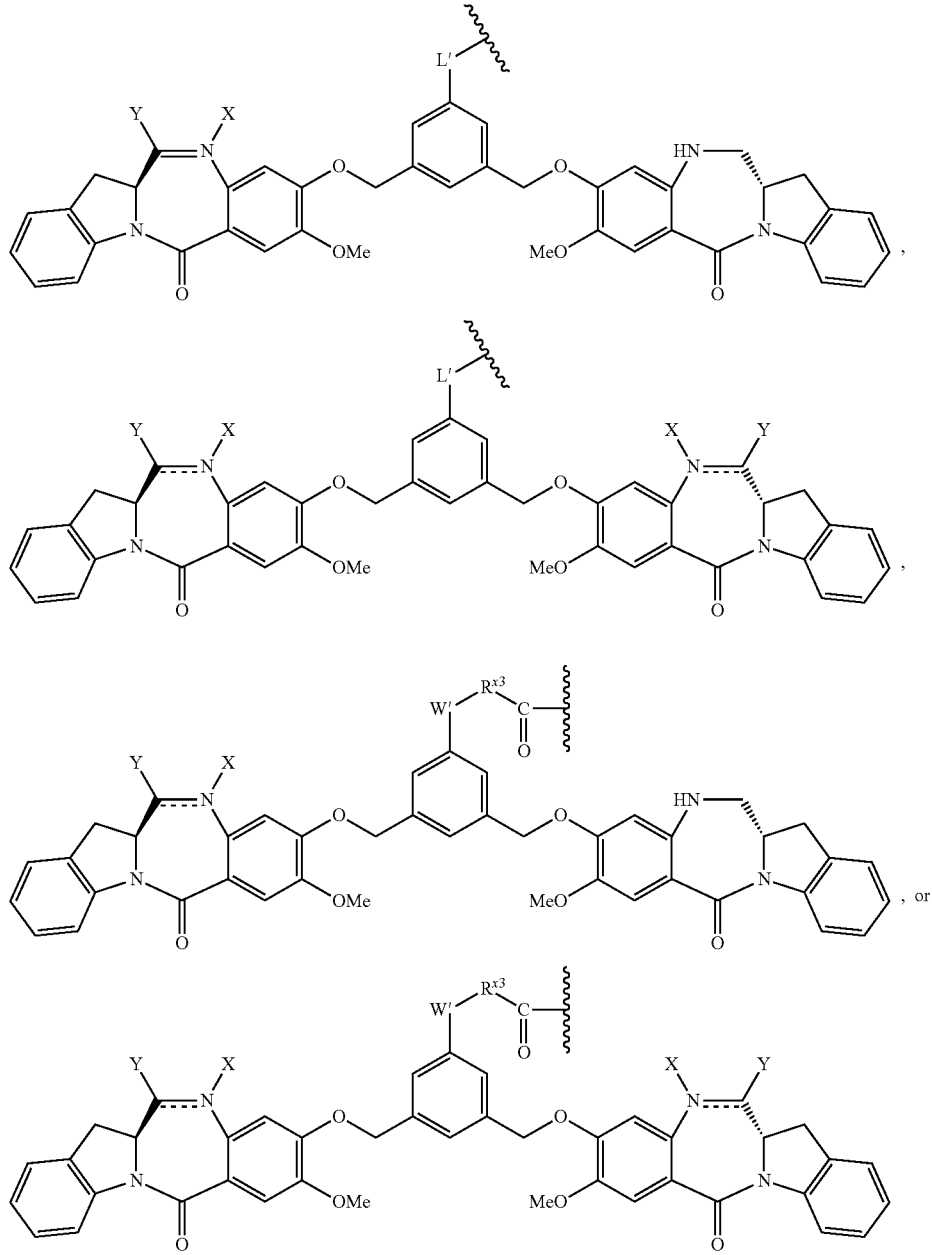

or a pharmaceutically acceptable salt thereof, wherein:

the double line ═ between N and C represents a single bond or a double bond, provided that when it is a double bond, X is absent and Y is —H or a (C₁-C₄)alkyl; and when it is a single bond, X is —H or an amine protecting moiety, and Y is —OH or —SO₃M;

W' is —NR$^{e'}$;
R$^{e'}$ is —(CH₂—CH₂—O)$_n$—R$^k$;
n is an integer from 2 to 6;
R$^k$ is —H or -Me;
R$^{x3}$ is a (C₁-C₆)alkyl;
L' is represented by the following formula:

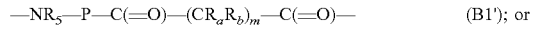   (B1'); or

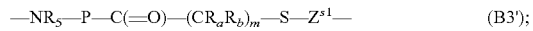   (B3');

R₅ is —H or a (C₁-C₃)alkyl;
P is an amino acid residue or a peptide containing between 2 to 20 amino acid residues;
R$_a$ and R$_b$, for each occurrence, are each independently —H, (C₁-C₃)alkyl, or a charged substituent or an ionizable group Q;
m is an integer from 1 to 6; and
Z$^{s1}$ is selected from any one of the following formulas:

wherein:

q is an integer from 1 to 5; and

M is H⁺ or a cation.

In certain embodiments, R$_a$ and R$_b$ are both H; and R₅ is H or Me.

In certain embodiments, P is a peptide containing 2 to 5 amino acid residues. For example, P may be selected from Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-N⁹-tosyl-Arg, Phe-N⁹-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 55), β-Ala-Leu-Ala-Leu (SEQ ID NO: 57), Gly-Phe-Leu-Gly (SEQ ID NO: 73), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. In certain embodiments, P is Gly-Gly-Gly, Ala-Val, Ala-Ala, Ala-D-Ala, D-Ala-Ala, or D-Ala-D-Ala.

In certain embodiments, Q is —SO₃M.

In certain embodiments, the immunoconjugate is represented by the following formula:

 (b1)

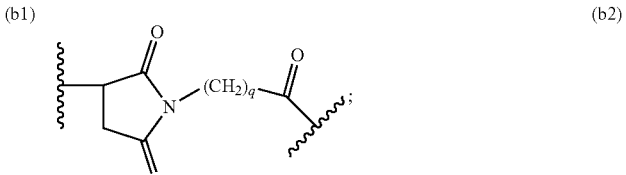 (b2)

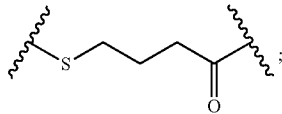 (b3)

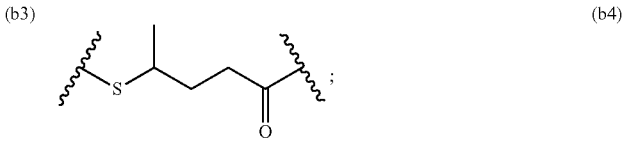 (b4)

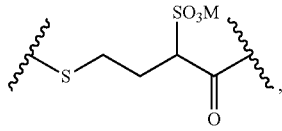 (b5)

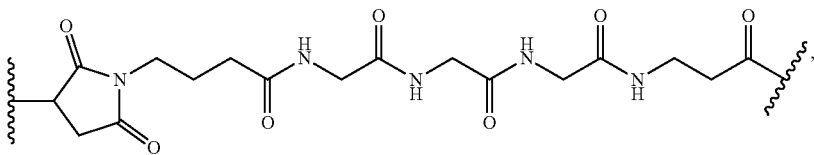 (b6)

 (b7)

 (b8)

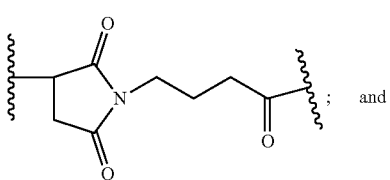 ; and (b9)

 (b10)

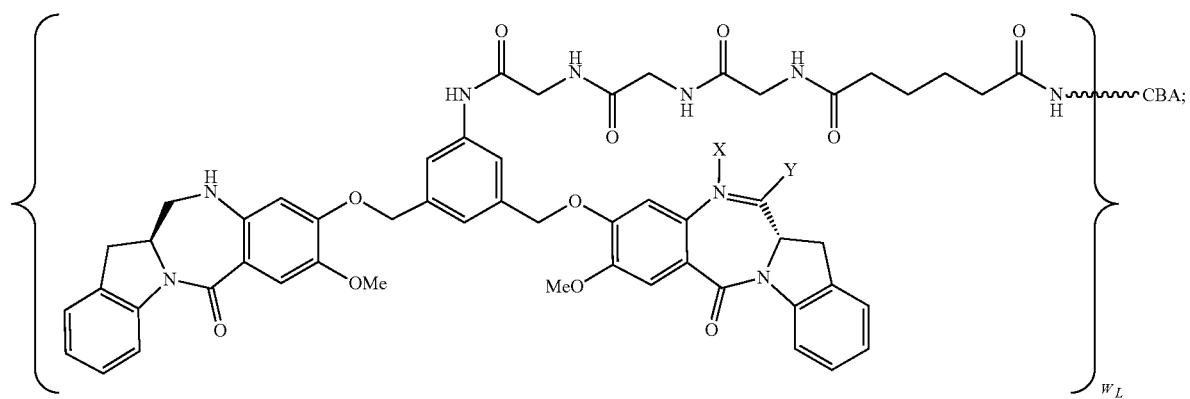
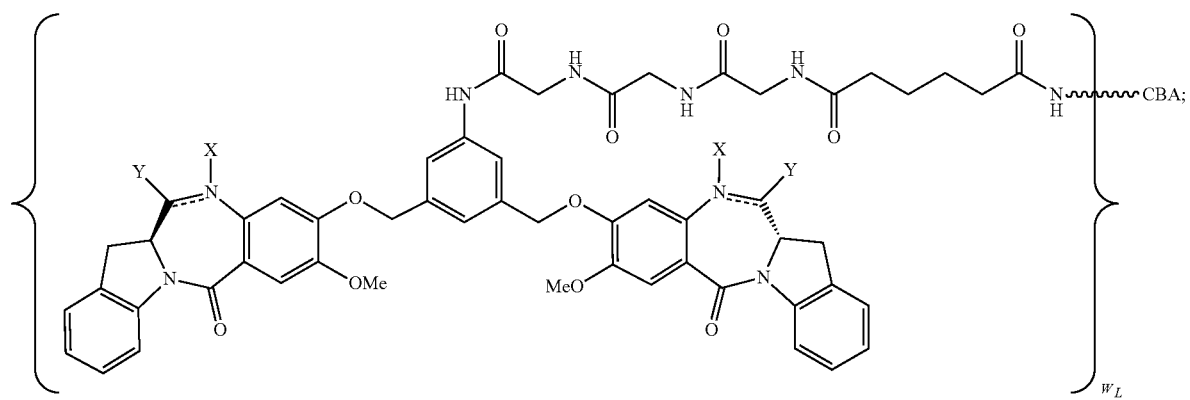
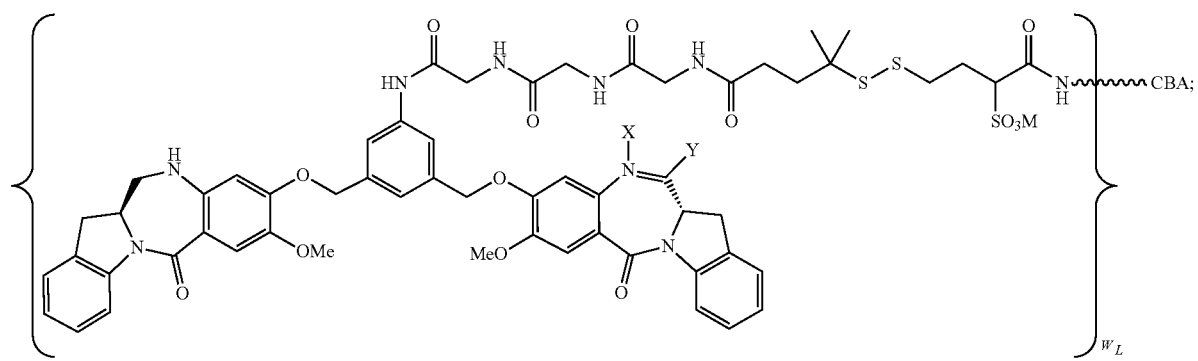
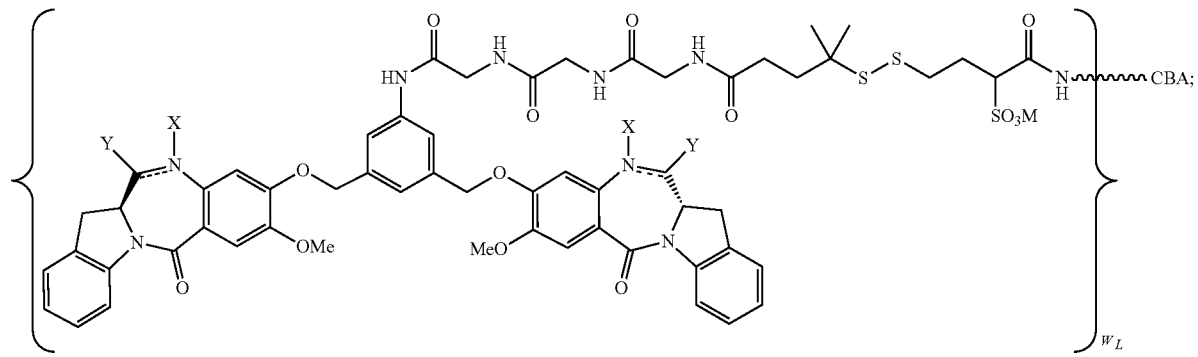

-continued
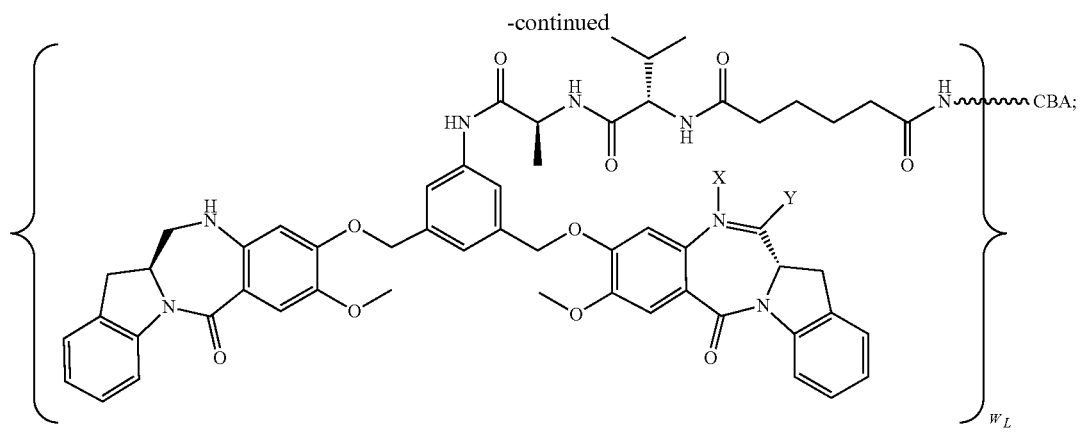
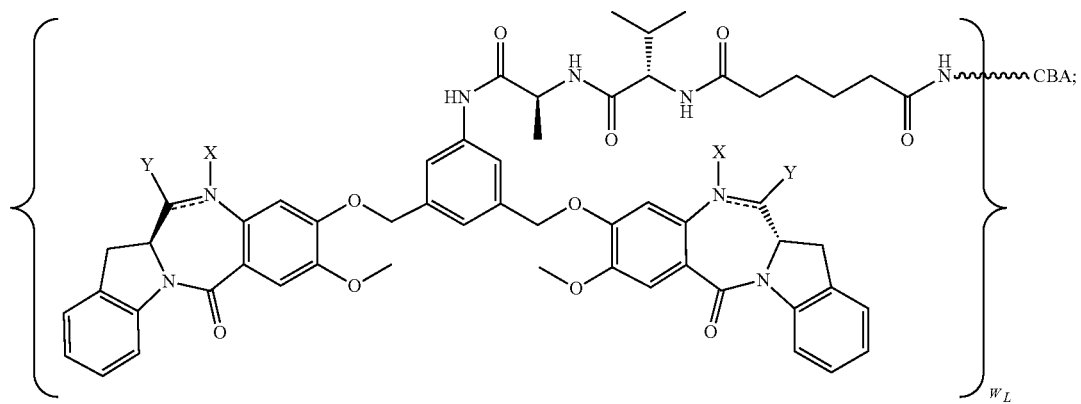
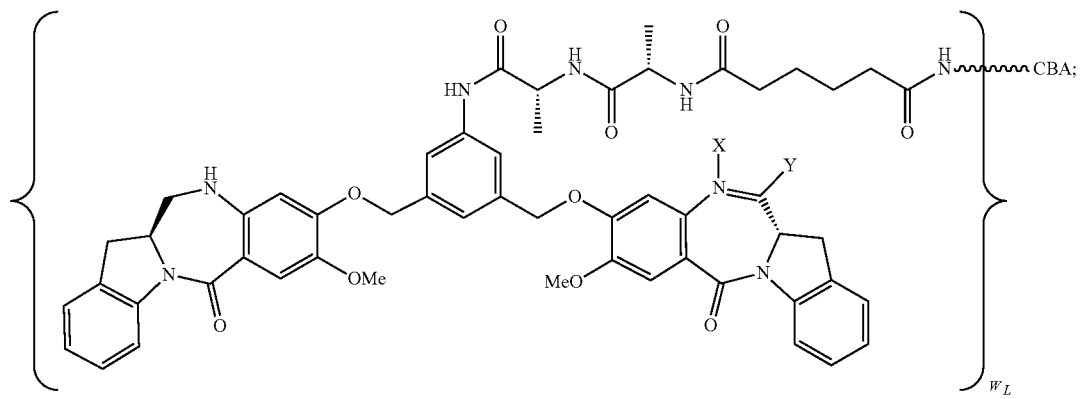
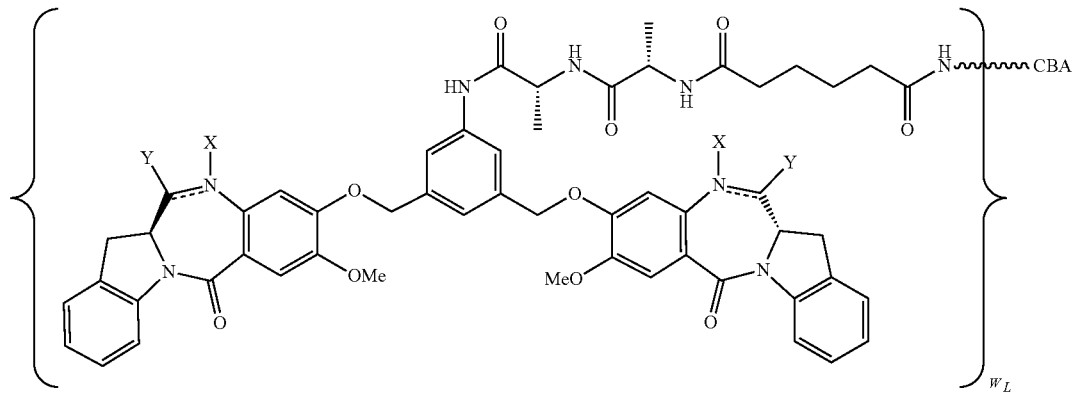

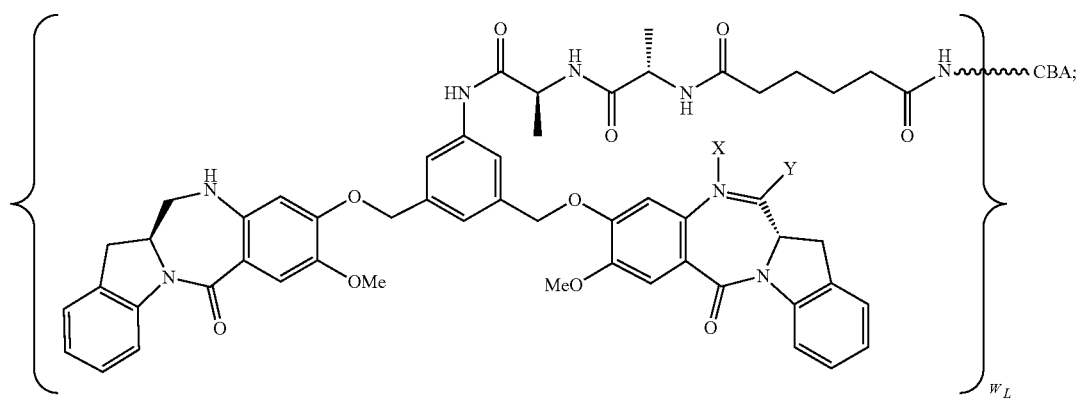
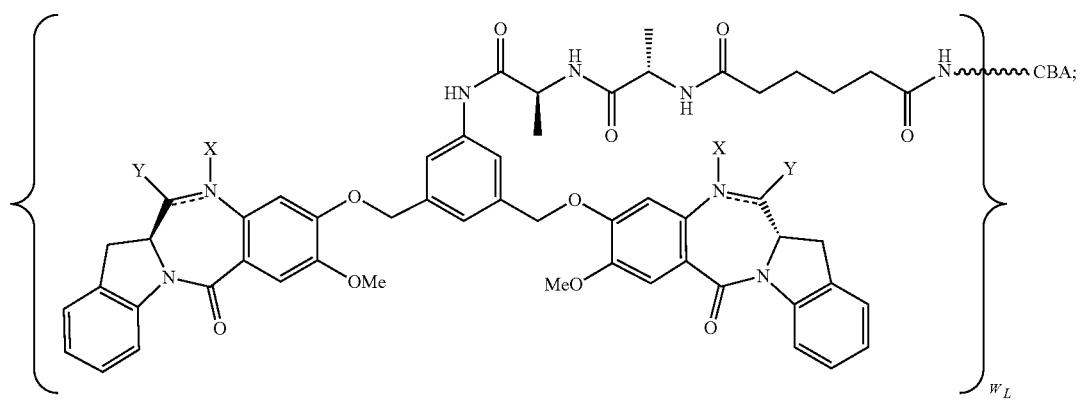
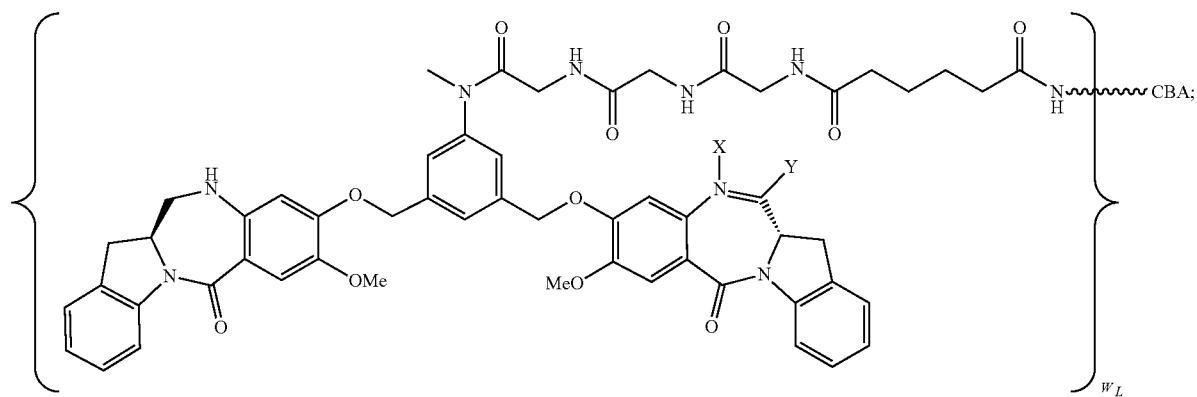
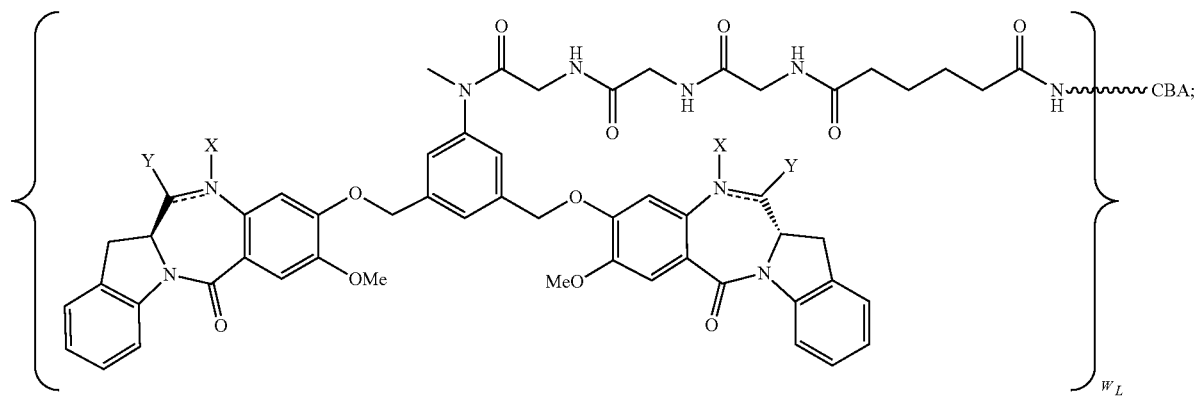

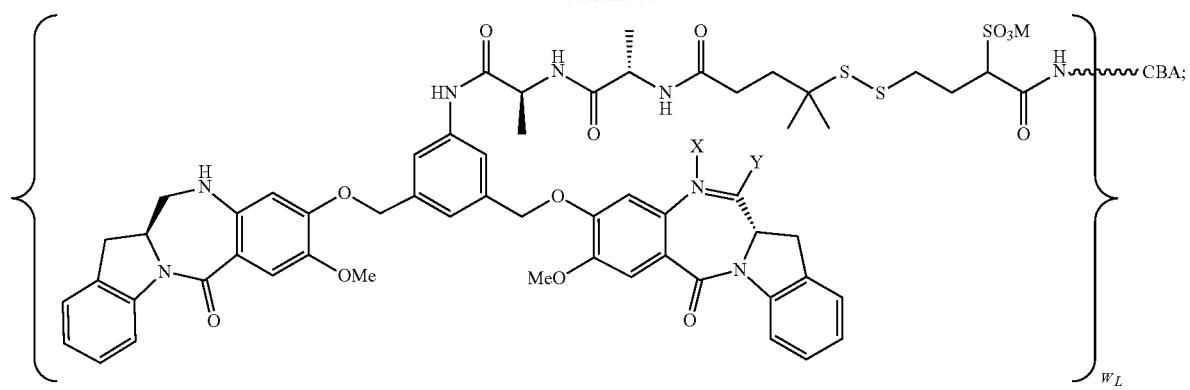
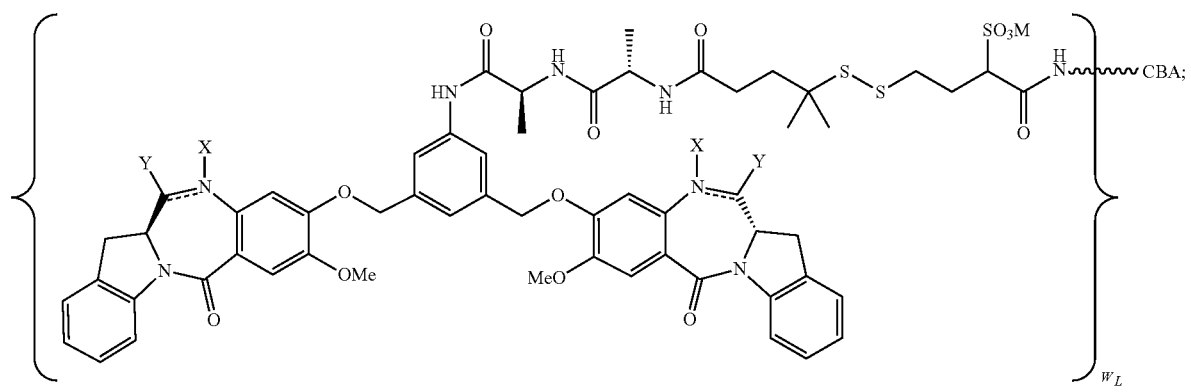
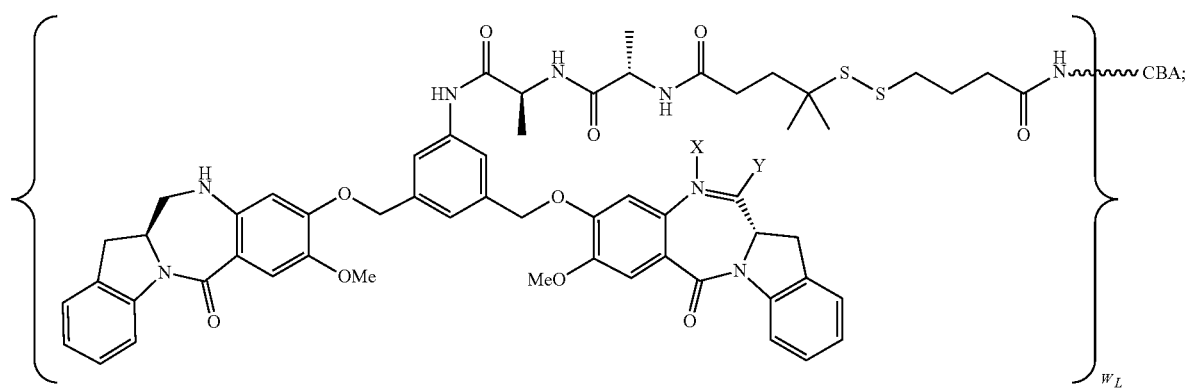
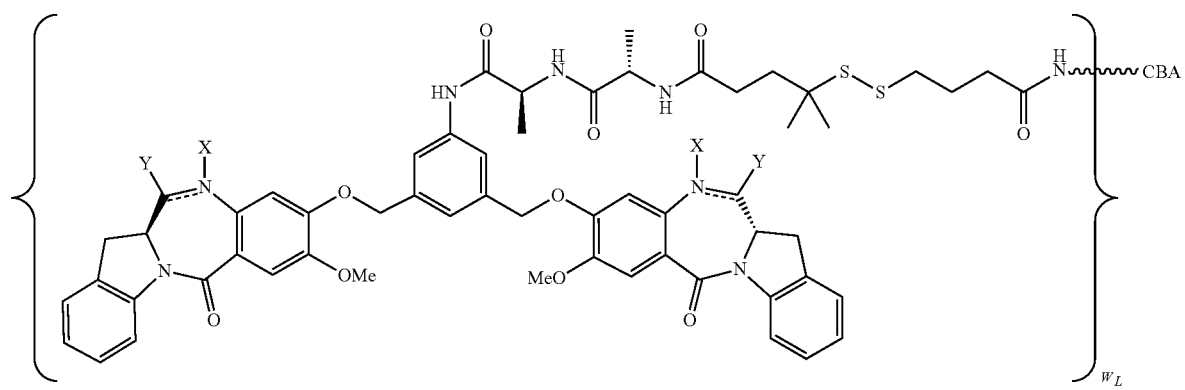

-continued
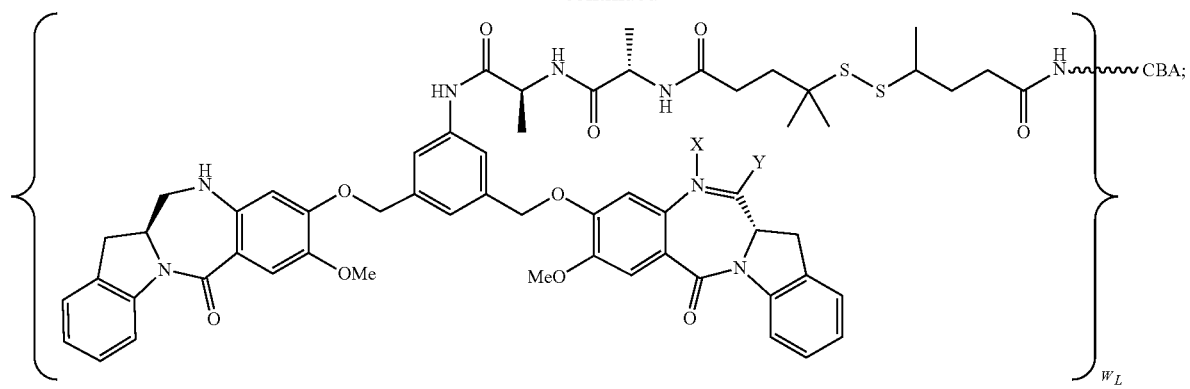
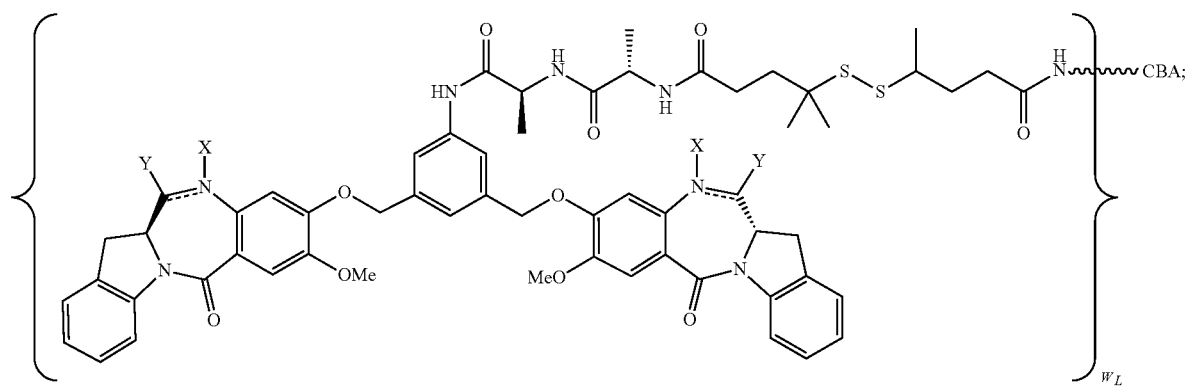
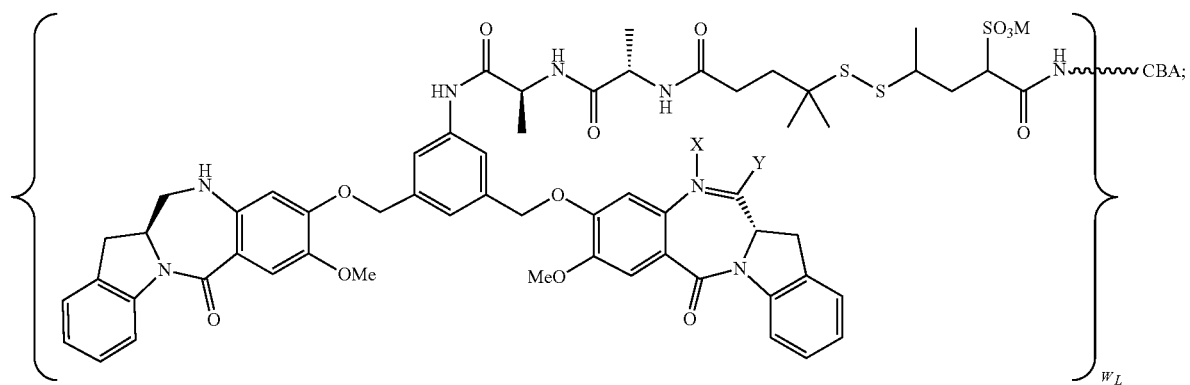
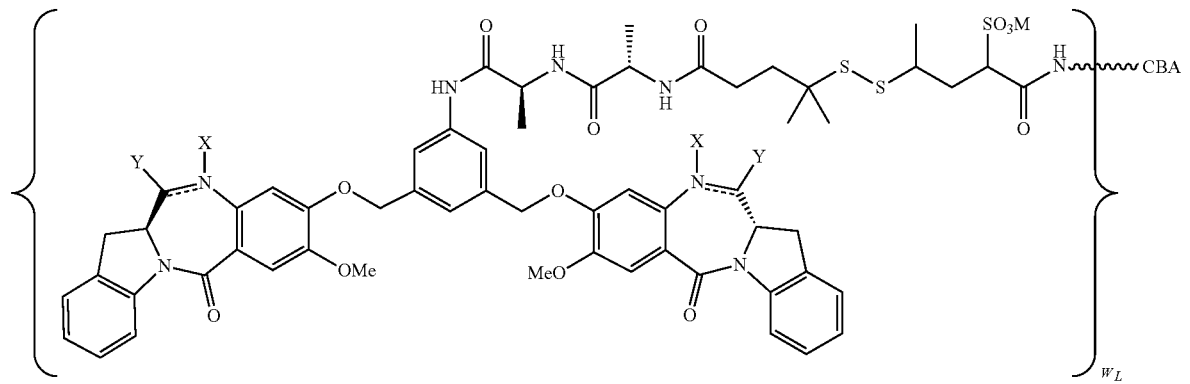

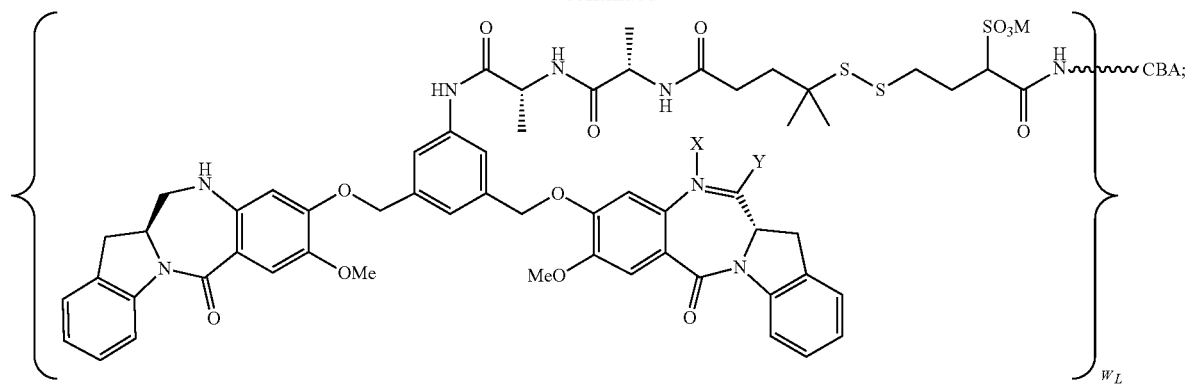
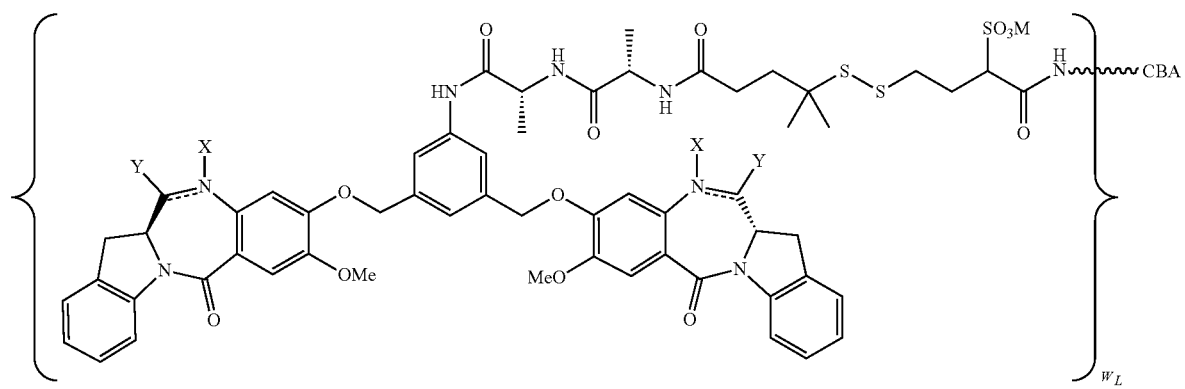
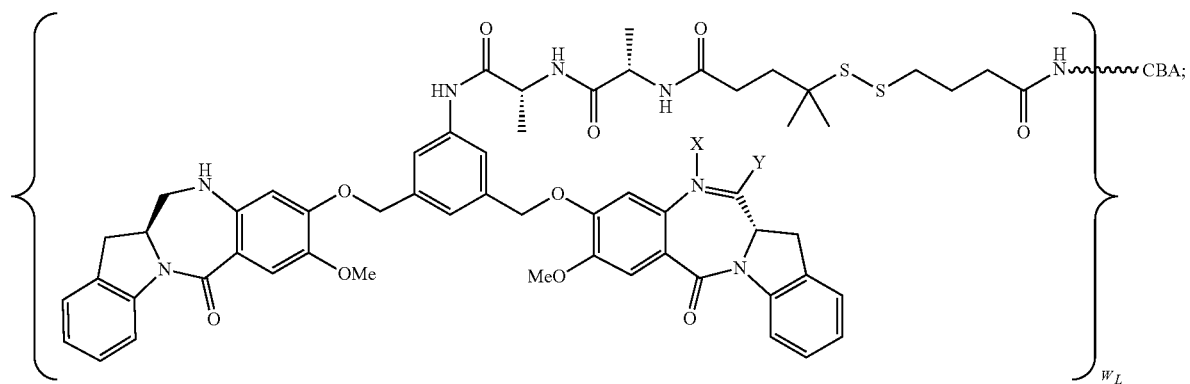
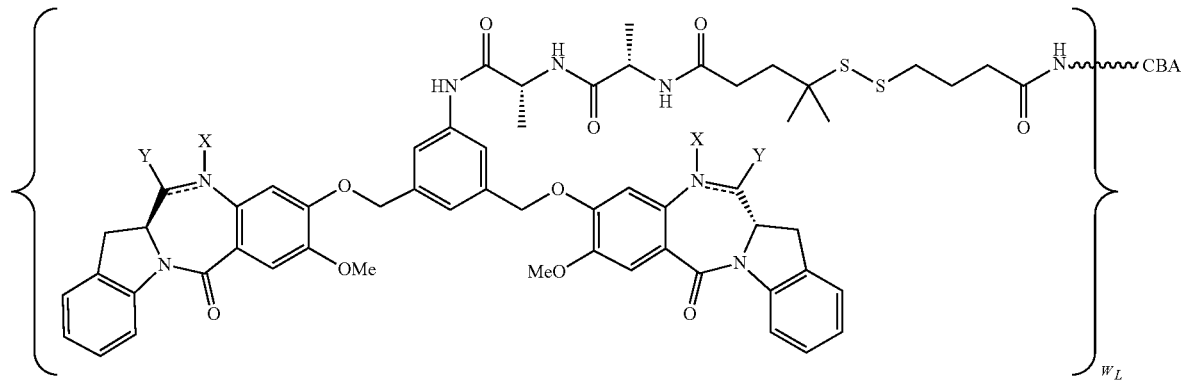

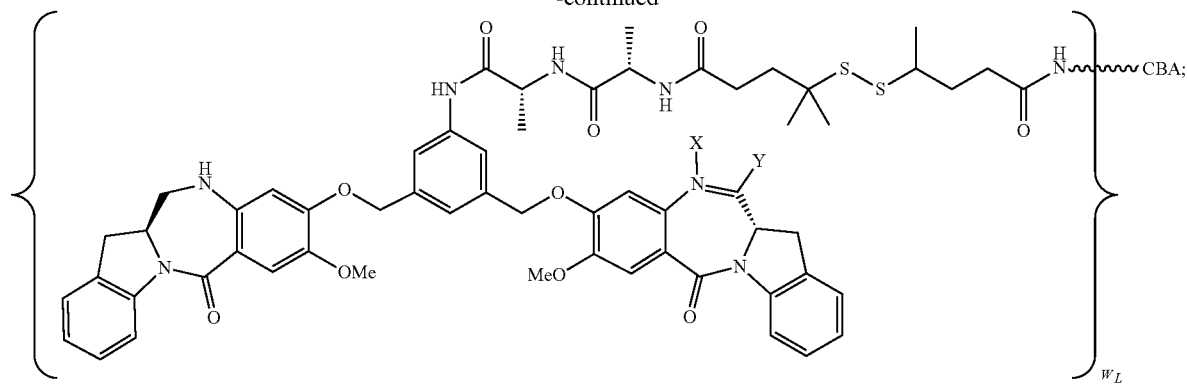
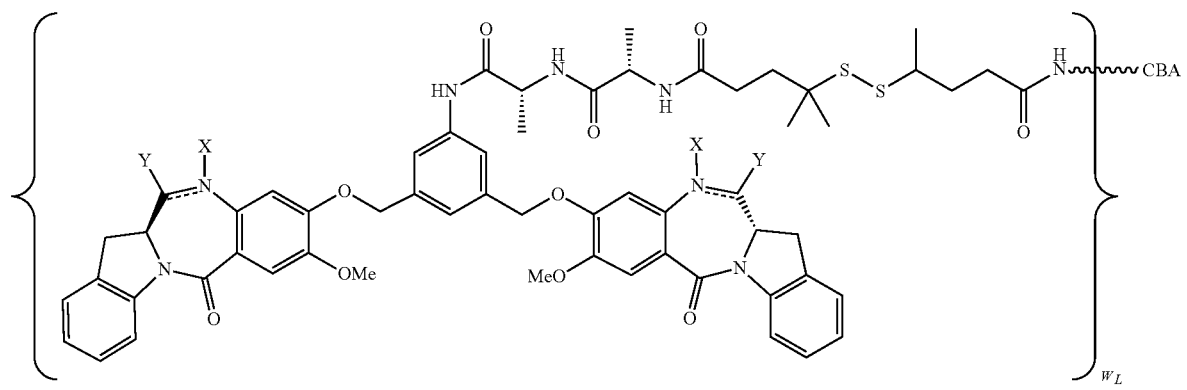
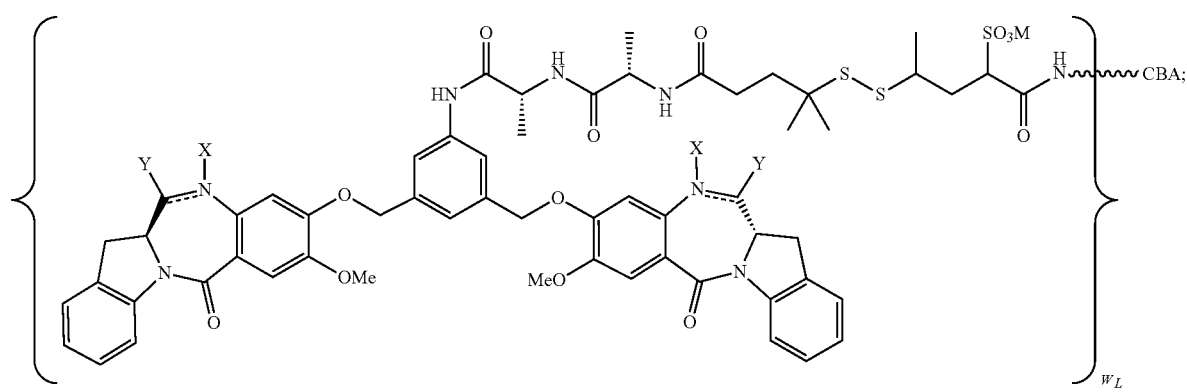

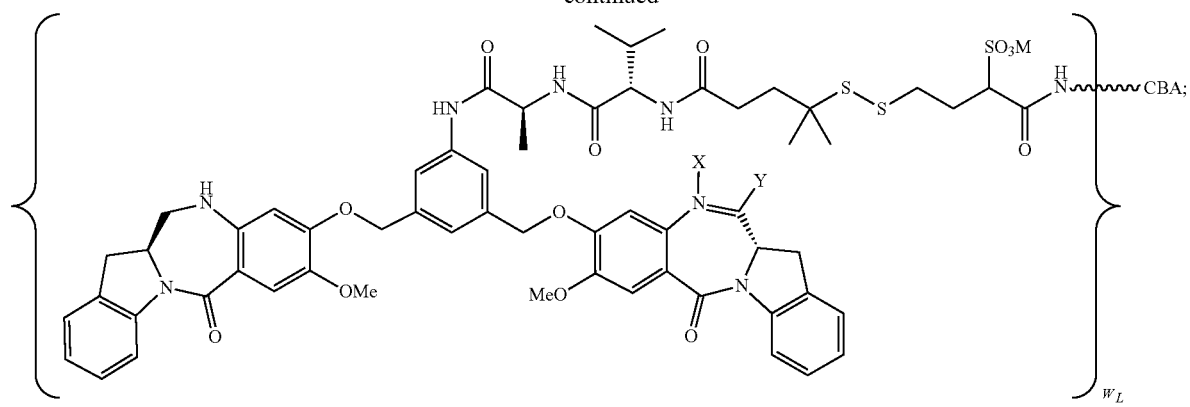
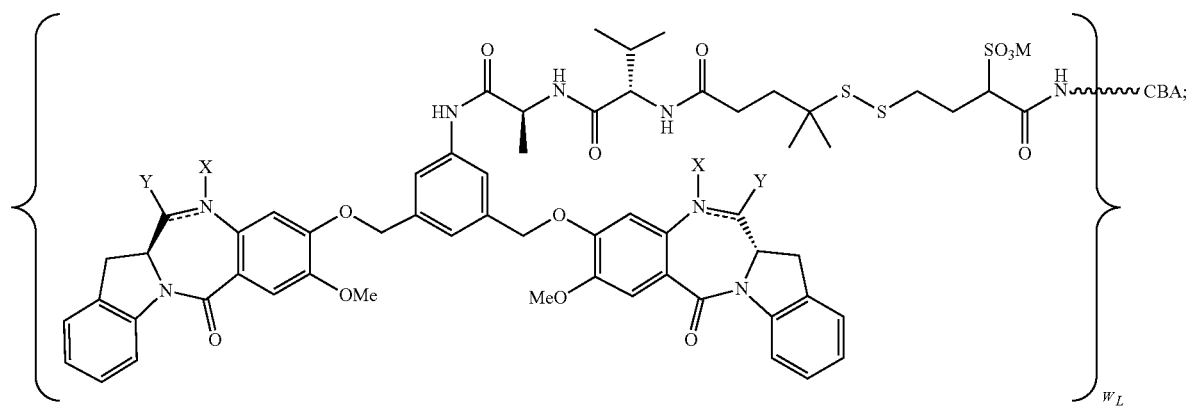
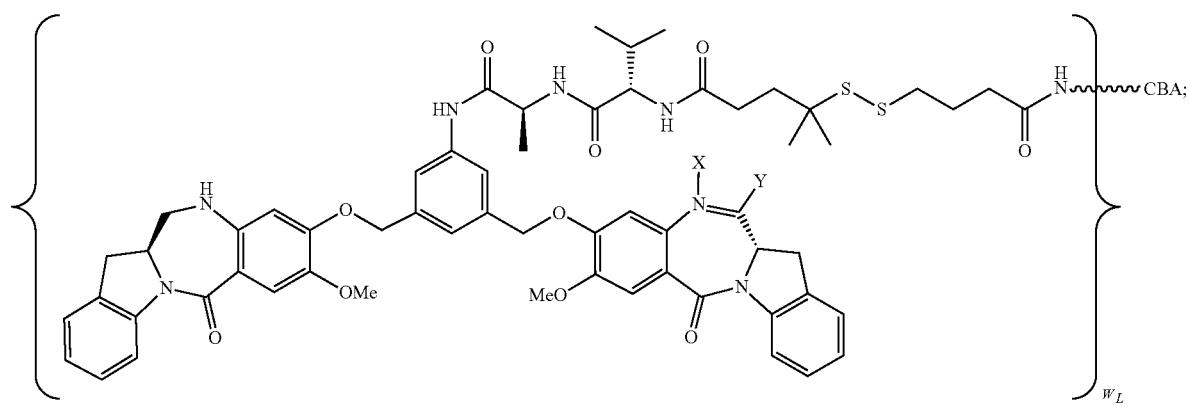
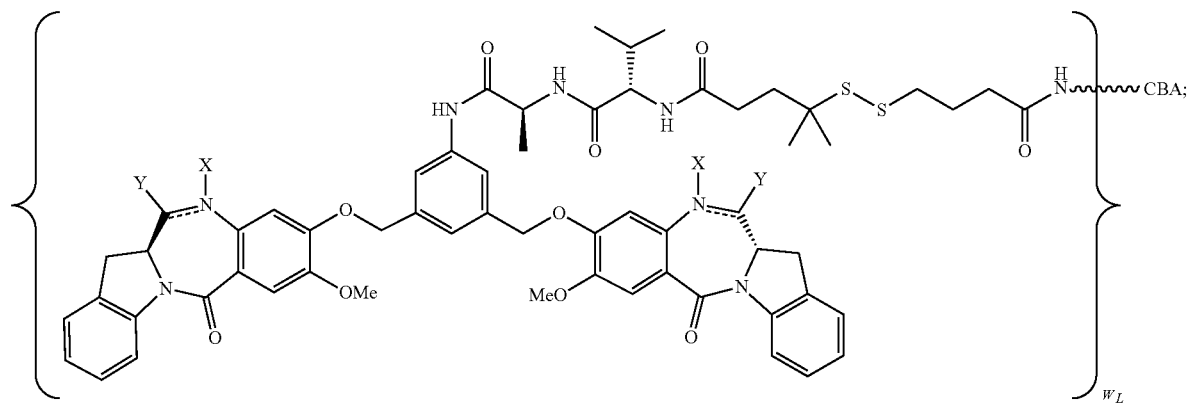

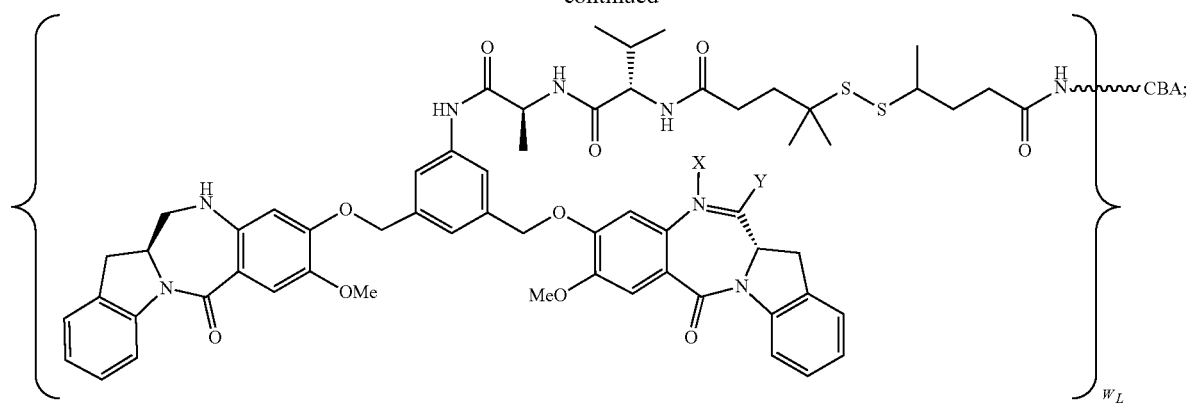
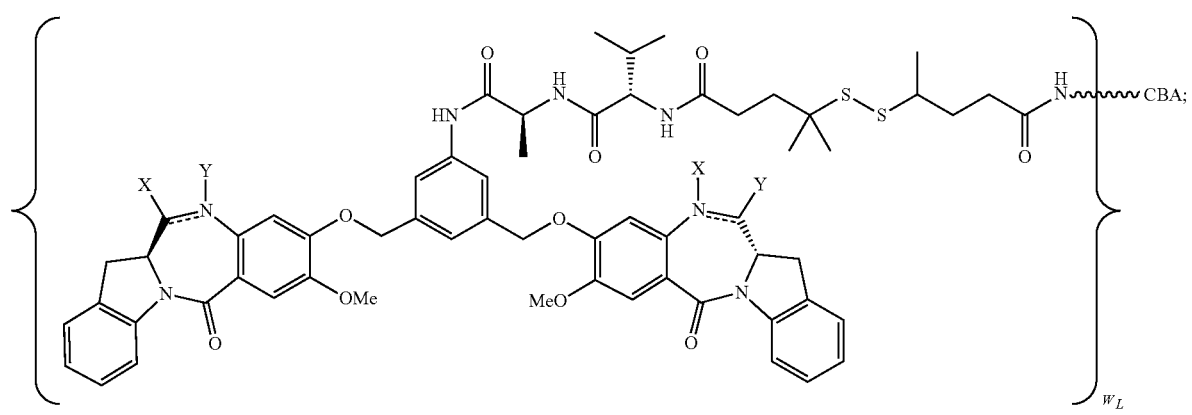
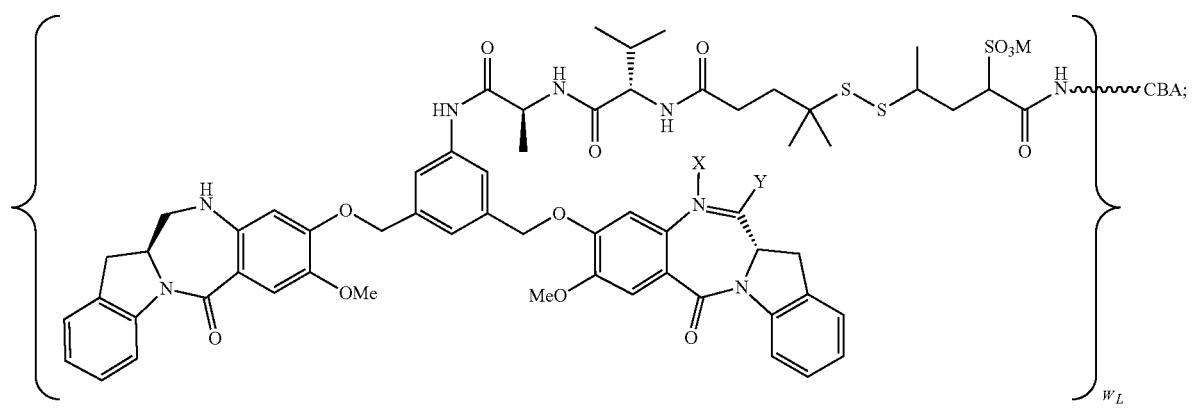
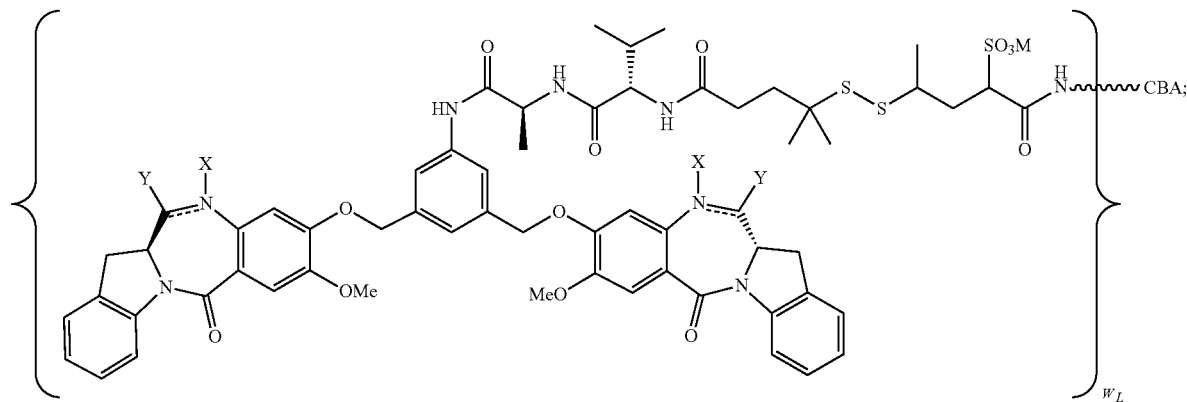

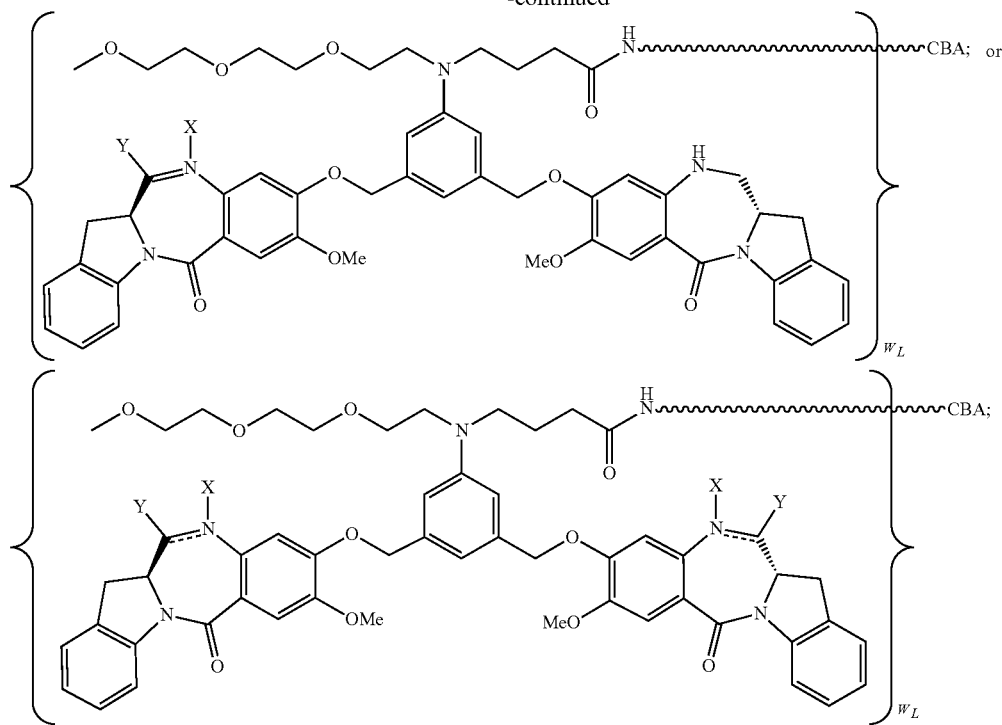

or a pharmaceutically acceptable salt thereof, wherein $W_L$ is an integer from 1 to 10; the double line ══ between N and C represents a single bond or a double bond, provided that when it is a double bond, X is absent and Y is —H; and when it is a single bond, X is —H, and Y is —OH or —SO$_3$M.

A related aspect provides an immunoconjugate having the formula:

$$CBA\text{-}(Cy^{L2})_{w_L},$$

wherein:
CBA is an antibody or antigen-binding fragment thereof of the invention, or the polypeptide thereof of the invention, that is covalently linked to $Cy^{L2}$ through a lysine residue;
$W_L$ is an integer from 1 to 20; and
$Cy^{L2}$ is represented by the following formula:

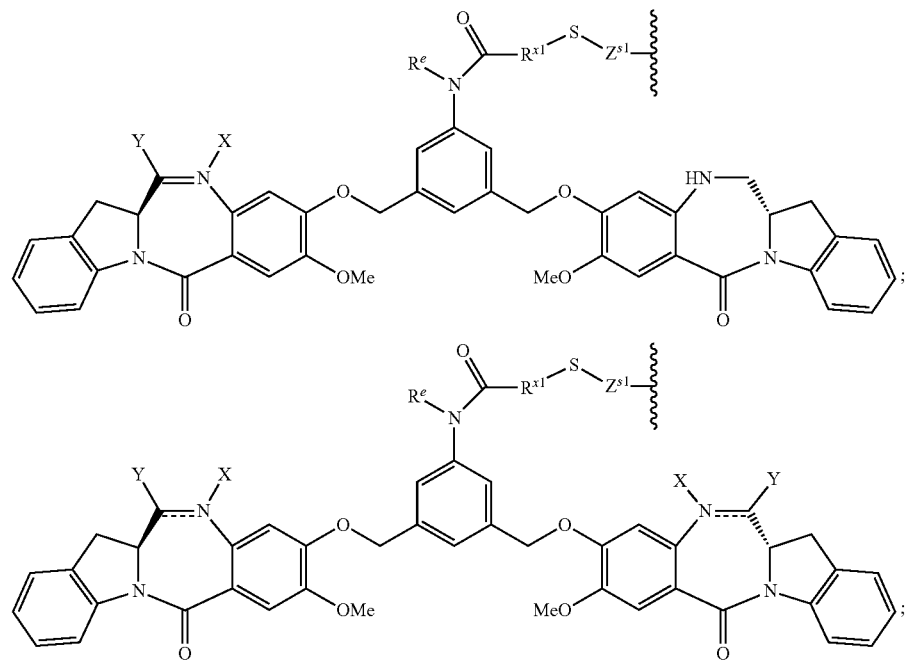

-continued

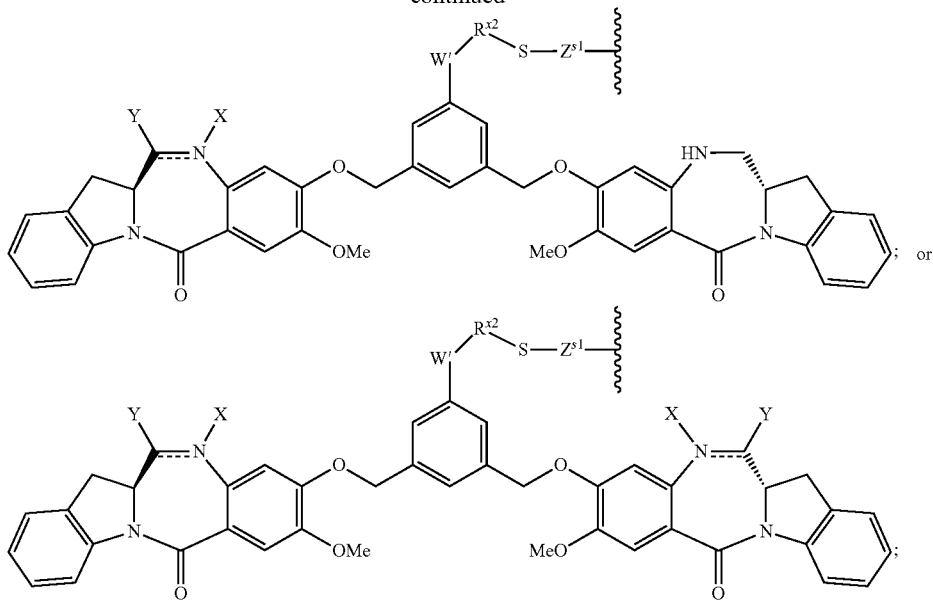

or a pharmaceutically acceptable salt thereof, wherein:

the double line ⚌ between N and C represents a single bond or a double bond, provided that when it is a double bond, X is absent and Y is —H or a ($C_1$-$C_4$) alkyl; and when it is a single bond, X is —H or an amine protecting moiety, and Y is —OH or —$SO_3$M;

$R^{x1}$ and R are independently ($C_1$-$C_6$)alkyl;

$R^e$ is —H or a ($C_1$-$C_6$)alkyl;

W' is —$NR^{e'}$, $R^{e'}$ is —($CH_2$—$CH_2$—O)$_n$—$R^k$;

n is an integer from 2 to 6;

$R^k$ is —H or -Me;

$Z^{s1}$ is selected from any one of the following formulas:

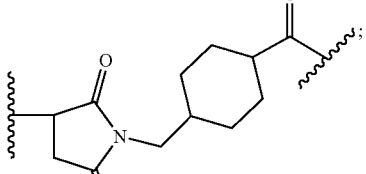 (b1)

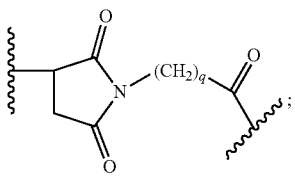 (b2)

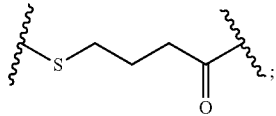 (b3)

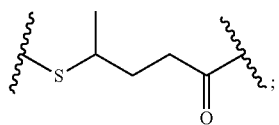 (b4)

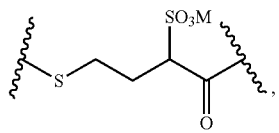 (b5)

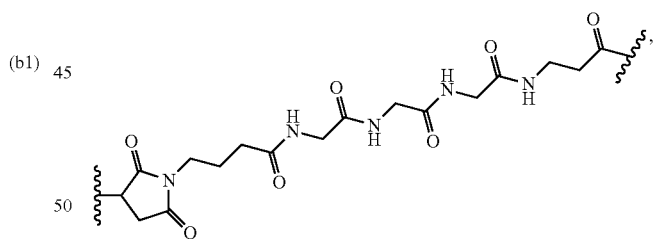 (b6)

 (b7)

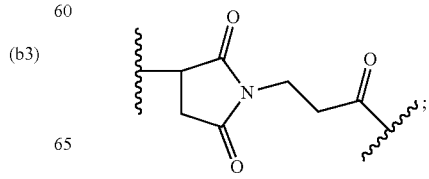 (b8)

-continued

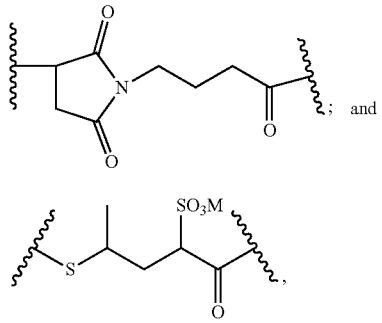

wherein:

q is an integer from 1 to 5; and

M is —H⁺ or a cation.

In certain embodiments, $R^e$ is H or Me; $R^{x1}$ and $R^{x2}$ are independently —$(CH_2)_p$—$(CR^fR^g)$—, wherein $R^f$ and $R^g$ are each independently —H or a ($C_1$-$C_4$)alkyl; and p is 0, 1, 2 or 3.

In certain embodiments, $R^f$ and $R^g$ are the same or different, and are selected from —H and -Me.

In certain embodiments, the immunoconjugate is represented by the following formula:

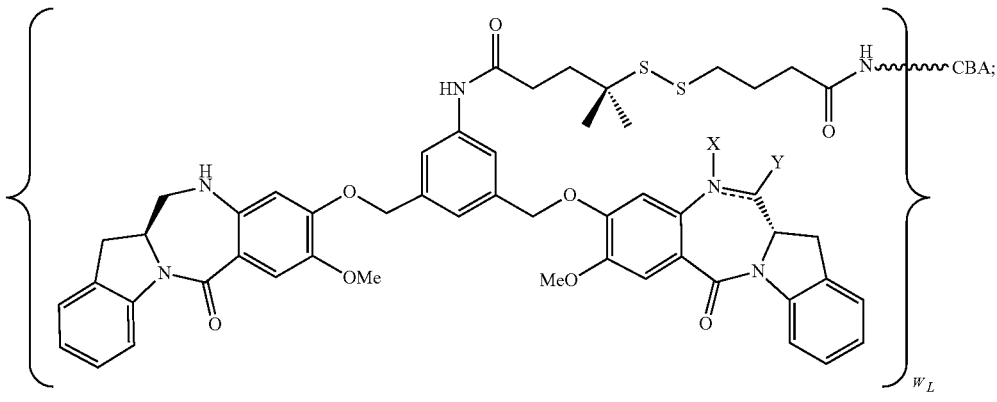

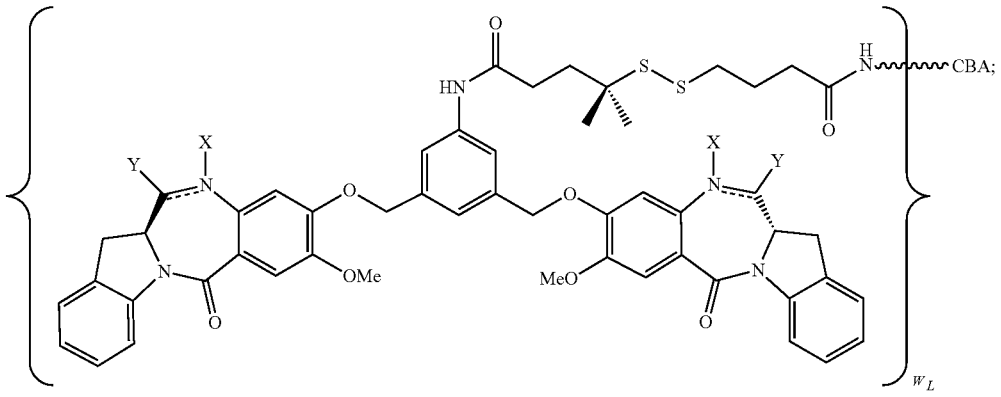

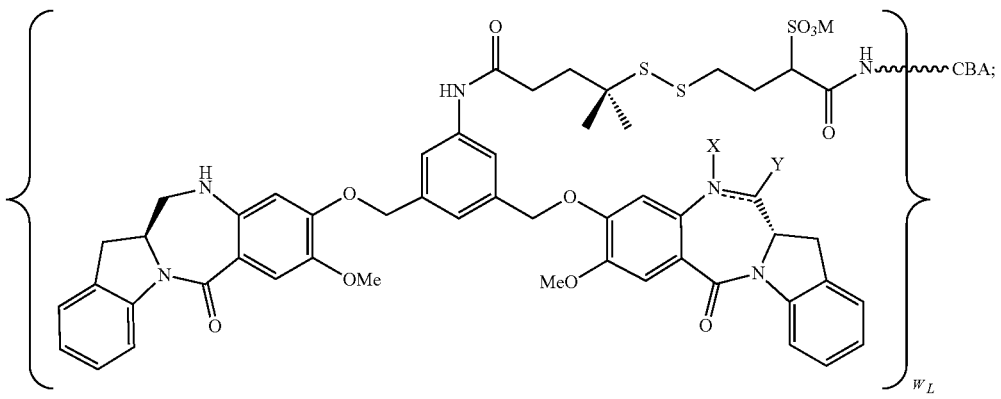

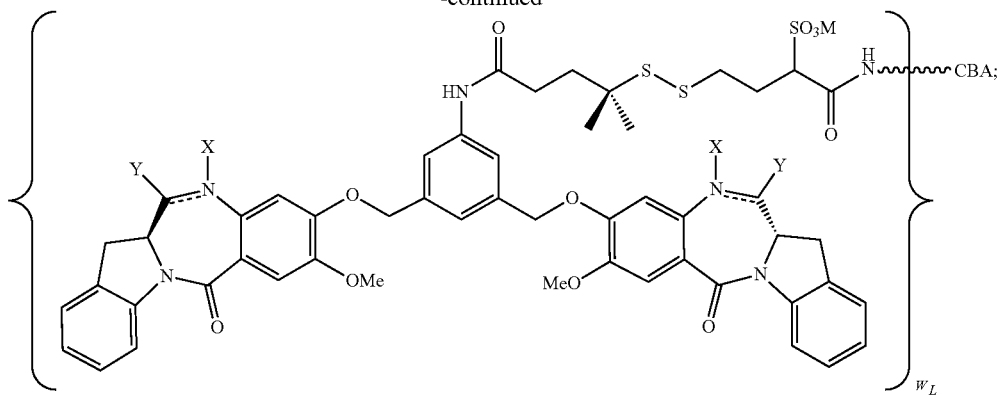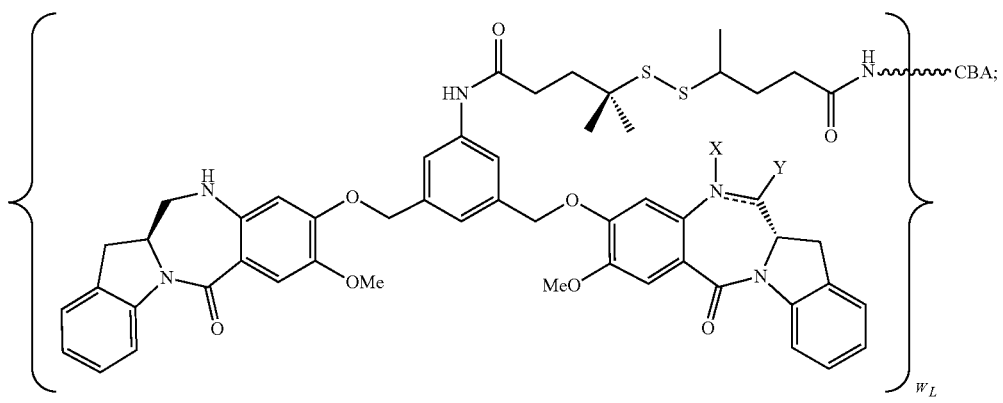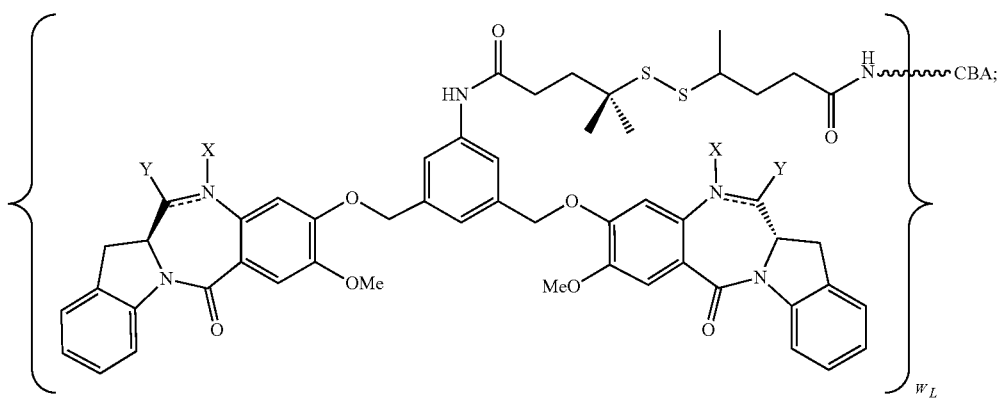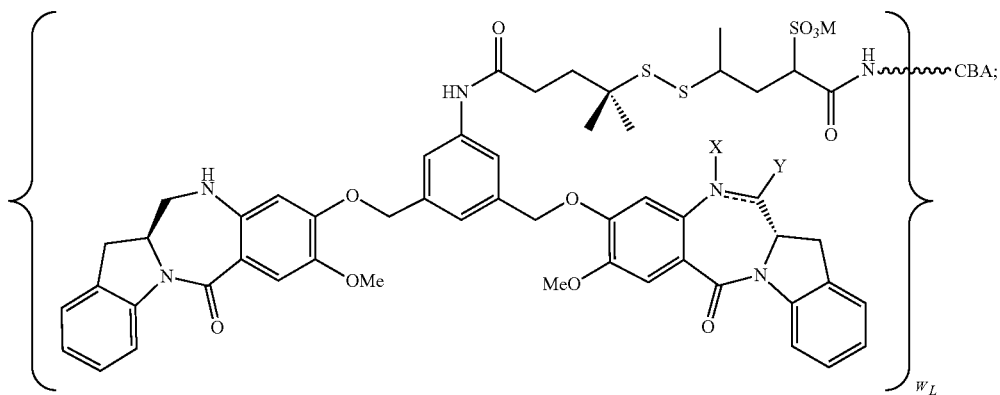

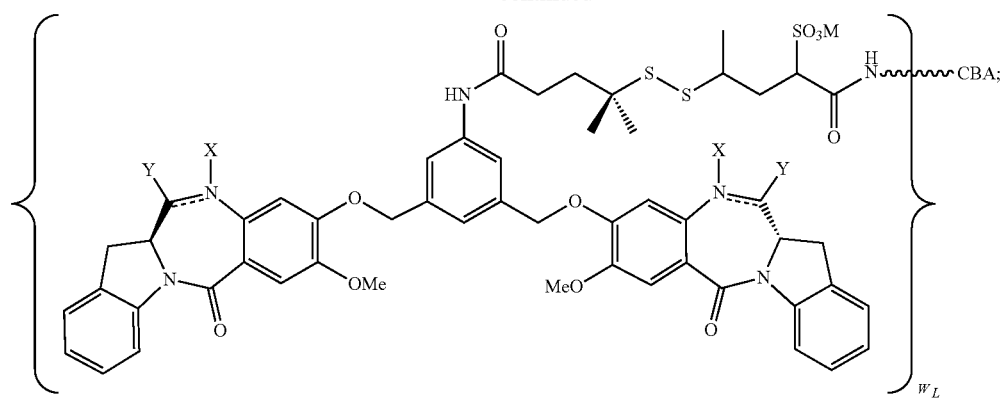
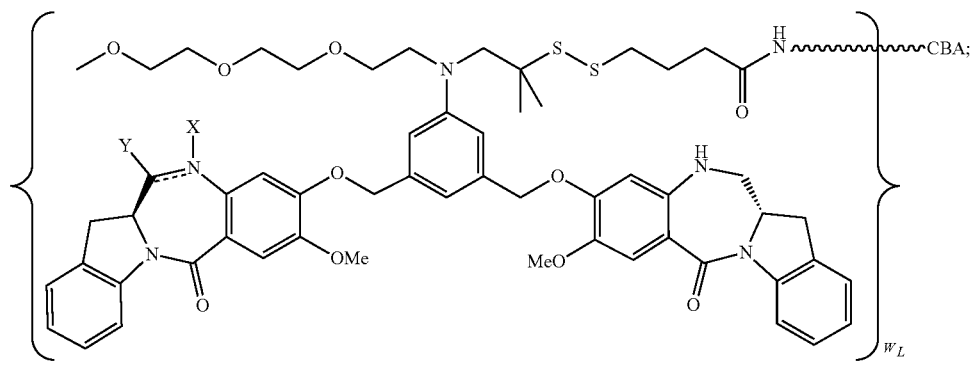
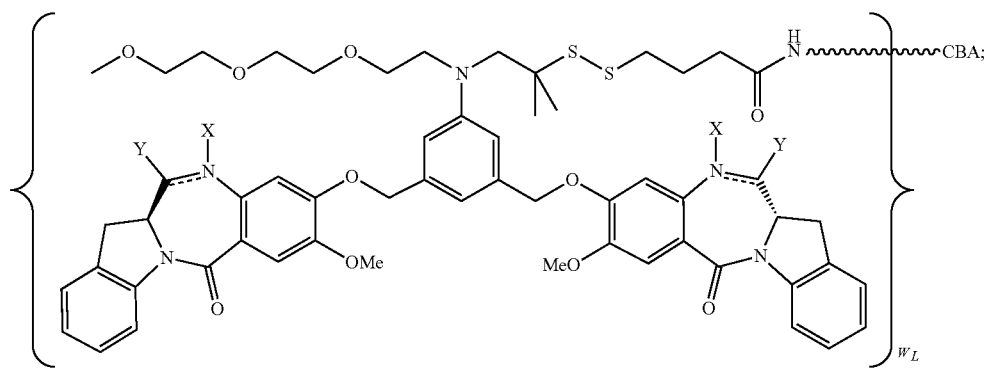
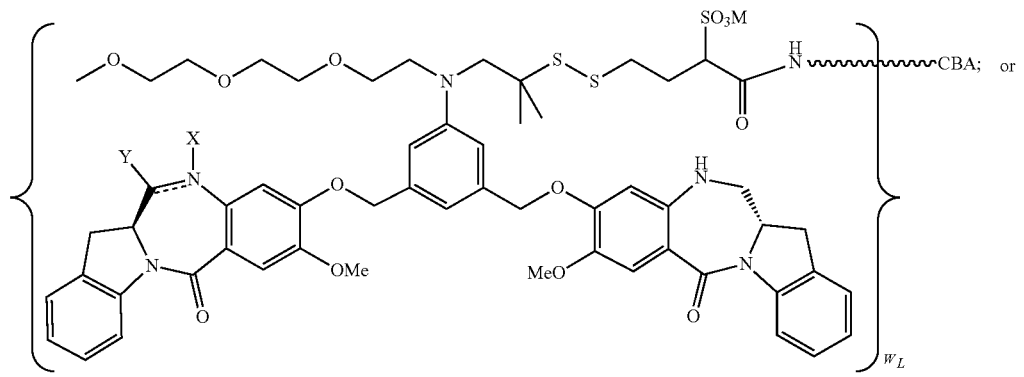

-continued

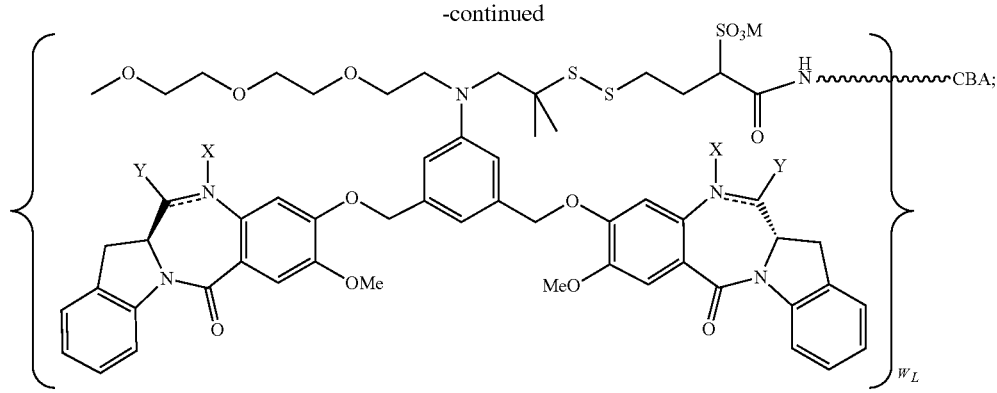

or a pharmaceutically acceptable salt thereof, wherein $W_L$ is an integer from 1 to 10; the double line ═ between N and C represents a single bond or a double bond, provided that when it is a double bond, X is absent and Y is —H; and when it is a single bond, X is —H and Y is —OH or —SO$_3$M.

In certain embodiments, the double line ═ between N and C represents a double bond, X is absent and Y is —H. In certain embodiments, the double line ═ between N and C represents a single bond, X is —H, and Y is —SO$_3$M. In certain embodiments, M is H$^+$, Na$^+$ or K$^+$.

Another related aspect of the invention provides an immunoconjugate having the formula:

$$CBA\!-\!(\!-\!Cy^{L3})_{w_L},$$

wherein:
  CBA is an antibody or antigen-binding fragment thereof of the invention, or the polypeptide of the invention, which is covalently linked to $Cy^{L3}$ through a Lys residue;
  $W_L$ is an integer from 1 to 20;
  $Cy^{L3}$ is represented by the following formula:

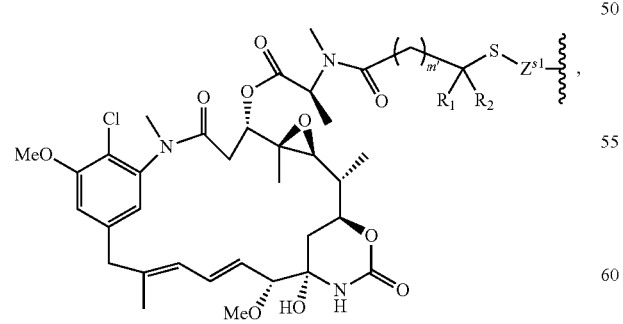

m' is 1 or 2;
  $R_1$ and $R_2$, are each independently H or a (C$_1$-C$_3$)alkyl; and $Z^{s1}$ is selected from any one of the following formulas:

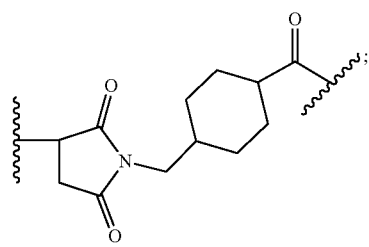 (b1)

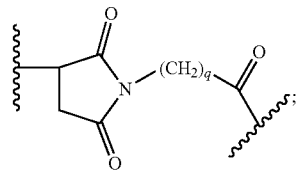 (b2)

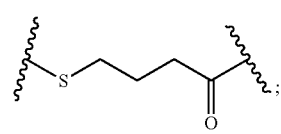 (b3)

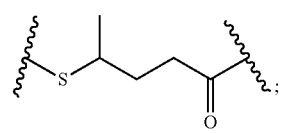 (b4)

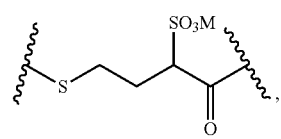 (b5)

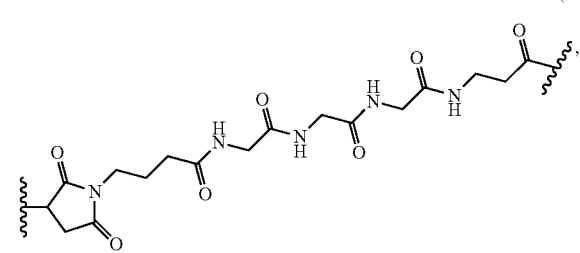 (b6)

41
-continued
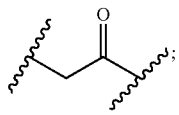
(b7)
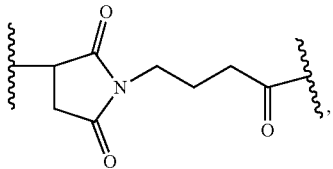
(b9)
(b8)
42
-continued
wherein:
q is an integer from 1 to 5; and
M is H⁺ or a cation.
In certain embodiments, m' is 1, and $R_1$ and $R_2$ are both H. In certain other embodiments, m' is 2, and $R_1$ and $R_2$ are both Me.
In certain embodiments, the immunoconjugate is represented by the following formula:
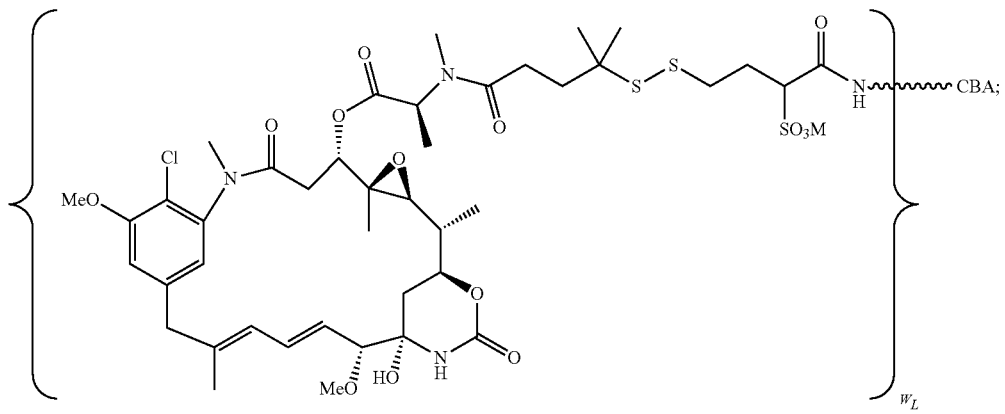
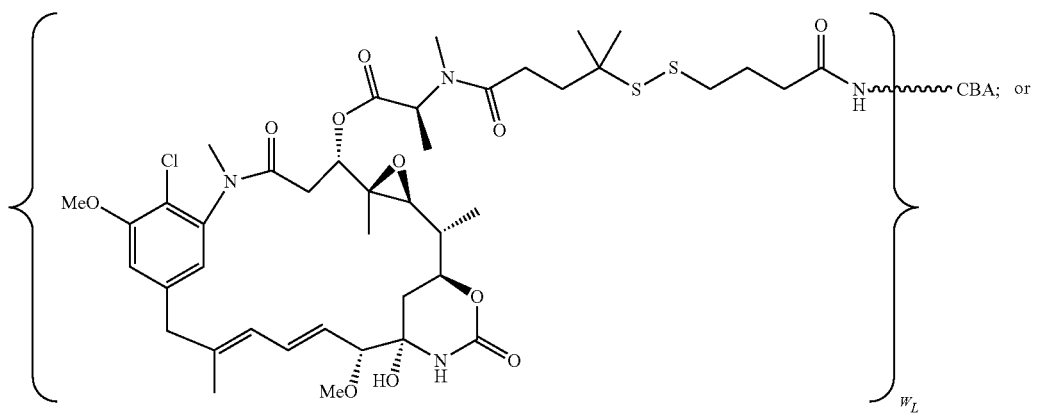
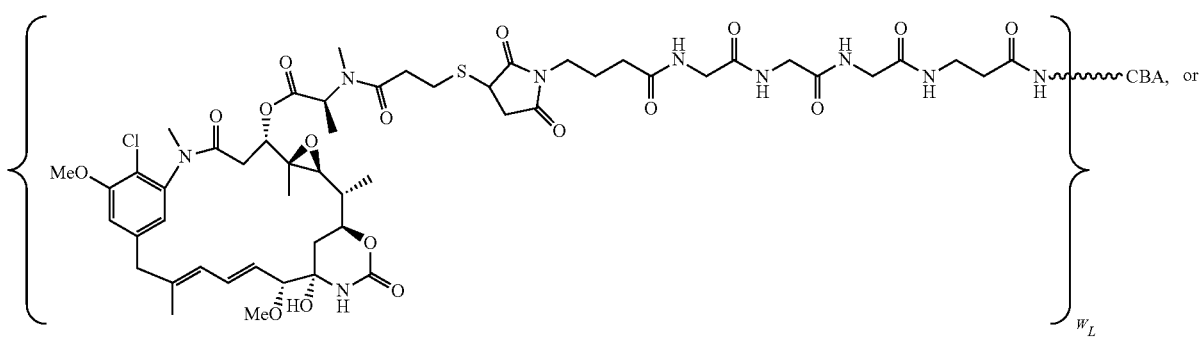

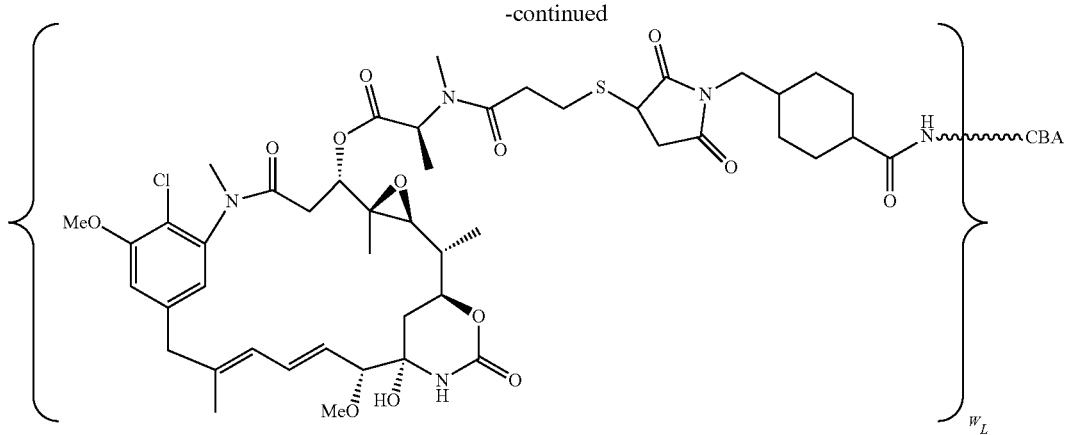

or a pharmaceutically acceptable salt thereof, wherein $W_L$ is an integer from 1 to 10.

In certain embodiments, M is $H^+$, $Na^+$ or $K^+$.

Another aspect of the invention provides an immunoconjugate having the following formula:

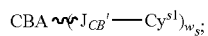

wherein:
- CBA is an antibody or antigen-binding fragment thereof of the invention, or the polypeptide thereof of the invention, covalently linked to the $J_{CB'}$ group;
- $W_S$ is 1, 2, 3, or 4;
- $J_{CB'}$ is a moiety formed by reacting an aldehyde group derived from oxidation of a 2-hydroxyethylamine moiety (wherein the 2-hydroxyethylamine moiety can be part of a senile, threonine, hydroxylysine, 4-hydroxyornithie or 2,4-diamino-5-hydroxy valeric acid residue) on an N-terminal of said antibody or antigen-binding fragment thereof of the invention, or the polypeptide thereof of the invention, and an aldehyde reactive group on $Cy^{s1}$, and is represented by the following formula:

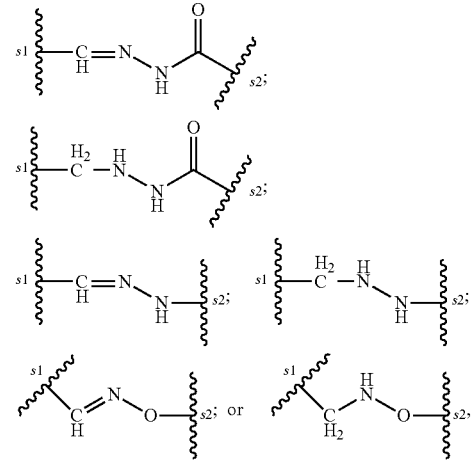

wherein s1 is the site covalently linked to the CBA; and s2 is the site covalently linked to $Cy^{s1}$;

$Cy^{s1}$ is represented by the following formula:

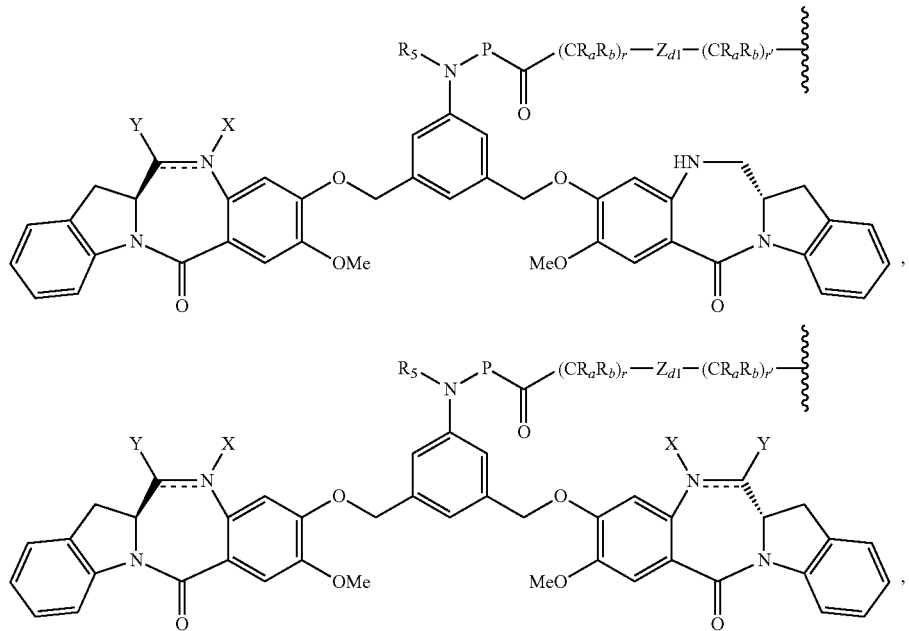

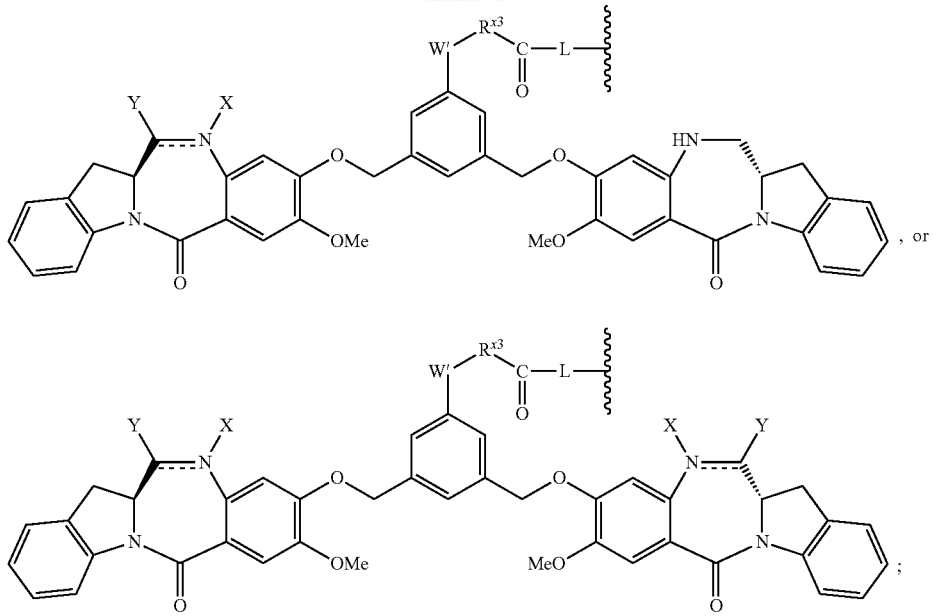

, or or a pharmaceutically acceptable salt thereof, wherein:
- the double line ══ between N and C represents a single bond or a double bond, provided that when it is a double bond, X is absent and Y is —H or a $(C_1\text{-}C_4)$alkyl; and when it is a single bond, X is —H or an amine protecting moiety, Y is —OH or —SO$_3$M, and M is H$^+$ or a cation;
- $R_5$ is —H or a $(C_1\text{-}C_3)$alkyl;
- P is an amino acid residue or a peptide containing 2 to 20 amino acid residues;
- $Z_{d1}$ is absent, —C(=O)—NR$_9$—, or —NR$_9$—C(=O)—;
- $R_9$ is —H or a $(C_1\text{-}C_3)$alkyl;
- $R_a$ and $R_b$, for each occurrence, are independently —H, $(C_1\text{-}C_3)$alkyl, or a charged substituent or an ionizable group Q;
- r and r' are independently an integer from 1 to 6;
- W' is —NR$^{e'}$;
- R$^{e'}$ is —(CH$_2$—CH$_2$—O)$_n$—R$^k$;
- n is an integer from 2 to 6;
- R$^k$ is —H or -Me;
- R$^{x3}$ is a $(C_1\text{-}C_6)$alkyl;
- L is —NR$_9$—(CR$_a$R$_b$)$_{r''}$— or absent; and
- r'' is an integer from 0 to 6.

For simplicity, in each instance below reciting Ser as the N-terminal residue, it should be understood that other 2-hydroxyethylamine moiety, as part of a serine, threonine, hydroxylysine, 4-hydroxyornithie or 2,4-diamino-5-hydroxy valeric acid residue, is contemplated where applicable, especially with respect to Thr.

In certain embodiments, $R_a$ and $R_b$ are both H, and $R_5$ and $R_9$ are both H or Me.

In certain embodiments, P is a peptide containing 2 to 5 amino acid residues. For example, P may be selected from the group consisting of: Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 55), β-Ala-Leu-Ala-Leu (SEQ ID NO: 57), Gly-Phe-Leu-Gly (SEQ ID NO: 73), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. In certain embodiments, P is Gly-Gly-Gly, Ala-Val, Ala-Ala, Ala-D-Ala, D-Ala-Ala, or D-Ala-D-Ala. In certain embodiments, Q is —SO$_3$M.

In certain embodiments, the immunoconjugate is represented by the following formula:

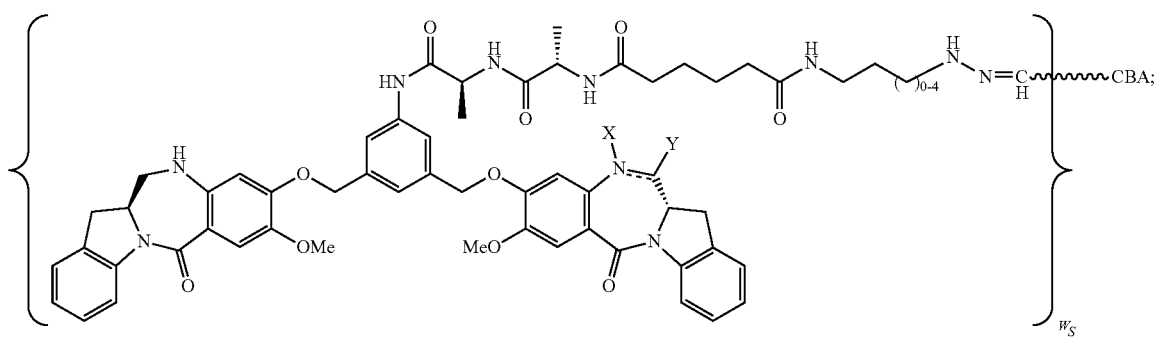

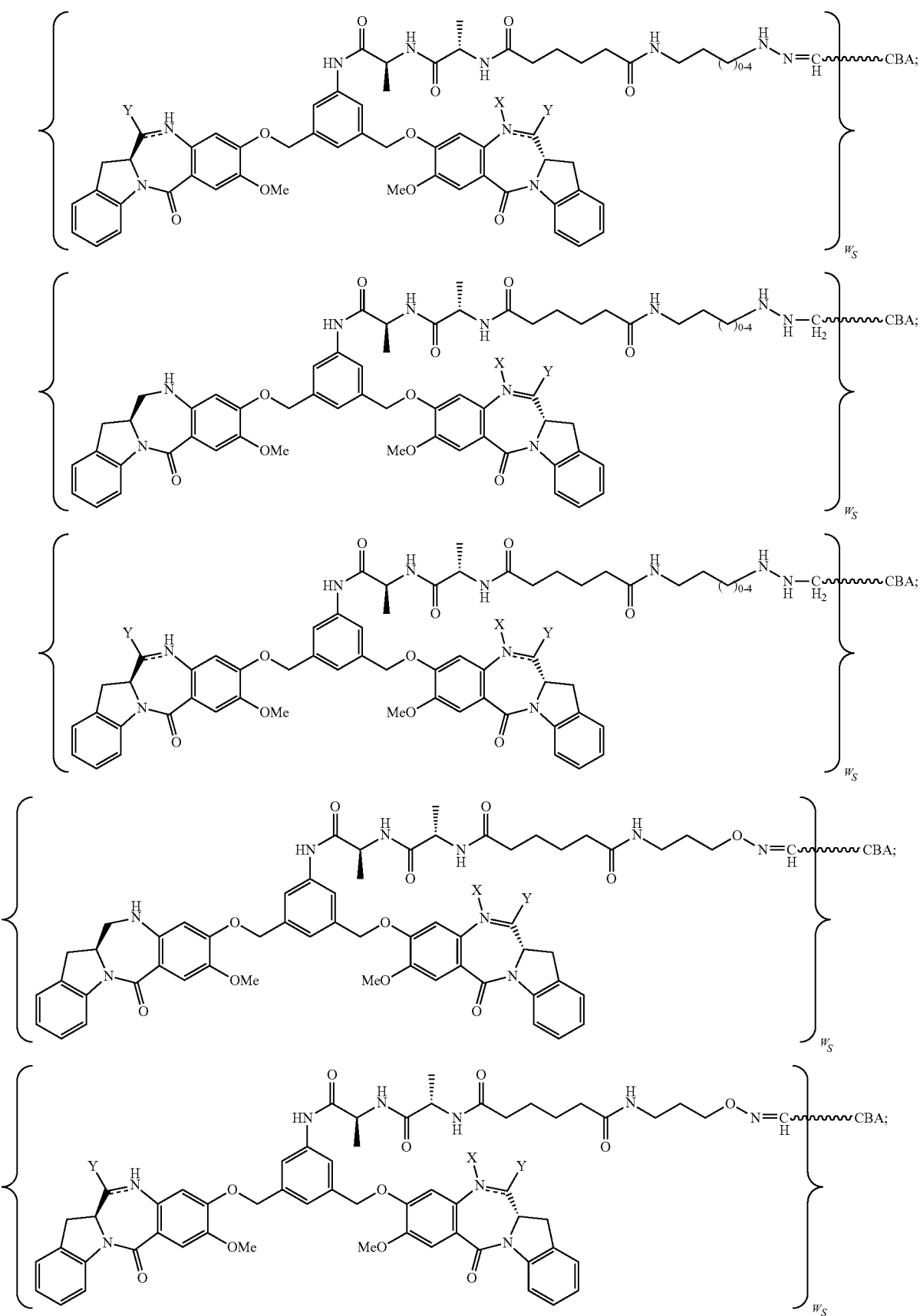

-continued
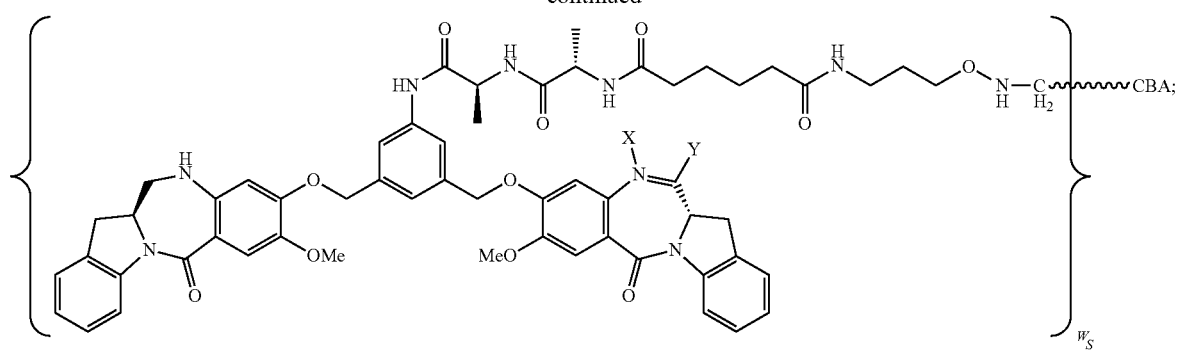
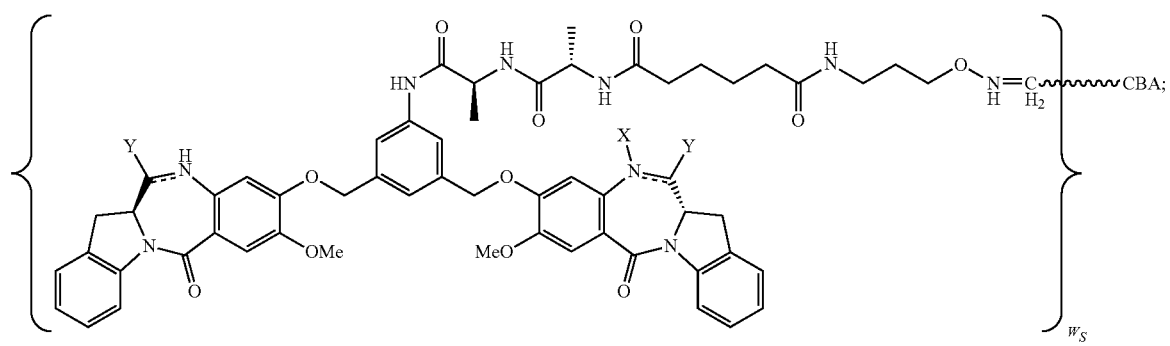
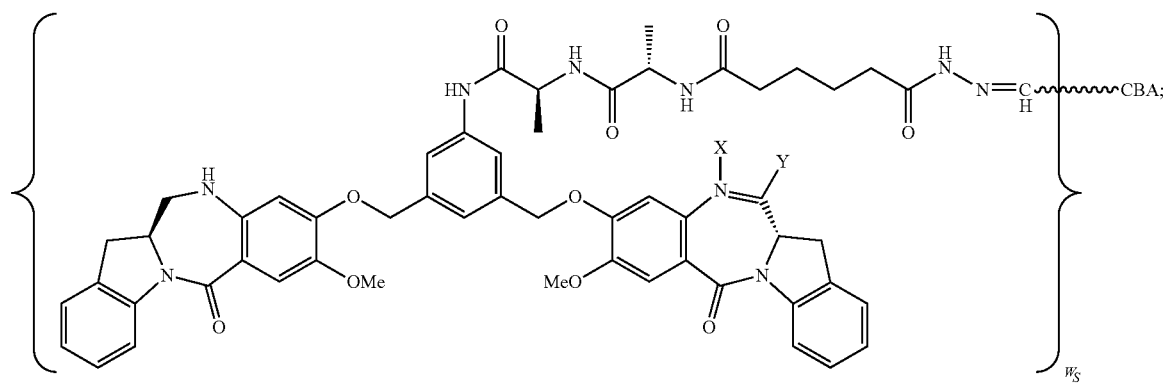
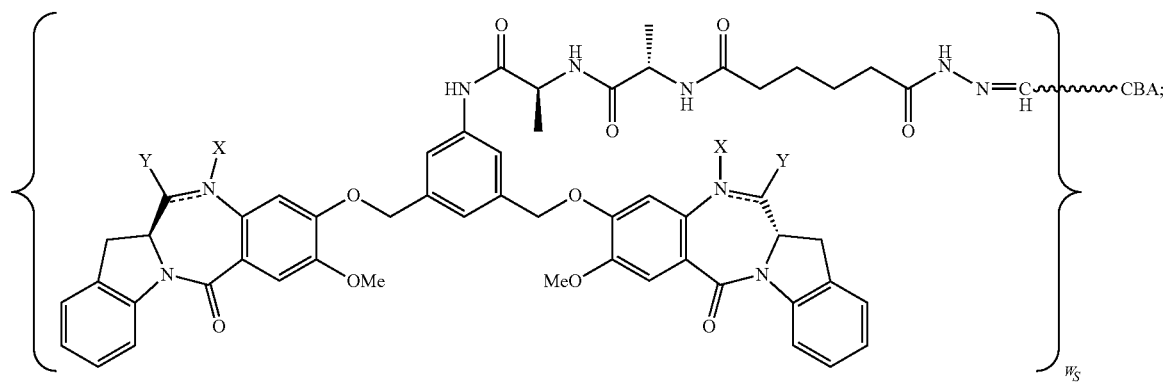

-continued
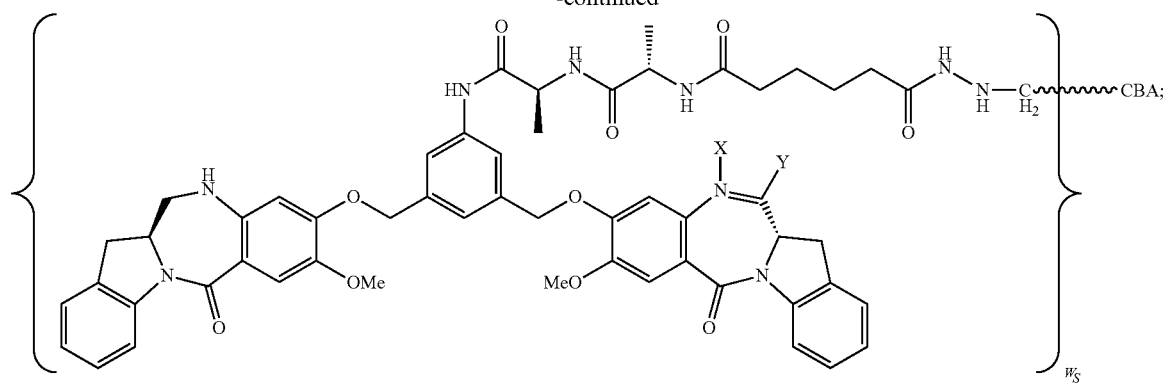
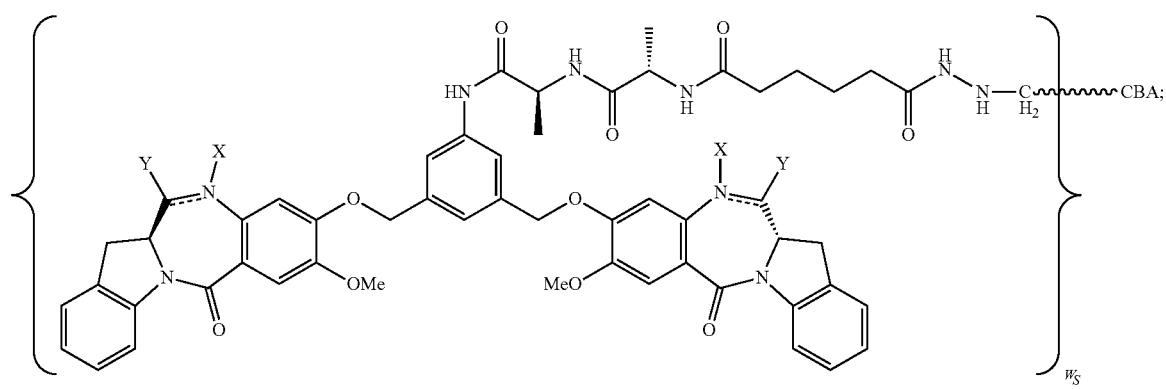
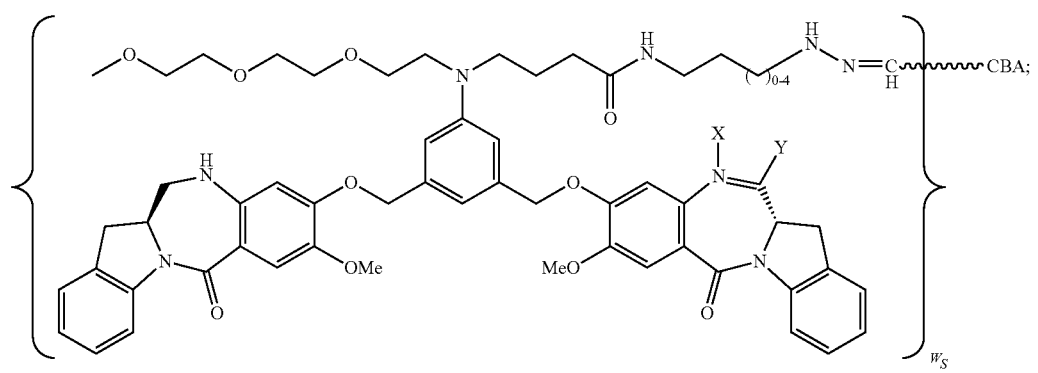
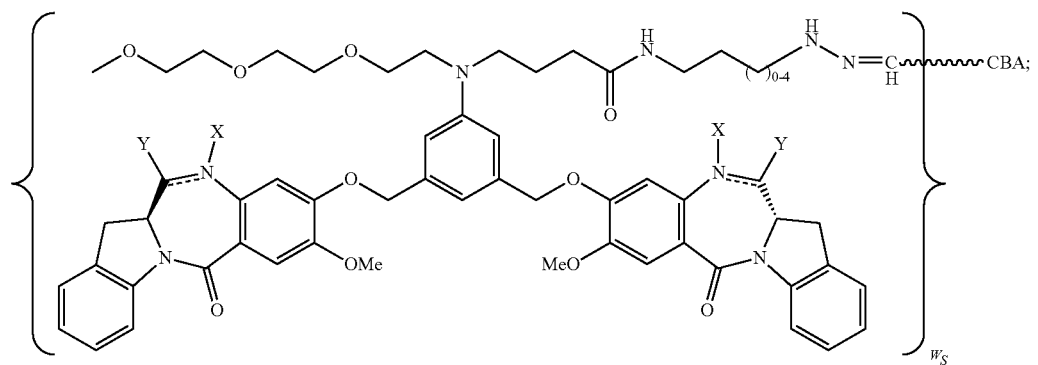

-continued
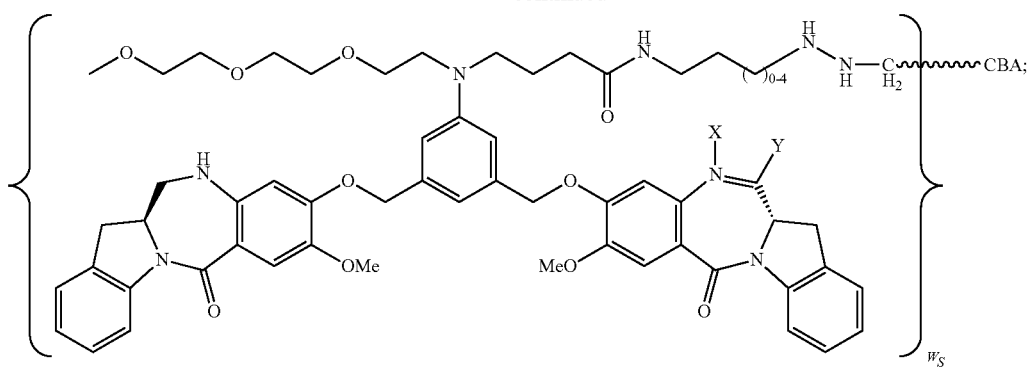
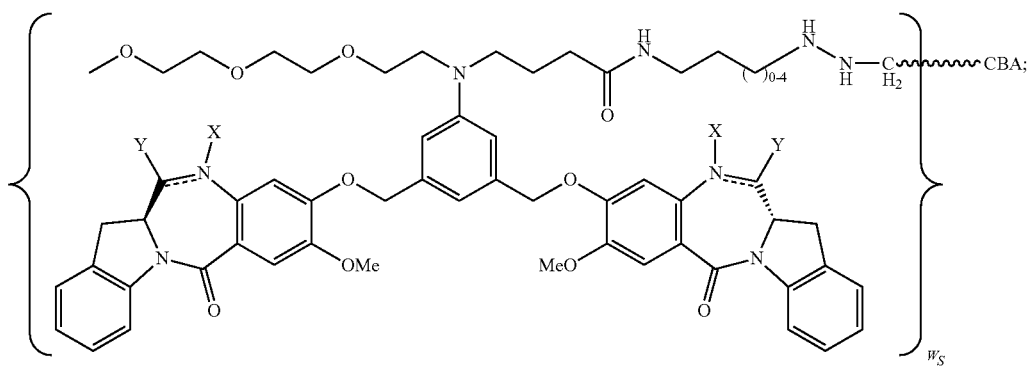
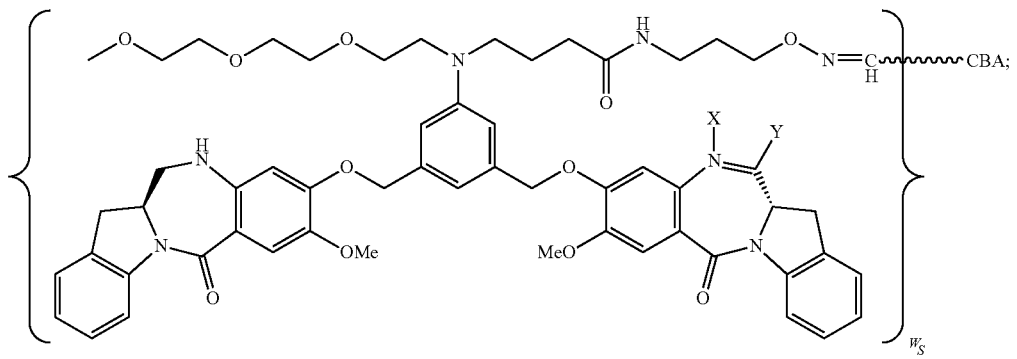
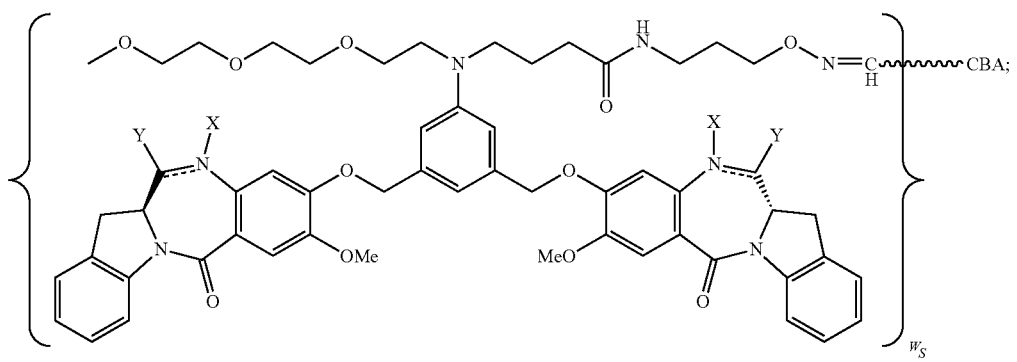

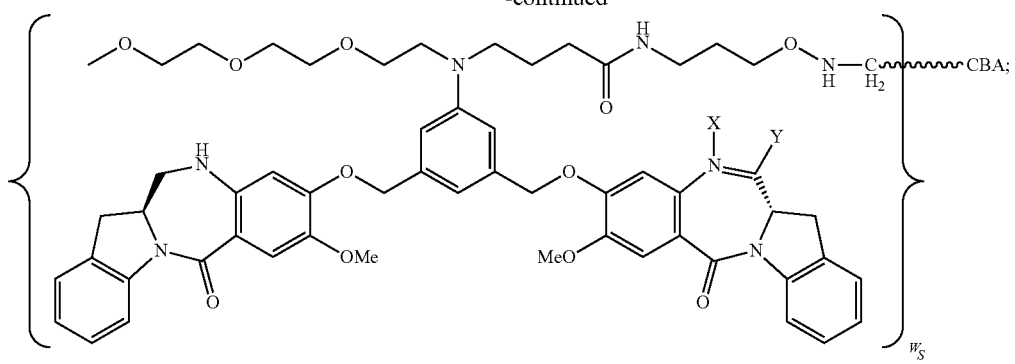
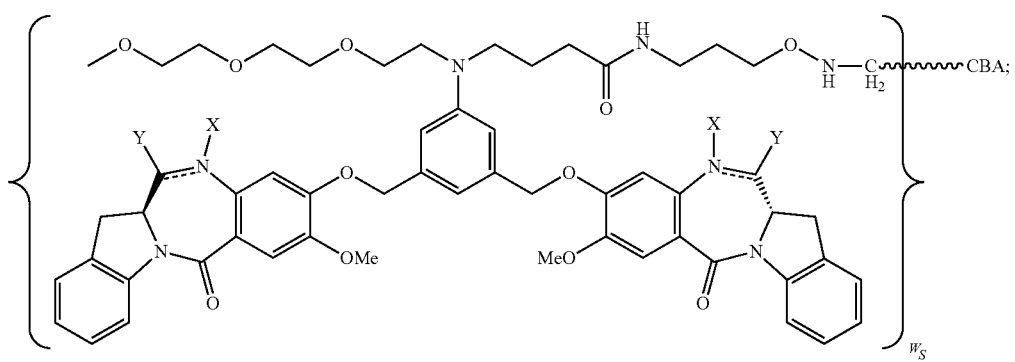
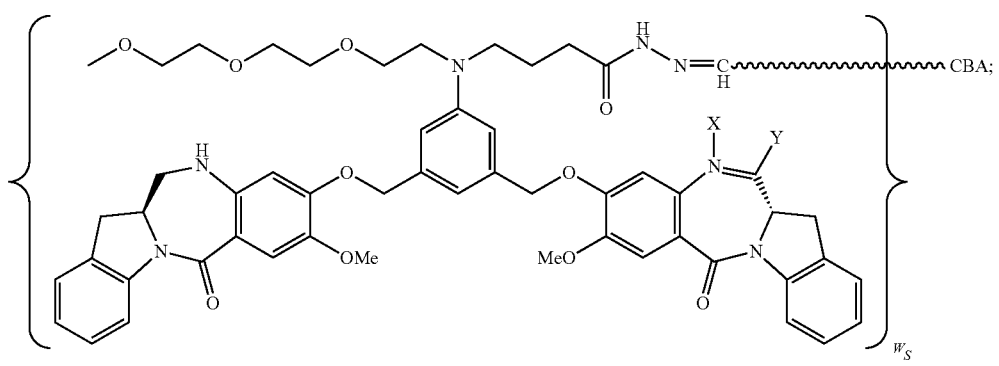

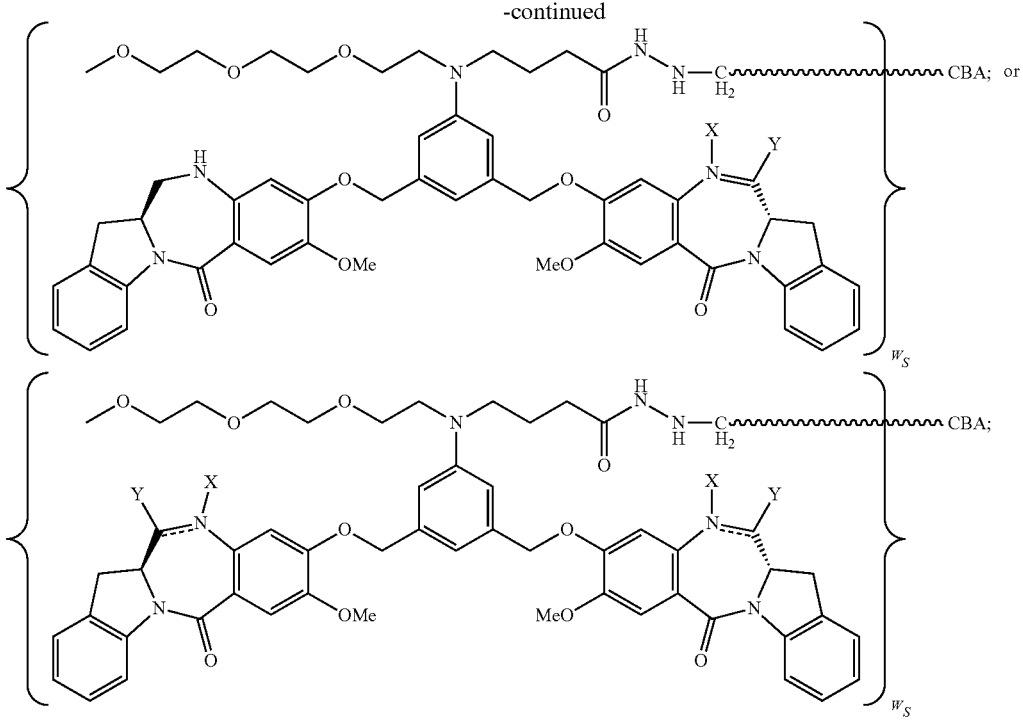

or a pharmaceutically acceptable salt thereof, wherein the double line ⚌ between N and C represents a single bond or a double bond, provided that when it is a double bond, X is absent and Y is —H, and when it is a single bond, X is —H, and Y is —OH or —SO$_3$M.

Another aspect of the invention provides an immunoconjugate having the following formula:

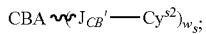

wherein:
CBA is the antibody or antigen-binding fragment thereof of the invention, or the polypeptide thereof of the invention, covalently linked to the J$_{CB'}$ group,
J$_{CB'}$ is a moiety formed by reacting an aldehyde group derived from oxidation of a 2-hydroxyethylamine moiety on an N-terminal of said antibody or antigen-binding fragment thereof of the invention, or the polypeptide thereof of the invention, and an aldehyde reactive group on Cy$^{s2}$, and is represented by the following formula:

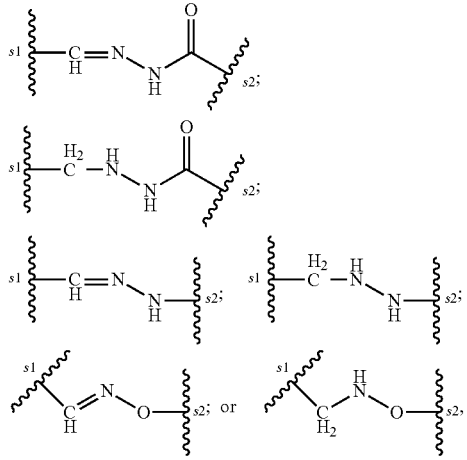

wherein s1 is the site covalently linked to the CBA; and s2 is the site covalently linked to Cy$^{s2}$;

Cy$^{s2}$ is represented by the following formula:

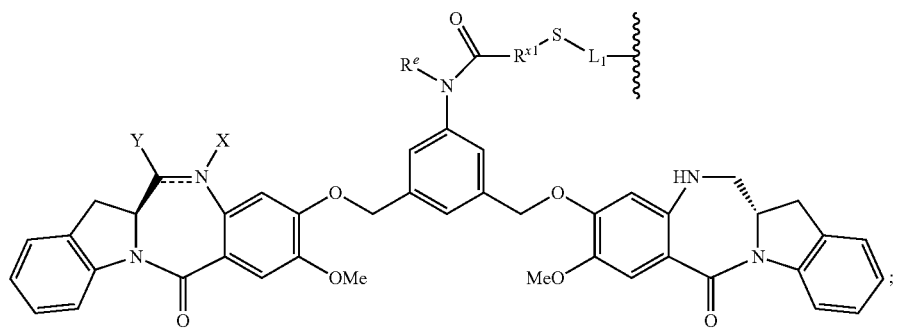

-continued

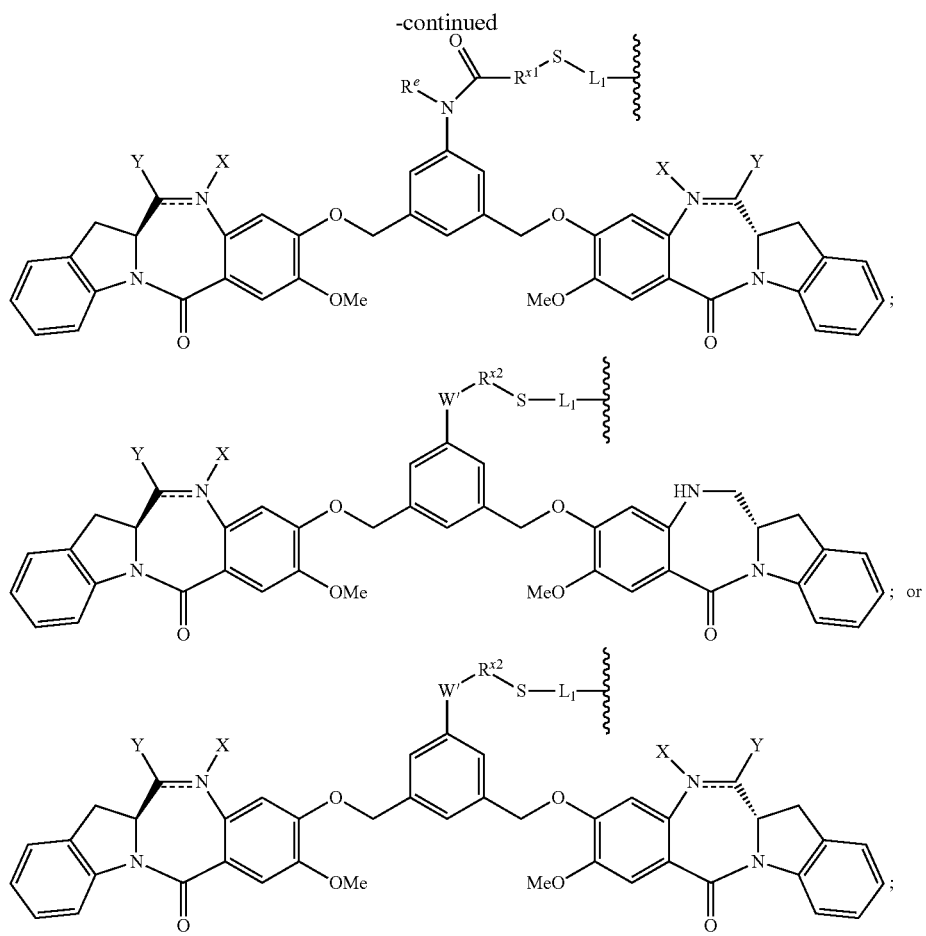

or a pharmaceutically acceptable salt thereof, wherein:
- the double line ═ between N and C represents a single bond or a double bond, provided that when it is a double bond, X is absent and Y is —H or a $(C_1-C_4)$alkyl; and when it is a single bond, X is —H or an amine protecting moiety, and Y is —OH or —SO$_3$M;
- M is H$^+$ or a cation;
- $R^{x1}$ is a $(C_1-C_6)$alkyl;
- $R^e$ is —H or a $(C_1-C_6)$alkyl;
- W' is —NR$^{e'}$;
- $R^{e'}$ is —(CH$_2$—CH$_2$—O)$_n$—R$^k$;
- n is an integer from 2 to 6;
- R$^k$ is —H or -Me;
- $R^{x2}$ is a $(C_1-C_6)$alkyl;
- L$_1$ is represented by the following formula:

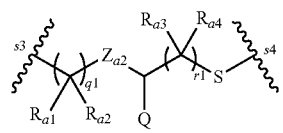

wherein:
- s3 is the site covalently linked to the group J$_{CB}$;
- s4 is the site covalently linked to the —S— group on Cy$^{s2}$;
- Z$_{a2}$ is absent, —C(═O)—NR$_9$—, or —NR$_9$—C(═O)—;
- R$_9$ is —H or a $(C_1-C_3)$alkyl;
- Q is H, a charged substituent or an ionizable group;
- R$_{a1}$, R$_{a2}$, R$_{a3}$, R$_{a4}$, for each occurrence, are independently H or $(C_1-C_3)$alkyl; and
- q1 and r1 are each independently an integer from 0 to 10, provided that q1 and r1 are not both 0.

In certain embodiments, -L$_1$- is represented by the following formula:

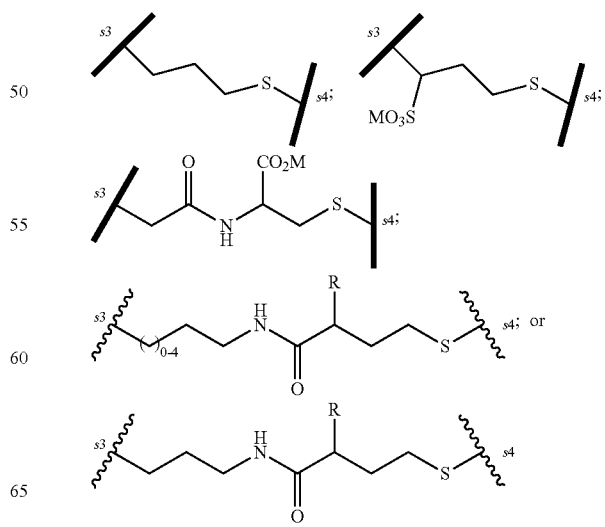

or a pharmaceutically acceptable salt thereof, wherein R is H or —SO₃M.

In certain embodiments, $R^e$ is H or Me; and $R^{x1}$ is —(CH₂)$_p$—(CR$^f$R$^g$)—, and $R^{x2}$ is —(CH₂)$_p$—(CR$^f$R$^g$)—, wherein $R^f$ and $R^g$ are each independently —H or a (C₁-C₄) alkyl; and p is 0, 1, 2 or 3. In certain embodiments, $R^f$ and $R^g$ are the same or different, and are selected from —H and -Me.

In certain embodiments, the immunoconjugate is represented by the following formula:

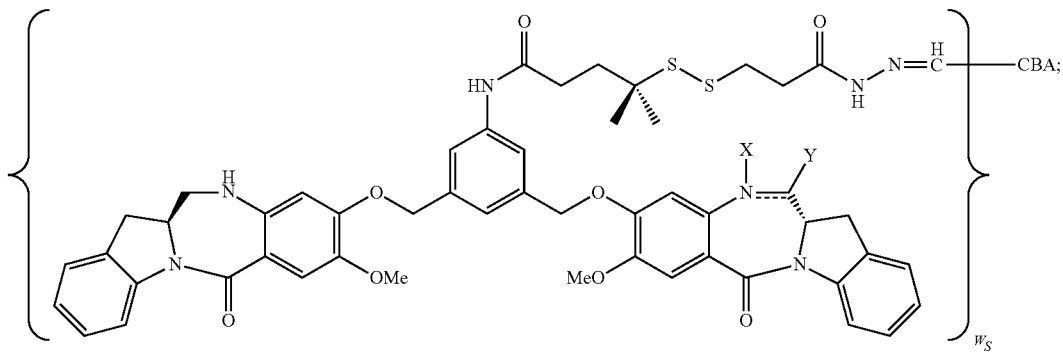

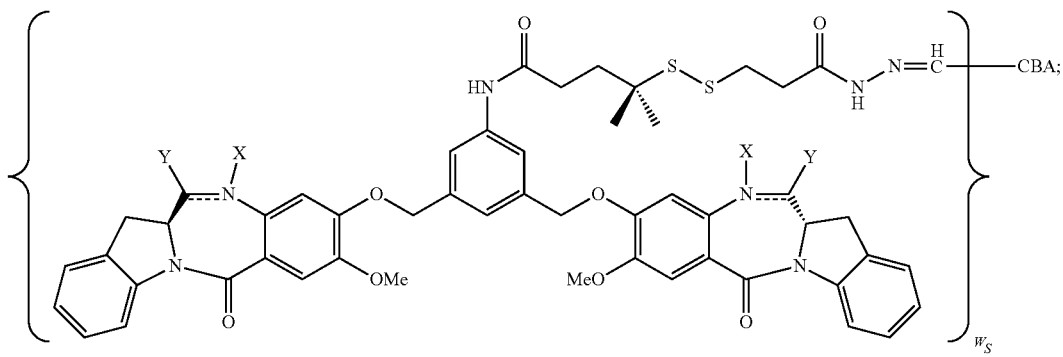

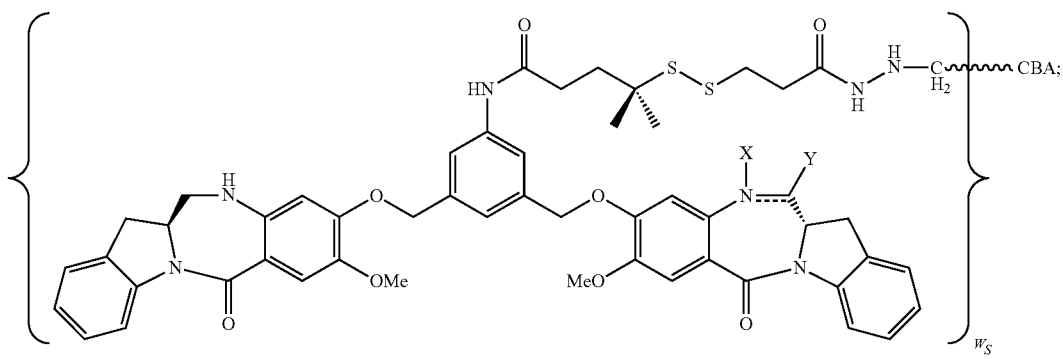

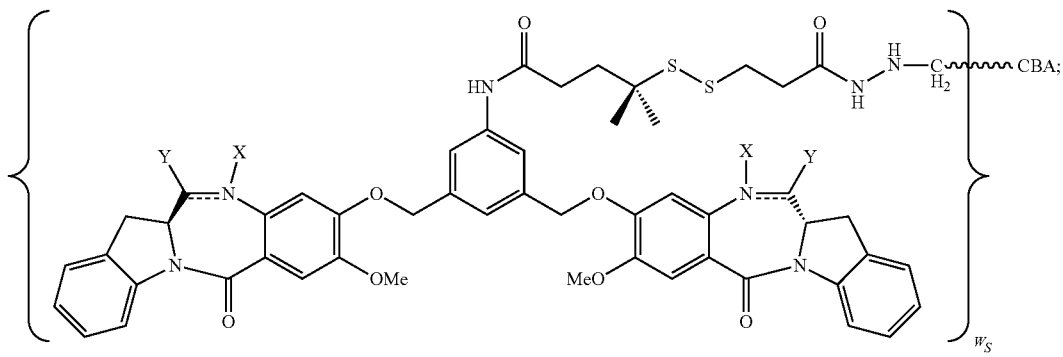

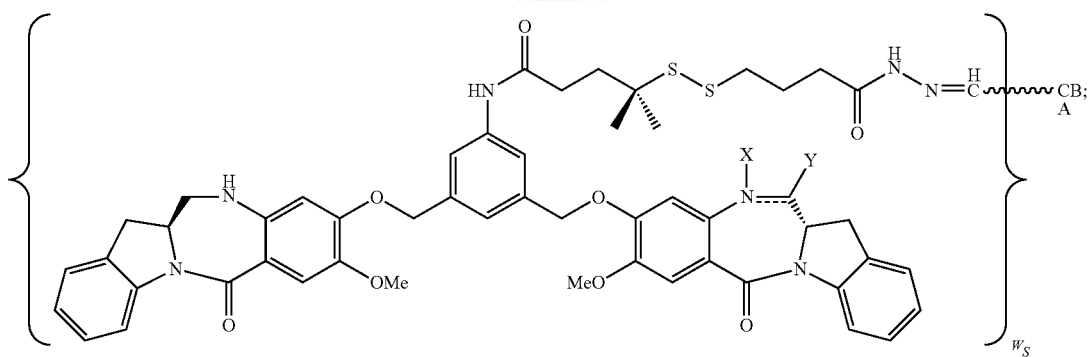
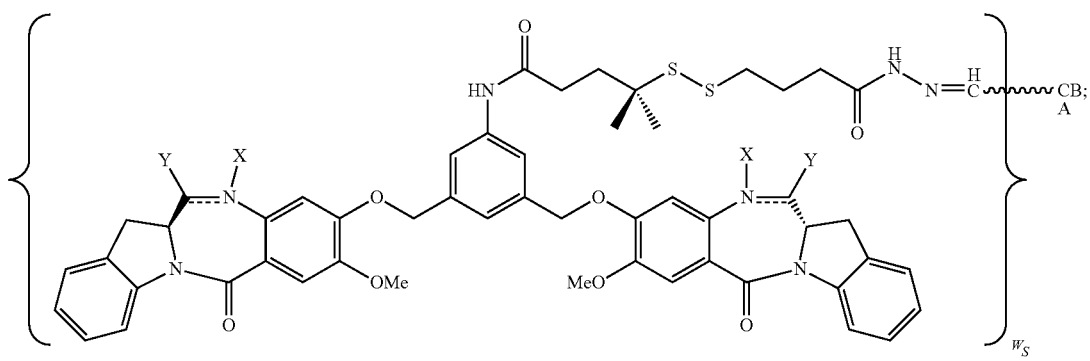
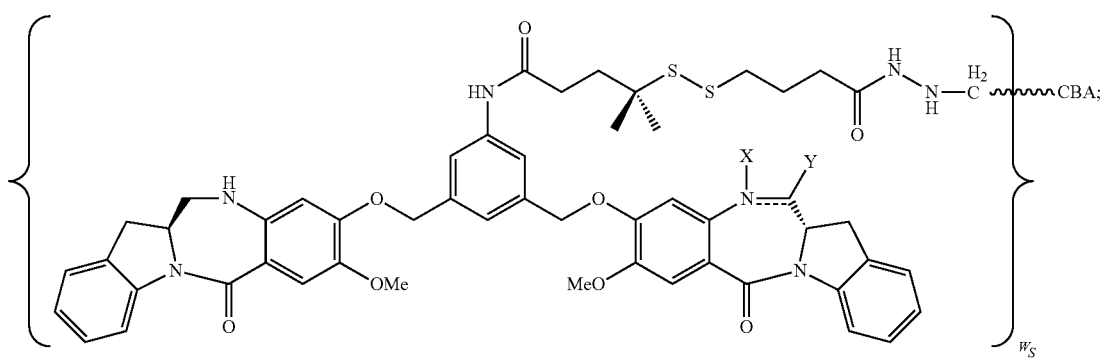
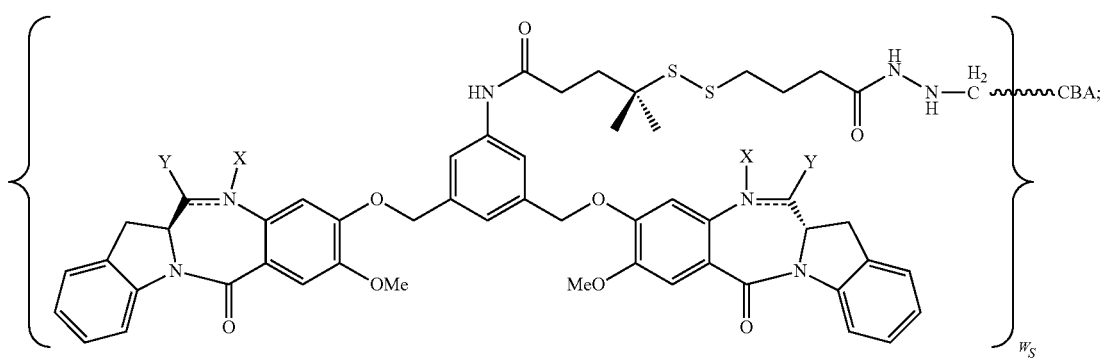

-continued
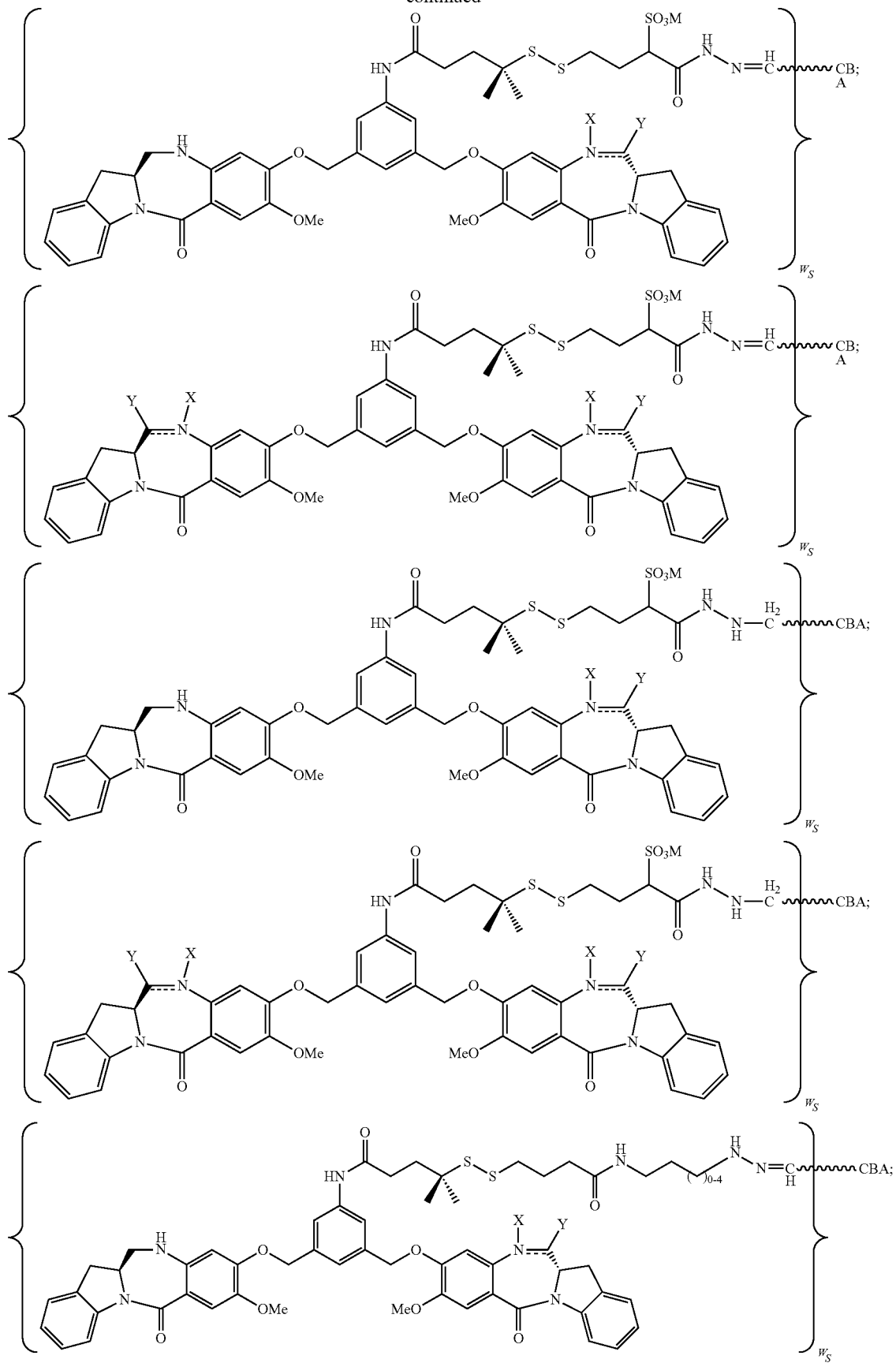

-continued
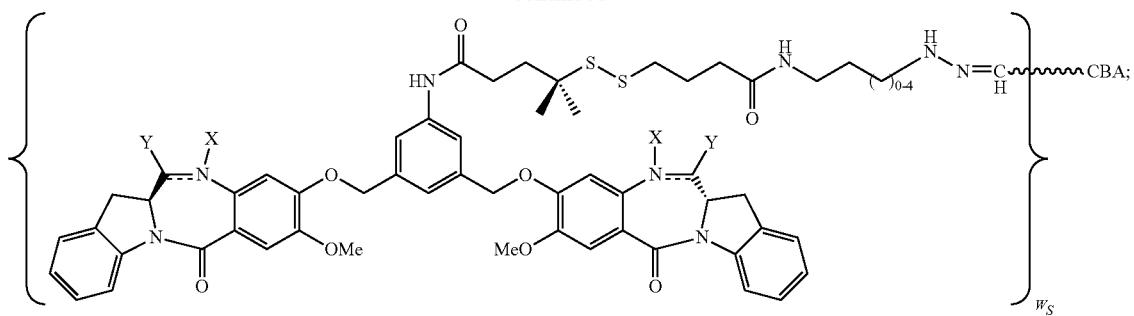
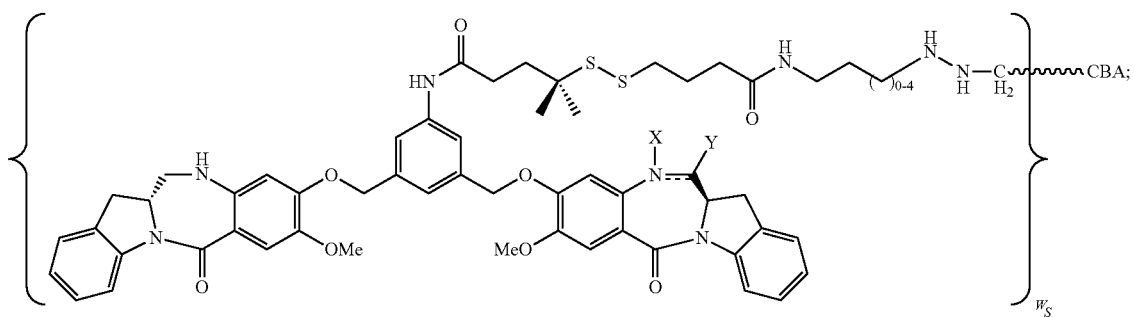
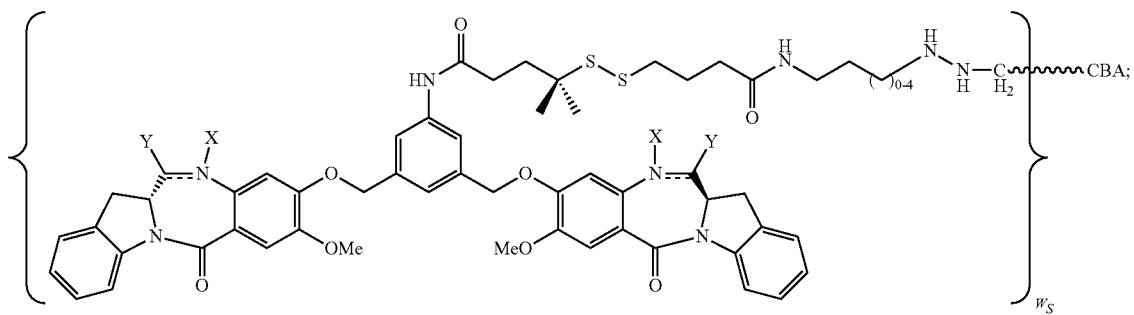
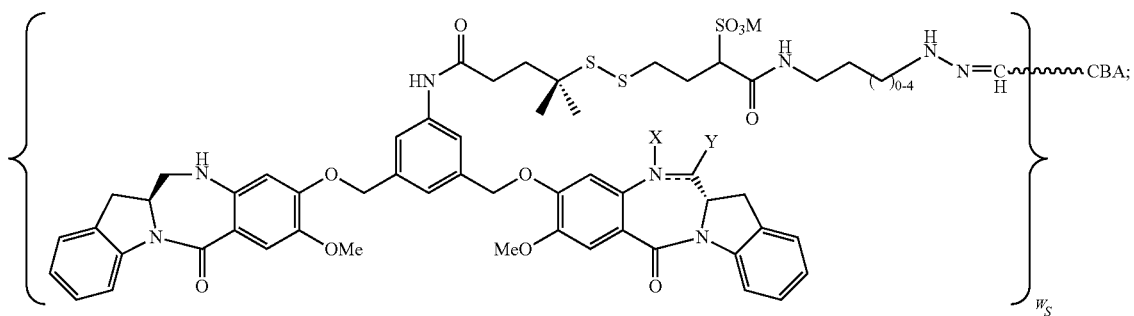
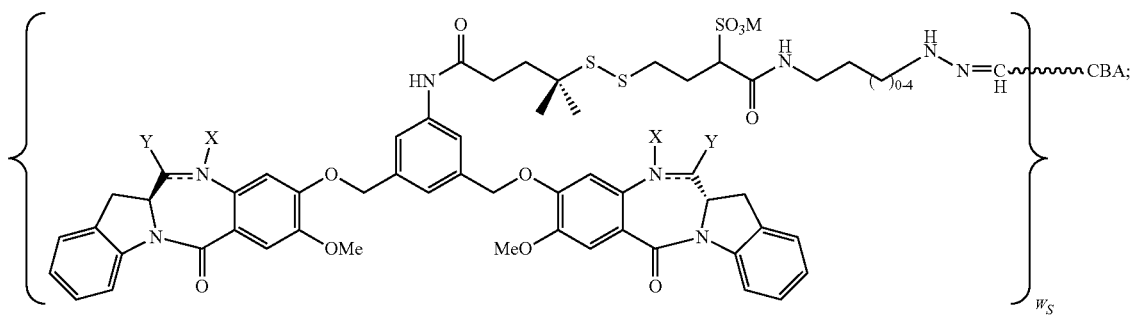

-continued
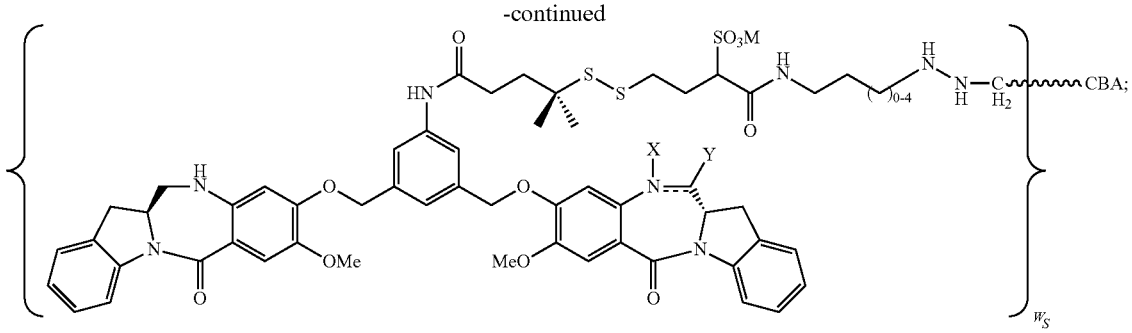
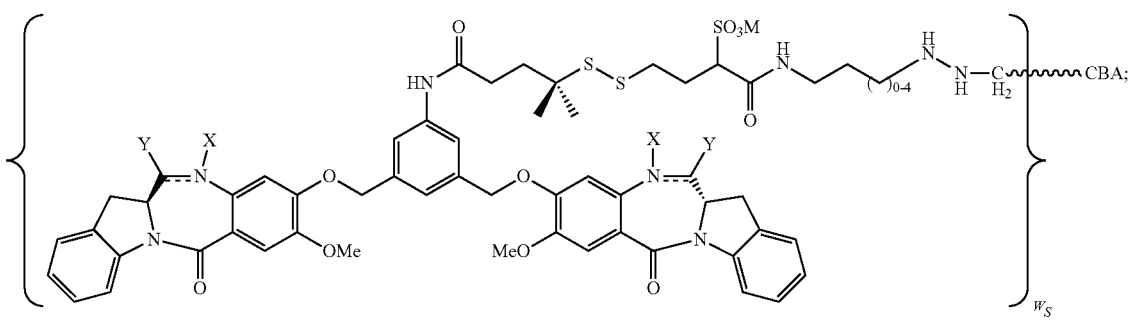
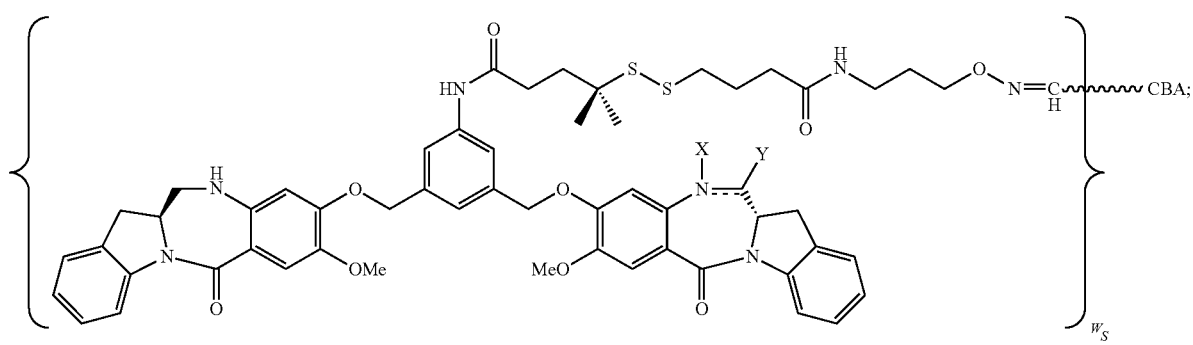
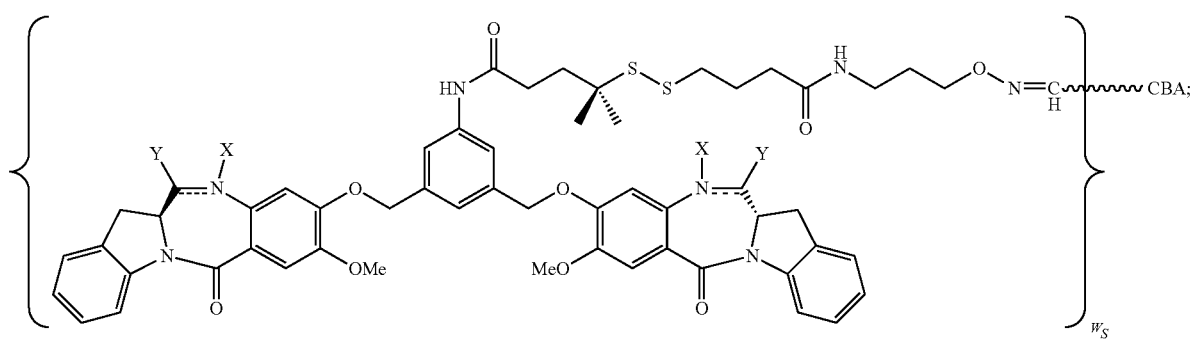
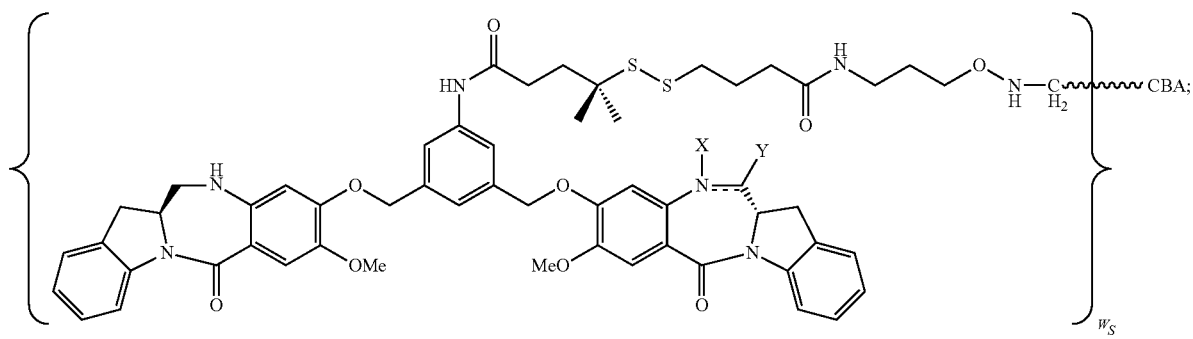

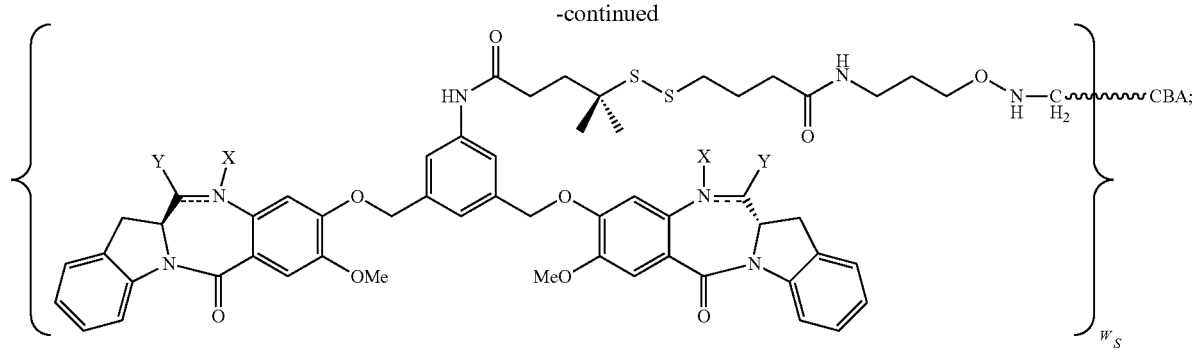
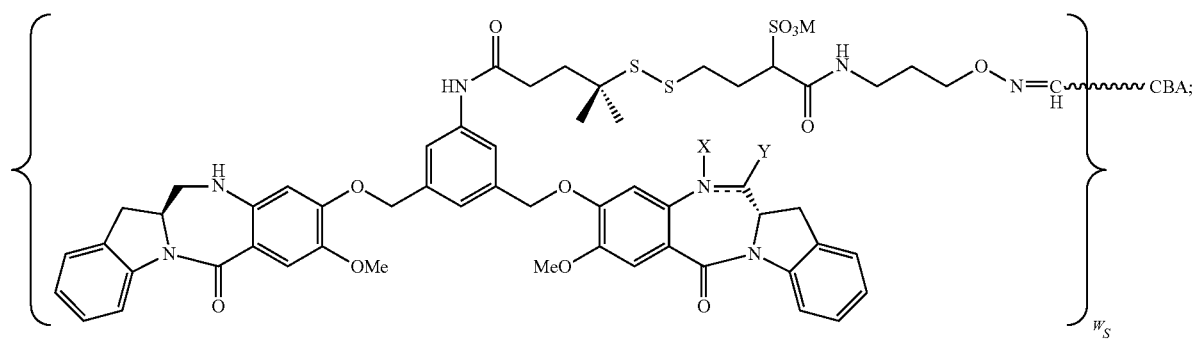
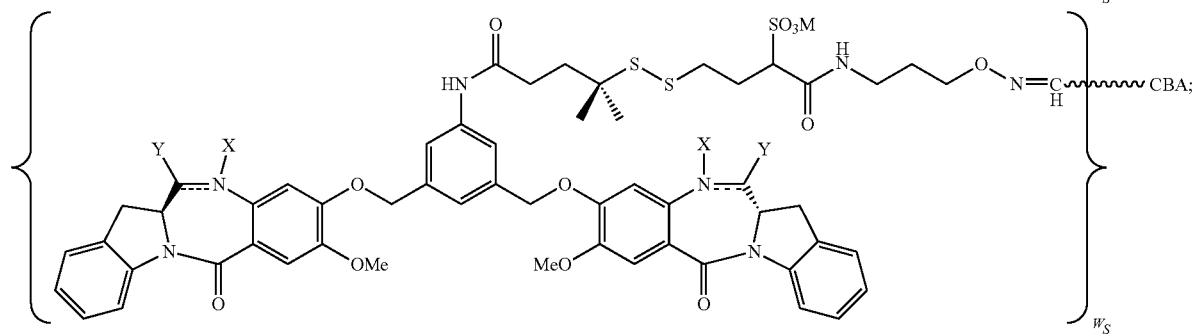
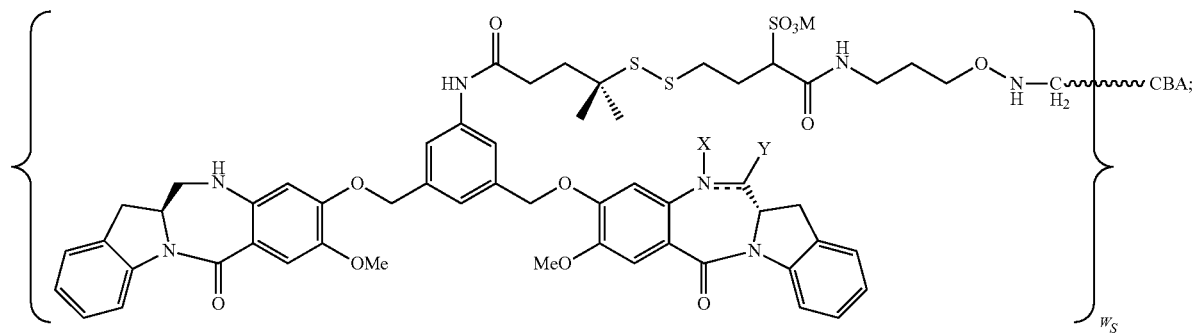
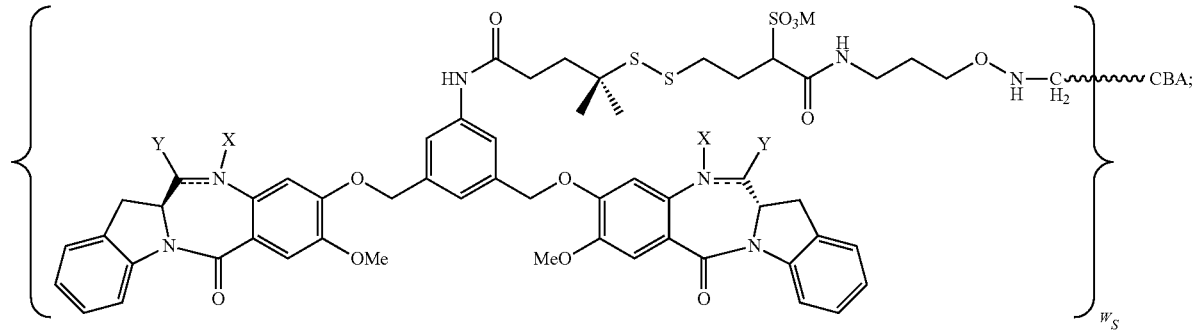

-continued
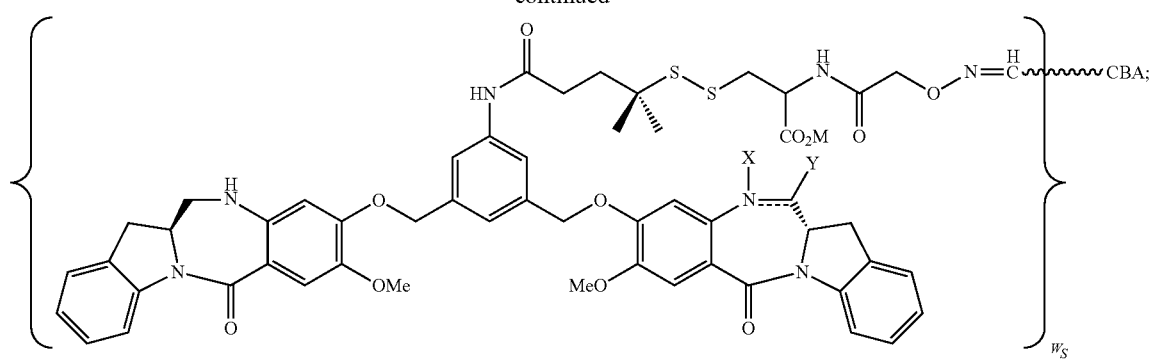
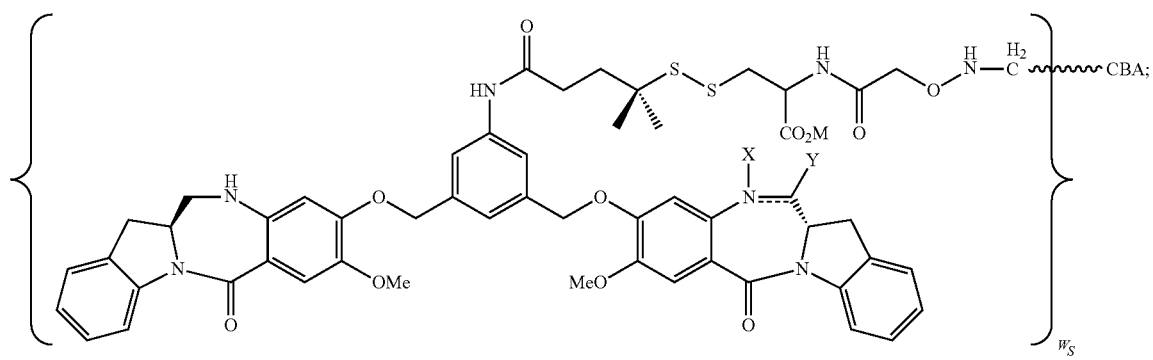
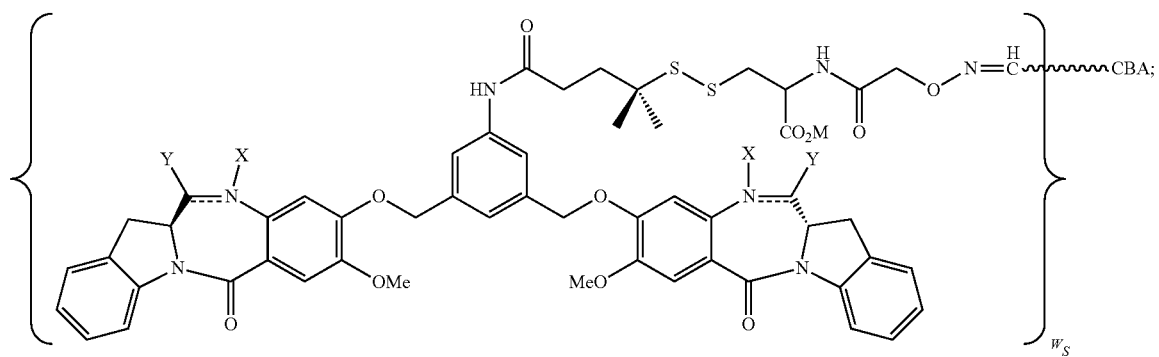
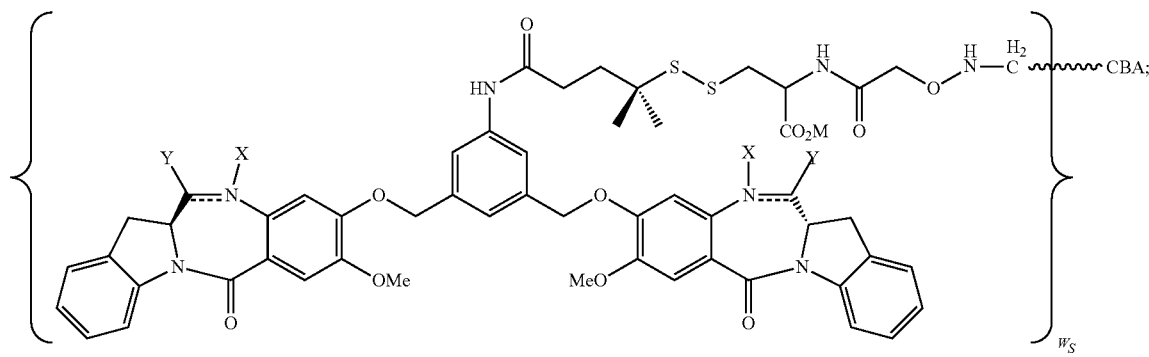

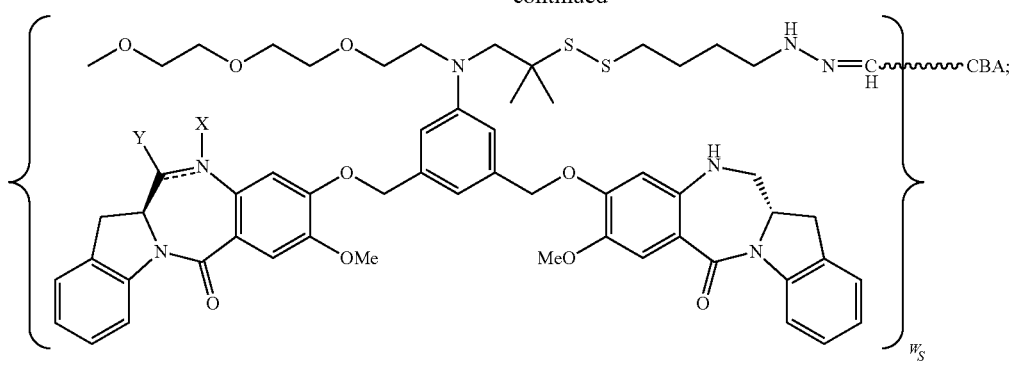
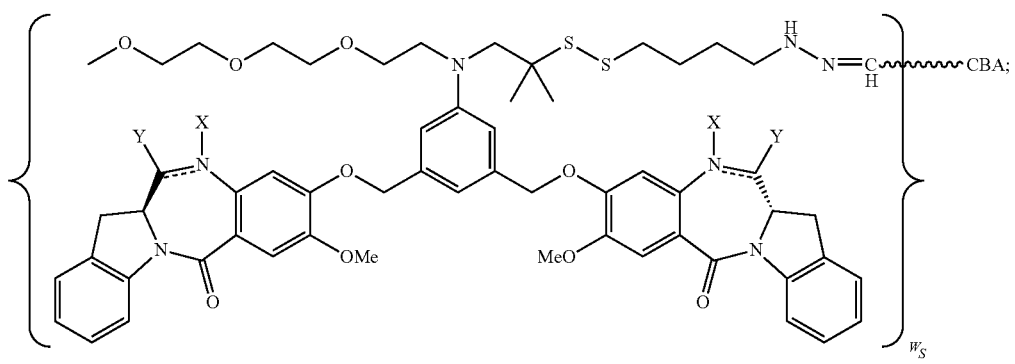
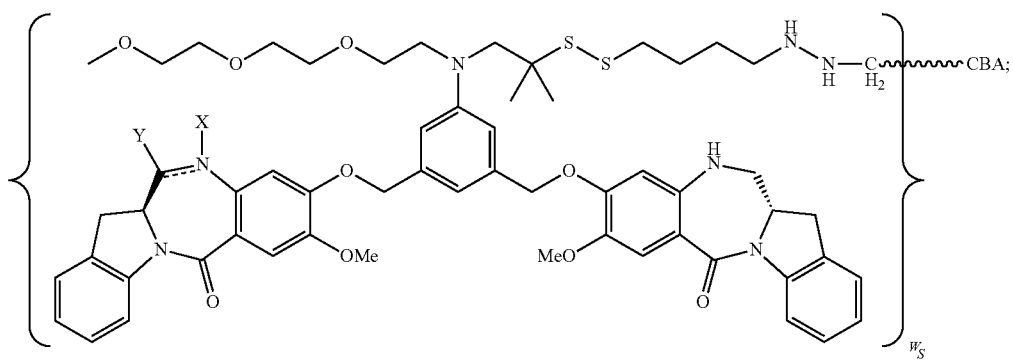
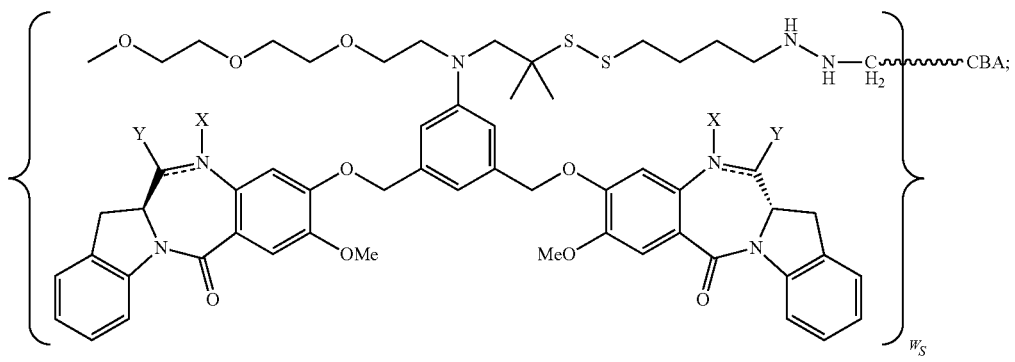

-continued
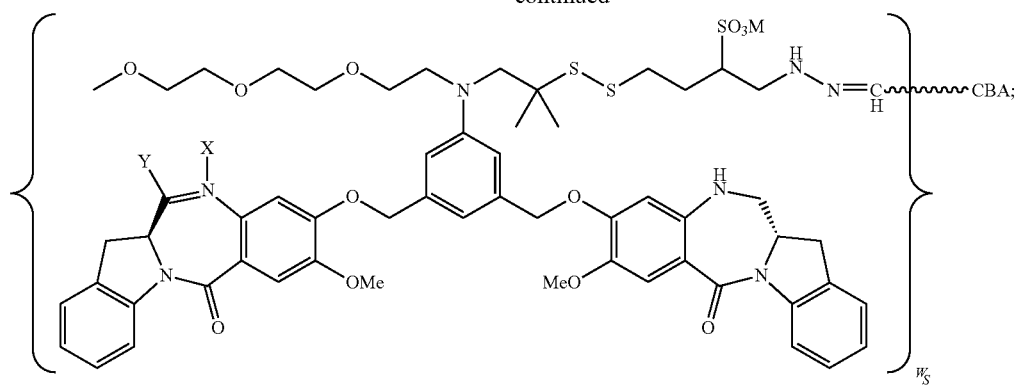
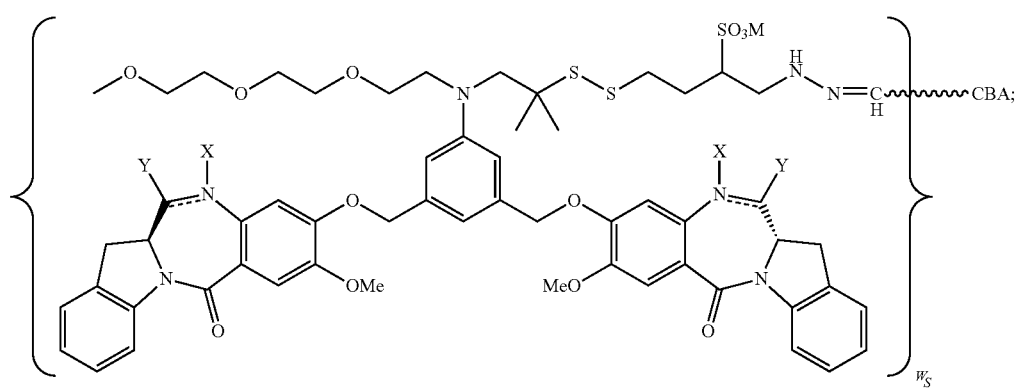
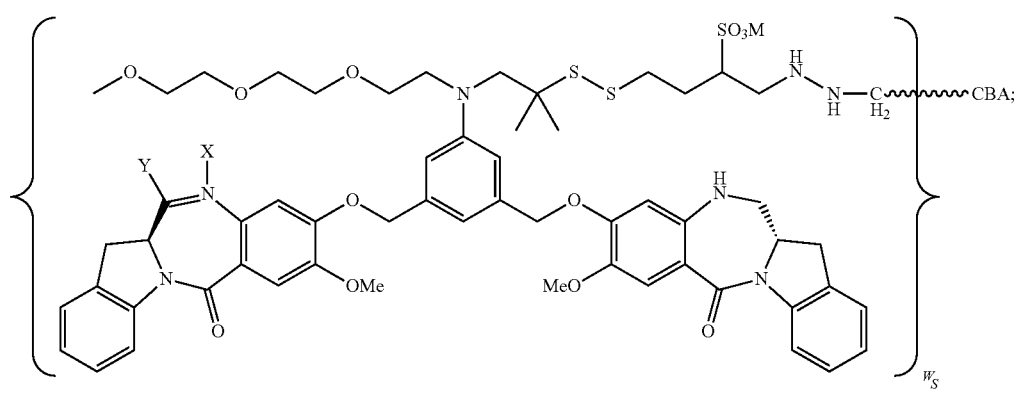
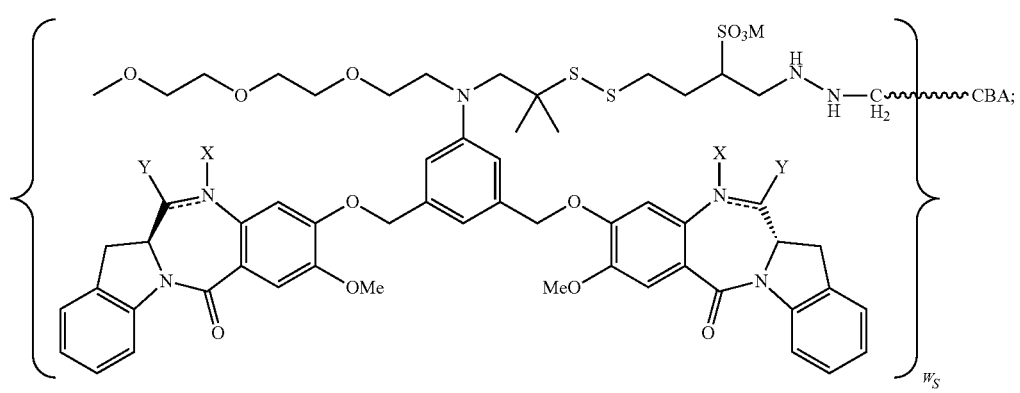

-continued
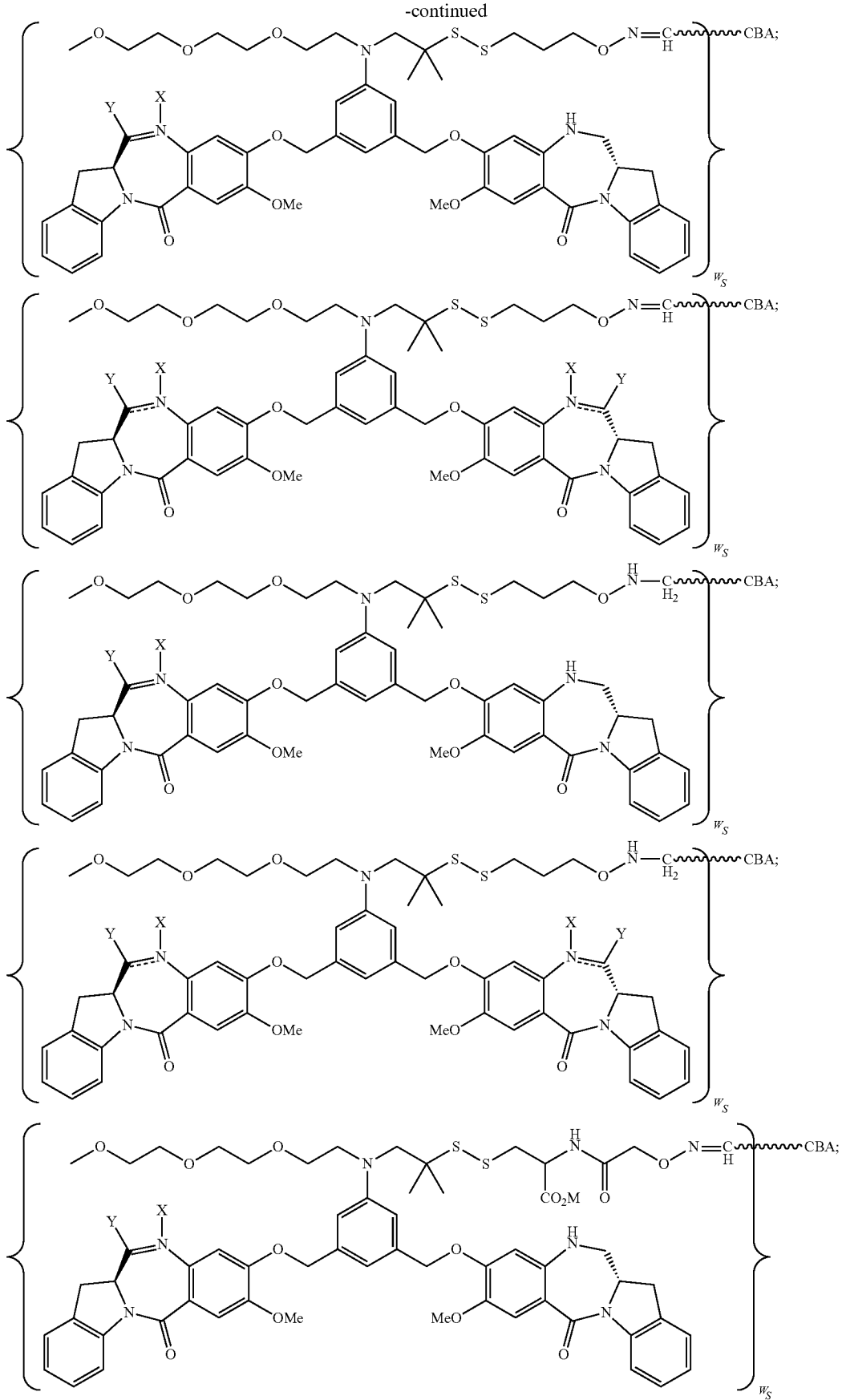

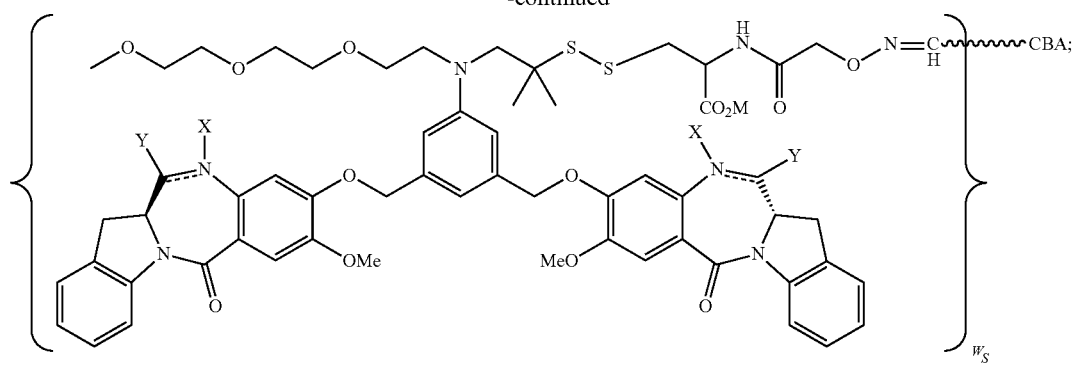
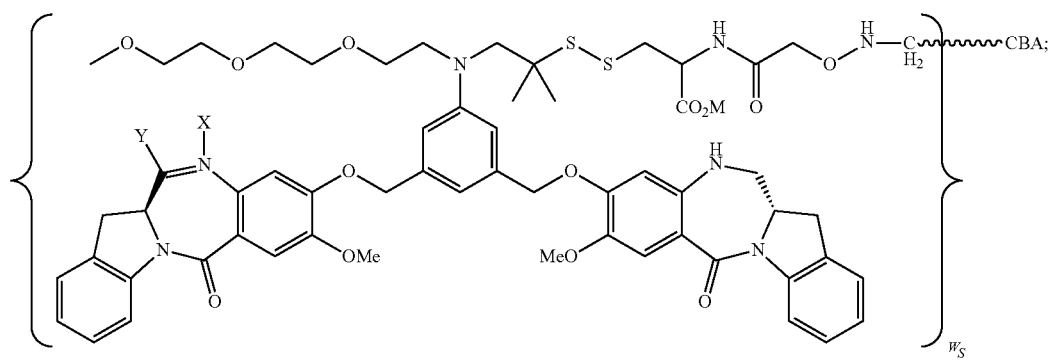
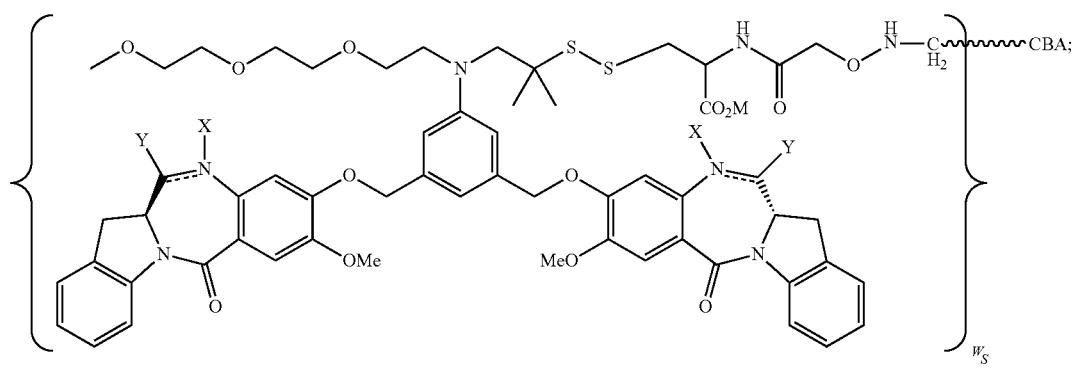
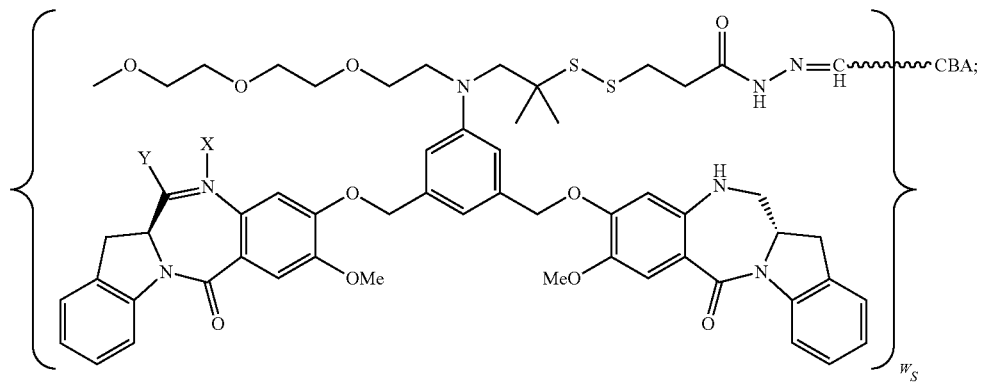

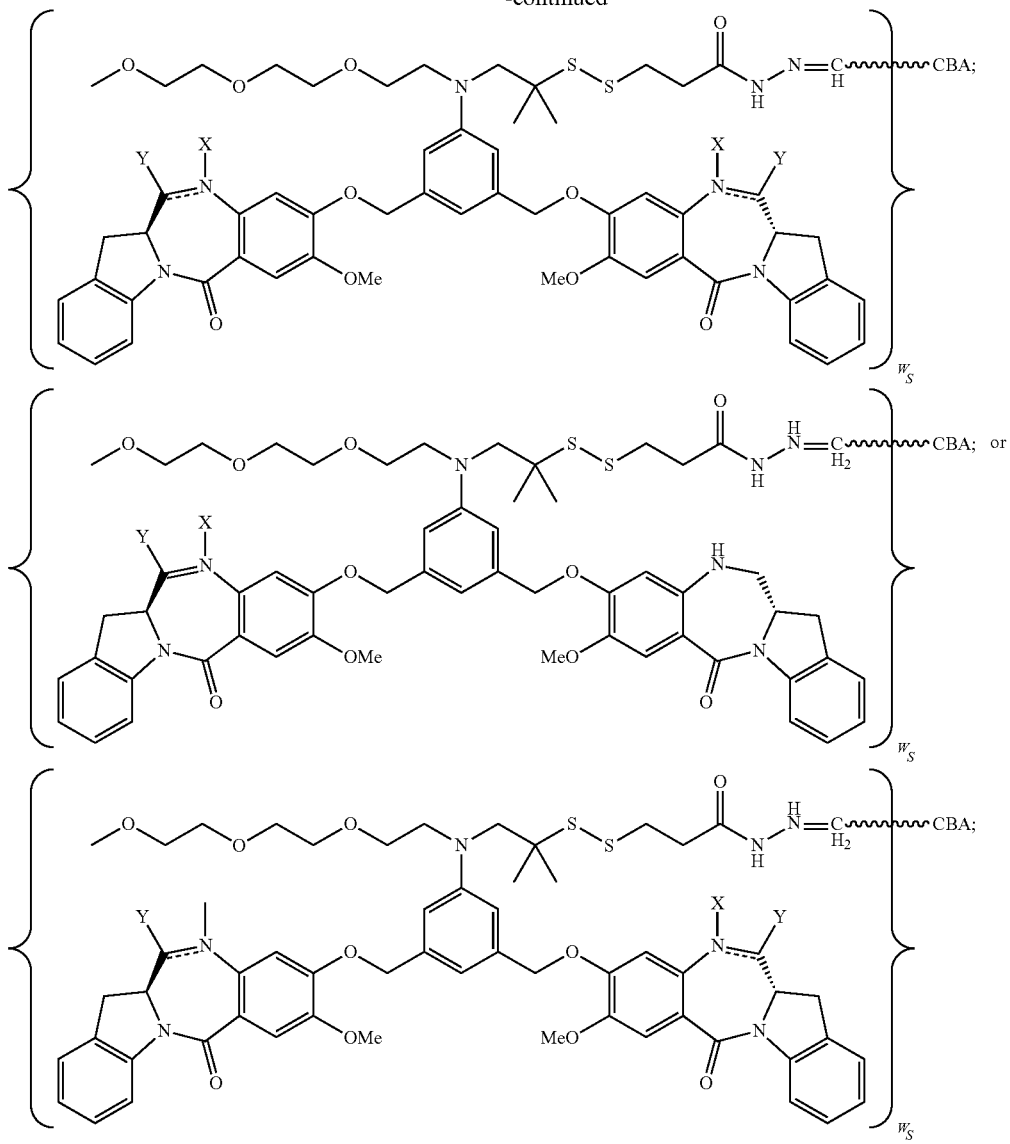

or a pharmaceutically acceptable salt thereof, wherein the
double line ═ between N and C represents a single bond or a double bond, provided that when it is a double bond, X is absent and Y is —H; and when it is a single bond, X is —H; and Y is —OH or —SO₃M.

In certain embodiments, the double line ═ between N and C represents a double bond, X is absent and Y is —H.

In certain embodiments, the double line ═ between N and C represents a single bond, X is —H and Y is —SO₃M. In certain embodiments, M is H⁺, Na⁺ or K⁺.

Another aspect of the invention provides an immunoconjugate having the following formula:

CBA～($J_{CB'}$—$Cy^{s3}$)$_{w_s}$;

wherein:
CBA is the antibody or antigen-binding fragment thereof of the invention, or the polypeptide thereof of the invention, covalently linked to the $J_{CB'}$ group;

$J_{CB'}$ is a moiety formed by reacting an aldehyde group derived from oxidation of a 2-hydroxyethylamine moiety on an N-terminal of said antibody or antigen-binding fragment thereof of the invention, or the polypeptide thereof of the invention, and an aldehyde reactive group on $Cy^{s3}$, and is represented by the following formula:

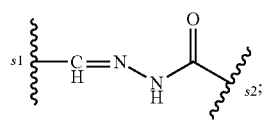

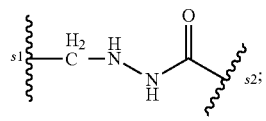

-continued

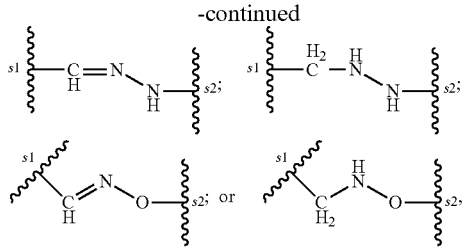

wherein s1 is the site covalently linked to the CBA; and s2 is the site covalently linked to $Cy^{s3}$;

$Cy^{s3}$ is represented by the following formula:

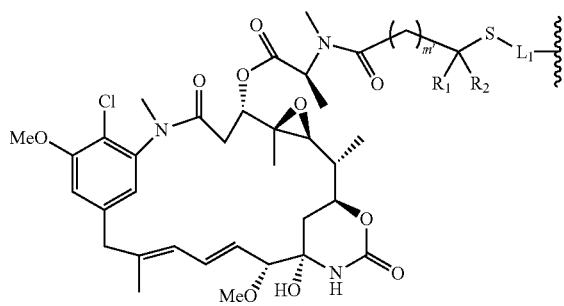

wherein:
m' is 1 or 2;
$R_1$ and $R_2$, are each independently H or a $(C_1-C_3)$alkyl;
$L_1$ is represented by the following formula:

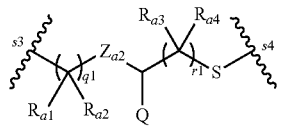

wherein:
s3 is the site covalently linked to the group $J_{CB'}$;
s4 is the site covalently linked to the —S— group on $Cy^{s3}$;
$Z_{a2}$ is absent, —C(=O)—$NR_9$—, or —$NR_9$—C(=O)—;
$R_9$ is —H or a $(C_1-C_3)$alkyl;
Q is H, a charged substituent or an ionizable group;
$R_{a1}$, $R_{a2}$, $R_{a3}$, $R_{a4}$, for each occurrence, are independently H or a $(C_1-C_3)$alkyl; and
q1 and r1 are each independently an integer from 0 to 10, provided that q1 and r1 are not both 0.

In certain embodiments, m' is 1 and $R_1$ and $R_2$ are both H.
In certain embodiments, m' is 2 and $R_1$ and $R_2$ are both Me.

In certain embodiments, -$L_1$- is represented by the following formula:

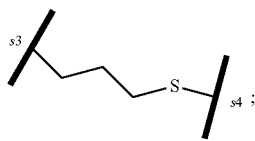

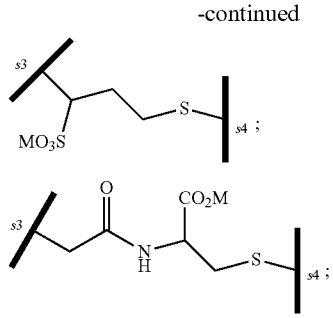

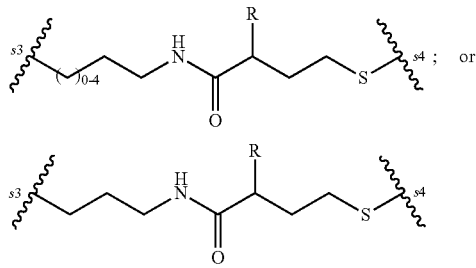

or a pharmaceutically acceptable salt thereof, wherein R is H or —$SO_3M$ and M is $H^+$ or a cation.

In certain embodiments, the immunoconjugate is represented by the following formula:

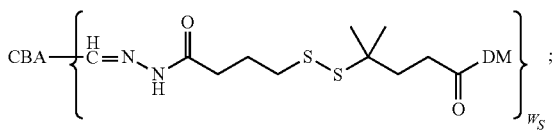

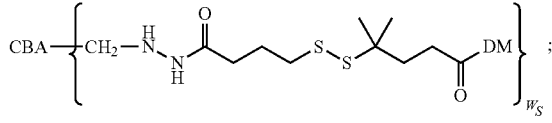

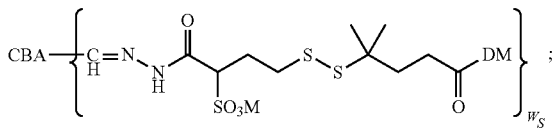

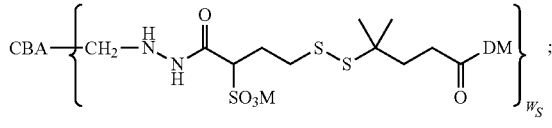

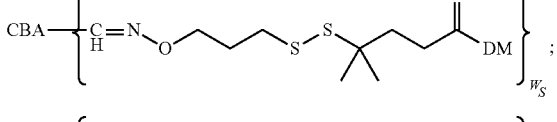

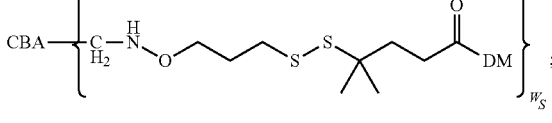

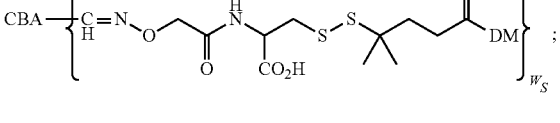

-continued

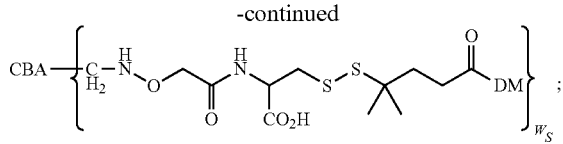

or a pharmaceutically acceptable salt thereof; wherein DM is represented by the following formula:

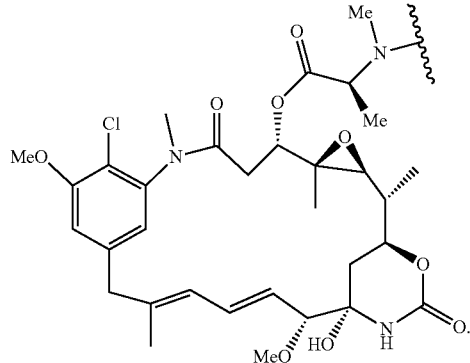 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

Another aspect of the invention provides an immunoconjugate having the following formula:

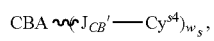

wherein:
CBA is the antibody or antigen-binding fragment thereof of the invention, or the polypeptide thereof of the invention, covalently linked to the $J_{CB'}$ group,
$J_{CB'}$ is a moiety formed by reacting an aldehyde group derived from oxidation of a 2-hydroxyethylamine moiety on an N-terminal of said antibody or antigen-binding fragment thereof of the invention, or the polypeptide thereof of the invention, and an aldehyde reactive group on $Cy^{s4}$ and is represented by the following formula:

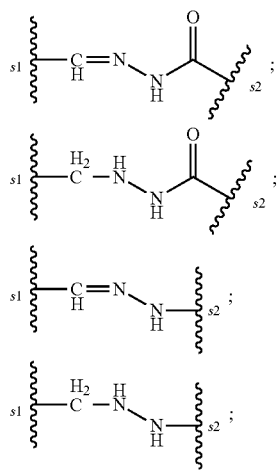

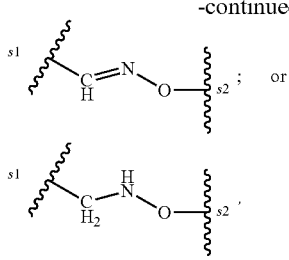

wherein s1 is the site covalently linked to the CBA; and s2 is the site covalently linked to $Cy^{s4}$.
$Cy^{s4}$ is represented by the following formula:

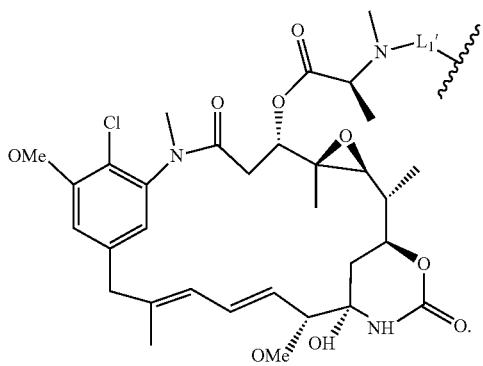

$L_{1'}$ is represented by the following formula:

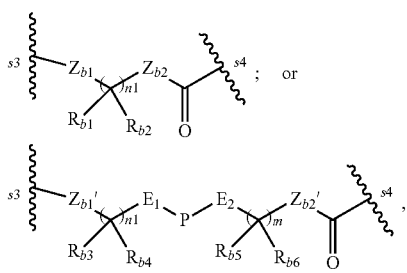

wherein:
s3 is the site covalently linked to the group $J_{CB'}$ group;
s4 is the site covalently linked to -NMe- group on $Cy^{s4}$;
$Z_{b1}$ and $Z_{b2}$ are both absent, or one of $Z_{b1}$ and $Z_{b2}$ is absent and the other is —$CH_2$—O— or —O—$CH_2$—;
$Z_{b1'}$ and $Z_{b2'}$ are each independently absent, —$CH_2$—O—, —O—$CH_2$—, —$NR_9$—C(=O)—$CH_2$—, or —$CH_2$—C(=O)—$NR_9$—;
$R_9$ is H or ($C_1$-$C_3$)alkyl;
n1 and m1 are each independently an integer from 1 to 6;
one of $E_1$ and $E_2$ is —C(=O)—, and the other is —$NR_9$—; or one of $E_1$ and $E_2$ is —C(=O)— or —$NR_9$—, and the other is absent;
P is an amino acid residue or a peptide containing between 2 to 20 amino acid residues; and
$R_{b1}$, $R_{b2}$, $R_{b3}$, $R_{b4}$, $R_{b5}$ and $R_{b6}$, for each occurrence, are each independently H or a ($C_1$-$C_3$)alkyl.
In certain embodiments, $R_{b1}$, $R_{b2}$, $R_{b3}$, $R_{b4}$, $R_{b5}$, and $R_{b6}$ are all H. In certain embodiments, $R_9$ is H.

In certain embodiments, $Z_{b1'}$ and $Z_{b2'}$ are both absent; or $Z_{b1'}$ is —CH$_2$—O—; and $Z_{b2'}$ is absent; or $Z_{b1'}$ is —CH$_2$—C(=O)—NR$_9$—; and $Z_{b2'}$ is —O—CH$_2$— or absent.

In certain embodiments, P is a peptide containing 2 to 5 amino acid residues. For example, P may be selected from Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 55), β-Ala-Leu-Ala-Leu (SEQ ID NO: 57), Gly-Phe-Leu-Gly (SEQ ID NO: 73), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. In certain embodiments, P is Gly-Gly-Gly, Ala-Val, Ala-Ala, Ala-D-Ala, D-Ala-Ala, and D-Ala-D-Ala.

In certain embodiments, immunoconjugate is represented by the following formula:

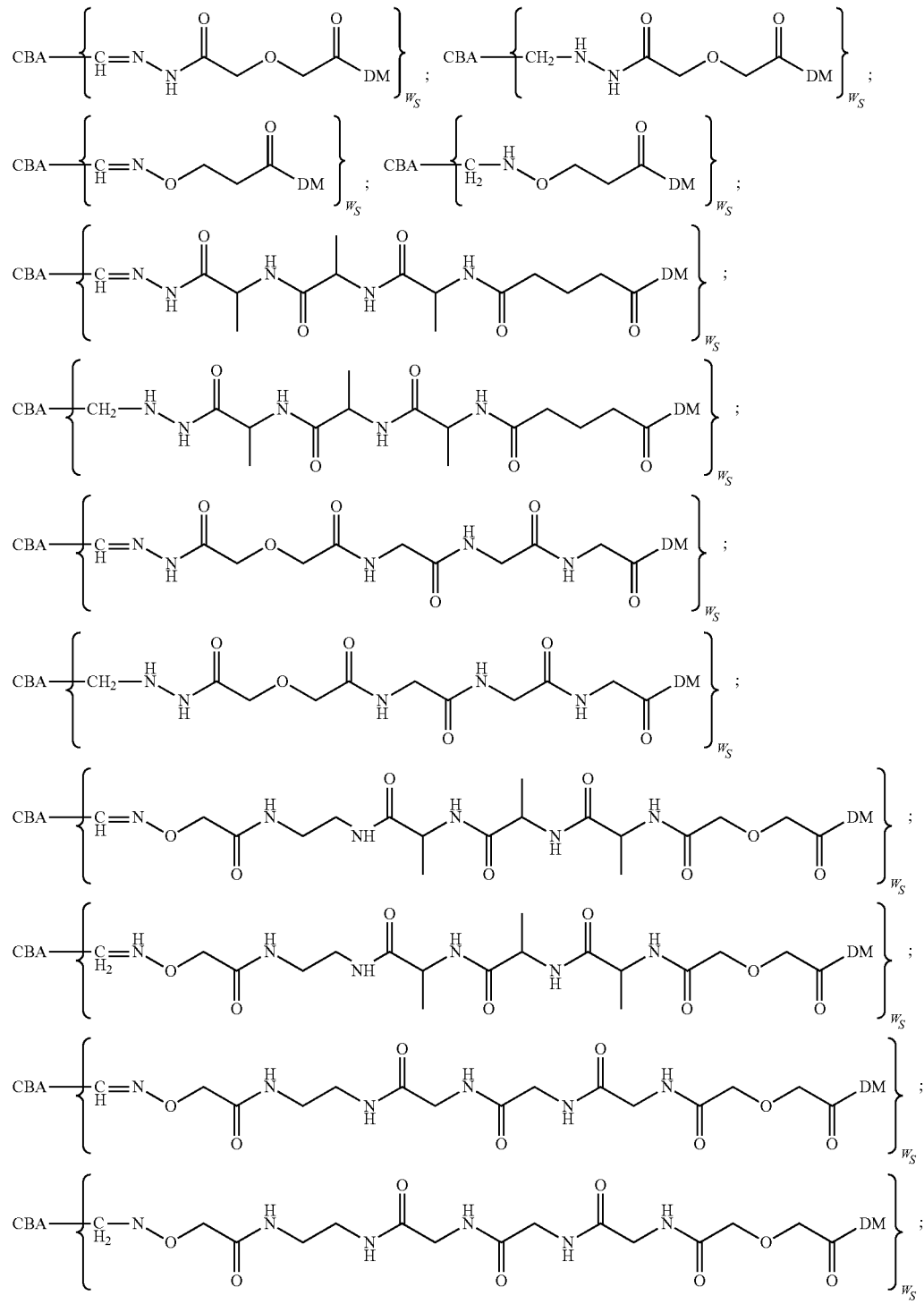

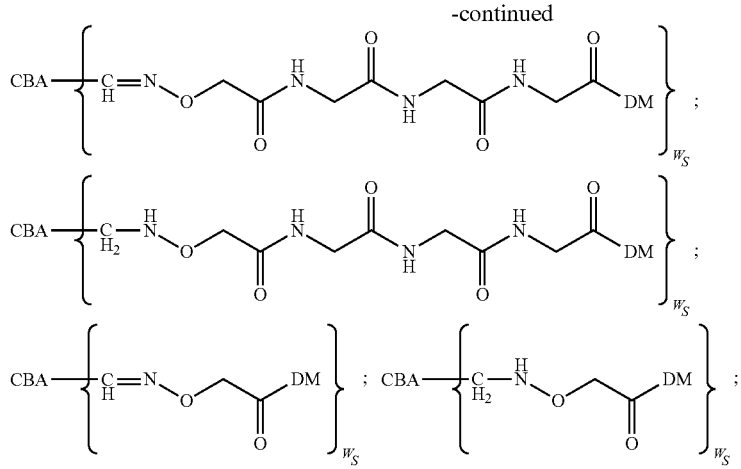

or a pharmaceutically acceptable salt thereof, wherein DM is represented by the following structural formula:

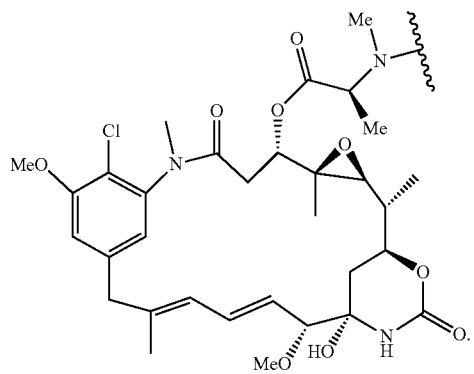 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

Another aspect of the invention provides an immunoconjugate represented by the following formula:

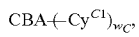

wherein:

CBA is an antibody or antigen-binding fragment thereof of the invention, or the polypeptide thereof of the invention, covalently linked to $Cy^{C1}$ through a cysteine residue;

$W_C$ is 1 or 2;

$Cy^{C1}$ is represented by the following formula:

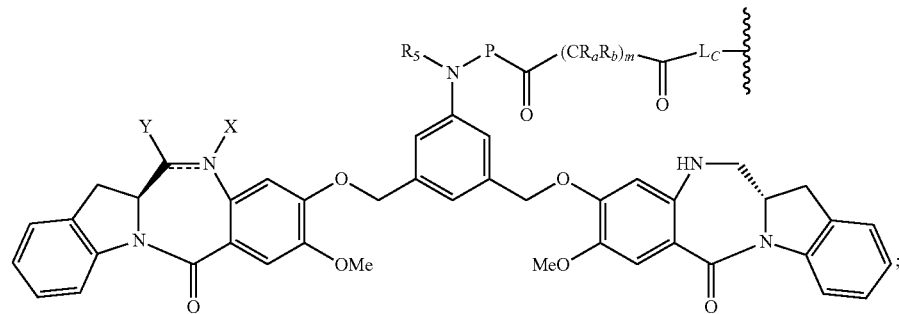

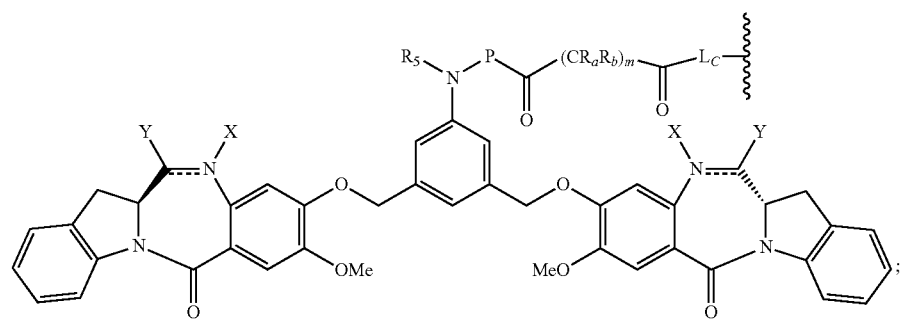

-continued

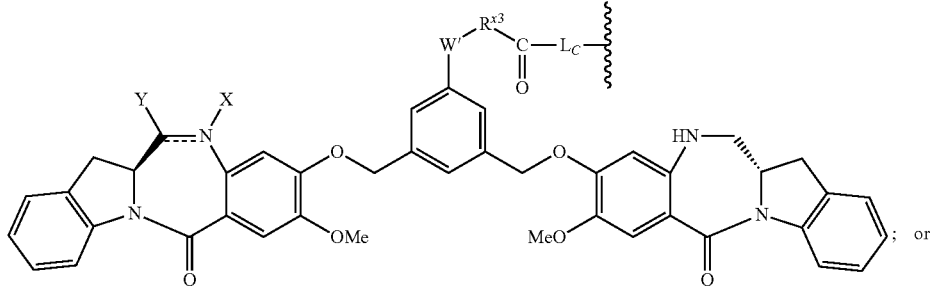

; or

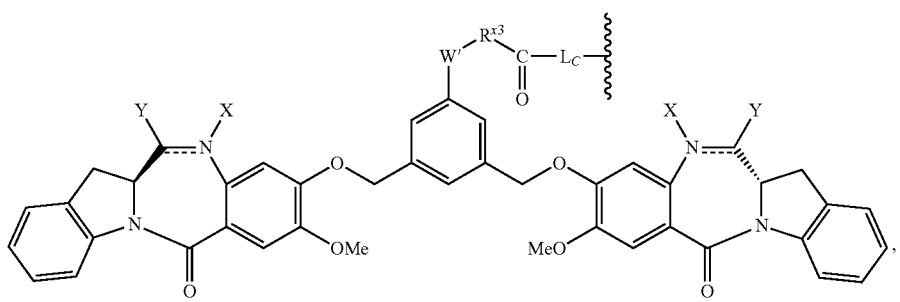

, or a pharmaceutically acceptable salt thereof, wherein:
the double line == between N and C represents a single bond or a double bond, provided that when it is a double bond, X is absent and Y is —H or a $(C_1-C_4)$alkyl; and when it is a single bond, X is —H or an amine protecting moiety, Y is —OH or —$SO_3M$, and M is $H^+$ or a cation;
$R_5$ is —H or a $(C_1-C_3)$alkyl;
P is an amino acid residue or a peptide containing 2 to 20 amino acid residues;
$R_a$ and $R_b$, for each occurrence, are independently —H, $(C_1-C_3)$alkyl, or a charged substituent or an ionizable group Q;
W' is —$NR^{e'}$,
$R^{e'}$ is —$(CH_2—CH_2—O)_n—R^k$;
n is an integer from 2 to 6;
$R^k$ is —H or -Me;
$R^{x3}$ is a $(C_1-C_6)$alkyl; and,
$L_C$ is represented by

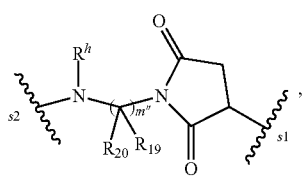

, s1 is the site covalently linked to CBA, and s2 is the site covalently linked to the —C(=O)— group on $Cy^{C1}$; wherein:

$R_{19}$ and $R_{20}$, for each occurrence, are independently —H or a $(C_1-C_3)$alkyl;
m" is an integer between 1 and 10; and
$R^h$ is —H or a $(C_1-C_3)$alkyl.

In certain embodiments, $R_a$ and $R_b$ are both H; and $R_5$ is H or Me.

In certain embodiments, P is a peptide containing 2 to 5 amino acid residues. For example, P may be selected from Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 55), β-Ala-Leu-Ala-Leu (SEQ ID NO: 57), Gly-Phe-Leu-Gly (SEQ ID NO: 73), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. In certain embodiments, P is Gly-Gly-Gly, Ala-Val, Ala-Ala, Ala-D-Ala, D-Ala-Ala, or D-Ala-D-Ala. In certain embodiments, Q is —$SO_3M$.

In certain embodiments, $R_{19}$ and $R_{20}$ are both H; and m" is an integer from 1 to 6.

In certain embodiments, -$L_C$- is represented by the following formula:

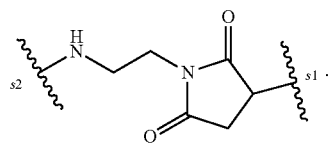 [SMILES: *NCCN1C(=O)CC(*)C1=O ; "."]
In certain embodiments, the immunoconjugate is represented by the following formula:
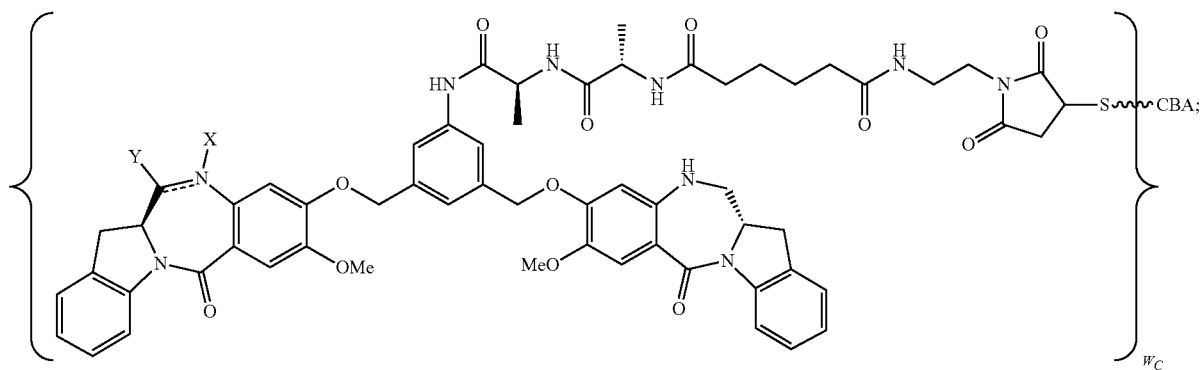
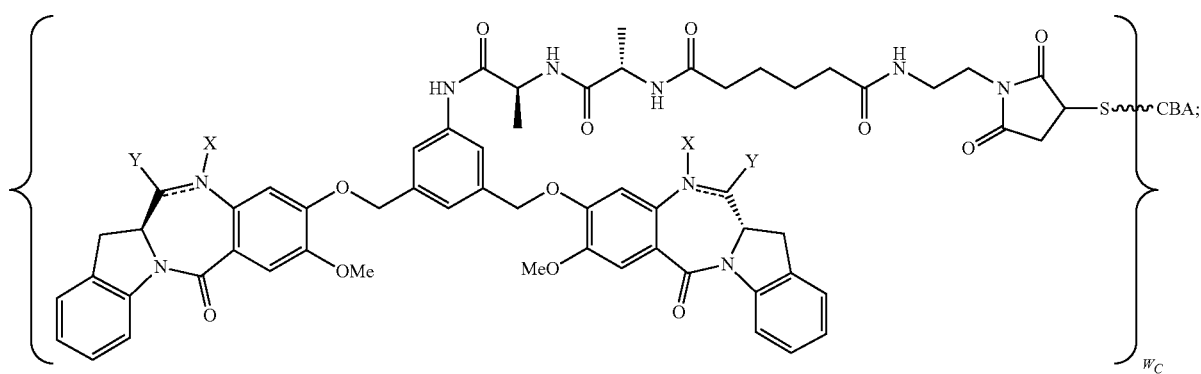
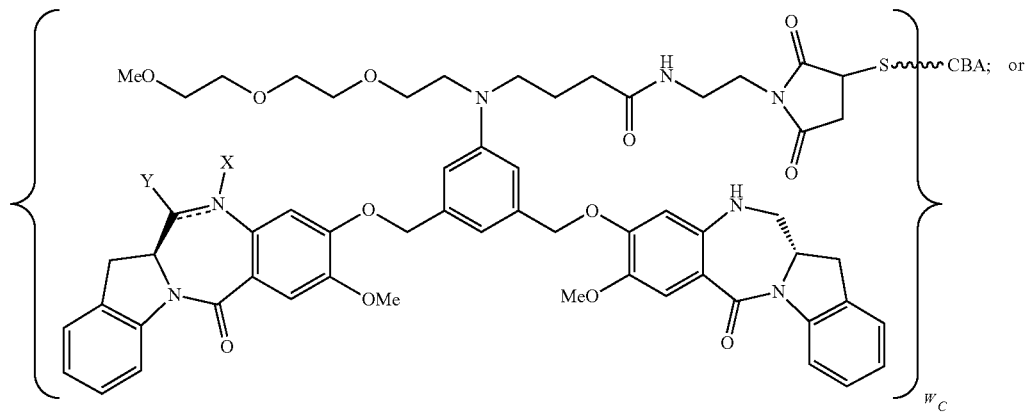

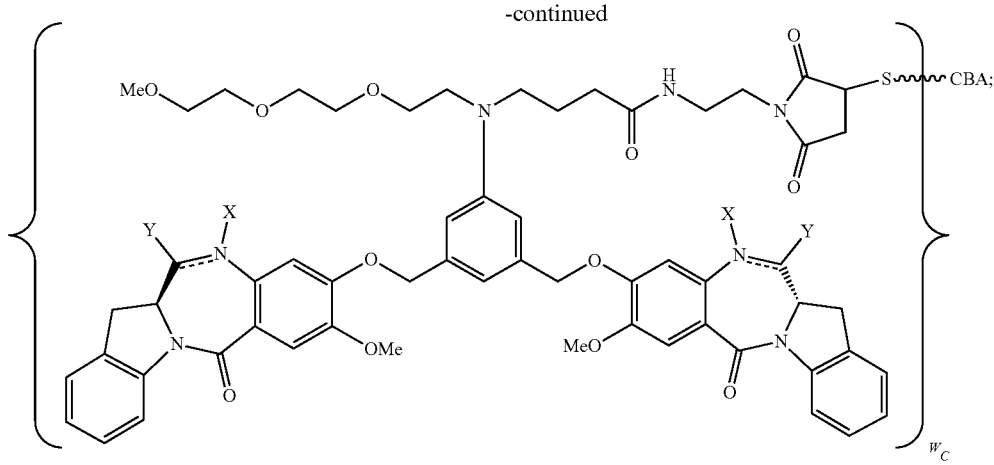

or a pharmaceutically acceptable salt thereof, wherein the double line ⚌ between N and C represents a single bond or a double bond, provided that when it is a double bond, X is absent and Y is —H, and when it is a single bond, X is —H, and Y is —OH or —$SO_3M$.

Another aspect of the invention provides an immunoconjugate represented by the following formula:

CBA—(—$Cy^{C2}$)$_{w_C}$, wherein:

CBA is an antibody or antigen-binding fragment thereof of the invention, or the polypeptide thereof of the invention, covalently linked to $Cy^{C2}$ through a cysteine residue;

$W_C$ is 1 or 2;

$Cy^{C2}$ is represented by the following formula:

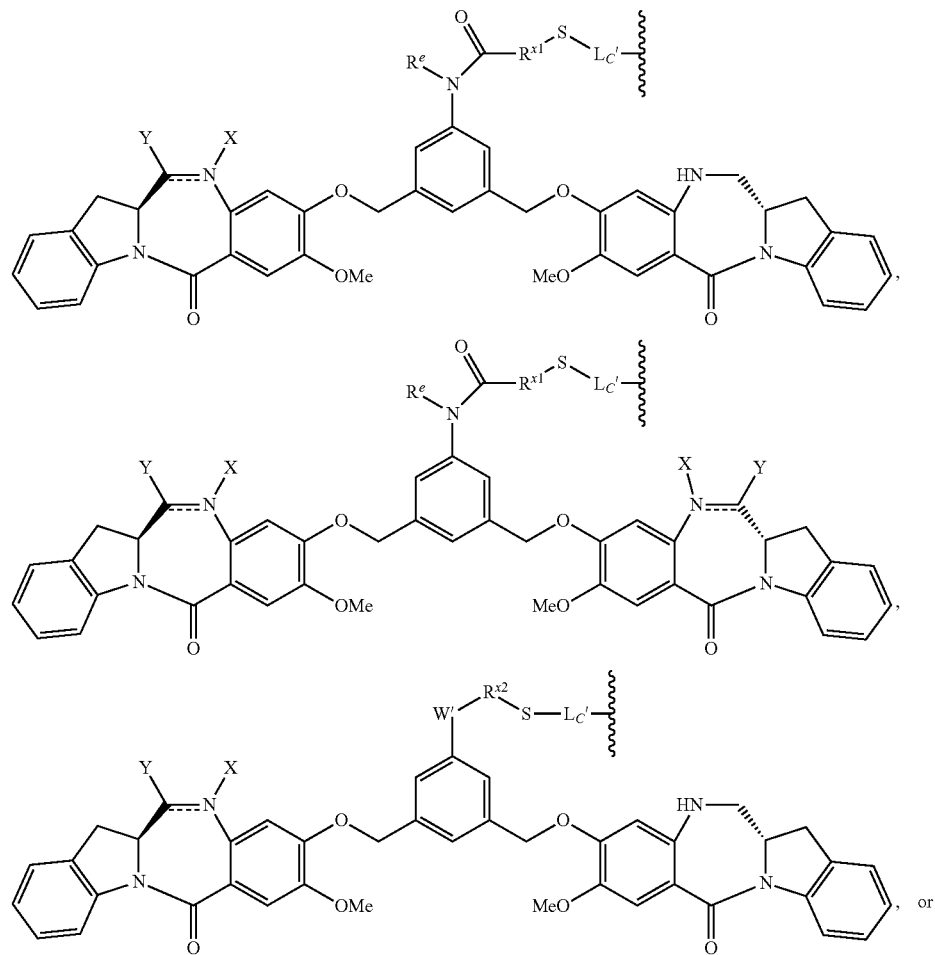

-continued

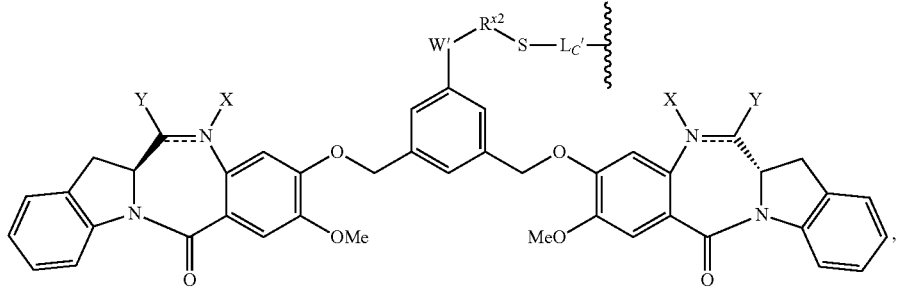

or a pharmaceutically acceptable salt thereof, wherein:

the double line between N and C represents a single bond or a double bond, provided that when it is a double bond, X is absent and Y is —H or a $(C_1-C_4)$alkyl; and when it is a single bond, X is —H or an amine protecting moiety, Y is —OH or —$SO_3M$, and M is $H^+$ or a cation;

$R^{x1}$ is a $(C_1-C_6)$alkyl;

$R^e$ is —H or a $(C_1-C_6)$alkyl;

W' is —$NR^{e'}$;

$R^{e'}$ is —$(CH_2—CH_2—O)_n—R^k$;

n is an integer from 2 to 6;

$R^k$ is —H or -Me;

$R^{x2}$ is a $(C_1-C_6)$alkyl;

$L_{C'}$ is represented by the following formula:

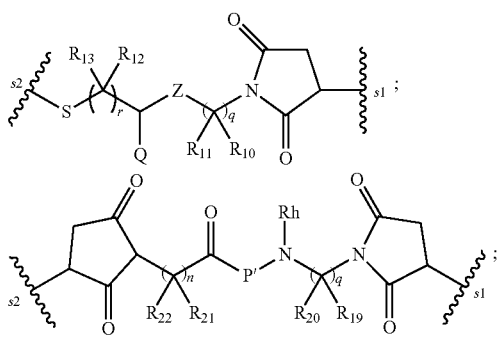

wherein:

s1 is the site covalently linked to the CBA and s2 is the site covalently linked to —S— group on $Cy^{C2}$;

Z is —C(=O)—$NR_9$—, or —$NR_9$—C(=O)—;

Q is —H, a charged substituent, or an ionizable group;

$R_9$, $R_{10}$, $R_{11}$, $R_{12}$, $R_{13}$, $R_{19}$, $R_{20}$, $R_{21}$ and $R_{22}$, for each occurrence, are independently —H or a $(C_1-C_3)$ alkyl;

q and r, for each occurrence, are independently an integer between 0 and 10;

m and n are each independently an integer between 0 and 10;

$R^h$ is —H or a $(C_1-C_3)$alkyl; and

P' is an amino acid residue or a peptide containing 2 to 20 amino acid residues.

In certain embodiments, P' is a peptide containing 2 to 5 amino acid residues. For example, P' may be selected from Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 55), β-Ala-Leu-Ala-Leu (SEQ ID NO: 57), Gly-Phe-Leu-Gly (SEQ ID NO: 73), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. In certain embodiments, P' is Gly-Gly-Gly, Ala-Val, Ala-Ala, Ala-D-Ala, D-Ala-Ala, or D-Ala-D-Ala.

In certain embodiments, in the immunoconjugate -$L_{C'}$- is represented by the following formula:

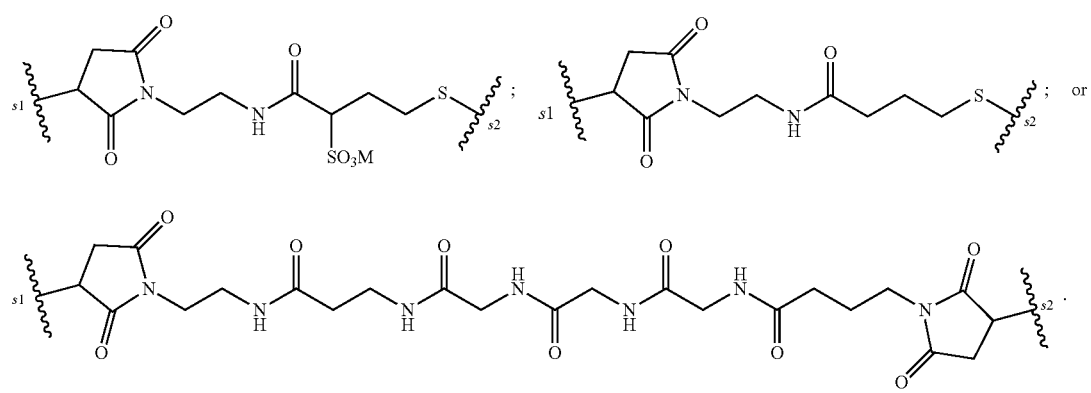

In certain embodiments, $R^e$ is H or Me; $R^{x1}$ is —$(CH_2)_p$—$(CR^fR^g)$—, and R is —$(CH_2)_p$—$(CR^fR^g)$—, wherein $R^f$ and $R^g$ are each independently —H or a ($C_1$-$C_4$) alkyl; and p is 0, 1, 2 or 3. In certain embodiments, $R^f$ and $R^g$ are the same or different, and are selected from —H and -Me.
In certain embodiments, the immunoconjugate is represented by the following formula:
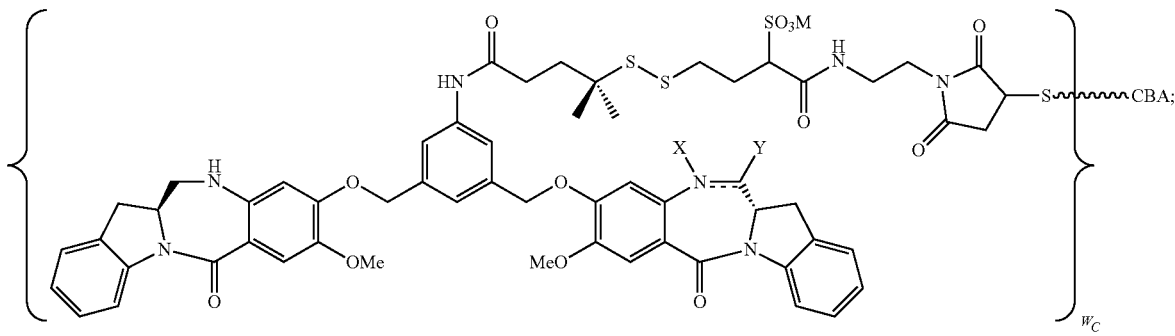
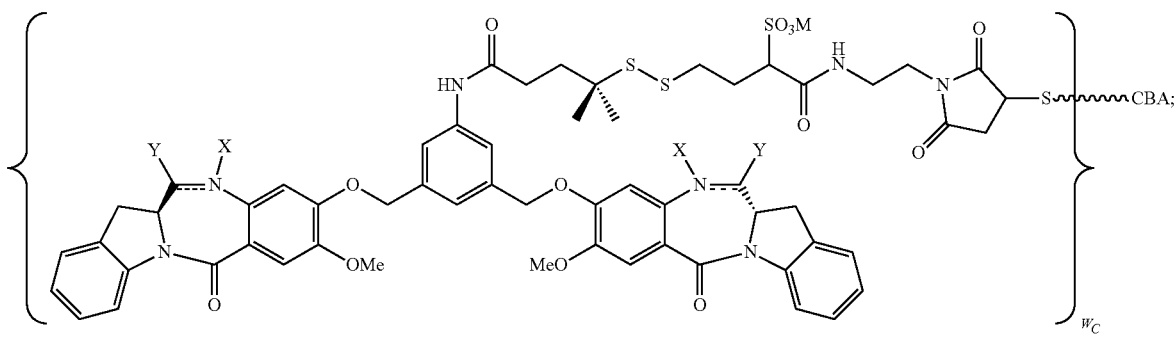
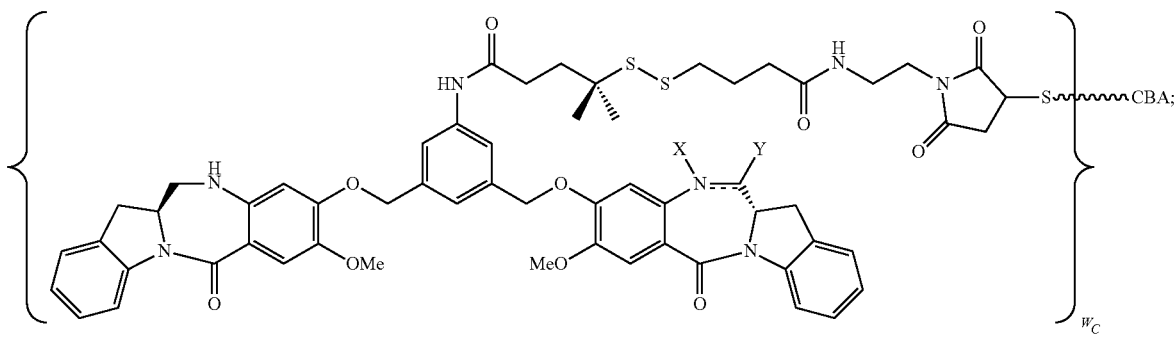
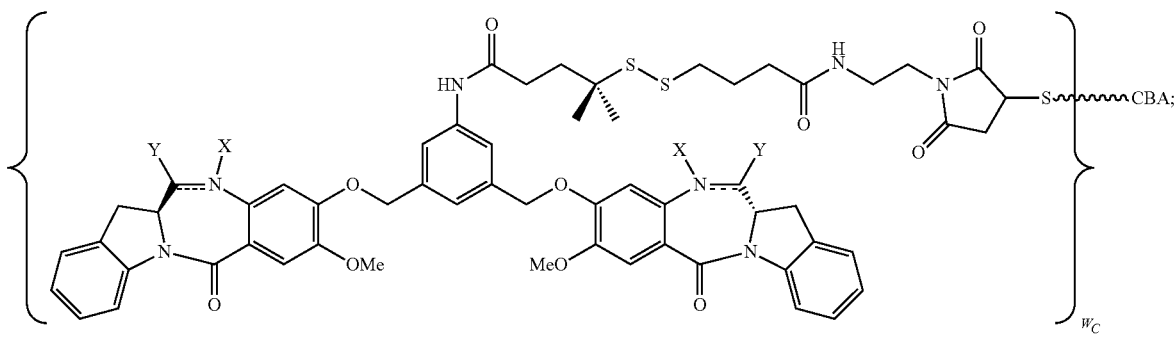

-continued
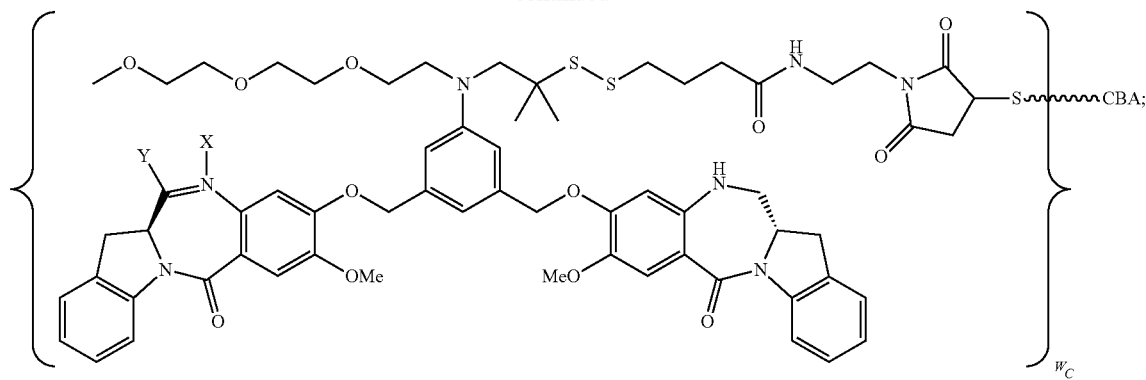
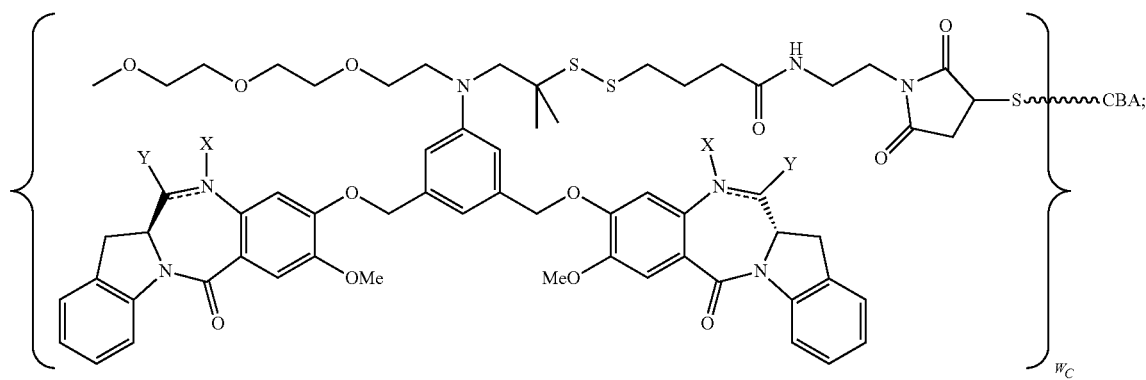
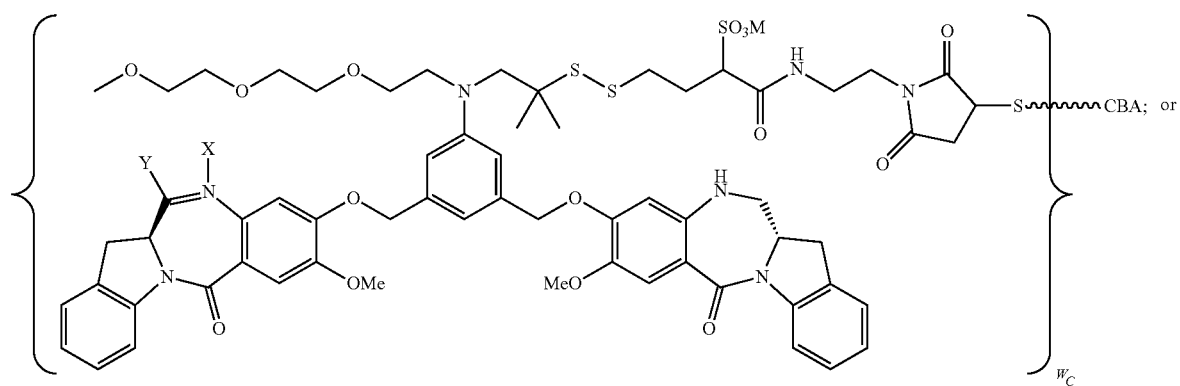
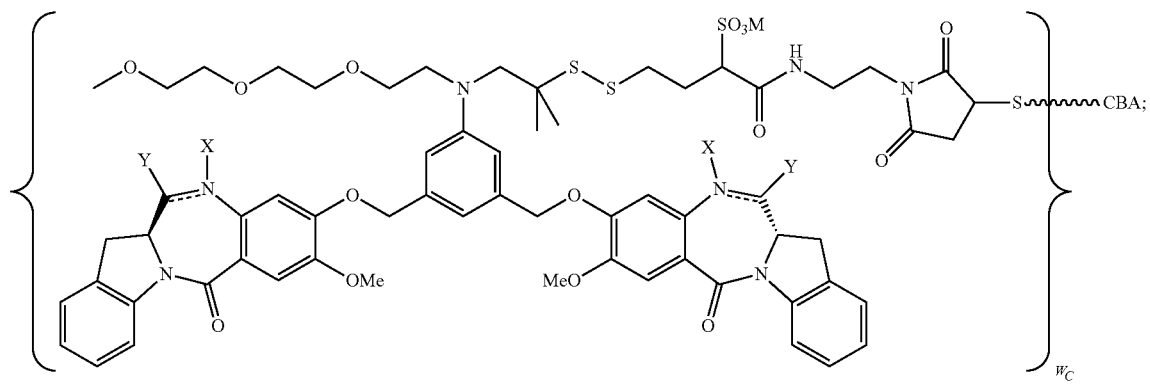

or a pharmaceutically acceptable salt thereof, wherein the double line 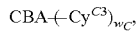 between N and C represents a single bond or a double bond, provided that when it is a double bond, X is absent and Y is —H, and when it is a single bond, X is —H, and Y is —OH or —SO$_3$M.

In certain embodiments, the double line == between N and C represents a double bond, X is absent and Y is —H.

In certain embodiments, the double line == between N and C represents a single bond, X is —H and Y is —SO$_3$M. In certain embodiments, M is H$^+$, Na$^+$ or K$^+$.

Another aspect of the invention provides an immunoconjugate having the following formula:

$$CBA-(Cy^{C3})_{wC},$$

wherein:

CBA is an antibody or antigen-binding fragment thereof of the invention, or the polypeptide thereof of the invention, covalently linked to Cy$^{C3}$ through a cysteine residue;

W$_C$ is 1 or 2;

Cy$^{C3}$ is represented by the following formula:

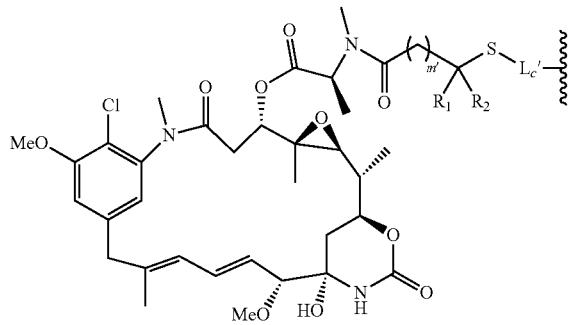

wherein:

m' is 1 or 2;

R$_1$ and R$_2$, are each independently —H or a (C$_1$-C$_3$) alkyl;

L$_{C'}$ is represented by the following formula:

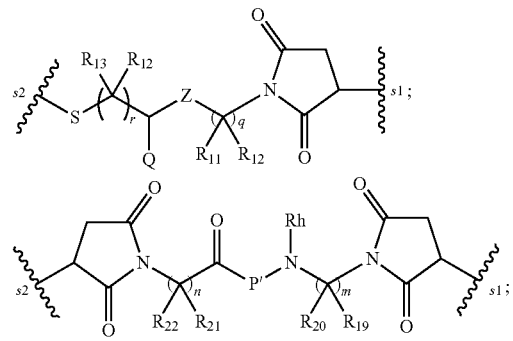

wherein:

s1 is the site covalently linked to the CBA and s2 is the site covalently linked to —S— group on Cy$^{C3}$;

Z is —C(=O)—NR$_9$—, or —NR$_9$—C(=O)—;

Q is H, a charged substituent, or an ionizable group;

R$_9$, R$_{10}$, R$_{11}$, R$_{12}$, R$_{13}$, R$_{19}$, R$_{20}$, R$_{21}$ and R$_{22}$, for each occurrence, are independently —H or a (C$_1$-C$_3$) alkyl;

q and r, for each occurrence, are independently an integer between 0 and 10;

m and n are each independently an integer between 0 and 10;

R$^h$ is —H or a (C$_1$-C$_3$)alkyl; and

P' is an amino acid residue or a peptide containing 2 to 20 amino acid residues.

In certain embodiments, P' is a peptide containing 2 to 5 amino acid residues. For example, P' is selected from Gly-Gly-Gly, Ala-Val, Val-Ala, Val-Cit, Val-Lys, Phe-Lys, Lys-Lys, Ala-Lys, Phe-Cit, Leu-Cit, Lle-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 55), β-Ala-Leu-Ala-Leu (SEQ ID NO: 57), Gly-Phe-Leu-Gly (SEQ ID NO: 73), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. In certain embodiments, P' is Gly-Gly-Gly, Ala-Val, Ala-Ala, Ala-D-Ala, D-Ala-Ala, or D-Ala-D-Ala.

In certain embodiments, -L$_{C'}$- is represented by the following formula:

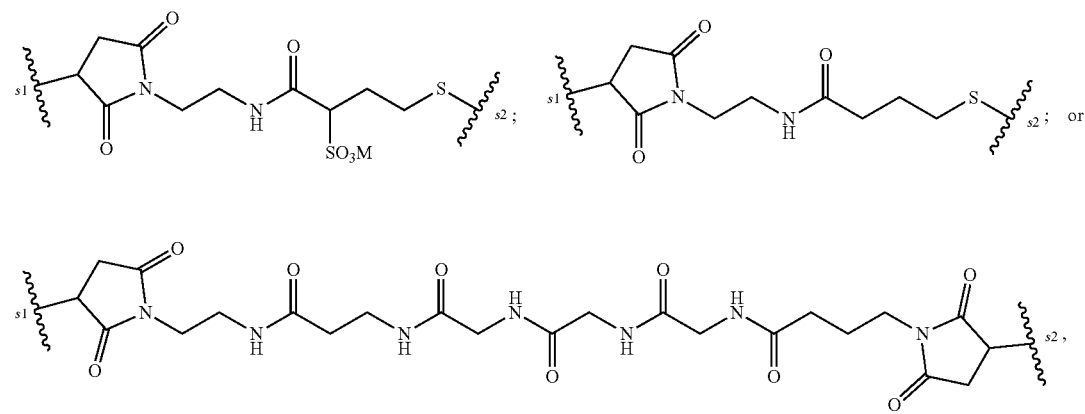

wherein M is H$^+$ or a cation.

In certain embodiments, m' is 1 and $R_1$ and $R_2$ are both H.

In certain embodiments, m' is 2 and $R_1$ and $R_2$ are both Me.

In certain embodiments, the immunoconjugate is represented by the following formula:

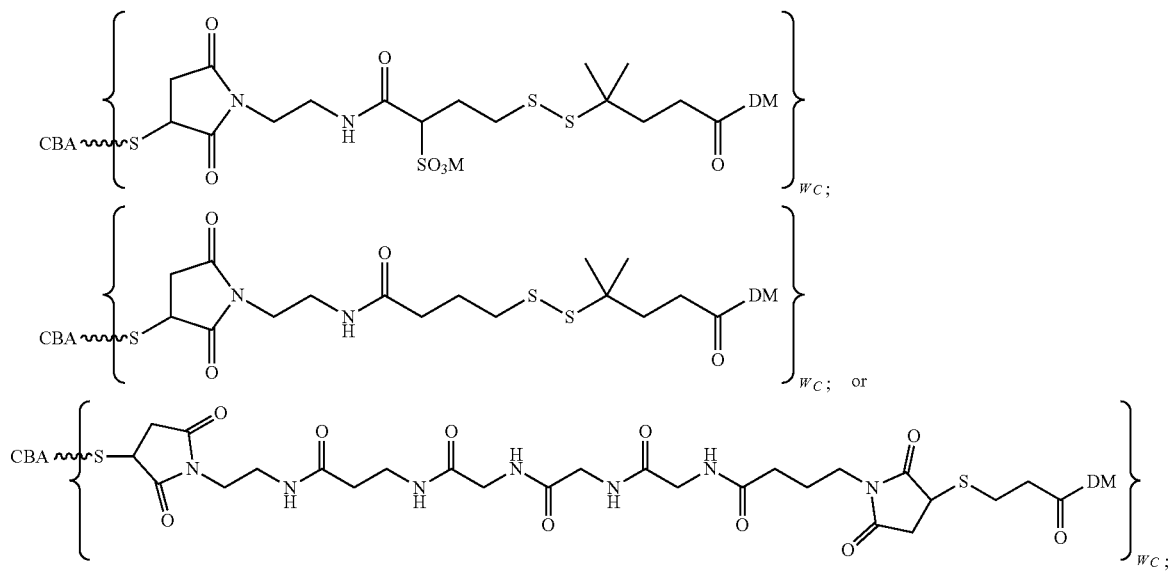

or a pharmaceutically acceptable salt thereof, wherein DM is a drug moiety represented by the following formula:

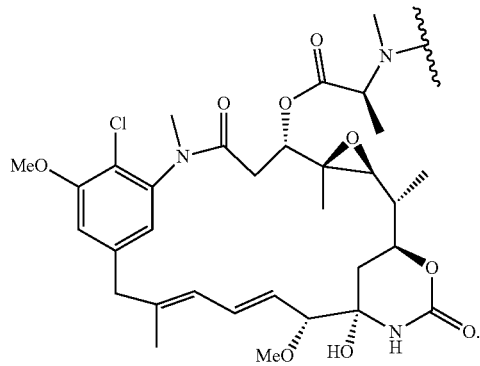 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

Another aspect of the invention provides a pharmaceutical composition comprising the antibody or antigen-binding fragment thereof of the invention, or the polypeptide of the invention, or the immunoconjugate of the invention, and a pharmaceutically acceptable carrier.

Another aspect of the invention provides a method for inhibiting the growth of a cell expressing CD123, comprising contacting the cell with the antibody or antigen-binding fragment thereof of the invention, or the polypeptide of the invention, or the immunoconjugate of the invention, or the pharmaceutical composition of the invention.

In certain embodiments, the cell is a tumor cell. In certain embodiments, the cell is a leukemia cell or a lymphoma cell.

Another aspect of the invention provides a method for treating a subject having cancer, wherein cells of the cancer expresses CD123, the method comprising administering to said subject a therapeutically effective amount of the antibody or antigen-binding fragment thereof of the invention, or the polypeptide of the invention, or the immunoconjugate of the invention, or the pharmaceutical composition of the invention.

In certain embodiments, the cancer or cell-proliferative disorder is leukemia or lymphoma. In certain embodiments, the cancer or cell-proliferative disorder is selected from the group consisting of: acute myeloid leukemia (AML); chronic myeloid leukemia (CML); acute lymphoblastic leukemia (ALL), including B-cell lineage acute lymphoblastic leukemia (B-ALL); chronic lymphocytic leukemia (CLL); hairy cell leukemia (HCL); myelodysplastic syndrome; basic plasmacytoid DC neoplasm (BPDCN) leukemia; non-Hodgkin lymphomas (NHL), including mantle cell lymphoma; and Hodgkin's leukemia (HL). In certain embodiments, the cancer is acute myeloid leukemia (AML). In certain embodiments, the cancer is B-cell acute lymphoblastic leukemia (B-ALL).

Another aspect of the invention provides a method for treating a cell-proliferative disorder in a subject, wherein cells of the cell-proliferative disorder expresses CD123, the method comprising administering to said subject a therapeutically effective amount of the antibody or antigen-binding fragment thereof of the invention, or the polypeptide of the invention, or the immunoconjugate of the invention, or the pharmaceutical composition of the invention, in an amount sufficient to treat said cell-proliferative disorder.

It is contemplated that any one embodiment described herein, including those described only in one aspect of the invention (but not in others or not repeated in others), and those described only in the Examples, can be combined with any one or more other embodiments of the invention, unless explicitly disclaimed or inapplicable.

BRIEF DESCRIPTION OF THE DRAWINGS

FIGS. 2A and 2B show that three murine anti-CD123 antibodies (muCD123-3, -6 and -14) inhibit IL-3 dependent proliferation of TF-1 cells at least as well as 7G3. FIG. 2A shows inhibition of TF-1 cells cultured in the presence of IL-3 (1 ng/mL) by the various anti-CD123 antibodies, including CD123-binding control antibodies 7G3, 6H6, and 9F5. FIG. 2B shows inhibition of TF-1 cells cultured in the presence of GM-CSF (2 ng/mL) by the same anti-CD123 antibodies.

FIG. 3 shows that murine anti-CD123 antibodies muCD123-3, -6, and -14 inhibit IL-3 (1 ng/mL) dependent proliferation of TF-1 cells in a dose-dependent manner, and to a higher degree than the 7G3 antibody. muCD123-16 is a negative control anti-CD123 antibody that binds CD123 but does not inhibit IL-3-dependent proliferation of TF-1 cells.

In FIG. 7C, the unconjugated huCD123-6Gv4.7 antibody has a heavy chain sequence of SEQ ID NO: 54, in which Xaa is Val. The conjugates with "53-SeriMab" have cytotoxin (in this case, the indolinobenzodiazepine or "IGN" compounds herein after) linkage through oxidized N-terminal Ser on light chain. The conjugates with "CysMab" have cytotoxin (in this case, the IGN compounds) linkage through the engineered Cys in the heavy chain (i.e., the Cys corresponding to the $5^{th}$ to the last Cys in SEQ ID NO: 54).

FIG. 9A shows expression constructs of IL-3Rα (CD123) extra-cellular domain and chimeric receptor proteins comprising IL-3Rα (gray) and GMRα domains (white). FIG. 9C shows that the CD123-3 antibody binds primarily to the CRM domain of IL-3Rα (residues 101-306). FIG. 9F shows that the 6H6 antibody binds exclusively to the N-terminal domain of IL-3Rα (residues 1-100).

FIG. 11B shows in vitro cytotoxicity of the various lysine- or cysteine-linked huCD123-6-IGN conjugates on multiple CD123-positive B-ALL cell lines. The non-binding KTI antibody based conjugates are included as negative controls.

FIG. 11C shows that the various Lys- or Cys-linked IGN compounds are highly active on P-gp (P-glycoprotein) positive AML cell lines Kasumi-3 and MOLM-1. The control curves with open data points are produced in the presence of excess unconjugated matching huCD123 antibodies.

FIG. 12B shows the $IC_{90}$ values for all AML patient samples treated with the conjugates.

FIGS. 13A-13C show that the IGN conjugate of CysMab of huCD123-6 (huCD123-6Gv4.6-CysMab-D5, filled black circle) is at least as active as the lysine-linked conjugate (huCD123-6Gv4.6-D2, filled black square) of the same antibody towards the AML cell line EOL-1 (FIG. 13A), the B-ALL cell line KOPN-8 (FIG. 13B), and the CML cell line MOLM-1 (FIG. 13C). The dotted curves connecting open data points in each figure represent activity of the respective conjugates (i.e., open circle for huCD123-6Gv4.6-CysMab-D5, and open square for huCD123-6Gv4.6-D2) in the presence of blocking concentration (500 nM) of the unconjugated chCD123-6 antibody.

FIGS. 14A-14C show that SeriMab of huCD123-6 (huCD123-6Rv1.1S2-SeriMab-D8, filled black circle) is at least as active as the lysine-linked conjugate (huCD123-6Rv1.1-D2, filled downward black triangle) of the same antibody in AML cell lines SHI-1 (FIG. 14A) and HNT-34 (FIG. 14B), as well as the CML cell line MOLM-1 (FIG. 14C). The dotted curves connecting open data points in each figure represent activity of the respective conjugates (i.e., open circle for huCD123-6Rv1.1S2-SeriMab-D8, and open downward triangle for huCD123-6Rv1.1-D2) in the presence of blocking concentration (500 nM) of the unconjugated huCD123-6 antibody.

FIG. 21 shows that the Cys-linked huCD123-6Gv4.7-CysMab-D5 conjugate is highly active on various CD123-positive AML cell lines with poor prognostic factors.

DETAILED DESCRIPTION OF THE INVENTION

1. Definitions

Figure 1:
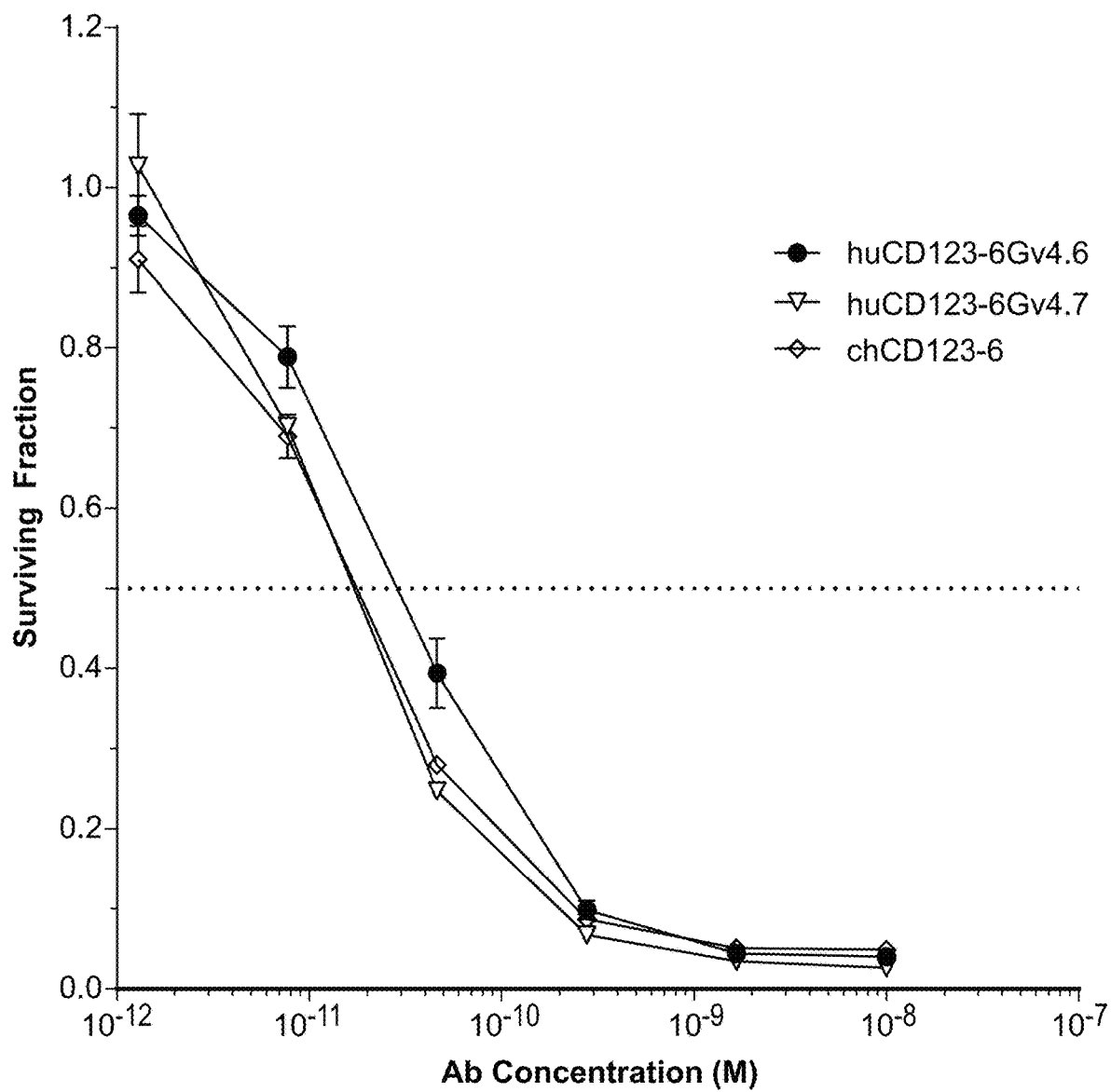
FIG. 1 shows inhibition of IL-3-dependent proliferation of TF-1 cells by chimeric CD123-6 antibody (chCD123-6) and its CDR-grafted huCD123-6 antibodies (huCD123-6Gv4.6 and huCD123-6Gv4.7).

To facilitate an understanding of the present invention, a number of terms and phrases are defined below.

The terms "(human) IL-3Rα," "Interleukine-3 Receptor alpha," or "CD123," as used interchangeably herein, refers to any native (human) IL-3Rα or CD123, unless otherwise indicated. The CD123 protein is an interleukin 3-specific subunit of a heterodimeric cytokine receptor (IL-3 Receptor, or IL-3R). The IL-3R is comprised of a ligand specific alpha subunit, and a signal transducing common beta subunit (also known as CD131) shared by the receptors for interleukin 3 (IL3), colony stimulating factor 2 (CSF2/GM-CSF), and interleukin 5 (IL5). The binding of CD123/IL-3Rα to IL3 depends on the beta subunit. The beta subunit is activated by the ligand binding, and is required for the biological activities of IL3.

All of these above terms for CD123 can refer to either a protein or nucleic acid sequence as indicated herein. The term "CD123/IL-3Rα" encompasses "full-length," unprocessed CD123/IL-3Rα, as well as any form of CD123/IL-3Rα that results from processing within the cell. The term also encompasses naturally occurring variants of CD123/IL-3Rα protein or nucleic acid, e.g., splice variants, allelic variants and isoforms. The CD123/IL-3Rα polypeptides and polynucleotides described herein can be isolated from a variety of sources, such as from human tissue types or from another source, or prepared by recombinant or synthetic methods. Examples of CD123/IL-3Rα sequences include, but are not limited to NCBI reference numbers NP_002174 & NM_002183 (protein and nucleic acid sequences for human CD123 variant 1), and NP_001254642 & NM_001267713 (protein and nucleic acid sequences for human CD123 variant 2).

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

In some embodiments, an antibody is a non-naturally occurring antibody. In some embodiments, an antibody is purified from natural components. In some embodiments, an antibody is recombinantly produced. In some embodiments, an antibody is produced by a hybridoma.

A "blocking" antibody or an "antagonist" antibody is one which inhibits or reduces biological activity of the antigen it binds, such as CD123/IL-3Rα. In a certain embodiment, blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "anti-CD123 antibody," "anti-IL-3Rα antibody" or "an antibody that (specifically) binds to CD123/IL-3Rα" refers to an antibody that is capable of binding CD123/IL-3Rα with sufficient affinity such that the antibody is useful as a diagnostic and/or therapeutic agent in targeting CD123/IL-3Rα. Unless otherwise specified, the extent of binding of an anti-CD123/IL-3Rα antibody to an unrelated, non-CD123/IL-3Rα protein is less than about 10% of the binding of the antibody to CD123/IL-3Rα as measured, e.g., by a radioimmunoassay (RIA). In certain embodiments, an antibody that binds to CD123/IL-3Rα has a dissociation constant ($K_d$) of ≤0.5 nM, ≤0.3 nM, ≤0.1 nM, ≤0.05 nM, or ≤0.01 nM. In one embodiment, the anti-CD123/IL-3Rα antibody does not bind the common beta chain CD131. In one embodiment, the anti-CD123/IL-3Rα antibody does not bind to the same epitope of CD123 that is bound by the known and commercially available CD123 antibodies such as 7G3 (mouse $IgG_{2a}$), 6H6 (mouse $IgG_1$), and 9F5 (mouse $IgG_1$) (Sun et al., *Blood* 87(1): 83-92, 1996).

The sequences of anti-CD123/IL-3Rα antibodies and antigen-binding fragments thereof of the invention are provided in Tables 1-6 below. The nomenclature for the various antibodies and immuno-conjugates of the invention are provided separately below.

The term "antibody fragment" refers to a portion of an intact antibody and refers to the antigenic determining variable regions of an intact antibody. Examples of antibody fragments include, but are not limited to, Fab, Fab', $F(ab')_2$, and $F_v$ fragments, linear antibodies, single chain antibodies, and multispecific antibodies formed from antibody fragments. The term "antigen-binding fragment" of an antibody includes one or more fragments of an antibody that retain the ability to specifically bind to an antigen. It has been shown that the antigen-binding function of an antibody can be performed by certain fragments of a full-length antibody. Examples of binding fragments encompassed within the term "antigen-binding fragment" of an antibody include (without limitation): (i) an Fab fragment, a monovalent fragment consisting of the $V_L$, $V_H$, $C_L$, and $C_{H1}$ domains (e.g., an antibody digested by papain yields three fragments: two antigen-binding Fab fragments, and one Fc fragment that does not bind antigen); (ii) a $F(ab')_2$ fragment, a bivalent fragment comprising two Fab fragments linked by a disulfide bridge at the hinge region (e.g., an antibody digested by pepsin yields two fragments: a bivalent antigen-binding $F(ab')_2$ fragment, and a pFc' fragment that does not bind antigen) and its related F(ab') monovalent unit; (iii) a $F_d$ fragment consisting of the $V_H$ and $C_{H1}$ domains (i.e., that portion of the heavy chain which is included in the Fab); (iv) a $F_v$ fragment consisting of the $V_L$ and $V_H$ domains of a single arm of an antibody, and the related disulfide linked $F_v$; (v) a dAb (domain antibody) or sdAb (single domain antibody) fragment (Ward et al., *Nature* 341:544-546, 1989), which consists of a $V_H$ domain; and (vi) an isolated complementarity determining region (CDR).

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', $F(ab')_2$, $F_v$), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and capability (Jones et al., *Nature* 321:522-525, 1986; Riechmann et al., *Nature* 332:323-327, 1988; Verhoeyen et al., *Science* 239:1534-1536, 1988).

In some instances, the $F_v$ framework region (FR) residues of a human immunoglobulin are replaced with the corresponding residues in an antibody from a non-human species that has the desired specificity, affinity, and capability. The humanized antibody can be further modified by the substitution of additional residues either in the $F_v$ framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain ($F_c$), typically that of a human immunoglobulin. Examples of methods used to generate humanized antibodies are described in U.S. Pat. Nos. 5,225,539 and 5,639,641, Roguska et al., *Proc. Natl. Acad. Sci. USA* 91(3):969-973, 1994; and Roguska et al., *Protein Eng.* 9(10):895-904, 1996 (all incorporated herein by reference). In some embodiments, a "humanized antibody" is a resurfaced antibody. In some embodiments, a "humanized antibody" is a CDR-grafted antibody.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. *Sequences of Proteins of Immunological Interest,* 5th ed., 1991, National Institutes of Health, Bethesda Md.); and (2) an approach based on crystallographic studies of antigen-antibody complexes (Al-lazikani et al., *J. Molec. Biol.* 273:927-948, 1997). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., *Sequences of Immunological Interest,* 5th Ed., Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., *Sequences of Proteins of Immunological Interest,* 5th Ed., Public Health Service, National Institutes of Health, Bethesda, Md. (1991) (incorporated herein by reference). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917, 1987). The end of the Chothia CDR-H1 loop when numbered using the Kabat numbering convention varies between H32 and H34 depending on the length of the loop. This is because the Kabat numbering scheme places the insertions at H35A and H35B—if neither 35A nor 35B is present, the loop ends at 32; if only 35A is present, the loop ends at 33; if both 35A and 35B are present, the loop ends at 34. The AbM hypervariable regions represent a compromise between the Kabat CDRs and Chothia structural loops, and are used by Oxford Molecular's AbM antibody modeling software.

| Loop | Kabat | AbM | Chiothia |
|------|-------|-----|----------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 (Kabat Numbering) |
| H1 | H31-H35 | H26-H35 | H26-H32 (Chothia Numbering) |
| H2 | H50-H65 | H50-H58 | H52-H56 |
| H3 | H9S-H102 | H95-H102 | H95-H102 |

The term "human antibody" means an antibody produced by a human or an antibody having an amino acid sequence corresponding to an antibody produced by a human made using any technique known in the art. In certain embodiments, the human antibody does not have non human sequence. This definition of a human antibody includes intact or full-length antibodies, or antigen-binding fragments thereof.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid or reduce the chance of eliciting an immune response in that species (e.g., human). In certain embodiments, chimeric antibody may include an antibody or antigen-binding fragment thereof comprising at least one human heavy and/or light chain polypeptide, such as, for example, an antibody comprising murine light chain and human heavy chain polypeptides.

The terms "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$) or the half-maximal effective concentration ($EC_{50}$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described herein.

"Or better" when used herein to refer to binding affinity refers to a stronger binding between a molecule and its binding partner. "Or better" when used herein refers to a stronger binding, represented by a smaller numerical $K_d$ value. For example, an antibody which has an affinity for an antigen of "0.3 nM or better," the antibody's affinity for the antigen is ≤0.3 nM, e.g., 0.29 nM, 0.28 nM, 0.27 nM etc., or any value equal to or less than 0.3 nM. In one embodiment, the antibody's affinity as determined by a $K_d$ will be between about $10^{-3}$ to about $10^{-12}$ M, between about $10^{-6}$ to about $10^{-11}$ M, between about $10^{-6}$ to about $10^{-10}$ M, between about $10^{-6}$ to about $10^{-9}$ M, between about $10^{-6}$ to about $10^{-8}$ M, or between about $10^{-6}$ to about $10^{-7}$ M.

By "specifically binds," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

In certain embodiments, an antibody or antigen-binding fragment of the invention "specifically binds" to a CD123 antigen, in that it has a higher binding specificity to the CD123 antigen (from any species) than that to a non-CD123 antigen. In certain embodiments, an antibody or antigen-binding fragment of the invention "specifically binds" to a human CD123 antigen, in that it has a higher binding specificity to the human CD123 antigen than that to a non human CD123 antigen (e.g., a mouse or a rat CD123).

By "preferentially binds," it is meant that the antibody specifically binds to an epitope more readily than it would bind to a related, similar, homologous, or analogous epitope.

Thus, an antibody which "preferentially binds" to a given epitope would more likely bind to that epitope than to a related epitope, even though such an antibody may cross-react with the related epitope. For example, in certain embodiments, an antibody or antigen-binding fragment of the invention "preferentially binds" to a human CD123 antigen over a mouse CD123.

An antibody is said to "competitively inhibit" binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same," as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristics measured by said values (e.g., $K_d$ values). The difference between said two values is less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate," "conjugate," or "ADC" as used herein refers to a compound or a derivative thereof that is linked to a cell binding agent (i.e., an anti-CD123/IL-3Rα antibody or fragment thereof) and is defined by a generic formula: A-L-C, wherein C=cytotoxin, L=linker, and A=cell binding agent (CBA), such as anti-CD123/IL-3Rα antibody or antibody fragment. Immunoconjugates can also be defined by the generic formula in reverse order: C-L-A.

A "linker" is any chemical moiety that is capable of linking a compound, usually a drug, such as a cytotoxic agent described herein (e.g., maytansinoid or IGN (indolinobenzodiazepine) compounds), to a cell-binding agent such as an anti-CD123/IL-3Rα antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

The terms "elevated" CD123/IL-3Rα, "increased expression" of CD123/IL-3Rα and "overexpression" of CD123/IL-3Rα refer to a sample which contains elevated levels of CD123 expression. The CD123 can be elevated, increased, or overexpressed as compared to a control value (e.g., expression level in a biological sample, tissue, or cell from a subject without cancer, a sample or cancer known to express no or low CD123/IL-3Rα, a normal sample, or a cancer that does not have elevated CD123/IL-3Rα values). For example, a sample (e.g., one from a hematological cancer such as leukemia and lymphoma) with increased expression can contain an increase of at least 2-, 3-, 4-, 5-, 10-, 15-, 20-, 25-, 30-, or at least 50-fold relative to a control/normal values.

A "reference sample" can be used to correlate and compare the results obtained in the methods of the invention from a test sample. Reference samples can be cells (e.g., cell lines, cell pellets) or tissue. The CD123/IL-3Rα levels in the "reference sample" can be an absolute or relative amount, a range of amount, a minimum and/or maximum amount, a mean amount, and/or a median amount of CD123/IL-3Rα. A "reference sample" can also serve as a baseline of CD123/IL-3Rα expression to which the test sample is compared. The "reference sample" can include a prior sample or baseline sample from the same patient, a normal reference with a known level of CD123/IL-3Rα expression, or a reference from a relevant patient population with a known level of CD123/IL-3Rα expression. CD123/IL-3Rα levels can also be expressed as values in a standard curve. A standard curve is a quantitative method of plotting assay data to determine the concentration of CD123/IL-3Rα in a sample. In one embodiment, a reference sample is an antigen standard comprising purified CD123/IL-3Rα. The diagnostic methods of the invention can involve a comparison between expression levels of CD123/IL-3Rα in a test sample and a "reference value." In some embodiments, the reference value is the expression level of the CD123/IL-3Rα in a reference sample. A reference value can be a predetermined value and can also be determined from reference samples (e.g., control biological samples or reference samples) tested in parallel with the test samples. A reference value can be a single cut off value, such as a median or mean or a range of values, such as a confidence interval. Reference values can be established for various subgroups of individuals.

The term "primary antibody" herein refers to an antibody that binds specifically to the target protein antigen in a sample. A primary antibody is generally the first antibody used in an ELISA assay or IHC procedure. In one embodiment, the primary antibody is the only antibody used in an IHC procedure.

The term "secondary antibody" herein refers to an antibody that binds specifically to a primary antibody, thereby forming a bridge or link between the primary antibody and a subsequent reagent, if any. The secondary antibody is generally the second antibody used in an immunohistochemical procedure.

A "sample" or "biological sample" of the present invention is of biological origin, in specific embodiments, such as from eukaryotic organisms. In some embodiments, the sample is a human sample, but animal samples may also be used. Non-limiting sources of a sample for use in the present invention include solid tissue, biopsy aspirates, ascites, fluidic extracts, blood, plasma, serum, spinal fluid, lymph fluid, the external sections of the skin, respiratory, intestinal, and genitourinary tracts, tears, saliva, milk, tumors, organs, cell cultures and/or cell culture constituents, for example. A "cancerous sample" is a sample that contains a cancerous cell. The method can be used to examine an aspect of expression of CD123/IL-3Rα or a state of a sample, including, but not limited to, comparing different types of cells or tissues, comparing different developmental stages, and detecting or determining the presence and/or type of disease or abnormality.

As used herein, the term "capture reagent" refers to a reagent capable of binding and capturing a target molecule in a sample such that under suitable condition, the capture reagent-target molecule complex can be separated from the rest of the sample. In one embodiment, the capture reagent is immobilized. In one embodiment, the capture reagent in a sandwich immunoassay is an antibody or a mixture of different antibodies against a target antigen.

As used herein, the term "detectable antibody" refers to an antibody that is capable of being detected either directly through a label amplified by a detection means, or indirectly through, e.g., another antibody that is labeled. For direct labeling, the antibody is typically conjugated to a moiety that is detectable by some means. In one embodiment, the detectable antibody is a biotinylated antibody.

As used herein, the term "detection means" refers to a moiety or technique used to detect the presence of the detectable antibody and includes detection agents that amplify the immobilized label such as label captured onto a microtiter plate. In one embodiment, the detection means is a fluorimetric detection agent such as avidin or streptavidin.

Commonly a "sandwich ELISA" employs the following steps: (1) microtiter plate is coated with a capture antibody; (2) sample is added, and any antigen present binds to capture antibody; (3) detecting antibody is added and binds to antigen; (4) enzyme-linked secondary antibody is added and binds to detecting antibody; and (5) substrate is added and is converted by enzyme to detectable form.

The word "label" when used herein refers to a detectable compound or composition which is conjugated directly or indirectly to the antibody so as to generate a "labeled" antibody. The label can be detectable by itself (e.g. radioisotope labels or fluorescent labels) or, in the case of an enzymatic label, can catalyze chemical alteration of a substrate compound or composition which is detectable.

By "correlate" or "correlating" is meant comparing, in any way, the performance and/or results of a first analysis with the performance and/or results of a second analysis. For example, one may use the results of a first analysis in carrying out the second analysis and/or one may use the results of a first analysis to determine whether a second analysis should be performed and/or one may compare the results of a first analysis with the results of a second analysis. In one embodiment, increased expression of CD123/IL-3Rα correlates with increased likelihood of effectiveness of a CD123/IL-3Rα-targeting therapy.

The terms "cancer" and "cancerous" refer to or describe the physiological condition in mammals in which a population of cells are characterized by unregulated cell growth. "Tumor" and "neoplasm" refer to one or more cells that result from excessive cell growth or proliferation, either benign (noncancerous) or malignant (cancerous) including pre-cancerous lesions.

Examples of cancer include lymphoma and leukemia. Examples of cancer or tumorigenic diseases which can be treated and/or prevented by the methods and reagents (e.g., anti-CD123 antibody, antigen-binding fragment thereof, or immuno-conjugate thereof) of the invention include AML, CML, ALL (e.g., B-ALL), CLL, myelodysplastic syndrome, basic plasmacytoid DC neoplasm (BPDCN) leukemia, B-cell lymphomas including non-Hodgkin lymphomas (NEIL), precursor B-cell lymphoblastic leukemia/lymphoma and mature B-cell neoplasms, such as B-cell chronic lymphocytic leukemia (B-CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia (HCL), diffuse large B-cell lymphoma, Burkitt's lymphoma, plasmacytoma, plasma cell myeloma, post-transplant lymphoproliferative disorder, Waldenstrom's macroglobulinemia, anaplastic large-cell lymphoma (ALCL), and Hodgkin's leukemia (HL).

Cancers also encompass cancers which contain cells having elevated CD123/IL-3Rα expression levels. Such CD123/IL-3Rα-elevated cancers include, but are not limited to, AML, CML, ALL (e.g., B-ALL), and CLL.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The term "pharmaceutical formulation" refers to a preparation which is in such form as to permit the biological activity of the active ingredient to be effective, and which contains no additional components which are unacceptably toxic to a subject to which the formulation would be administered. Such formulation can be sterile.

An "effective amount" of an antibody or immunoconjugate as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP), or any combination thereof. See the definition herein of "treating." To the extent the drug can prevent growth and/or kill existing cancer cells, it can be cytostatic and/or cytotoxic.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "respond favorably" generally refers to causing a beneficial state in a subject. With respect to cancer treatment, the term refers to providing a therapeutic effect on the subject. Positive therapeutic effects in cancer can be measured in a number of ways (See, W. A. Weber, *J. Nucl. Med.* 50: 1S-10S (2009)). For example, tumor growth inhibition, molecular marker expression, serum marker expression, and molecular imaging techniques can all be used to assess therapeutic efficacy of an anti-cancer therapeutic. With respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. A favorable response can be assessed, for example, by increased progression-free survival (PFS), disease-free survival (DFS), or overall survival (OS), complete response (CR), partial response (PR), or, in some cases, stable disease (SD), a decrease in progressive disease (PD), a reduced time to progression (TTP), or any combination thereof.

PFS, DFS, and OS can be measured by standards set by the National Cancer Institute and the U.S. Food and Drug Administration for the approval of new drugs. See Johnson et al., (2003) *J. Clin. Oncol.* 21(7): 1404-1411.

"Progression free survival" (PFS) refers to the time from enrollment to disease progression or death. PFS is generally measured using the Kaplan-Meier method and Response Evaluation Criteria in Solid Tumors (RECIST) 1.1 standards. Generally, progression free survival refers to the situation wherein a patient remains alive, without the cancer getting worse.

A "complete response" or "complete remission" or "CR" indicates the disappearance of all signs of tumor or cancer in response to treatment. This does not always mean the cancer has been cured.

A "partial response" or "PR" refers to a decrease in the size or volume of one or more tumors or lesions, or in the extent of cancer in the body, in response to treatment.

"Stable disease" refers to disease without progression or relapse. In stable disease there is neither sufficient tumor shrinkage to qualify for partial response nor sufficient tumor increase to qualify as progressive disease.

"Progressive disease" refers to the appearance of one more new lesions or tumors and/or the unequivocal progression of existing non-target lesions. Progressive disease can also refer to a tumor growth of more than 20 percent since treatment began, either due to an increases in mass or in spread of the tumor.

"Disease free survival" (DFS) refers to the length of time during and after treatment that the patient remains free of disease.

"Overall Survival" (OS) refers to the time from patient enrollment to death or censored at the date last known alive. OS includes a prolongation in life expectancy as compared to naive or untreated individuals or patients. Overall survival refers to the situation wherein a patient remains alive for a defined period of time, such as one year, five years, etc., e.g., from the time of diagnosis or treatment.

A "chemotherapeutic agent" is a chemical compound useful in the treatment of cancer, regardless of mechanism of action. Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with the disorder, and may also include those who have minimal residual disease, or resistant disease, or replased disease. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

Prophylactic or preventative measures refer to measures that prevent and/or slow the development of a targeted pathologic condition or disorder. Thus, those in need of prophylactic or preventative measures include those prone to have the disorder and those in whom the disorder is to be prevented.

Prophylactic or preventative measures refer to therapeutic measures that prevent and/or slow the development of a targeted pathologic condition or disorder. Thus, those in need of prophylactic or preventative measures include those prone to have the disorder and those in whom the disorder is to be prevented.

As used herein, the term "healthcare provider" refers to individuals or institutions which directly interact with and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

In some aspects, a healthcare provider can administer or instruct another healthcare provider to administer a therapy to treat a cancer. "Administration" of a therapy, as used herein, includes prescribing a therapy to a subject as well as delivering, applying, or giving the therapy to a subject. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/ measuring/quantifying one or more samples, provide the comparison/score from one or more samples, obtain the comparison/score from one or more samples, administer a therapy or therapeutic agent (e.g., a CD123/IL-3Rα binding agent), commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent. These actions can be performed by a healthcare provider automatically using a computer-implemented method (e.g., via a web service or stand-alone computer system).

"Polynucleotide" or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-0-methyl-, 2'-0-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR*, CO or CH$_2$ ("formacetal"), in which each R or R is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains. In some embodiments, a polypeptide, peptide, or protein is non-naturally occurring. In some embodiments, a polypeptide, peptide, or protein is purified from other naturally occurring components. In some embodiments, the polypeptide, peptide, or protein is recombinantly produced.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al., *Proc. Natl. Acad. Sci.* 87:2264-2268, 1990, as modified in Karlin et al., *Proc. Natl. Acad. Sci.* 90:5873-5877, 1993, and incorporated into the NBLAST and XBLAST programs (Altschul et al., *Nucleic Acids Res.* 25:3389-3402, 1991). In certain embodiments, Gapped BLAST can be used as described in Altschul et al., *Nucleic Acids Res.* 25:3389-3402, 1997; BLAST-2, WU-BLAST-2 (Altschul et al., *Methods in Enzymology* 266:460-480, 1996), ALIGN, ALIGN-2 (Genentech, South San Francisco, California) or Megalign (DNASTAR) are additional publicly available software programs that can be used to align sequences. In certain embodiments, the percent identity between two nucleotide sequences is determined using the GAP program in GCG software (e.g., using a NWSgap-dna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453, 1970) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17, 1989). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, WI 53711). Bestfit uses the local homology algorithm of Smith and Waterman, *Advances in Applied Mathematics* 2: 482-489, 1981, to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In certain embodiments, identity exists over a region of the sequences that is at least about 10, about 20, about 40-60 residues in length or any integral value therebetween, or over a longer region than 60-80 residues, at least about 90-100 residues, or the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the invention do not abrogate the binding of the polypeptide or antibody containing the amino acid sequence, to the antigen(s), i.e., the CD123/IL-3Rα to which the polypeptide or antibody binds. Methods of identifying nucleotide and amino acid conservative substitutions which do not eliminate antigen-binding are well-known in the art (see, e.g., Brummell et al., *Biochem.* 32:1180-1187, 1993; Kobayashi et al., *Protein Eng.* 12(10):879-884, 1999; and Burks et al., *Proc. Natl. Acad. Sci. USA* 94:412-417, 1997).

As used herein, "P-glycoprotein 1," also known as "permeability glycoprotein," "P-gp or Pgp," "multidrug resistance protein 1 (MDR1)," "ATP-binding cassette sub-family B member 1 (ABCB1)," or "cluster of differentiation 243 (CD243)," is an ABC-transporter of the MDR/TAP subfamily that transports a wide variety of substrates across extra- and intracellular membranes. It is an ATP-dependent efflux pump with broad substrate specificity. P-gp is extensively distributed and expressed in the intestinal epithelium where it pumps xenobiotics (such as toxins or drugs) back into the intestinal lumen, in liver cells where it pumps them into bile ducts, in the cells of the proximal tubule of the kidney where it pumps them into urine-conducting ducts, and in the capillary endothelial cells composing the blood-brain barrier and blood-testis barrier, where it pumps them back into the capillaries. Some cancer cells also express large amounts of P-gp, which renders these cancers multi-drug resistant.

"Alkyl" as used herein refers to a saturated linear or branched-chain monovalent hydrocarbon radical of one to twenty carbon atoms. Examples of alkyl include, but are not limited to, methyl, ethyl, 1-propyl, 2-propyl, 1-butyl, 2-methyl-1-propyl, —$CH_2CH(CH_3)_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms. More preferably, the alkyl has one to four carbon atoms.

The number of carbon atoms in a group can be specified herein by the prefix "$C_{x-xx}$", wherein x and xx are integers. For example, "$C_{1-4}$alkyl" is an alkyl group having from 1 to 4 carbon atoms.

The term "compound" or "cytotoxic compound," are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, and salts (e.g., pharmaceutically acceptable salts) of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt", "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "chiral" refers to molecules that have the property of non-superimposability of the mirror image partner, while the term "achiral" refers to molecules that are superimposable on their mirror image partner.

The term "stereoisomer" refers to compounds that have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as crystallization, electrophoresis and chromatography.

"Enantiomers" refer to two stereoisomers of a compound that are non-superimposable mirror images of one another.

Stereochemical definitions and conventions used herein generally follow S. P. Parker, Ed., McGraw-Hill, *Dictionary of Chemical Terms* (1984) McGraw-Hill Book Company, New York; and Eliel, E. and Wilen, S., *Stereochemistry of Organic Compounds*, John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies that are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "imine reactive reagent" refers to a reagent that is capable of reacting with an imine group. Examples of imine reactive reagent includes, but is not limited to, sulfites ($H_2SO_3$, $H_2SO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono, di, tri, and tetra-thiophosphates ($PO_3SH_3$, $PO_2S_2H_3$, $POS_3H_3$, $PS_4H_3$ or a salt of $PO_3S^{3-}$, $PO_2S_2^{3-}$, $POS_3^{3-}$ or $PS_4^{3-}$ formed with a cation), thio phosphate esters (($R^iO)_2PS(OR^i)$, $R^iSH$, $R^iSOH$, $R^iSO_2H$, $R^iSO_3H$), various amines (hydroxyl amine (e.g., $NH_2OH$), hydrazine (e.g., $NH_2NH_2$), $NH_2O-R^i$, $R^{i'}NH-R^i$, $NH_2-R^i$), $NH_2-CO-NH_2$, $NH_2-C(=S)-NH_2$, thiosulfate ($H_2S_2O_3$ or a salt of $S_2O_3^{2-}$ formed with a cation), dithionite ($H_2S_2O_4$ or a salt of $S_2O_4^{2-}$ formed with a cation), phosphorodithioate ($P(=S)(OR^k)(SH)(OH)$ or a salt thereof formed with a cation), hydroxamic acid ($R^kC(=O)NHOH$ or a salt formed with a cation), hydrazide ($R^kCONHNH_2$), formaldehyde sulfoxylate ($HOCH_2SO_2H$ or a salt of $HOCH_2SO_2^-$ formed with a cation, such as $HOCH_2SO_2^-Na^+$), glycated nucleotide (such as GDP-mannose), fludarabine or a mixture thereof, wherein $R^i$ and $R^{i'}$ are each independently a linear or branched alkyl having 1 to 10 carbon atoms and are substituted with at least one substituent selected from $-N(R^j)_2$, $-CO_2H$, $-SO_3H$, and $-PO_3H$; $R^i$ and $R^{i'}$ can be further optionally substituted with a substituent for an alkyl described herein; $R^j$ is a linear or branched alkyl having 1 to 6 carbon atoms; and $R^k$ is a linear, branched or cyclic alkyl, alkenyl or alkynyl having 1 to 10 carbon atoms, aryl, heterocyclyl or heteroaryl (preferably, $R^k$ is a linear or branched alkyl having 1 to 4 carbon atoms; more preferably, $R^k$ is methyl, ethyl or propyl). Preferably, the cation is a monovalent cation, such as $Na^+$ or $K^+$. Preferably, the imine reactive reagent is selected from sulfites, hydroxyl amine, urea and hydrazine. More preferably, the imine reactive reagent is $NaHSO_3$ or $KHSO_3$.

The phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt can involve the inclusion of another molecule such as an acetate ion, a succinate ion or other counter ion. The counter ion can be any organic or inorganic moiety that stabilizes the charge on the parent compound. Furthermore, a pharmaceutically acceptable salt can have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt can be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt can be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound that further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

A "metabolite" or "catabolite" is a product produced through metabolism or catabolism in the body of a specified compound, a derivative thereof, or a conjugate thereof, or salt thereof. Metabolites of a compound, a derivative thereof, or a conjugate thereof, can be identified using routine techniques known in the art and their activities determined using tests such as those described herein. Such products can result for example from the oxidation, hydroxylation, reduction, hydrolysis, amidation, deamidation, esterification, deesterification, enzymatic cleavage, and the like, of the administered compound. Accordingly, the invention includes metabolites of compounds, a derivative thereof, or a conjugate thereof, of the invention, including compounds, a derivative thereof, or a conjugate thereof, produced by a process comprising contacting a compound, a derivative thereof, or a conjugate thereof, of this invention with a mammal for a period of time sufficient to yield a metabolic product thereof.

The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amine-protecting group" or an "amino-protecting moiety" is a substituent attached to an amino group that blocks or protects the amino functionality in the compound. Such groups are well known in the art (see for example P. Wuts and T. Greene, 2007, *Protective Groups in Organic Synthesis*, Chapter 7, J. Wiley & Sons, NJ) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P. G. M. Wuts & T. W. Greene, *Protective Groups in Organic Synthesis*, John Wiley & Sons, New York, 2007.

The term "amino acid" refers to naturally occurring amino acids or non-naturally occurring amino acid. In one embodiment, the amino acid is represented by $NH_2-C(R^{aa'}R^{aa})-C(=O)OH$, wherein $R^{aa}$ and $R^{aa'}$ are each independently H, an optionally substituted linear, branched or cyclic alkyl, alkenyl or alkynyl having 1 to 10 carbon atoms, aryl, heteroaryl or heterocyclyl or $R^{aa}$ and the N-terminal nitrogen atom can together form a heteroycyclic ring (e.g., as in proline). The term "amino acid residue" refers to the corresponding residue when one hydrogen atom is removed from the amine and/or carboxy end of the amino acid, such as $-NH-C(R^{aa'}R^{aa})-C(=O)O-$.

The term "cation" refers to an ion with positive charge. The cation can be monovalent (e.g., $Na^+$, $K^+$, $NH_4^+$ etc.), bi-valent (e.g., $Ca^{2+}$, $Mg^{2+}$, etc.) or multi-valent (e.g., $Al^{3+}$ etc.). Preferably, the cation is monovalent.

The term "reactive ester group" refers to a group an ester group that can readily react with an amine group to form amide bond. Exemplary reactive ester groups include, but are not limited to, N-hydroxysuccinimide esters, N-hydroxyphthalimide esters, N-hydroxy sulfo-succinimide esters, para-nitrophenyl esters, dinitrophenyl esters, pentafluorophenyl esters and their derivatives, wherein said derivatives facilitate amide bond formation. In certain embodiments, the reactive ester group is a N-hydroxysuccinimide ester or a N-hydroxy sulfo-succinimide ester.

The term "amine reactive group" refers to a group that can react with an amine group to form a covalent bond. Exemplary amine reactive groups include, but are not limited to, reactive ester groups, acyl halides, sulfonyl halide, imidoester, or a reactive thioester groups. In certain embodiments, the amine reactive group is a reactive ester group. In one embodiment, the amine reactive group is a N-hydroxysuccinimide ester or a N-hydroxy sulfo-succinimide ester.

The term "thiol-reactive group" refers to a group that can react with a thiol (—SH) group to form a covalent bond. Exemplary thiol-reactive groups include, but are not limited to, maleimide, haloacetyl, aloacetamide, vinyl sulfone, vinyl sulfonamide or vinyal pyridine. In one embodiment, the thiol-reactive group is maleimide.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Antibodies, Compounds, and Immunoconjugates Nomenclature

As used herein, the nomenclature used for the anti-CD123 antibodies, cytotoxic compounds, and their immunoconjugates generally adopt the following meanings.

CD123-3, -6, and -14 (or CD123 Mu-3, -6, and -14; or muCD123-3, -6, and 14) are three murine anti-CD123 monoclonal antibodies. The CDR1-3 sequences of the heavy and light chains (VH-CDR1-3, and VL-CDR1-3) are provided in Tables 1 and 2, with the associated SEQ ID NOs: 1-25. The heavy chain variable region (HCVR) sequences are provided in Table 3A with the associated SEQ ID NOs: 26, 28, and 30. Their light chain variable region (LCVR) sequences are provided in Table 4A with the associated SEQ ID NOs: 27, 29, and 31. The full length heavy chain (HC) sequences of the murine antibodies are provided in Table 5 (SEQ ID NOs: 42, 44, and 46), and the full length light chain (LC) sequences of the murine antibodies are provided in Table 6 (SEQ ID NOs: 43, 45, and 47).

chCD123-3, -6, and -14 are the corresponding murine-human chimeric antibodies having the murine heavy and light chain variable regions and the human constant region sequences. For example, the chimeric antibody chCD123-6 is comprised of the mouse HCVR and LCVR of SEQ ID NOs: 28 and 29, respectively, together with the human IgG1 and Kappa constant sequences for the heavy and light chains, respectively. See Example 3.

huCD123-3, -6, and -14 are the corresponding humanized antibodies. When the humanization is by way of CDR grafting of the 6 corresponding murine CDR regions (HC and LC CDR1-3), the letter "G" immediately follows the clone designation, which is in turn followed by a version number that designates the origin of the human light chain and heavy chain variable region sequences. Thus huCD123-6Gv4.6 refers to the humanized CD123 antibody based on grafting ("G") the 6 CDR regions from the corresponding muCDR123-6 antibody, onto the human light chain variable region Gv4 and the heavy chain variable region Gv6. Similarly, -Gv4.7 comprises human light chain variable region Gv4 and heavy chain variable region Gv7; and -Gv1.1 comprises human light chain variable region Gv1 and heavy chain variable region Gv1.

The three HCVR sequences, huCD123-6Gv1, -Gv6, and -Gv7 are provided in Table 3A (SEQ ID NOs: 32 and 34, with SEQ ID NO: 34 representing both -Gv6 and -Gv7 since they differ only at the $2^{nd}$ residue Xaa), and their DNA coding sequences in Table 3B (SEQ ID NOs: 62, 64, and 66). The three full length HC sequences, huCD123-6Gv1, -Gv6, and -Gv7 are provided in Table 5 (SEQ ID NOs: 48 and 50, with SEQ ID NO: 50 representing both full length -Gv6 and -Gv7 since they differ only at the $2^{nd}$ residue Xaa).

The two LCVR sequences, huCD123-6Gv1 and -Gv4, are provided in Table 4A (SEQ ID NOs: 33 and 35, and their DNA coding sequences in Table 4B (SEQ ID NOs: 63, and 65). The two full length LC sequences, huCD123-6Gv1 and -Gv4, are provided in Table 6 (SEQ ID NOs: 49 and 51).

When humanization is by way of resurfacing, the resurfaced heavy chain sequences are designated by "rh" immediately following the murine CD123 antibody clone number, and are further designated by one of two version of the resurfaced sequences, v1.0 or v1.1. Thus huCD123-6rhv1.0 and -rhv1.1 are resurfaced heavy chain sequences with CDR regions corresponding to the muCD123-6 antibody, with version designation of 1.0 and 1.1 respectively. See HCVR SEQ ID NOs: 39 and 40 in Table 3A, and SEQ ID NOs: 68 and 69 in Table 3B. Also see full length HC SEQ ID NOs: 59 and 60 in Table 5.

Likewise, the only version of the resurfaced light chain sequence, huCD123-6r1v1.0, has LCVR SEQ ID NO: 41 in Table 4A, and full length LC SEQ ID NO: 61 in Table 6.

A resurfaced antibody having huCD123-6rhv1.0 and huCD123-6r1v 1.0 is huCD123-6Rv1.0; and a resurfaced antibody having huCD123-6rhv1.1 and huCD123-6r1v1.0 is huCD123-6Rv1.1.

NTS2 or "S2" for short refers to an antibody having an engineered Ser at the N-terminus of heavy chain. The S2 variant of the huCD123-6Gv6/7 has HCVR sequence SEQ ID NO: 38 in Table 3A, and full length HC protein sequence SEQ ID NO: 53 in Table 5.

Likewise, NTS3 or "S3" for short refers to an antibody having an engineered Ser at the N-terminus of light chain. The S3 variant of the huCD123-6Gv4 has LCVR sequence SEQ ID NO: 37 in Table 4A, and full length LC protein sequence SEQ ID NO: 58 in Table 6.

An antibody comprising an engineered N-terminal Ser (either S2 or S3) may be conjugated with a cytotoxic drug/agent through either the oxidized N-terminal Ser, or through the "conventional" Lys linkage. If the drug linkage is through oxidized N-terminal Ser, the conjugate name contains a "SeriMab" designation. If the drug linkage is through Lys, then the conjugate name does not contain SeriMab (despite the fact that there is an S2 or S3 designation to signal the presence of engineered Ser at the N-terminus). The particular linkage type will also be apparent based on the cytotoxin reactive group. For example, huCD123-6Gv4.7S3-SeriMab-D8 refers to conjugate between D8 and the humanized CD123 antibody huCD123-6Gv4.7S3, through the oxidized N-terminal Ser on the light chain. The humanized CD123 antibody has the grafted murine CD123-6 CDR regions, the human LC Gv4 and heavy chain Gv7, and the N-terminal of the light chain has an engineered Ser (S3). In contrast, huCD123-6Gv4.7S3-sSPDB-D1 refers to conjugate between D1 and the same humanized CD123 antibody huCD123-6Gv4.7S3, through Lys linkage via a sulfonated SPDB linker.

In certain embodiments, if both the light chain and heavy chain N-termini contain the engineered Ser, "S2S3" or "S2S3-SeriMab" may appear in the antibody name.

Certain antibodies of the invention have an engineered Cys in the heavy chain CH3 domain, at a position corresponding to the same Kabat position of the $5^{th}$ to the last Cys in SEQ ID NO: 54. Such HCs or antibodies comprising such HCs contain the designation CysMab. Thus huCD123-6Gv4.6-CysMab is a humanized CD123 antibody that has grafted muCD123-6 CDR regions, is based on the human light chain Gv4 and heavy chain Gv6 sequences, wherein an engineered Cys is located in the HC CH3 region at a position corresponding to the $5^{th}$ to the last Cys in SEQ ID NO: 54. Similarly, its heavy chain sequence is huCD123-6Gv6-CysMab. In addition, huCD123-6Gv4.6S2-CysMab is otherwise identical, but has an engineered Ser at the N-terminus of the heavy chain, and its heavy chain sequence is huCD123-6Gv6S2-CysMab.

The resurfaced antibody described above may be further engineered to contain N-terminal Ser at either the light chain (S3 variant of the resurfaced antibody) or the heavy chain (S2 variant of the resurfaced antibody), or both (see below). Alternatively or in addition, the resurfaced antibody may have an engineered Cys in the heavy chain CH3 domain at a position corresponding to the same Kabat position of the $5^{th}$ to the last Cys of SEQ ID NO: 54 (the CysMab version of the resurfaced antibody). A resurfaced antibody can have both engineered Cys and N-terminal Ser.

In the conjugates formed between such CysMab and cytotoxin, however, at least in theory, the cytotoxin can be linked to the CysMab either through the Cys or through the conventional Lys. As used herein, however, without specific indication, a conjugate with a CysMab designation refers to a conjugate between a CysMab and a cytotoxin though the Cys-linkage (not the Lys linkage). The particular linkage type will also be apparent based on the cytotoxin reactive group.

Other variations or combinations of the above general nomenclature are also contemplated and will be readily apparent to one of skill in the art. For example, huCD123-6Rv1.1-CysMab is the resurfaced version of huCD123-6 (v1.1) that has an engineered Cys located in the HC CH3 region at a position corresponding to the $5^{th}$ to the last Cys in SEQ ID NO: 54.

The antibodies or antigen-binding fragments thereof of the invention may be conjugated to certain cytotoxic agents, either through linkage with the Lys side chain amino group, the Cys side chain thiol group, or an oxidized N-terminal Ser/Thr. Certain representative (non-limiting) cytotoxic agents described in the specification (including the examples) are listed below for illustration purpose. Note that most compounds such as D1, D2, D4, DGN462, D3, D6, etc., may be sulfonated (not shown here, but see FIG. 17 compound sD1, FIG. 15 compound sDGN462, and the FIG. 16 compound sD8) at one of the indolinobenzodiazepine monomers in certain examples. For compound D5', both indolinobenzodiazepine monomers may be sulfonated.

| Compound No. | Structure |
|---|---|
| D1 | 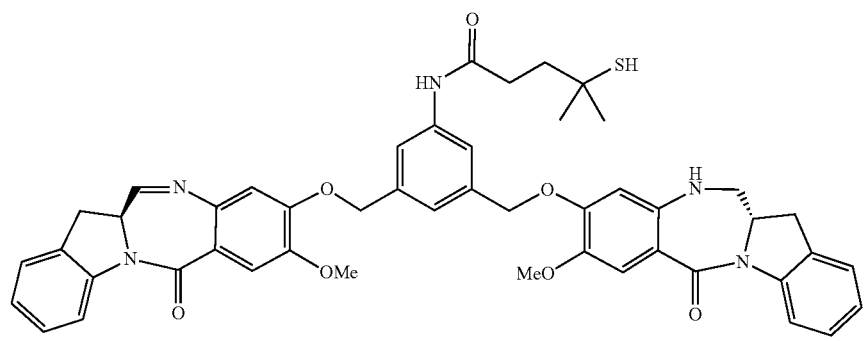 [SMILES: COc1cc2c(cc1OCc1cc(COc3cc4c(cc3OC)C(=O)N3c5ccccc5C[C@H]3CN4)cc(NC(=O)CCC(C)(C)S)c1)N=C[C@@H]1Cc3ccccc3N1C2=O] |
| D2 | 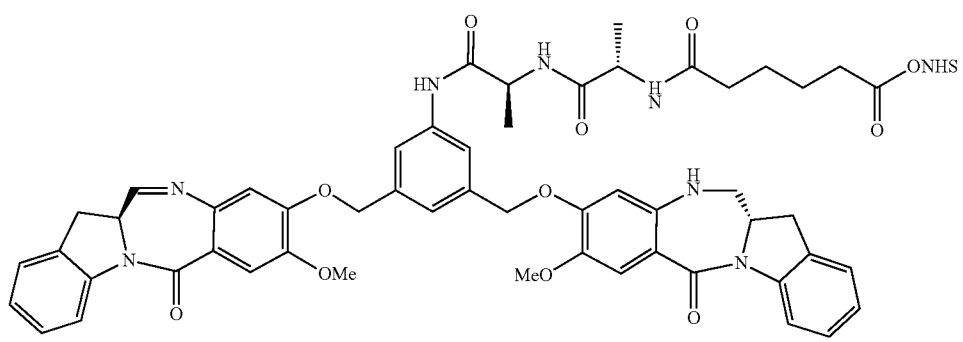 |
| DGN462 | 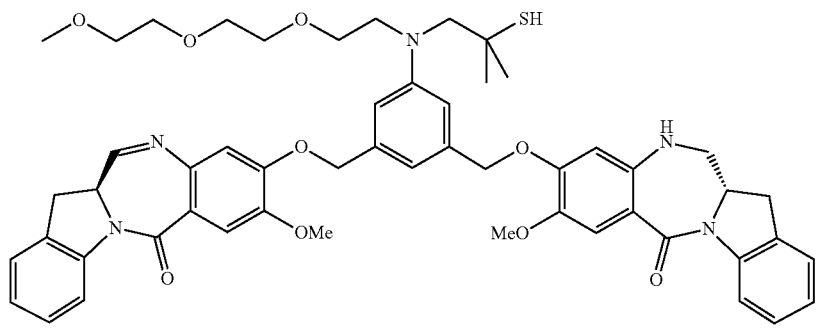 [SMILES: COCCOCCOCCN(CC(C)(C)S)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1] |
| D3 | 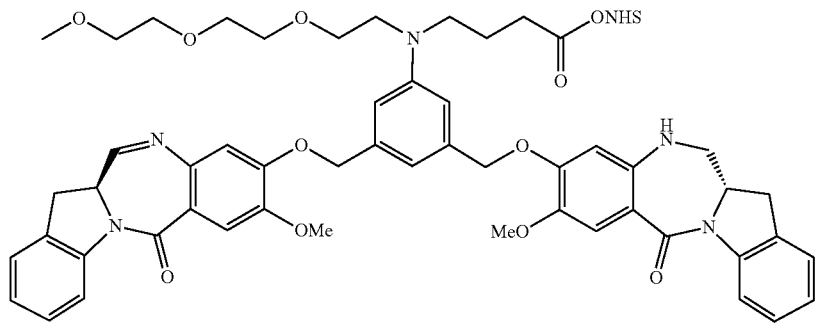 |

-continued
| Compound No. | Structure |
|---|---|
| D4 | 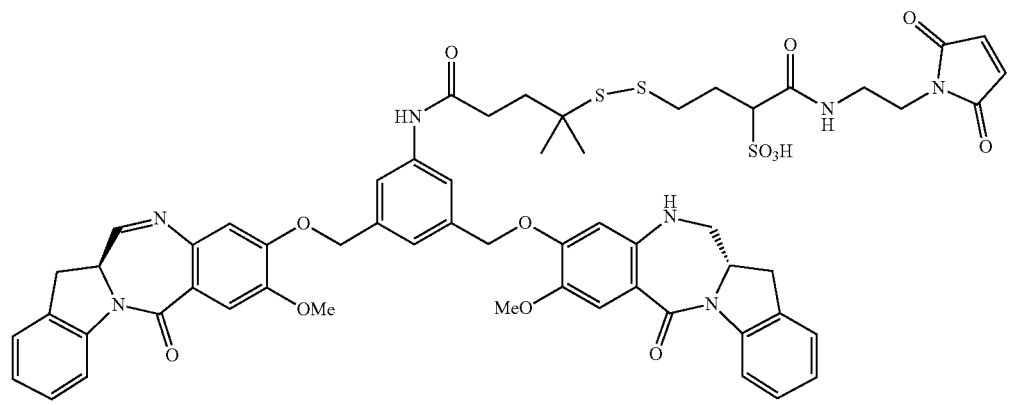 [SMILES: COc1cc2c(cc1OCc1cc(COc3cc4c(cc3OC)C(=O)N3c5ccccc5C[C@H]3CN4)cc(NC(=O)CCC(C)(C)SSCCC(C(=O)NCCN3C(=O)C=CC3=O)S(=O)(=O)O)c1)N=C[C@@H]1Cc3ccccc3N1C2=O] |
| D5 | 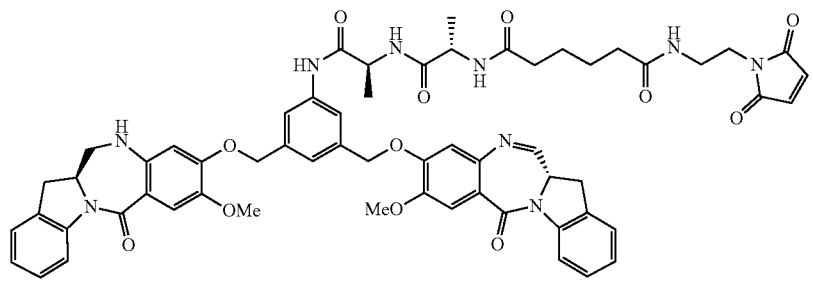 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O] |
| D5' | 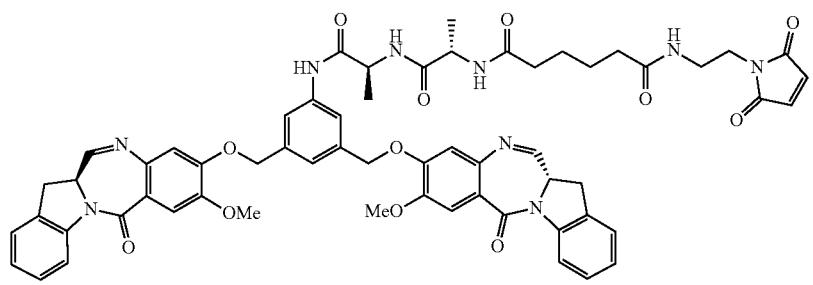 [SMILES: COc1cc2c(cc1OCc1cc(COc3cc4c(cc3OC)C(=O)N3c5ccccc5C[C@H]3C=N4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O] |
| D6 | 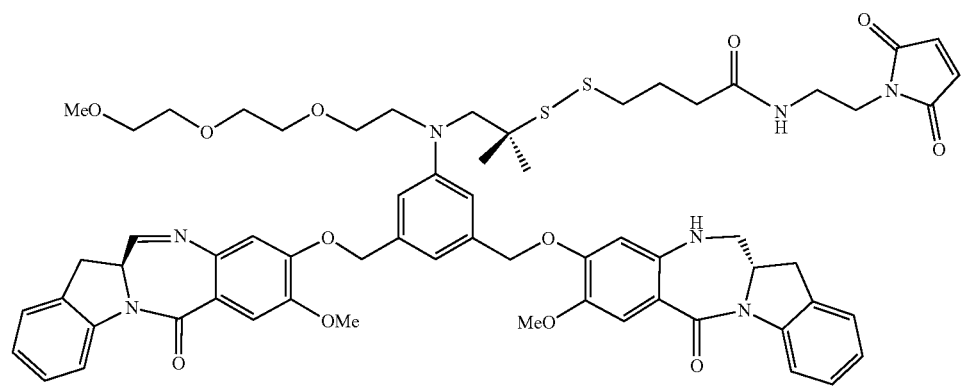 |

| Compound No. | Structure |
|---|---|
| D7 | (chemical structure) |
| D8 | (chemical structure) |
| D9 | (chemical structure) |

Note that several agents only differ slightly due to the different linkage chemistry required for linking the cytotoxin to different antibody side chains (i.e., Lys-linkage, Cys-linkage, oxidized N-terminal Ser linkage). Nevertheless, these related cytotoxins are given different "D" designations. See D1 and D4, as well as D2, D5, and D8.

Conjugates of the subject antibodies and the cytotoxic agents generally follow the nomenclature of the antibodies and cytotoxic agents as described above.

For example, huCD123-6Gv4.6-sulfo-SPDB-D1 is a conjugate of the huCD123-6Gv4.6 antibody to compound D1 through a sulfonated SPDB linker, at one or more Lys residues of the antibody. huCD123-6-CX1-1-DM1 is a conjugate of the huCD123-6 antibody conjugated with the cytotoxic agent DM1 via a triglycyl linker named "CX1-1 linker," at one or more of the Lys residues of the antibody. See Example 9e.

Figure 7A:
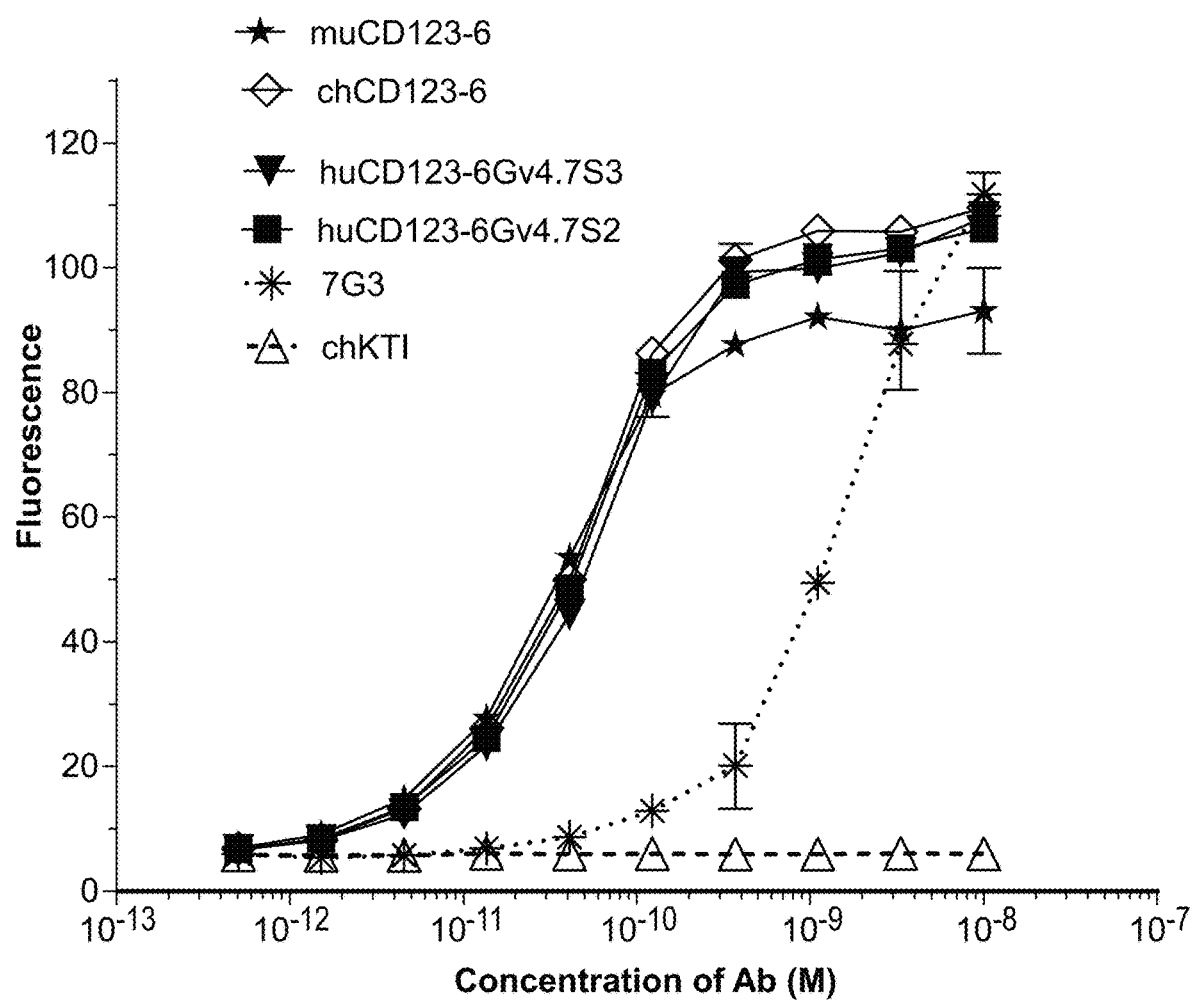
FIG. 7A shows that the murine (muCD123-6), chimeric (chCD123-6), and CDR-grafted huCD123-6 antibodies (huCD123-6Gv4.7S2 and huCD123-6Gv4.7S3) all have higher affinity than 7G3 to CD123-expressing HNT-34 cells. Chimeric antibody chKTI, which does not bind CD123, was included as negative control.
Figure 7B:
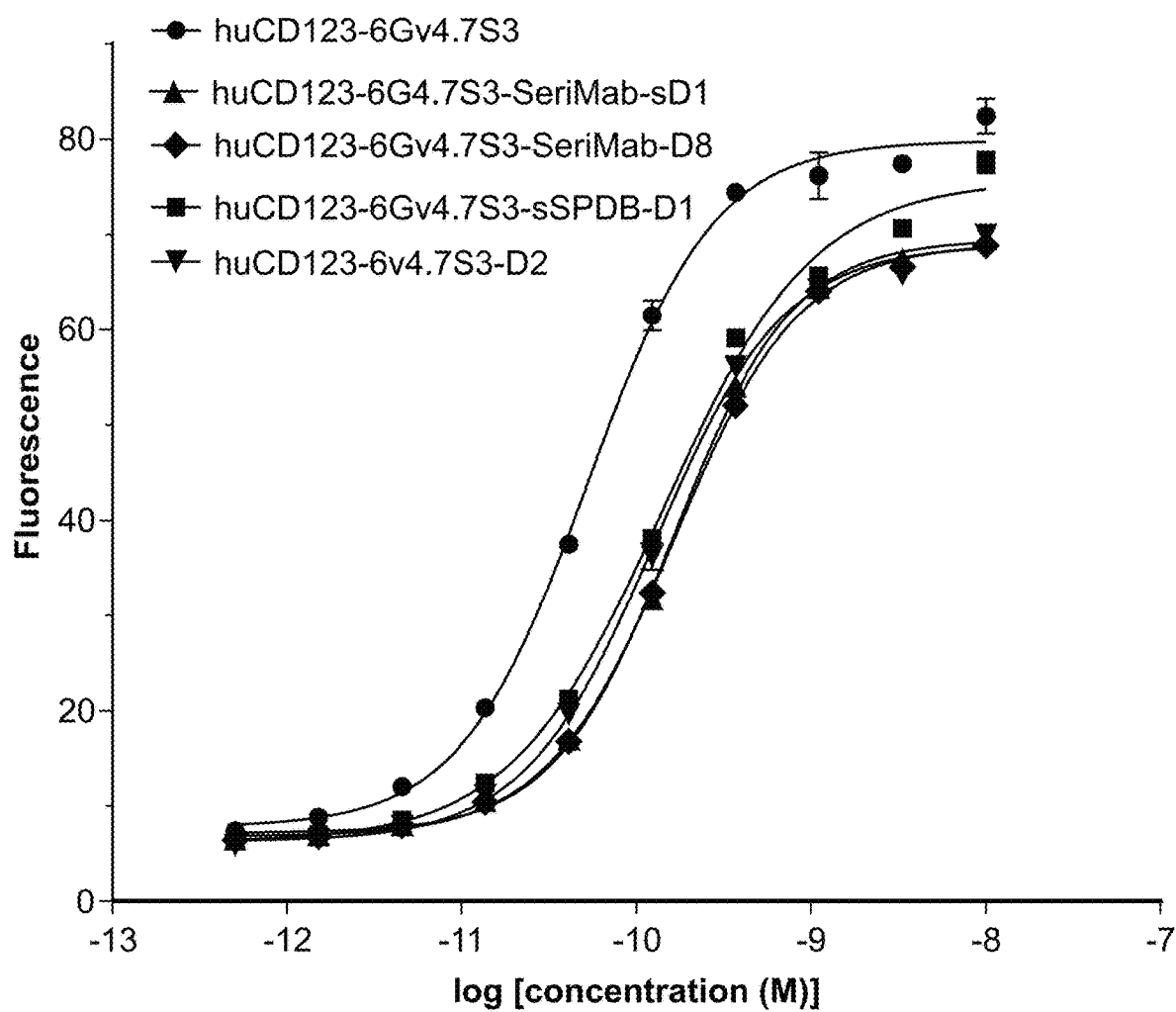
FIGS. 7B and 7C show that conjugation of the huCD123-6Gv4.7S3 or the -Gv4.7 antibody to the D1 or D2 compounds through Lys-, Ser-, or Cys-linkage only moderately affected the binding affinities of these ADC conjugates, i.e., the Ser-linked huCD123-6Gv4.7S3-SeriMab-sD1 (see structure in FIG. 17) and huCD123-6Gv4.7S3-SeriMab-D8, and the Lys-linked huCD123-6Gv4.7S3-sSPDB-D1, and huCD123-6Gv4.7S3-D2 in FIG. 7B; and the Cys-linked huCD123-6Gv4.7-CysMab-D4 and huCD123-6Gv4.7-CysMab-D5 in FIG. 7C.
Figure 17:
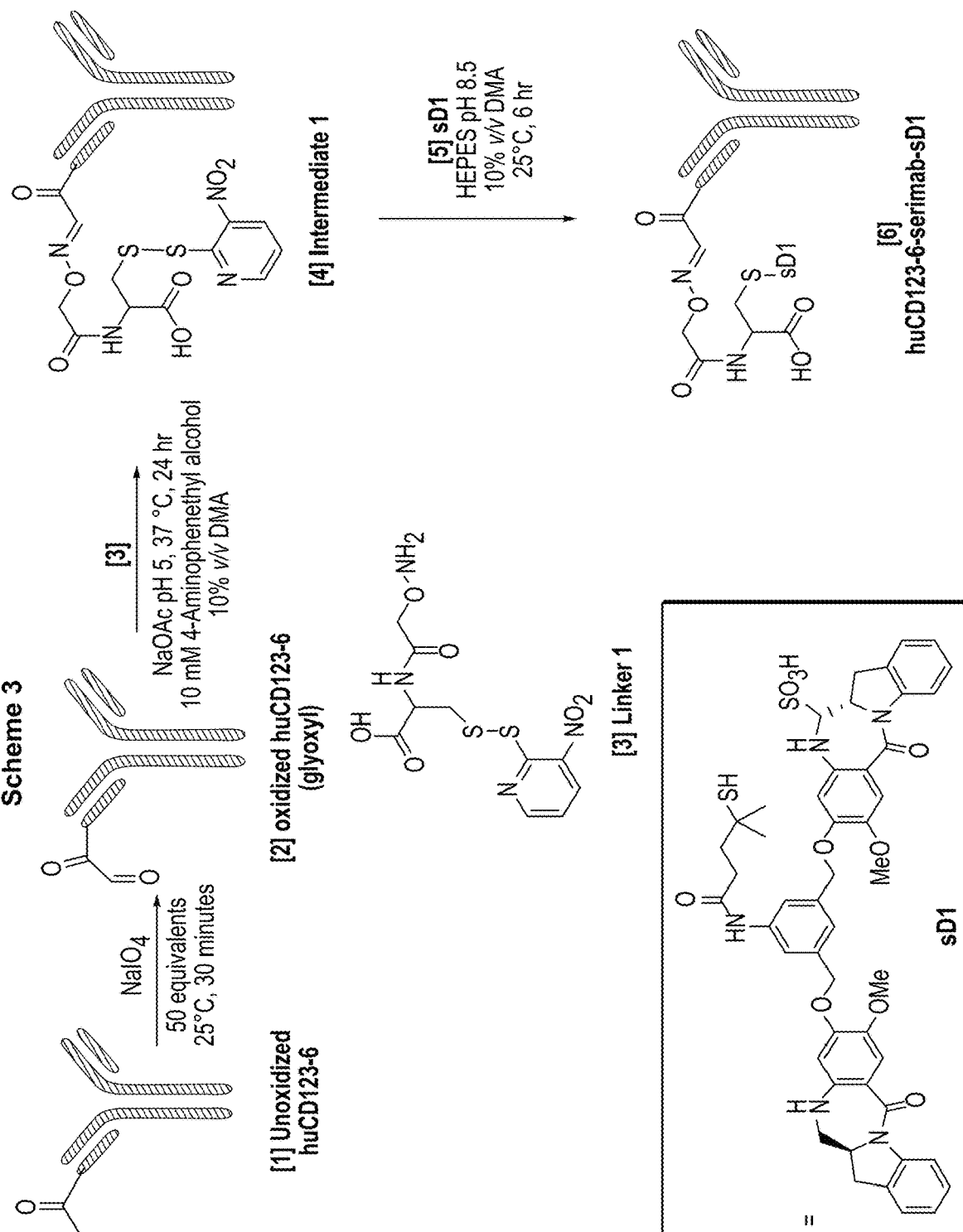
FIG. 17 shows a schematic drawing to show the general steps that can be used to synthesize a Ser-linkage conjugate of the invention.

One notable exception is the conjugate huCD123-6-SeriMab-sD1 shown in FIGS. 7B and 17, in which the short linker sequence between the huCD123-6-SeriMab and the sD1 cytotoxin is not explicitly recited in the conjugate name.

Figure 15:
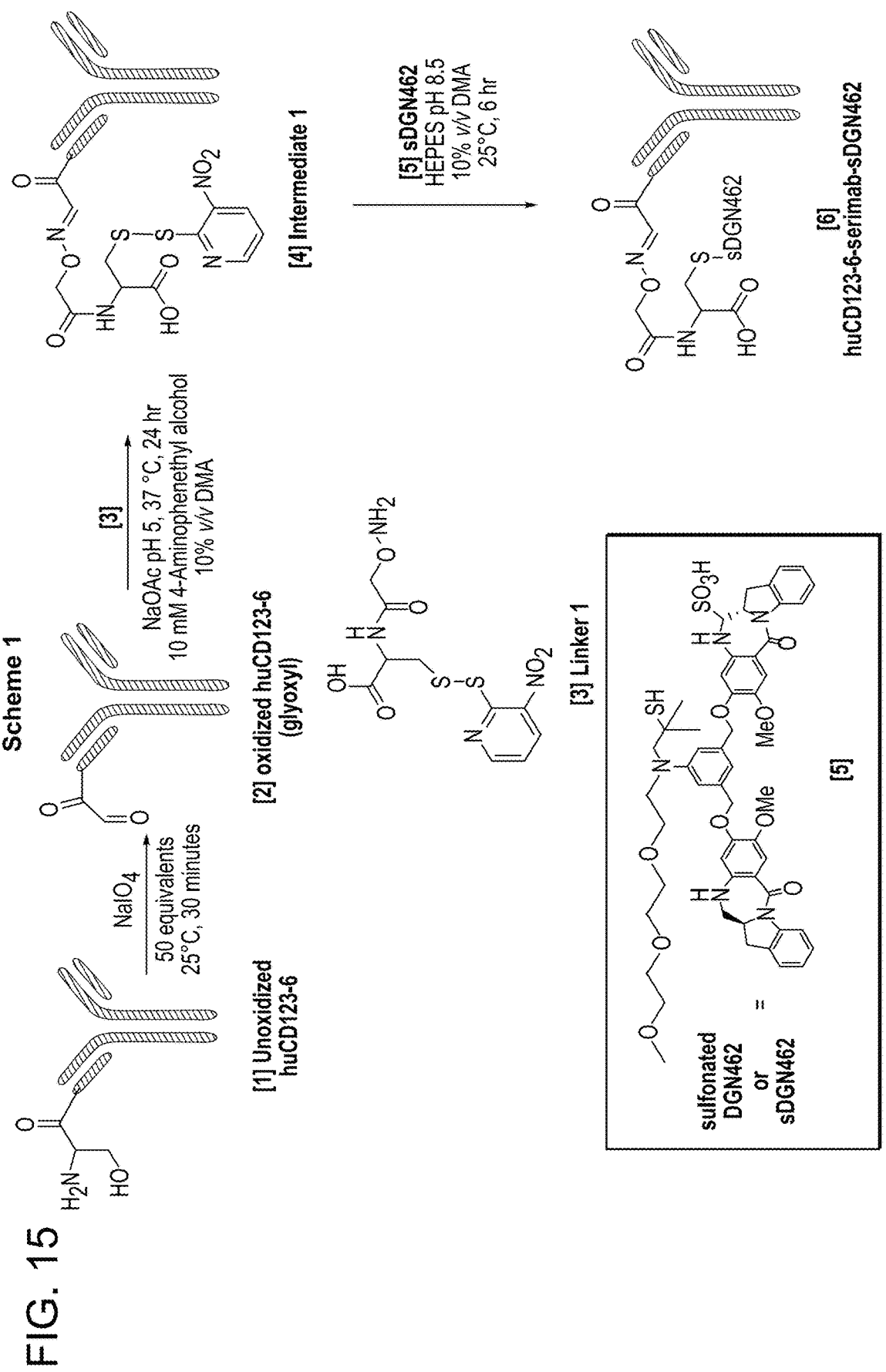
FIG. 15 shows a schematic drawing to show the general steps that can be used to synthesize a Ser-linkage conjugate of the invention.
Figure 16:
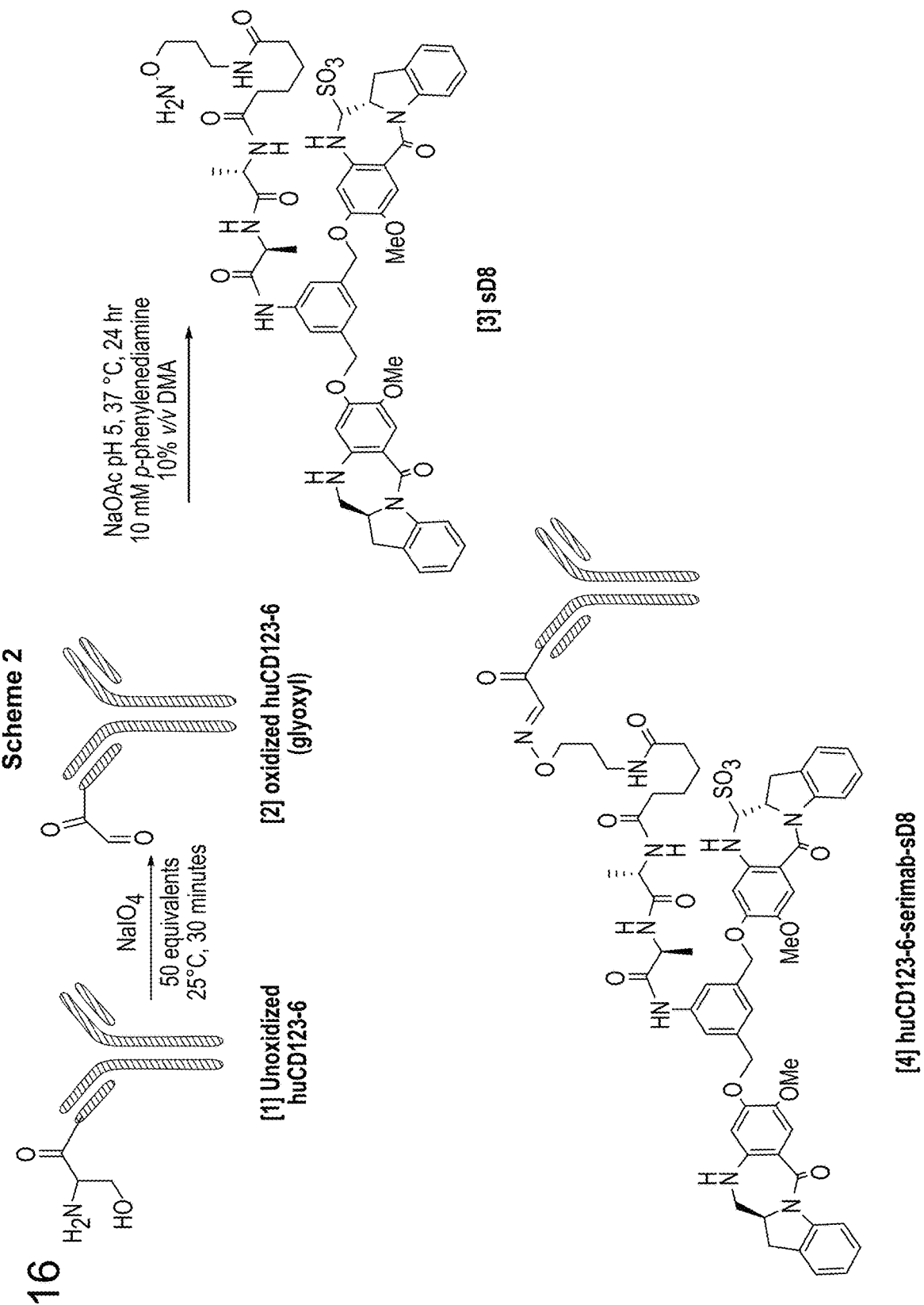
FIG. 16 shows a schematic drawing to show the general steps that can be used to synthesize a Ser-linkage conjugate of the invention.

Similarly, conjugate huCD123-6-SeriMab-sDGN462 in FIG. 15 is also an exception to the general rules above.

2. CD123 Binding Agents

In a first aspect, the present invention provides agents that specifically bind CD123/IL-3Ra, such as human CD123/IL-3Rα. These agents are generally referred to herein as "CD123/IL-3Rα-binding agents." In certain embodiments, the CD123/IL-3Rα-binding agents are antibodies or antigen-binding fragments thereof (or "antibodies" for simplicity), immunoconjugates thereof or polypeptides thereof.

The amino acid and nucleotide sequences for human and other species of CD123/IL-3Rα are known in the art. For example, the human CD123/IL-3Rα splicing variant 1 protein sequence as depicted in NCBI RefSeq NP_002174 is reproduced below:

(SEQ ID NO: 36)
1   MVLLWLTLLL IALPCLLQTK EDPNPPITNL RMKAKAQQLT
    WDLNRNVTDI ECVKDADYSM

-continued

```
 61  PAVNNSYCQF GAISLCEVTN YTVRVANPPF STWILFPENS
     GKPWAGAENL TCWIHDVDFL

121  SCSWAVGPGA PADVQYDLYL NVANRRQQYE CLHYKTDAQG
     TRIGCRFDDI SRLSSGSQSS

181  HILVRGRSAA FGIPCTDKFV VFSQIEILTP PNMTAKCNKT
     HSFMHWKMRS HFNRKFRYEL

241  QIQKRMQPVI TEQVRDRTSF QLLNPGTYTV QIRARERVYE
     FLSAWSTPQR FECDQEEGAN

301  TRAWRTSLLI ALGTLLALVC VFVICRRYLV MQRLFPRIPH
     MKDPIGDSFQ NDKLVVWEAG

361  KAGLEECLVT EVQVVQKT
```

The above sequence shows the CD123/IL-3R alpha precursor chain protein, which is composed by 378 amino acids, containing the extracellular domain (residues 1-306, including an 18-residue N-terminal signal peptide), a 20 amino acid transmembrane domain, and a short cytoplasmic tail of 52 amino acids.

The human CD123/IL-3Rα splicing variant 1 nucleic acid sequence as depicted in NCBI RefSeq NM_002183 is reproduced below:

```
                                     (SEQ ID NO: 52)
   1  GTCAGGTTCA TGGTTACGAA GCTGCTGACC CCAGGATCCC
      AGCCCGTGGG AGAGAAGGGG

61  GTCTCTGACA GCCCCCACCC CTCCCCACTG CCAGATCCTT
      ATTGGGTCTG AGTTTCAGGG

121  GTGGGGCCCC AGCTGGAGGT TATAAAACAG CTCAATCGGG
      GAGTACAACC TTCGGTTTCT

181  CTTCGGGGAA AGCTGCTTTC AGCGCACACG GGAAGATATC
      AGAAACATCC TAGGATCAGG

241  ACACCCCAGA TCTTCTCAAC TGGAACCACG AAGGCTGTTT
      CTTCCACACA GTACTTTGAT

301  CTCCATTTAA GCAGGCACCT CTGTCCTGCG TTCCGGAGCT
      GCGTTCCCGA TGGTCCTCCT

361  TTGGCTCACG CTGCTCCTGA TCGCCCTGCC CTGTCTCCTG
      CAAACGAAGG AAGATCCAAA

421  CCCACCAATC ACGAACCTAA GGATGAAAGC AAAGGCTCAG
      CAGTTGACCT GGGACCTTAA

481  CAGAAATGTG ACCGATATCG AGTGTGTTAA AGACGCCGAC
      TATTCTATGC CGGCAGTGAA

541  CAATAGCTAT TGCCAGTTTG GAGCAATTTC CTTATGTGAA
      GTGACCAACT ACACCGTCCG

601  AGTGGCCAAC CCACCATTCT CCACGTGGAT CCTCTTCCCT
      GAGAACAGTG GGAAGCCTTG

661  GGCAGGTGCG GAGAATCTGA CCTGCTGGAT TCATGACGTG
      GATTTCTTGA GCTGCAGCTG

721  GGCGGTAGGC CCGGGGGCCC CCGCGGACGT CCAGTACGAC
      CTGTACTTGA ACGTTGCCAA

781  CAGGCGTCAA CAGTACGAGT GTCTTCACTA CAAAACGGAT
      GCTCAGGGAA CACGTATCGG

841  GTGTCGTTTC GATGACATCT CTCGACTCTC CAGCGGTTCT
      CAAAGTTCCC ACATCCTGGT

901  GCGGGGCAGG AGCGCAGCCT TCGGTATCCC CTGCACAGAT
      AAGTTTGTCG TCTTTTCACA

961  GATTGAGATA TTAACTCCAC CCAACATGAC TGCAAAGTGT
      AATAAGACAC ATTCCTTTAT
```

```
1021  GCACTGGAAA ATGAGAAGTC ATTTCAATCG CAAATTTCGC
      TATGAGCTTC AGATACAAAA

1081  GAGAATGCAG CCTGTAATCA CAGAACAGGT CAGAGACAGA
      ACCTCCTTCC AGCTACTCAA

1141  TCCTGGAACG TACACAGTAC AAATAAGAGC CCGGGAAAGA
      GTGTATGAAT TCTTGAGCGC

1201  CTGGAGCACC CCCCAGCGCT TCGAGTGCGA CCAGGAGGAG
      GGCGCAAACA CACGTGCCTG

1261  GCGGACGTCG CTGCTGATCG CGCTGGGGAC GCTGCTGGCC
      CTGGTCTGTG TCTTCGTGAT

1321  CTGCAGAAGG TATCTGGTGA TGCAGAGACT CTTTCCCCGC
      ATCCCTCACA TGAAAGACCC

1381  CATCGGTGAC AGCTTCCAAA ACGACAAGCT GGTGGTCTGG
      GAGGCGGGCA AAGCCGGCCT

1441  GGAGGAGTGT CTGGTGACTG AAGTACAGGT CGTGCAGAAA
      ACTTGAGACT GGGGTTCAGG

1501  GCTTGTGGGG GTCTGCCTCA ATCTCCCTGG CCGGGCCAGG
      CGCCTGCACA GACTGGCTGC

1561  TGGACCTGCG CACGCAGCCC AGGAATGGAC ATTCCTAACG
      GGTGGTGGGC ATGGGAGATG

1621  CCTGTGTAAT TTCGTCCGAA GCTGCCAGGA AGAAGAACAG
      AACTTTGTGT GTTTATTTCA

1681  TGATAAAGTG ATTTTTTTTT TTTTAACCCA AAA
```

Proteins and nucleic acid sequences of CD123/IL-3Rα from other non-human species can be readily retrieved from public database such as GenBank, using sequence search tools known in the art (such as NCBI BLASTp or BLASTn) and the above protein and nucleic acid sequences as query sequences, respectively.

Such sequences from the non-human species can be aligned with the human sequences using any of many art-recognized sequence alignment tools, such as those described herein and above, such that any amino acid residues or nucleotides "corresponding to" any given human sequences or regions of sequences can be readily obtained.

Thus, one aspect of the invention provides an antibody or antigen-binding fragment thereof that: (a) binds an epitope within amino acids 101 to 346 of human CD123 antigen, and (b) inhibits IL3-dependent proliferation in antigen-positive TF-1 cells.

In some embodiments, an anti-CD123/IL-3Rα antibody or antigen-binding fragment thereof can specifically binds to an epitope of SEQ ID NO: 36. In certain embodiments, the epitope is within a region corresponding to residues 101-346 of human CD123/IL-3Rα. In certain embodiments, the epitope is within a region corresponding to residues 101-204 of SEQ ID NO: 36. In certain other embodiments, the epitope is within a region corresponding to residues 205-346 of SEQ ID NO: 36. In certain embodiments, the epitope is not within a region corresponding to residues 1-100 of human CD123/IL-3Rα.

In certain embodiments, the CD123/IL-3Rα-binding agents (e.g., antibodies) inhibit IL3-dependent signaling, such as IL-3-dependent proliferation of CD123-positive TF-1 cells. While not wishing to be bound by any particular theory, the CD123/IL-3Rα-binding agents (e.g., antibodies) of the invention bind to CD123, such as within a CD123 region corresponding to residues 101-346 (e.g., residues 101-204, or 205-346) of human CD123/IL-3Rα, and prevents, reduces, diminishes, or otherwise inhibits productive binding between CD123 and the IL-3 ligand, and/or productive binding between CD123 and the common beta chain CD131, leading to reduced or abolished IL-3 dependent signaling.

In a related aspect, the invention provides an antibody or antigen-binding fragment thereof that: (a) binds an epitope within amino acids 1 to 100 of human CD123 antigen, and (b) inhibits IL3-dependent proliferation in antigen-positive TF-1 cells, with an $IC_{50}$ value of 0.1 nM or less (e.g., 0.08 nM, 0.05 nM, 0.03 nM).

In certain embodiments, binding by the CD123/IL-3Rα-binding agents (e.g., antibodies) of the invention inhibits (e.g., preferentially inhibits) the proliferation of leukemic stem cells (LSCs), leukemia progenitors (LPs), or leukemic blasts, but do not substantially inhibit the proliferation of the normal hematopoietic stem cells (HSCs).

Inhibition of cell proliferation can be conducted using any standard assays known in the art, including but are not limited to flow cytometry. For example, normal HSCs, LSCs, LPs, and leukemia blasts can be separated using flow cytometry based on the difference on expression of cell surface markers, and the relative number of the surviving or remaining cells, after incubating with the testing agents, can be quantitatively measured and compared.

Inhibition of cell proliferation of the LSCs, LPs, or leukemia blasts as compared to normal HSCs can also be assayed using in vitro potency assay on primary cancer cells, such as primary AML cells. For example, AML cells (or normal human bone marrow samples containing normal HSCs) can be exposed to various concentrations of the subject anti-CD123 antibodies, antigen-binding fragments thereof, immuno-conjugates thereof, or polypeptide comprising the antibodies or antigen-binding fragments for 24 hrs. Non-targeting (isotype-matched) antibodies, or immuno-conjugates (ADC) control can also be used in the assay. Samples can be divided into a short-term liquid culture (STLC) assay to measure the cytotoxicity toward the LSCs, LPs, or leukemia blasts; and a long-term liquid culture (LTLC) assay to measure the effect on the LSCs and normal HSCs. STLC can be used to measure colony forming units 10-14 days in cells, e.g., following plating in semi-solid MethoCult H4230 medium (Stemcell technologies). The LTLC assays can be performed similarly with the addition of growth factors for long-term culture 5-7 weeks. In both assays, colonies can be counted to determine colony forming units per number of cells initially plated. LTLC colonies can be further analyzed for the presence of cancer (e.g., AML) molecular markers using PCR or FISH or both.

In certain embodiments, the antibody or antigen-binding fragment thereof binds to human CD123 antigen-positive cells with a dissociation constant ($K_d$) of 0.3 nM or lower. In certain embodiments, the antibodies or antigen-binding fragments thereof bind to human CD123 with a $K_d$ between 0.05 and 0.3 nM, or between 0.05 and 0.2 nM, or between 0.05 and 0.1 nM, or between 0.01 nM and 0.3 nM, or between 0.01 nM and 0.2 nM, or between 0.01 nM and 0.1 nM.

In certain embodiments, the antibodies or antigen-binding fragments thereof bind to cynomolgus monkey CD123. In certain embodiments, the antibodies or antigen-binding fragments thereof bind to cynomolgus monkey CD123 with a $K_d$ between 0.05 and 0.3 nM, or between 0.05 and 0.2 nM, or between 0.05 and 0.1 nM.

In certain embodiments, the antibodies or antigen-binding fragments thereof bind both human and cynomolgus monkey CD123 with a substantially similar binding affinity. In certain embodiments, the antibodies or antigen-binding fragments thereof bind to both human and cynomolgus monkey CD123 with $K_d$ between 0.05 and 0.3 nM, or between 0.05 and 0.2 nM, or between 0.05 and 0.1 nM.

In certain embodiments, the $K_d$ value is based on cell-based binding assay. In certain embodiments, the $K_d$ value is measured by flow cytometry. In certain embodiments, the $K_d$ value is measured by surface plasmon resonance (such as by using the BIOCORE™ surface plasmon resonance system). In certain embodiments, the $K_d$ value is measured by radio-immunoassay (RIA). In certain embodiments, the $K_d$ is measured by any other art-recognized methods.

In certain embodiments, the antibody or antigen-binding fragment thereof inhibits at least 50% of IL3-dependent proliferation in antigen-positive TF-1 cells at a concentration of 0.5 nM or lower.

In certain embodiments, the CD123/IL-3Rα-binding agents are CD123/IL-3Rα antibodies or antigen-binding fragments thereof that comprise a heavy chain variable region (HCVR) and a light chain variable region (LCVR), each comprising three CDR regions (e.g., CDR1-CDR3 for the HCVR, and CDR1-CDR3 for the LCVR), wherein the composite CDRs for the HCVR and LCVR are any of the sequences provided in Tables 1 and 2 below.

TABLE 1

Heavy Chain Variable Region CDR Amino Acid Sequences

| Antibody | Alt Name | VH-CDR1 | VH-CDR2 | VH-CDR3 |
|---|---|---|---|---|
| CD123-3 | CD123Mu-3 | SYVMH (SEQ ID NO: 1) | YIKPYKDGTK (SEQ ID NO: 2) YIKPYKDGTKYNEKFKG (Kabat) (SEQ ID NO: 3) | EGENGYYDAMDY (SEQ ID NO: 4) |
| CD123-6 | CD123Mu-6 | SSIMH (SEQ ID NO: 5) | YIKPYNDGTK Murine + Grafted (SEQ ID NO: 6) YIRPYNDGTR (resurfaced version 1.0) (SEQ ID NO: 7) YIKPYNDGTKYNEKFKG (Kabat Murine + Grafted) (SEQ ID NO: 8) YIRPYNDGTRYNQKFQG (Kabat - resurfaced v1.0) (SEQ ID NO: 9) YIKPYNDGTKYNQKFQG (Kabat - resurfaced v1.1) (SEQ ID NO: 10) | EGGNDYYDTMDY (SEQ ID NO: 11) |

TABLE 1-continued

Heavy Chain Variable Region CDR Amino Acid Sequences

| Antibody | Alt Name | VH-CDR1 | VH-CDR2 | VH-CDR3 |
|---|---|---|---|---|
| CD123-14 | CD123Mu-14 | NYAMS (SEQ ID NO: 12) | TINSGGSFTY (SEQ ID NO: 13) TINSGGSFTYYPDSVKG (Kabat) (SEQ ID NO: 14) | QSEAYYGYDKRT (SEQ ID NO: 15) QSEAYYGYDKRTW FAY (SEQ ID NO: 70) |

TABLE 2

Light Chain Variable Region CDR Amino Acid Sequences

| Antibody | Alt Name | VL-CDR1 | VL-CDR2 | VL-CDR3 |
|---|---|---|---|---|
| CD123-3 | CD123Mu-3 | KASQDINKYIA (SEQ ID NO: 16) | YTSTLQP (SEQ ID NO: 17) | LQYDNLLYT (SEQ ID NO: 18) |
| CD123-6 | CD123Mu-6 | KASQDINSYLS (SEQ ID NO: 19) RASQDINSYLS Humanized (SEQ ID NO: 20) RASQDINSYLA (SEQ ID NO: 72) | RVNRLVD (SEQ ID NO: 21) RVNRLVS (SEQ ID NO: 71) | LQYDAFPYT (SEQ ID NO: 22) |
| CD123-14 | CD123Mu-14 | RASQSVGTSIH (SEQ ID NO: 23) | YASESIS (SEQ ID NO: 24) | QQSKSWPLT (SEQ ID NO: 25) |

In certain embodiments, the anti-CD123/IL-3Rα antibodies and antigen-binding fragments thereof comprise: a) at least one heavy chain variable region or fragment thereof comprising three sequential complementarity-determining regions (CDR) CDR1, CDR2, and CDR3, respectively, wherein, with the exception of 1, 2, or 3 conservative amino acid substitutions, CDR1 is selected from the group consisting of: SEQ ID NOs: 1, 5, and 12, CDR2 is selected from the group consisting of: SEQ ID NOs: 2-3, 6-10, and 13-14, and, optionally, CDR3 is selected from the group consisting of: SEQ ID NOs: 4, 11, 15 and 70; and b) at least one light chain variable region or fragment thereof comprising three sequential complementarity-determining regions (CDR) CDR1, CDR2, and CDR3, respectively, wherein, with the exception of 1, 2, or 3 conservative amino acid substitutions, CDR1 is selected from the group consisting of: SEQ ID NOs: 16, 19-20, 23 and 72, CDR2 is selected from the group consisting of: SEQ ID NOs: 17, 21, 24 and 71, and, optionally, CDR3 is selected from the group consisting of: SEQ ID NOs: 18, 22, and 25.

In certain embodiments, the anti-CD123/IL-3Rα antibodies and antigen-binding fragments thereof comprise: a) at least one heavy chain variable region or fragment thereof comprising three sequential complementarity-determining regions (CDR) CDR1, CDR2, and CDR3, respectively, wherein, with the exception of 1, 2, or 3 conservative amino acid substitutions, CDR1 is selected from the group consisting of: SEQ ID NOs: 1, 5, and 12, CDR2 is selected from the group consisting of: SEQ ID NOs: 2-3, 6-10, and 13-14, and, optionally, CDR3 is selected from the group consisting of: SEQ ID NOs: 4, 11, and 15; and b) at least one light chain variable region or fragment thereof comprising three sequential complementarity-determining regions (CDR) CDR1, CDR2, and CDR3, respectively, wherein, with the exception of 1, 2, or 3 conservative amino acid substitutions, CDR1 is selected from the group consisting of: SEQ ID NOs: 16, 19-20, and 23, CDR2 is selected from the group consisting of: SEQ ID NOs: 17, 21, and 24, and, optionally, CDR3 is selected from the group consisting of: SEQ ID NOs: 18, 22, and 25.

In certain embodiments, the conservative amino acid substitutions comprise a substitution of a Lys in a CDR by an Arg (such as the Lys-to-Arg substitutions in SEQ ID NOs: 6 and 7, 8 and 9, and 19 and 20). In certain embodiments, the antibody is a CDR-grafted humanized antibody comprising mouse CDR regions, and wherein one or more (e.g., 1, 2, 3, 4, 5, 6, 7, or 8) heavy chain and/or light chain framework region vernier zone residues of the antibody is of mouse origin.

In certain embodiments, the anti-CD123/IL-3Rα antibodies and antigen-binding fragments thereof comprise: a) an immunoglobulin heavy chain variable region comprising a CDR1 having an amino acid sequence set forth in SEQ ID NO: 1, a CDR2 having an amino acid sequence set forth in SEQ ID NO: 2 or 3, and, optionally, a CDR3 having an amino acid sequence set forth in SEQ ID NO: 4; and 2) an immunoglobulin light chain variable region comprising a CDR1 having an amino acid sequence set forth in SEQ ID NO: 16, a CDR2 having an amino acid sequence set forth in SEQ ID NO: 17, and, optionally, a CDR3 having an amino acid sequence set forth in SEQ ID NO: 18. In certain embodiments, CDR2 of the heavy chain variable region is SEQ ID NO: 2. In certain embodiments, CDR2 of the heavy chain variable region is SEQ ID NO: 3.

In certain embodiments, the anti-CD123/IL-3Rα antibodies and antigen-binding fragments thereof comprise: a) an immunoglobulin heavy chain variable region comprising a CDR1 having an amino acid sequence set forth in SEQ ID NO: 5, a CDR2 having an amino acid sequence set forth in SEQ ID NO: 6, 7, 8, 9, or 10, and, optionally, a CDR3 having an amino acid sequence set forth in SEQ ID NO: 11; and 2) an immunoglobulin light chain variable region comprising a CDR1 having an amino acid sequence set forth in SEQ ID NO: 19 or 20, a CDR2 having an amino acid sequence set forth in SEQ ID NO: 21, and, optionally, a CDR3 having an amino acid sequence set forth in SEQ ID NO: 22. In certain embodiments, CDR2 of the heavy chain variable region is SEQ ID NO: 6, and CDR1 of the light chain variable region is SEQ ID NO: 19. In certain embodiments, CDR2 of the heavy chain variable region is SEQ ID NO: 7, and CDR1 of the light chain variable region is SEQ ID NO: 19. In certain embodiments, CDR2 of the heavy chain variable region is SEQ ID NO: 8, and CDR1 of the light chain variable region is SEQ ID NO: 19. In certain embodiments, CDR2 of the heavy chain variable region is SEQ ID NO: 9, and CDR1 of the light chain variable region is SEQ ID NO: 19. In certain embodiments, CDR2 of the heavy chain variable region is SEQ ID NO: 10, and CDR1 of the light chain variable region is SEQ ID NO: 19. In certain embodiments, CDR2 of the heavy chain variable region is SEQ ID NO: 6, and CDR1 of the light chain variable region is SEQ ID NO: 20. In certain embodiments, CDR2 of the heavy chain variable region is SEQ ID NO: 7, and CDR1 of the light chain variable region is SEQ ID NO: 20. In certain embodiments, CDR2 of the heavy chain variable region is SEQ ID NO: 8, and CDR1 of the light chain variable region is SEQ ID NO: 20. In certain embodiments, CDR2 of the heavy chain variable region is SEQ ID NO: 9, and CDR1 of the light chain variable region is SEQ ID NO: 20. In certain embodiments, CDR2 of the heavy chain variable region is SEQ ID NO: 10, and CDR1 of the light chain variable region is SEQ ID NO: 20. For each pairwise combinations of heavy chain variable region CDR2 with light chain variable region CDR1 above, the heavy chain variable region CDR1 and 3 are SEQ ID NOs: 5 and 11, respectively, and the light chain variable region CDR2 and 3 are SEQ ID NOs: 21 and 22, respectively.

In certain embodiments, the anti-CD123/IL-3Rα antibodies and antigen-binding fragments thereof comprise: a) an immunoglobulin heavy chain variable region comprising a CDR1 having an amino acid sequence set forth in SEQ ID NO: 12, a CDR2 having an amino acid sequence set forth in SEQ ID NO: 13 or 14, and, optionally, a CDR3 having an amino acid sequence set forth in SEQ ID NO: 15; and 2) an immunoglobulin light chain variable region comprising a CDR1 having an amino acid sequence set forth in SEQ ID NO: 23, a CDR2 having an amino acid sequence set forth in SEQ ID NO: 24, and, optionally, a CDR3 having an amino acid sequence set forth in SEQ ID NO: 25. In certain embodiments, CDR2 of the heavy chain variable region is SEQ ID NO: 13. In certain embodiments, CDR2 of the heavy chain variable region is SEQ ID NO: 14.

In certain embodiments, CDR1 sequences from the light chain and heavy chain of one antibody (such as SEQ ID NOs: 5 and 19) can be combined with CDR2 sequences from the light chain and heavy chain of another antibody (such as SEQ ID NOs: 2 and 17), and optionally can be combined with CDR3 sequences from the light chain and heavy chain of the same (e.g., SEQ ID NOs: 4 and 18, or 11 and 22) or yet another antibody (e.g., SEQ ID NOs: 15 and 25). All possible combinations based on SEQ ID NOs: 1-25 in Table 1, particularly those pertaining to the same antibody number (e.g., all six light chain and heavy chain CDRs come from CD123-3, or from CD123-6, or from CD123-14) are contemplated herein without exhaustively enumerating all the specific combinations.

In certain embodiments, the anti-CD123/IL-3Rα antibodies and antigen-binding fragments thereof have conserved amino acid substitutions over 1, 2, or 3 consecutive residues in any one or more CDR sequences above. That is, in some embodiments, the subject antibodies and antigen-binding fragments thereof may have conserved amino acid substitutions over 1, 2, or 3 consecutive residues, in any one or more of SEQ ID NOs: 1-25.

In certain embodiments, the CD123/IL-3Rα-binding agents are CD123/IL-3Rα antibodies or antigen-binding fragments thereof that comprise a heavy chain variable region (HCVR) and a light chain variable region (LCVR), wherein the HCVR and LCVR are any of the sequences provided in Tables 3A and 4A below. Selected corresponding nucleic acid sequences encoding the HCVR and LCVR are in Tables 3B and 4B.

TABLE 3A

Heavy Chain Variable Region Amino Acid Sequences

| Antibody | Alt Name | VH Amino Acid Sequence (SEQ ID NO) |
|---|---|---|
| CD123-3 | CD123Mu-3 | EFQLQQSGPEVVKPGASVKMSCKASGYTFTSYVMHWMKQ KPGQGLEWIGYIKPYKDGTKYNEKFKGKATLISDKPSSTAY MELSSLTSEDSAVYYCAREGENGYYDAMDYWGQGTSVTV SS (SEQ ID NO: 26) |
| CD123-6 | CD123Mu-6 | EFQLQQSGPELVKPGASVKMSCKASGYIFTSSIMHWMKQK PGQGLEWIGYIKPYNDGTKYNEKFKGKATLTSDKSSSTAN MELNSLTSEDSAVYYCAREGGNDYYDTMDYWGQGTSVT VSS (SEQ ID NO: 28) |
| CD123-14 | CD123Mu-14 | EVKLVESGGDLVKPGGSLKLSCAASGFTFSNYAMSWVRQ NSEKRLEWVATINSGGSFTYYPDSVKGRFTISRDNAKDSLY LQMSSLNSEDTAMYYCARQSEAYYGYDKRTWFAYWGQG TLVTVSS (SEQ ID NO: 30) |
| huCD123-6Gv1 | | QVQLVQSGAEVKKPGASVKVSCKASGYGFTSSIMHWVRQ APGQGLEWMGYIKPYNDGTKYNEKFKGRVTMTRDTSTST VYMELSSLRSEDTAVYYCAREGGNDYYDTMDYWGQGTL VTVSS (SEQ ID NO: 32) |
| huCD123-6Gv6/7 | | QXQLVQSGAEVKKPGASVKVSCKASGYIFTSSIMHWVRQA PGQGLEWIGYIKPYNDGTKYNEKFKGRATLTSDRSTSTAY MELSSLRSEDTAVYYCAREGGNDYYDTMDYWGQGTLVT VSS (SEQ ID NO: 34) |
| huCD123-6 Gv6/7-NTS2 | | SXQLVQSGAEVKKPGASVKVSCKASGYIFTSSIMHWVRQA PGQGLEWIGYIKPYNDGTKYNEKFKGRATLTSDRSTSTAY MELSSLRSEDTAVYYCAREGGNDYYDTMDYWGQGTLVT VSS (SEQ ID NO: 38) |

TABLE 3A-continued

Heavy Chain Variable Region Amino Acid Sequences

| Antibody | Alt Name | VH Amino Acid Sequence (SEQ ID NO) |
|---|---|---|
| huCD123-6rhv1.0 | | QVQLVQSGAEVVKPGASVKMSCKASGYTFTSSIMHWMKQ KPGQGLEWIGYIRPYNDGTRYNQKFQGKATLTSDRSSSTA NMELNSLTSEDSAVYYCAREGGNDYYDTMDYWGQGTSV TVSS (SEQ ID NO: 39) |
| huCD123-6rhv1.1 | | QFQLVQSGAEVVKPGASVKMSCKASGYTFTSSIMHWMKQ KPGQGLEWIGYIKPYNDGTKYNQKFQGKATLTSDKSSSTA NMELNSLTSEDSAVYYCAREGGNDYYDTMDYWGQGTSV TVSS (SEQ ID NO: 40) |

* In all sequences above in which the $2^{nd}$ residue from the N-terminus is X (or Xaa), e.g., SEQ ID NOs: 34 and 38, X is F for Gv6 sequences, while X is V for Gv7 sequences.

TABLE 3B

Selected Heavy Chain Variable Region Nucleic Acid Sequences

| Antibody | VH DNA Sequence (SEQ ID NO) |
|---|---|
| huCD123-6 $V_H$Gv1 | AAGCTTGCCACCATGGGATGGTCCTGCATTATCCTGTTCCT TGTAGCAACTGCAACAGGAGTCCACAGCCAGGTCCAACTG GTGCAGTCCGGGGCCGAGGTGAAGAAACCAGGCGCATCCG TGAAGGTCAGCTGTAAAGCCAGCGGCTATGGTTTTACCAG CTCAATCATGCACTGGGTCAGGCAAGCCCCAGGACAGGGT CTCGAATGGATGGGATACATTAAGCCTTACAATGATGGTA CAAAATATAATGAAAATTTAAGGGTCGTGTTACCATGAC AAGGGATACATCAACTAGCACTGTCTATATGGAACTGAGC TCTCTCAGGTCCGAGGATACTGCAGTATATTACTGCGCCCG GGAGGGAGGCAACGACTATTACGACACCATGGACTATTGG GGGCAGGGCACACTGGTTACTGTATCCAGCGCCTCTACTA AGGGCCC (SEQ ID NO: 62) |
| huCD123-6 $V_H$Gv6 | AAGCTTGCCACCATGGGCTGGTCCTGTATCATCCTGTTCCT CGTTGCAACAGCAACTGGCGTGCACAGCCAGTTCCAGCTT GTGCAGAGTGGCGCCGAAGTCAAGAAACCAGGCGCTAGTG TCAAGGTGTCCTGTAAGGCATCAGGCTACATCTTTACCAGC TCCATCATGCATTGGGTCAGACAGGCTCCTGGACAGGGCC TGGAGTGGATTGGGTATATCAAGCCATACAATGATGGGAC AAAATACAATGAAAAGTTTAAAGGGCGAGCCACTCTGACA TCTGATCGGAGTACAAGCACTGCCTACATGGAATTGAGCT CACTGCGGTCCGAAGACACTGCTGTGTATTATTGCGCTCGG GAGGGAGGGAACGACTACTACGATACCATGGACTACTGGG GCCAGGGCACCCTGGTTACCGTCAGCAGCGCTTCCACTAA GGGCCC (SEQ ID NO: 64) |
| huCD123-6 $V_H$Gv7 | AAGCTTGCCACCATGGGCTGGTCCTGTATCATCCTGTTCCT CGTTGCAACAGCAACTGGCGTGCACAGCCAGGTCCAACTT GTGCAGAGTGGCGCCGAAGTCAAGAAACCAGGCGCTAGTG TCAAGGTGTCCTGTAAGGCATCAGGCTACATCTTTACCAGC TCCATCATGCATTGGGTCAGACAGGCTCCTGGACAGGGCC TGGAGTGGATTGGGTATATCAAGCCATACAATGATGGGAC AAAATACAATGAAAAGTTTAAAGGGCGAGCCACTCTGACA TCTGATCGGAGTACAAGCACTGCCTACATGGAATTGAGCT CACTGCGGTCCGAAGACACTGCTGTGTATTATTGCGCTCGG GAGGGAGGGAACGACTACTACGATACCATGGACTACTGGG GCCAGGGCACCCTGGTTACCGTCAGCAGCGCTTCCACTAA GGGCCC (SEQ ID NO: 66) |
| huCD123-6 $V_H$rhv1.0 | AAGCTTGCCACCATGGGGTGGAGCTGCATTATTCTGTTCTT GGTCGCCACCGCAACTGGCGTCCACTCTCAGGTCCAGCTC GTCCAGTCTGGGGCAGAAGTGGTCAAGCCCGGTGCATCTG TGAAAATGTCCTGCAAAGCTAGCGGGTATACATTCACATCT AGTATCATGCATTGGATGAAACAGAAGCCTGGCCAGGGTC TGGAGTGGATAGGATATATCAGGCCTTACAACGATGGCAC TCGATACAACCAAAAGTTCCAGGGTAAAGCTACACTGACC TCAGACCGCTCAAGCAGTACAGCAAACATGGAACTGAACA GTCTTACCTCTGAGGACAGTGCCGTTTACTATTGCGCCAGG GAGGGTGGCAATGACTACTATGATACTATGGACTACTGGG GACAGGGTACCTCTGTAACAGTTTCAAGCGCCAGCACTAA GGGCCC (SEQ ID NO: 68) |

TABLE 3B-continued

Selected Heavy Chain Variable Region Nucleic Acid Sequences

| Antibody | VH DNA Sequence (SEQ ID NO) |
|---|---|
| huCD123-6 V$_H$rhv1.1 | AAGCTTGCCACCATGGGCTGGTCTTGTATTATTCTGTTTCT<br>GGTGGCCACCGCAACAGGCGTTCACAGTCAATTCCAGCTG<br>GTCCAGTCCGGCGCCGAGGTTGTCAAACCTGGTGCCAGCG<br>TAAAGATGTCTTGCAAAGCTAGCGGCTATACTTTCACTTCT<br>TCAATTATGCACTGGATGAAGCAAAAGCCTGGACAGGGCC<br>TGGAATGGATCGGCTACATTAAACCTTATAACGACGGCAC<br>AAAGTACAATCAGAAGTTCCAAGGAAAGGCAACCCTGACC<br>TCAGACAAGTCTTCATCCACTGCCAACATGGAACTTAATAG<br>TCTTACCTCTGAGGATTCCGCTGTCTATTATTGCGCTCGGG<br>AGGGGGGGAACGACTATTACGACACCATGGACTACTGGGG<br>ACAGGGCACCAGTGTTACCGTGTCCAGCGCTAGCACCAAG<br>GGCCC (SEQ ID NO: 69) |

* The bolded bases mark the first codon of the mature variable region amino acid sequence

TABLE 4A

Light Chain Variable Region Amino Acid Sequences

| Antibody | Alt Name | VL Amino Acid Sequence (SEQ ID NO) |
|---|---|---|
| CD123-3 | | DIQMTQSPSSLSASLGGKVTITCKASQDINKYIAWYQHKPG<br>KGPRLLIHYTSTLQPGIPSRFSGSGSGRDYSFSISNLEPEDIAT<br>YYCLQYDNLLYTFGGGTKLELKR (SEQ ID NO: 27) |
| CD123-6 | | DIKMTQSPSSMYASLGERVTITCKASQDINSYLSWFQQKPG<br>KSPKTLIYRVNRLVDGVPSRFSGSGSGQDYSLTISSLEYED<br>MGIYYCLQYDAFPYTFGGGTKLEIKR (SEQ ID NO: 29) |
| CD123-14 | | DILLTQSPAILSVSPGTRVSFSCRASQSVGTSIHWYQQRPNG<br>FPRLLIKYASESISGIPSRFSGSGSGTDFTLNINSVESEDIADY<br>YCQQSKSWPLTFGAGTKLELKR (SEQ ID NO: 31) |
| huCD123-6Gv1 | | DIQMTQSPSSLSASVGDRVTITCRASQDINSYLAWFQQKPG<br>KAPKSLIYRVNRLVSGVPSRFSGSGSGTDFTLTISSLQPEDF<br>ATYYCLQYDAFPYTFGQGTKVEIKR (SEQ ID NO: 33) |
| huCD123-6Gv4 | | DIQMTQSPSSLSASVGDRVTITCRASQDINSYLSWFQQKPG<br>KAPKTLIYRVNRLVDGVPSRFSGSGSGNDYTLTISSLQPEDF<br>ATYYCLQYDAFPYTFGQGTKVEIKR (SEQ ID NO: 35) |
| huCD123-6Gv4-NTS3 | | SIQMTQSPSSLSASVGDRVTITCRASQDINSYLSWFQQKPG<br>KAPKTLIYRVNRLVDGVPSRFSGSGSGNDYTLTISSLQPEDF<br>ATYYCLQYDAFPYTFGQGTKVEIKR (SEQ ID NO: 37) |
| huCD123-6r1v1.0 | | DIQMTQSPSSMSASVGERVTITCRASQDINSYLSWFQQKPG<br>KSPKTLIYRVNRLVDGVPSRFSGSGSGQDYSLTISSLEPEDM<br>GIYYCLQYDAFPYTFGQGTKLEIKR (SEQ ID NO: 41) |

TABLE 4B

Selected Light Chain Variable Region Nucleic Acid Sequences

| Antibody | Alt Name | VL DNA Sequence (SEQ ID NO) |
|---|---|---|
| huCD123-6 V$_L$Gv1 | | GAATTCGCCACCATGGGTTGGTCTTGTATAATCCTGTTCC<br>TGGTCGCTACCGCAACAGGGGTTCACTCAGACATCCAGA<br>TGACCCAGAGTCCCTCTTCTCTGAGCGCTTCTGTTGGGG<br>ACCGGGTGACCATCACCTGTCGGGCATCCCAGGACATCA<br>ATTCTTACCTGGCTTGGTTCCAGCAGAAGCCCGGAAAAG<br>CCCCTAAATCTCTCATTTACCGGGTAAACCGTTTGGTCTC<br>CGGAGTGCCTTCAAGGTTTAGTGGATCTGGATCAGGTAC<br>AGACTTCACTCTCACCATAAGCAGCCTGCAACCAGAGGA<br>TTTCGCAACTTACTACTGCTTGCAGTATGACGCCTTCCCT<br>TACACTTTCGGGCAGGGGACCAAAGTGGAAATAAAGCG<br>TACG (SEQ ID NO: 63) |
| huCD123-6 V$_L$Gv4 | | GAATTCGCCACCATGGGTTGGTCCTGTATCATCCTCTTTC<br>TGGTGGCAACTGCAACCGGCGTCCATAGCGACATTCAG<br>ATGACACAGTCTCCTTCTTCCCTGAGCGCCAGCGTCGGG<br>GACCGCGTGACTATACATGTCGGGCCTCCCAGGACATT<br>AACTCTTACCTCTCCTGGTTCCAGCAGAAGCCTGGGAAA |

TABLE 4B-continued

Selected Light Chain Variable Region Nucleic Acid Sequences

| Antibody | Alt Name | VL DNA Sequence (SEQ ID NO) |
|---|---|---|
| | | GCCCCAAAGACACTGATATACAGGGTAAATCGTTTGGTT GACGGTGTACCATCACGATTTTCCGGTAGTGGGTCTGGA AACGATTACACTCTCACAATTAGCAGCCTGCAACCAGAG GACTTTGCAACATACTATTGCCTGCAGTACGATGCTTTTC CTTATACCTTCGGTCAGGGTACCAAGGTGGAAATTAAAC GTACG (SEQ ID NO: 65) |
| huCD123-6V$_L$ (resurfaced) | | GAATTCGCCACCATGGGCTGGTCATGTATTATCCTGTTTC TGGTTGCAACCGCAACAGGAGTACACTCTGATATCCAGA TGACTCAGTCTCCCTCTTCTATGTCTGCTTCTGTGGGAGA GAGAGTCACCATCACCTGTCGCGCTTCCCAAGATATTAA TAGCTATCTGTCTTGGTTCCAACAGAAACCTGGCAAATC ACCCAAGACTCTGATTTATCGGGTTAACCGCCTGGTGGA CGGTGTGCCTTCACGCTTCTCCGGCAGCGGTAGTGGACA AGACTATAGCCTGACAATTTCTTCTCTTGAACCCGAGGA CATGGGAATCTACTATTGCTTGCAGTATGACGCTTTTCCT TATACATTCGGCCAGGGCACAAAGCTGGAAATCAAACG TACG (SEQ ID NO: 67) |

* The bolded bases mark the first codon of the mature variable region amino acid sequence.

In certain embodiments, the anti-CD123/IL-3Rα antibodies and antigen-binding fragments thereof comprises: (a) a V$_H$ sequence at least 95% identical to a reference V$_H$ sequence selected from a group having amino acid sequences represented by SEQ ID NOs: 26, 28, 30, 32, 34, 38, 39, and 40 (or SEQ ID NOs: 26, 28, 30, 32, 34, and 38); and/or (b) a V$_L$ sequence at least 95% identical to a reference V$_L$ sequence selected from the group having amino acid sequences represented by SEQ ID NOs: 27, 29, 31, 33, 35, 37, and 41 (or SEQ ID NOs: 27, 29, 31, 35, and 37).

In certain embodiments, the anti-CD123/IL-3Rα antibodies and antigen-binding fragments thereof comprises: (a) a V$_H$ sequence at least 96% identical to a reference V$_H$ sequence selected from a group having amino acid sequences represented by SEQ ID NOs: 26, 28, 30, 32, 34, 38, 39, and 40 (or SEQ ID NOs: 26, 28, 30, 32, 34, and 38); and/or (b) a V$_L$ sequence at least 96% identical to a reference V$_L$ sequence selected from the group having amino acid sequences represented by SEQ ID NOs: 27, 29, 31, 33, 35, 37, and 41 (or SEQ ID NOs: 27, 29, 31, 35, and 37).

In certain embodiments, the anti-CD123/IL-3Rα antibodies and antigen-binding fragments thereof comprises: (a) a V$_H$ sequence at least 97% identical to a reference V$_H$ sequence selected from a group having amino acid sequences represented by SEQ ID NOs: 26, 28, 30, 32, 34, 38, 39, and 40 (or SEQ ID NOs: 26, 28, 30, 32, 34, and 38); and/or (b) a V$_L$ sequence at least 97% identical to a reference V$_L$ sequence selected from the group having amino acid sequences represented by SEQ ID NOs: 27, 29, 31, 33, 35, 37, and 41 (or SEQ ID NOs: 27, 29, 31, 35, and 37).

In certain embodiments, the anti-CD123/IL-3Rα antibodies and antigen-binding fragments thereof comprises: (a) a V$_H$ sequence at least 98% identical to a reference V$_H$ sequence selected from a group having amino acid sequences represented by SEQ ID NOs: 26, 28, 30, 32, 34, 38, 39, and 40 (or SEQ ID NOs: 26, 28, 30, 32, 34, and 38); and/or (b) a V$_L$ sequence at least 98% identical to a reference V$_L$ sequence selected from the group having amino acid sequences represented by SEQ ID NOs: 27, 29, 31, 33, 35, 37, and 41 (or SEQ ID NOs: 27, 29, 31, 35, and 37).

In certain embodiments, the anti-CD123 antibodies and antigen-binding fragments thereof comprises: (a) a V$_H$ sequence at least 99% identical to a reference V$_H$ sequence selected from a group having amino acid sequences represented by SEQ ID NOs: 26, 28, 30, 32, 34, 38, 39, and 40 (or SEQ ID NOs: 26, 28, 30, 32, 34, and 38); and/or (b) a V$_L$ sequence at least 99% identical to a reference V$_L$ sequence selected from the group having amino acid sequences represented by SEQ ID NOs: 27, 29, 31, 33, 35, 37, and 41 (or SEQ ID NOs: 27, 29, 31, 35, and 37).

In certain embodiments, the CD123/IL-3Rα antibody/antigen-binding fragment thereof having a certain percentage of sequence identity to SEQ ID NOs: 26, 28, 30, 32, 34, 38, 39, and 40 (preferably SEQ ID NOs: 26, 28, 30, 32, 34, and 38) and/or 27, 29, 31, 33, 35, 37, and 41 (or SEQ ID NOs: 27, 29, 31, 35, and 37) differs from SEQ ID NOs: 26, 28, 30, 32, 34, 38, 39, and 40 (or SEQ ID NOs: 26, 28, 30, 32, 34, and 38) and/or 27, 29, 31, 33, 35, 37, and 41 (or SEQ ID NOs: 27, 29, 31, 35, and 37) by conservative amino acid substitutions only, such as 1, 2, or 3 conservative amino acid substitutions. In certain embodiments, the conservative amino acid substitutions are substitutions of 1, 2, or 3 consecutive amino acids in one or more CDR regions of the heavy and/or light chains.

In certain embodiments, the anti-CD123/IL-3Rα antibodies and antigen-binding fragments thereof comprises: (a) a V$_H$ sequence identical to a reference V$_H$ sequence selected from a group having amino acid sequences represented by SEQ ID NOs: 26, 28, 30, 32, 34, 38, 39, and 40 (or SEQ ID NOs: 26, 28, 30, 32, 34, and 38); and/or (b) a V$_L$ sequence identical to a reference V$_L$ sequence selected from the group having amino acid sequences represented by SEQ ID NOs: 27, 29, 31, 33, 35, 37, and 41 (or SEQ ID NOs: 27, 29, 31, 35, and 37).

In certain embodiments, the anti-CD123/IL-3Rα antibodies and antigen-binding fragments thereof comprises: a V$_H$ sequence as set forth in SEQ ID NO: 26, and/or a V$_L$ sequence as set forth in SEQ ID NO: 27.

In certain embodiments, the anti-CD123/IL-3Rα antibodies and antigen-binding fragments thereof comprises: a V$_H$ sequence as set forth in SEQ ID NO: 28, and/or a V$_L$ sequence as set forth in SEQ ID NO: 29.

In certain embodiments, the anti-CD123/IL-3Rα antibodies and antigen-binding fragments thereof comprises: a V$_H$ sequence as set forth in SEQ ID NO: 30, and/or a V$_L$ sequence as set forth in SEQ ID NO: 31.

In certain embodiments, the anti-CD123/IL-3Rα antibodies and antigen-binding fragments thereof comprises: a V$_H$ sequence as set forth in SEQ ID NO: 34, and/or a $V_L$ sequence as set forth in SEQ ID NO: 35.

In certain embodiments, the anti-CD123/IL-3Rα antibodies and antigen-binding fragments thereof comprises a $V_H$ sequence and a $V_L$ sequence with a combination of SEQ ID NOs. selected from the group consisting of: 32/33, 34/33, 38/33, 39/33, 40/33, 32/35, 34/35, 38/35, 39/35, 40/35, 32/37, 34/37, 38/37, 39/37, 40/37, 39/33, 39/35, 39/37, 39/41, 40/33, 40/35, 40/37, and 40/41.

For example, in one embodiment, the anti-CD123/IL-3Rα antibodies and antigen-binding fragments thereof comprises: a) an immunoglobulin heavy chain variable region having the amino acid sequence set forth in SEQ ID NO: 39 or 40; and, b) an immunoglobulin light chain variable region having the amino acid sequence set forth in SEQ ID NO: 41. In certain embodiments, the $V_H$ sequence is set forth in SEQ ID NO: 39, and the $V_L$ sequence is set forth in SEQ ID NO: 41. In certain embodiments, the $V_H$ sequence is set forth in SEQ ID NO: 40, and the $V_L$ sequence is set forth in SEQ ID NO: 41.

In a related embodiment, the anti-CD123/IL-3Rα antibodies and antigen-binding fragments thereof comprises: a) an immunoglobulin heavy chain variable region having the amino acid sequence set forth in SEQ ID NO: 34; and, b) an immunoglobulin light chain variable region having the amino acid sequence set forth in SEQ ID NO: 35. In certain embodiments, Xaa in SEQ ID NO: 34 is Phe (F). In certain embodiments, Xaa in SEQ ID NO: 34 is Val (V).

In another embodiment, the anti-CD123/IL-3Rα antibodies and antigen-binding fragments thereof comprises: a) an immunoglobulin heavy chain variable region having the amino acid sequence set forth in SEQ ID NO: 39 or 40, except that the first residue is replaced by Ser (S); and, b) an immunoglobulin light chain variable region having the amino acid sequence set forth in SEQ ID NO: 41.

In another embodiment, the anti-CD123/IL-3Rα antibodies and antigen-binding fragments thereof comprises: a) an immunoglobulin heavy chain variable region having the amino acid sequence set forth in SEQ ID NO: 39 or 40; and, b) an immunoglobulin light chain variable region having the amino acid sequence set forth in SEQ ID NO: 41, except that the first residue is replaced by Ser (S).

In another embodiment, the anti-CD123/IL-3Rα antibodies and antigen-binding fragments thereof comprises: a) an immunoglobulin heavy chain region having the amino acid sequence set forth in SEQ ID NO: 59 or 60, except that the N-terminal residue is Ser, and except that the residue corresponding to the $5^{th}$ to the last residue of SEQ ID NO: 54 is Cys; and b) an immunoglobulin light chain variable region having the amino acid sequence set forth in SEQ ID NO: 41.

In another embodiment, the anti-CD123/IL-3Rα antibodies and antigen-binding fragments thereof comprises: a) an immunoglobulin heavy chain region having the amino acid sequence set forth in SEQ ID NO: 59 or 60, except that the residue corresponding to the $5^{th}$ to the last residue of SEQ ID NO: 54 is Cys; and b) an immunoglobulin light chain variable region having the amino acid sequence set forth in SEQ ID NO: 41, except that the N-terminal residue is Ser.

In another embodiment, the anti-CD123/IL-3Rα antibodies and antigen-binding fragments thereof comprises: a) an immunoglobulin heavy chain variable region having the amino acid sequence set forth in SEQ ID NO: 38; and, b) an immunoglobulin light chain variable region having the amino acid sequence set forth in SEQ ID NO: 35. In certain embodiments, Xaa in SEQ ID NO: 38 is Phe (F). In certain embodiments, Xaa in SEQ ID NO: 38 is Val (V).

In another embodiment, the anti-CD123/IL-3Rα antibodies and antigen-binding fragments thereof comprises: a) an immunoglobulin heavy chain variable region having the amino acid sequence set forth in SEQ ID NO: 34; and, b) an immunoglobulin light chain variable region having the amino acid sequence set forth in SEQ ID NO: 37. In certain embodiments, Xaa in SEQ ID NO: 34 is Phe (F). In certain embodiments, Xaa in SEQ ID NO: 34 is Val (V).

In another embodiment, the anti-CD123/IL-3Rα antibodies and antigen-binding fragments thereof comprises: a) an immunoglobulin heavy chain region having the amino acid sequence set forth in SEQ ID NO: 56; and, b) an immunoglobulin light chain variable region having the amino acid sequence set forth in SEQ ID NO: 35. In certain embodiments, Xaa in SEQ ID NO: 56 is Phe (F). In certain embodiments, Xaa in SEQ ID NO: 56 is Val (V).

In another embodiment, the anti-CD123/IL-3Rα antibodies and antigen-binding fragments thereof comprises: a) an immunoglobulin heavy chain region having the amino acid sequence set forth in SEQ ID NO: 54; and, b) an immunoglobulin light chain variable region having the amino acid sequence set forth in SEQ ID NO: 37. In certain embodiments, Xaa in SEQ ID NO: 54 is Phe (F). In certain embodiments, Xaa in SEQ ID NO: 54 is Val (V).

In another embodiment, the anti-CD123/IL-3Rα antibodies and antigen-binding fragments thereof comprises: a) an immunoglobulin heavy chain region having the amino acid sequence set forth in SEQ ID NO: 59 or 60, except that the residue corresponding to the $5^{th}$ to the last residue of SEQ ID NO: 54 is Cys; and b) an immunoglobulin light chain variable region having the amino acid sequence set forth in SEQ ID NO: 41.

In another embodiment, the anti-CD123/IL-3Rα antibodies and antigen-binding fragments thereof comprises: a) an immunoglobulin heavy chain region having the amino acid sequence set forth in SEQ ID NO: 54; and, b) an immunoglobulin light chain variable region having the amino acid sequence set forth in SEQ ID NO: 35. In certain embodiments, Xaa in SEQ ID NO: 54 is Phe (F). In certain embodiments, Xaa in SEQ ID NO: 54 is Val (V).

In another embodiment, the anti-CD123/IL-3Rα antibodies and antigen-binding fragments thereof comprises: a) an immunoglobulin heavy chain region having the amino acid sequence set forth in SEQ ID NO: 56; and, b) an immunoglobulin light chain variable region having the amino acid sequence set forth in SEQ ID NO: 35. In certain embodiments, Xaa in SEQ ID NO: 56 is Phe (F). In certain embodiments, Xaa in SEQ ID NO: 56 is Val (V).

In another embodiment, the anti-CD123/IL-3Rα antibodies and antigen-binding fragments thereof comprises: a) an immunoglobulin heavy chain region having the amino acid sequence set forth in SEQ ID NO: 54; and, b) an immunoglobulin light chain variable region having the amino acid sequence set forth in SEQ ID NO: 37. In certain embodiments, Xaa in SEQ ID NO: 54 is Phe (F). In certain embodiments, Xaa in SEQ ID NO: 54 is Val (V).

In certain embodiments, the anti-CD123/IL-3Rα antibodies and antigen-binding fragments thereof specifically binds CD123/IL-3Rα. In certain embodiments, the CD123/IL-3Ra antibody or antigen-binding fragment thereof is a murine, chimeric, humanized, or human antibody or antigen-binding fragment thereof that specifically binds CD123/IL-3Rα. In certain embodiments, the humanized antibody or antigen-binding fragment thereof is a CDR-grafted or resurfaced antibody or antigen-binding fragment thereof.

In certain embodiments, the anti-CD123/IL-3Rα antibodies are full-length antibodies. The full-length antibodies may comprise any of the antibodies above defined by the 1-4 CDR (e.g., CDR1 and CDR2 of the heavy chain; CDR1 and CDR2 of the heavy and light chains), 1-6 CDR sequences (e.g., CDR1-CDR3 of the heavy chain; CDR1-CDR3 of the heavy and light chains), or any of the antibodies above defined by the LCVR and/or the HCVR, or any of the full-length antibodies having a heavy chain sequence in Table 5, or any of the full-length antibodies having a light chain sequence in Table 6, or any of the full-length antibodies having a heavy chain sequence in Table 5 and a light chain sequence in Table 6.

TABLE 5

Full-Length Heavy Chain Amino Acid Sequences

| Antibody | Full-Length Heavy Chain Amino Acid Sequence (SEQ ID NO) |
|---|---|
| CD123-3 | EFQLQQSGPEVVKPGASVKMSCKASGYTFTSYVMHWMKQKPGQGLEWIGY IKPYKDGTKYNEKFKGKATLISDKPSSTAYMELSSLTSEDSAVYYCAREGEN GYYDAMDYWGQGTSVTVSSAKTTPPSVYPLAPGSAAQTNSMVTLGCLVKG YFPEPVTVTWNSGSLSSGVHTFPAVLESDLYTLSSSVTVPSSPRPSETVTCNVA HPASSTKVDKKIVPRDCGCKPCICTVPEVSSVFIFPPKPKDVLTITLTPKVTCV VVDISKDDPEVQFSWFVDDVEVHTAQTQPREEQFNSTFRSVSELPIMHQDWL NGKEFKCRVNSAAFPAPIEKTISKTKGRPKAPQVYTIPPPKEQMAKDKVSLTC MITDFFPEDITVEWQWNGQPAENYKNTQPIMNTNGSYFVYSKLNVQKSNWE AGNTFTCSVLHEGLHNHEITEKSLSHSPGK (SEQ ID NO: 42) |
| CD123-6 | EFQLQQSGPELVKPGASVKMSCKASGYIFTSSIMHWMKQKPGQGLEWIGYIK PYNDGTKYNEKFKGKATLTSDKSSSTANMELNSLTSEDSAVYYCAREGGND YYDTMDYWGQGTSVTVSSAKTTPPSVYPLAPGSAAQTNSMVTLGCLVKGYF PEPVTVTWNSGSLSSGVHTFPAVLESDLYTLSSSVTVPSSMRPSETVTCNVAH PASSTKVDKKIVPRDCGCKPCICTVPEVSSVFIFPPKPKDVLTITLTPKVTCVV VDISKDDPEVQFSWFVDDVEVHTAQTQPREEQFNSTFRSVSELPIMHQDWLN GKEFKCRVNSAAFPAPIEKTISKTKGRPKAPQVYTIPPPKEQMAKDKVSLTCM ITDFFPEDITVEWQWNGQPAENYKNTQPIMNTNGSYFVYSKLNVQKSNWEA GNTFTCSVLHEGLHNHHTEKSLSHSPGK (SEQ ID NO: 44) |
| CD123-14 | EVKLVESGGDLVKPGGSLKLSCAASGFTFSNYAMSWVRQNSEKRLEWVATI NSGGSFTYYPDSVKGRFTISRDNAKDSLYLQMSSLNSEDTAMYYCARQSEAY YGYDKRTWFAYWGQGTLVTVSSAKTTPPSVYPLAPGSAAQTNSMVTLGCLV KGYFPEPVTVTWNSGSLSSGVHTFPAVLESDLYTLSSSVTVPSSPRPSETVTCN VAHPASSTKVDKKIVPRDCGCKPCICTVPEVSSVFIFPPKPKDVLTITLTPKVT CVVVDISKDDPEVQFSWFVDDVEVHTAQTQPREEQFNSTFRSVSELPIMHQD WLNGKEFKCRVNSAAFPAPIEKTISKTKGRPKAPQVYTIPPPKEQMAKDKVSL TCMITDFFPEDITVEWQWNGQPAENYKNTQPIMNTNGSYFVYSKLNVQKSN WEAGNTFTCSVLHEGLHNHHTEKSLSHSPGK (SEQ ID NO: 46) |
| huCD123-6Gv1 | QVQLVQSGAEVKKPGASVKVSCKASGYGFTSSIMHWVRQAPGQGLEWMGY IKPYNDGTKYNEKFKGRVTMTRDTSTSTVYMELSSLRSEDTAVYYCAREGG NDYYDTMDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYSK LTVDKSRWQQGNVFSCSVMHEALHNHYTQKSLSLSPG (SEQ ID NO: 48) |
| huCD123-6Gv6/7 | QXQLVQSGAEVKKPGASVKVSCKASGYIFTSSIMHWVRQAPGQGLEWIGYIK PYNDGTKYNEKFKGRATLTSDRSTSTAYMELSSLRSEDTAVYYCAREGGND YYDTMDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTV LHQDWLNGKEYKCKVSNKALPAPIEKTISKAKGQPREPQVYTLPPSRDELTK NQVSLTCLVKGFYPSDIAVEWESNGQPENNYKTTPPVLDSDGSFFLYSKLTV DKSRWQQGNVFSCSVMHEALHNHYTQKSLSLSPG (SEQ ID NO: 50) |
| huCD123-6 Gv6/7-NTS2 (or "S2") | SXQLVQSGAEVKKPGASVKVSCKASGYIFTSSIMEIWVRQAPGQGLEWIGYIK PYNDGTKYNEKFKGRATLTSDRSTSTAYMELSSLRSEDTAVYYCAREGGND YYDTMDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTV LHQDWLNGKEYKCKVSNKALPAPIEKTISKAKGQPREPQVYTLPPSRDELTK NQVSLTCLVKGFYPSDIAVEWESNGQPENNYKTTPPVLDSDGSFFLYSKLTV DKSRWQQGNVFSCSVMHEALHNHYTQKSLSLSPG (SEQ ID NO: 53) |
| huCD123-6 Gv6/7-CysMab | QXQLVQSGAEVKKPGASVKVSCKASGYIFTSSIMHWVRQAPGQGLEWIGYIK PYNDGTKYNEKFKGRATLTSDRSTSTAYMELSSLRSEDTAVYYCAREGGND YYDTMDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTV LHQDWLNGKEYKCKVSNKALPAPIEKTISKAKGQPREPQVYTLPPSRDELTK |

TABLE 5-continued

Full-Length Heavy Chain Amino Acid Sequences

| Antibody | Full-Length Heavy Chain Amino Acid Sequence (SEQ ID NO) |
|---|---|
| | NQVSLTCLVKGFYPSDIAVEWESNGQPENNYKTTPPVLDSDGSFFLYSKLTV<br>DKSRWQQGNVFSCSVMHEALHNHYTQKSLCLSPG (SEQ ID NO: 54) |
| huCD123-<br>6 Gv6/7S2-<br>CysMab | SXQLVQSGAEVKKPGASVKVSCKASGYIFTSSIMHWVRQAPGQGLEWIGYIK<br>PYNDGTKYNEKFKGRATLTSDRSTSTAYMELSSLRSEDTAVYYCAREGGND<br>YYDTMDYWGQGTLVTVSSASTKGPSVFPLAPSSKSTSGGTAALGCLVKDYFP<br>EPVTVSWNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTLMISRTPE<br>VTCVVVDVSHEDPEVKFNWYVDGVEVHNAKTKPREEQYNSTYRVVSVLTV<br>LHQDWLNGKEYKCKVSNKALPAPIEKTISKAKGQPREPQVYTLPPSRDELTK<br>NQVSLTCLVKGFYPSDIAVEWESNGQPENNYKTTPPVLDSDGSFFLYSKLTV<br>DKSRWQQGNVFSCSVMHEALHNHYTQKSLCLSPG (SEQ ID NO: 56) |
| huCD123-<br>6rhv1.0 | QVQLVQSGAEVVKPGASVKMSCKASGYTFTSSIMHWMKQKPGQGLEWIGYI<br>RPYNDGTRYNQKFQGKATLTSDRSSSTANMELNSLTSEDSAVYYCAREGGN<br>DYYDTMDYWGQGTSVTVSSASTKGPSVFPLAPSSKSTSGGTAALGCLVKDY<br>FPEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMISR<br>TPEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRDE<br>LTKNQVSLTCLVKGFYPSDIAVEWESNGQPENNYKTTPPVLDSDGSFFLYSKL<br>TVDKSRWQQGNVFSCSVMHEALHNHYTQKSLSLSPG (SEQ ID NO: 59) |
| huCD123-<br>6rhv1.1 | QFQLVQSGAEVVKPGASVKMSCKASGYTFTSSIMHWMKQKPGQGLEWIGYI<br>KPYNDGTKYNQKFQGKATLTSDKSSTANMELNSLTSEDSAVYYCAREGGN<br>DYYDTMDYWGQGTSVTVSSASTKGPSVFPLAPSSKSTSGGTAALGCLVKDY<br>FPEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMISR<br>TPEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRDE<br>LTKNQVSLTCLVKGFYPSDIAVEWESNGQPENNYKTTPPVLDSDGSFFLYSKL<br>TVDKSRWQQGNVFSCSVMHEALHNHYTQKSLSLSPG (SEQ ID NO: 60) |

\* In all sequences above in which the $2^{nd}$ residue from the N-terminus is X (or Xaa),
e.g., SEQ ID NOs: 50, 53, 54, and 56, X is F for Gv6 sequences, while X is V for
Gv7 sequences. In some embodiments, the Met (bolded) in SEQ ID NO: 44 is Pro.

TABLE 6

Full-Length Light Chain Amino Acid Sequences

| Antibody | Full-length Light Chain Amino Acid Sequence (SEQ ID NO) |
|---|---|
| CD123-3 | DIQMTQSPSSLSASLGGKVTITCKASQDINKYIAWYQHKPGKGPRLLIHYTS<br>TLQPGIPSRFSGSGSGRDYSFSISNLEPEDIATYYCLQYDNLLYTFGGGTKLE<br>LKRADAAPTVSIFPPSSEQLTSGGASVVCFLNNFYPKDINVKWKIDGSERQN<br>GVLNSWTDQDSKDSTYSMSSTLTLTKDEYERHNSYTCEATFIKTSTSPIVKS<br>FNRNEC (SEQ ID NO: 43) |
| CD123-6 | DIKMTQSPSSMYASLGERVTITCKASQDINSYLSWFQQKPGKSPKTLIYRVN<br>RLVDGVPSRFSGSGSGQDYSLTISSSLEYEDMGIYYCLQYDAFPYTFGGGTK<br>LEIKRADAAPTVSIFPPSSEQLTSGGASVVCFLNNFYPKDINVKWKIDGSER<br>QNGVLNSWTDQDSKDSTYSMSSTLTLTKDEYERHNSYTCEATHKTSTSPIV<br>KSFNRNEC (SEQ ID NO: 45) |
| CD123-14 | DILLTQSPAILSVSPGTRVSFSCRASQSVGTSIHWYQQRPNGFPRLLIKYASE<br>SISGIPSRFSGSGSGTDFTLNINSVESEDIADYYCQQSKSWPLTFGAGTKLEL<br>KRADAAPTVSIFPPSSEQLTSGGASVVCFLNNFYPKDINVKWKIDGSERQN<br>GVLNSWTDQDSKDSTYSMSSTLTLTKDEYERHNSYTCEATEIKTSTSPIVKS<br>FNRNEC (SEQ ID NO: 47) |
| huCD123-<br>6Gv1 | DIQMTQSPSSLSASVGDRVTITCRASQDINSYLAWFQQKPGKAPKSLIYRVN<br>RLVSGVPSRFSGSGSGTDFTLTISSLQPEDFATYYCLQYDAFPYTFGQGTKV<br>EIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVT<br>KSFNRGEC (SEQ ID NO: 49) |
| huCD123-<br>6Gv4 | DIQMTQSPSSLSASVGDRVTITCRASQDINSYLSWFQQKPGKAPKTLIYRVN<br>RLVDGVPSRFSGSGSGNDYTLTISSLQPEDFATYYCLQYDAFPYTFGQGTK<br>VEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPV<br>TKSFNRGEC (SEQ ID NO: 51) |

TABLE 6-continued

Full-Length Light Chain Amino Acid Sequences

| Antibody | Full-length Light Chain Amino Acid Sequence (SEQ ID NO) |
|---|---|
| huCD123-6Gv4-NTS3 (or "S3") | SIQMTQSPSSLSASVGDRVTITCRASQDINSYLSWFQQKPGKAPKTLIYRVN RLVDGVPSRFSGSGSGNDYTLTISSLQPEDFATYYCLQYDAFPYTFGQGTK VEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPV TKSFNRGEC (SEQ ID NO: 58) |
| huCD123-6rlv1.0 | DIQMTQSPSSMSASVGERVTITCRASQDINSYLSWFQQKPGKSPKTLIYRVN RLVDGVPSRFSGSGSGQDYSLTISSLEPEDMGIYYCLQYDAFPYTFGQGTKL EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC (SEQ ID NO: 61) |

In certain embodiments, the anti-CD123/IL-3Rα antibodies are full-length antibodies comprising: (a) a heavy chain having at least about 90%, 95%, 96%, 97%, 98%, or 99% sequence identity to any of the full-length heavy chain sequences above, such as any of the full-length heavy chain sequences in Table 5; and/or (b) a light chain having at least about 90%, 95%, 96%, 97%, 98%, or 99% sequence identity to any of the full-length light chain sequences above, such as any of the full-length light chain sequences in Table 6. In certain embodiments, the anti-CD123/IL-3Rα antibodies are full-length antibodies comprising a full-length heavy chain sequence and a full-length light chain sequence combination selected from the group consisting of SEQ ID NOs: 42/43, 44/45, 46/47, 48/49, 50/49, 53/49, 54/49, 56/49, 59/49, 60/49, 48/51, 50/51, 53/51, 54/51, 56/51, 59/51, 60/51, 48/58, 50/58, 53/58, 54/58, 56/58, 59/58, 60/58, 59/49, 59/51, 59/58, 59/61, 60/49, 60/51, 60/58, and 60/61, or antibodies with at least about 90%, 95%, 96%, 97%, 98%, or 99% sequence identity to any of the full-length heavy chain sequences and/or light chain sequences thereof.

In certain embodiments, the anti-CD123/IL-3Rα antibodies are full-length antibodies comprising a full-length heavy chain sequence and a full-length light chain sequence combination selected from the group consisting of SEQ ID NOs: 59/61, and 60/61, or antibodies with at least about 90%, 95%, 96%, 97%, 98%, or 99% sequence identity to any of the full-length heavy chain sequences and/or light chain sequences thereof. Such antibodies may further comprise engineered N-terminal Ser/Thr in the light chain, heavy chain, or both. Such antibodies may further comprise engineered Cys in the heavy chain CH3 domain in a position corresponding to the 5$^{th}$ to the last Cys of SEQ ID NO: 54.

In certain embodiments, the anti-CD123/IL-3Rα antibody is a murine, chimeric, humanized, or human antibody that specifically binds CD123/IL-3Rα. In certain embodiments, the anti-CD123/IL-3Rα antibody having a certain percentage of sequence identity to any of the full-length SEQ ID NOs differs from such SEQ ID NOs by conservative amino acid substitutions only, e.g., by 1, 2, 3, 4, or 5 consecutive conservative amino acid substitutions only. In certain embodiments, the conservative amino acid substitutions are outside the CDRs.

In certain embodiments, the antigen-binding fragment thereof is or comprises a Fab, Fd, Fab', F(ab')$_2$, single chain Fv or scFv, disulfide linked Fv, V-NAR domain, IgNar, intrabody, IgGΔCH2, minibody, F(ab')$_3$, tetrabody, triabody, diabody, single-domain antibody, DVD-Ig, Fcab, mAb2, (scFv)$_2$, or scFv-Fc, of any one of the above antibodies.

In a related aspect, the invention also provides a polypeptide comprising any of the antibodies or antigen-binding fragments thereof, any of the V$_H$ and/or V$_L$ sequences above, any of the HCVR and/or LCVR above, or any of the CDR sequence(s) of the HCVR and/or LCVR above. The polypeptide maybe, for example, a fusion with a non-antibody protein or domain. In certain embodiments, the fusion protein is not a fusion with a *pseudomonas* toxin.

The affinity or avidity of an antibody for an antigen can be determined experimentally using any suitable method well known in the art, e.g., flow cytometry, enzyme-linked immunoabsorbent assay (ELISA), or radioimmunoassay (RIA), or kinetics (e.g., BIACORE™ analysis). Direct binding assays as well as competitive binding assay formats can be readily employed. See, for example, Berzofsky et al., "Antibody-Antigen Interactions," in *Fundamental Immunology*, Paul, W. E., Ed., Raven Press: New York, N.Y. (1984); Kuby, Janis *Immunology*, W. H. Freeman and Company: New York, N.Y. (1992); and methods described herein.

The measured affinity of a particular antibody-antigen interaction can vary if measured under different conditions (e.g., salt concentration, pH, temperature). Thus, measurements of affinity and other antigen-binding parameters (e.g., $K_D$ or $K_d$, $k_{on}$, $k_{off}$) are made with standardized solutions of antibody and antigen, and a standardized buffer, as known in the art and such as the buffer described herein.

In one aspect, binding assays can be performed using flow cytometry on cells expressing the CD123/IL-3Rα antigen on the surface. For example, CD123/IL-3Rα-positive cells can be incubated with varying concentrations of anti-CD123/IL-3Rα antibodies using 1×10$^5$ cells per sample in 100 μL FACS buffer (e.g., RPMI-1640 medium supplemented with 2% normal goat serum). Then, the cells can be pelleted, washed, and incubated for 1 hr with 100 μL of FITC-conjugated goat-anti-mouse or goat-anti-human IgG-antibody (such as is obtainable from, for example Jackson Laboratory, 6 μg/mL in FACS buffer). The cells are then pelleted again, washed with FACS buffer and resuspended in 200 μL of PBS containing 1% formaldehyde. Samples can be acquired, for example, using a FACSCalibur flow cytometer with the HTS multiwell sampler and analyzed using CellQuest Pro (all from BD Biosciences, San Diego, US). For each sample the mean fluorescence intensity for FL1 (MFI) can be exported and plotted against the antibody concentration in a semi-log plot to generate a binding curve. A sigmoidal dose-response curve is fitted for binding curves and EC$_{50}$ values are calculated using programs such as GraphPad Prism v4 with default parameters (GraphPad software, San Diego, CA). EC$_{50}$ values can be used as a measure for the apparent dissociation constant "$K_d$" or "$K_D$" for each antibody.

Monoclonal antibodies can be prepared using hybridoma methods, such as those described by Kohler and Milstein (1975) Nature 256:495. Using the hybridoma method, a mouse, hamster, or other appropriate host animal, is immunized to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g., radioimmunoassay (MA); enzyme-linked immunosorbent assay (ELISA)) can then be propagated either in vitro culture using standard methods (Goding, *Monoclonal Antibodies: Principles and Practice*, Academic Press, 1986) or in vivo as ascites tumors in an animal. The monoclonal antibodies can then be purified from the culture medium or ascites fluid as described for polyclonal antibodies.

Alternatively monoclonal antibodies can also be made using recombinant DNA methods as described in U.S. Pat. No. 4,816,567. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., Nature 348:552-554, 1990; Clackson et al., Nature, 352:624-628, 1991; and Marks et al., *J. Mol. Biol.* 222:581-597, 1991).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody, or, 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the human CD123/IL-3Rα is a humanized antibody. In certain embodiments, such antibodies are used therapeutically to reduce antigenicity and HAMA (human anti-mouse antibody) responses when administered to a human subject.

Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing CD123/IL-3Rα binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the antigen CD123/IL-3Rα and other favorable biological properties. To achieve this goal, humanized (or human) or engineered anti-CD123/IL-3Rα antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as CD123/IL-3Rα. In this way, framework (FR) residues can be selected and combined from the consensus and import sequences so that the desired antibody characteristic, such as increased affinity for the target antigen(s), is achieved.

Humanization, resurfacing or engineering of antibodies of the present invention can be performed using any known method, such as but not limited to those described in, Winter (Jones et al., Nature 321:522, 1986; Riechmann et al., Nature 332:323, 1988; Verhoeyen et al., Science 239:1534, 1988, Sims et al., *J. Immunol.* 151:2296, 1993; Chothia and Lesk, *J. Mol. Biol.* 196:901, 1987, Carter et al., *Proc. Natl. Acad. Sci. U.S.A.* 89:4285, 1992; Presta et al., *J. Immunol.* 151:2623, 1993; Raguska et al., *Proc. Natl. Acad. Sci. U.S.A.* 91(3):969-973, 1994; U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567; PCT/: US98/16280; US96/18978; US91/09630; US91/05939; US94/01234; GB89/01334; GB91/01134; GB92/01755; WO90/14443; WO90/14424; WO90/14430; EP 229246; 7,557,189; 7,538,195; and 7,342,110, each of which is entirely incorporated herein by reference, including the references cited therein.

In certain alternative embodiments, the antibody to CD123/IL-3Rα is a human antibody. Human antibodies can be directly prepared using various techniques known in the art. Immortalized human B lymphocytes immunized in vitro or isolated from an immunized individual that produce an antibody directed against a target antigen can be generated (See, e.g., Cole et al., *Monoclonal Antibodies and Cancer Therapy*, Alan R. Liss, p. 77 (1985); Boemer et al., 1991, *J. Immunol*, 147 (1):86-95; and U.S. Pat. No. 5,750,373). Also, the human antibody can be selected from a phage library, where that phage library expresses human antibodies, as described, for example, in Vaughan et al., *Nat. Biotech.* 14:309-314, 1996, Sheets et al., *Proc. Nat'l. Acad. Sci.*

95:6157-6162, 1998, Hoogenboom and Winter, *J. Mol. Biol.* 227:381, 1991, and Marks et al., *J. Mol. Biol.* 222:581, 1991). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., *J. Mol. Bio.* doi: 10.1016/j.jmb.2007.12.018, 2007 (each of which is incorporated by reference in its entirety). Affinity maturation strategies and chain shuffling strategies (Marks et al., *Bio/Technology* 10:779-783, 1992, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments are provided an antibody fragment to, for example, increase tumor penetration. Various techniques are known for the production of antibody fragments. Traditionally, these fragments are derived via proteolytic digestion of intact antibodies (for example Morimoto et al., *Journal of Biochemical and Biophysical Methods* 24: 107-117, 1993; Brennan et al., *Science* 229:81, 1985). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from antibody phage libraries. The antibody fragment can also be linear antibodies as described in U.S. Pat. No. 5,641,870, for example, and can be monospecific or bispecific. Other techniques for the production of antibody fragments will be apparent to the skilled practitioner.

For the purposes of the present invention, it should be appreciated that modified antibodies can comprise any type of variable region that provides for the association of the antibody with the polypeptides of a human CD123/IL-3Rα. In this regard, the variable region can comprise or be derived from any type of mammal that can be induced to mount a humoral response and generate immunoglobulins against the desired tumor associated antigen. As such, the variable region of the modified antibodies can be, for example, of human, murine, non human primate (e.g., cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and in certain embodiments from an antibody from a different species. It may not be necessary to replace all of the CDRs with the complete CDRs from the donor variable region to transfer the antigen-binding capacity of one variable domain to another. Rather, it may only be necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein can comprise alterations or modifications to one or more of the three heavy chain constant domains (CH1, CH2, or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ACH2 constructs). In some embodiments, the omitted constant region domain will be replaced by a short amino acid spacer (e.g., 10 residues) that provides some of the molecular flexibility typically imparted by the absent constant region.

It will be noted that in certain embodiments, the modified antibodies can be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies of the present invention can be provided by the partial deletion or substitution of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g., complement C1Q binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified, e.g., through the mutation or substitution of one or more amino acids, which may enhance the profile of the resulting construct. In this respect it may be possible to disrupt the activity provided by a conserved binding site (e.g., Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art, such as those defined hereinabove.

The polypeptides of the present invention can be recombinant polypeptides, natural polypeptides, or synthetic polypeptides comprising an antibody, or fragment thereof, against a human CD123/IL-3Rα. It will be recognized in the art that some amino acid sequences of the invention can be varied without significant effect of the structure or function of the protein. Thus, the invention further includes variations of the polypeptides which show substantial activity or which include regions of an antibody, or fragment thereof, against a CD123 antigen, such as a human CD123. Such mutants include deletions, insertions, inversions, repeats, and type substitutions.

The polypeptides and analogs can be further modified to contain additional chemical moieties not normally part of the protein. Those derivatized moieties may improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, PA (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., *Proc. Nat'l. Acad. Sci. USA* 81:5662 5066, 1984, and U.S. Pat. No. 4,588,585.

In some embodiments a DNA sequence encoding a polypeptide of interest (e.g., antibody, antigen-binding fragment, or polypeptide of the invention) would be completely or partially constructed by chemical synthesis using an oligo-nucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human CD123/IL-3Rα. Recombinant expression vectors are replicable DNA constructs which have synthetic or cDNA-derived DNA fragments encoding a polypeptide chain of an anti-CD123/IL-3Rα antibody, or fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a CD123/IL-3Rα-binding polypeptide or antibody (or a CD123/IL-3Rα protein to use as an antigen) include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin, such as CHO cells. Cell-free translation systems could also be employed. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23: 175, 1981), and other cell lines including, for example, L cells, CI 27, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *Bio/Technology* 6:47 (1988).

Thus one aspect of the invention also provides a cell producing any one of the subject antibody or antigen-binding fragment thereof, or any one of the subject polypeptide. In certain embodiments, the cell is a mammalian cell. In certain embodiments, the cell is a HEK-293 or HEK-293T cell, a COS-7 cell, an L cell, a CI 27 cell, a 3T3 cell, a Chinese hamster ovary (CHO) cell, a HeLa cell, or a BHK cell. In certain embodiments, the cell is a CHO cell.

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a CD123/IL-3Ra-binding agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

In certain embodiments, the CD123/IL-3Rα-binding agent of the present invention have a N-terminal serine, which can be oxidized with an oxidizing agent to form an oxidized CD123/IL-3Rα-binding agent having a N-terminal aldehyde group.

Any suitable oxidizing agent can be used in step (a) of the methods described above. In certain embodiments, the oxidizing agent is a periodate. More specifically, the oxidizing agent is sodium periodate.

Excess molar equivalents of the oxidizing agent relative to the CD123/IL-3Rα-binding agent can be used. In certain embodiments, about 2-100, 5-80, 10-50, 1-10 or 5-10 molar equivalents of the oxidizing agent can be used. In certain embodiments, about 10 or about 50 equivalents of the oxidizing agent can be used. When large amount of the oxidizing agent is used, short reaction time is used to avoid over-oxidation. For example, when 50 equivalents of the oxidizing agent is used, the oxidation reaction is carried out for about 5 to about 60 minutes. Alternatively, when 10 equivalents of the oxidizing agent is used, the reaction is carried out for about 30 minutes to about 24 hours. In one embodiment, 5-10 molar equivalents of the oxidizing agent is used and the oxidation reaction is carried out for about 5 to about 60 minutes (e.g., about 10 to about 30 minutes, about 20 to about 30 minutes).

In certain embodiments, the oxidation reaction does not lead to significant non-targeted oxidation. For example, no signification extent (e.g., less than 20%, less than 10%, less than 5%, less than 3%, less than 2% or less than 1%) of methionine and/or glycans are oxidized during the oxidation process of N-terminal serine to generate the oxidized CD123/IL-3Rα-binding agent having a N-terminal aldehyde group.

In certain embodiments, the CD123/IL-3Rα-binding agent of the present invention have a recombinantly engineered Cys residue, such as a Cys residue corresponding to the $5^{th}$ to the last Cys in, for example, SEQ ID NO: 54 or 56 (i.e, a Cys residue at EU/OU numbering position 442). Thus the term "cysteine engineered antibody" includes an antibody with at least one Cys that is not normally present at a given residue of the antibody light chain or heavy chain. Such Cys, which may also be referred to as "engineered Cys," can be engineered using any conventional molecular biology or recombinant DNA technology (e.g., by replacing the coding sequence for a non-Cys residue at the target residue with a coding sequence for Cys). For example, if the original residue is Ser with a coding sequence of 5'-UCU-3', the coding sequence can be mutated (e.g., by site-directed mutagenesis) to 5'-UGU-3', which encodes Cys. In certain embodiments, the Cys engineered antibody of the invention has an engineered Cys in the heavy chain. In certain embodiments, the engineered Cys is in or near the $CH_3$ domain of the heavy chain. In certain embodiments, the engineered Cys corresponding to the 5th to the last Cys in, for example, SEQ ID NO: 54 or 56. The engineered antibody heavy (or light) chain sequence can be inserted into a suitable recombinant expression vector to produce the engineered antibody having the engineered Cys residue in place of the original Ser residue.

3. Immunoconjugates

In a second aspect, the present invention also provides immunoconjugates comprising CD123/IL-3Rα-binding agents described herein covalently linked to one or more molecules of the cytototoxic agents described herein.

In a first embodiments, the immuoconjugate of the present invention comprises a CD123/IL-3Rα-binding agents (including antibody, antigen-binding fragment thereof, or polypeptide comprising the antibody or antigen-binding fragment thereof) described herein covalently linked to a cytotoxic agent described herein through the ε-amino group of one or more lysine residues located on the CD123/IL-3Rα-binding agents.

In a 1st specific embodiment of the first embodiment, the immunoconjugate of the present invention is represented by the following formula:

(L1), wherein:
CBA is a CD123/IL-3Rα-binding agent (e.g. a subject antibody or antigen-binding fragment thereof described herein above, or a subject polypeptide thereof described above), that is covalently linked through a lysine residue to $Cy^{L1}$;
$W_L$ is an integer from 1 to 20; and
$Cy^{L1}$ is a cytotoxic compound represented by the following formula:

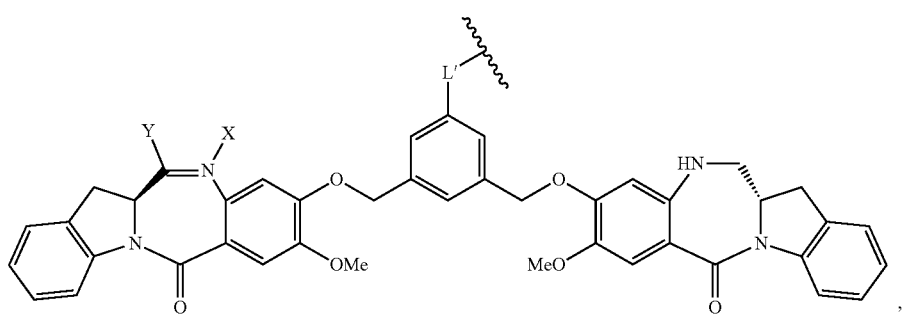
(L1a)

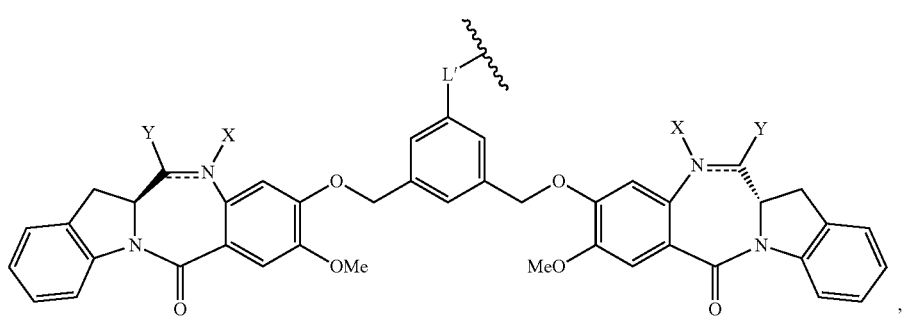
(L1a1)

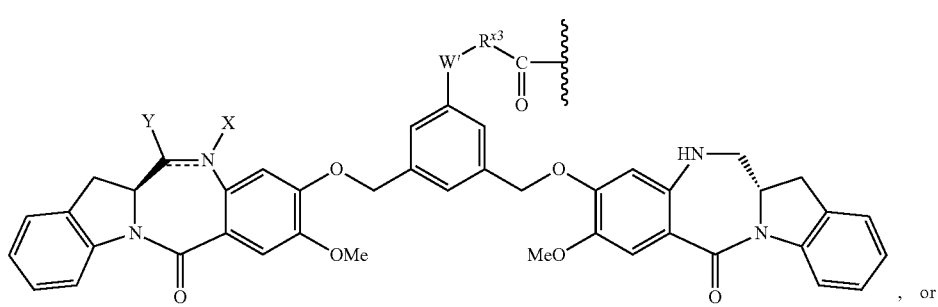
(L1b)

, or (L1b1)

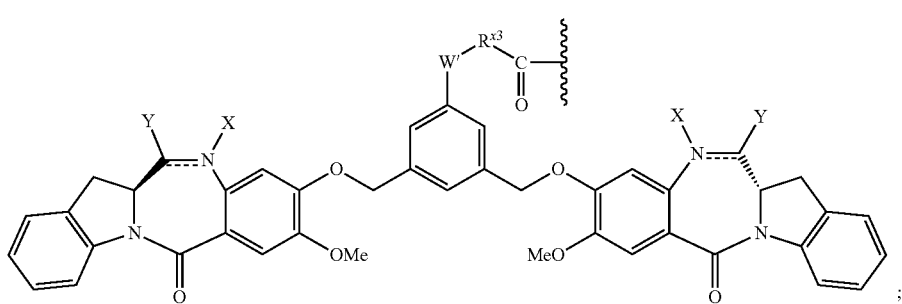

or a pharmaceutically acceptable salt thereof, wherein:
the double line $\doubleequal$ between N and C represents a single bond or a double bond, provided that when it is a double bond, X is absent and Y is —H or a ($C_1$-$C_4$) alkyl; and when it is a single bond, X is —H or an amine protecting moiety, and Y is —OH or —$SO_3$M;
W' is —$NR^e$,
$R^{e'}$ is —($CH_2$—$CH_2$—O)$_n$—$R^k$;
n is an integer from 2 to 6;
$R^k$ is —H or -Me;
$R^{x3}$ is a ($C_1$-$C_6$)alkyl;
L' is represented by the following formula:

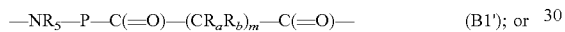  (B1'); or

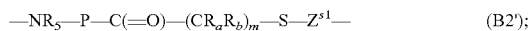  (B2');

$R_5$ is —H or a ($C_1$-$C_3$)alkyl;
P is an amino acid residue or a peptide containing between 2 to 20 amino acid residues;
$R_a$ and $R_b$, for each occurrence, are each independently —H, ($C_1$-$C_3$)alkyl, or a charged substituent or an ionizable group Q;
m is an integer from 1 to 6; and
$Z^{s1}$ is selected from any one of the following formulas:

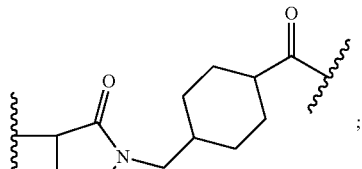 (b1)

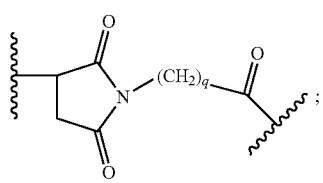 (b2)

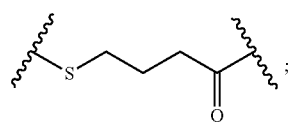 (b3)

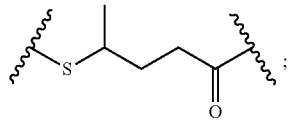 (b4)

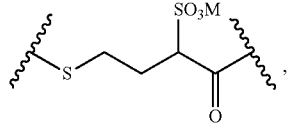 (b5)

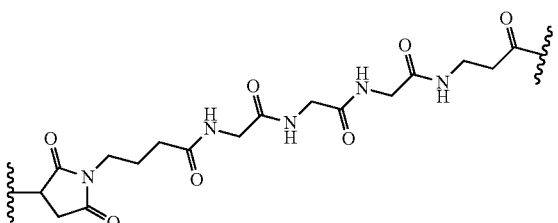 (b6)

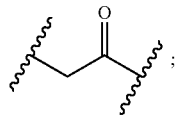 (b7)

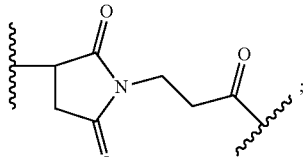 (b8)

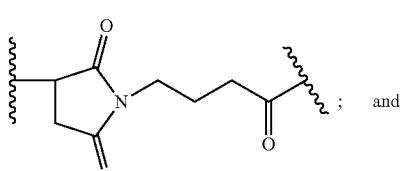 (b9) ; and

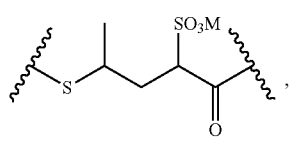 (b10)

wherein:
q is an integer from 1 to 5; and
M is $H^+$ or a cation.

In a 2nd specific embodiment, for conjugates of formula (L1), $Cy^{L1}$ is represented by formula (L1a) or (L1a1); and the remaining variables are as described above in the 1st specific embodiment.

In a 3rd specific embodiment, for conjugates of formula (L1), $Cy^{L1}$ is represented by formula (L1b) or (L1b1); and the remaining variables are as described above in the 1st specific embodiment. More specifically, $R^{x3}$ is a $(C_2-C_4)$ alkyl.

In a 4th specific embodiment, for conjugates of formula (L1), $Cy^{L1}$ is represented by formula (L1a); $R_a$ and $R_b$ are both H; $R_5$ is H or Me, and the remaining variables are as described above in the 1st specific embodiment.

In a 5th specific embodiment, P is a peptide containing 2 to 5 amino acid residues; and the remaining variables are described above in the 1st, 2nd or 4th specific embodiment. In a more specific embodiment, P is selected from the group consisting of Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 55), β-Ala-Leu-Ala-Leu (SEQ ID NO: 57), Gly-Phe-Leu-Gly (SEQ ID NO: 73), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. More specifically, P is Gly-Gly-Gly, Ala-Val, Ala-Ala, Ala-D-Ala, D-Ala-Ala, or D-Ala-D-Ala.

In a 6th specific embodiment, Q is —SO$_3$M; and the remaining variables are as described above in the 1st, 2nd, 4th or 5th specific embodiment or any more specific embodiments described therein.

In a 7th specific embodiment, the immunoconjugate of the first embodiment is represented by the following formula:

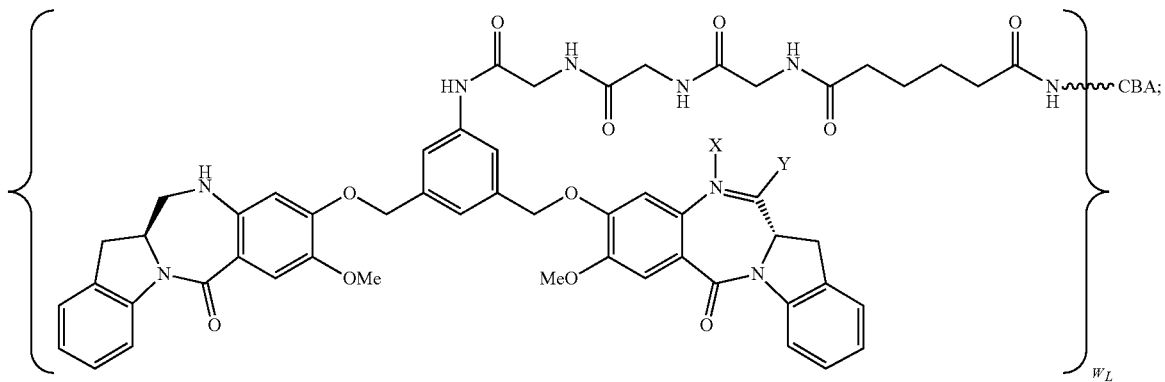

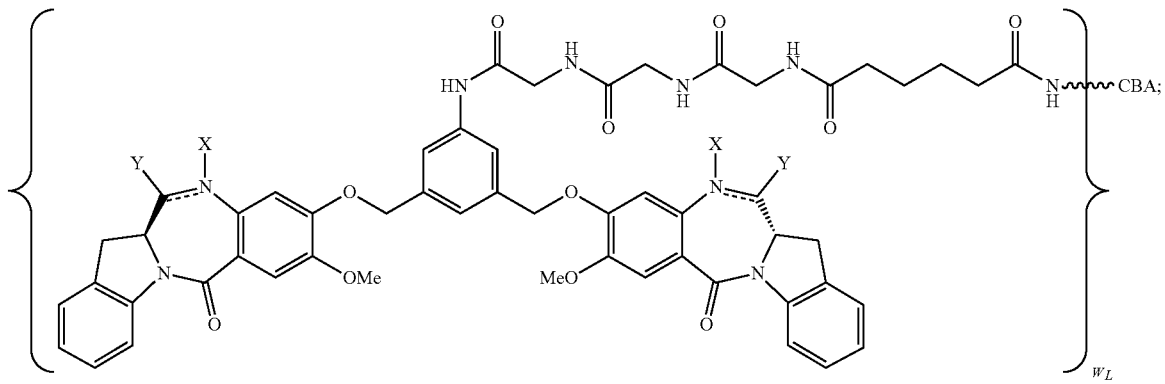

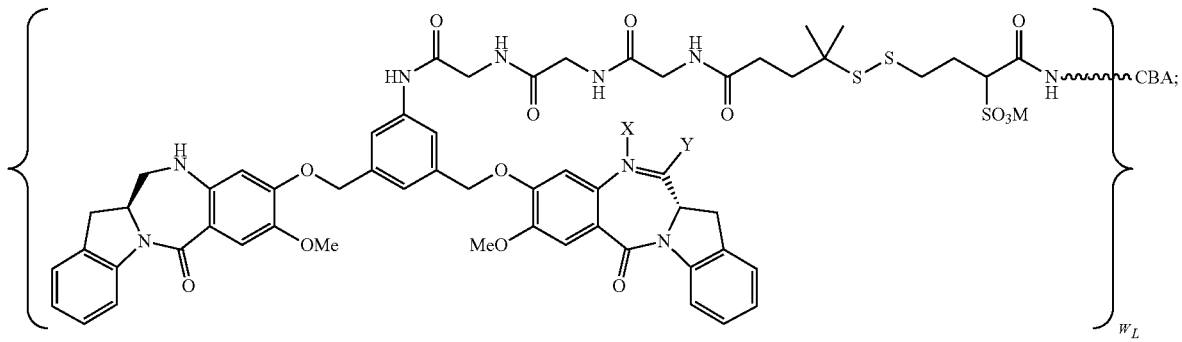

175 176
-continued
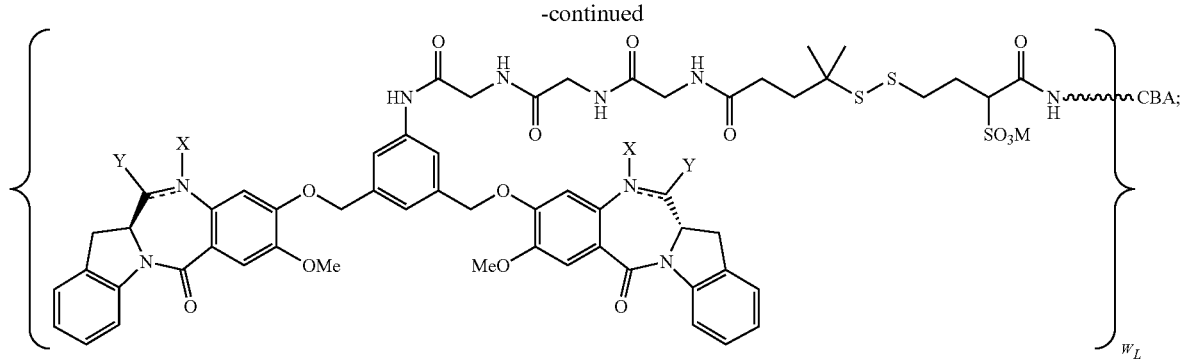
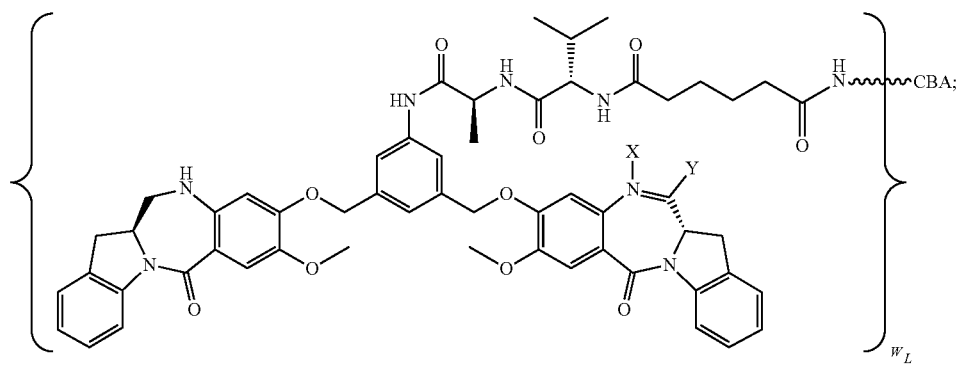
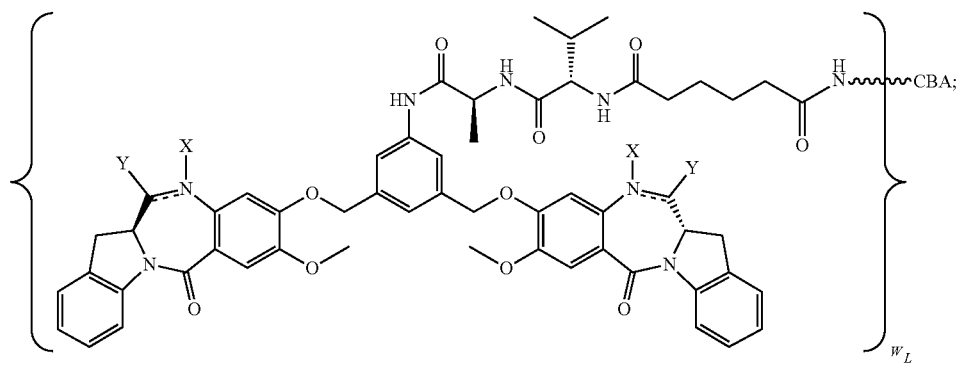
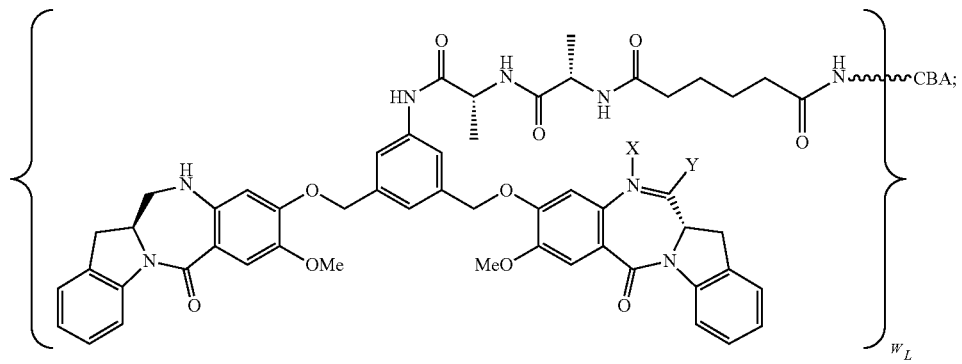

-continued
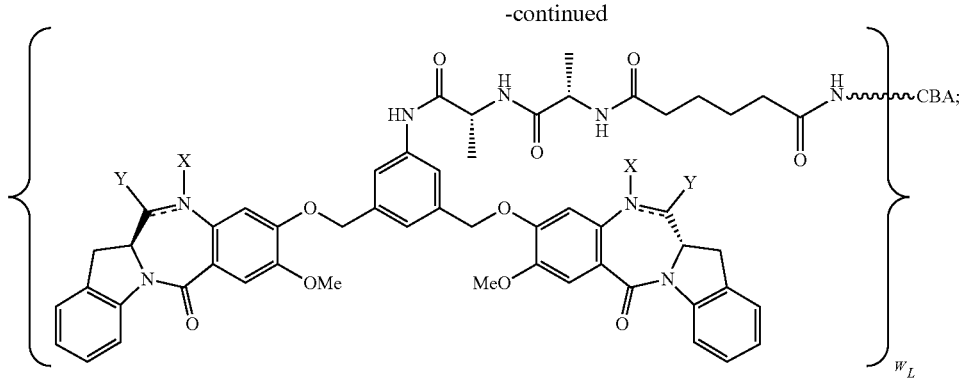
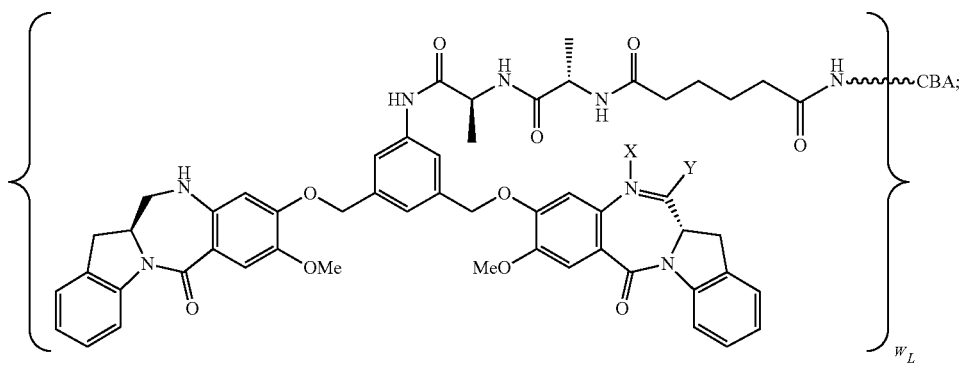
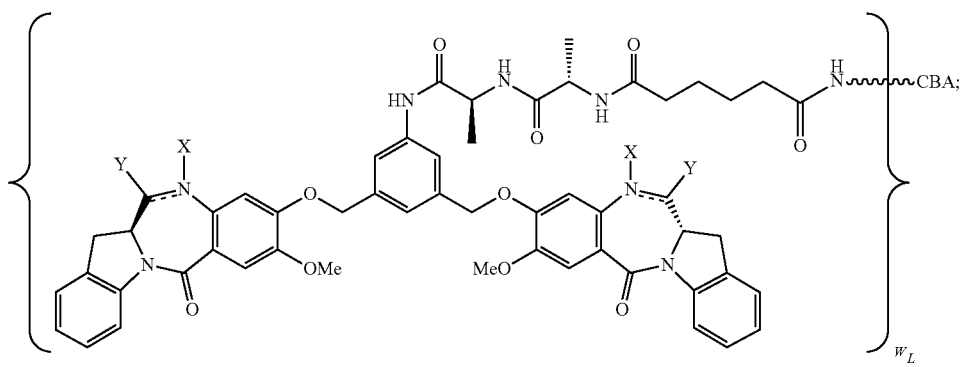
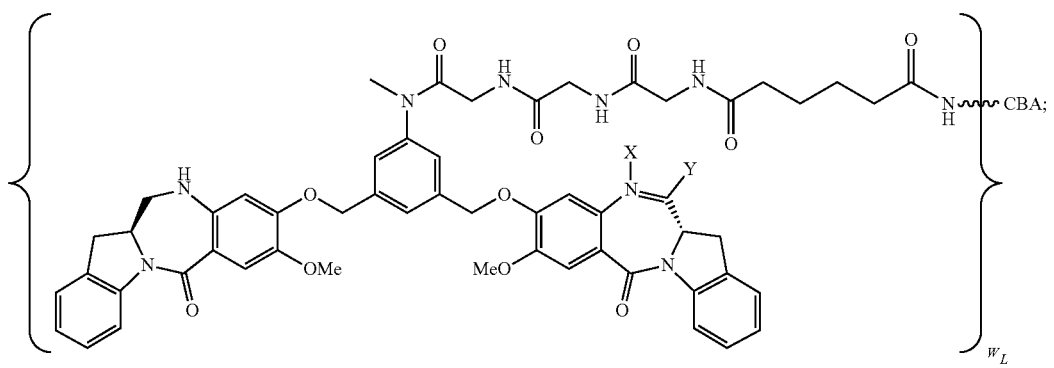

-continued
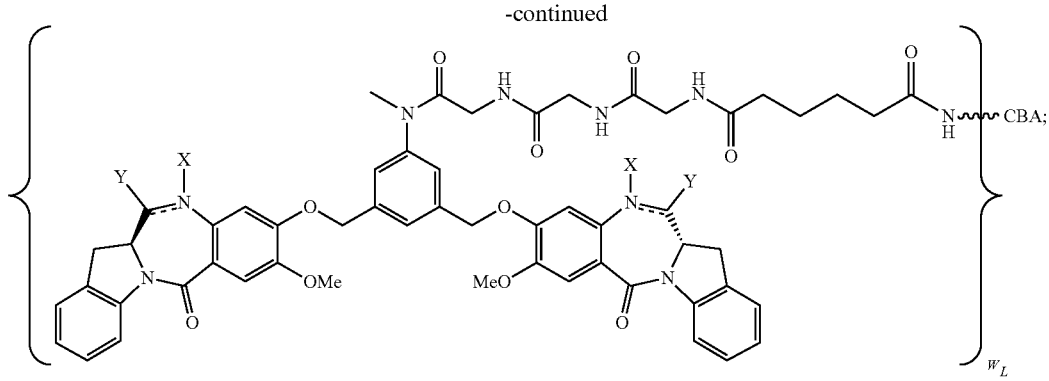
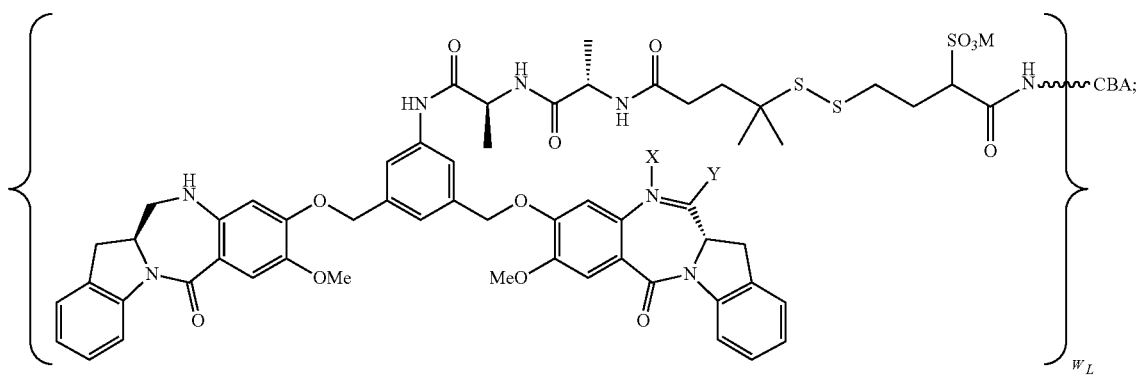
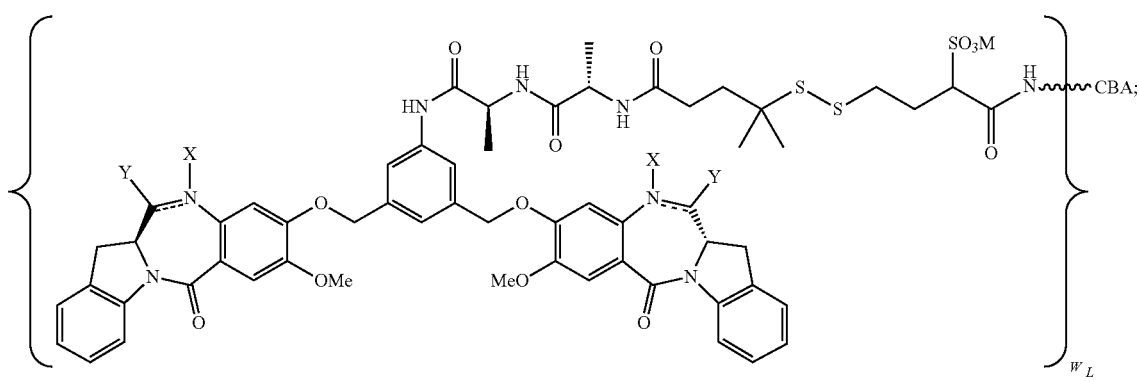
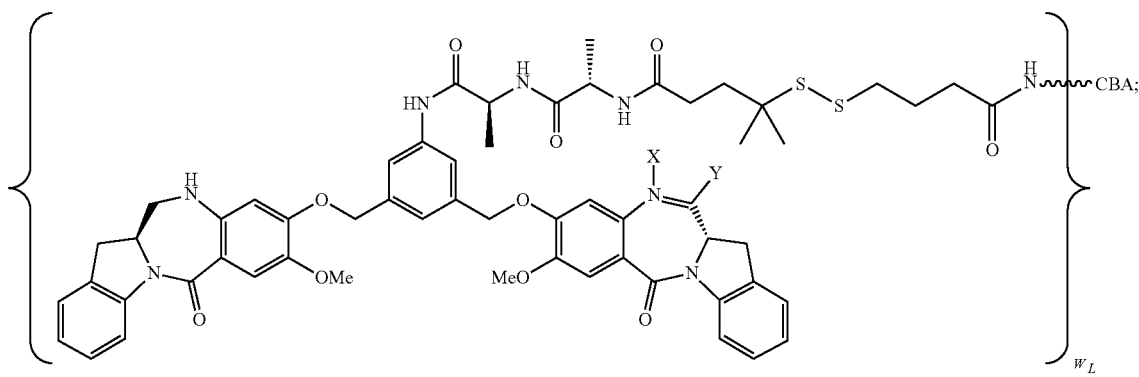

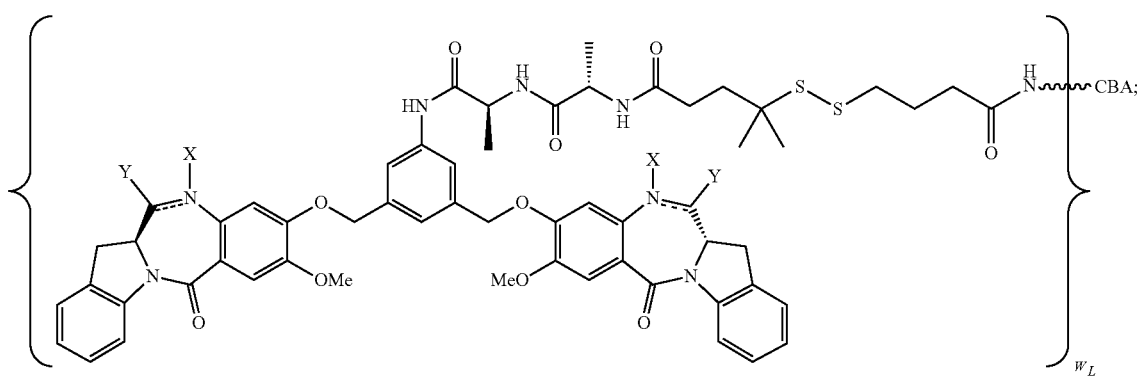
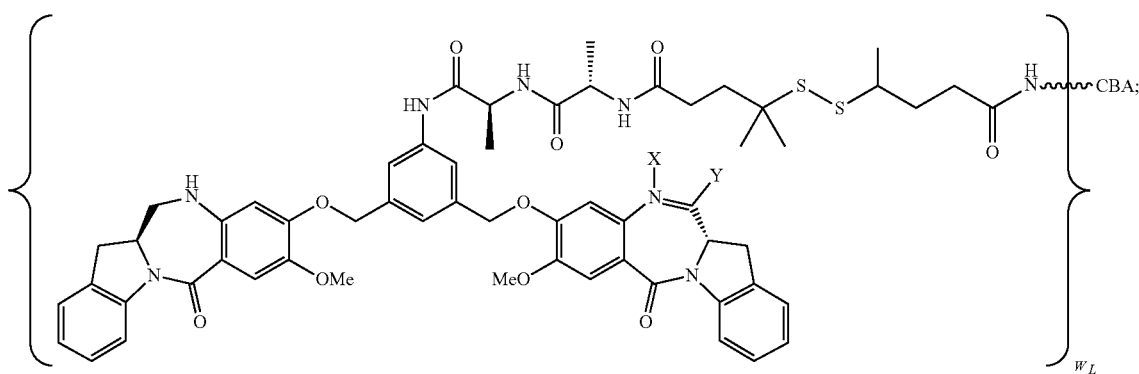
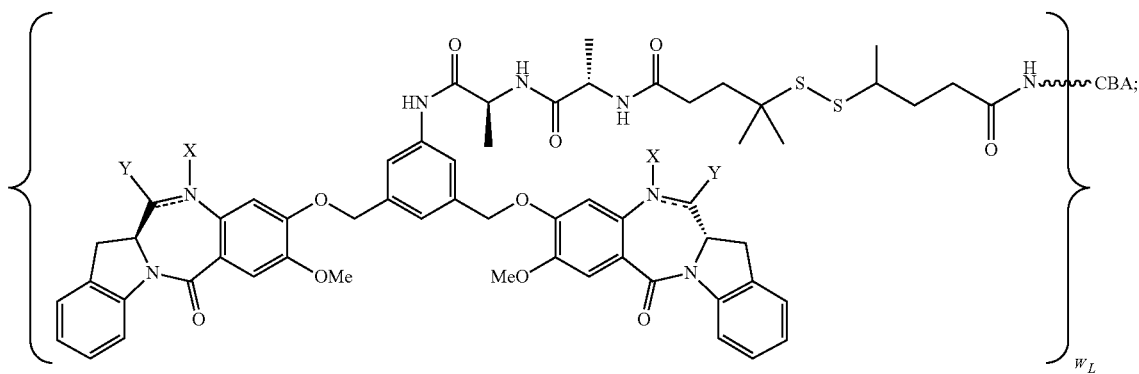
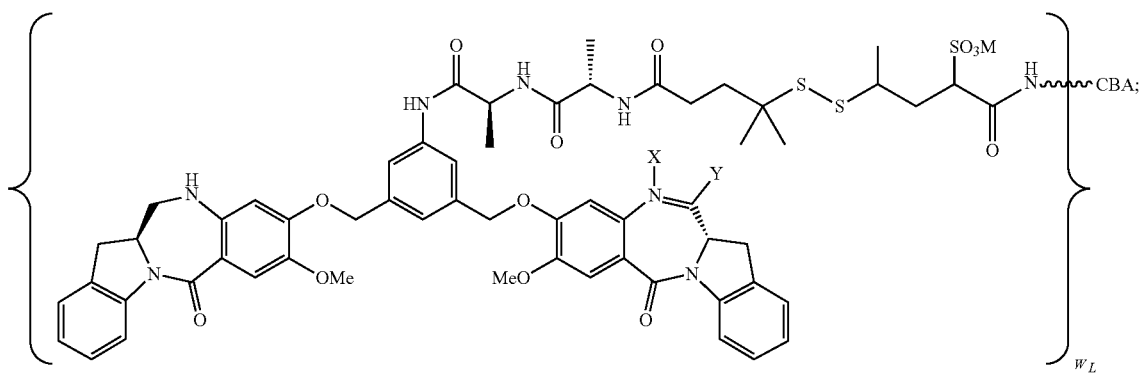

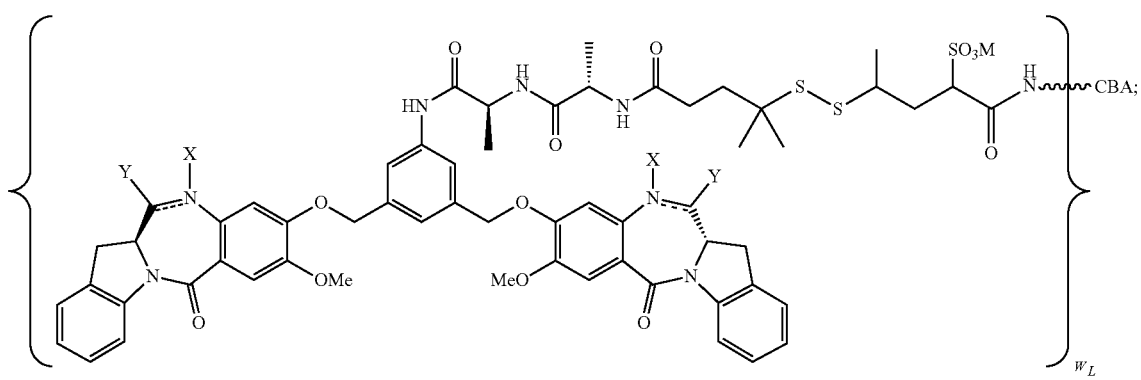
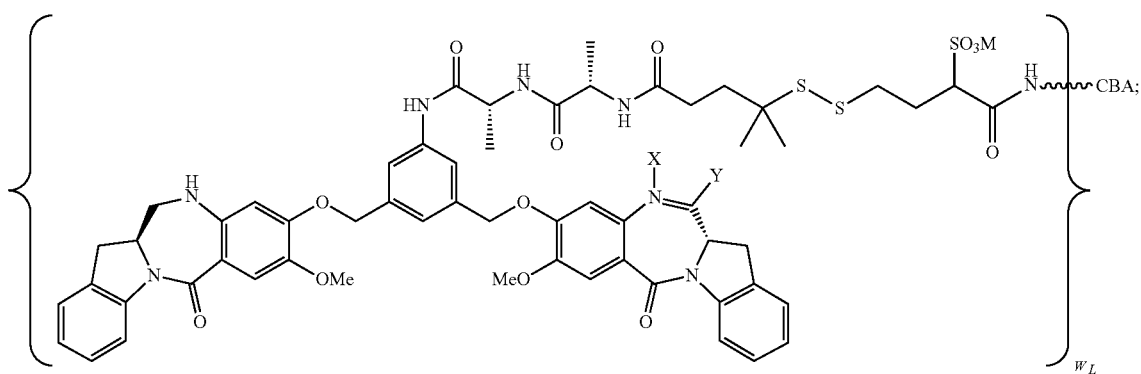
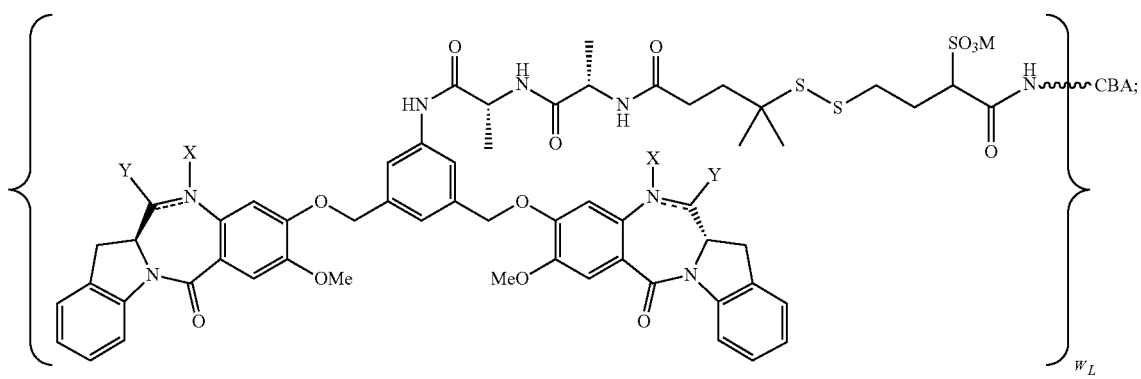
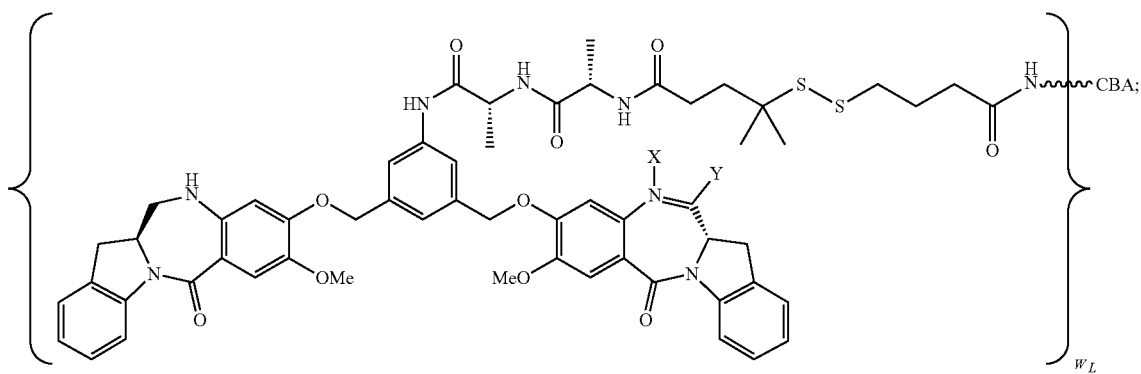

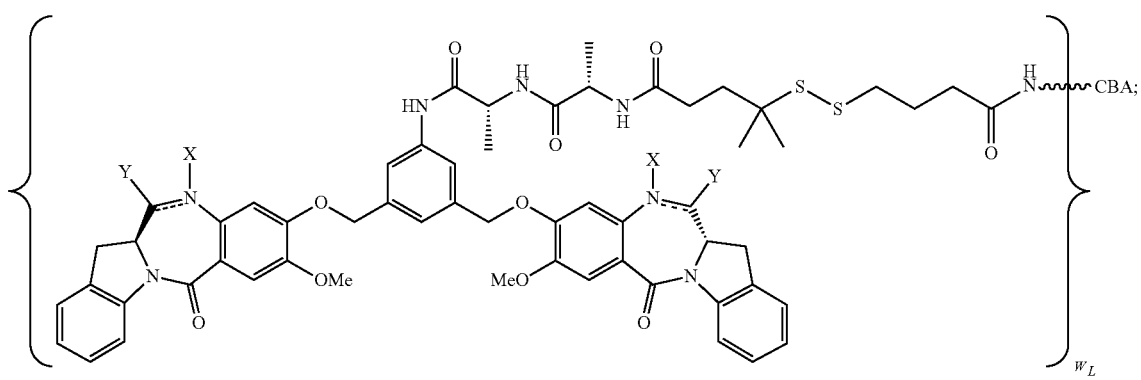
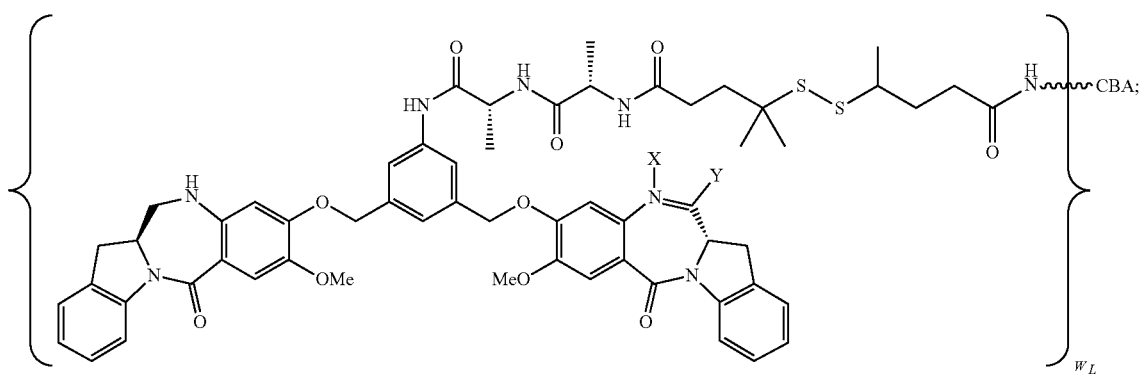
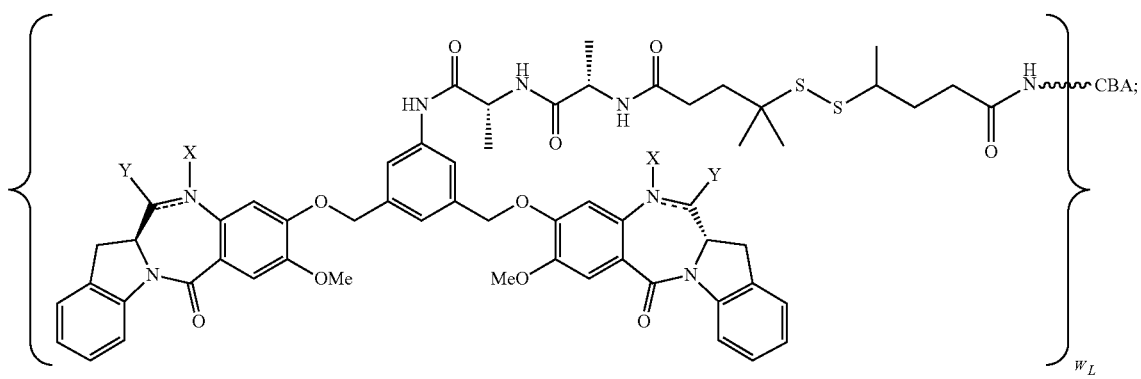
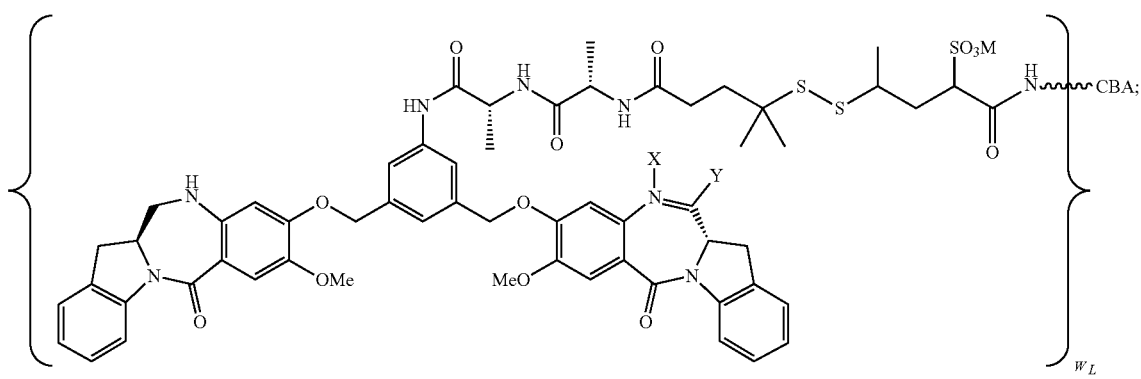

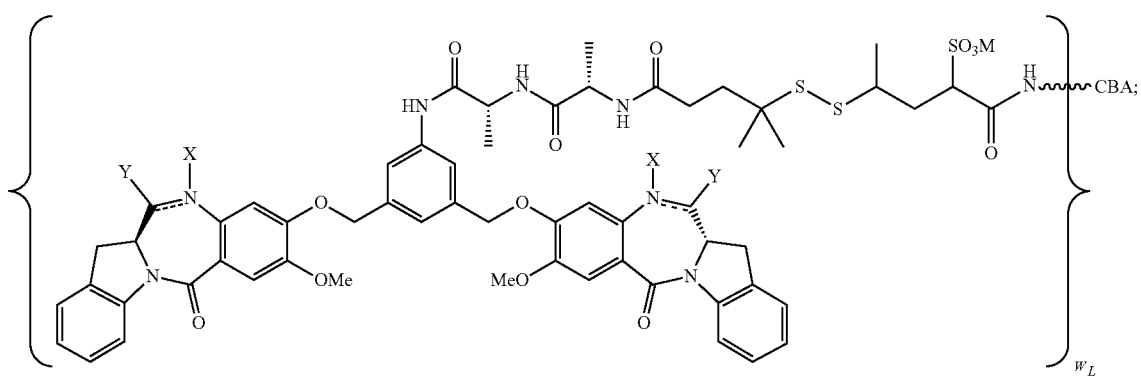
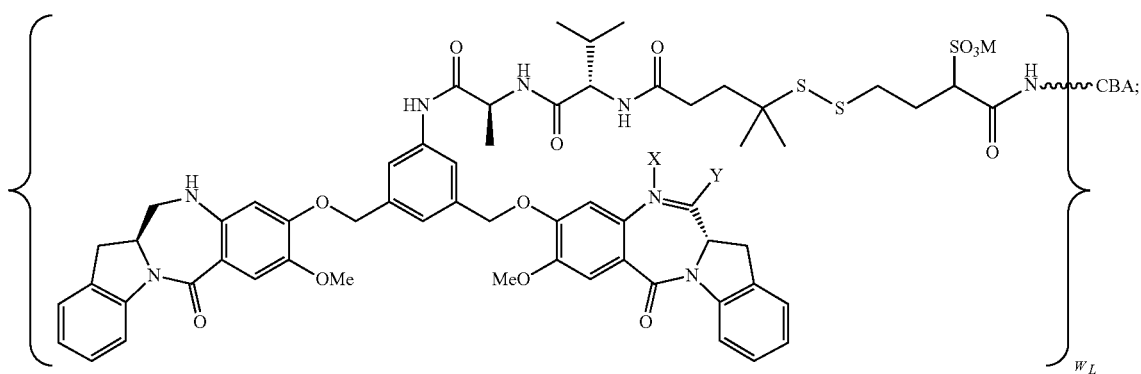
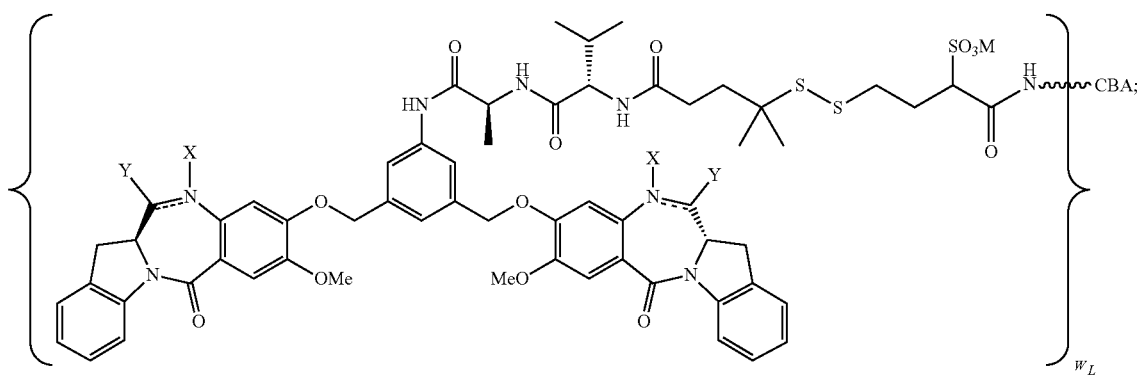
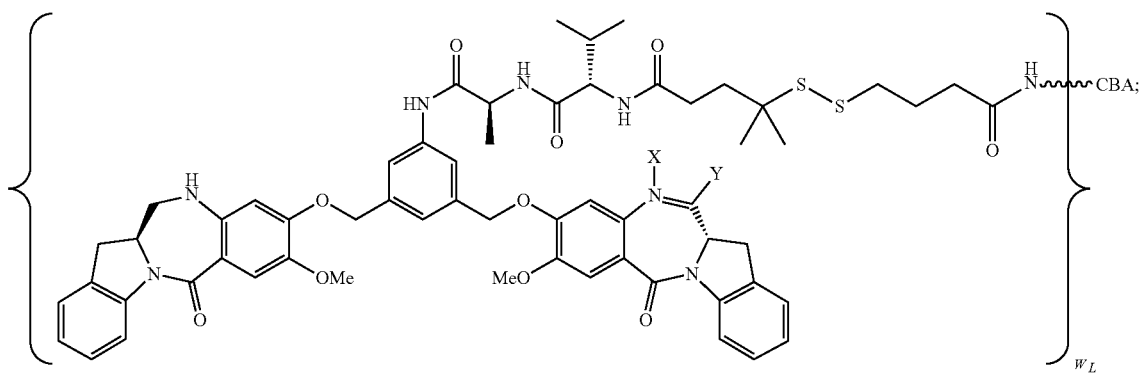

-continued
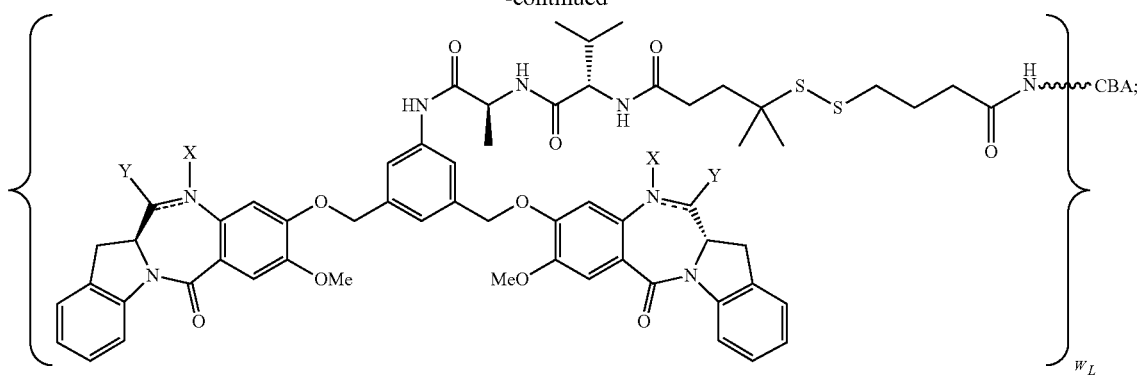
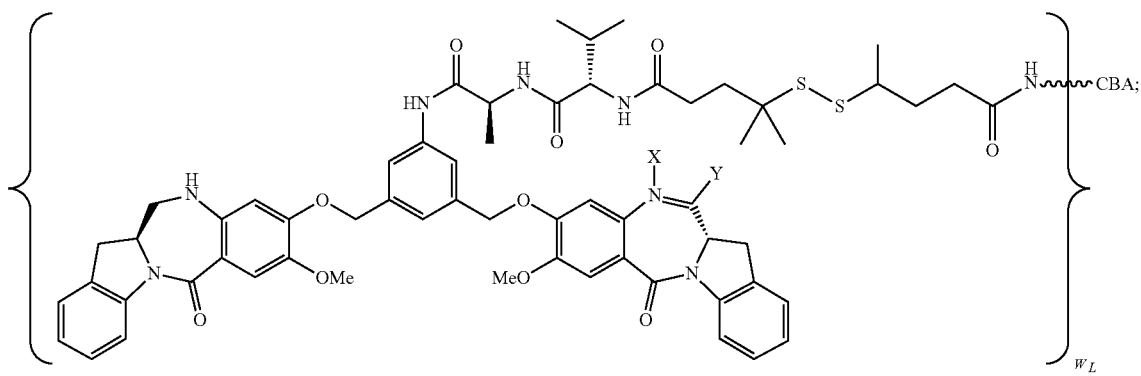
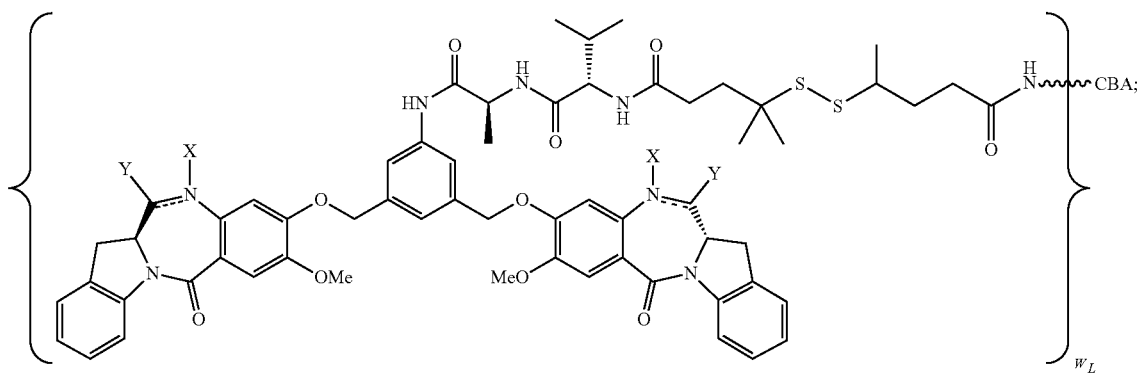
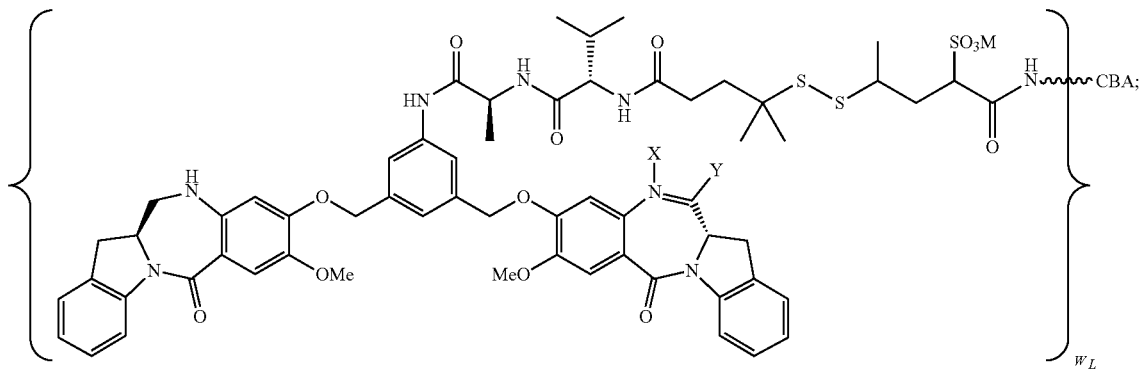

-continued

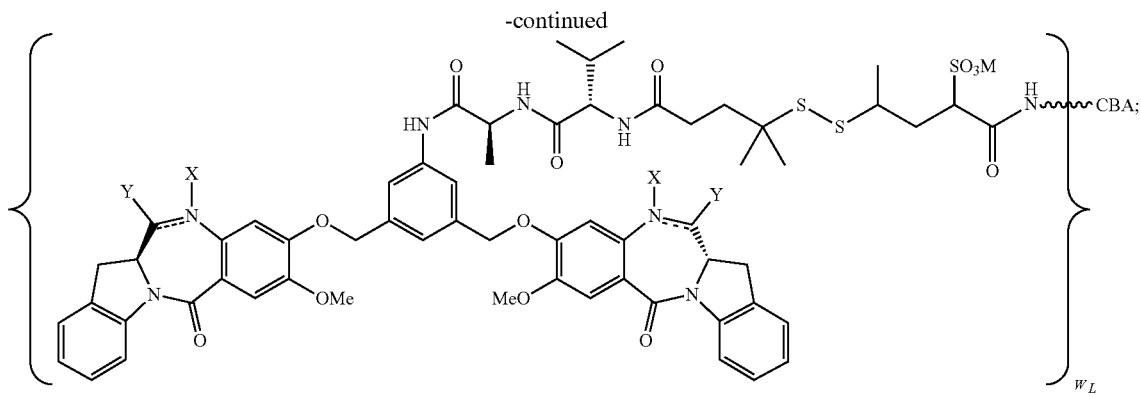

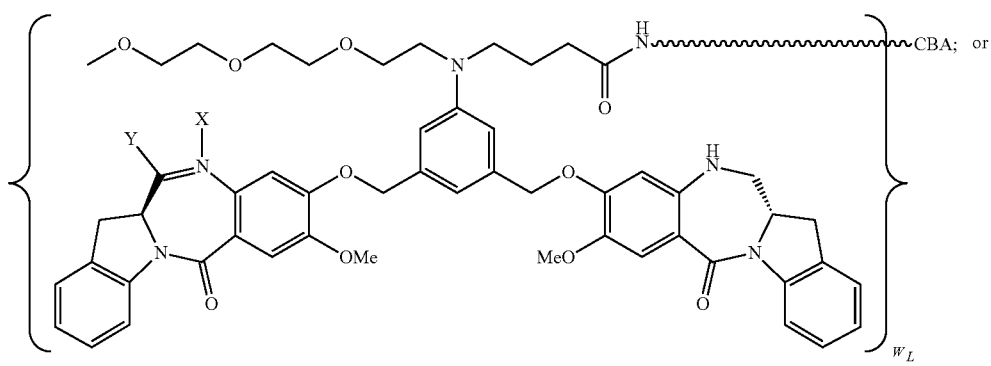

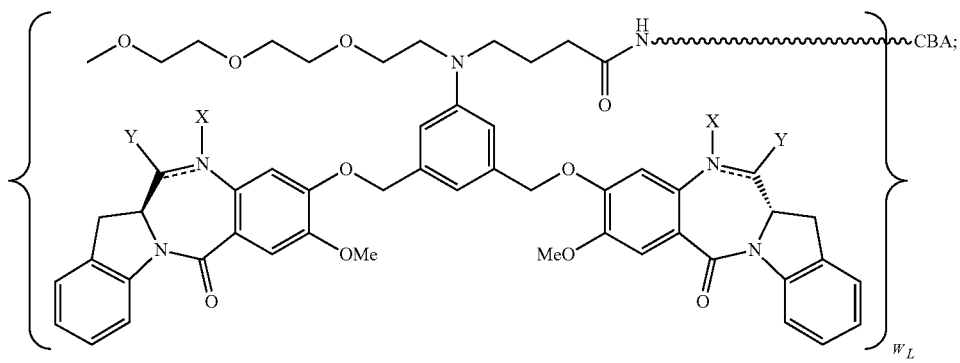

or a pharmaceutically acceptable salt thereof, wherein $W_L$ is an integer from 1 to 10; the double line ═ between N and C represents a single bond or a double bond, provided that when it is a double bond, X is absent and Y is —H; and when it is a single bond, X is —H, and Y is —OH or —SO₃M. In a more specific embodiment, the double line ═ between N and C represents a double bond, X is absent and Y is —H. In another more specific embodiment, the double line ═ between N and C represents a single bond, X is —H and Y is —SO₃M.

In a 8$^{th}$ specific embodiment, the immunoconjugate of the first embodiment is represented by the following formula:

 (L2), wherein:

CBA is a CD123/IL-3Rα-binding agent described in the first aspect of the present invention (e.g. a subject antibody or antigen-binding fragment thereof described herein above, or a subject polypeptide thereof described above), that is covalently linked to $Cy^{L2}$ through a lysine residue;

$W_L$ is an integer from 1 to 20; and $Cy^{L2}$ is a cytotoxic compound represented by the following formula:

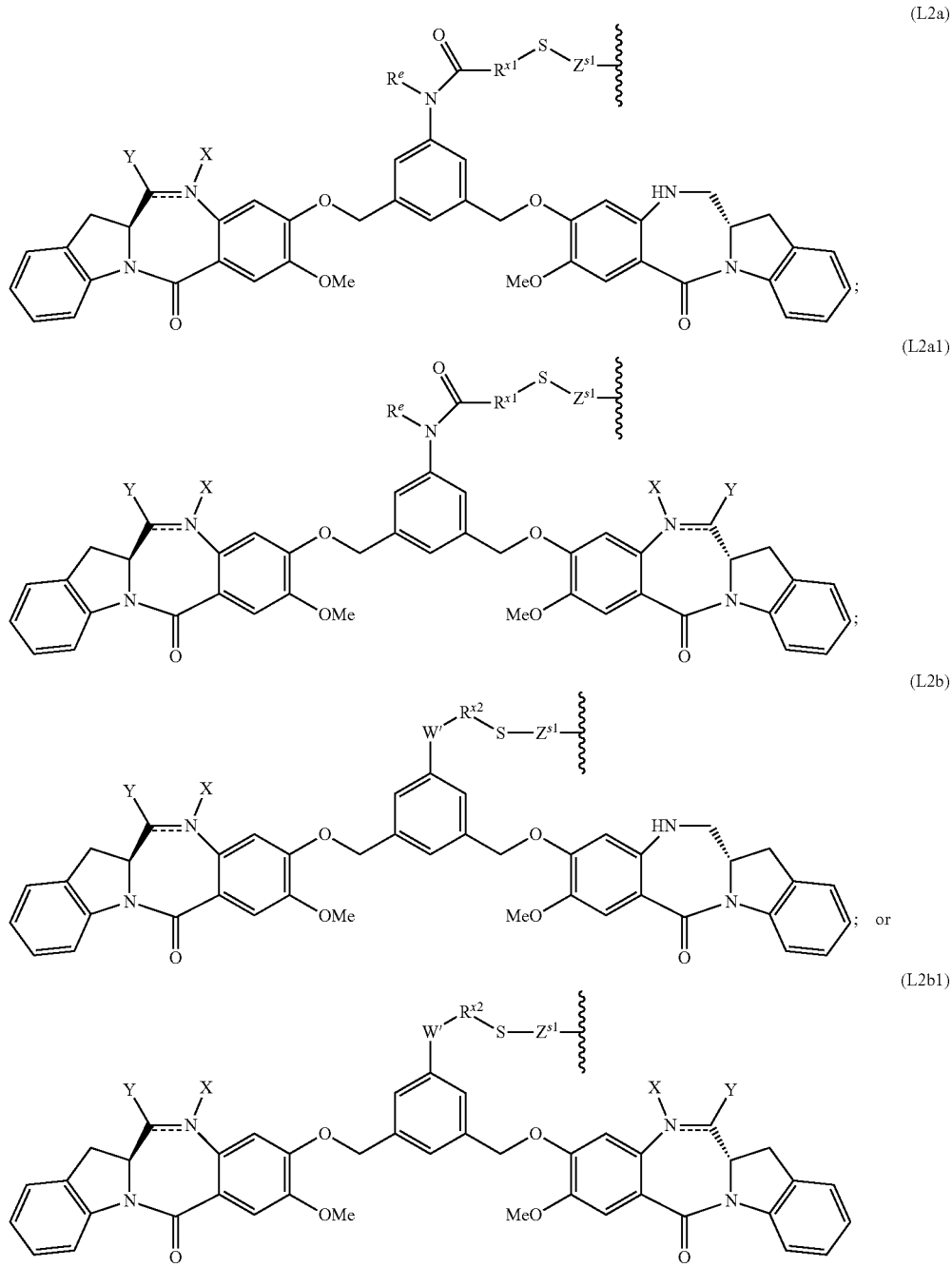

or a pharmaceutically acceptable salt thereof, wherein:

the double line ═ between N and C represents a single bond or a double bond, provided that when it is a double bond, X is absent and Y is —H or a $(C_1-C_4)$ alkyl; and when it is a single bond, X is —H or an amine protecting moiety, and Y is —OH or —$SO_3M$;

$R^{x1}$ and $R^{x2}$ are independently $(C_1-C_6)$alkyl;

$R^e$ is —H or a $(C_1-C_6)$alkyl;

W' is —$NR^{e'}$, $R^{e'}$ is —$(CH_2-CH_2-O)_n-R^k$;

n is an integer from 2 to 6;

$R^k$ is —H or -Me;

$Z^{s1}$ is selected from any one of the following formulas:

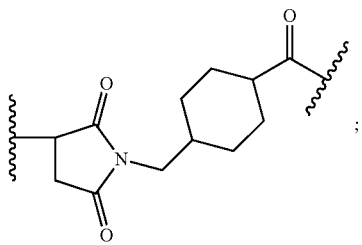

(b1)

(b2) 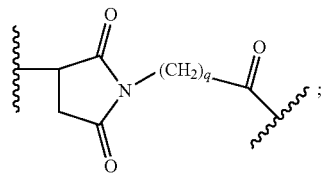

(b3) 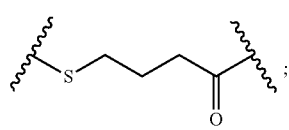

(b4) 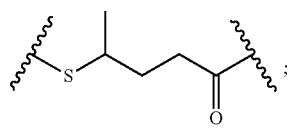

(b5) 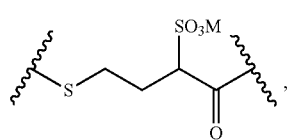

(b6) 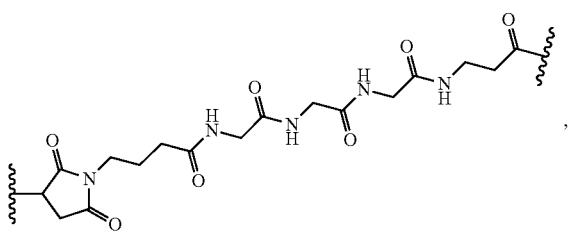

(b7) 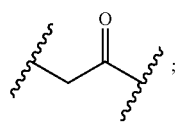

(b8) 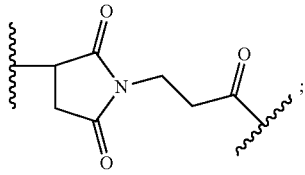

(b9) 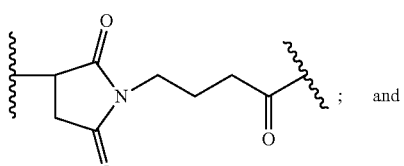; and (b10) 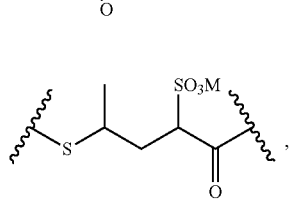

wherein:

q is an integer from 1 to 5; and

M is —H⁺ or a cation.

In a 9th specific embodiment, for immunoconjugates of formula (L2), $Cy^{L2}$ is represented by formula (L2a) or (L2a1); and the remaining variables are as described above in the 8th specific embodiment.

In a 10th specific embodiment, for immunoconjugates of formula (L2), $Cy^{L2}$ is represented by formula (L2b) or (L2b1); and the remaining variables are as described above in the 8th specific embodiment.

In a 11th specific embodiment, for immunoconjugates of formula (L2), $R^e$ is H or Me; $R^{x1}$ and $R^{x2}$ are independently —(CH$_2$)$_p$—(CR$^f$R$^g$)—, wherein $R^f$ and $R^g$ are each independently —H or a (C$_1$-C$_4$)alkyl; and p is 0, 1, 2 or 3; and the remaining variables are as described above in the 8th, 9th or 10th specific embodiment. More specifically, $R^f$ and $R^g$ are the same or different, and are selected from —H and -Me.

In a 12th specific embodiment, the immunoconjugate of the first embodiment is represented by the following formula:

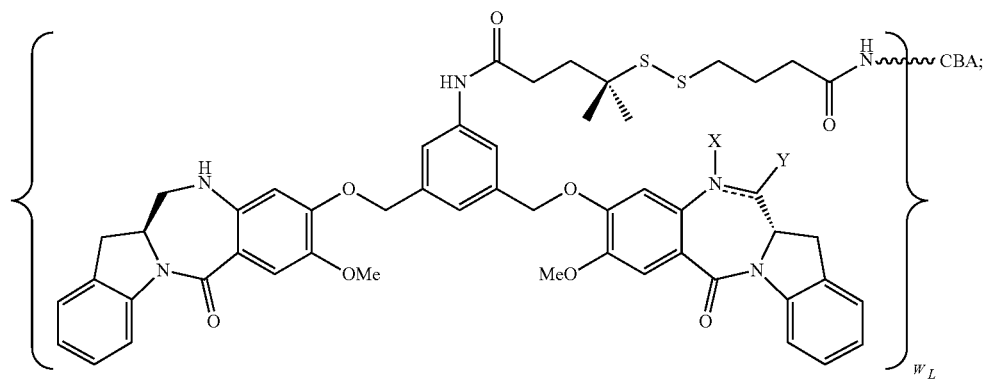

-continued
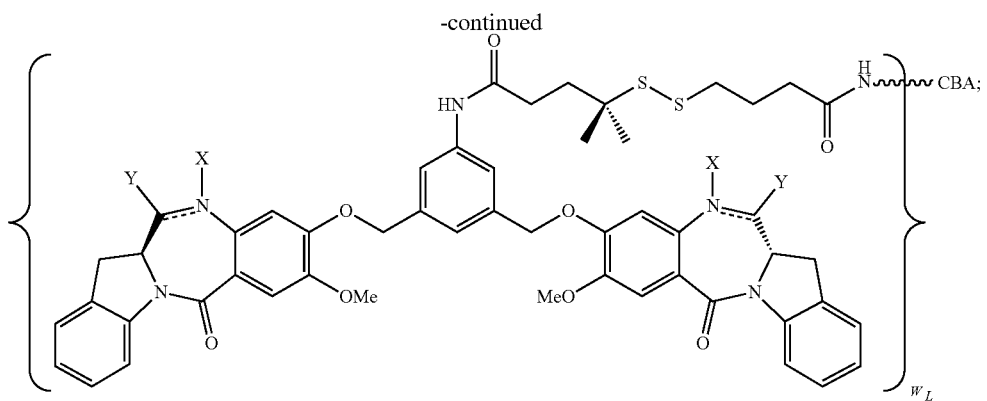
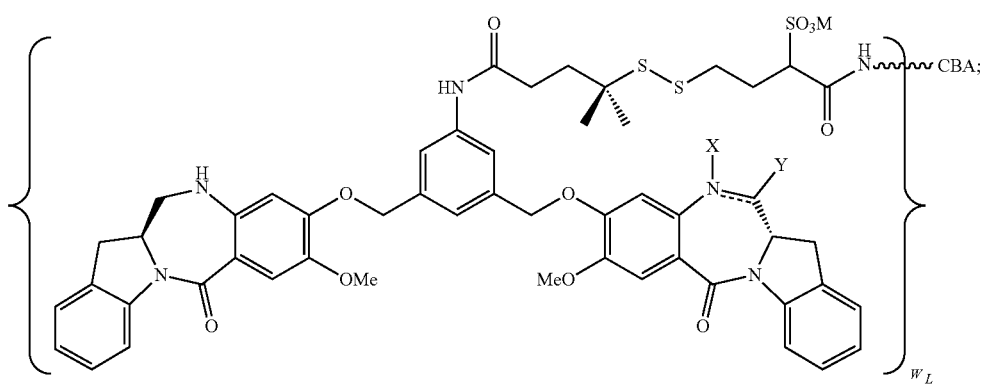
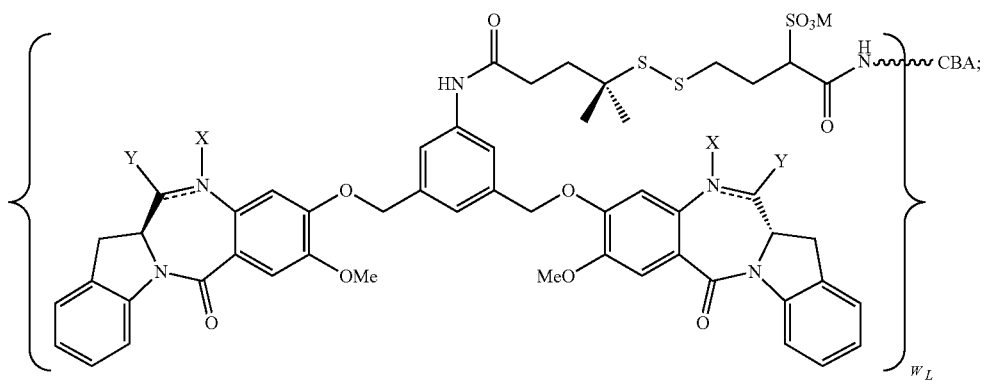
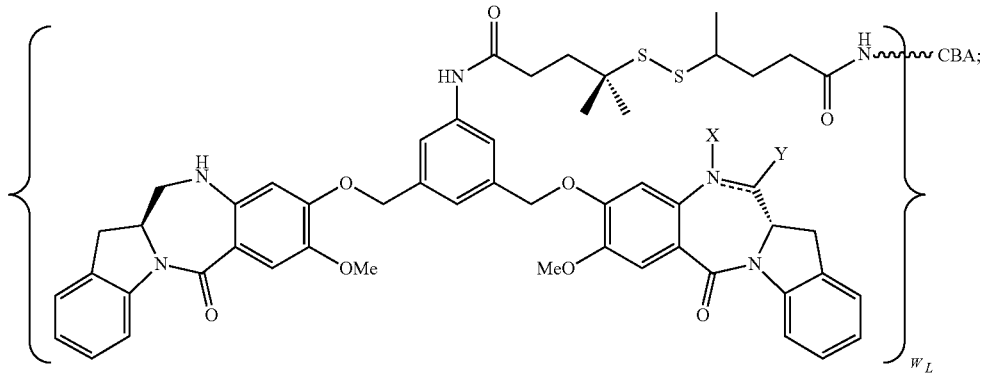

-continued
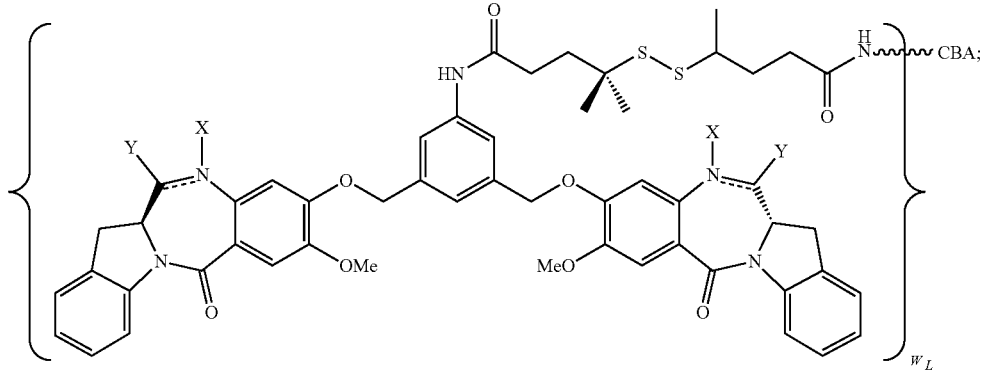
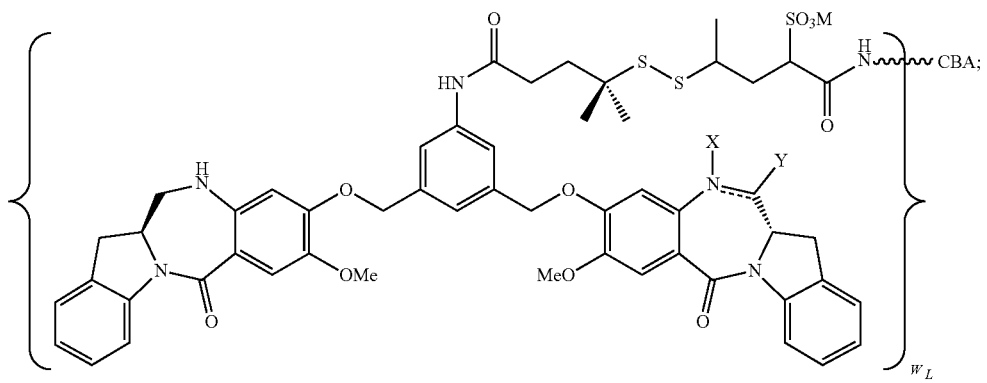
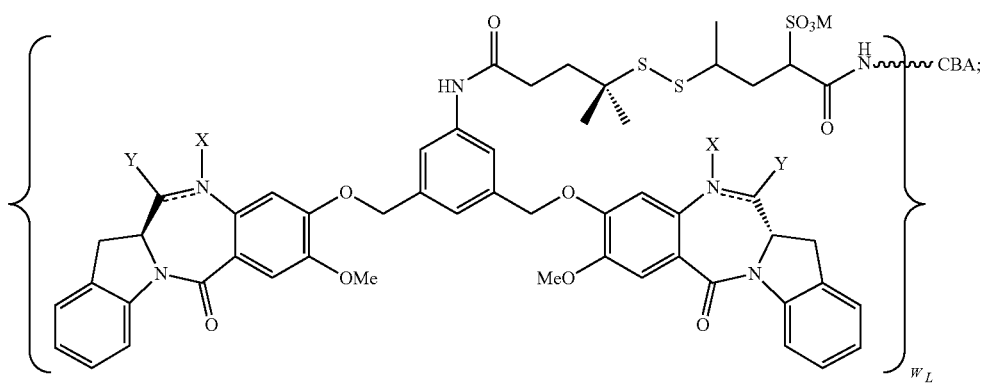
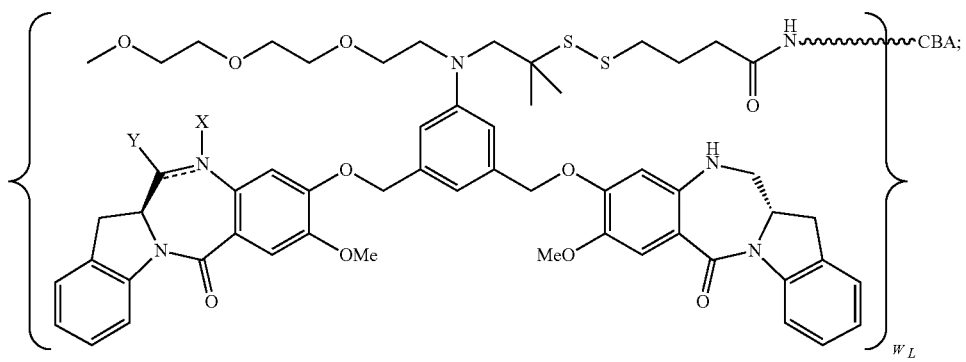

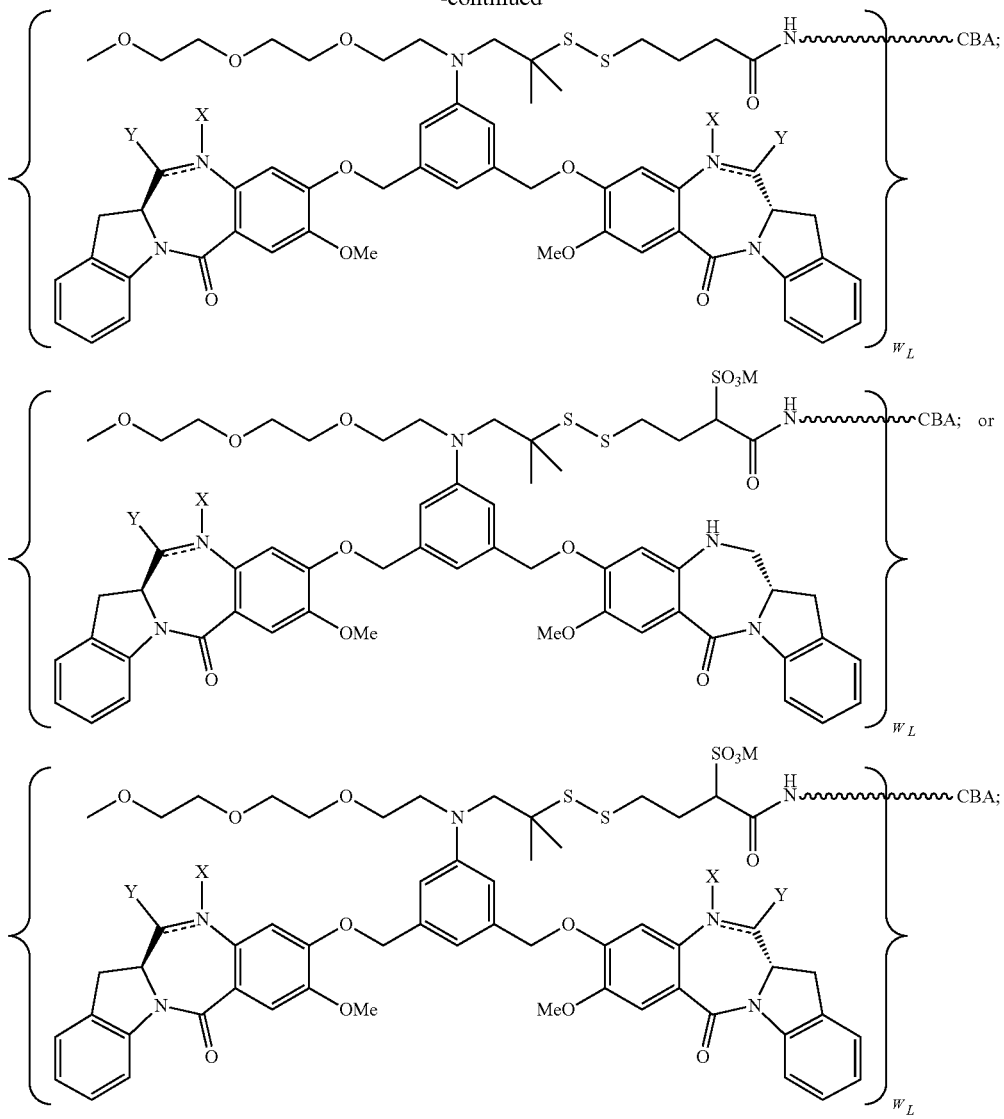

or a pharmaceutically acceptable salt thereof, wherein $W_L$ is an integer from 1 to 10; the double line ═ between N and C represents a single bond or a double bond, provided that when it is a double bond, X is absent and Y is —H; and when it is a single bond, X is —H and Y is —OH or —SO$_3$M. In a more specific embodiment, the double line ═ between N and C represents a double bond. In another more specific embodiment, the double line ═ between N and C represents a single bond, X is —H and Y is —SO$_3$M.

In a 13$^{th}$ specific embodiment, the immunoconjugates of the first embodiment is represented by the following formula:

$$CBA \text{-}(\text{-}Cy^{L3})_{w_L} \quad (L3),$$

wherein:
CBA is a CD123/IL-3Rα-binding agents described in the first aspect of the present invention (e.g. a subject antibody or antigen-binding fragment thereof described herein above, or a subject polypeptide thereof described above), which is covalently linked to Cy$^{L3}$ through a Lys residue;
$W_L$ is an integer from 1 to 20;

Cy$^{L3}$ is represented by the following formula:

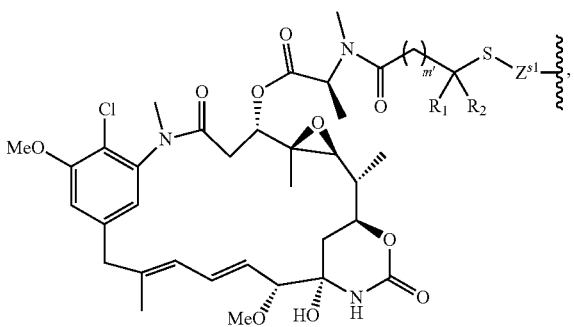

m' is 1 or 2;

R$_1$ and R$_2$, are each independently H or a (C$_1$-C$_3$)alkyl; and $Z^{s1}$ is selected from any one of the following formulas:

(b1)
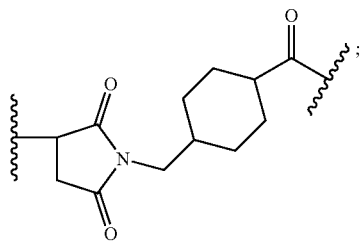

(b2)

(b3)
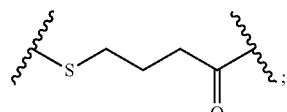

(b4)

(b5)
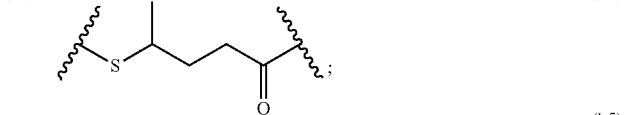

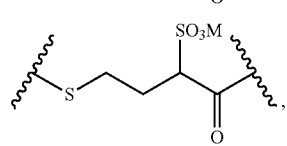

(b6)

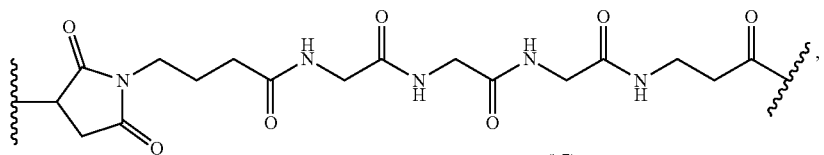

(b7)
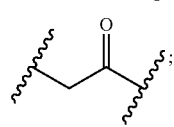

(b8)

(b9)

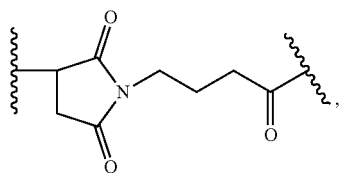

wherein:
q is an integer from 1 to 5; and
M is $H^+$ or a cation.

In a 14th specific embodiment, for immunoconjugates of formula (L3), m' is 1, and $R_1$ and $R_2$ are both H; and the remaining variables are as described above in the 13th specific embodiment.

In a 15th specific embodiment, for immunoconjugates of formula (L3), m' is 2, and $R_1$ and $R_2$ are both Me; and the remaining variables are as described above in the 13th specific embodiment.

In a 16th specific embodiment, the immunoconjugates of the first embodiment is represented by the following formula:

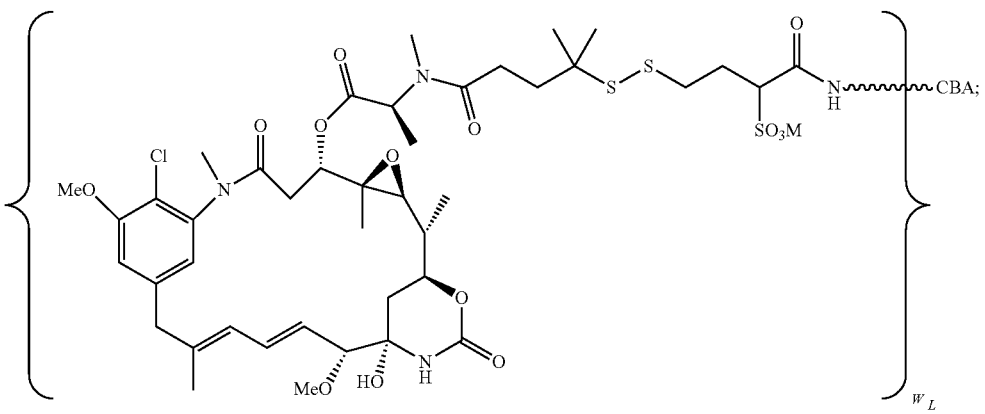

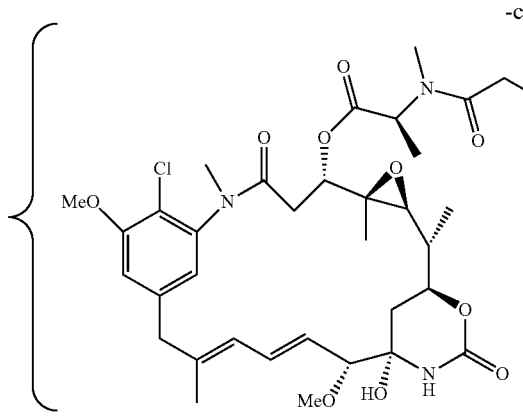

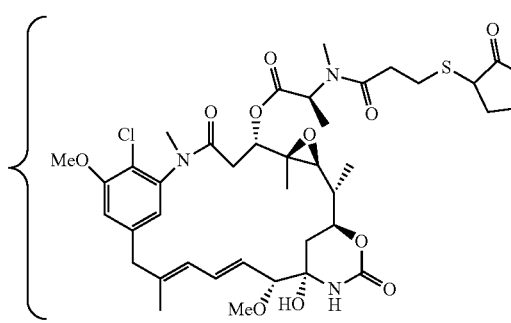

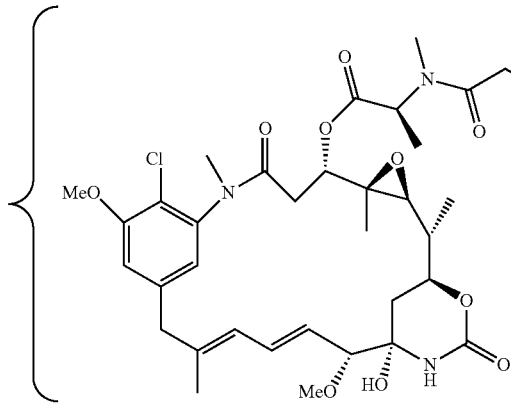

or a pharmaceutically acceptable salt thereof, wherein $W_L$ is an integer from 1 to 10.

In a 17th specific embodiment, for immunoconjugates of the first embodiment, M is $H^+$, $Na^+$ or $K^+$; and the remaining variables are as described above in any one of the 1st to 16th specific embodiment or any more specific embodiments described therein.

In any of the above 1st to the 17th specific embodiments, the subject antibody or antigen-binding fragment thereof may have one or more of (e.g., substantially all of, or 100% of) the Lys residues in any of the six light chain and heavy chain CDR regions (if any) substituted by Arg. The subject antibody or antigen-binding fragment thereof may comprise an immunoglobulin heavy chain variable region (HCVR) having the amino acid sequence set forth in SEQ ID NO: 39 or 40; and an immunoglobulin light chain variable region (LCVR) having the amino acid sequence set forth in SEQ ID NO: 41. The subject antibody or antigen-binding fragment thereof may also comprise an Ig HCVR having the amino acid sequence set forth in SEQ ID NO: 34; and an Ig LCVR having the amino acid sequence set forth in SEQ ID NO: 35. The subject antibody or antigen-binding fragment thereof may further comprise an Ig HCVR having the amino acid sequence set forth in SEQ ID NO: 32, 34, 38, 39, or 40; and an Ig LCVR having the amino acid sequence set forth in SEQ ID NO: 33, 35, 37, or 41. In certain embodiments, the second residue from the N-terminus of SEQ ID NO: 34 is Phe, while in certain other embodiments, the second residue from the N-terminus of SEQ ID NO: 34 is Val.

The immunoconjugates described the first embodiment or any specific embodiments descried therein can be prepared according to any methods known in the art, see, for example, WO 2012/128868 and WO2012/112687, which are incorporate herein by reference.

In certain embodiments, the immunoconjugates of the first embodiment can be prepared by a first method comprising the steps of reacting the CBA with a cytotoxic agent having an amine reactive group.

In one embodiment, for the first method described above, the reaction is carried out in the presence of an imine reactive reagent, such as $NaHSO_3$.

In one embodiment, for the first method described above the cytotoxic agent having an amine reactive reagent is represented by the following formula:

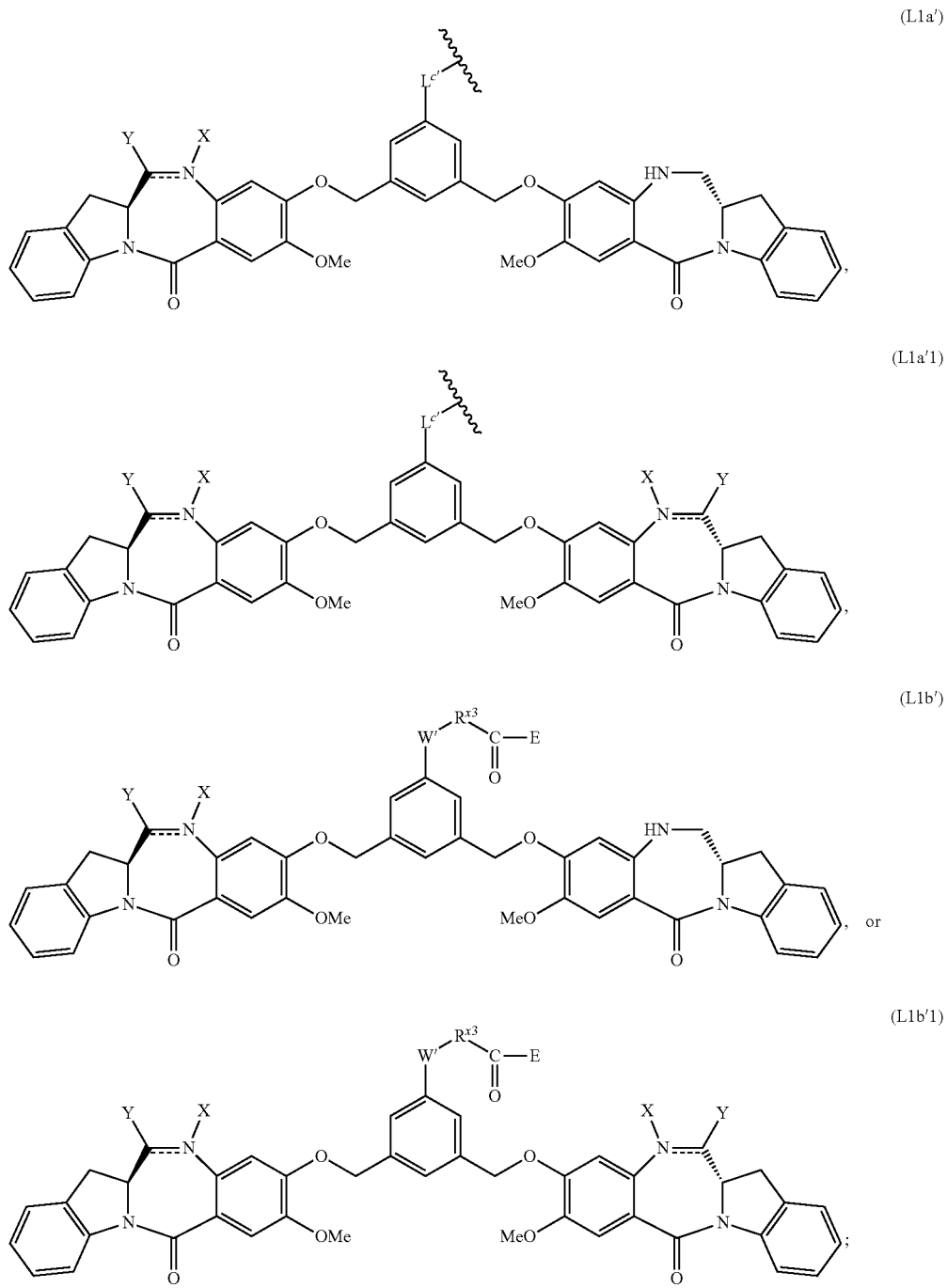

or a pharmaceutically acceptable salt thereof, wherein:

$L^{c'}$ is represented by the following formula:

$$-NR_5-P-C(=O)-(CR_aR_b)_m-C(=O)E \quad (B1); or$$

$$-NR_5-P-C(=O)-(CR_aR_b)_m-S-Z^s \quad (B2)$$

C(=O)E is a reactive ester group, such as N-hydroxysuccinimde ester, N-hydroxy sulfosuccinimide ester, nitrophenyl (e.g., 2 or 4-nitrophenyl) ester, dinitrophenyl (e.g., 2,4-dinitrophenyl) ester, sulfo-tetraflurophenyl (e.g., 4-sulfo-2,3,5,6-tetrafluorophenyl) ester, or pentafluorophenyl ester, preferably N-hydroxysuccinimide ester;

$Z^s$ is represented by the following formula:

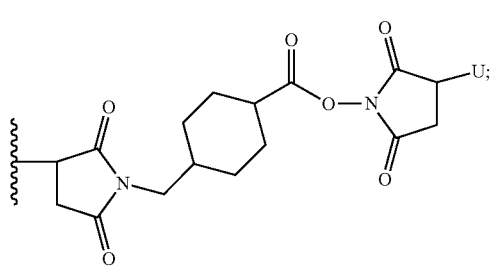
(a1)

(a2)

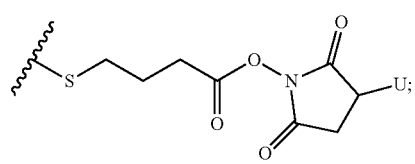
(a3)

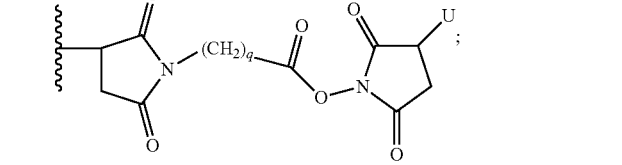
(a4)

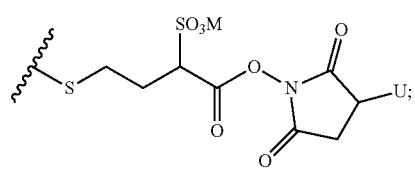
(a5)

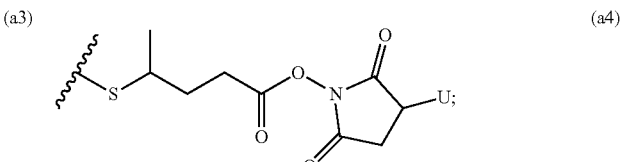
(a6)

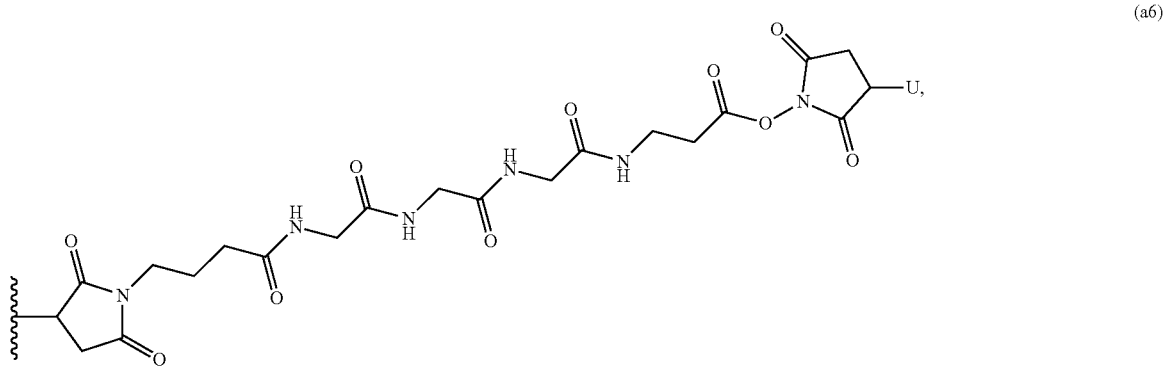

(a7)

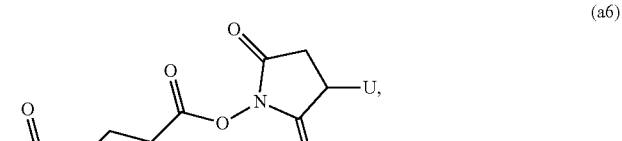
(a8)

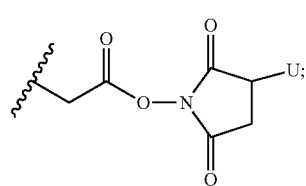
(a9)

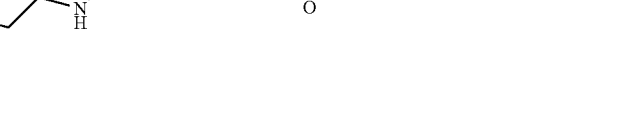
(a10)

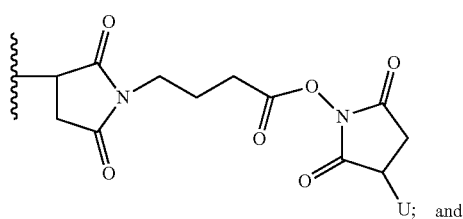
and

, wherein:

q is an integer from 1 to 5; and

U is —H or SO$_3$M; and the remaining variables are as described in any one of the 1$^{st}$ to 7$^{th}$ and 17$^{th}$ specific embodiments or any more specific embodiments described therein.

In certain embodiments, the immunoconjugates of the first embodiment can be prepared by a second method comprising the steps of:

(a) reacting a cytotoxic agent with a linker compound having an amine reactive group and a thiol reactive group to form a cytotoxic agent-linker compound having the amine reactive group bound thereto; and (b) reacting the CBA with the cytotoxic agent-linker compound.

In one embodiment, for the second method described above, the reaction in step (a) is carried out in the presence of an imine reactive reagent.

In one embodiment, for the second method described above, the cytotoxic agent-linker compound is reacted with the CBA without purification. Alternatively, the cytotoxic agent-linker compound is first purified before reacting with the CBA.

In certain embodiments, the immunoconjugates of the first embodiment can be prepared by a third method comprising the steps of:
(a) reacting the CBA with a linker compound having an amine reactive group and a thiol reactive group to form a modified CBA having a thiol reactive group bound thereto; and
(b) reacting the modified CBA with the cytotoxic agent.

In one embodiment, for the third method described above, the reaction in step (b) is carried out in the presence of an imine reactive reagent.

In certain embodiments, the immunoconjugates of the first embodiment can be prepared by a fourth method comprising the steps of reacting the CBA, a cytotoxic compound and a linker compound having an amine reactive group and a thiol reactive group.

In one embodiment, for the fourth method, the reaction is carried out in the presence of an imine reactive agent.

In certain embodiments, for the second, third or fourth embodiment, described above, the linker compound having an amine reactive group and a thiol reactive group is represented by the following formula:

(a1L)
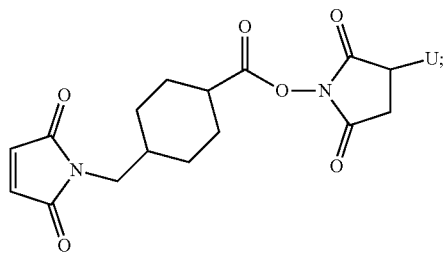

(a2L)
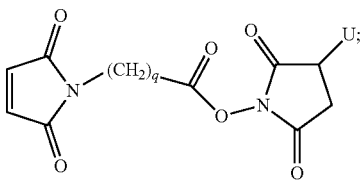

(a3L)
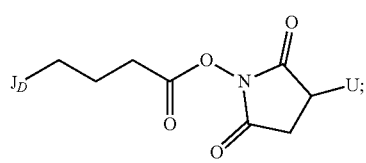

(a4L)
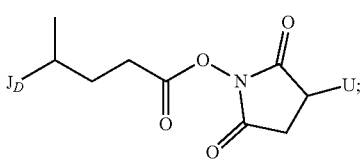

(a5L)
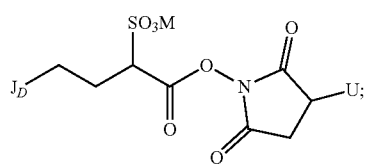

(a6L)
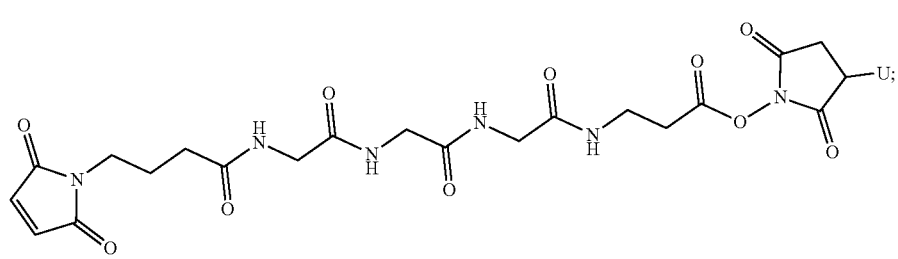

(a7L)
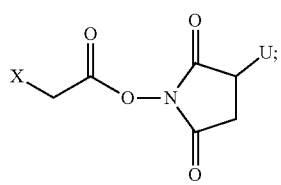

(a8L)
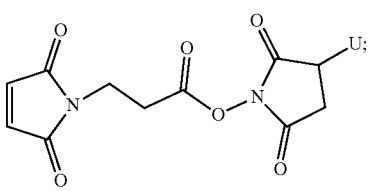

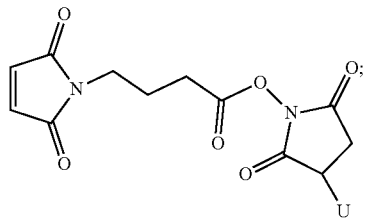 (a9L) and 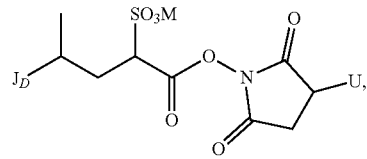 (a10L)
wherein X is halogen; $J_D$-SH, —SSR$^d$, or —SC(=O)R$^g$; R$^d$ is phenyl, nitrophenyl, dinitrophenyl, carboxynitrophenyl, pyridyl or nitropyridyl; R$^g$ is an alkyl; and the remaining variables are as described above for formula (a1)-(a10); and the cytotoxic agent is represented by the following formula:
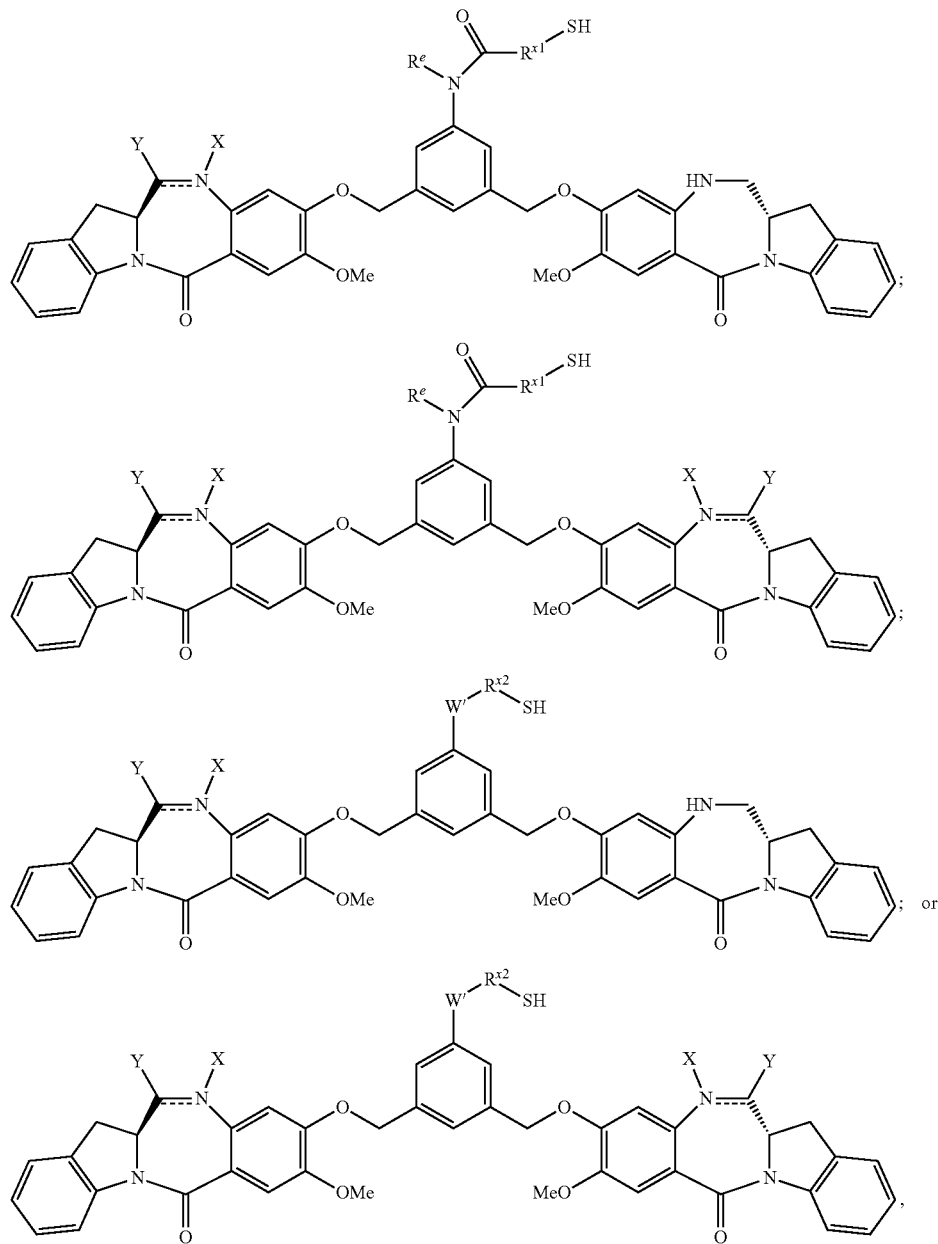

or a pharmaceutically acceptable salt thereof, wherein the variables are as described in any one of the 8th to 12th and 17th specific embodiments and any more specific embodiments described therein.

In certain embodiments, for the second, third or fourth methods described above, the linker compound having an amine reactive group and a thiol reactive group is represented by any one of the formula (a1L)-(a10L) and the cytotoxic agent is represented by the following formula:

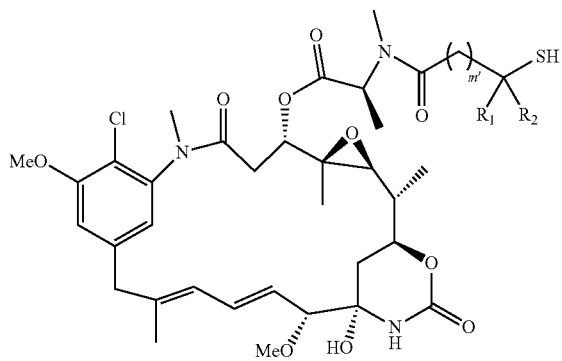

Wherein the variables are as described above in any one of the 13th to 17th specific embodiments and any more specific embodiments described therein.

In a second embodiment, the immuonoconjugate of the present invention comprises an oxidized CD123/IL-3Rα-binding agent (including antibody, antigen-binding fragment thereof, or polypeptide comprising the antibody or antigen-binding fragment thereof) described in the first aspect of the present invention described herein (e.g., oxidized antibody or antigen-binding fragment thereof, or the polypeptide thereof) covalently linked to a cytotoxic agent described herein through one or more aldehyde groups located on the oxidized CD123-binding agent. The aldehyde groups located on the oxidized CD123/IL-3Rα-binding agent can be generated by oxidizing one or more 2-hydroxyethylamine moiety of the CD123/IL-3Rα-binding agent, wherein the 2-hydroxyethylamine moiety is part of a serine, threonine, hydroxylysine, 4-hydroxyornithie or 2,4-diamino-5-hydroxy valeric acid residue. In one embodiment, the aldehyde groups can be generated by oxidizing the 2-hydroxyethyl-amine moiety of one or more N-terminal serine residue(s) located on the CD123/IL-3Rα-binding agent (e.g., 1, 2, 3, or up to 4 Ser residues at the N-termini of the light chains and/or the heavy chains).

In a 1st specific embodiment of the second embodiment, the immunoconjugate of the present invention is represented by the following formula:

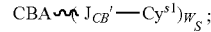 (S1)

wherein:
CBA is the oxidized CD123/IL-3Rα-binding agent described in the first aspect of the invention (e.g. a subject oxidized antibody or antigen-binding fragment thereof described herein above, or a subject oxidized polypeptide thereof described above);

$W_S$ is 1, 2, 3, or 4;

$J_{CB'}$ is a moiety formed by reacting an aldehyde group on the CBA with an aldehyde reactive group on $Cy^{s1}$, and is represented by the following formula:

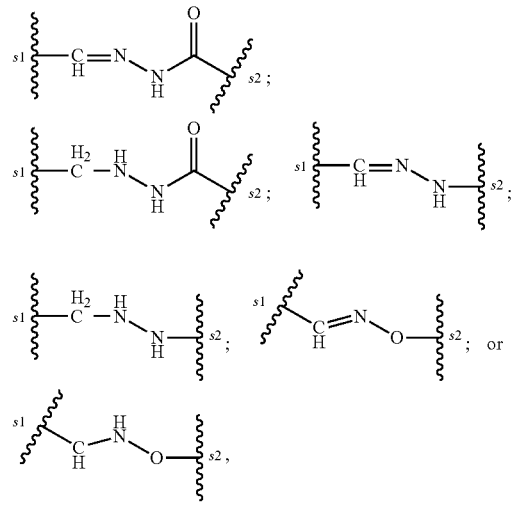

wherein s1 is the site covalently linked to the CBA; and s2 is the site covalently linked to $Cy^{s1}$;

$Cy^{s1}$ is represented by the following formula:

(S1a)

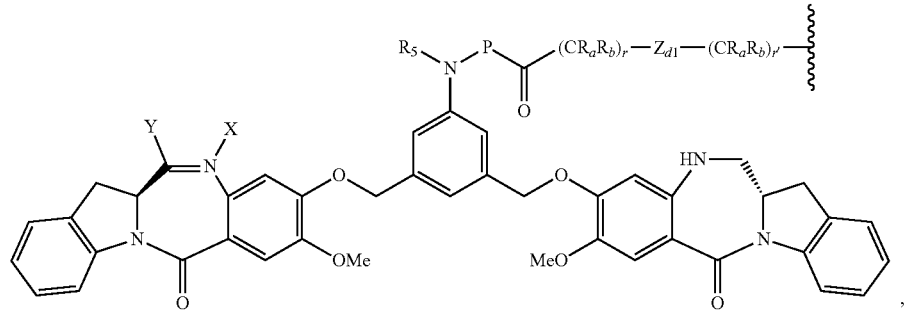

,

-continued

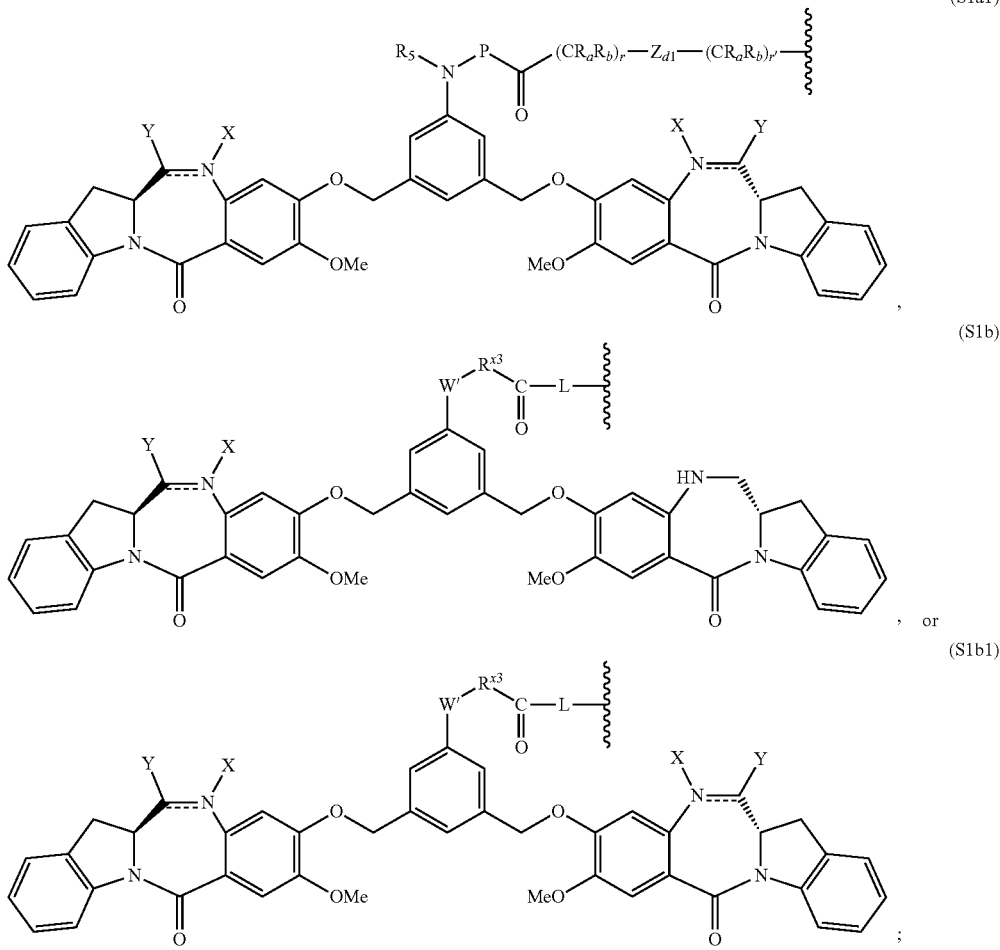

or a pharmaceutically acceptable salt thereof, wherein:
the double line <img> between N and C represents a single bond or a double bond, provided that when it is a double bond, X is absent and Y is —H or a $(C_1\text{-}C_4)$ alkyl; and when it is a single bond, X is —H or an amine protecting moiety, Y is —OH or —$SO_3M$, and M is $H^+$ or a cation;
$R_5$ is —H or a $(C_1\text{-}C_3)$alkyl;
P is an amino acid residue or a peptide containing 2 to 20 amino acid residues;
$Z_{d1}$ is absent, —C(=O)—$NR_9$—, or —$NR_9$—C(=O)—;
$R_9$ is —H or a $(C_1\text{-}C_3)$alkyl;
$R_a$ and $R_b$, for each occurrence, are independently —H, $(C_1\text{-}C_3)$alkyl, or a charged substituent or an ionizable group Q;
r and r' are independently an integer from 1 to 6;
W' is —$NR^{e'}$,
$R^{e'}$ is —$(CH_2\text{—}CH_2\text{—}O)_n\text{—}R^k$;
n is an integer from 2 to 6;
$R^k$ is —H or -Me;
$R^{x3}$ is a $(C_1\text{-}C_6)$alkyl;
L is —$NR_9$—$(CR_aR_b)_{r''}$— or absent; and
r'' is an integer from 0 to 6.

In a $2^{nd}$ specific embodiment, for immunoconjugates of formula (S1), $Cy^{s1}$ is represented by formula (S1a) or (S1a1); and the remaining variables are as described above in the $1^{st}$ specific embodiment.

In a $3^{rd}$ specific embodiment, for immunoconjugates of formula (S1), $Cy^{s1}$ is represented by formula (S1b) or (S1b1); and the remaining variables are as described above in the $1^{st}$ specific embodiment. More specifically, $R^{x3}$ is a $(C_2\text{-}C_4)$alkyl.

In a $4^{th}$ specific embodiment, for immunoconjugates of formula (S1), $R_a$ and $R_b$ are both H, and $R_5$ and $R_9$ are both H or Me; and the remaining variables are as described above in the $1^{st}$ or $2^{nd}$ specific embodiment.

In a $5^{th}$ specific embodiment, for immunoconjugates of formula (S1), P is a peptide containing 2 to 5 amino acid residues; and the remaining variables are as described above in the $1^{st}$, $2^{nd}$ or $4^{th}$ specific embodiment. In a more specific embodiment, P is selected from the group consisting of Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 55), β-Ala-Leu-Ala-Leu (SEQ ID NO: 57), Gly-Phe-Leu-Gly (SEQ ID NO: 73), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. Even more specifically, P is Gly-Gly-Gly, Ala-Val, Ala-Ala, Ala-D-Ala, D-Ala-Ala, or D-Ala-D-Ala.

In a $6^{th}$ specific embodiment, for immunoconjugates of formula (S1), Q is —$SO_3M$; and the remaining variables are as described above in the $1^{st}$, $2^{nd}$, $4^{th}$ or $5^{th}$ specific embodiment.

In a $7^{th}$ specific embodiment, the immunoconjugate of the second embodiment is represented by the following formula:

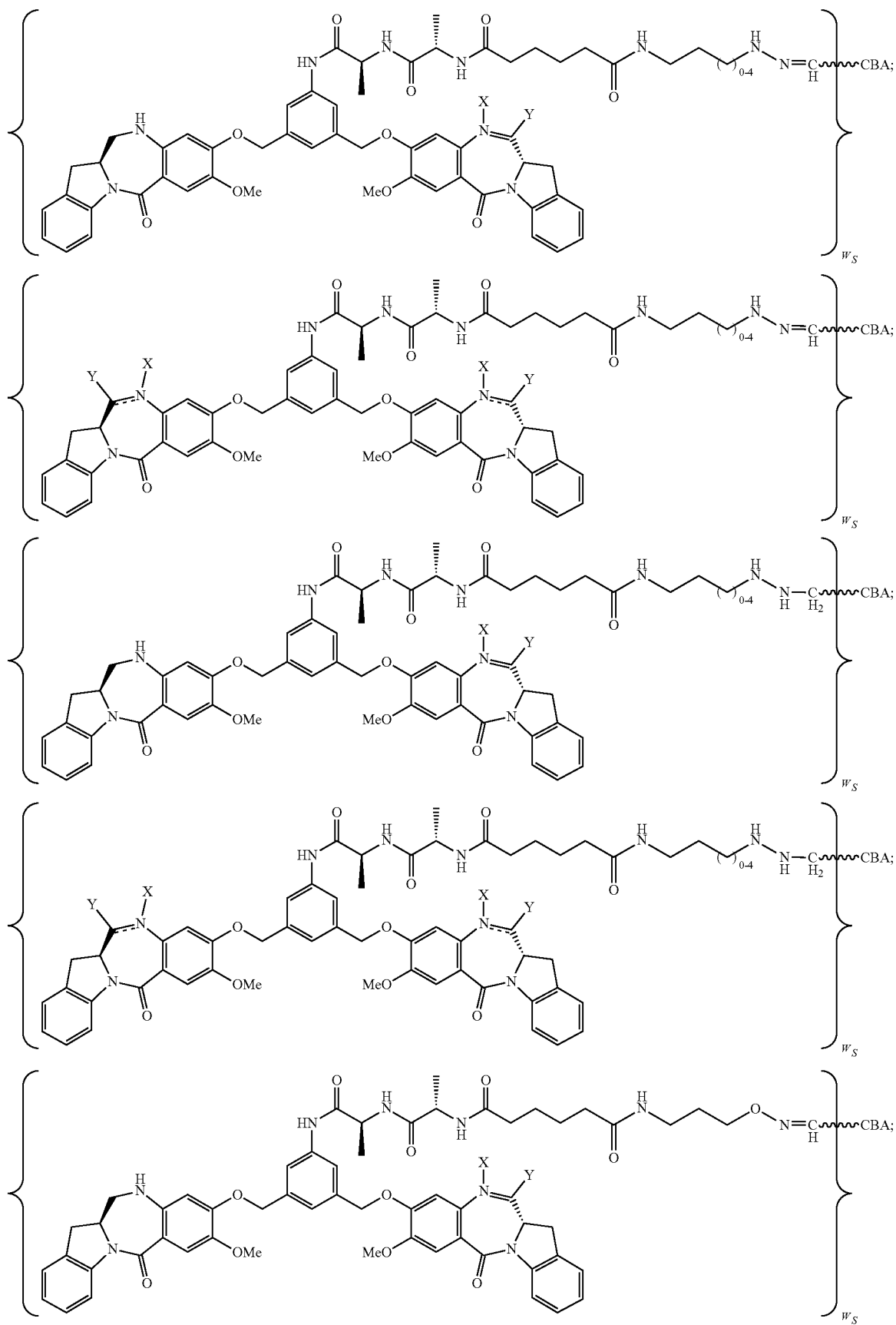

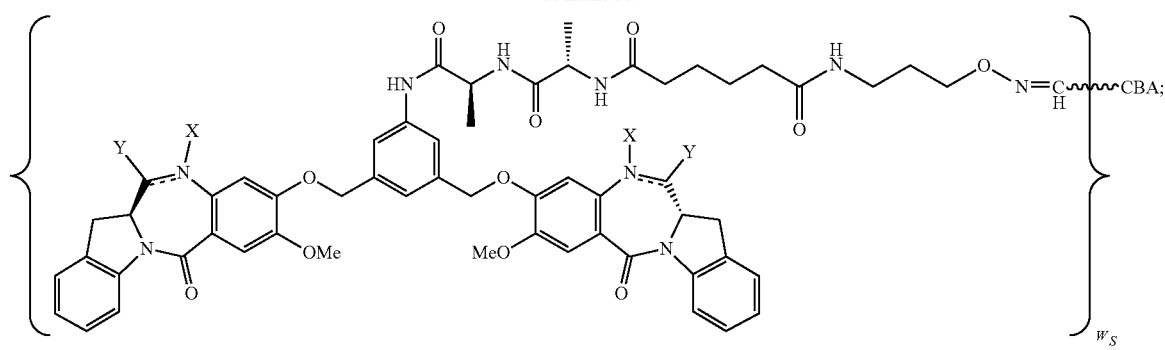
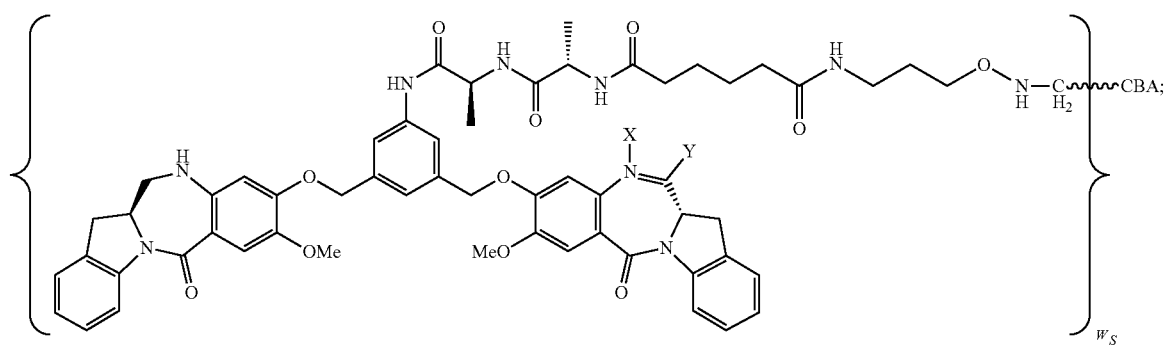
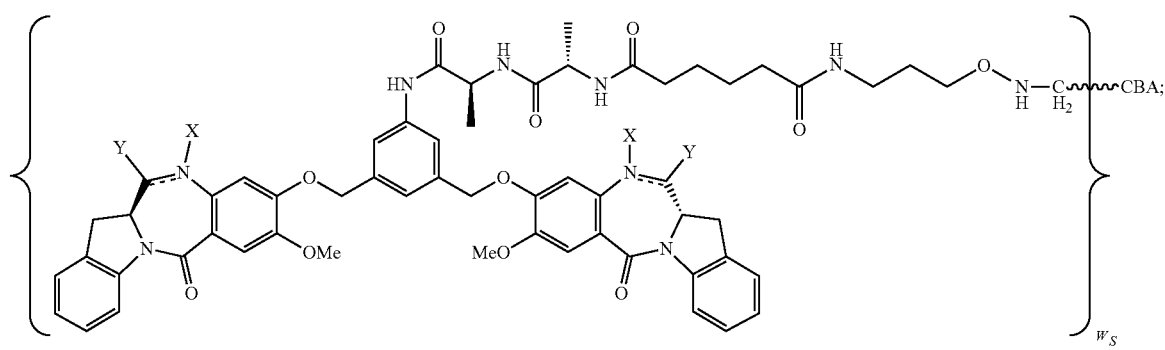
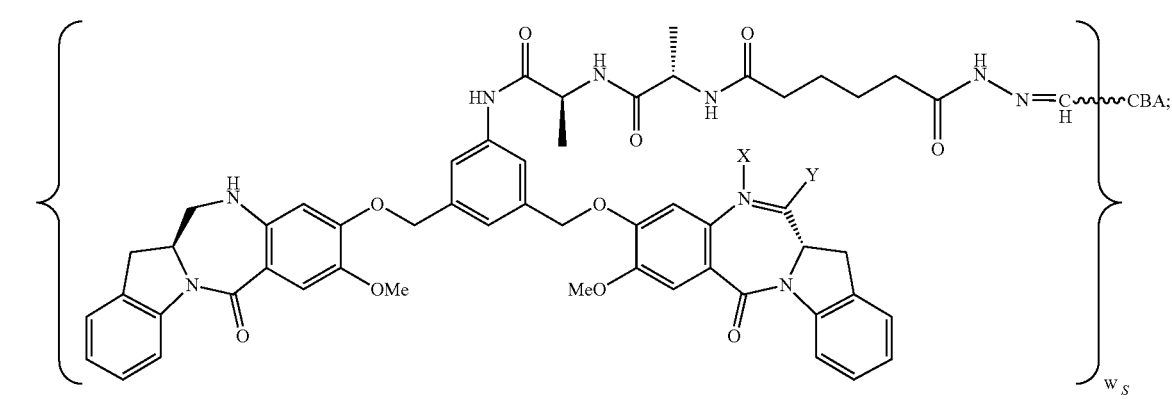

-continued
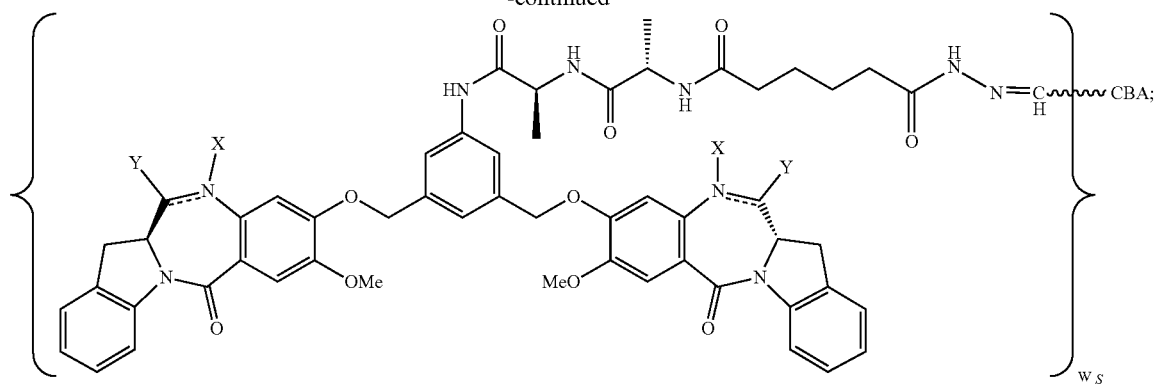
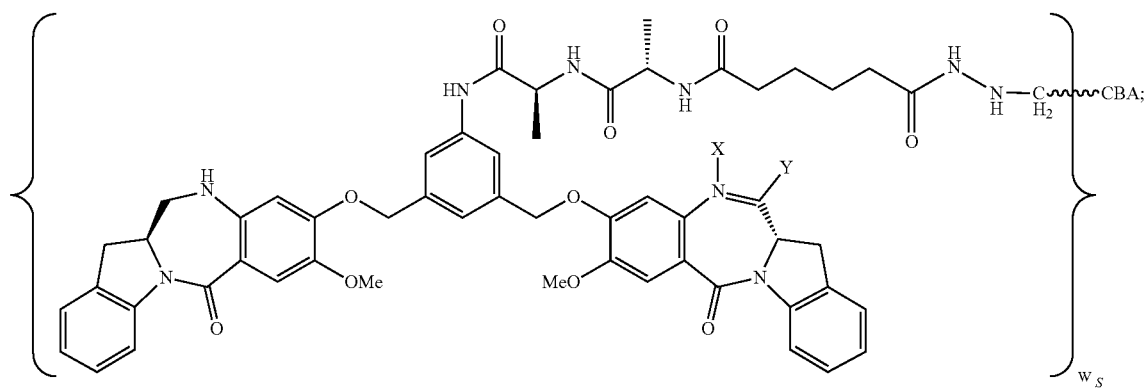
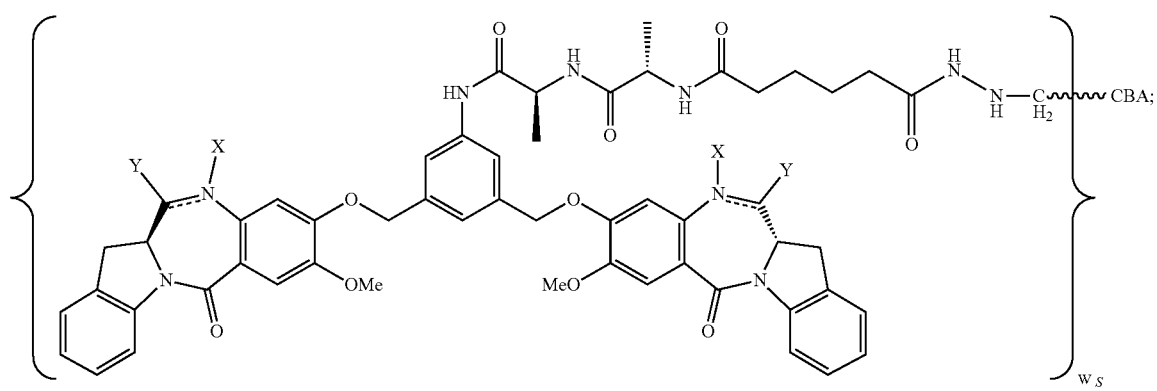
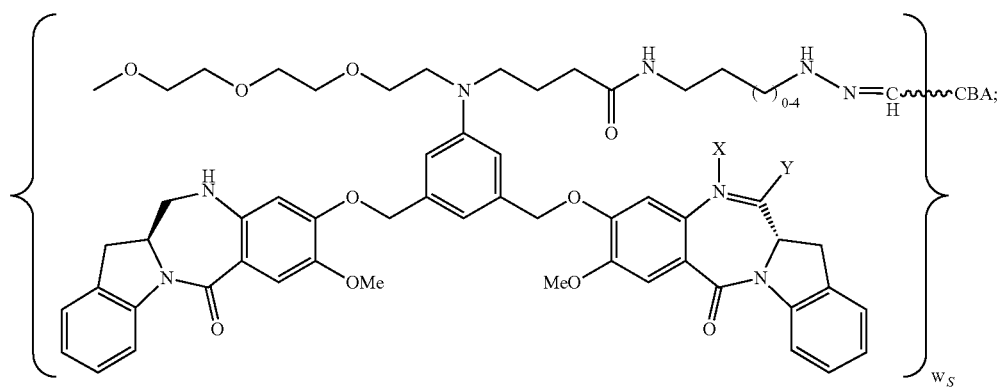

-continued
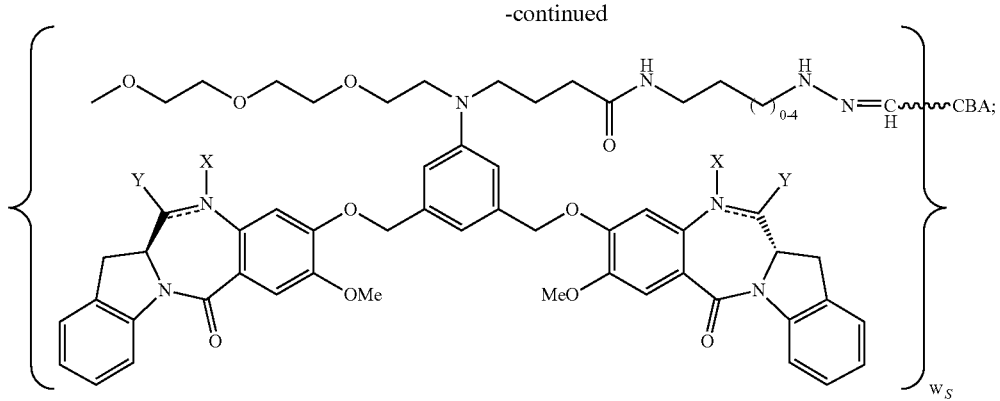
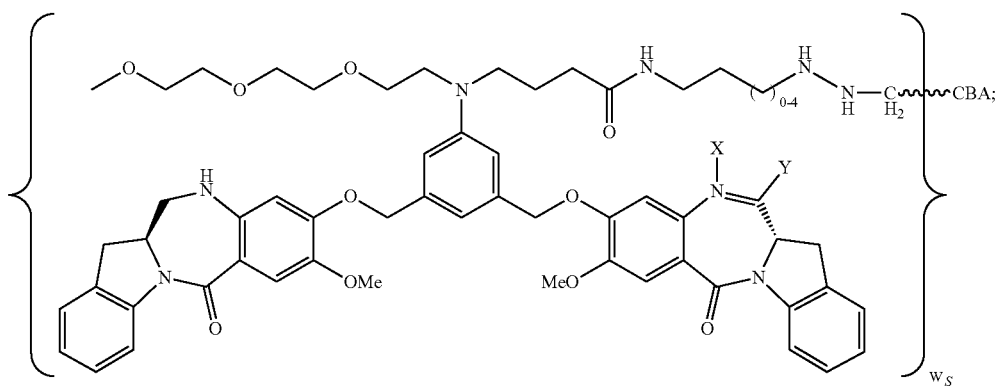
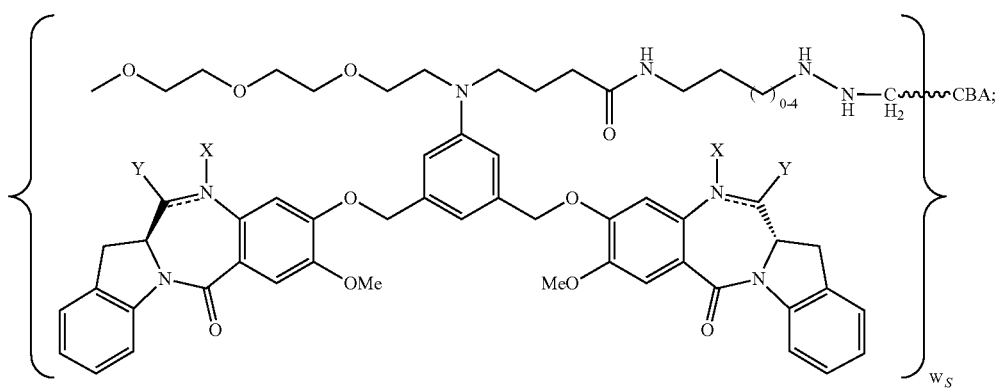
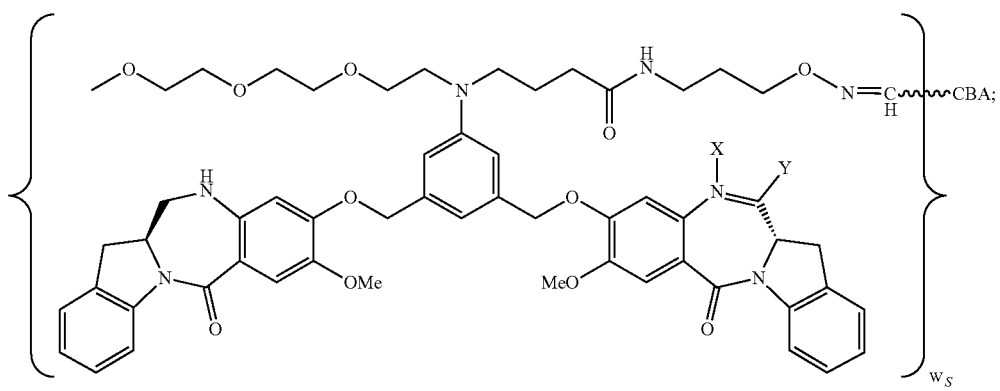

-continued
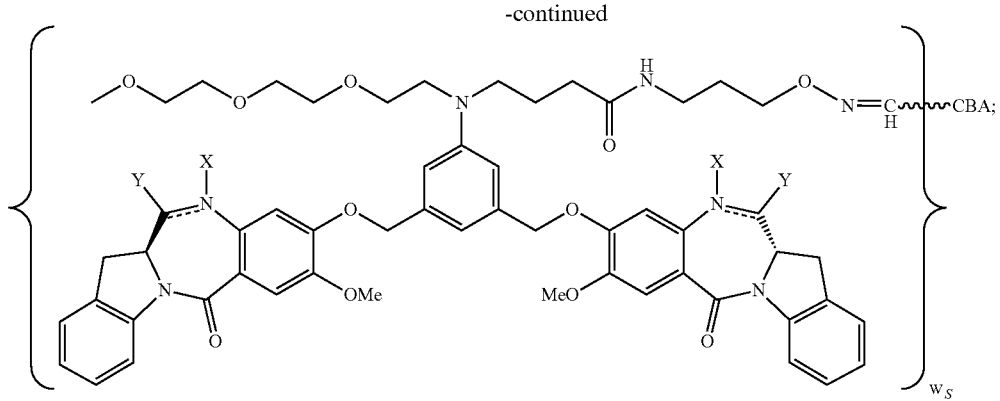
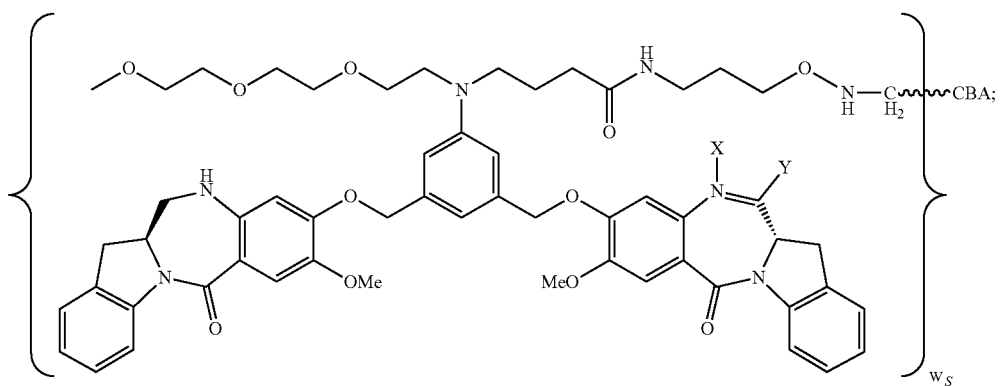
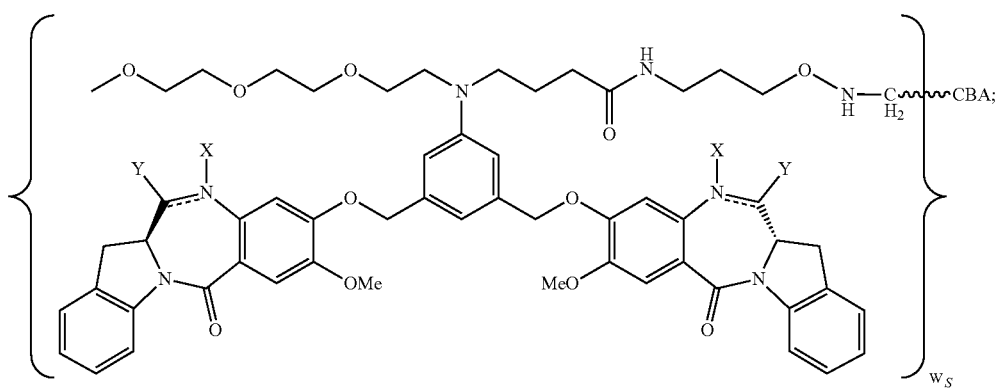
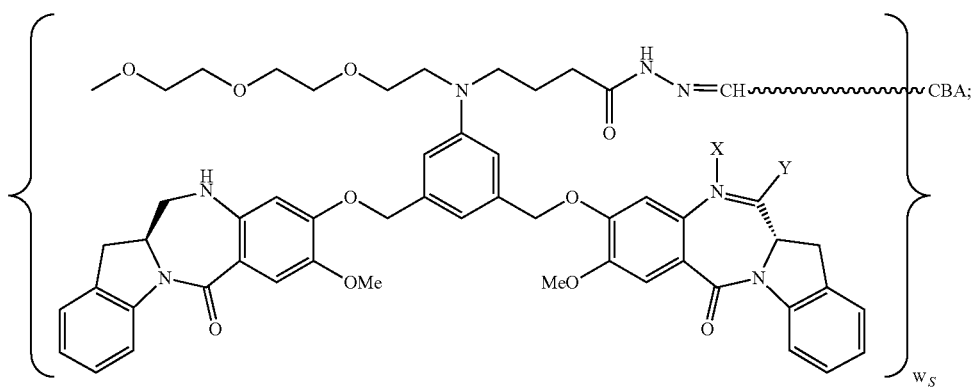

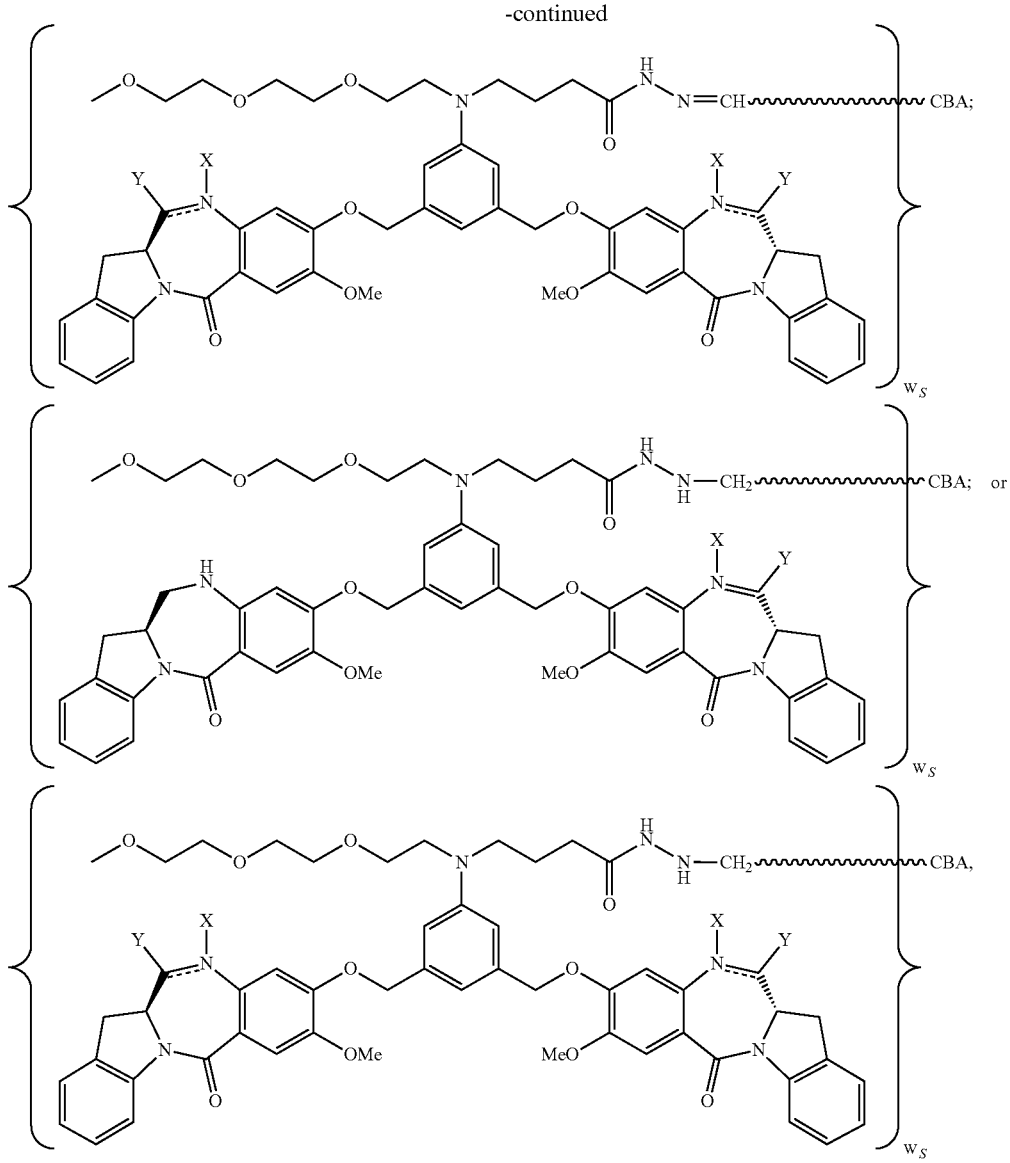

or a pharmaceutically acceptable salt thereof, wherein the double line ⚌ between N and C represents a single bond or a double bond, provided that when it is a double bond, X is absent and Y is —H, and when it is a single bond, X is —H, and Y is —OH or —SO$_3$M. In a more specific embodiment, the double line ⚌ between N and C represents a double bond, X is absent and Y is —H. In another more specific embodiment, the double line ⚌ between N and C represents a single bond, X is —H and Y is —SO$_3$M.

In an 8$^{th}$ specific embodiment, the immunoconjugates of the present invention is represented by the following formula:

$$CBA \sim (J_{CB'} - Cy^{s1})_{W_S};$$  (S2)

wherein:
CBA is the oxidized CD123/IL-3Rα-binding agent described in the first aspect of the invention (e.g. a subject oxidized antibody or antigen-binding fragment thereof described herein above, or a subject oxidized polypeptide thereof described above);

$J_{CB'}$ is a moiety formed by reacting an aldehyde group on the CBA and an aldehyde reactive group on Cy$^{s2}$, and is represented by the following formula:

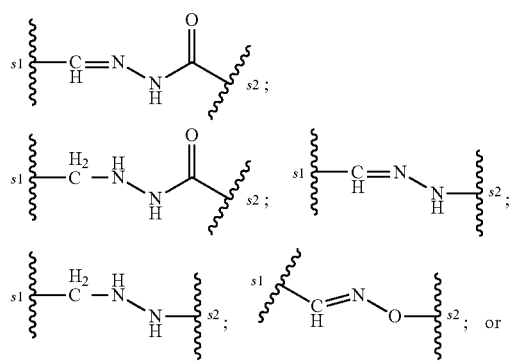

-continued

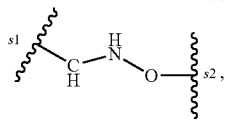

wherein s1 is the site covalently linked to the CBA; and s2 is the site covalently linked to Cy$^{s2}$;

Cy$^{s2}$ is represented by the following formula:

$R^{x1}$ is a $(C_1-C_6)$alkyl;
$R^e$ is —H or a $(C_1-C_6)$alkyl;
W' is —NR$^{e'}$,
$R^{e'}$ is —(CH$_2$—CH$_2$—O)$_n$—R$^k$;
n is an integer from 2 to 6;
$R^k$ is —H or -Me;
$R^{x2}$ is a $(C_1-C_6)$alkyl;

(S2a)

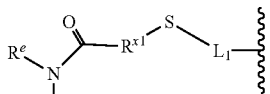
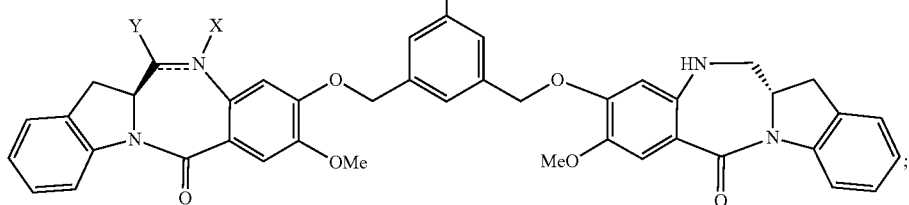

(S2a1)

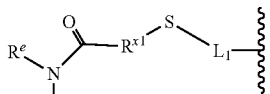
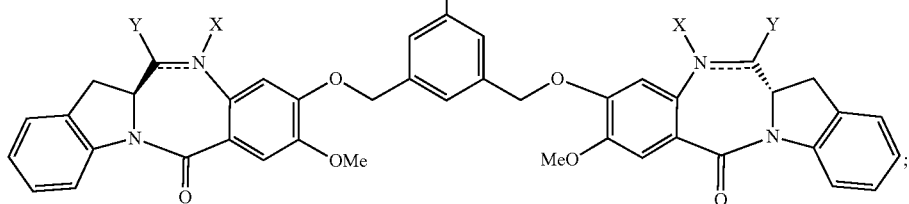

(S2b)

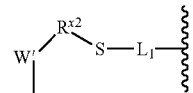
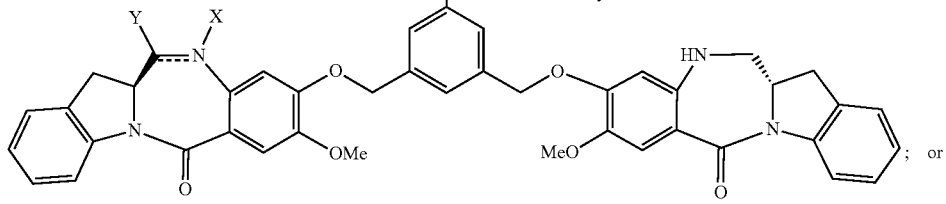
; or (S2b1)

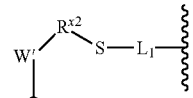
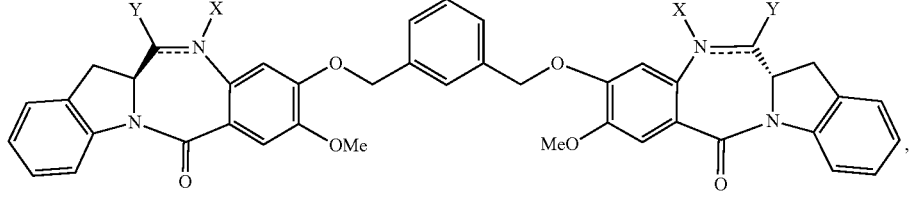
, or a pharmaceutically acceptable salt thereof, wherein:

the double line ═ between N and C represents a single bond or a double bond, provided that when it is a double bond, X is absent and Y is —H or a $(C_1-C_4)$ alkyl; and when it is a single bond, X is —H or an amine protecting moiety, and Y is —OH or —SO$_3$M;

M is H$^+$ or a cation;

$L_1$ is represented by the following formula:

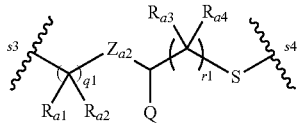

wherein:
s3 is the site covalently linked to the group $J_{CB}$;
s4 is the site covalently linked to the —S— group on $Cy^{s2}$;
$Z_{a2}$ is absent, —C(=O)—$NR_9$—, or —$NR_9$—C(=O)—;
$R_9$ is —H or a $(C_1-C_3)$alkyl;
Q is H, a charged substituent or an ionizable group;
$R_{a1}$, $R_{a2}$, $R_{a3}$, $R_{a4}$, for each occurrence, are independently H or $(C_1-C_3)$alkyl; and
q1 and r1 are each independently an integer from 0 to 10, provided that q1 and r1 are not both 0.

In a more specific embodiment, $Z_{a2}$ is absent; q1 and r1 are each independent an integer from 0 to 3, provided that q1 and r1 are not both 0; and the remaining variables are as described above in the 8th specific embodiments. Even more specifically, $R_{a1}$, $R_{a2}$, $R_{a3}$, $R_{a4}$ are all —H.

In another more specific embodiment, $Z_{a2}$ is —C(=O)—NH—, or —$NH_9$—C(=O)—; q1 and r1 are each independently an integer from 1 to 6; and the remaining variables are as described above in the 8th specific embodiments. Even more specifically, $R_{a1}$, $R_{a2}$, $R_{a3}$, $R_{a4}$ are all —H.

In a 9th specific embodiment, for immunoconjugate of formula (S2), $Cy^{s2}$ is represented by formula (S2a) or (S2a1); and the remaining variables are as described above in the 8th specific embodiment or any more specific embodiments described therein.

In a 10th specific embodiment, for immunoconjugate of formula (S2), $Cy^{s2}$ is represented by formula (S2b) or (S2b1); and the remaining variables are as described above in the 8th specific embodiment or any more specific embodiments described therein.

In an 11th specific embodiment, for immunoconjugate of formula (S2), -$L_1$- is represented by the following formula:

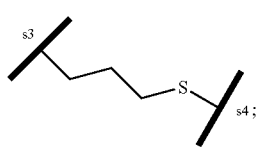

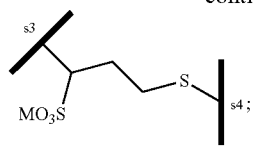

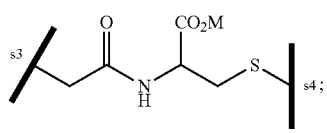

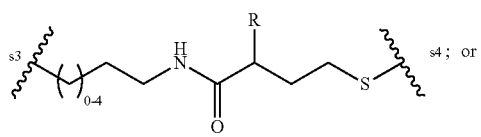

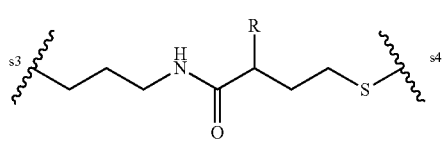

or a pharmaceutically acceptable salt thereof, wherein R is H or —$SO_3M$; and the remaining variables are as described above in the 8th, 9th or 10th specific embodiment or any more specific embodiments described therein.

In a 12th specific embodiment, for immunoconjugate of formula (S2), $R^e$ is H or Me; and $R^{x1}$ is —$(CH_2)_p$—$(CR^fR^g)$—, and $R^{x2}$ is —$(CH_2)_p$—$(CR^fR^g)$—, wherein $R^f$ and $R^g$ are each independently —H or a $(C_1-C_4)$alkyl; and p is 0, 1, 2 or 3. More specifically, $R^f$ and $R^g$ are the same or different, and are selected from —H and -Me.

In a 13th specific embodiment, the immunoconjugate of the second embodiment is represented by the following formula:

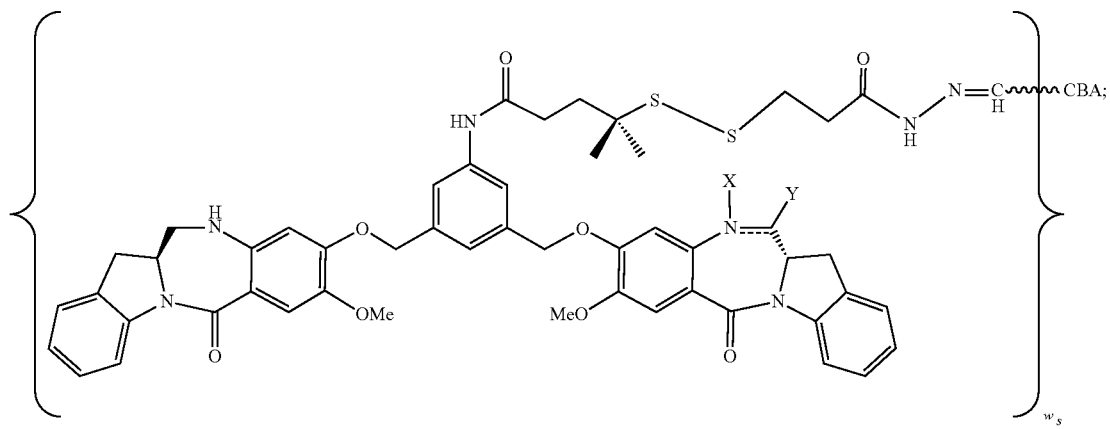

235 236
-continued
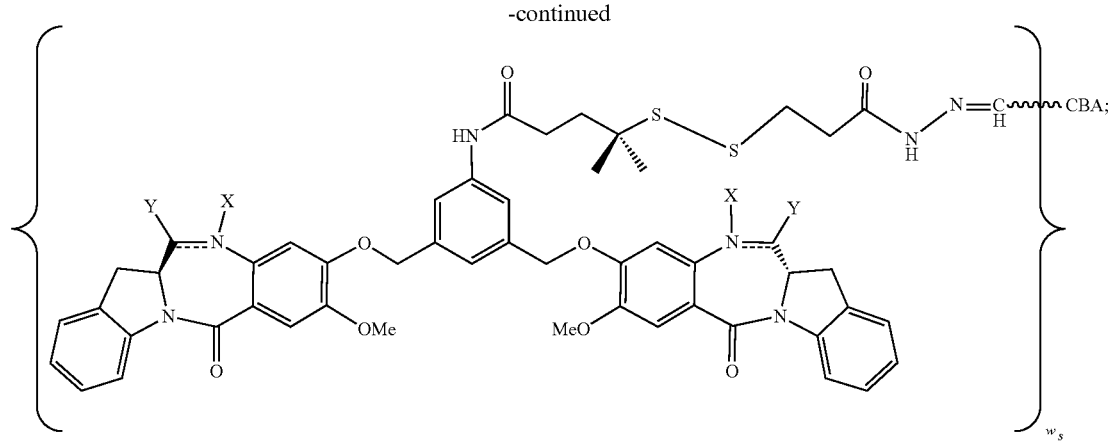
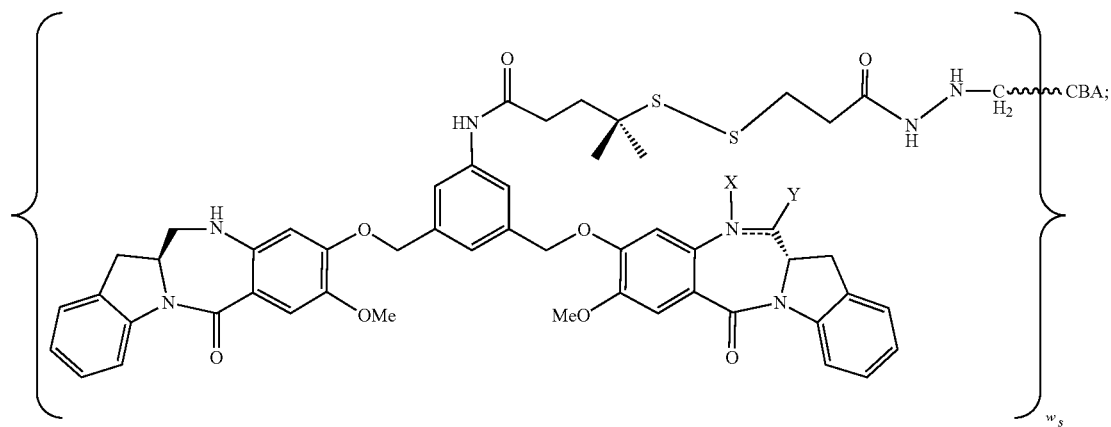
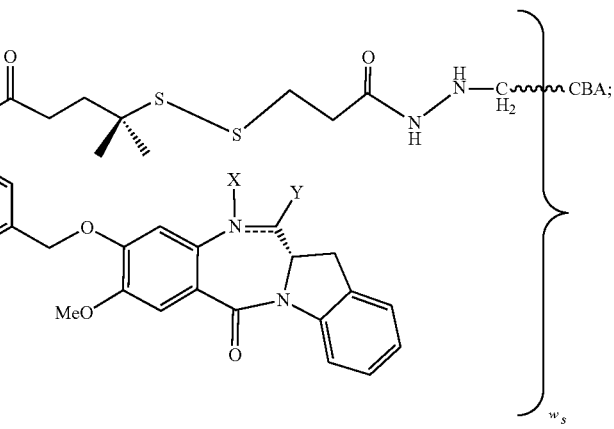
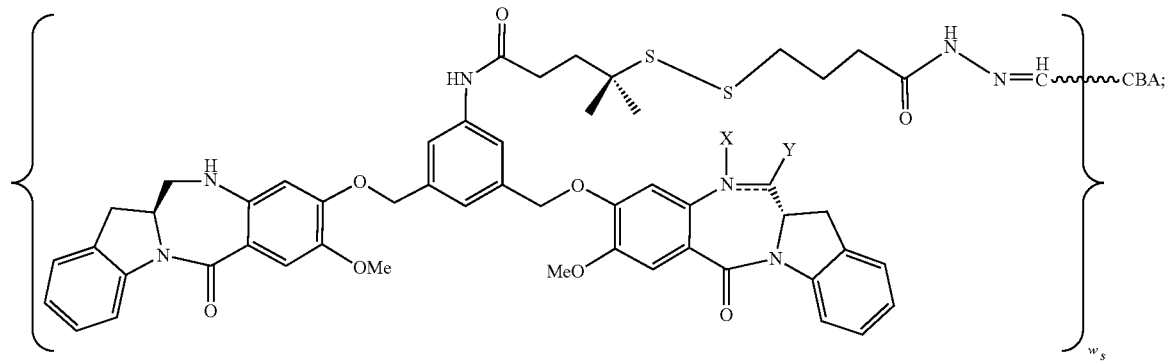

-continued
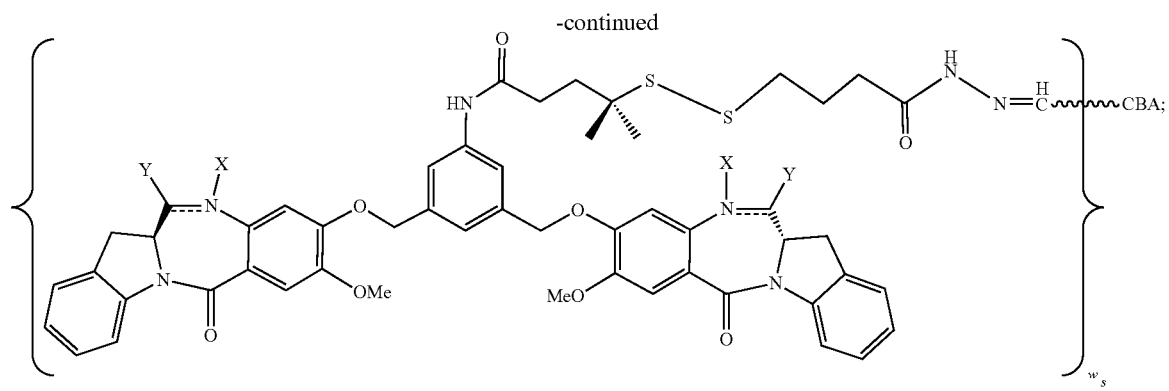
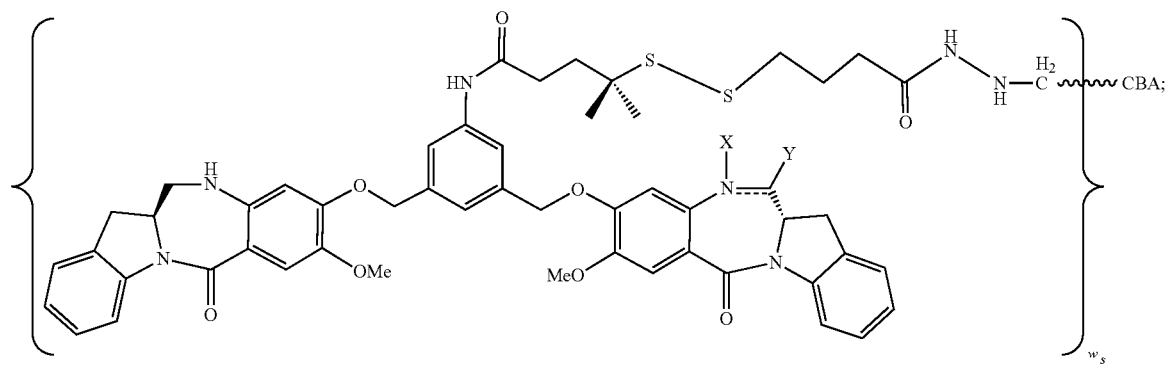
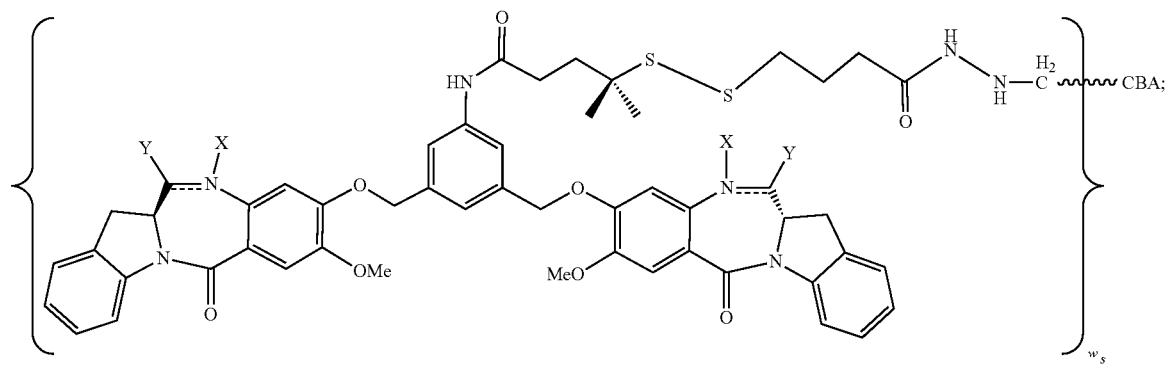
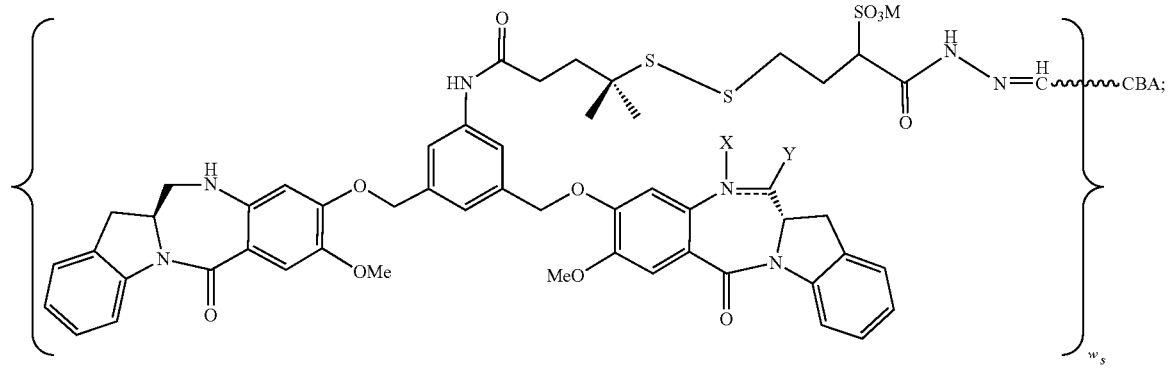

-continued
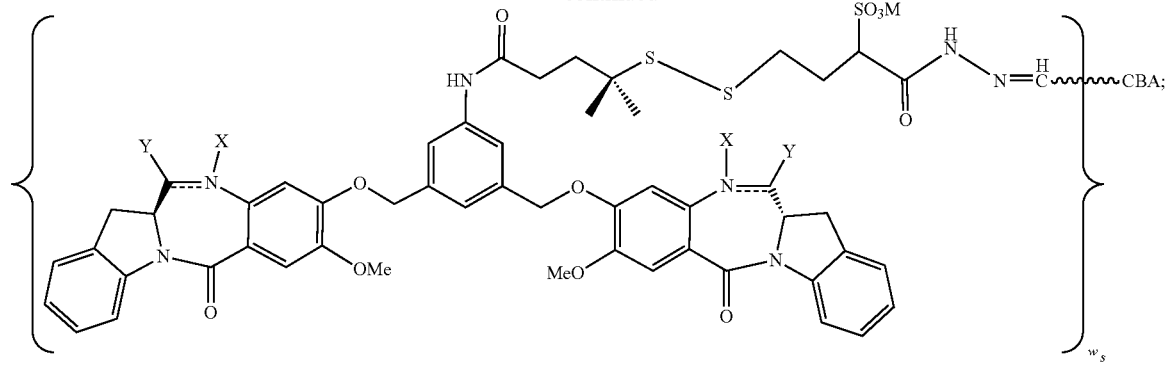
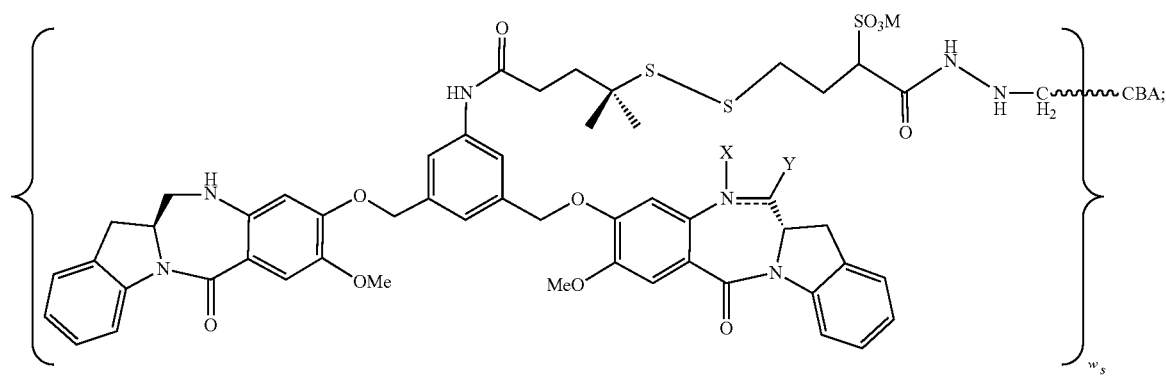
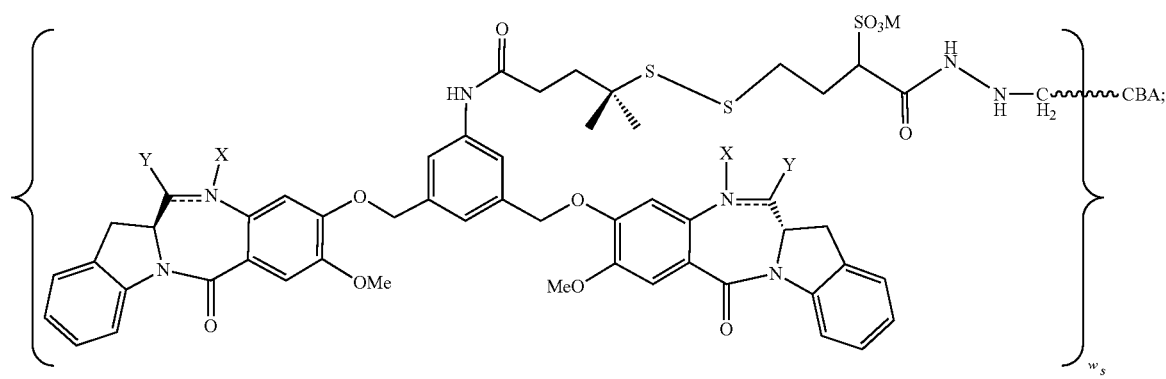
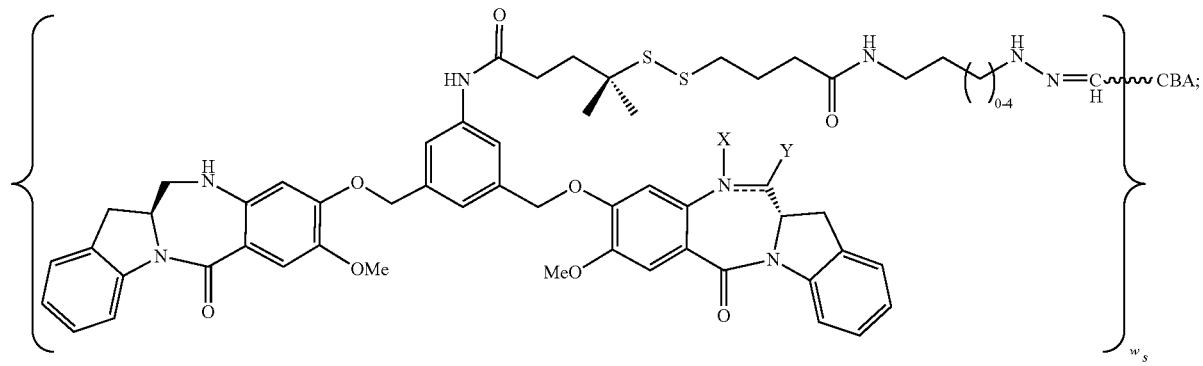

-continued
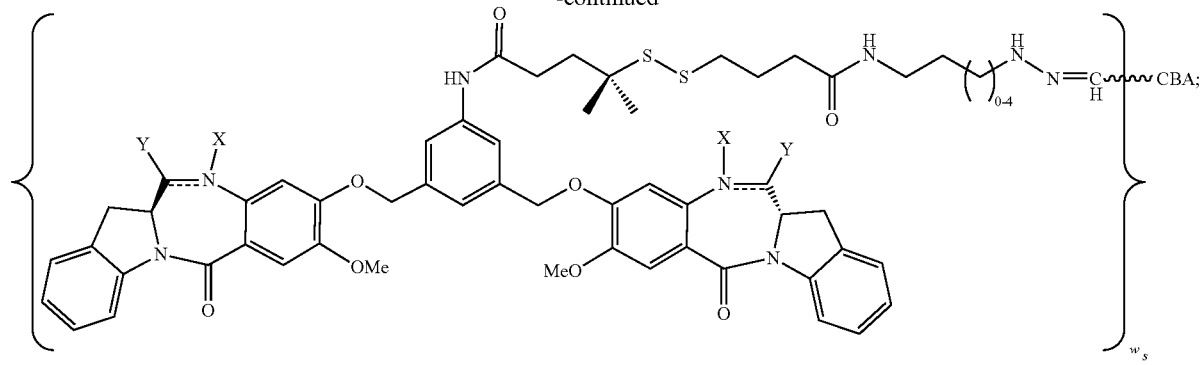
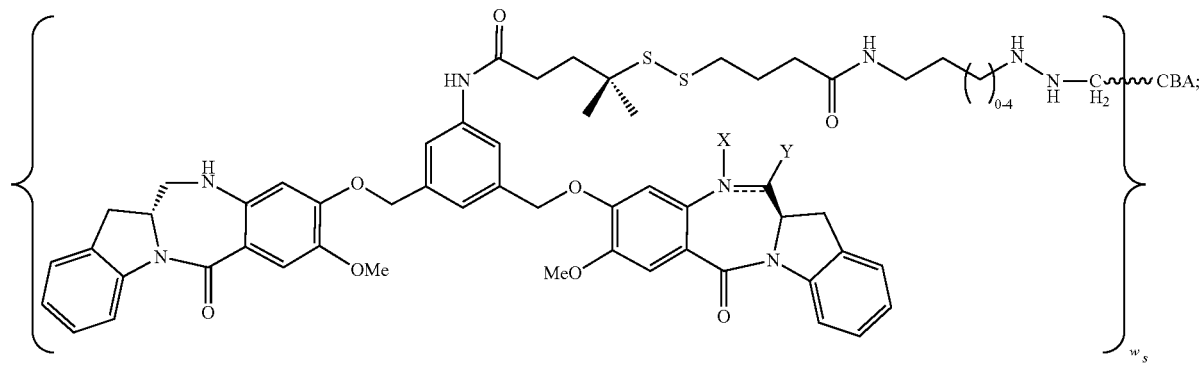
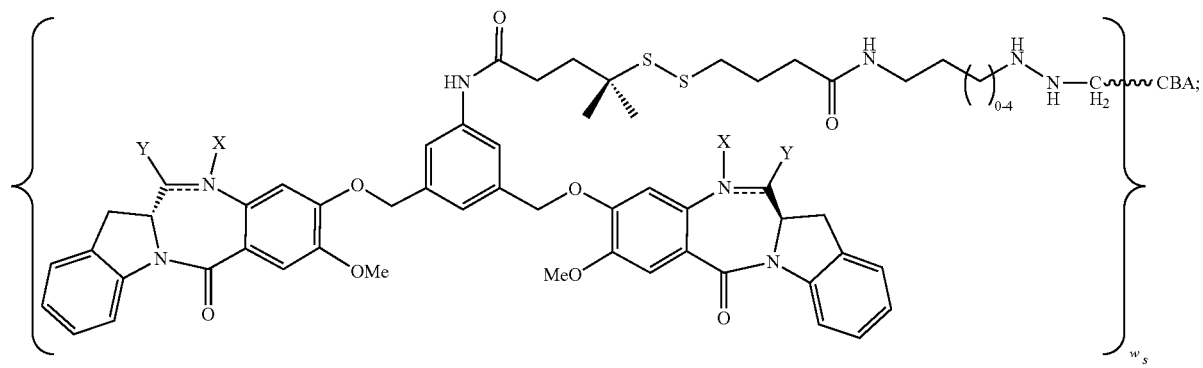
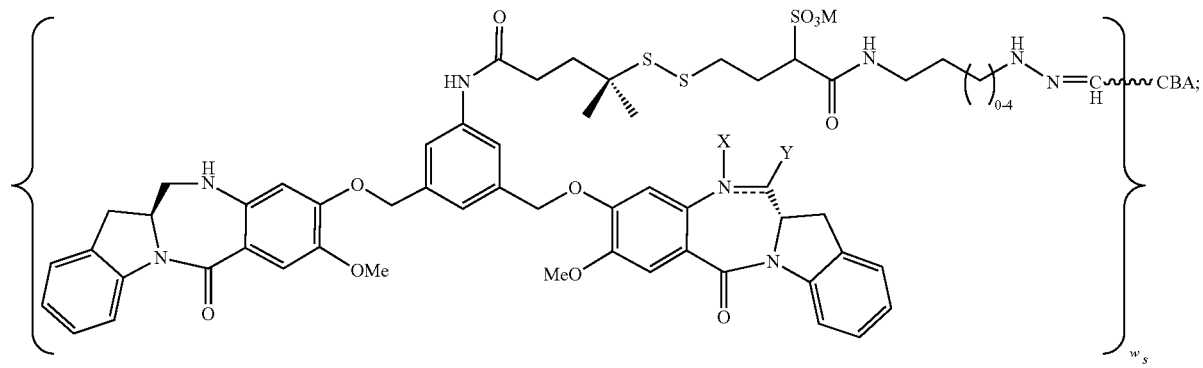

-continued
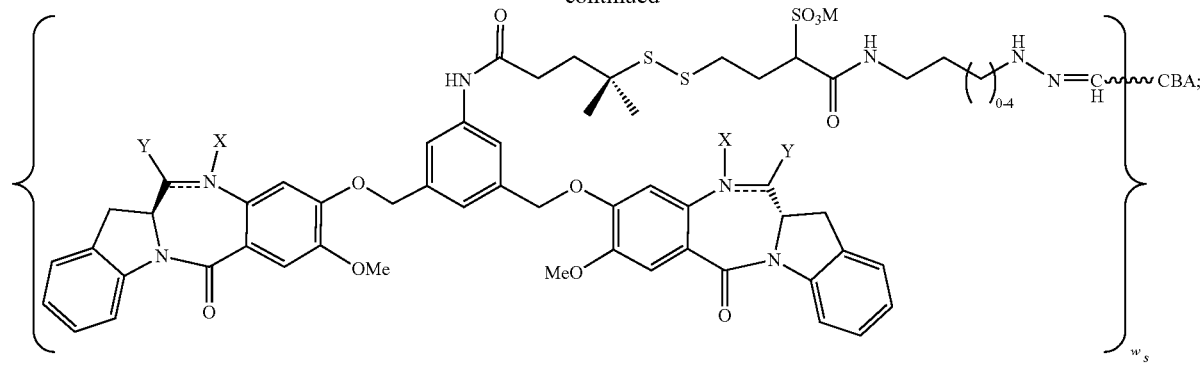
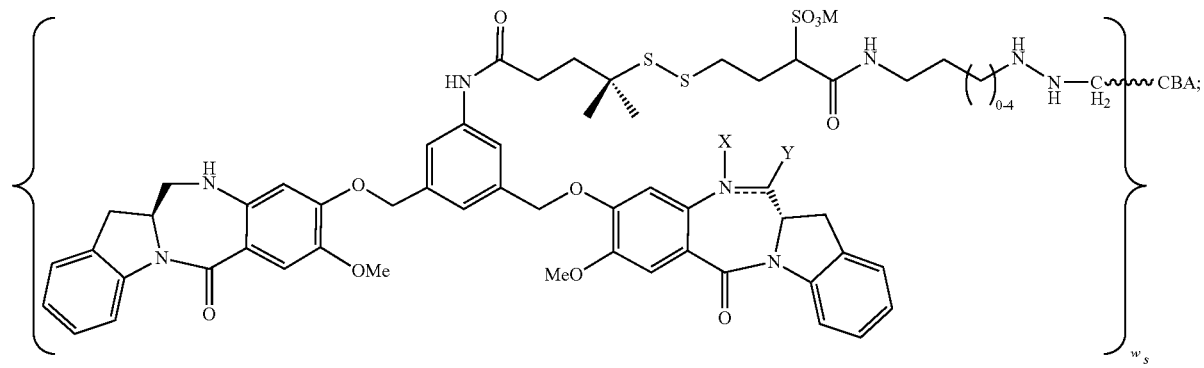
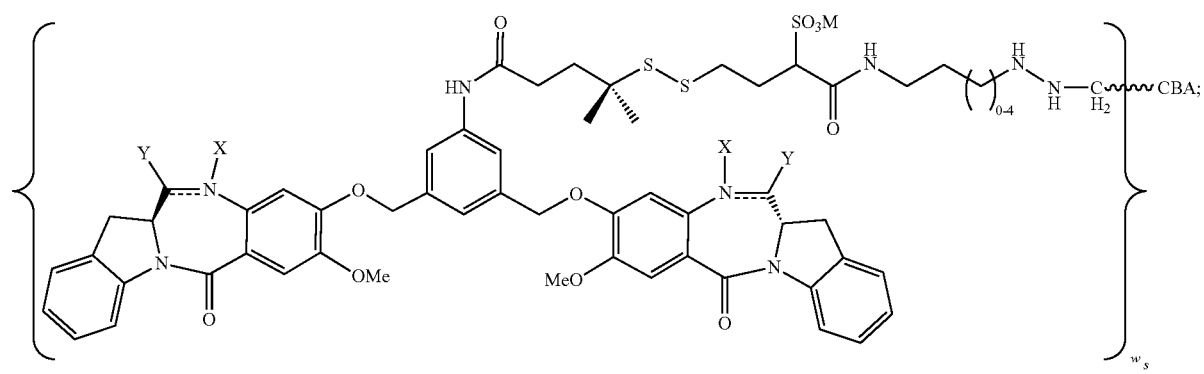
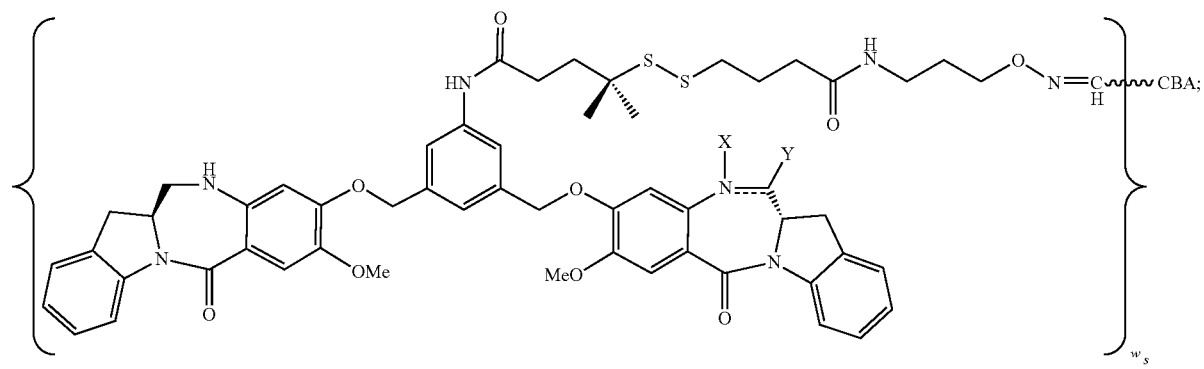

-continued
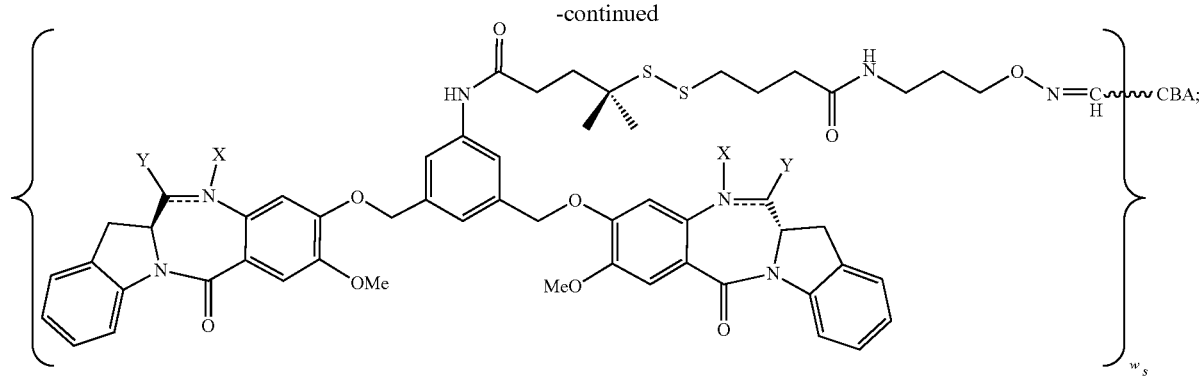
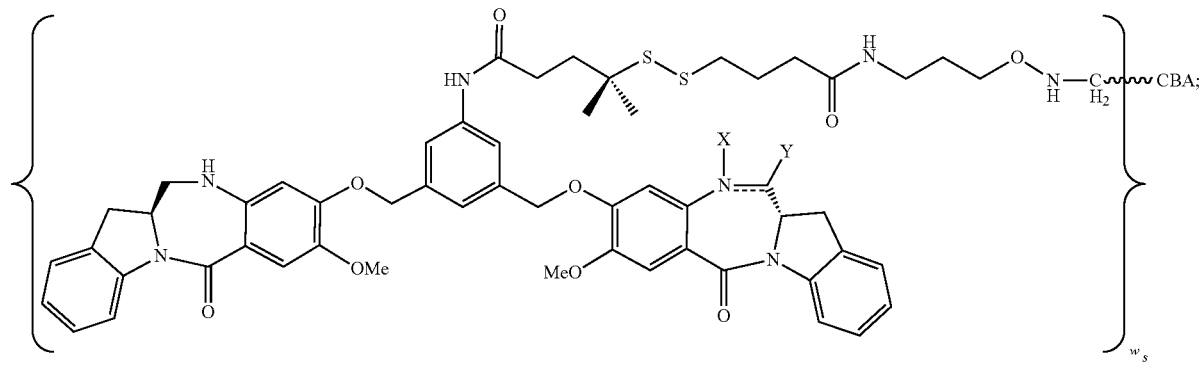
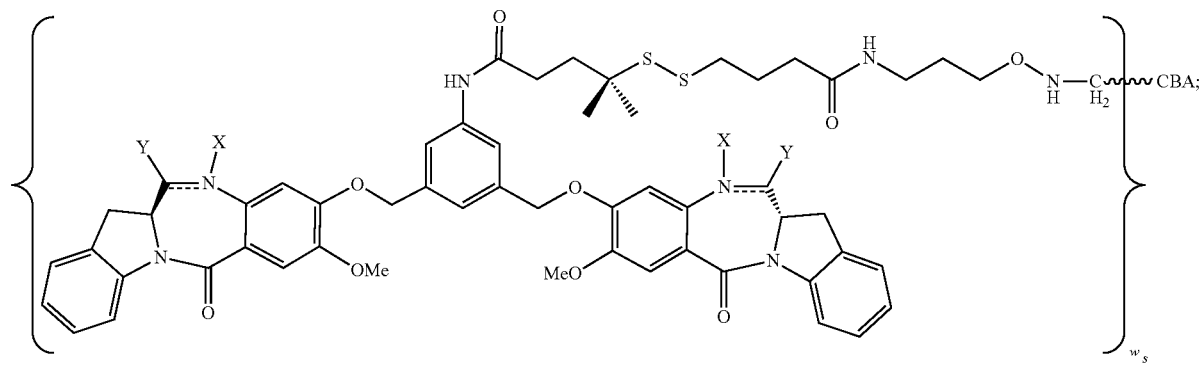
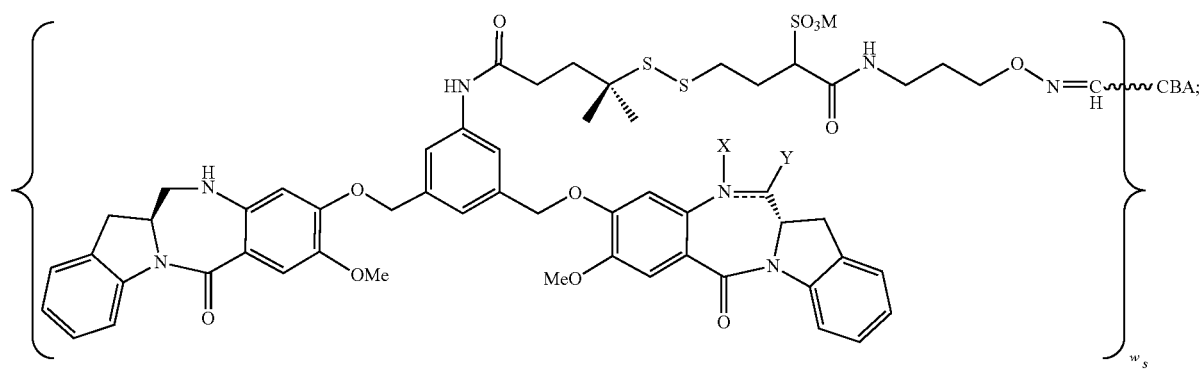

-continued
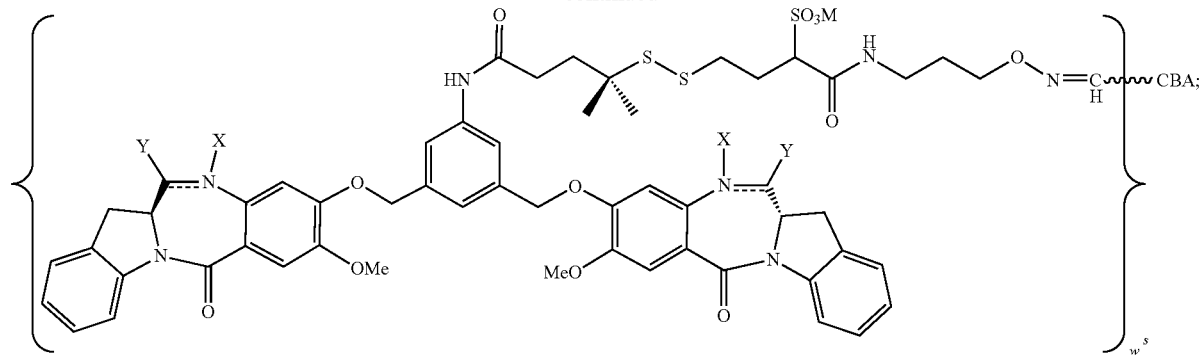
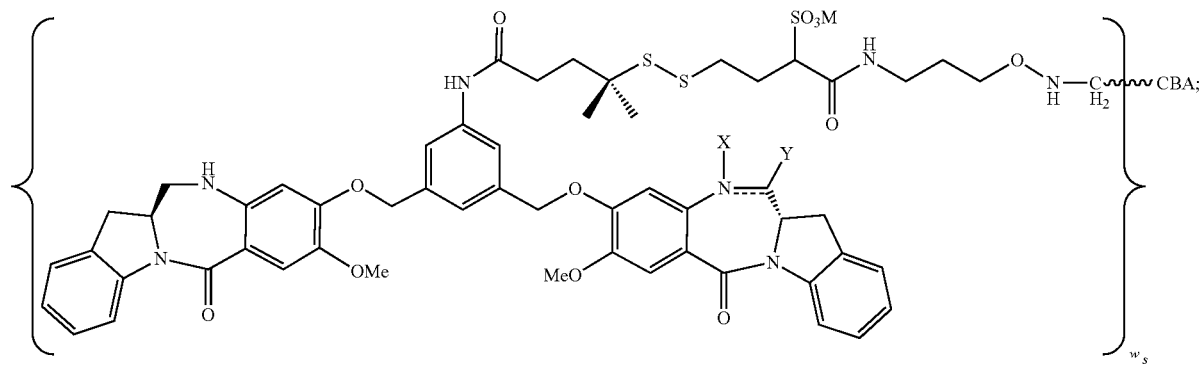
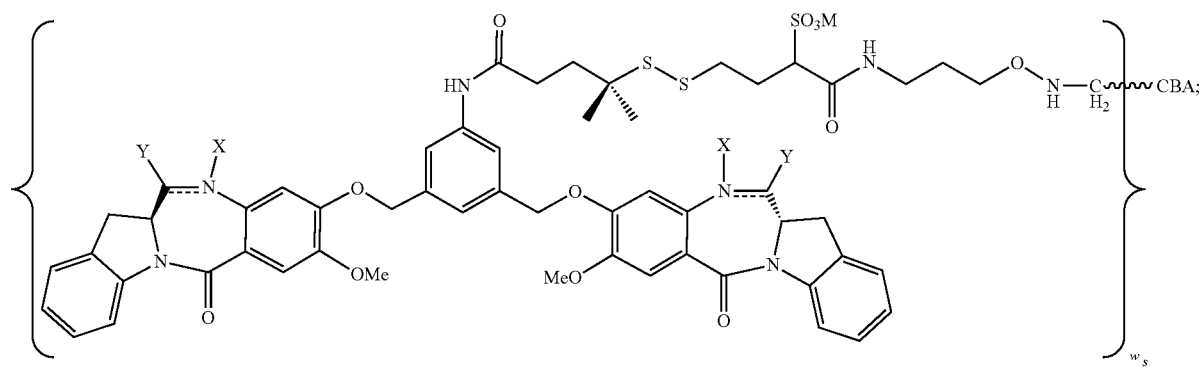
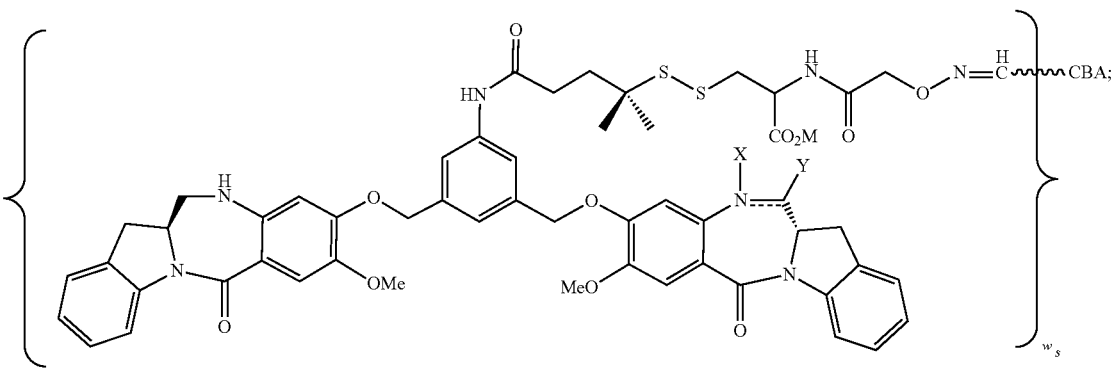

-continued
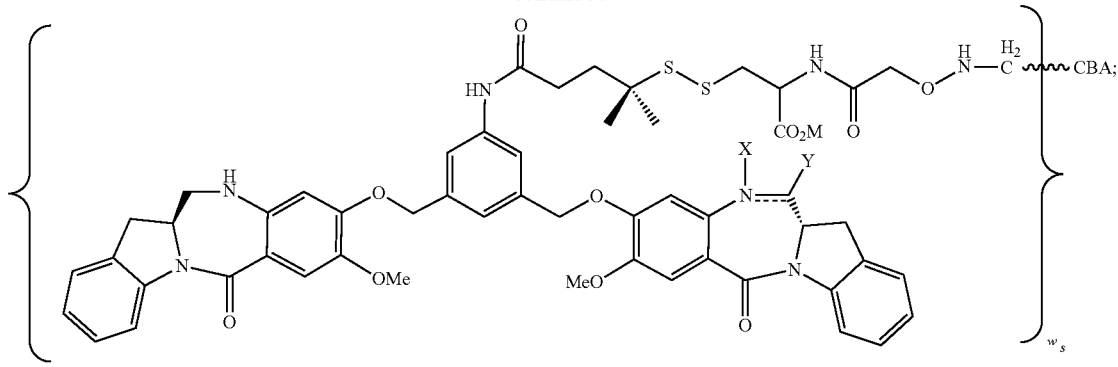
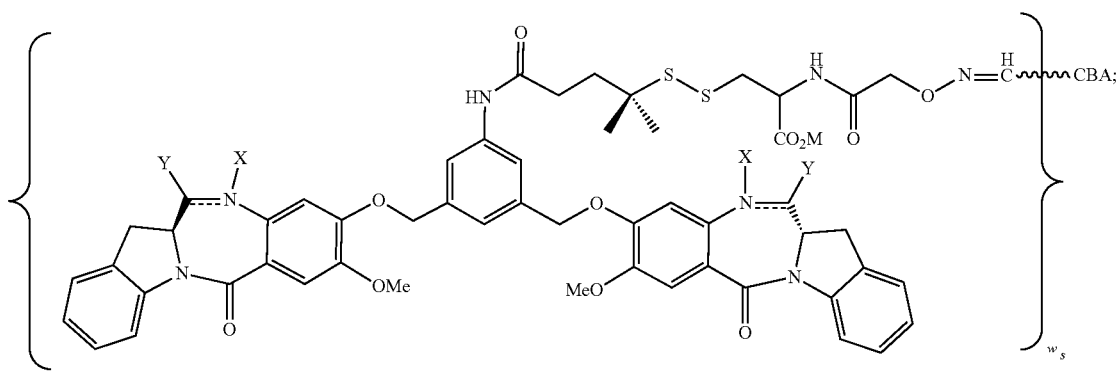
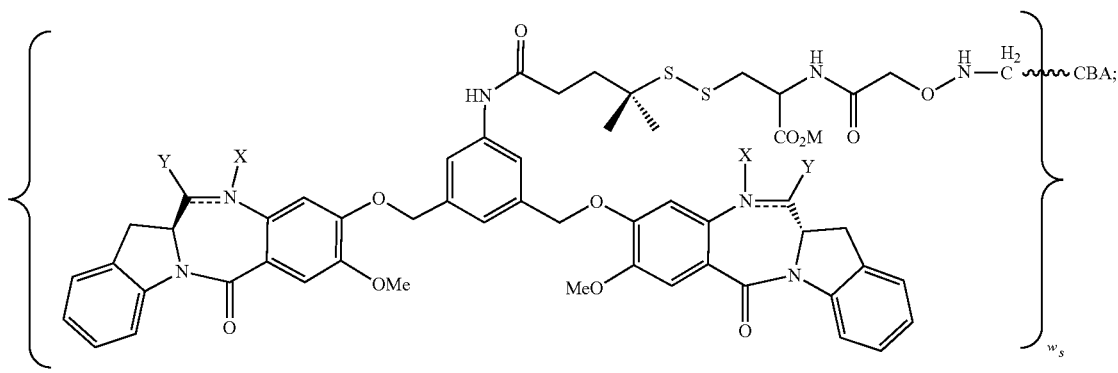
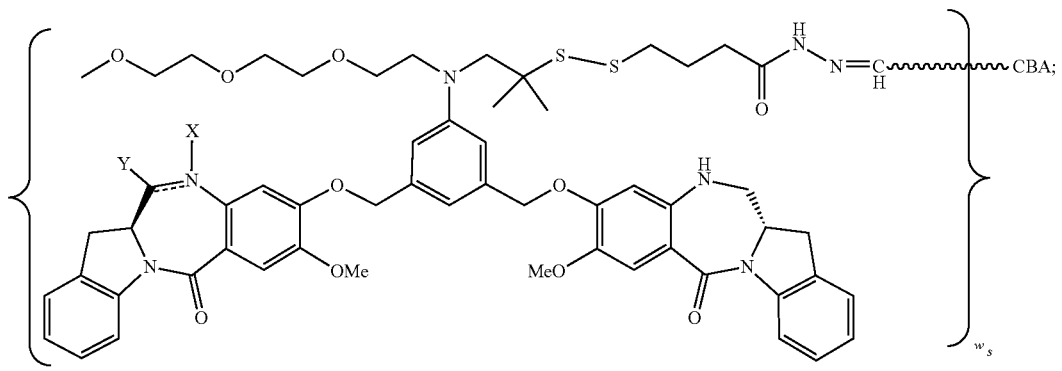

-continued
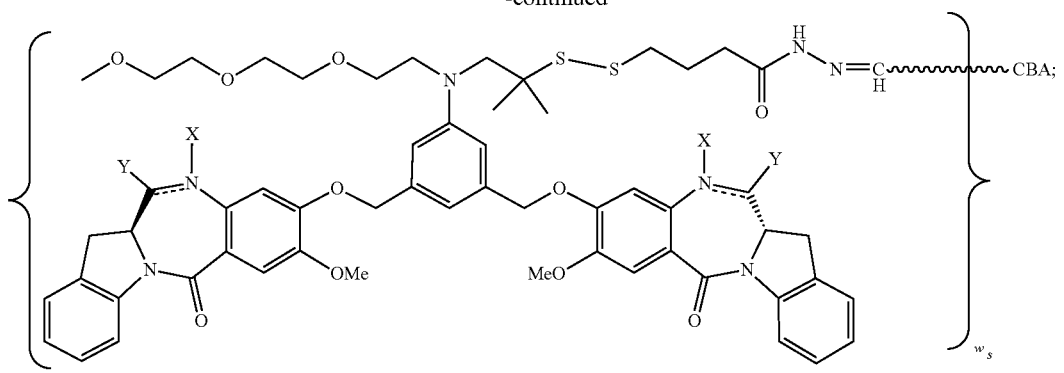
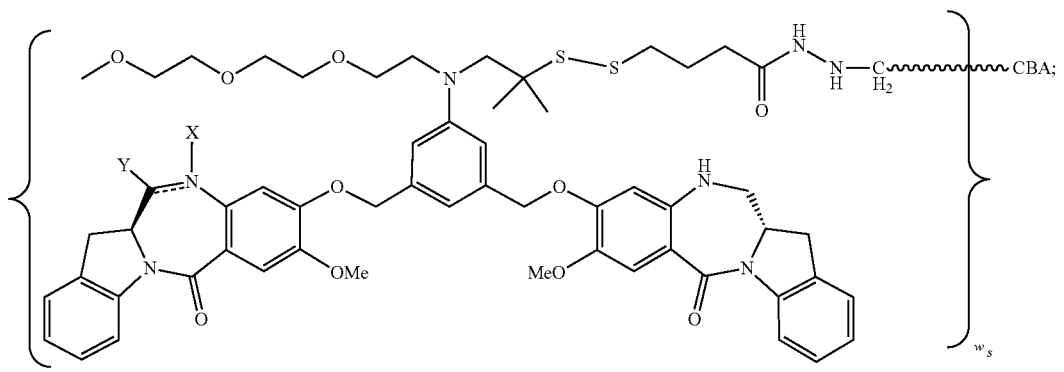
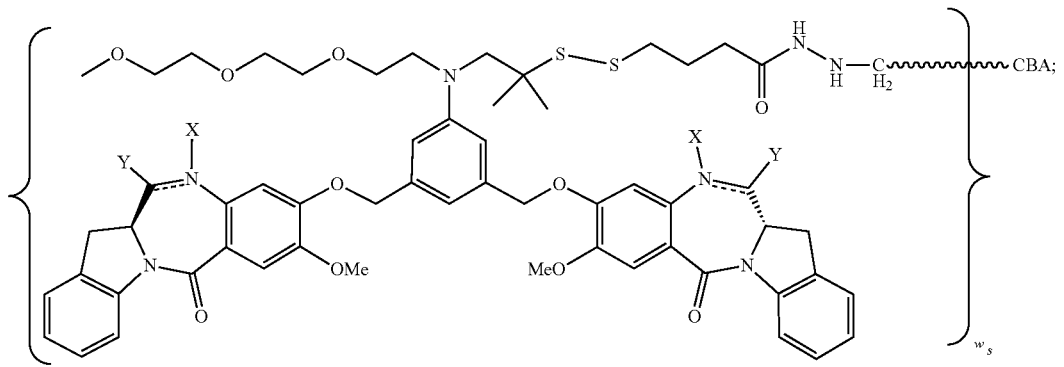
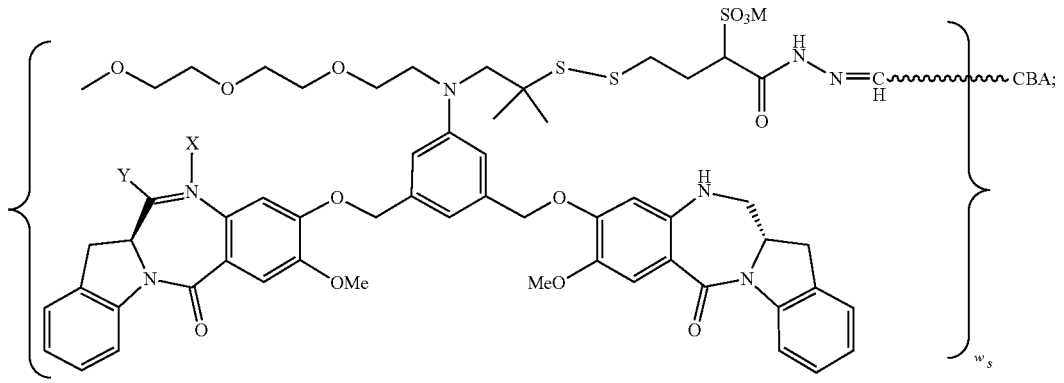

-continued
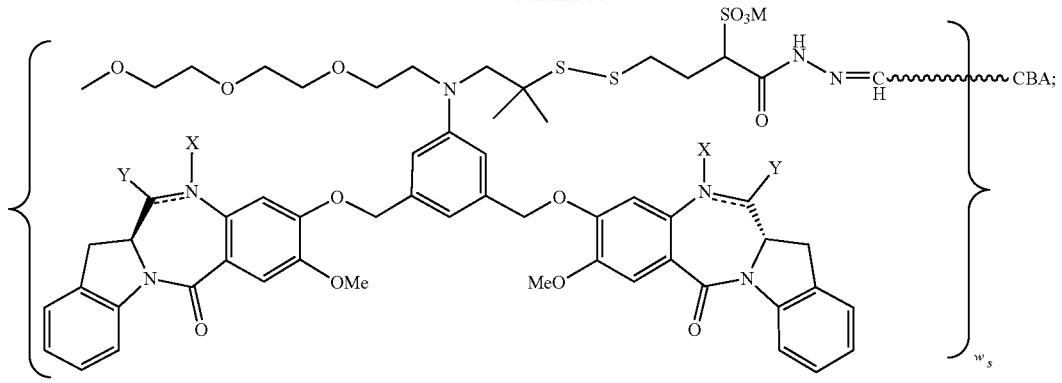
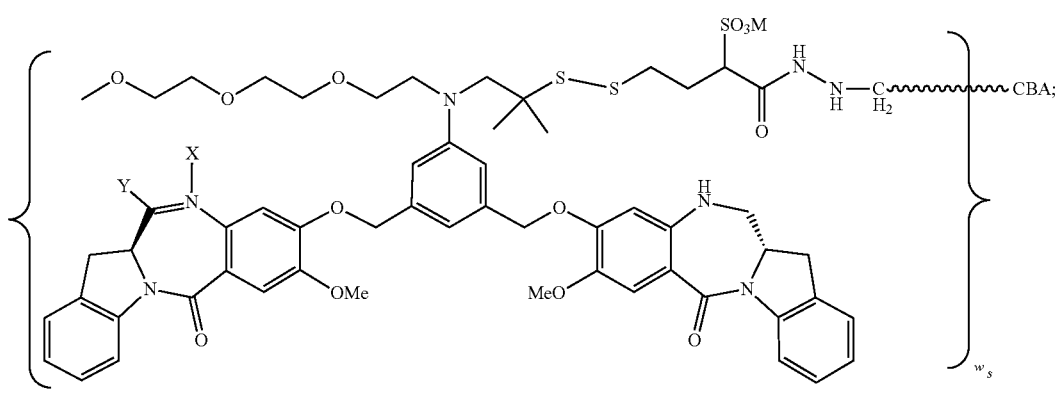
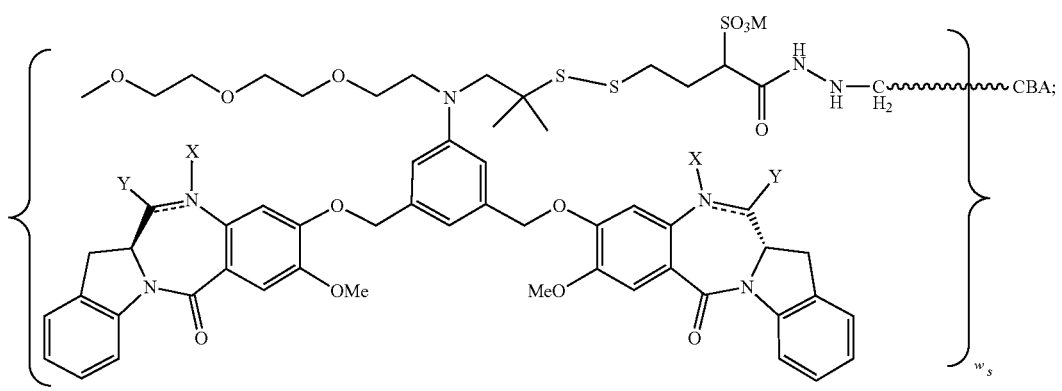
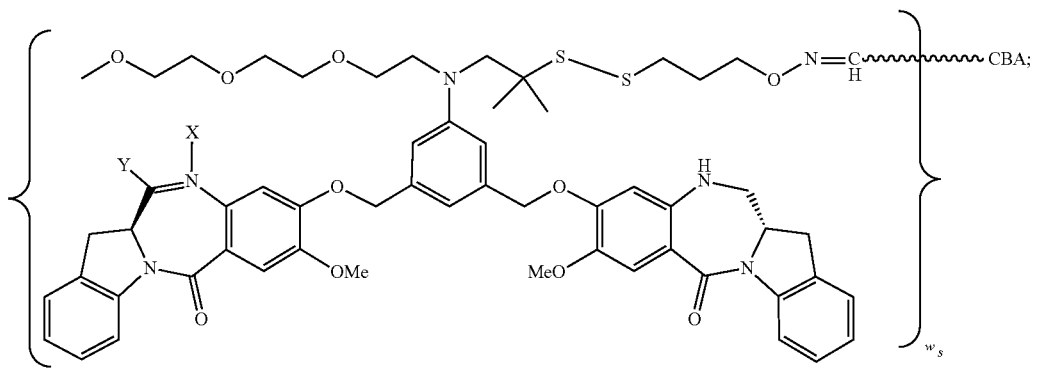

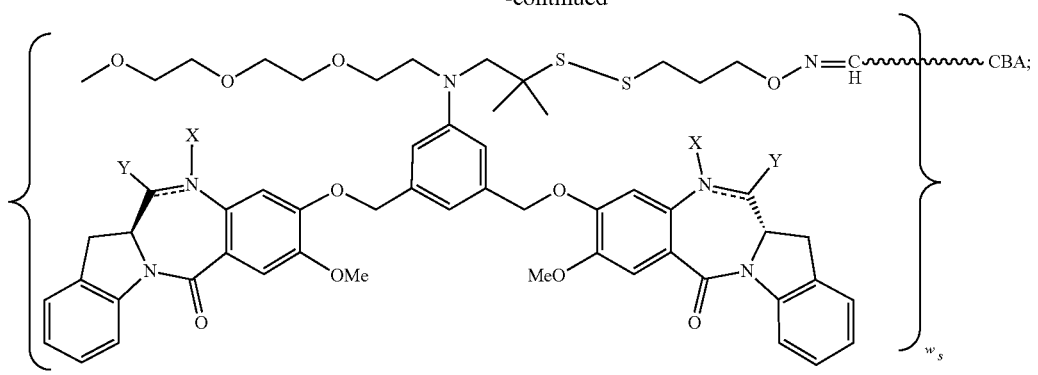
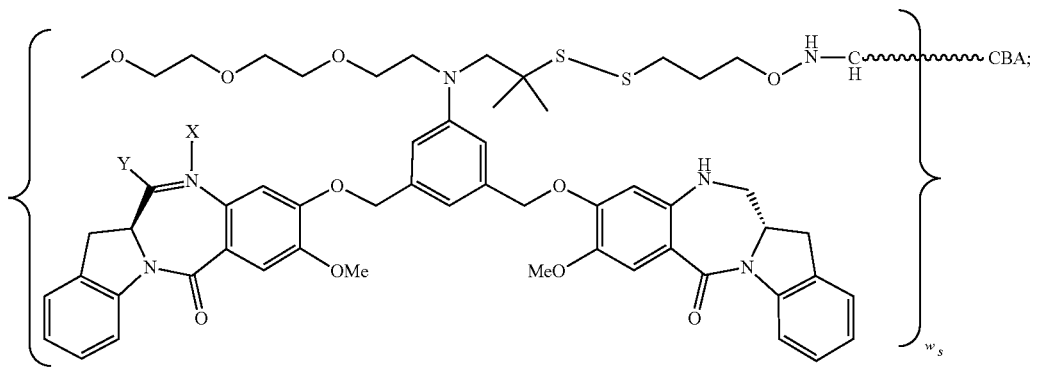
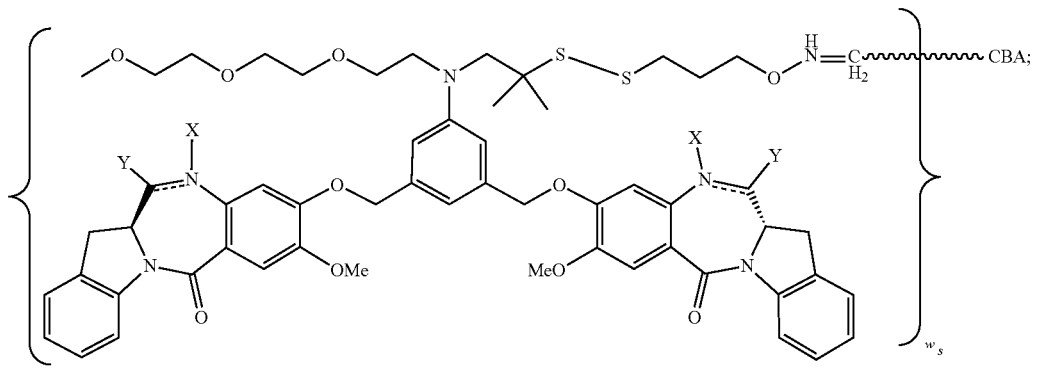
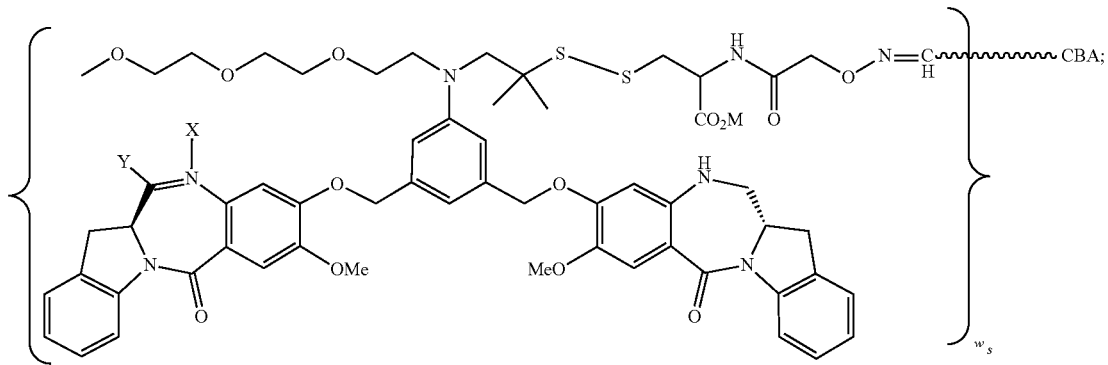

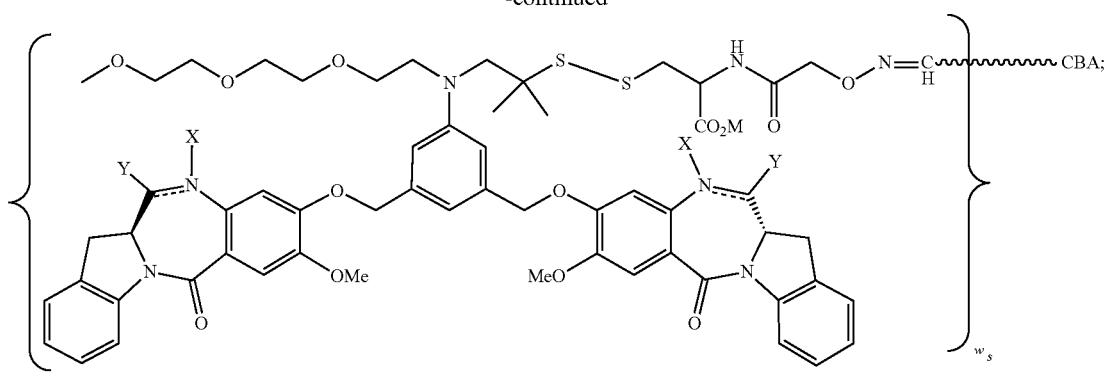
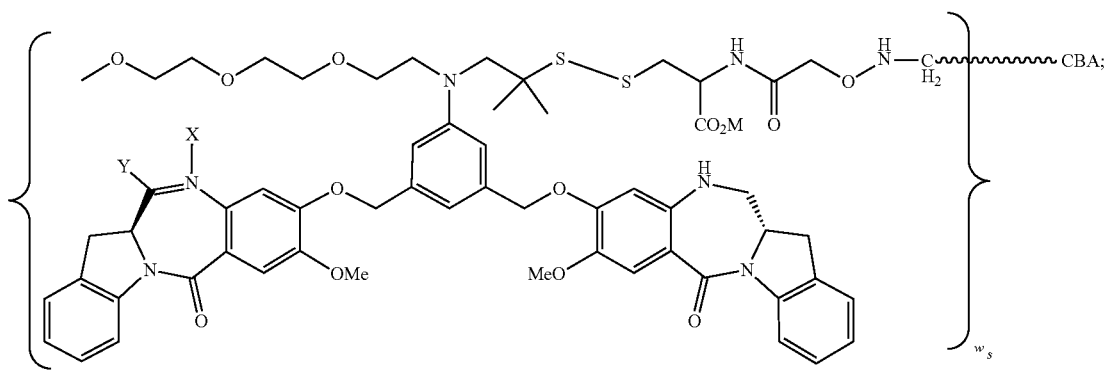
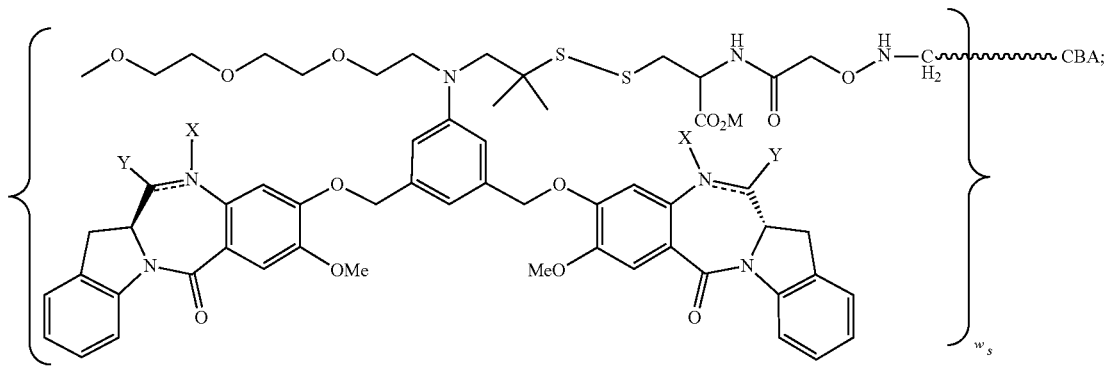
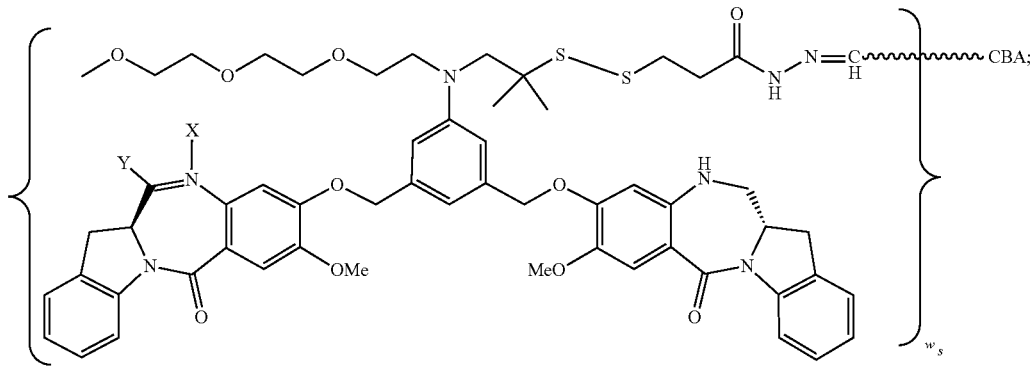

-continued

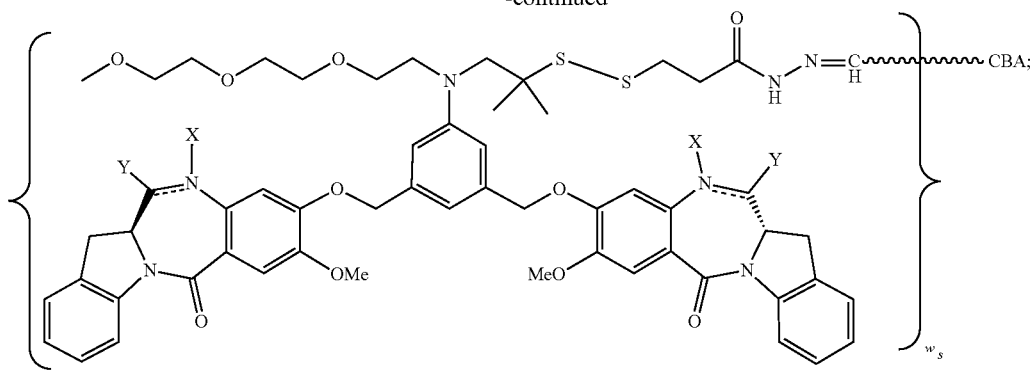

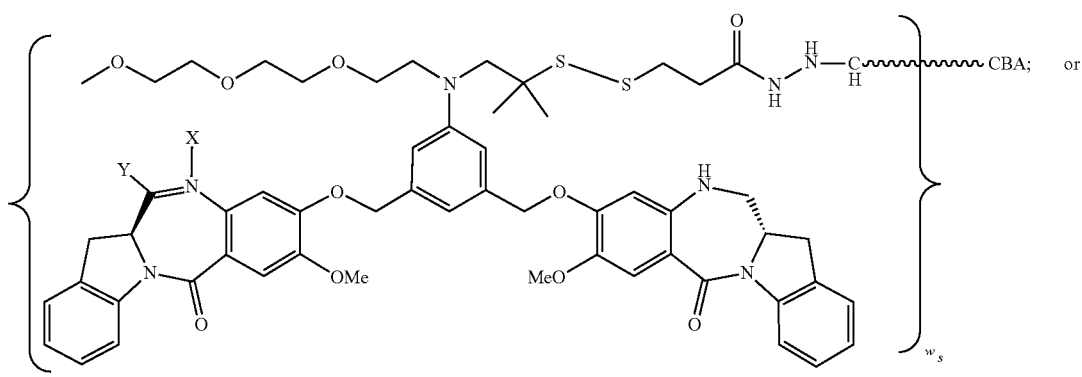

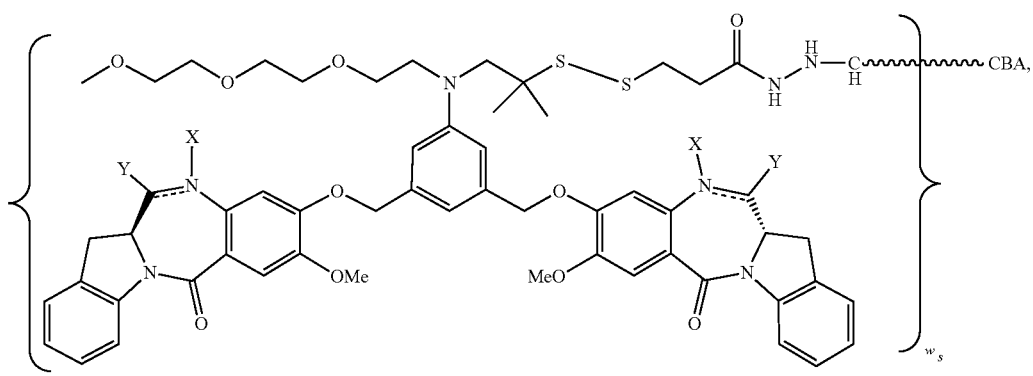

or a pharmaceutically acceptable salt thereof, wherein the double line ═ between N and C represents a single bond or a double bond, provided that when it is a double bond, X is absent and Y is —H; and when it is a single bond, X is —H; and Y is —OH or —SO₃M. In a more specific embodiment, the double line ═ between N and C represents a double bond, X is absent and Y is —H. In another more specific embodiment, the double line ═ between N and C represents a single bond, X is —H and Y is —SO₃M.

In a 14$^{th}$ specific embodiment, the immunoconjugate of the second embodiment is represented by the following formula:

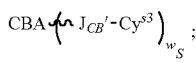 (S3)

wherein:
CBA is the oxidized CD123/IL-3Rα-binding agent described in the first aspect of the invention (e.g. a subject oxidized antibody or antigen-binding fragment thereof described herein above, or a subject oxidized polypeptide thereof described above);

$J_{CB'}$ is a moiety formed by reacting an aldehyde group on the CBA and an aldehyde reactive group on $Cy^{s3}$, and is represented by the following formula:

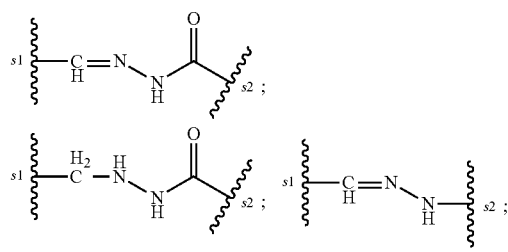

-continued

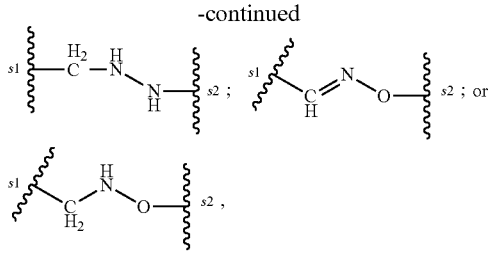

wherein s1 is the site covalently linked to the CBA; and s2 is the site covalently linked to $Cy^{s3}$;

$Cy^{s3}$ is represented by the following formula:

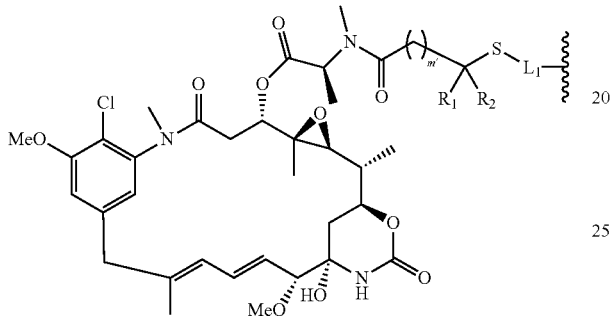

wherein:
m' is 1 or 2;
$R_1$ and $R_2$, are each independently H or a $(C_1$-$C_3)$alkyl;
$L_1$ is represented by the following formula:

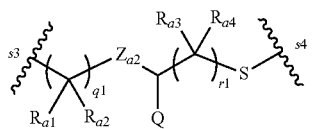

wherein:
s3 is the site covalently linked to the group $J_{CB}$;
s4 is the site covalently linked to the —S— group on $Cy^{s3}$;
$Z_{a2}$ is absent, —C(=O)—$NR_9$—, or —$NR_9$—C(=O)—;
$R_9$ is —H or a $(C_1$-$C_3)$alkyl;
Q is H, a charged substituent or an ionizable group;
$R_{a1}$, $R_{a2}$, $R_{a3}$, $R_{a4}$, for each occurrence, are independently H or a $(C_1$-$C_3)$alkyl; and
q1 and r1 are each independently an integer from 0 to 10, provided that q1 and r1 are not both 0.

In a more specific embodiment, $Z_a2$ is absent; q1 and r1 are each independent an integer from 0 to 3, provided that q1 and r1 are not both 0; and the remaining variables are as described above in the 14$^{th}$ specific embodiments. Even more specifically, $R_{a1}$, $R_{a2}$, $R_{a3}$, $R_{a4}$ are all —H.

In another more specific embodiment, $Z_{a2}$ is —C(=O)—NH—, or —$NH_9$—C(=O)—; q1 and r1 are each independently an integer from 1 to 6; and the remaining variables are as described above in the 14$^{th}$ specific embodiments. Even more specifically, $R_{a1}$, $R_{a2}$, $R_{a3}$, $R_{a4}$ are all —H.

In a 15$^{th}$ specific embodiment, for immunoconjugates of formula (S3), m' is 1; $R_1$ and $R_2$ are both H; and the remaining variables are as described above in the 14$^{th}$ specific embodiment or any more specific embodiments described therein.

In a 16$^{th}$ specific embodiment, for immunoconjugates of formula (S3), m' is 2; $R_1$ and $R_2$ are both Me; and the remaining variables are as described above in the 14$^{th}$ specific embodiment or any more specific embodiments described therein.

In a 17$^{th}$ specific embodiment, for immunoconjugates of formula (S3), -$L_1$- is represented by the following formula:

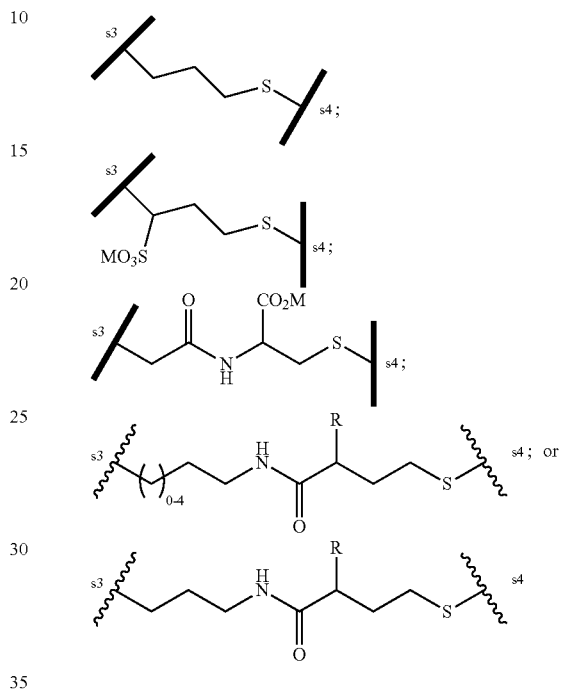

or a pharmaceutically acceptable salt thereof, wherein R is H or —$SO_3M$ and M is $H^+$ or a cation.

In a 18$^{th}$ specific embodiment, the immunoconjugate of the second embodiment is represented by the following formula:

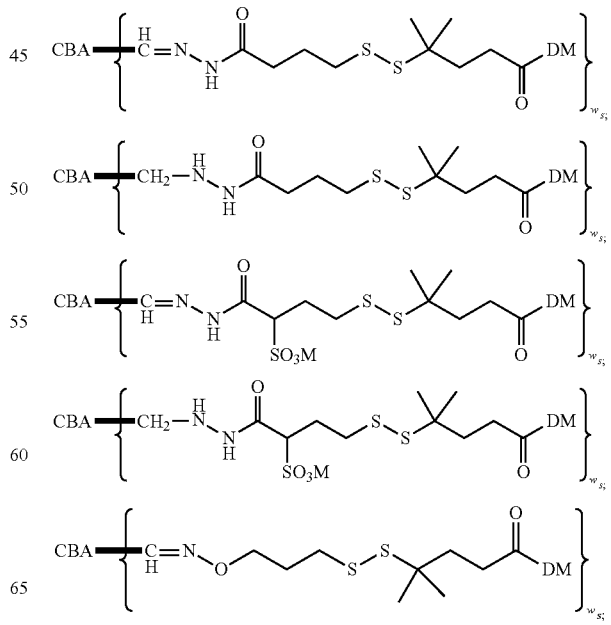

-continued

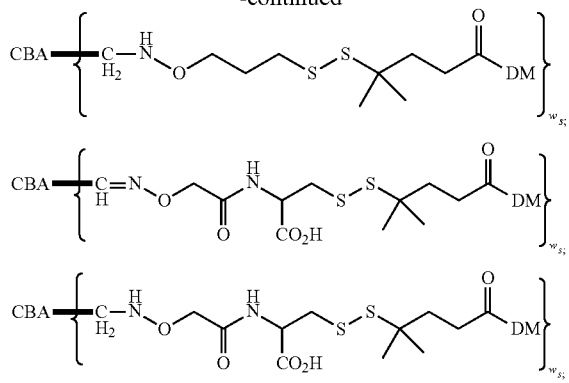

or a pharmaceutically acceptable salt thereof; wherein DM is represented by the following formula:

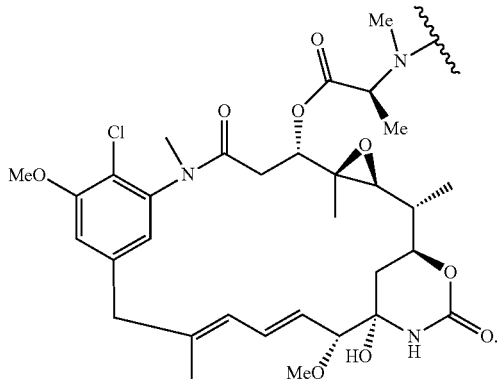 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In a 19th specific embodiment, the immunoconjugate of the second embodiment is represented by the following formula:

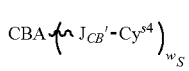
(S4)

wherein:
CBA is the oxidized CD123/IL-3Rα-binding agent described in the first aspect of the invention (e.g. a subject oxidized antibody or antigen-binding fragment thereof described herein above, or a subject oxidized polypeptide thereof described above);
$J_{CB'}$ is a moiety formed by reacting an aldehyde group on the CBA and an aldehyde reactive group on $Cy^{s4}$ and is represented by the following formula:

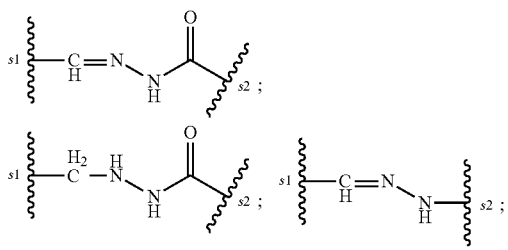

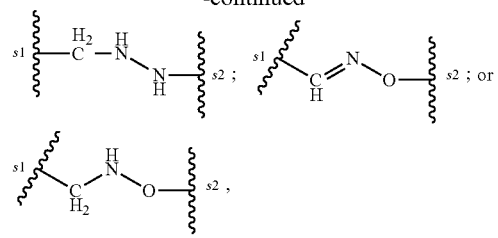

wherein s1 is the site covalently linked to the CBA; and s2 is the site covalently linked to $Cy^{s4}$;
$Cy^{s4}$ is represented by the following formula:

(S4a)

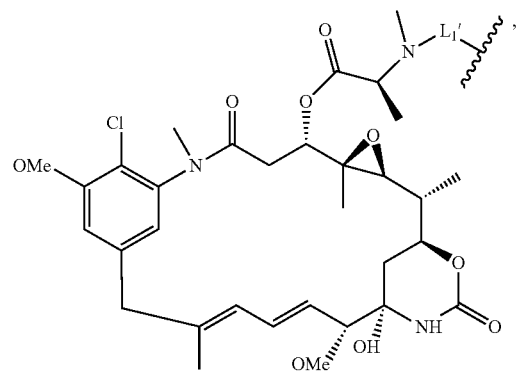

$L_{1'}$ is represented by the following formula:

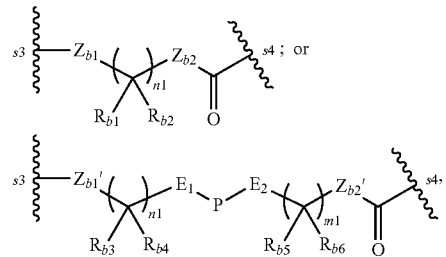

wherein:
s3 is the site covalently linked to the group $J_{CB'}$ group;
s4 is the site covalently linked to -NMe- group on $Cy^{s4}$;
$Z_{b1}$ and $Z_{b2}$ are both absent, or one of $Z_{b1}$ and $Z_{b2}$ is absent and the other is —$CH_2$—O— or —O—$CH_2$—;
$Z_{b1'}$ and $Z_{b2'}$ are each independently absent, —$CH_2$—O—, —O—$CH_2$—, —$NR_9$—C(=O)—$CH_2$—, or —$CH_2$—C(=O)—$NR_9$—;
$R_9$ is H or ($C_1$-$C_3$)alkyl;
n1 and m1 are each independently an integer from 1 to 6;
one of $E_1$ and $E_2$ is —C(=O)—, and the other is —$NR_9$—; or one of $E_1$ and $E_2$ is —C(=O)— or —$NR_9$—, and the other is absent;
P is an amino acid residue or a peptide containing between 2 to 20 amino acid residues; and
$R_{b1}$, $R_{b2}$, $R_{b3}$, $R_{b4}$, $R_{b5}$ and $R_{b6}$, for each occurrence, are each independently H or a ($C_1$-$C_3$)alkyl.
In a 20th specific embodiment, for immunoconjugates of formula (S4), $R_{b1}$, $R_{b2}$, $R_{b3}$, $R_{b4}$, $R_{b5}$, and $R_{b6}$ are all H; and the remaining variables are as described above in the 19th specific embodiment.

In a 21$^{st}$ specific embodiment, for immunoconjugates of formula (S4), $R_9$ is H; and the remaining variables are as described above in the 19$^{th}$ or 20$^{th}$ specific embodiment.

In a 22$^{nd}$ specific embodiment, for immunoconjugates of formula (S4), $Z_{b1'}$ and $Z_{b2'}$ are both absent; or $Z_{b1'}$ is —CH$_2$—O— and $Z_{b2'}$ is absent; or $Z_{b1'}$ is —CH$_2$—C(=O)—NR$_9$—; and $Z_{b2'}$ is —O—CH$_2$— or absent; and the remaining variables are as described above in the 19$^{th}$, 20$^{th}$ or 21$^{st}$ specific embodiment.

In a 23$^{rd}$ specific embodiment, for immunoconjugates of formula (S4), P is a peptide containing 2 to 5 amino acid residues; and the remaining variables are as described above in the 19$^{th}$, 20$^{th}$, 21$^{st}$ or 22$^{nd}$ specific embodiment. In a more specific embodiment, P is selected from the group consisting of Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 55), β-Ala-Leu-Ala-Leu (SEQ ID NO: 57), Gly-Phe-Leu-Gly (SEQ ID NO: 73), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala; and the remaining variables are as described above in the 23$^{rd}$ specific embodiment. Even more specifically, P is Gly-Gly-Gly, Ala-Val, Ala-Ala, Ala-D-Ala, D-Ala-Ala, or D-Ala-D-Ala.

In a 24$^{th}$ specific embodiment, the immunoconjugate of the second embodiment is represented by the following formula:

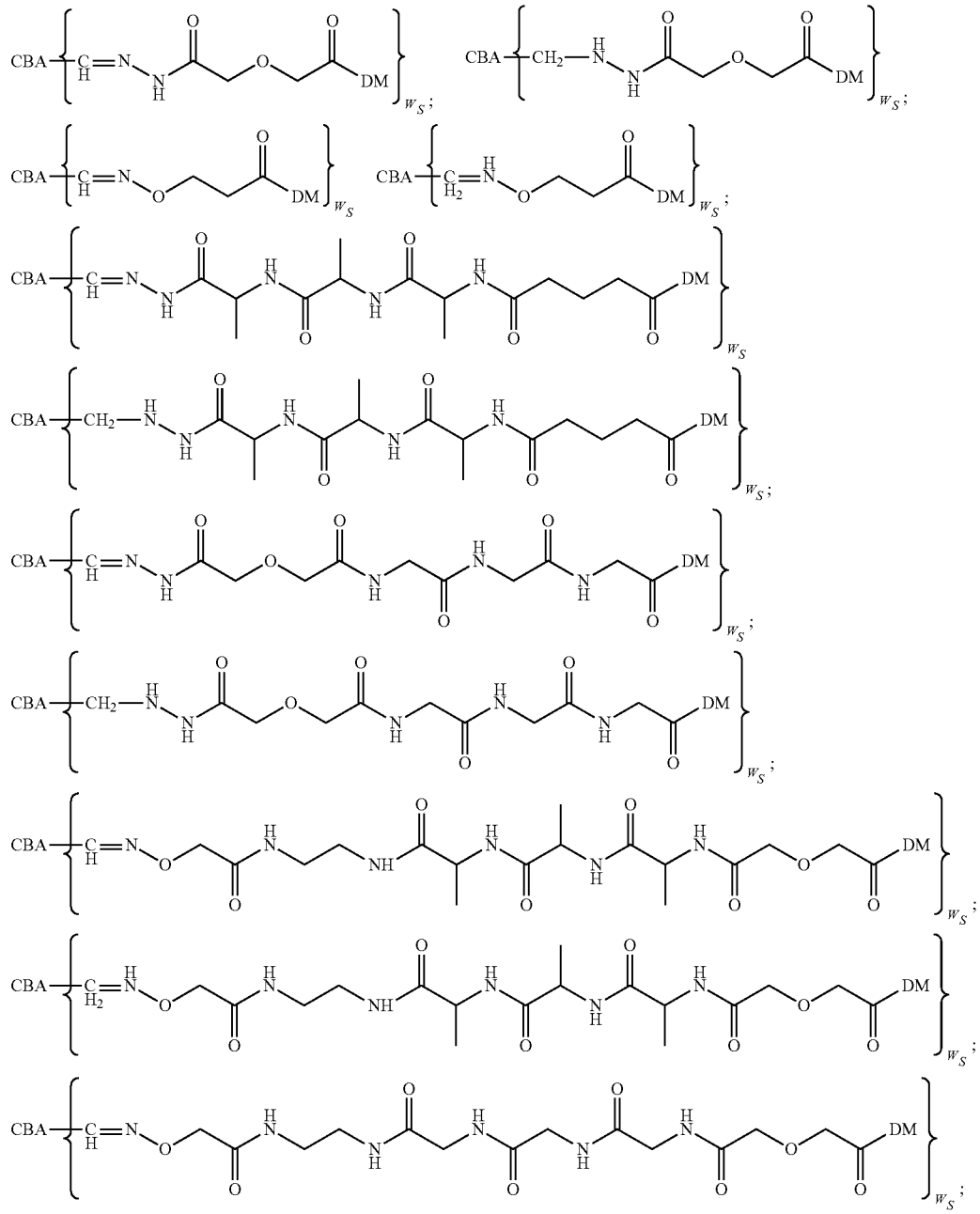

-continued

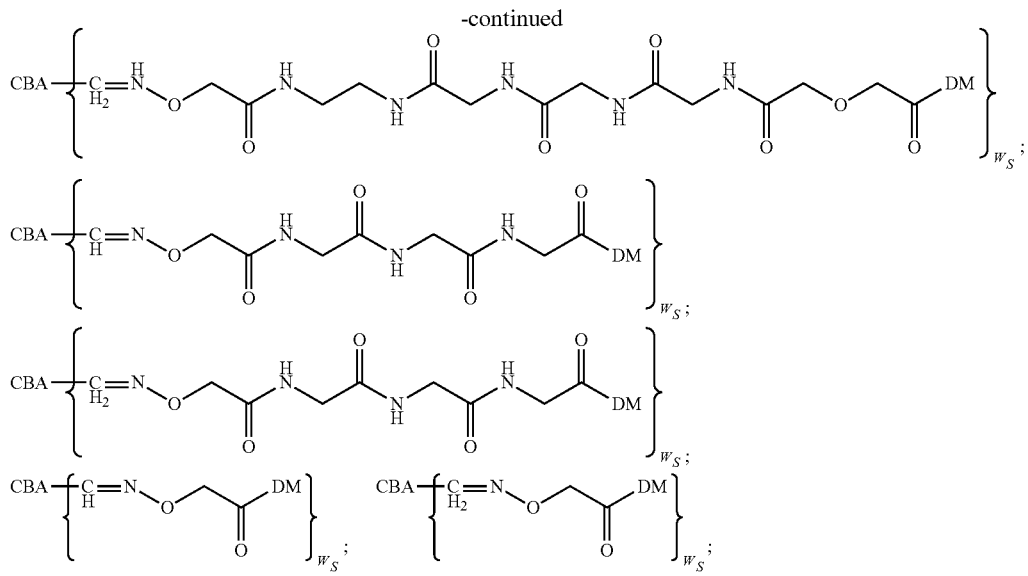

or a pharmaceutically acceptable salt thereof, wherein DM is represented by the following structural formula:

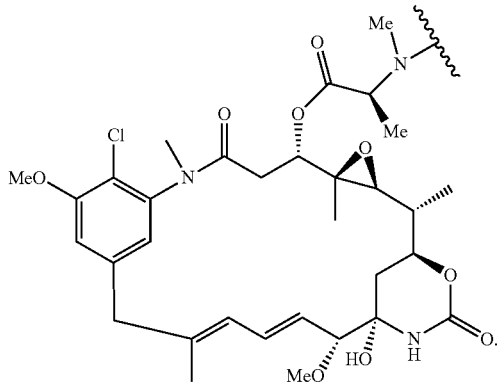 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In a 25$^{th}$ specific embodiment, for immunoconjugates of the second embodiment, M is H$^+$, Na$^+$ or K$^+$; and the remaining variables are as described above in any one of the 1$^{st}$ to 24$^{th}$ specific embodiment or any more specific embodiments described therein.

In any of the above 1$^{st}$ to the 25$^{th}$ specific embodiments, the subject oxidized antibody or antigen-binding fragment thereof may have 1, 2, 3, or up to 4 N-terminal 2-hydroxyethylamine moieties oxidized to aldehyde group(s), for linking covalently to a cytotoxic agent described herein. The N-terminal 2-hydroxyethylamine moiety may be part of a serine, threonine, hydroxylysine, 4-hydroxyornithine or 2,4-diamino-5-hydroxy valeric acid residue, preferably Ser or Thr. For simplicity, the description below, including the oxidation reaction and any subsequent conjugation with linkers or cytotoxic agents, may refer to Ser as a specific example of such N-terminal 2-hydroxyethylamine moieties, but should generally be construed as referring to all N-terminal 2-hydroxyethylamine moieties. The subject antibody or antigen-binding fragment thereof may comprise an immunoglobulin heavy chain variable region (HCVR) having the amino acid sequence set forth in SEQ ID NO: 38; and an immunoglobulin light chain variable region (LCVR) having the amino acid sequence set forth in SEQ ID NO: 33, 35, 37, or 41 (preferably SEQ ID NO: 35 or 37). The subject antibody or antigen-binding fragment thereof may also comprise an Ig HCVR having the amino acid sequence set forth in SEQ ID NO: 32, 34, 38, 39, or 40 (preferably SEQ ID NO: 34); and an Ig LCVR having the amino acid sequence set forth in SEQ ID NO: 37. The subject antibody or antigen-binding fragment thereof may also comprise an Ig heavy chain (HC) region having the amino acid sequence set forth in SEQ ID NO: 53 or 56; and an Ig LCVR having the amino acid sequence set forth in SEQ ID NO: 33, 35, 37, or 41 (preferably SEQ ID NO: 35 or 37). The subject antibody or antigen-binding fragment thereof may also comprise an Ig HC region having the amino acid sequence set forth in SEQ ID NO: 48, 50, 53, 54, 56, 59, or 60 (preferably SEQ ID NO: 53); and an Ig LCVR having the amino acid sequence set forth in SEQ ID NO: 37. In certain embodiments, the second residue from the N-terminus of SEQ ID NOs: 34, 38, 50, 53, 54, or 56 is Phe, while in certain other embodiments, the second residue from the N-terminus of SEQ ID NOs: 34, 38, 50, 53, 54, or 56 is Val.

In certain embodiments, the immunoconjugates of the second embodiment can be prepared by a first method comprising reacting an oxidized CD123/IL-3Rα-binding agent having an N-terminal aldehyde described in the first aspect of the invention with a cytotoxic agent having an aldehyde reactive group.

In certain embodiments, the immunoconjugates of the second embodiment can be prepared by a second method comprising reacting an oxidized CD123/IL-3Rα-binding agent having an N-terminal aldehyde described in the first aspect of the invention with a linker compound having an aldehyde reactive group to form a modified CD123/IL-3Rα-binding agent having a linker bound thereto, followed by reacting the modified CD123/IL-3Rα-binding agent with a cytotoxic agent.

In certain embodiments, the immunoconjugates of the second embodiment can be prepared by a third method comprising contacting an oxidized CD123/IL-3Rα-binding agent having an N-terminal aldehyde described in the first aspect of the invention with a cytotoxic agent followed by addition of a linker compound having an aldehyde reactive group.

In certain embodiments, the immunoconjugates of the second embodiment can be prepared by a fourth method comprising the steps of:
(a) oxidizing a CD123/IL-3Rα-binding agent having a N-terminal 2-hydroxyethylamine moiety (e.g., Ser/Thr) with an oxidizing agent to form an oxidized CD123/IL-3Rα-binding agent having a N-terminal aldehyde group; and
(b) reacting the oxidized CD123/IL-3Rα-binding agent having the N-terminal aldehyde group with a cytotoxic agent having an aldehyde reactive group.

In certain embodiments, the immunoconjugates of the second embodiment can be prepared by a fifth method comprising the steps of:
(a) oxidizing a CD123/IL-3Rα-binding agent having a N-terminal 2-hydroxyethylamine moiety (e.g., Ser/Thr) with an oxidizing agent to form an oxidized CD123/IL-3Rα-binding agent having a N-terminal aldehyde group;
(b) reacting the oxidized CD123/IL-3Rα-binding agent having the N-terminal aldehyde group with a linker compound having an aldehyde reactive group to form a modified CD123/IL-3Rα-binding agent having a linker bound thereto, followed by reacting the modified CD123/IL-3Rα-binding agent with a cytotoxic agent.

In certain embodiments, the immunoconjugates of the second embodiment can be prepared by a sixth method comprising the steps of:
(a) oxidizing the CD123/IL-3Rα-binding agent having a N-terminal 2-hydroxyethylamine moiety (e.g., Ser/Thr) with an oxidizing agent to form an oxidized CD123/IL-3Rα-binding agent having a N-terminal aldehyde group;
(b) contacting the oxidized CD123/IL-3Rα-binding agent having the N-terminal aldehyde group with a cytotoxic agent followed by addition of a linker compound having an aldehyde reactive group.

In one embodiment, for the first or fourth method described above, the cytotoxic agent having an aldehyde reactive group is represented by the following formula:

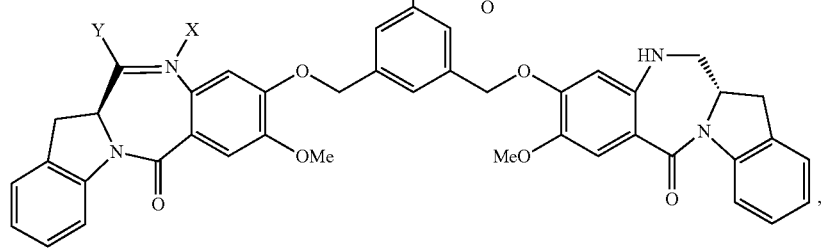

(S1a′)

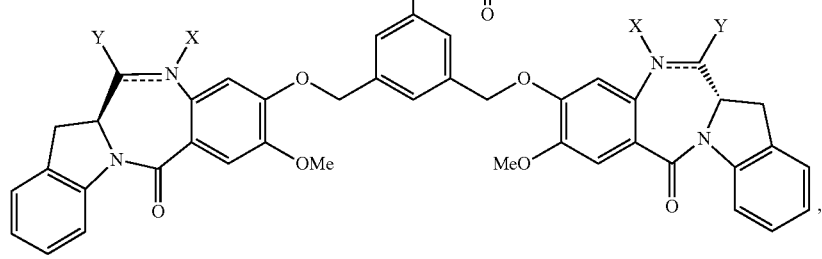

(S1a′1)

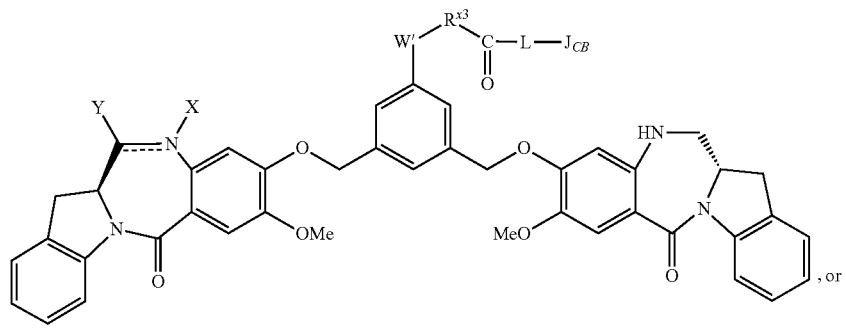

(S1b′)

, or (S1b'1)

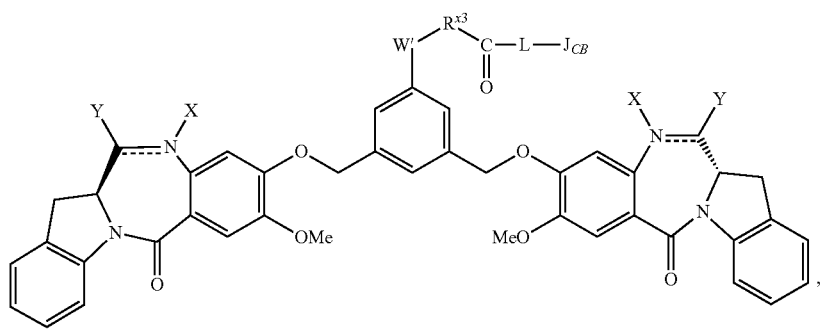

or a pharmaceutically acceptable salt thereof, wherein $J_{CB}$ is represented by the following formula:

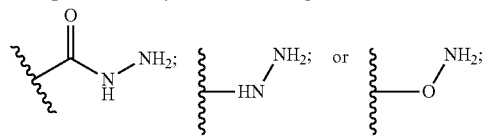

and the remaining variables are as described above in any one of $1^{st}$ to $7^{th}$ and $25^{th}$ specific embodiments and any more specific embodiments described therein.

In another embodiment, for the first or fourth method described above, the cytotoxic agent having an aldehyde reactive group is represented by the following formula:

(S4a')

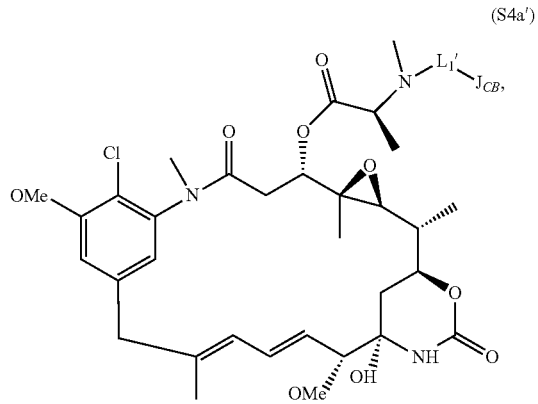

or a pharmaceutically acceptable salt thereof, wherein $J_{CB}$ is as described above and the remaining variables are as described in the any one of the $19^{th}$ to $25^{th}$ specific embodiments and any more specific embodiments described therein.

In one embodiment, for the second, third, fifth or sixth method described above, the linker compound is represented by the following formula:

($L^s$a)

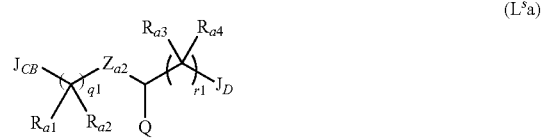

wherein $J_D$-SH, —$SSR^d$, or —$SC(=O)R^g$; $R^d$ is phenyl, nitrophenyl, dinitrophenyl, carboxynitrophenyl, pyridyl or nitropyridyl; $R^g$ is an alkyl; $J_{CB}$ is as described above; the cytotoxic agent is represented by the following formula:

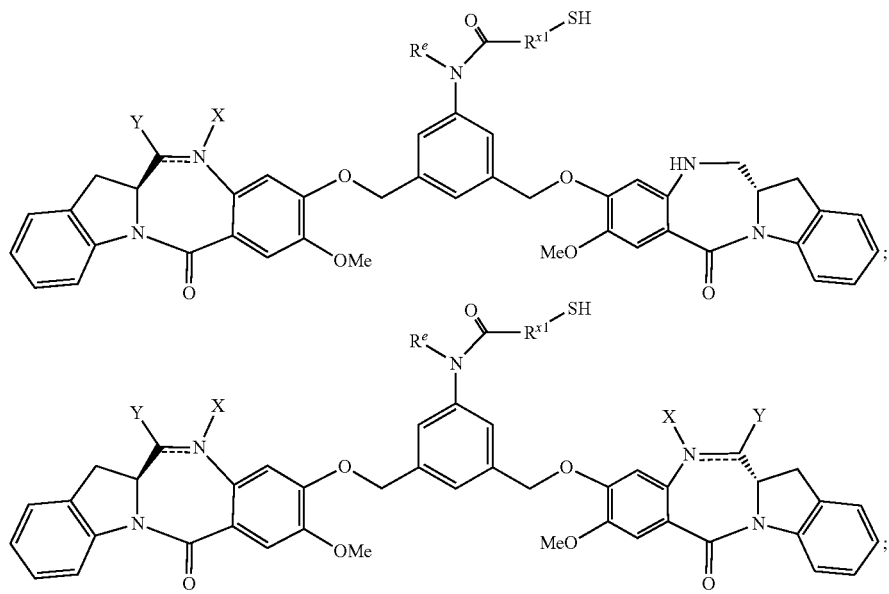

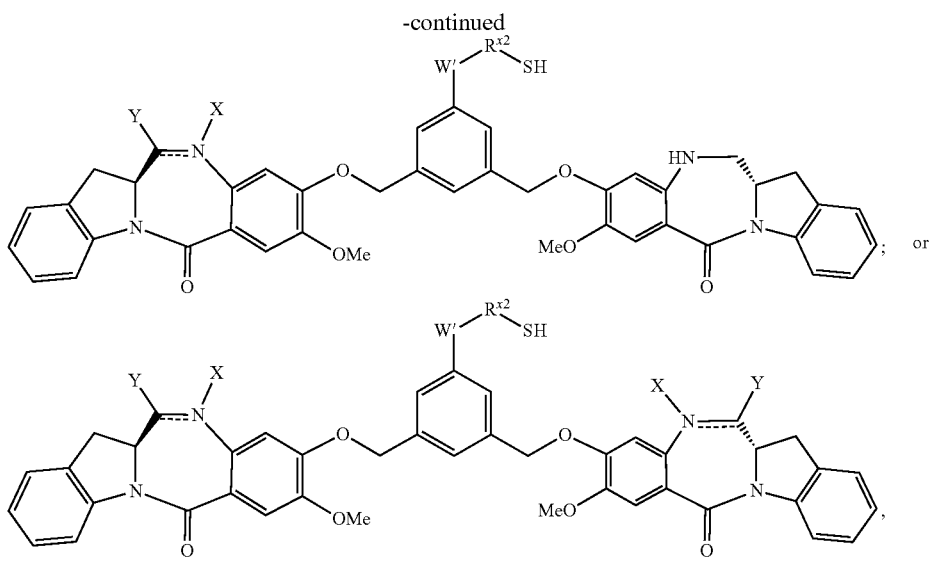

and the remaining variables are as described above in any one of the 8$^{th}$ to 13$^{th}$ and 25$^{th}$ specific embodiments and any more specific embodiments described therein.

In another embodiment, for the second, third, fifth or sixth method described above, the linker compound is represented by formula (L$^s$a) above; the cytotoxic compound is represented by the following formula:

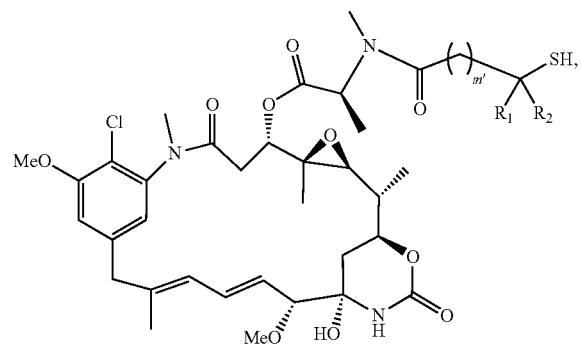

and the remaining variables are as described in any one of the 14$^{th}$ to 18$^{th}$ and 25$^{th}$ specific embodiments and any more specific embodiments described therein.

In one embodiment, for the first or fourth methods described above, the cytotoxic agent is reacted with an imine-reactive reagent, such as NaHSO$_3$, to form a modified cytotoxic agent before reacting with the oxidized CD123/IL-3Rα-binding agent having the N-terminal aldehyde. In one embodiment, the modified cytotoxic agent is not purified before reacting with the oxidized CBA having the N-terminal aldehyde. Alternatively, the modified cytotoxic agent is purified before reacting with the oxidized CBA having the N-terminal aldehyde.

In another embodiment, for the second or fifth method described above, the cytotoxic agent is reacted with an imine-reactive reagent, such as NaHSO$_3$, to form a modified cytotoxic agent before reacting with the modified CD123/IL-3Rα-binding agent having a linker bound thereto. In one embodiment, the modified cytotoxic agent is purified before reacting with the modified CD123/IL-3Rα-binding agent having a linker bound thereto. Alternatively, the modified cytotoxic agent is not purified before reacting with the oxidized CD123/IL-3Rα-binding agent having the N-terminal aldehyde.

In yet another embodiment, for the third or sixth methods described above, the reaction of the oxidized CD123/IL-3Rα-binding agent, the cytotoxic agent and the linker compound is carried out in the presence of an imine reactive reagent, such as NaHSO$_3$.

Any suitable oxidizing agent can be used in step (a) of the fourth, fifth or sixth method described above. In certain embodiments, the oxidizing agent is a periodate. More specifically, the oxidizing agent is sodium periodate.

Excess molar equivalents of the oxidizing agent relative to the CD123/IL-3Rα-binding agent can be used. In certain embodiments, about 2-100, 5-80, 10-50, 1-10 or 5-10 molar equivalents of the oxidizing agent can be used. In certain embodiments, about 10 or about 50 equivalents of the oxidizing agent can be used. When large amount of the oxidizing agent is used, short reaction time is used to avoid over-oxidation. For example, when 50 equivalents of the oxidizing agent is used, the oxidation reaction is carried out for about 5 to about 60 minutes. Alternatively, when 10 equivalents of the oxidizing agent is used, the reaction is carried out for about 30 minutes to about 24 hours. In one embodiment, 5-10 molar equivalents of the oxidizing agent is used and the oxidation reaction is carried out for about 5 to about 60 minutes (e.g., about 10 to about 30 minutes, about 20 to about 30 minutes).

In certain embodiments, a catalyst is present in the reaction in the first, second or third method described above or in the reaction of step (b) in the fourth, fifth or sixth method described above. Any suitable catalyst in the art can be used. In one embodiment, the catalyst is an aniline or substituted aniline. Exemplary aniline catalyst include, but are not limited to, aniline, o-phenylenediamine, m-phenylenediamine, 3,5-diaminobenzoic acid, p-phenylenediamine, 2-methyl-p-phenylenediamine, N-methyl-p-phenylenediamine, o-aminophenol, m-aminophenol, p-aminophenol, p-methoxyaniline, 5-methoxy-anthranilic acid, o-aminobenzoid acid, and 4-aminophenethylalcohol. In one embodiment, the catalyst is 4-aminophenethylalcohol. In certain embodiments, the reaction of step (b) is carried out at pH about 5.0 to about 6.5. In certain embodiments, the reaction of step (b) is carried out at pH about 5.0.

In certain embodiments, for the reaction in the first, second or third method described above or in the reaction of step (b) in the fourth, fifth or sixth method described above, the compound having an aldehyde reactive group (e.g., cytotoxic agent, or the linker compound described herein) is used in molar excess relative to the oxidized cell-binding agent (e.g., oxidized antibody or oxidized antigen binding portion). In certain embodiments, the ratio for the compound having an aldehyde reactive group to the oxidized cell-binding agent is between about 10:1 to about 1.1:1, between about 5:1 to about 2:1. In one embodiment, the ratio is about 4:1.

In a third embodiment, the immunoconjugates of the present invention comprises a CD123/IL-3Rα-binding agent (including antibody, antigen-binding fragment thereof, or polypeptide comprising the antibody or antigen-binding fragment thereof) described in the first aspect of the invention covalently linked to a cytotoxic agent described herein through the thiol group (—SH) of one or more cysteine residues located on the CD123-binding agent.

In a 1$^{st}$ specific embodiment, the immunoconjugate of the third embodiment is represented by the following formula:

$$CBA\text{-}(Cy^{C1})_{w_C} \quad (C1),$$

wherein:
CBA is a CD123/IL-3Rα-binding agent described in the first aspect of the invention (e.g. a subject antibody or antigen-binding fragment thereof described herein above, or a subject polypeptide thereof described above), covalently linked to $Cy^{C1}$ through a cysteine residue;
$W_C$ is 1 or 2;
$Cy^{C1}$ is represented by the following formula:

(C1a)
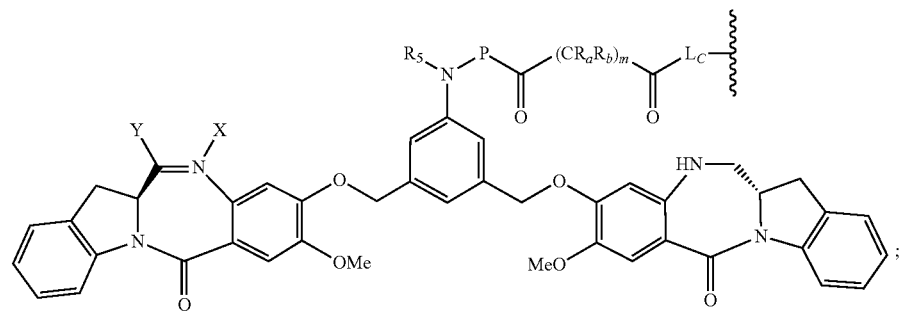

(C1a1)
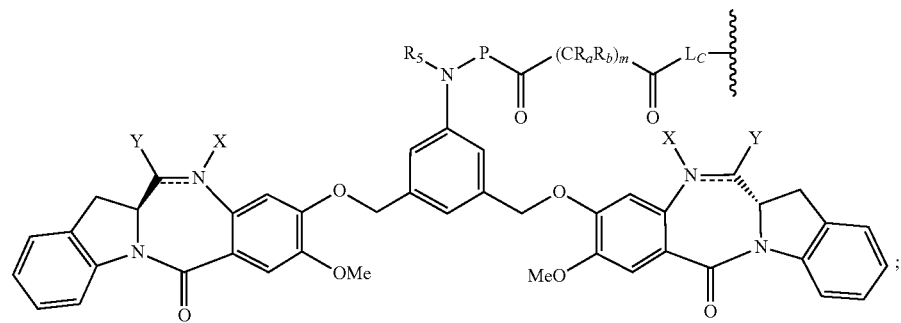

(C1b)
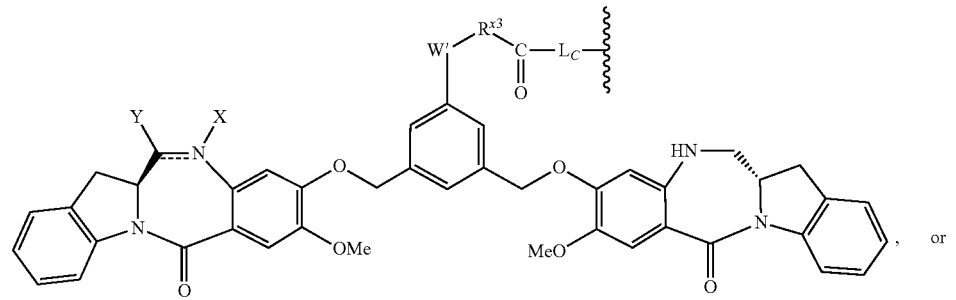

or (C1b1)
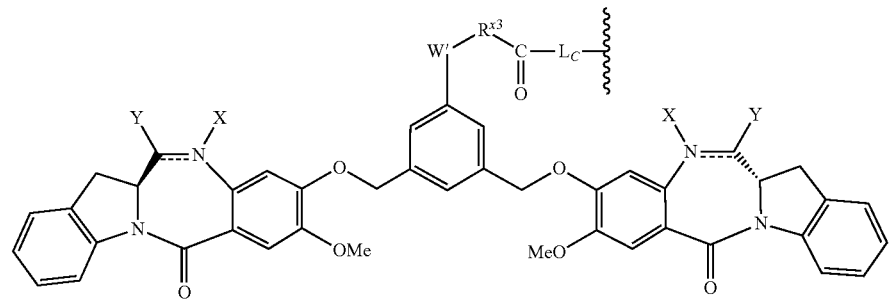

or a pharmaceutically acceptable salt thereof, wherein:
the double line == between N and C represents a single bond or a double bond, provided that when it is a double bond, X is absent and Y is —H or a ($C_1$-$C_4$)

alkyl; and when it is a single bond, X is —H or an amine protecting moiety, Y is —OH or —SO₃M, and M is H⁺ or a cation;

$R_5$ is —H or a $(C_1\text{-}C_3)$alkyl;

P is an amino acid residue or a peptide containing 2 to 20 amino acid residues;

$R_a$ and $R_b$, for each occurrence, are independently —H, $(C_1\text{-}C_3)$alkyl, or a charged substituent or an ionizable group Q;

W' is —NR$^{e'}$,

R$^{e'}$ is —(CH₂—CH₂—O)$_n$—R$^k$;

n is an integer from 2 to 6;

R$^k$ is —H or -Me;

R$^{x3}$ is a $(C_1\text{-}C_6)$alkyl; and, $L_C$ is represented by:

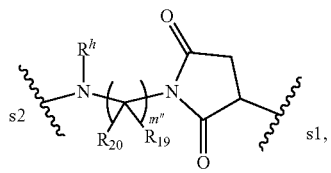

wherein s1 is the site covalently linked to CBA, and s2 is the site covalently linked to the —C(=O)— group on Cy$^{C1}$; wherein:

$R_{19}$ and $R_{20}$, for each occurrence, are independently —H or a $(C_1\text{-}C_3)$alkyl;

m" is an integer between 1 and 10; and

R$^h$ is —H or a $(C_1\text{-}C_3)$alkyl.

In a 2$^{nd}$ specific embodiment, for immunoconjugate of formula (C1), Cy$^{C1}$ is represented by formula (C1a) or (C1a1); and the remaining variables are as described above in the 1$^{st}$ specific embodiment.

In a 3$^{rd}$ specific embodiment, for immunoconjugate of formula (C1), Cy$^{C1}$ is represented by formula (C1b) or (C1b1); and the remaining variables are as described above in the 1$^{st}$ specific embodiment.

In a 4$^{th}$ specific embodiment, for immunoconjugate of formula (C1), Cy$^{C1}$ is represented by formula (C1a) or (C1a1); $R_a$ and $R_b$ are both H; and $R_5$ is H or Me; and the remaining variables are as described above in the 1$^{st}$ or 2$^{nd}$ specific embodiment.

In a 5$^{th}$ specific embodiment, for immunoconjugate of formula (C1), P is a peptide containing 2 to 5 amino acid residues; and the remaining variables are as described above in the 1$^{st}$, 2$^{nd}$ or 4$^{th}$ specific embodiment. In a more specific embodiment, P is selected from Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-N⁹-tosyl-Arg, Phe-N⁹-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 55), β-Ala-Leu-Ala-Leu (SEQ ID NO: 57), Gly-Phe-Leu-Gly (SEQ ID NO: 73), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. In another more specific embodiment, P is Gly-Gly-Gly, Ala-Val, Ala-Ala, Ala-D-Ala, D-Ala-Ala, or D-Ala-D-Ala.

In a 6$^{th}$ specific embodiment, for immunoconjugates of formula (C1), Q is —SO₃M; and the remaining variables are as describe above in the 1$^{st}$, 2$^{nd}$, 4$^{th}$ or 5$^{th}$ specific embodiment or any more specific embodiments described therein.

In a 7$^{th}$ specific embodiment, for immunoconjugates of formula (C1), $R_{19}$ and $R_{20}$ are both H; and m" is an integer from 1 to 6; and the remaining variables are as described above in the 1$^{st}$, 2$^{nd}$, 3$^{rd}$, 4$^{th}$, 5$^{th}$ or 6$^{th}$ specific embodiment or any more specific embodiments described therein.

In a 8$^{th}$ specific embodiment, for immunoconjugates of formula (C1), -L-$L_C$- is represented by the following formula:

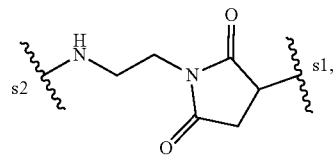 [SMILES: *NCCN1C(=O)CC(*)C1=O]

and the remaining variables are as described above in the 1$^{st}$, 2$^{nd}$, 3$^{rd}$, 4$^{th}$, 5$^{th}$, 6$^{th}$ or 7$^{th}$ specific embodiment or any more specific embodiments described therein.

In a 9$^{th}$ specific embodiment, the immunoconjugate of the third embodiment is represented by the following formula:

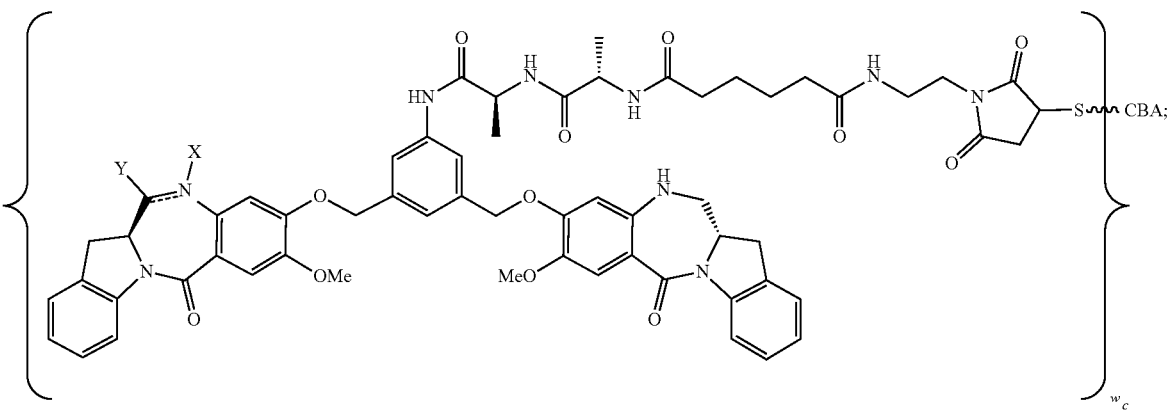

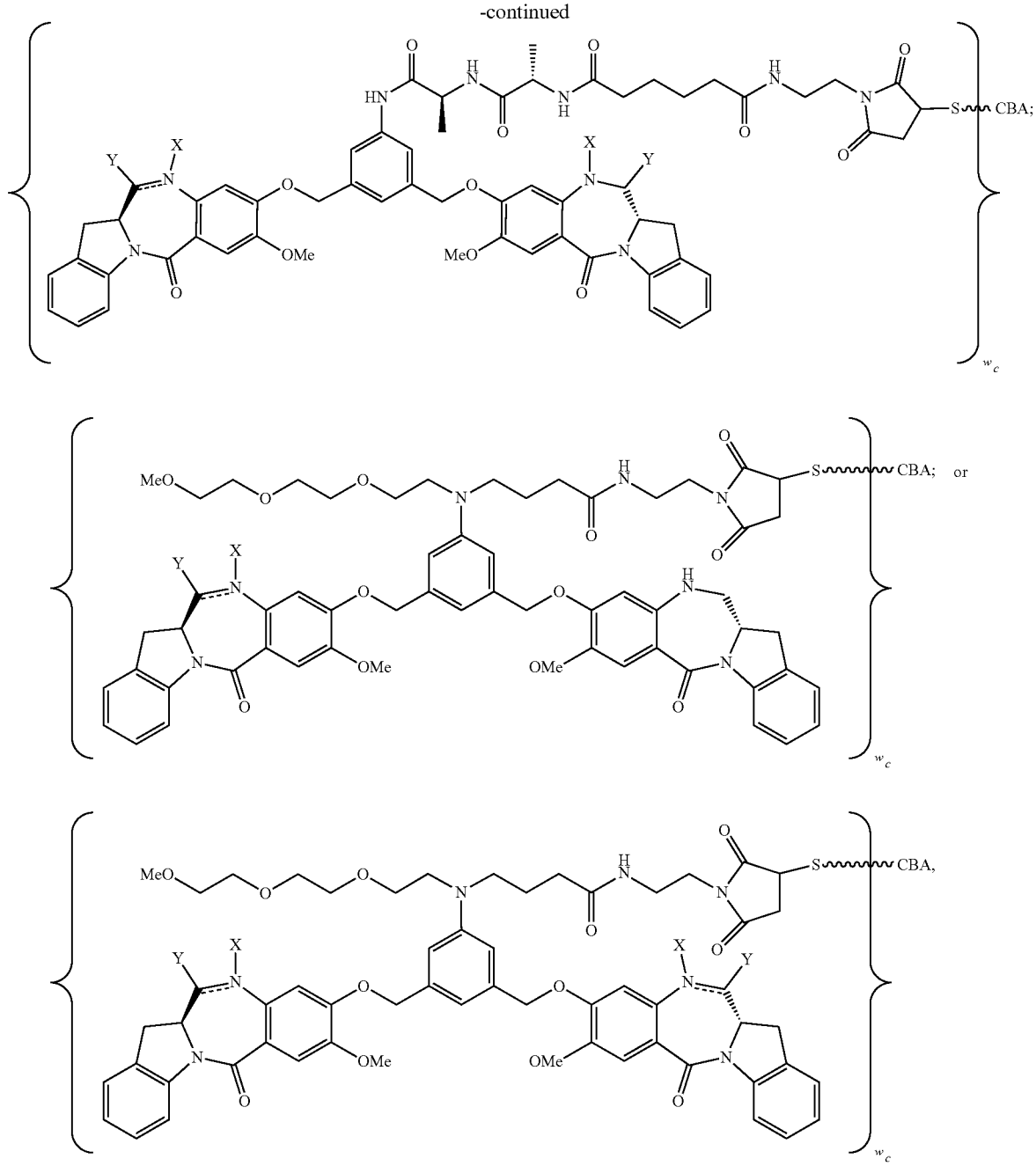

or a pharmaceutically acceptable salt thereof wherein the double line ⹀ between N and C represents a single bond or a double bond, provided that when it is a double bond, X is absent and Y is —H, and when it is a single bond, X is —H, and Y is —OH or —SO₃M. In a more specific embodiment, the double line ⹀ between N and C represents a double bond, X is absent and Y is —H. In another more specific embodiment, the double line ⹀ between N and C represents a single bond, X is —H and Y is —SO₃M.

In a 10$^{th}$ specific embodiment, the immunoconjugate of the third embodiment is represented by the following formula:

$$CBA\text{-}(Cy^{C2})_{w_C} \qquad (C2),$$

wherein:

CBA is a CD123/IL-3Rα-binding agent described in the first aspect of the invention (e.g., a subject antibody or antigen-binding fragment thereof described herein above, or a subject polypeptide thereof described above), covalently linked to Cy$^{C2}$ through a cysteine residue;

$W_C$ is 1 or 2;

Cy$^{C2}$ is represented by the following formula:

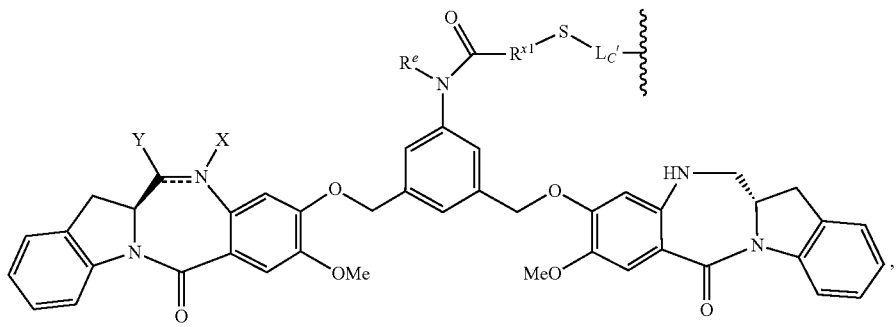

(C2a)

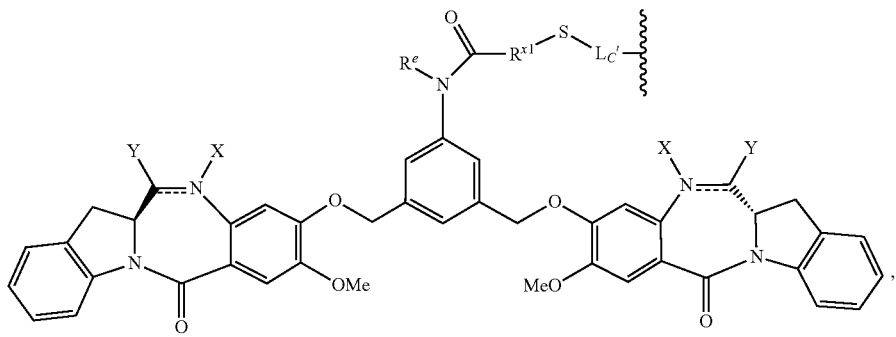

(C2a1)

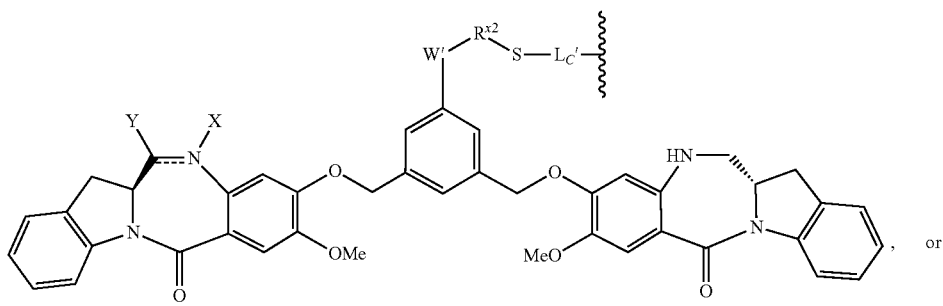

(C2b)

, or

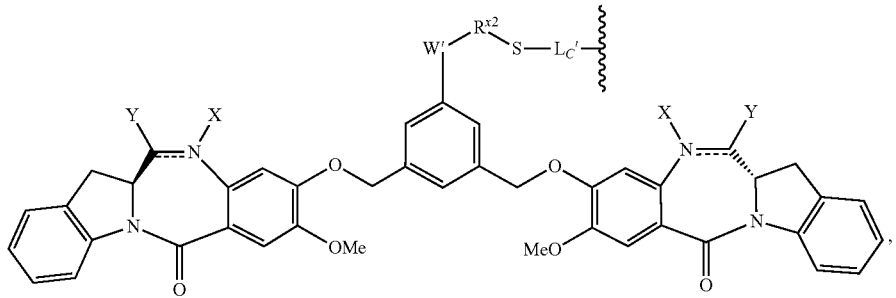

(C2b1)

, or a pharmaceutically acceptable salt thereof, wherein:
the double line ═ between N and C represents a single bond or a double bond, provided that when it is a double bond, X is absent and Y is —H or a ($C_1$-$C_4$) alkyl; and when it is a single bond, X is —H or an amine protecting moiety, Y is —OH or —$SO_3$M, and M is H$^+$ or a cation;
R$^{x1}$ is a ($C_1$-$C_6$)alkyl;
R$^e$ is —H or a ($C_1$-$C_6$)alkyl;
W' is —NR$^{e'}$;
R$^{e'}$ is —($CH_2$—$CH_2$—O)$_n$—R$^k$;
n is an integer from 2 to 6;

R$^k$ is —H or -Me;
R$^{x2}$ is a ($C_1$-$C_6$)alkyl;
L$_{C'}$ is represented by the following formula:

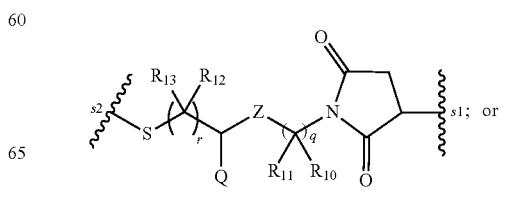

s1; or

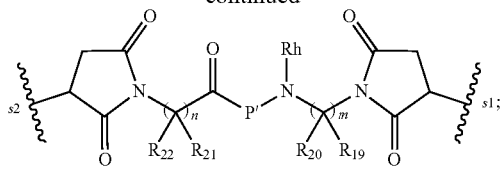

wherein:
  s1 is the site covalently linked to the CBA and s2 is the site covalently linked to —S— group on $Cy^{C2}$;
  Z is —C(=O)—$NR_9$—, or —$NR_9$—C(=O)—;
  Q is —H, a charged substituent, or an ionizable group;
  $R_9$, $R_{10}$, $R_{11}$, $R_{12}$, $R_{13}$, $R_{19}$, $R_{20}$, $R_{21}$ and $R_{22}$, for each occurrence, are independently —H or a ($C_1$-$C_3$)alkyl;
  q and r, for each occurrence, are independently an integer between 0 and 10;
  m and n are each independently an integer between 0 and 10;
  $R^h$ is —H or a ($C_1$-$C_3$)alkyl; and
  P' is an amino acid residue or a peptide containing 2 to 20 amino acid residues.

In a more specific embodiment, q and r are each independently an integer between 1 to 6, more specifically, an integer between 1 to 3. Even more specifically, $R_{10}$, $R_{11}$, $R_{12}$ and $R_{13}$ are all H.

In another more specific embodiment, m and n are each independently an integer between 1 and 6, more specifically, an integer between 1 to 3. Even more specifically, $R_{19}$, $R_{20}$, $R_{21}$ and $R_{22}$ are all H.

In a 11$^{th}$ specific embodiment, for immunoconjugates of formula (C2), $Cy^{C2}$ is represented by formula (C2a) or (C2a1); and the remaining variables are as described above in the 10$^{th}$ specific embodiment or any more specific embodiments described therein.

In a 12$^{th}$ specific embodiment, for immunoconjugates of formula (C2), $Cy^{C2}$ is represented by formula (C2b) or (C2b1); and the remaining variables are as described above in the 10$^{th}$ specific embodiment.

In a 13$^{th}$ specific embodiment, for immunoconjugates of formula (C2), P' is a peptide containing 2 to 5 amino acid residues; and the remaining variables are as described in the 10$^{th}$, 11$^{th}$ or 12$^{th}$ specific embodiment or any more specific embodiments described therein. In a more specific embodiment, P' is selected from Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 55), β-Ala-Leu-Ala-Leu (SEQ ID NO: 57), Gly-Phe-Leu-Gly (SEQ ID NO: 73), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. In another more specific embodiment, P' is Gly-Gly-Gly, Ala-Val, Ala-Ala, Ala-D-Ala, D-Ala-Ala, or D-Ala-D-Ala.

In a 14$^{th}$ specific embodiment, for immunoconjugates of formula (C2), -$L_{C'}$- is represented by the following formula:

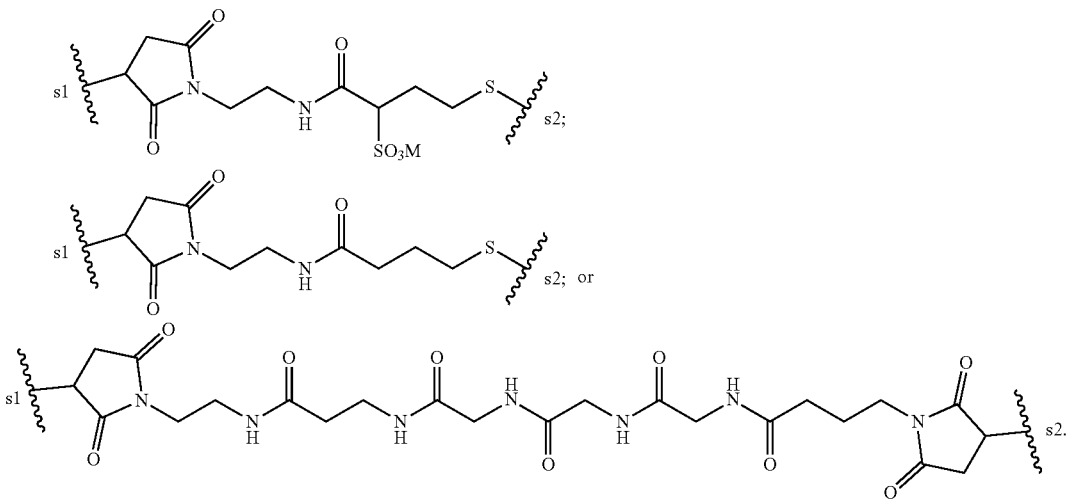

In a 15$^{th}$ specific embodiment, for immunoconjugates of ($C_2$), $R^e$ is H or Me; $R^{x1}$ is —($CH_2$)$_p$—($CR^fR^g$)—, and $R^{x2}$ is —($CH_2$)$_p$—($CR^fR^g$)—, wherein $R^f$ and $R^g$ are each independently —H or a ($C_1$-$C_4$)alkyl; and p is 0, 1, 2 or 3; and the remaining variables are as described above in the 10$^{th}$, 11$^{th}$, 12$^{th}$, 13$^{th}$, or 14$^{th}$ specific embodiment. More specifically, $R^f$ and $R^g$ are the same or different, and are selected from —H and -Me.

In a 16$^{th}$ specific embodiment, the immunoconjugate of the third embodiment is represented by the following formula:

285 286
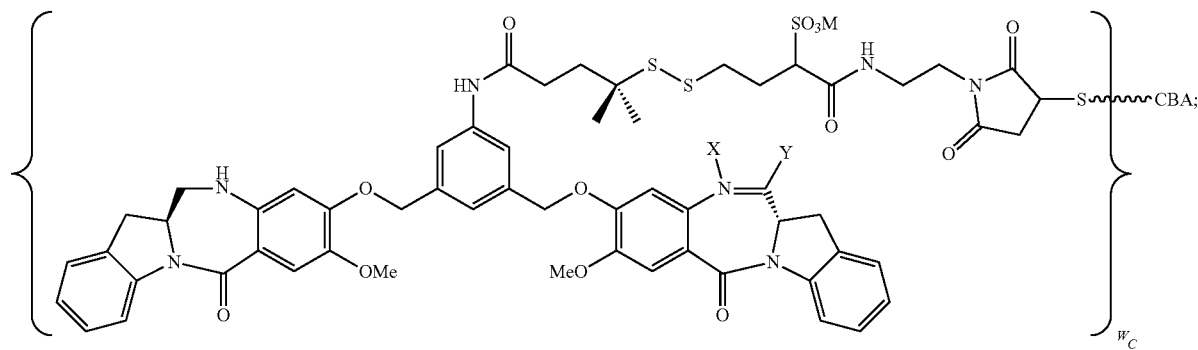
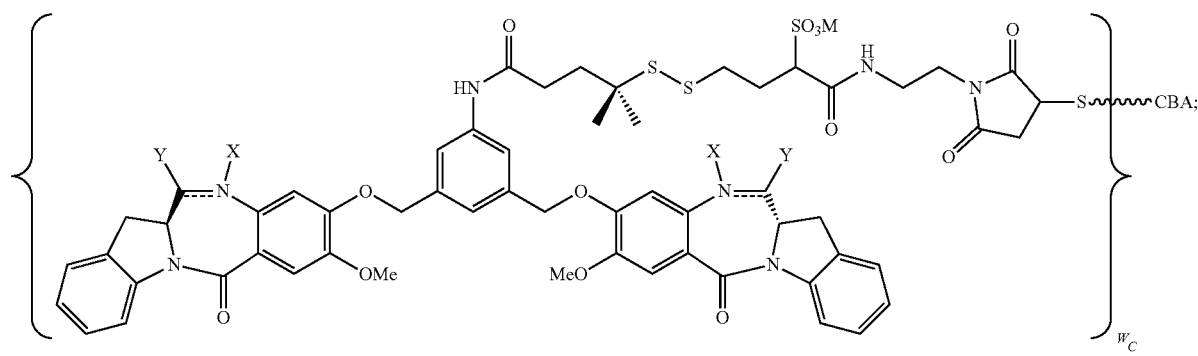
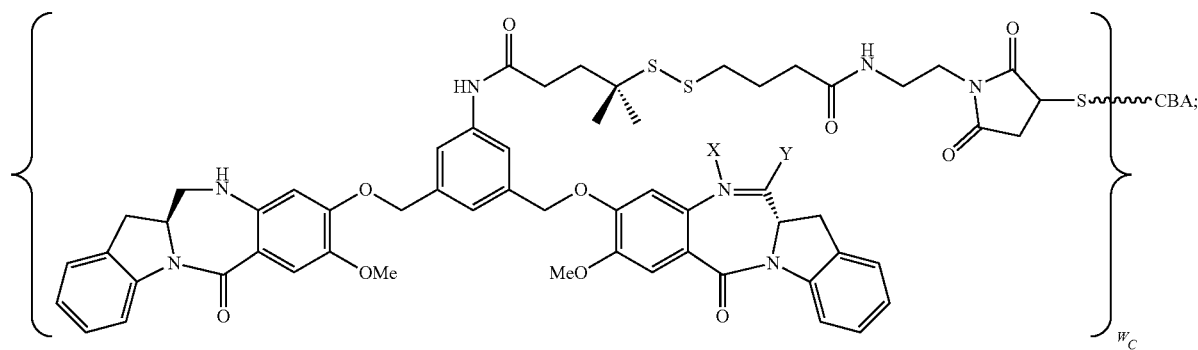
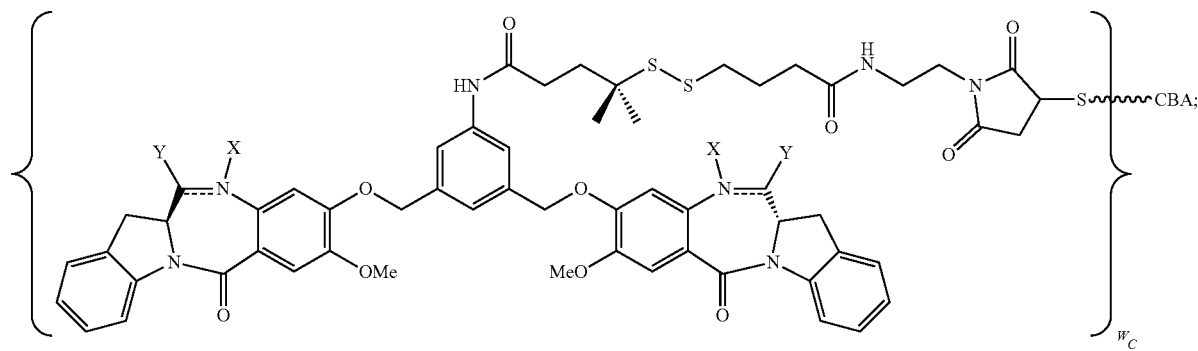

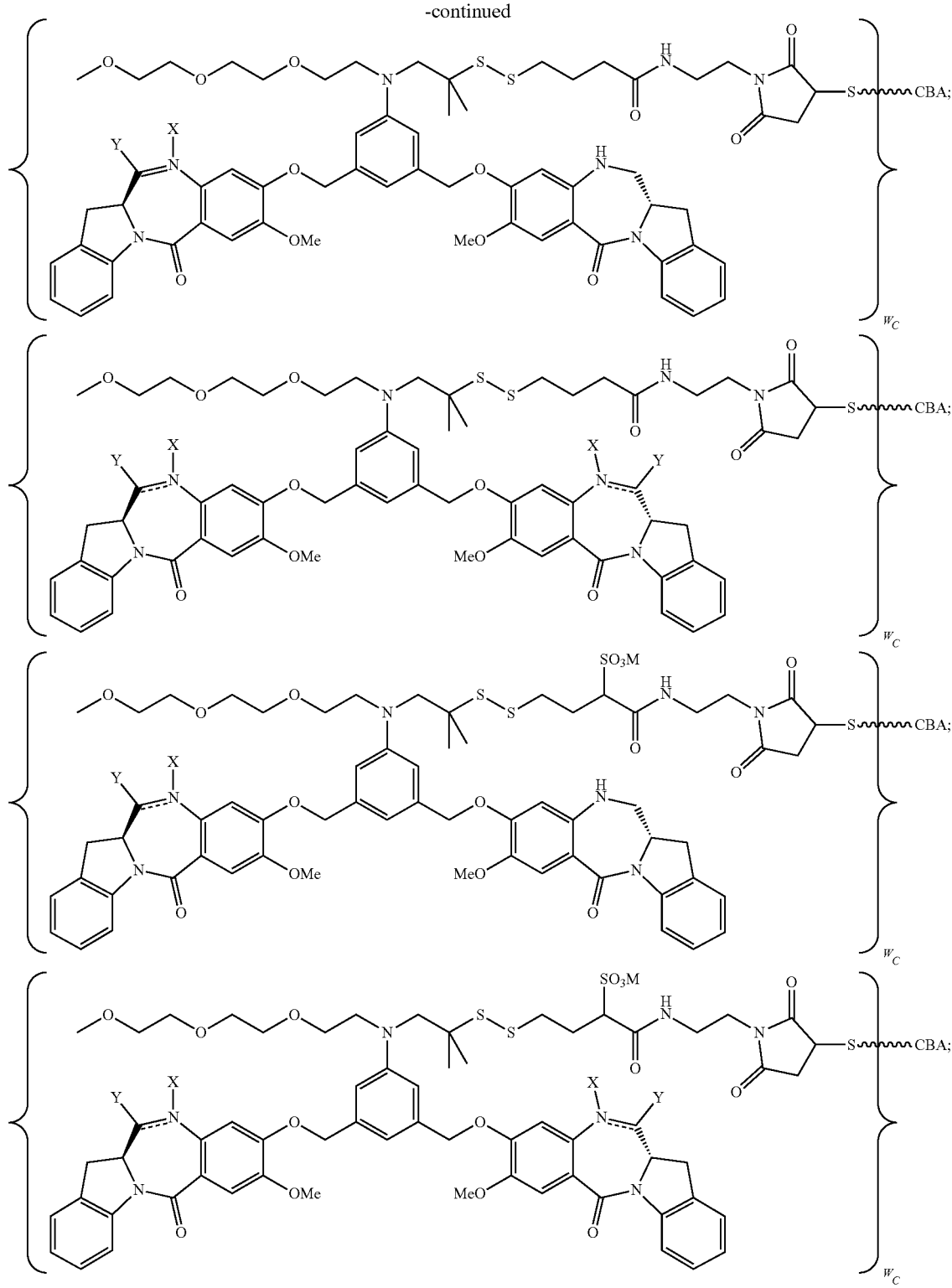

or a pharmaceutically acceptable salt thereof, wherein the double line ══ between N and C represents a single bond or a double bond, provided that when it is a double bond, X is absent and Y is —H, and when it is a single bond X is —H, and Y is —OH or —SO$_3$M. In a more specific embodiment, the double line ══ between N and C represents a double bond, X is absent and Y is —H. In another specific embodiment, the double line ══ between N and C represents a single bond, X is —H and Y is —SO$_3$M.

In a 17$^{th}$ specific embodiment, the immunoconjugate of the third embodiment is represented by the following formula:

CBA—(—Cy$^{C3}$)$_{wC}$  (C3), wherein:
CBA is a CD123/IL-3Rα-binding agent described in the first aspect of the invention (e.g., a subject antibody or antigen-binding fragment thereof described herein above, or a subject polypeptide thereof described above), covalently linked to Cy$^{C3}$ through a cysteine residue;
$W_C$ is 1 or 2;
Cy$^{C3}$ is represented by the following formula:

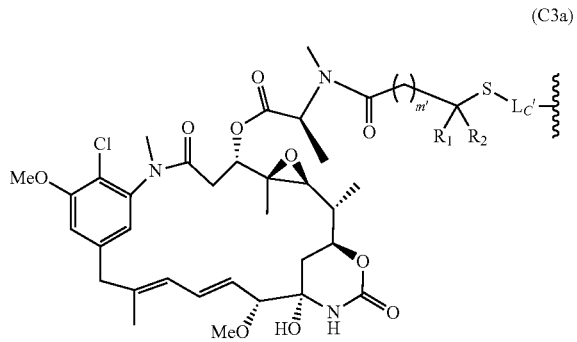
(C3a)

wherein:
m' is 1 or 2;
$R_1$ and $R_2$, are each independently —H or a $(C_1$-$C_3)$alkyl;
$L_{C'}$ is represented by the following formula:

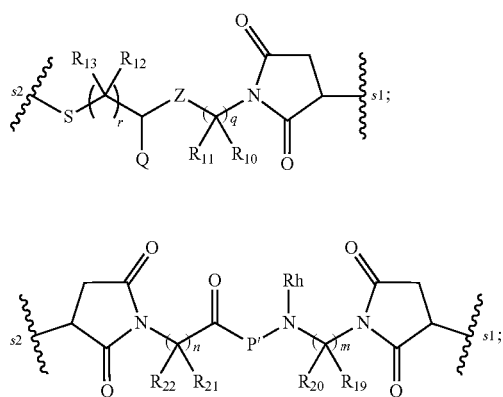

wherein:
s1 is the site covalently linked to the CBA and s2 is the site covalently linked to —S— group on Cy$^{C3}$;
Z is —C(=O)—NR$_9$—, or —NR$_9$—C(=O)—;
Q is H, a charged substituent, or an ionizable group;
$R_9$, $R_{10}$, $R_{11}$, $R_{12}$, $R_{13}$, $R_{19}$, $R_{20}$, $R_{21}$ and $R_{22}$, for each occurrence, are independently —H or a $(C_1$-$C_3)$alkyl;
q and r, for each occurrence, are independently an integer between 0 and 10;
m and n are each independently an integer between 0 and 10;
$R^h$ is —H or a $(C_1$-$C_3)$alkyl; and
P' is an amino acid residue or a peptide containing 2 to 20 amino acid residues.

In a more specific embodiment, q and r are each independently an integer between 1 to 6, more specifically, an integer from 1 to 3. Even more specifically, $R_{10}$, $R_{11}$, $R_{12}$ and $R_{13}$ are all H.

In another more specific embodiment, m and n are each independently an integer between 1 and 6, more specifically, an integer from 1 to 3. Even more specifically, $R_{19}$, $R_{20}$, $R_{21}$ and $R_{22}$ are all H.

In a 18$^{th}$ specific embodiment, for immunoconjugates of formula (C3), P' is a peptide containing 2 to 5 amino acid residues; and the remaining variables are as described above in the 17$^{th}$ specific embodiment or any more specific embodiments described therein. In a more specific embodiment, P' is selected from Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 55), β-Ala-Leu-Ala-Leu (SEQ ID NO: 57), Gly-Phe-Leu-Gly (SEQ ID NO: 73), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. In another more specific embodiment, P' is Gly-Gly-Gly, Ala-Val, Ala-Ala, Ala-D-Ala, D-Ala-Ala, or D-Ala-D-Ala.

In a 19$^{th}$ specific embodiment, for immunoconjugates of formula (C3), -$L_{C'}$- is represented by the following formula:

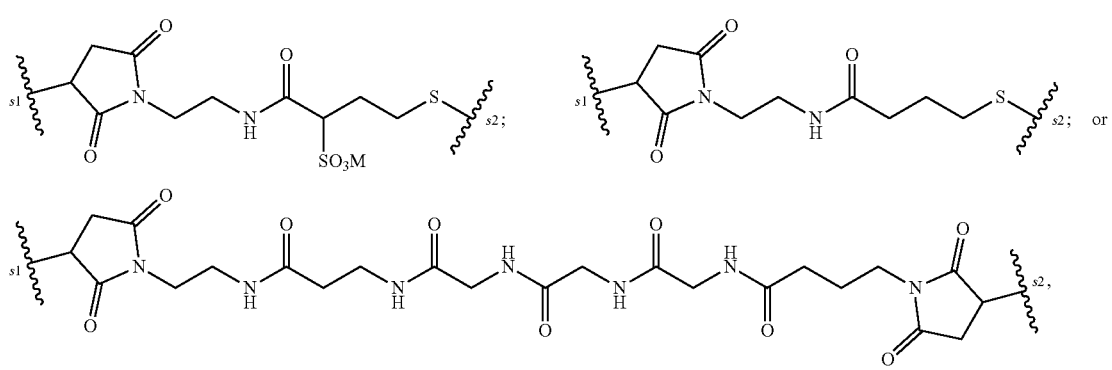

wherein M is H⁺ or a cation; and the remaining variables are as described above in the 17$^{th}$ or 18$^{th}$ specific embodiment or any more specific embodiments described therein.

In a 20$^{th}$ specific embodiment, for immunoconjugates of formula (C3), m' is 1 and $R_1$ and $R_2$ are both H; and the remaining variables are as described above in the 17$^{th}$, 18$^{th}$ or 19$^{th}$ specific embodiment or any more specific embodiments described therein.

In a 21$^{st}$ specific embodiment, for immunoconjugates of formula (C3), m' is 2 and $R_1$ and $R_2$ are both Me; and the remaining variables are as described above in the 17$^{th}$, 18$^{th}$ or 19$^{th}$ specific embodiment or any more specific embodiments described therein.

In a 22$^{nd}$ specific embodiment, the immunoconjugate of the third embodiment is represented by the following formula:

In a 23$^{rd}$ specific embodiment, for the immunoconjugates of the third embodiment, M is H⁺, Na⁺ or K⁺; and the remaining variables are as described in any one of the 1$^{st}$ to 22$^{nd}$ specific embodiments or any more specific embodiments described therein.

In any of the above 1$^{st}$ to the 23$^{rd}$ specific embodiments, the subject antibody or antigen-binding fragment thereof, or polypeptide comprising the subject antibody or antigen-binding fragment thereof, has a Cys residue at a location corresponding to the engineered Cys in the heavy chain CH3 domain (i.e., the 5$^{th}$ to the last residue) of SEQ ID NOs: 54 or 56. The subject antibody or antigen-binding fragment thereof may comprise an immunoglobulin heavy chain region (HC) having the amino acid sequence set forth in SEQ ID NO: 54; and an immunoglobulin light chain variable region (LCVR) having the amino acid sequence set

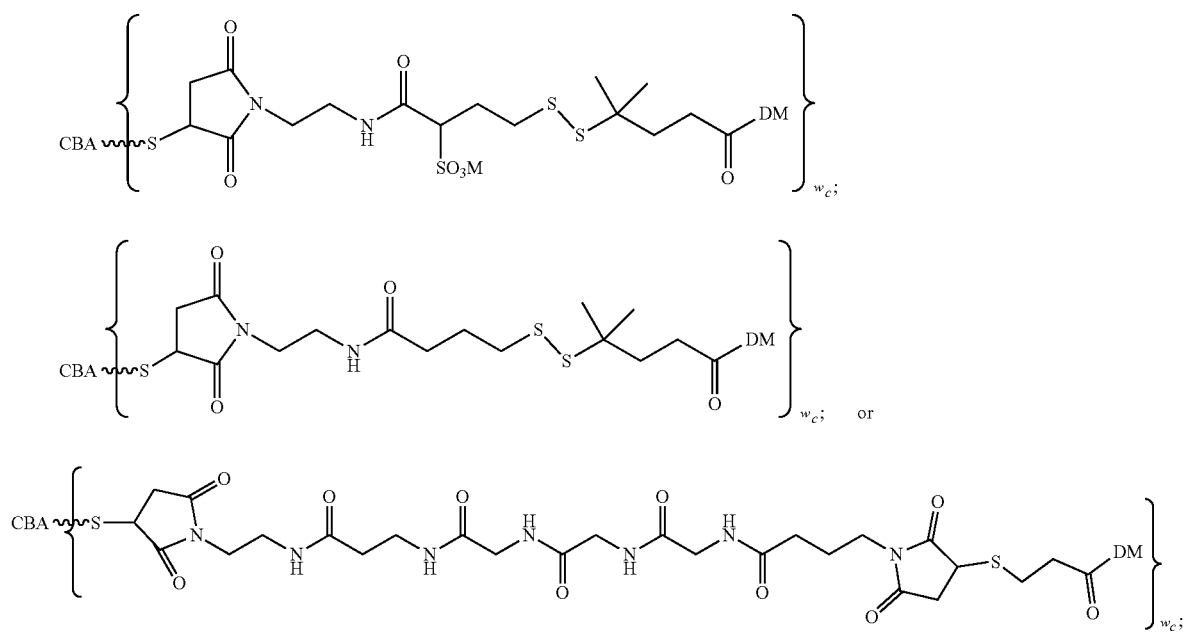

or a pharmaceutically acceptable salt thereof, wherein DM is a drug moiety represented by the following formula:

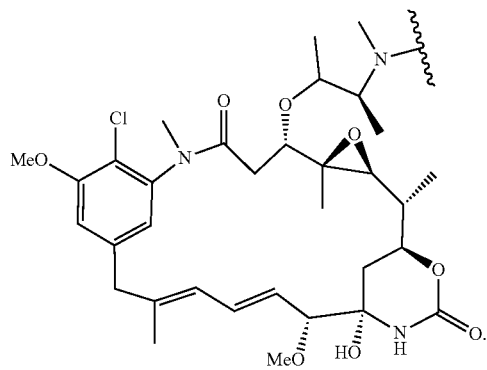 [SMILES: *N(C)[C@@H](C)C(C)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

forth in SEQ ID NO: 33, 35, 37, or 41 (preferably SEQ ID NO: 35 or 37). The subject antibody or antigen-binding fragment thereof may also comprise an Ig heavy chain region having the amino acid sequence set forth in SEQ ID NO: 56; and an Ig LCVR having the amino acid sequence set forth in SEQ ID NO: 33, 35, 37, or 41 (preferably SEQ ID NO: 35 or 37). In certain embodiments, the second residue from the N-terminus of SEQ ID NOs: 54 and 56 is Phe, while in certain other embodiments, the second residue from the N-terminus of SEQ ID NOs: 54 and 56 is Val.

The immunoconjugates of the third embodiment described above (e.g., immunoconjugates of any one of the 1$^{st}$ to 23$^{rd}$ specific embodiments or any more specific embodiments described therein) can be prepared by reacting the CBA having one or more free cysteine with a cytotoxic agent having a thiol-reactive group described herein.

In one embodiment, the cytotoxic agent having a thiol-reactive group is represented by the following formula:

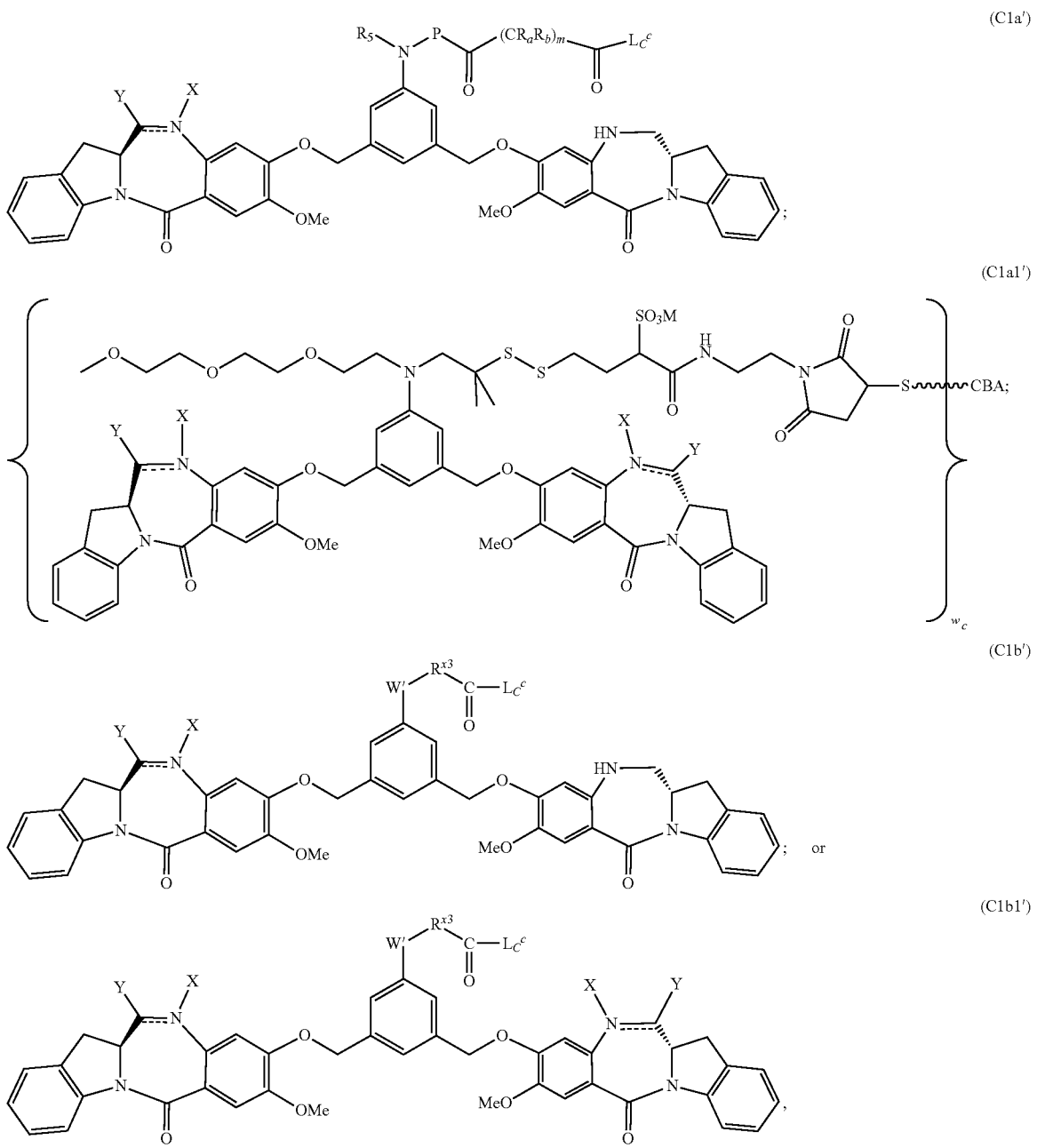
or a pharmaceutically acceptable salt thereof, wherein -L$_C^c$ is represented by the following formula:
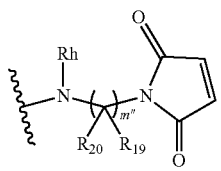
wherein the variables are as described above in any one of the 1$^{st}$ to 9$^{th}$ and 23$^{rd}$ specific embodiments or any more specific embodiments described therein.

In another embodiment, the cytotoxic agent having a thiol-reactive group is represented by the following formula:

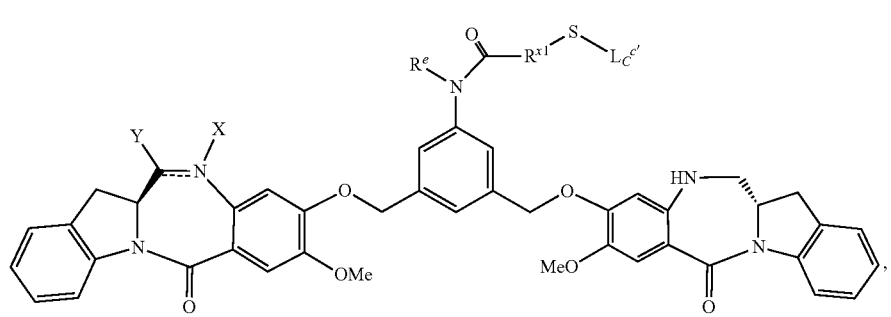

(C2a″)

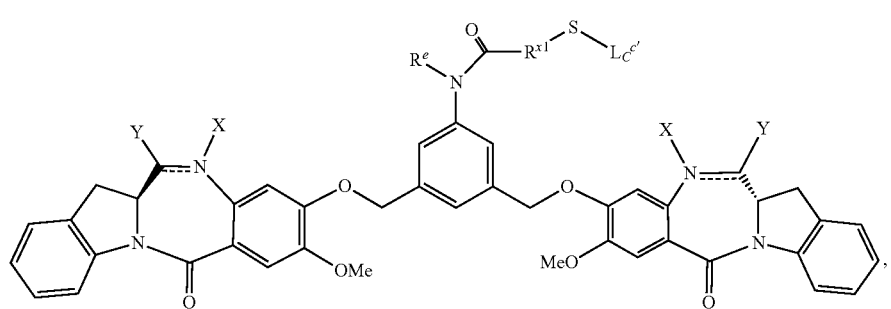

(C2a″1)

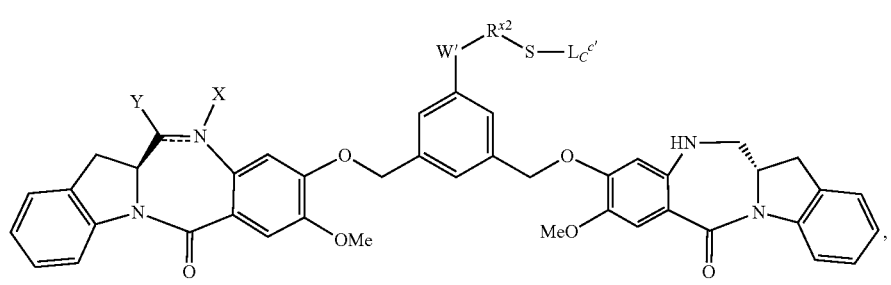

(C2b″)

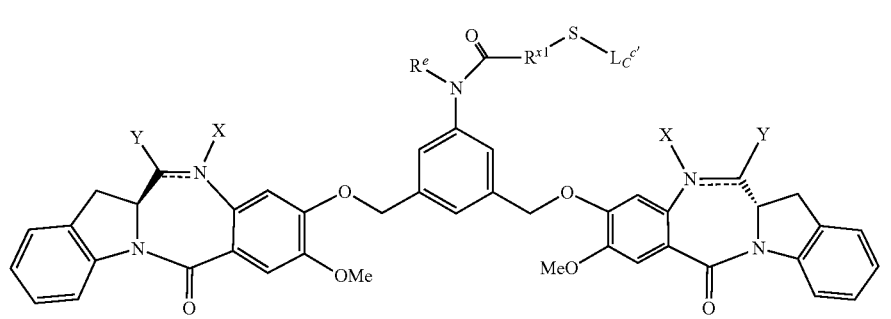

(C2b″1)

or a pharmaceutically acceptable salt thereof, wherein $L_C^{c'}$ is represented by the following formula:

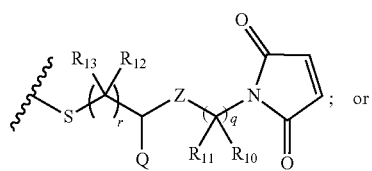

; or

-continued

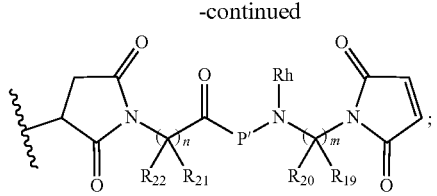

;

wherein the variables are as described above in any one of the $10^{th}$ to $16^{th}$ and $23^{rd}$ specific embodiment or any more specific embodiments described therein.

In yet another embodiment, the cytotoxic agent having a thiol-reactive group is represented by the following formula:

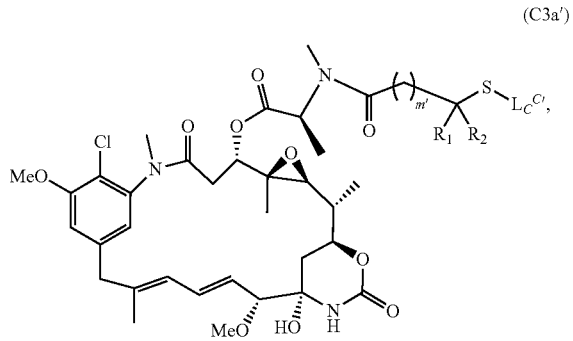

(C3a')

or a pharmaceutically acceptable salt thereof, wherein $L_C^{c'}$ is described above and the remaining variables are as described above in any one of the $17^{th}$ to $23^{rd}$ specific embodiments or any more specific embodiments described therein.

In certain embodiments, organic solvents are used in the reaction of the CBA and the cytotoxic agent to solubilize the cytotoxic agent. Exemplary organic solvents include, but are not limited to, dimethylacetamide (DMA), propylene glycol, etc. In one embodiment, the reaction of the CBA and the cytotoxic agent is carried out in the presence of DMA and propylene glycol.

4. Compositions and Methods of Use

The present invention includes a composition (e.g., a pharmaceutical composition) comprising the subject antibodies or antigen-binding fragments thereof, or immunoconjugates thereof (e.g., conjugates of Formulas (L1), (L2), (L3), (S1), (S2), (S3), (S4), (C1), (C2), and (C3)) described herein, and a carrier (a pharmaceutically acceptable carrier). The present invention also includes a composition (e.g., a pharmaceutical composition) comprising the subject antibodies or antigen-binding fragments thereof, or conjugate of Formulas (L1), (L2), (L3), (S1), (S2), (S3), (S4), (C1), (C2), and (C3)), and a carrier (a pharmaceutically acceptable carrier), and further comprising a second therapeutic agent. The present compositions are useful for inhibiting abnormal cell growth or treating a proliferative disorder in a mammal (e.g., human), including hematologic cancer, leukemia, or lymphoma.

In particular, the present invention provides pharmaceutical compositions comprising one or more of the CD123-binding agents or immuno-conjugates thereof described herein. In certain embodiments, the pharmaceutical compositions further comprise a pharmaceutically acceptable vehicle. These pharmaceutical compositions find use in inhibiting tumor growth and treating cancer in human patients, including hematologic cancer, leukemia, or lymphoma.

In certain embodiments, formulations are prepared for storage and use by combining a purified antibody, or immuno-conjugate thereof of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g., octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g., Zn-protein complexes); and non-ionic surfactants such as TWEEN or polyethylene glycol (PEG).

The pharmaceutical compositions described herein can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration. In some particular embodiments, the administration is intravenous. The pharmaceutical compositions described herein can also be used in vitro or in ex vivo.

An antibody or immunoconjugate of the invention can be combined in a pharmaceutical combination formulation, or dosing regimen as combination therapy, with a second compound, such as one that is known to be effective in treating a disease or disorder of interest. In some embodiments, the second compound is a anti-cancer agent. In some embodiments, the methods encompass administration of the second compound and an immunoconjugate of the invention that results in a better efficacy as compared to administration of the immunoconjugate alone. The second compound can be administered via any number of ways, including for example, topical, pulmonary, oral, parenteral, or intracranial administration. In some embodiments, the administration is oral. In some embodiments, the administration is intravenous. In some embodiments, the administration is both oral and intravenous.

An antibody or immunoconjugate can also be combined in a pharmaceutical combination formulation, or dosing regimen as combination therapy, with an analgesic, or other medications.

An antibody or immunoconjugate can be combined in a pharmaceutical combination formulation, or dosing regimen as combination therapy, with a second compound having anti cancer properties. The second compound of the pharmaceutical combination formulation or dosing regimen can have complementary activities to the ADC of the combination such that they do not adversely affect each other. Pharmaceutical compositions comprising the CD123-binding agent and the second anti-cancer agent are also provided.

The present invention includes a method of inhibiting abnormal cell growth or treating a proliferative disorder in a mammal (e.g., human) comprising administering to said mammal a therapeutically effective amount of the subject antibodies or antigen-binding fragments thereof, or immuno-conjugates (e.g., conjugates of formulas (L1), (L2), (L3), (S1), (S2), (S3), (S4), (C1), (C2), and (C3)) described herein, or a composition thereof, alone or in combination with a second therapeutic agent.

In certain embodiments, the abnormal cell growth or proliferative disorder in a mammal is a disease or condition associated with or characterized by the expression of CD123, such as cancer, including hematologic cancer, leukemia, or lymphoma. In certain embodiments, the proliferative disorder is a cancer of a lymphatic organ, or a hematological malignancy.

For example, the cancer may be selected from the group consisting of: acute myeloid leukemia (AML, including CD33-low AML, P-glycoprotein positive AML, relapsed AML, or refractory AML), chronic myelogenous leukemia (CML), including blastic crisis of CML and Abelson oncogene associated with CML (Bcr-ABL translocation), myelodysplastic syndrome (MDS), acute B lymphoblastic leukemia or B-cell acute lymphoblastic leukemia (B-ALL), chronic lymphocytic leukemia (CLL), including Richter's syndrome or Richter's transformation of CLL, hairy cell leukemia (HCL), acute promyelocytic leukemia (APL), B-cell chronic lymphoproliferative disease (B-CLPD), atypical chronic lymphocytic leukemia (preferably with a marked CD11c expression), blastic plasmacytoid dendritic cell neoplasm (BPDCN), non-Hodgkin lymphomas (NHL), including mantel cell leukemia (MCL), and small lymphocytic lymphoma (SLL), Hodgkin's lymphoma, systemic mastocytosis, and Burkitt's lymphoma.

In certain embodiments, the B-ALL is a CD19 positive B-ALL. In certain other embodiments, the B-ALL is a CD19 negative B-ALL.

In certain embodiments, the cancer has at least one negative prognostic factor, e.g., overexpression of P-glycoprotein, overexpression of EVI1, a p53 alteration, DNMT3A mutation, FLT3 internal tandem duplication.

In certain embodiments, the therapeutically effective amount of the subject antibodies or antigen-binding fragments thereof, or immuno-conjugates (e.g., conjugates of formulas (L1), (L2), (L3), (S1), (S2), (S3), (S4), (C1), (C2), and (C3)) described herein, or a composition thereof, alone or in combination with a second therapeutic agent, preferentially inhibits the proliferation of leukemic stem cells (LSCs), leukemia progenitors (LPs), and/or leukemic blasts, over normal hematopoietic stem cells (HSCs). In certain embodiments, $IC_{50}$ value or the half maximum concentration of the above subject agents to inhibit the proliferation of leukemic stem cells (LSCs), leukemia progenitors (LPs), and/or leukemic blasts, is at least 10-, 20-, 30-, 40-, 50-, 60-, 70-, 80-, 90-, 100-, 150-, 300-, 500-fold or more lower than that for the normal hematopoietic stem cells (HSCs).

In certain embodiments, an anti-leukemia therapy of the invention not only targets and kills leukemic blasts, but preferably also targets and kills leukemic progenitors (LP) and leukemic stem sells (LSCs). In certain embodiments, the therapy is also less selective against normal HSCs. In certain embodiments, CD123 expression on LSCs, LPs and leukemia blasts are much higher (e.g., at least 20-25 fold higher in LSC, AML progenitors, and AML blasts) as compared to normal lymphocytes (which may be close to negative). In certain embodiments, CD123 expression levels on LPs and LSCs are at least as high as those on leukemic blasts.

Similarly, the present invention provides a method for inducing cell death in selected cell populations comprising contacting target cells or tissue containing target cells with an effective amount of the subject antibodies or antigen-binding fragments thereof, or immuno-conjugates of the present invention. The target cells are cells to which the cell-binding agent of the conjugates can bind.

If desired, other active agents, such as other anti-tumor agents, may be administered along with the conjugate.

Cancer therapies and their dosages, routes of administration and recommended usage are known in the art and have been described in such literature as the *Physician's Desk Reference* (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include: Comprehensive index; Manufacturer; Products (by company's or trademarked drug name); Category index; Generic/chemical index (non-trademark common drug names); Color images of medications; Product information, consistent with FDA labeling; Chemical information; Function/action; Indications & Contraindications; Trial research, side effects, warnings.

Examples of in vitro uses include treatments of autologous bone marrow prior to their transplant into the same patient in order to kill diseased or malignant cells: treatments of bone marrow prior to their transplantation in order to kill competent T cells and prevent graft-versus-hostdisease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 μM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic compounds or conjugates of the invention will be supplied as a solution or a lyophilized powder that are tested for sterility and for endotoxin levels.

Suitable pharmaceutically acceptable carriers, diluents, and excipients are well known and can be determined by those of ordinary skill in the art as the clinical situation warrants. Examples of suitable carriers, diluents and/or excipients include: (1) Dulbecco's phosphate buffered saline, pH about 7.4, containing or not containing about 1 mg/mL to 25 mg/mL human serum albumin, (2) 0.9% saline (0.9% w/v NaCl), and (3) 5% (w/v) dextrose; and may also contain an antioxidant such as tryptamine and a stabilizing agent such as Tween 20.

The method of the invention for inducing cell death in selected cell populations, for inhibiting cell growth, and/or for treating cancer, can be practiced in vitro, in vivo, or ex vivo.

EXAMPLES

Example 1 Generation of Mouse Monoclonal Antibodies Against Human and Cynomolgus CD123 Antigen To produce murine anti-CD123 antibodies, wild type BALB/c female mice (Charles River Laboratory, Wilmington, MA) were injected subcutaneously with human CD123 expressing stable 300-19 cell line, which is a BALB/c derived pre-B cell line (M. G. Reth et al., 1985, *Nature*, 317: 353-355), in PBS at dose of $5 \times 10^6$ cells/mouse every 2 weeks for five times. Three days before being sacrificed for hybridoma generation, the immunized mice received intraperitoneal injection of another dose of antigen. The spleen from the mouse was collected according to standard animal protocols and was ground between two sterile, frosted microscopic slides to obtain a single cell suspension in RPMI-1640 medium. After the red blood cells were lysed with ACK lysing buffer, the spleen cells were then mixed with murine myeloma P3X63Ag8.653 cells (P3 cells) (J. F. Kearney et al., 1979, *J. Immunol*, 123: 1548-1550) at ratio of 1 P3 cells:3 spleen cells. The mixture of spleen cells and P3 cells was washed and treated with pronase in fusion media (0.3 M mannitol/D-sorbitol, 0.1 mM $CaCl_2$, 0.5 mM $MgCl_2$ and 1 mg/mL BSA) at room temperature for 3 min. The reaction was stopped by addition of Fetal Bovine Serum (FBS, Invitrogen); cells were then washed, resuspended in 2 mL cold fusion media and fused with BTX ECM 2001 electrofusion machine (Harvard Apparatus). The fused cells were added gently to RPMI-1640 selection medium containing hypoxanthine-aminopterin-thymidine (HAT) (Sigma Aldrich), incubated for 20 min at 37° C., and then seeded into flat bottom 96-well plates at 200 µL/well. The plates were then incubated in 5% $CO_2$ incubator at 37° C. until hydridoma clones were ready for antibody screening. Other techniques of immunization and hybridoma production can also be used, including those described in J. Langone and H. Vunakis (Eds., *Methods in Enzymology, Vol. 121, Immunochemical Techniques, Part I*, Academic Press, Florida); and E. Harlow and D. Lane (*Antibodies: A Laboratory Manual*, 1988, Cold Spring Harbor Laboratory Press, New York, NY).

Hybridoma Screening and Selection

Hybridoma screening was done using flow cytometric binding assay with human CD123 expressing stable 300-19 cell lines and wild-type 300-19 cells. In brief, the wild-type 300-19 cells were first labeled with CELLTRACE™ far red DDAO-SE (Invitrogen), mixed with untreated cells at 1:1 ratio and incubated with the hybridoma supernatant for 2 hours on ice. Cells were then washed, incubated with PE-labeled anti mouse IgG (Jackson Immunoresearch), washed, fixed with formalin and analyzed using FACS array (BD Bioscience). The hybridoma with specific reactivity to human CD123 antigen were expanded and the supernatants were rescreened by flow cytometric binding assay using three independent cell lines: human CD123 expressing stable 300-19 cell line, cynomolgus CD123 expressing stable 300-19 cell line and wild type 300-19 cell line. The hybridoma with positive binding to human and cynomolgus CD123 antigens but negative on wild type 300-19 cells were further subcloned by limiting dilution. One subclone from each hybridoma, which showed specific binding to human and cynomolgus CD123 antigens, was selected for subsequent analysis.

A total of six fusions were conducted over the course of this investigation. Approximately 6,000 hybridomas were screened, 33 hybridomas specific for human and cynomolgus CD123 antigens were generated and 18 hybridomas were subcloned. Stable subclones were cultured and the isotype of the monoclonal antibody was identified using commercial mouse IgG isotyping reagents (such as the IsoStrip Mouse Monoclonal Antibody Isotyping Kit by Roche Diagnostics GmbH, Germany, Product No. 11493027001).

Antibody Purification

Antibodies were purified from hybridoma subclone supernatants using standard methods, such as, for example Protein A or G chromatography (HiTrap Protein A or G HP, 1 mL, Amersham Biosciences). Briefly, supernatant was prepared for chromatography by the addition of 1/10 volume of 1 M Tris/HCl buffer, pH 8.0. The pH-adjusted supernatant was filtered through a 0.22 µm filter membrane and loaded onto column equilibrated with binding buffer (PBS, pH 7.3). The column was washed with binding buffer until a stable baseline was obtained with no absorbance at 280 nm. Antibody was eluted with 0.1 M acetic acid buffer containing 0.15 M NaCl, pH 2.8, using a flow rate of 0.5 mL/min. Fractions of approximately 0.25 mL were collected and neutralized by the addition of 1/10 volume of 1M Tris/HCl, pH 8.0. The peak fraction(s) was dialyzed overnight twice against 1×PBS and sterilized by filtering through a 0.2 µm filter membrane. Purified antibody was quantified by absorbance at A280.

Protein A purified fractions were further polished using ion exchange chromatography (IEX) with quaternary ammonium (Q) chromatography for murine antibodies. Briefly, samples from protein A purification were buffer exchanged into binding buffer (10 mM Tris, 10 mM sodium chloride, pH 8.0) and filtered through 0.22 µm filer. The prepared sample was then loaded onto a Q fast flow resin (GE Lifesciences) that was equilibrated with binding buffer at a flow rate of 120 cm/hr. Column size was chosen to have sufficient capacity to bind all the MAb in the sample. The column was then washed with binding buffer until a stable baseline was obtained with no absorbance at 280 nm. Antibody was eluted by initiating a gradient from 10 mM to 500 mM sodium chloride in 20 column volume (CV). Peak fractions were collected based on absorbance measurement at 280 nm (A280). The percentage of monomer was assessed with size exclusion chromatography (SEC) on a TSK gel G3000SWXL, 7.8×300 mm with a SWXL guard column, 6.0×40 mm (Tosoh Bioscience, Montgomeryville, PA) using an Agilent HPLC 1100 system (Agilent, Santa Clara, CA). Fractions with monomer content above 95% were pooled, buffer exchanged to PBS (pH 7.4) using a TFF system, and sterilized by filtering through a 0.2 µm filter membrane. The IgG concentration of purified antibody was determined by A280 using an extinction coefficient of 1.47. Alternative methods such as ceramic hydroxyapatite (CHT) were also used to polish antibodies with good selectivity. Type II CHT resin with 40 μm particle size (Bio-Rad Laboratories) were used with a similar protocol as described for IEX chromatography. The binding buffer for CHT corresponds to 20 mM sodium phosphate, pH 7.0 and antibody was eluted with a gradient of 20-160 mM sodium phosphate over 20 CV.

Example 2 Cloning and Sequencing of the $V_L$ and $V_H$ Regions of the Anti-CD123 Antibodies Cloning of the $V_L$ and $V_H$ Regions Total cellular RNA was prepared from 5×10⁶ cells of the CD123 hybridomas using an RNeasy kit (QIAgen) according to the manufacturer's protocol. cDNA was subsequently synthesized from total RNA using the SuperScript II cDNA synthesis kit (Invitrogen).

The PCR procedures for amplifying the antibody variable region cDNAs derived from hybridoma cells were based on methods described in Wang et al. ((2000) *J Immunol Methods*. 233:167-77) and Co et al. ((1992) *J Immunol*. 148: 1149-54). The $V_L$ and $V_H$ sequences were amplified by degenerate primers on the 5'-end and either murine kappa or IgG₁ constant region specific primers respectively on the 3'-end. The purified amplicons were sent to Beckman Coulter Genomics for sequencing.

Since the degenerate primers used to clone the $V_L$ and $V_H$ cDNA sequences alter the 5'-end, additional sequencing efforts were needed to verify the complete cDNA sequences. The preliminary sequences were entered into a search query of the NCBI IgBlast site to identify the murine germline sequences from which the antibody sequences had been derived. PCR primers were then designed to anneal to the germline linked leader sequence of the murine antibody so that this new PCR reaction would yield a complete variable region cDNA sequence, unaltered by the PCR primers.

Mass Determination for Sequence Confirmation

The variable regions cDNA sequences obtained for each of the anti-CD123 antibodies were combined with germline constant region sequences to obtain full length antibody cDNA sequences. The molecular weights of the heavy and light chains were then calculated from translations of the cDNA sequences and compared with the molecular weights obtained by LC/MS analyses of the purified murine anti-CD123 antibodies. The observed molecular weights for each of the light and heavy chains matched the expected values.

Example 3 Antibody Humanization

Recombinant Antibody Expression

The confirmed variable region amino acid sequences for the murine CD123 antibodies were codon-optimized, synthesized and cloned in-frame with human antibody constant regions by Blue Heron Biotechnology to build chimeric versions of the CD123 antibodies. The vectors, constant regions, and cloning schemes used for the chimeric CD123 antibodies were identical to those used for the humanized CD123 antibodies described below. The chimeric antibody chCD123-6 is comprised of the mouse variable region sequences of SEQ ID NOs: 28 and 29, respectively, together with the human IgG1 and Kappa constant sequences for the heavy and light chains, respectively. The light chain variable region was cloned into the EcoRI and BsiWI sites of the pAbKZeo plasmid and the heavy chain variable region was cloned into the HindIII and ApaI sites of the pAbG1Neo plasmid. These expression constructs were transiently produced in either adherent HEK-293T cells using suspension adapted HEK-293T cells using a modified PEI procedure in shake flasks. The PEI transient transfections were performed as previously described (Durocher et al., *Nucleic Acids Res.* 30(2):E9 (2002)), except the HEK-293T cells were grown in Freestyle 293 (Invitrogen) and the culture volume was left undiluted after the addition of the PEI-DNA complexes. The transfections were incubated for a week and then the cleared supernatants were purified by standard Protein A chromatography followed by polishing chromatography procedures.

Antibody Humanization

The murine CD123-6 antibody was humanized using complementary determining region (CDR) grafting procedures substantially as described in Jones et al., *Nature* 321: 604-608, 1986, Verhoeyen et al., *Science* 239: 1534-1536, 1988, U.S. Pat. Nos. 5,225,539, and 5,585,089. CDR grafting generally consists of replacing the Fv framework regions (FRs) of a mouse antibody with human antibody Fv framework regions while preserving the mouse CDR residues critical for the specific antigen-binding properties of the parent antibody. Exemplary CDRs of the CD123-6 antibody following the Kabat numbering scheme and the Kabat CDR definitions are as indicated in Table A below.

TABLE A

CD123-6 CDRs (CDR grafting)

Light Chain

CDR-L1:
Murine: KASQDINSYLS (SEQ ID NO: 19)
CDR grafted: RASQDINSYLS (SEQ ID NO: 20)
CDR-L2: RVNRLVD (SEQ ID NO: 21)
CDR-L3: LQYDAFPYT (SEQ ID NO: 22)

Heavy Chain

CDR-H1: SSIMH (SEQ ID NO: 5)
CDR-H2: YIKPYNDGTKYNEKFKG (SEQ ID NO: 8)
CDR-H3: EGGNDYYDTMDY (SEQ ID NO: 11)

The CDR-grafting process begins by selecting appropriate human acceptor frameworks, typically those derived from human antibody genes sharing the highest sequence homology to the parent murine antibody. The human immunoglobulin germline light and heavy chain sequences with the highest homology to the murine CD123-6 antibody was identified utilizing the interactive tool, DomainGapAlign, of the International ImMunoGeneTics information System® (IMGT (http column double slash imgt dot cines dot fr slash) as described in Ehrenmann et al., *Nucleic Acids Res.* 38: D301-307 (2010). The human germline sequences selected as the acceptor frameworks for the $V_L$ and $V_H$ domains of CD123-6 antibody were IGKV1-16*01 and IGHV1-46*03, respectively.

Sequence alignment among the relevant portion of the original muCD123-6 $V_L$ sequence, the corresponding human germline sequence IGKV1-16*01, and the corresponding huCD123-6VLGv1 and huCD123-6VLGv4 sequences is shown below.

```
                      1                                                           61
muCD123-6 VL    (1) DIKMTQSPSSMYASLGERVTITCKASQDINSYLSWFQQKPGKSPKTLIYRVNRLVDGVPSR SEQ ID NO: 79
huCD123-6VLGv1  (1) --Q-------LS--V-D------R---------A--------A--S----------S-----(SEQ ID NO: 80)
huCD123-6VLGv4  (1) --Q-------LS--V-D------R------------------A-------------------(SEQ ID NO: 81)
IGKV1-16*01     (1) --Q-------LS--V-D------R---G-SN--A--------A--S----AASS-QS-----(SEQ ID NO: 82)

62                                          108
muCD123-6 VL   (62) FSGSGSGQDYSLTISSLEYEDMGIYYCLQYDAFPYTFGGGTKLEIKR(SEQ ID NO: 83)
huCD123-6VLGv1 (62) -------T-FT------QP--FAT--------------Q---V----(SEQ ID NO: 84)
huCD123-6VLGv4 (62) -------N--T------QP--FAT--------------Q---V----(SEQ ID NO: 85)
IGKV1-16*01    (62) -------T-FT------QP--FAT---Q--NSY-             (SEQ ID NO: 86)
```

Sequence alignment among the relevant portion of the original muCD123-6 $V_H$ sequence, the corresponding human germline sequence IGHV1-46*03, and the corresponding huCD123-6VHGv1, huCD123-6VHGv6, and huCD123-6VHGv7 sequences is shown below.

```
                      1                                                           61
muCD123-6 VH    (1) EFQLQQSGPELVKPGASVKMSCKASGYIFTSSIMHWMKQKPGQGLEWIGYIKPYNDGTKYN (SEQ ID NO: 87)
huCD123-6VHGv1  (1) QV--V---A-VK------V-------G--------VR-A-------M-------------- (SEQ ID NO: 88)
huCD123-6VHGv6  (1) Q---V---A-VK------V----------------VR-A--------------------- (SEQ ID NO: 89)
huCD123-6VHGv7  (1) QV--V---A-VK------V----------------VR-A--------------------- (SEQ ID NO: 90)
IGHV1-46*03     (1) QV--V---A-VK------V-------T---YV---VR-A-------M-I-N-SGGS-S-A (SEQ ID NO: 91)

62                                             121
muCD123-6 VH   (62) EKFKGKATLTSDKSSTANMELNSLTSEDSAVYYCAREGGNDYYDTMDYWGQGTSVTVSS(SEQ ID NO: 92)
huCD123-6VHGv1 (62) -----RV-M-R-T-T--VY---S---R---T-----------------------L-----(SEQ ID NO: 93)
huCD123-6VHGv6 (62) -----R------R-T---Y---S---R---T-----------------------L-----(SEQ ID NO: 94)
huCD123-6VHGv7 (62) -----R------R-T---Y---S---R---T-----------------------L-----(SEQ ID NO: 95)
IGHV1-46*03    (62) Q--Q-RV-M-R-T-T--VY---S---R---T-------                       (SEQ ID NO: 96)
```

The humanized DNA constructs were synthesized, expressed, and the recombinant antibodies purified as described above for subsequent CD123 binding analysis compared with the parent antibody.

It is well established that framework residues can also make structural contributions to antigen-binding and may be re-introduced as back-mutations to maximally preserve antigen-binding affinity. Foote and Winter, *J. Mol. Biol.* 224: 487-499 (1992). A platform of residues directly underneath the CDRs, referred to as vernier zone residues, may help to preserve the conformation of the CDR loops that direct the specificity and affinity of the antibody. Thus variants containing one or more back-mutations of the vernier zone residues were made, and subsequently evaluated for antigen-binding as well as for the functional IL3 inhibition activity. The vernier zone residue back-mutations tested included 3 residues in the $V_L$ (position 46 in FW-L2, and positions 69, 71 in FW-L3) and 8 residues in the $V_H$ (positions 2, 28 in FW-H1, position 48 in FW-H2, and positions 67, 69, 71, 73, 78 in FW-H3). Several CDR-grafted CD123-6 antibodies with vernier zone back-mutations exhibited IL3 inhibition activity on TF-1 cells as exemplified by version 4.6 or referred to as "Gv4.6" herein ($V_L$ Gv4 and $V_H$ Gv6) and version 4.7 or referred to as "Gv4.7" herein ($V_L$ Gv4 and $V_H$ Gv7) (FIG. 1).

The specific framework residue usage of the CDR-grafted CD123-6 antibodies described are given in Tables B and C below.

TABLE B

CDR-grafting of CD123-6 antibody $V_L$
CD123-6-$V_L$

| Kabat position | Murine residue | Human (CDR-graft) v1 residue | Human (CDR-graft) v4 residue |
|---|---|---|---|
| 3 | K | Q | Q |
| 11 | M | L | L |

TABLE B-continued

CDR-grafting of CD123-6 antibody $V_L$
CD123-6-$V_L$

| Kabat position | Murine residue | Human (CDR-graft) v1 residue | Human (CDR-graft) v4 residue |
|---|---|---|---|
| 12 | Y | S | S |
| 15 | L | V | V |
| 17 | E | D | D |
| 43 | S | A | A |
| 46 | T | S | _T_ |
| 69 | Q | T | _N_ |
| 71 | Y | F | _Y_ |
| 72 | S | T | T |
| 79 | E | Q | Q |
| 80 | Y | P | P |
| 83 | M | F | F |
| 84 | G | A | A |
| 85 | I | T | T |
| 100 | G | Q | Q |
| 104 | L | V | V |
| 24 | K | R | R |

TABLE C

CDR-grafting of CD123-6 antibody $V_H$
CD123-6-$V_H$

| Kabat position | Murine residue | Human (CDR-graft) v1 residue | Human (CDR-graft) v6 residue | Human (CDR-graft) v7 residue |
|---|---|---|---|---|
| 1 | E | Q | Q | Q |
| 2 | F | V | _V_ | V |
| 5 | Q | V | _V_ | V |
| 9 | P | A | A | A |
| 11 | L | V | V | V |
| 12 | V | K | K | K |

TABLE C-continued

CDR-grafting of CD123-6 antibody V$_H$
CD123-6-V$_H$

| Kabat position | Murine residue | Human (CDR-graft) v1 residue | Human (CDR-graft) v6 residue | Human (CDR-graft) v7 residue |
|---|---|---|---|---|
| 20 | M | V | V | V |
| 28 | I | G | <u>I</u> | <u>I</u> |
| 37 | M | V | V | V |
| 38 | K | R | R | R |
| 40 | K | A | A | A |
| 48 | I | M | <u>I</u> | <u>I</u> |
| 66 | K | R | R | R |
| 67 | A | V | <u>A</u> | <u>A</u> |
| 69 | L | M | <u>L</u> | <u>L</u> |
| 71 | S | R | <u>S</u> | <u>S</u> |
| 73 | K | T | <u>R</u> | <u>R</u> |
| 75 | S | T | T | T |
| 78 | A | V | <u>A</u> | <u>A</u> |
| 79 | N | Y | <u>Y</u> | <u>Y</u> |
| 82a | N | S | S | S |
| 83 | T | R | R | R |
| 87 | S | T | T | T |
| 108 | S | L | L | L |

Additionally, to minimize concerns about the impact of conjugating lysines that fall in CDRs, lysine 24 in murine CD123-6 antibody CDR-L1 was replaced with arginine in CDR grafting (see Table A above).

The CD123-6 antibody was also humanized by variable domain resurfacing, following methods previously described, Roguska et al., *Proc. Natl. Acad. Sci., USA*, 91(3):969-973, 1994 and Roguska et al., *Protein Eng.* 9(10): 895-904, 1996. Resurfacing generally involves identification of the variable region framework surface residues in both the light and heavy chains and replacing them with human equivalents. The murine CDRs and buried framework residues are preserved in the resurfaced antibody. Exemplary CDRs of CD123-6 antibodies are defined as indicated in Table D.

TABLE D

CD123-6 antibody CDRs (Resurfacing)

Light Chain

CDR-L1:
Murine: KASQDINSYLS (SEQ ID NO: 19)
Resurfaced: RASQDINSYLS (SEQ ID NO: 20)
CDR-L2: RVNRLVD (SEQ ID NO: 21)
CDR-L3: LQYDAFPYT (SEQ ID NO: 22)

Heavy Chain

CDR-H1: SSIMH (SEQ ID NO: 5)
CDR-H2:
Murine and resurfaced v1.1: YIKPYNDGTK
(SEQ ID NO: 6)
Resurfaced v1.0: YIRPYNDGTR (SEQ ID NO: 7)
CDR-H3: EGGNDYYDTMDY (SEQ ID NO: 11)

Kabat CD123-6 CDR-H2

Murine CDR-H2: YIKPYNDGTK<u>YNEKFKG</u> (SEQ ID NO: 8)
Resurfaced v1.0 CDR-H2: YIRPYNDGTR<u>YNQKFQG</u>
(SEQ ID NO: 9)
Resurfaced v1.1 CDR-H2: YIKPYNDGTK<u>YNQKFQG</u>
(SEQ ID NO: 10)

*The double underlined sequence marks the portion of the Kabat heavy chain CDR-H2 that was not considered a CDR for resurfacing.

To minimize concerns about the impact of conjugating lysines that fall within CDRs, lysine 24 of the murine CD123-6 antibody light chain CDR-L1 was replaced with arginine. Similarly, lysines 52 and 59 of the murine CD123-6 antibody heavy chain CDR-H2 were replaced with arginines for resurfaced version 1.0. The AbM heavy chain CDR-H2 definition was employed for resurfacing so the table provides those as well as exemplary Kabat defined heavy chain CDR-H2 sequences for both the murine and human versions of CD123-6 antibody.

Surface residue positions were defined as any position with a relative accessibility of 30% or greater (Pedersen et al., *J. Mol. Biol.* 235: 959-973, 1994). The calculated surface residues were then aligned with human germline surface sequences to identify the most homologous human surface sequence. The human germline sequence used as the replacement surface for the light chain variable domain of CD123-6 antibody was IGKV1-16*01 while IGHV1-69*10 was used as the replacement surface for heavy chain variable domain. The specific framework surface residue changes are given in Tables E and F below.

TABLE E

Resurfacing of CD123-6 antibody V$_L$
CD123-6 V$_L$

| Kabat position | Murine residue | Human (resurface) residue |
|---|---|---|
| 1 | D | D |
| 3 | K | <u>Q</u> |
| 5 | T | T |
| 9 | S | S |
| 12 | Y | <u>S</u> |
| 15 | L | <u>V</u> |
| 18 | R | R |
| 40 | P | P |
| 41 | G | G |
| 57 | G | G |
| 60 | S | S |
| 67 | S | S |
| 80 | Y | <u>P</u> |
| 81 | E | E |
| 100 | G | <u>Q</u> |
| 103 | K | K |
| 107 | K | K |
| 108 | R | R |
| 24 | K | <u>R</u> |

TABLE F

Resurfacing of CD123-6 antibody V$_H$
CD123-6 V$_H$

| Kabat position | Murine residue | Human v1.0 (resurface) residue | Human v1.1 (resurface) residue |
|---|---|---|---|
| 1 | E | <u>Q</u> | <u>Q</u> |
| 2 | F | <u>V</u> | F |
| 3 | Q | Q | Q |
| 5 | Q | <u>V</u> | <u>V</u> |
| 9 | P | <u>A</u> | <u>A</u> |
| 11 | L | <u>V</u> | <u>V</u> |
| 13 | K | K | K |
| 14 | P | P | P |
| 19 | K | K | K |
| 23 | K | K | K |
| 28 | I | <u>T</u> | <u>T</u> |
| 41 | P | P | P |

TABLE F-continued

Resurfacing of CD123-6 antibody $V_H$

CD123-6 $V_H$

| Kabat position | Murine residue | Human v1.0 (resurface) residue | Human v1.1 residue |
|---|---|---|---|
| 42 | G | G | G |
| 43 | Q | Q | Q |
| 61 | E | *Q* | *Q* |
| 62 | K | K | K |
| 64 | K | *Q* | *Q* |
| 65 | G | G | G |
| 73 | K | *R* | K |
| 74 | S | S | S |
| 82B | S | S | S |
| 84 | S | S | S |
| 85 | E | E | E |
| 105 | Q | Q | Q |
| 112 | S | S | S |
| 52 | K | *R* | K |
| 59 | K | *R* | K |

Sequence alignments below show the resurfaced sequences for CD123-6 antibody variable domain of both light ($V_L$) and heavy ($V_H$) chain with their murine counterparts. See SEQ ID NO: 41 for the resurfaced huCD123-6 $V_L$ sequence, and SEQ ID NOs: 39 and 40 for the resurfaced huCD123-6 $V_H$ sequences.

```
            1                                                           61
muCD123-6 VL  DIKMTQSPSSMYASLGERVTITCKASQDINSYLSWFQQKPGKSPKTLIYRVNRLVDGVPSR(SEQ ID NO: 79)
huCD123-6 VL  --Q--------S--V--------R------------------------------------(SEQ ID NO: 74)

62                                             108
muCD123-6 VL  FSGSGSGQDYSLTISSLEYEDMGIYYCLQYDAFPYTFGGGTKLEIKR(SEQ ID NO: 83)
huCD123-6 VL  ------------------P------------------Q--------(SEQ ID NO: 75)

1                                                           61
muCD123-6 VH    EFQLQQSGPELVKPGASVKMSCKASGYIFTSSIMHWMKQKPGQGLEWIGYIKPYNDGTKYN(SEQ ID NO: 87)
huCD123-6 VHv1.0 QV--V---A-V----------------T----------------------R------R--(SEQ ID NO: 76)
huCD123-6 VHv1.1 QV--V---A-V----------------T--------------------------------(SEQ ID NO: 77)

62                                                      121
muCD123-6 VH    EKFKGKATLTSDKSSSTANMELNSLTSEDSAVYYCAREGGNDYYDTMDYWGQGTSVTVSS(SEQ ID NO: 92)
huCD123-6 VHv1.0 Q--Q--------R-----------------------------------------------(SEQ ID NO: 78)
huCD123-6 VHv1.1 Q--Q--------------------------------------------------------(SEQ ID NO: 97)
```

Example 4 Screen for Anti-CD123 Antibodies that Inhibit IL3-Mediated Signaling and Proliferation The ability of anti-CD123 antibodies to inhibit IL3-mediated signaling and proliferation was examined in vitro using the erythroleukemia cell line TF-1 that can proliferate only in the presence of one of the following growth factors, either IL-3 or GM-CSF. TF-1 cells were cultured in the complete RPMI medium (RPMI-1640, 10% fetal bovine serum and 50 µg/mL gentamicin sulfate; all reagents were from Invitrogen) supplemented with GM-CSF (2 ng/mL). Prior to setting up the proliferation assays, the cells were washed and then starved of the growth factors overnight. To block Fc receptors on the cell surface, the culture medium was supplemented with 100 nM chKTI antibody (a non-binding antibody of the same isotype). TF-1 cells were plated at 6,000 cells per well in the complete RPMI medium in either the presence or absence of 10 µg/mL of an anti-CD123 antibody. A growth factor, either IL-3 (1 ng/mL) or GM-CSF (2 ng/mL), was added to the cells to initiate cell proliferation. Cells were incubated at 37° C. in a humidified 5% $CO_2$ incubator for 3 days. The relative numbers of viable cells in each well were determined by the colorimetric WST-8 assay (Dojindo Molecular Technologies, Inc., Rockville, MD, US). WST-8 is reduced by dehydrogenases in viable cells to an orange formazan product that is soluble in tissue culture medium. The amount of formazan produced is directly proportional to the number of viable cells. WST-8 was added into the wells at 10% of the final volume, and the plates were incubated at 37° C. in a humidified 5% $CO_2$ incubator for an additional 2-6 hours. Then the absorbance was measured on a plate-reader spectrophotometer in the dual wavelength mode 450 nm/650 nm, and the absorbance at the 650 nm (non-specific light scattering by cells) was subtracted from that at the 450 nm. The relative cell number in each well was calculated by first correcting for the medium background absorbance, and then dividing the value of each sample treated with an antibody by the average values of wells with the untreated cells (control).

Figure 2B:
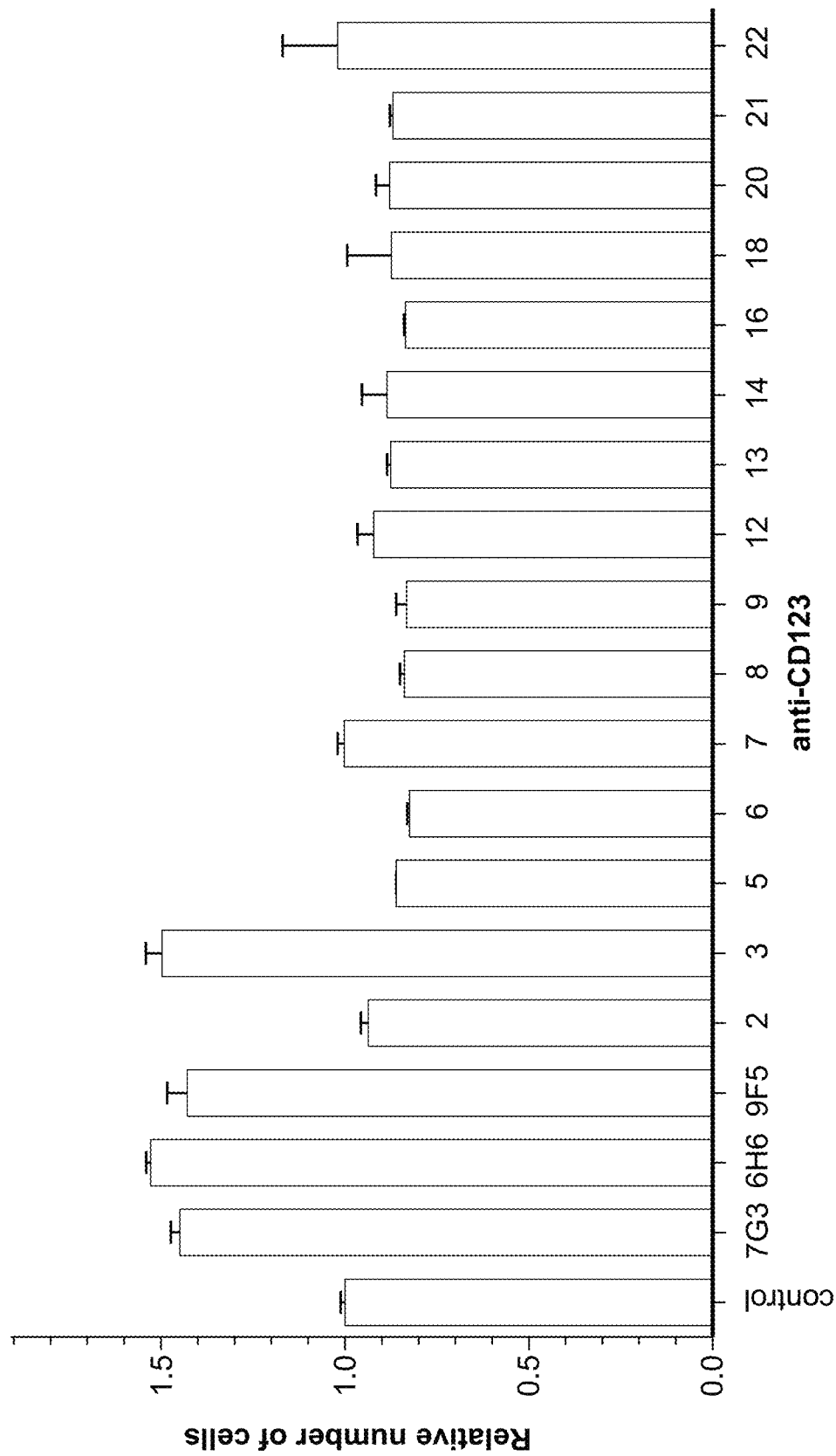

The results from a typical assay are presented in FIGS. 2A and 2B. Consistent with the previously reported data (Sun et al. 1996), the 7G3 but not 6H6 or 9F5 antibody substantially inhibited IL-3 dependent proliferation. Unexpectedly, several anti-CD123 antibodies generated in this study were able to inhibit IL-3 dependent proliferation of TF-1 cells even more significantly than 7G3 (FIG. 2A). For example, the antibody 3, 6 and 14 reduced the number of TF-1 cells to less than 5% of that in the control (TF-1 cells grown in the absence of an antibody), whereas 7G3 antibody reduced the number of cells to 15% of that in the control. In contrast, treatment with the other anti-CD123 antibodies (e.g., the antibodies 2, 5, 7, 8, 9, 12, 13, 16, 18, 20, 21 and 22) had only a minimal effect on the cell proliferation or no effect at all.

The inhibition of TF-1 cell proliferation by the antibodies 3, 6, 14 and 7G3 was IL-3 dependent, as these antibodies had no inhibitory effect when the cells were grown in the presence of another growth factor GM-CSF (FIG. 2B).

Next, the concentrations of the antibodies 3, 6, 14 (renamed muCD123-3, muCD123-6, muCD123-14, respectively) and 7G3 that were needed to inhibit IL3-dependent proliferation were determined. TF-1 cells were plated at 6,000 cells per well in 100 µL culture medium. The antibodies were diluted into the culture medium using 6-fold dilution series and 50 µL of the diluted material was added per well. Then IL3 was added to the cells at the final concentration 1 ng/mL. The final antibody concentration typically ranged from $6 \times 10^{-8}$ M to $8 \times 10^{-12}$ M. Cells were incubated at 37° C. in a humidified 5% $CO_2$ incubator for 3 days. Relative cell number in each well was determined by WST-8 assay as described above. The relative cell number value was plotted against the antibody concentration and presented in FIG. 3. It is apparent, that muCD123-3, muCD123-6, muCD123-14, and 7G3 inhibit IL-3 dependent proliferation of TF-1 cells substantially and in a dose-dependent manner, while a control non-functional anti- CD123 antibody had no such effect. For example, treatment with 7G3 reduced the relative cell number to 18% at the highest antibody concentration tested, with the $IC_{50}$ value of 0.33 nM. Treatment with muCD123-3 reduced the relative cell number to 2% at the highest antibody concentration tested, with the $IC_{50}$ value of 0.26 nM. Likewise, treatment with muCD123-14 or muCD123-6 reduced the relative cell number to less than 1% at the highest antibody concentration tested, with the $IC_{50}$ values of 0.08 nM or 0.05 nM, respectively. Therefore, muCD123-3, muCD123-6, and muCD123-14 inhibit IL-3 dependent proliferation of TF-1 cells to a significantly higher degree than the 7G3 antibody.

Example 5 Binding Affinity of Murine Anti-CD123 Antibodies

Figure 4A:
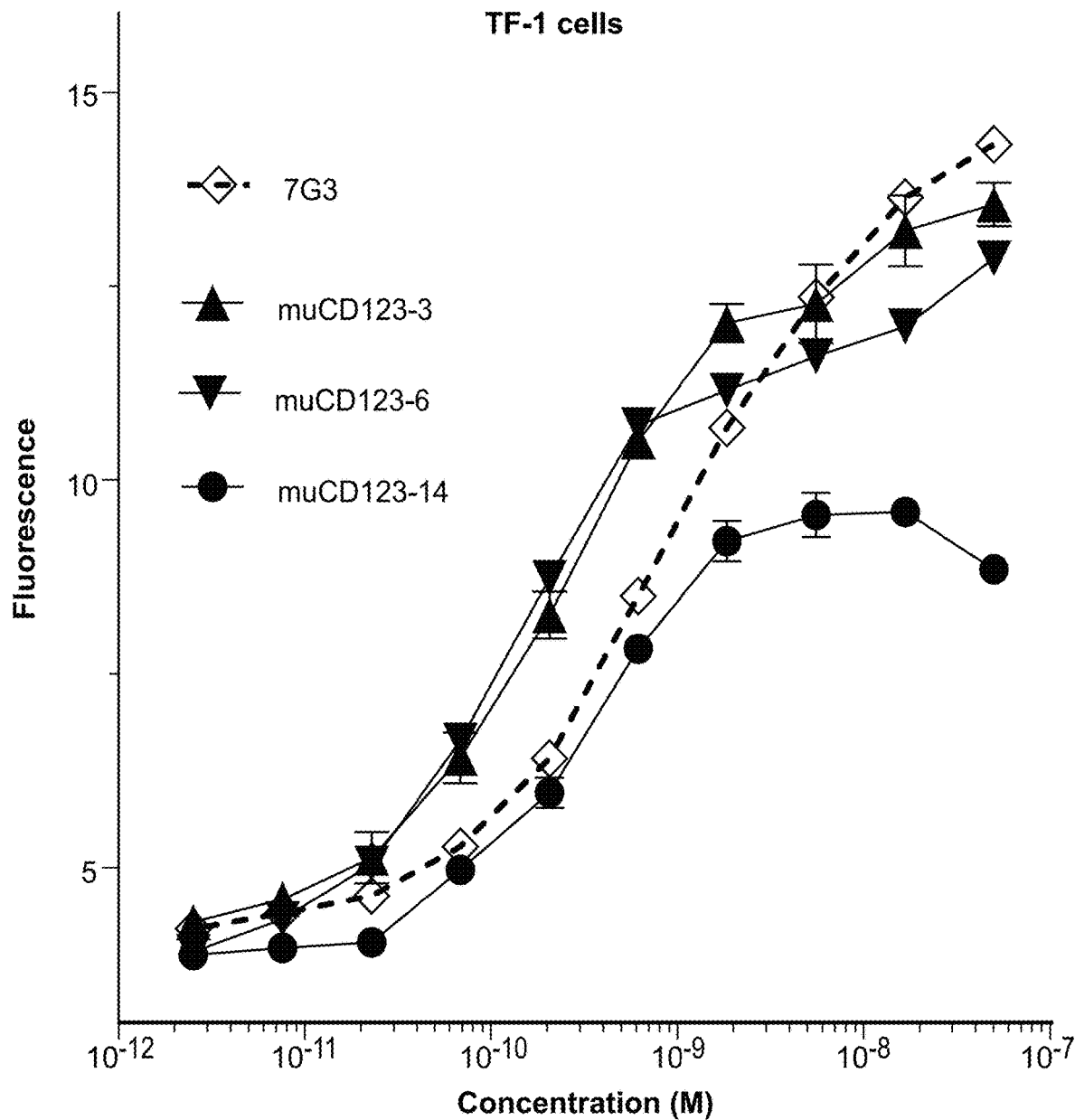
FIGS. 4A and 4B show that the murine muCD123-3, -6, and -14 antibodies have higher binding affinity to CD123-positive AML cells than that of the 7G3 antibody in CD123-expressing TF-1 (FIG. 4A) and HNT-34 (FIG. 4B) cells.
Figure 4B:
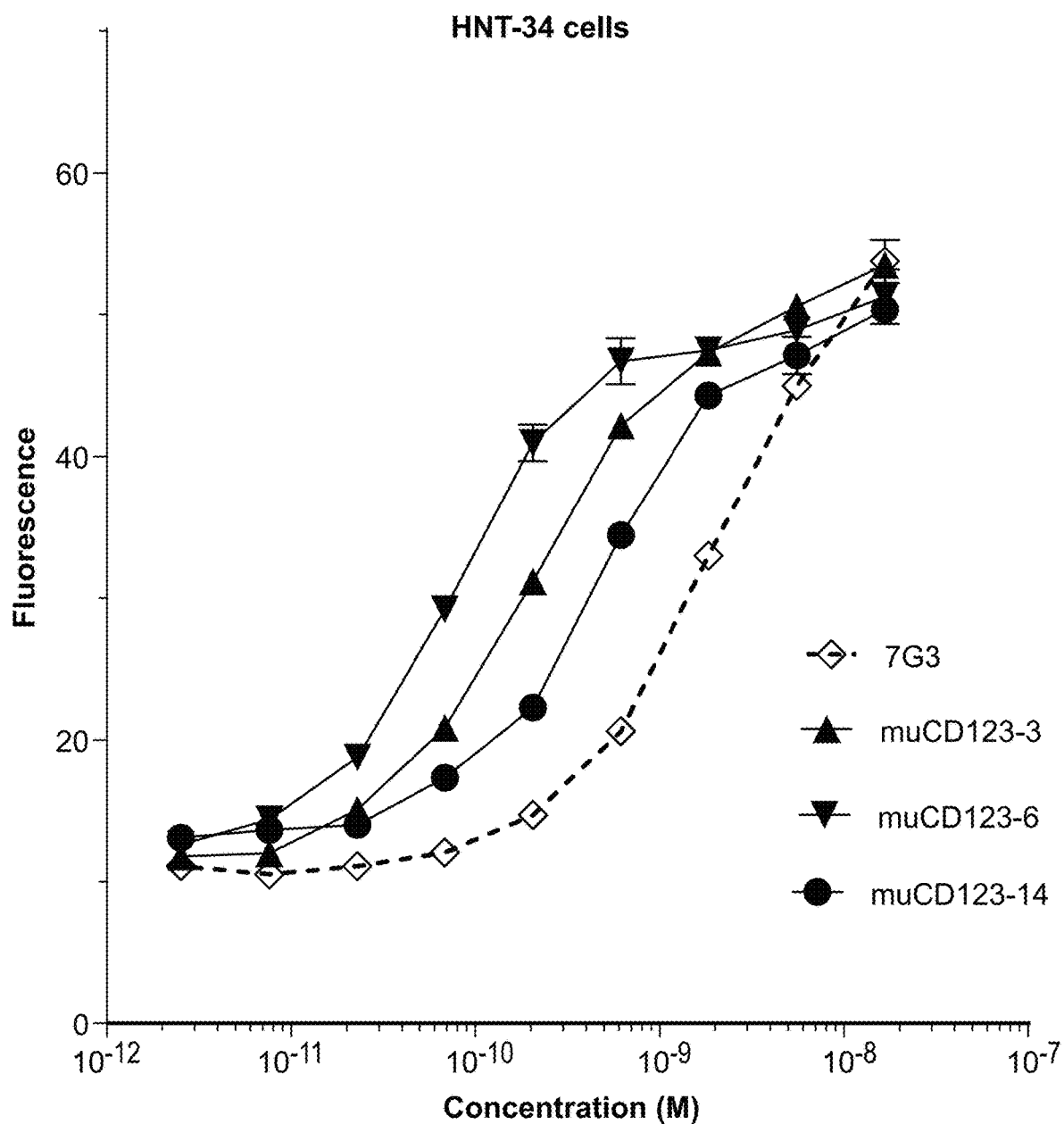

Binding affinity was tested by flow cytometry using purified antibodies. FACS histograms demonstrating the binding of muCD123-3, muCD123-6, muCD123-14, and 7G3 to CD123-expressing TF-1 and HNT-34 cells are shown in FIGS. 4A and 4B, respectively. TF-1 cells ($5 \times 10^4$ cells per sample) were incubated with varying concentrations of murine antibodies in 200 µL FACS buffer (DMEM medium supplemented with 2% normal goat serum). The cells were then pelleted, washed twice, and incubated for 1 hr with 100 µL of phycoerythrin (PE)-conjugated goat anti-mouse IgG-antibody (Jackson Laboratory). The cells were pelleted again, washed with FACS buffer and resuspended in 200 µL of PBS containing 1% formaldehyde. Samples were acquired using a FACSCalibur flow cytometer with the HTS multiwell sampler, or a FACS array flow cytometer, and analyzed using CellQuest Pro (all from BD Biosciences, San Diego, US). For each sample the geomean fluorescence intensity for FL2 was calculated and plotted against the antibody concentration in a semi-log plot. A dose-response curve was generated by non-linear regression and the $EC_{50}$ value of each curve, which corresponds to the apparent dissociation constant ($K_d$) of each antibody, was calculated using GraphPad Prism v4 (GraphPad software, San Diego, CA). A strong binding was observed for all antibodies tested and the $K_d$ values correspond to 0.3 nM, 0.1 nM, 0.3 nM, and 0.9 nM for muCD123-3, muCD123-6, muCD123-14, and 7G3 antibodies, respectively (FIG. 4A). Thus in this experiment, the binding by the subject murine CD123 antibodies are at least 3-9 times better than that by the 7G3 antibody.

Likewise, strong binding was also observed when another CD123-positive acute myeloid leukemia cell line, HNT-34, was used for the same flow cytometry assay described above. The $K_d$ values, calculated as described above, were 0.2 nM, 0.07 nM, 0.5 nM, and 2 nM for muCD123-3, muCD123-6, muCD123-14, and 7G3, respectively (FIG. 4B). Thus in this experiment, the binding by the subject murine CD123 antibodies are at least 4-28 times better than that by the 7G3 antibody.

These data demonstrate that muCD123-3, muCD123-6, and muCD123-14 have lower $K_d$ (which represent higher affinity) than the 7G3 antibody to CD123-positive AML cells.

Example 6 Binding Affinity of Chimeric Anti-CD123 Antibodies

Figure 5A:
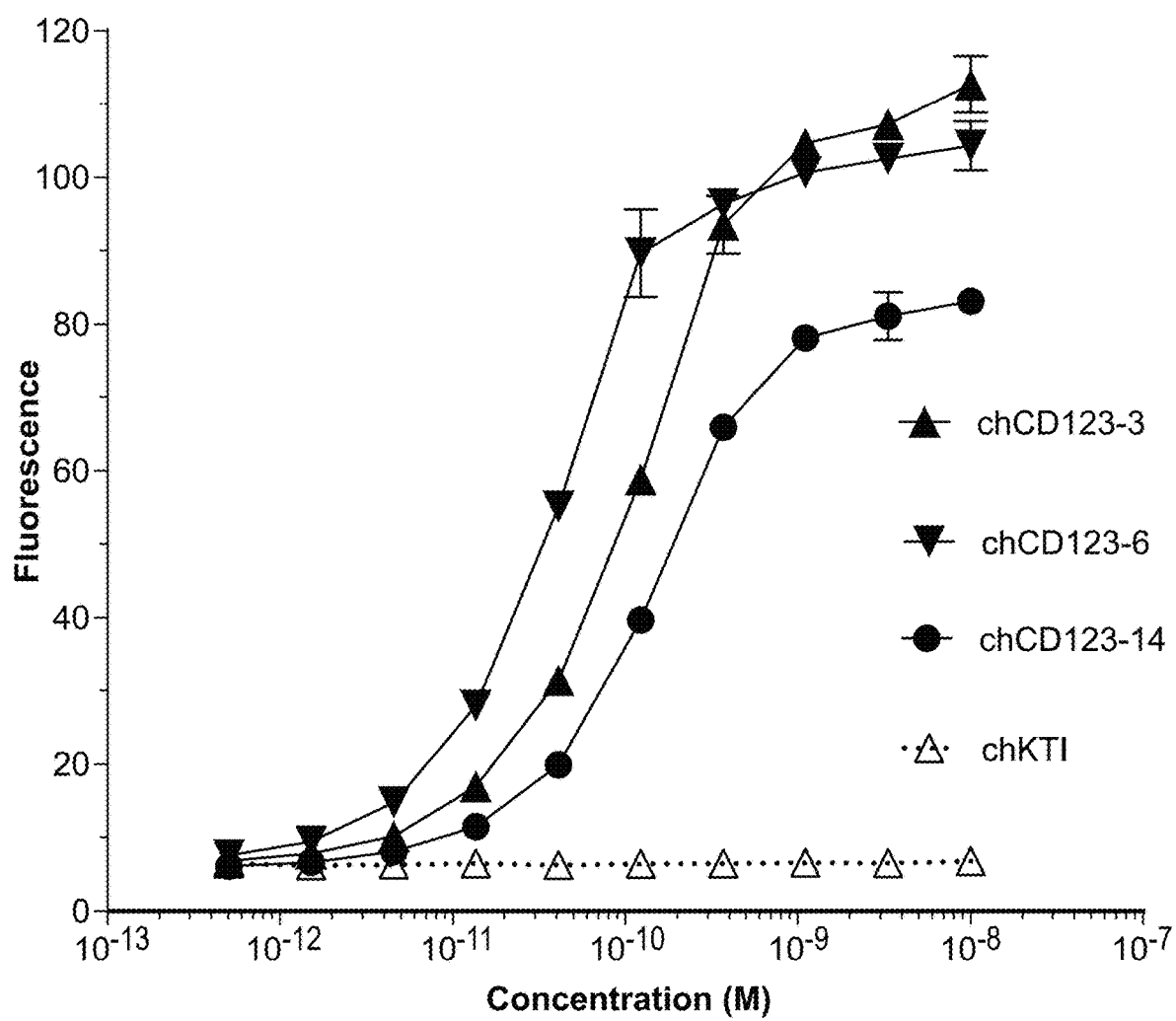
FIGS. 5A and 5B show that chimeric anti-CD-123 antibodies chCD123-3, -6, and -14 retain high binding affinity of their murine counterparts, using either HNT-34 cells (FIG. 5A) or the CD123-positive acute myeloid leukemia (AML) cell line MOLM-13 (FIG. 5B). Chimeric antibody chKTI, which does not bind CD123, was included as negative control.

The chimeric antibodies chCD123-3, chCD123-6, and chCD123-14 were assayed for their binding affinity to HNT-34 cells in comparison to a chimeric isotype control IgG (chKTI). Flow cytometry binding assays were carried out and analyzed as described in Example 5 using secondary PE-conjugated goat-anti-human antibodies. FIG. 5A depicts the dose-response curves for each antibody. The value for the apparent dissociation constant ($K_d$) of each antibody was calculated using GraphPad Prism v4 (GraphPad software, San Diego, CA). The data show that chimerization only moderately affected the binding affinities of these antibodies. The $K_d$ values for chCD123-3, chCD123-6, and chCD123-14 were 0.1 nM, 0.04 nM, and 0.2 nM, respectively. These values were at most 2.5 fold different from those for their murine counterparts reported in the Example 5. As expected, the chKTI antibody did not bind to the cells at the tested concentrations (FIG. 5A).

Figure 5B:
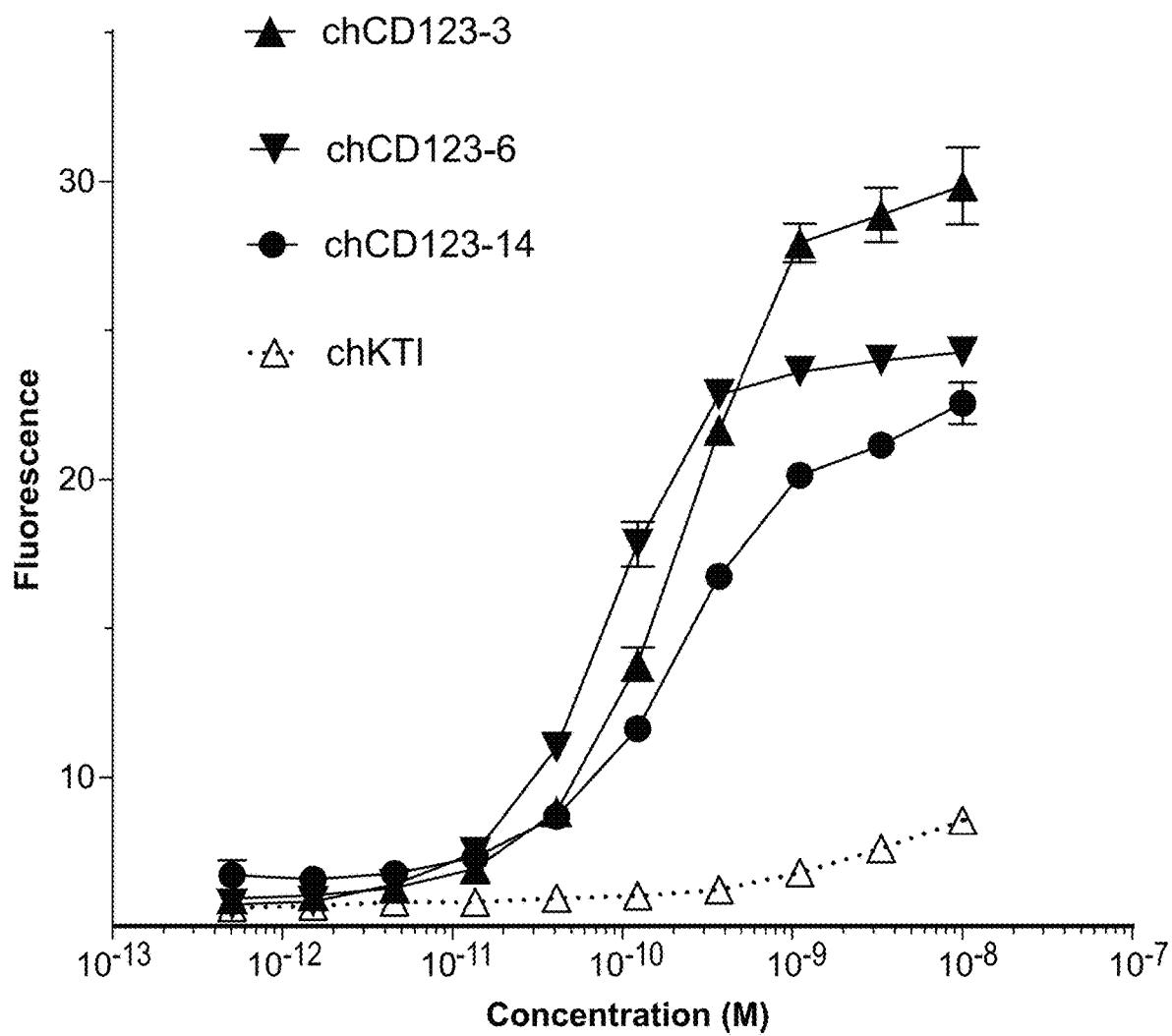

The high affinity of chCD123-3, chCD123-6, and chCD123-14 to AML cells was confirmed using another CD123-positive acute myeloid leukemia cell line, MOLM-13. Flow cytometry binding assays were carried out and analyzed as described above. FIG. 5B depicts the dose-response curves for each antibody. The values for the apparent dissociation constant ($K_d$) of chCD123-3, chCD123-6, and chCD123-14 were 0.2 nM, 0.08 nM, and 0.2 nM, respectively. Only marginal binding was observed for chimeric isotype control IgG (chKTI antibody) at the highest concentration tested (10 nM).

Thus, chCD123-3, chCD123-6, and chCD123-14 retain the high affinity of their murine counterparts.

Figure 6:
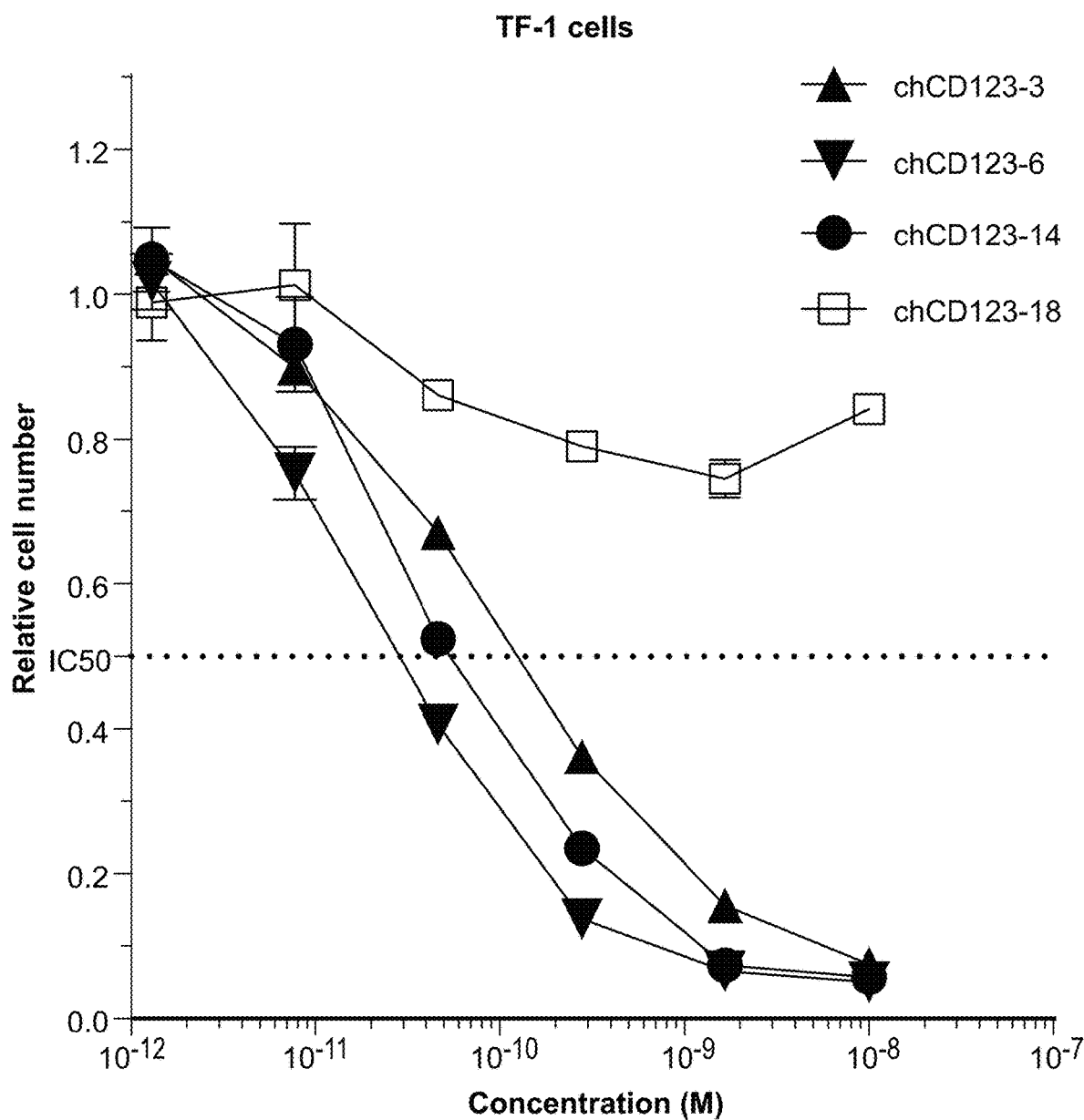
FIG. 6 shows that the chimeric chCD123-3, -6, and -14 anti-CD-123 antibodies retain functional activity of their murine counterparts, as evidenced by their ability to inhibit IL-3 dependent proliferation of TF-1 cells. A non-functional chimeric anti-CD123 antibody (chCD123-18) that binds CD123 but does not inhibit IL-3-dependent proliferation of TF-1 cells was included as negative control.

Functional Activity of Chimeric Antibodies chCD123-3, chCD123-6, and chCD123-14 and a non-functional anti-CD123 antibody, used as a negative control, were assayed for their ability to inhibit IL3-dependent proliferation of TF-1 cells. The assays were carried out and analyzed as described in Example 4. The treatment with chCD123-3, chCD123-6, and chCD123-14 reduced the relative cell number in a dose-dependent manner with the $IC_{50}$ values of 0.1 nM, 0.03, and 0.05 nM, respectively (FIG. 6). The control non-functional antibody did not affect the cell growth. Therefore, chCD123-3, chCD123-6, and chCD123-14 retained the functional activity of their murine counterparts.

Example 7 Binding Affinity of Humanized Anti-CD123 Antibodies

The binding affinity of the exemplary humanized anti-CD123 antibodies, huCD123-6Gv4.7S2 and huCD123-6Gv4.7S3, to HNT-34 cells was compared to that of their murine and chimeric counterparts, muCD123-6 and chCD123-6, respectively. The 7G3 antibody and a chimeric isotype control IgG (chKTI) were tested in parallel. Flow cytometry binding assays were carried out and analyzed as described in Example 5. FIG. 7A depicts the dose-response curves for each antibody. These data show that humanization did not affect the binding affinity of the antibody as the $K_d$ for huCD123-6Gv4.7S2, huCD123-6Gv4.7S3, chCD123-6, and muCD123-6 are approximately 0.06 nM. The apparent $K_d$ for the 7G3 antibody was significantly higher, approximately 2 nM. The chKTI antibody did not bind to the cells at the tested concentrations. Therefore, both huCD123-6Gv4.7 clones retain the high affinity of the murine and chimeric counterparts and have a higher affinity (e.g., at least about 30-fold higher) than the 7G3 antibody to CD123-expressing cells.

Figure 7C:
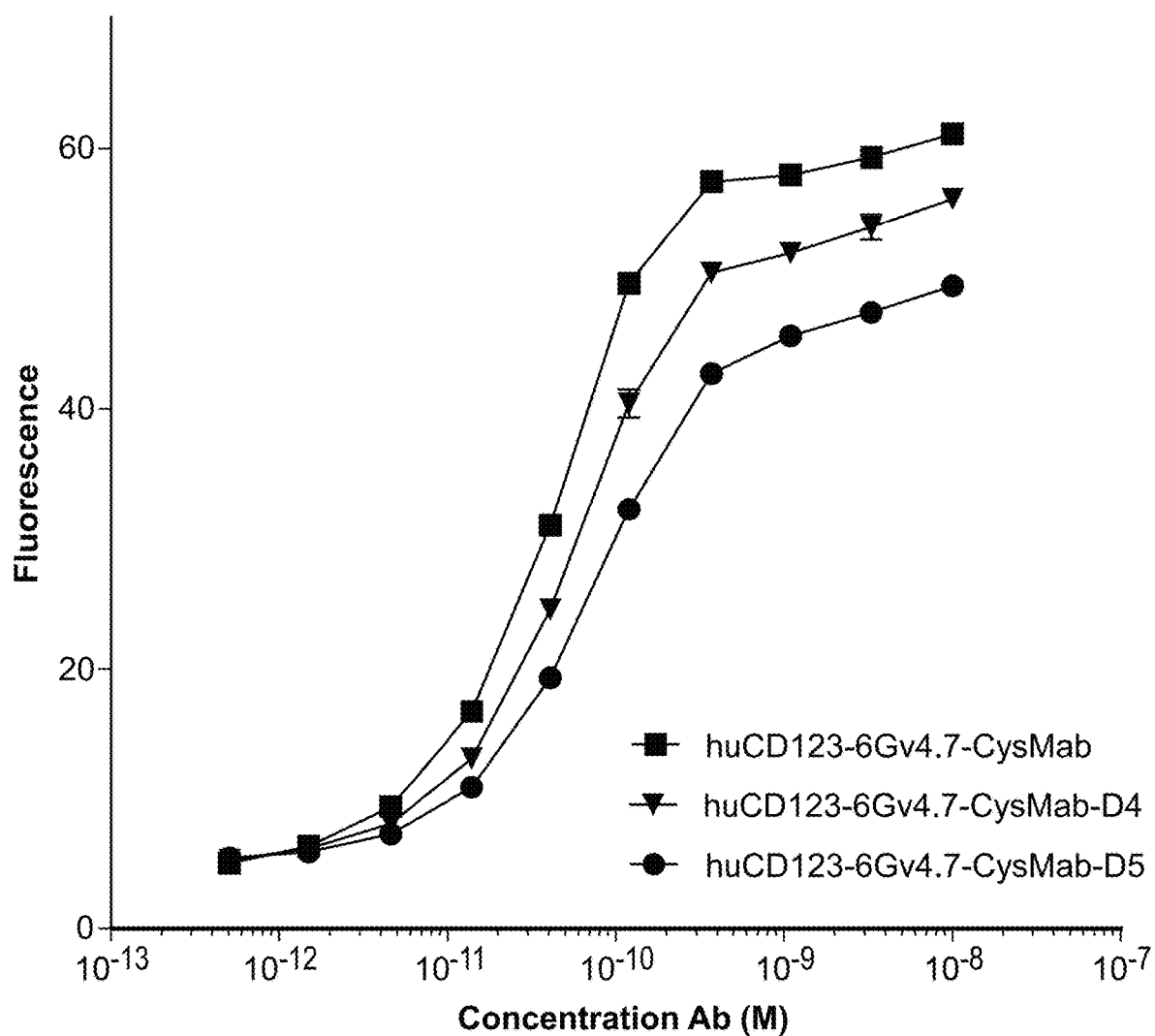

Similarly, the binding affinities of the ADC conjugates of the exemplary humanized huCD123-6Gv4.7 antibody were assayed using HNT-34 cells, in comparison to that of the unconjugated huCD123-6Gv4.7. Flow cytometry binding assays were carried out and analyzed as described in Example 5 using secondary PE-conjugated goat-anti-human antibodies. FIGS. 7B and 7C depict the dose-response curves for each antibody and the corresponding conjugates. The data show that conjugation only moderately affected the binding affinities of these antibodies.

Functional Activity of Humanized Anti-CD123 Antibodies

The functional activity (the ability to inhibit IL3-dependent proliferation of TF-1 cells) of the exemplary humanized anti-CD123 antibodies, huCD123-6Gv4.7S2 and huCD123-6Gv4.7S3, was compared to that of their chimeric counterpart, the chCD123-6 antibody. The 7G3 antibody was tested in parallel. The assays were carried out and analyzed as described in Example 4.

Figure 8A:
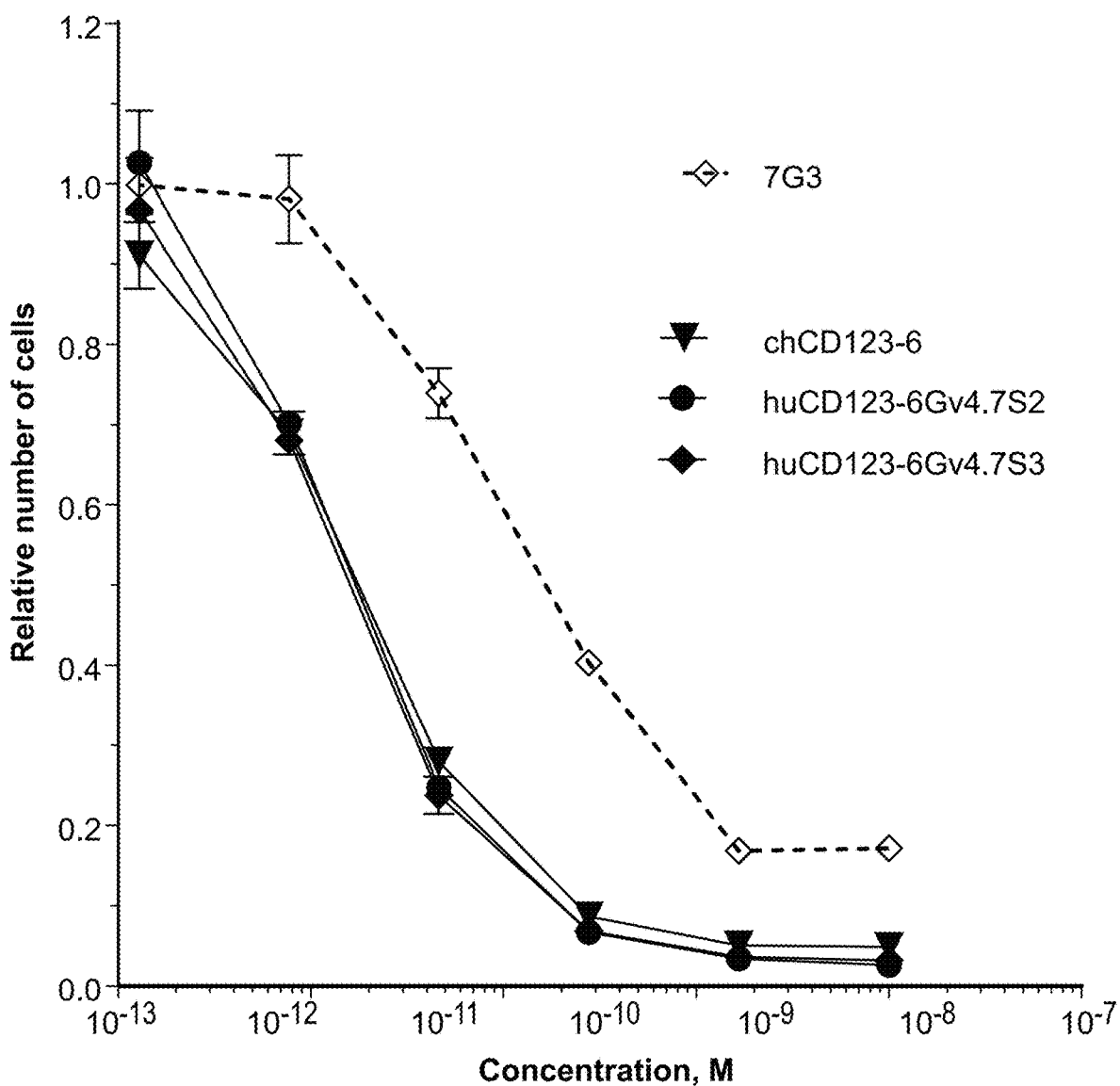
FIG. 8A shows that the chimeric (chCD123-6) and CDR-grafted (huCD123-6Gv4.7S2 and huCD123-6Gv4.7S3) huCD123-6 antibodies inhibit IL-3 dependent proliferation of TF-1 cells better than the 7G3 antibodies. The inhibition is IL-3 dependent, as these antibodies had no inhibitory effect when the cells were grown in the presence of GM-CSF (FIG. 8B).

The treatment with huCD123-6Gv4.7S2, huCD123-6Gv4.7S3, and chCD123-6 inhibited IL-3 dependent proliferation similarly: the proliferation was completely inhibited at 1 nM with an $IC_{50}$ of 0.02 nM (FIG. 8A). However, the treatment with 7G3 did not have such a profound effect on the proliferation of the cells: the antibody $IC_{50}$ was 0.2 nM and it was not able to inhibit the cell proliferation completely, but only reduced the cell number to 18% at the highest concentration (10 nM).

Figure 8B:
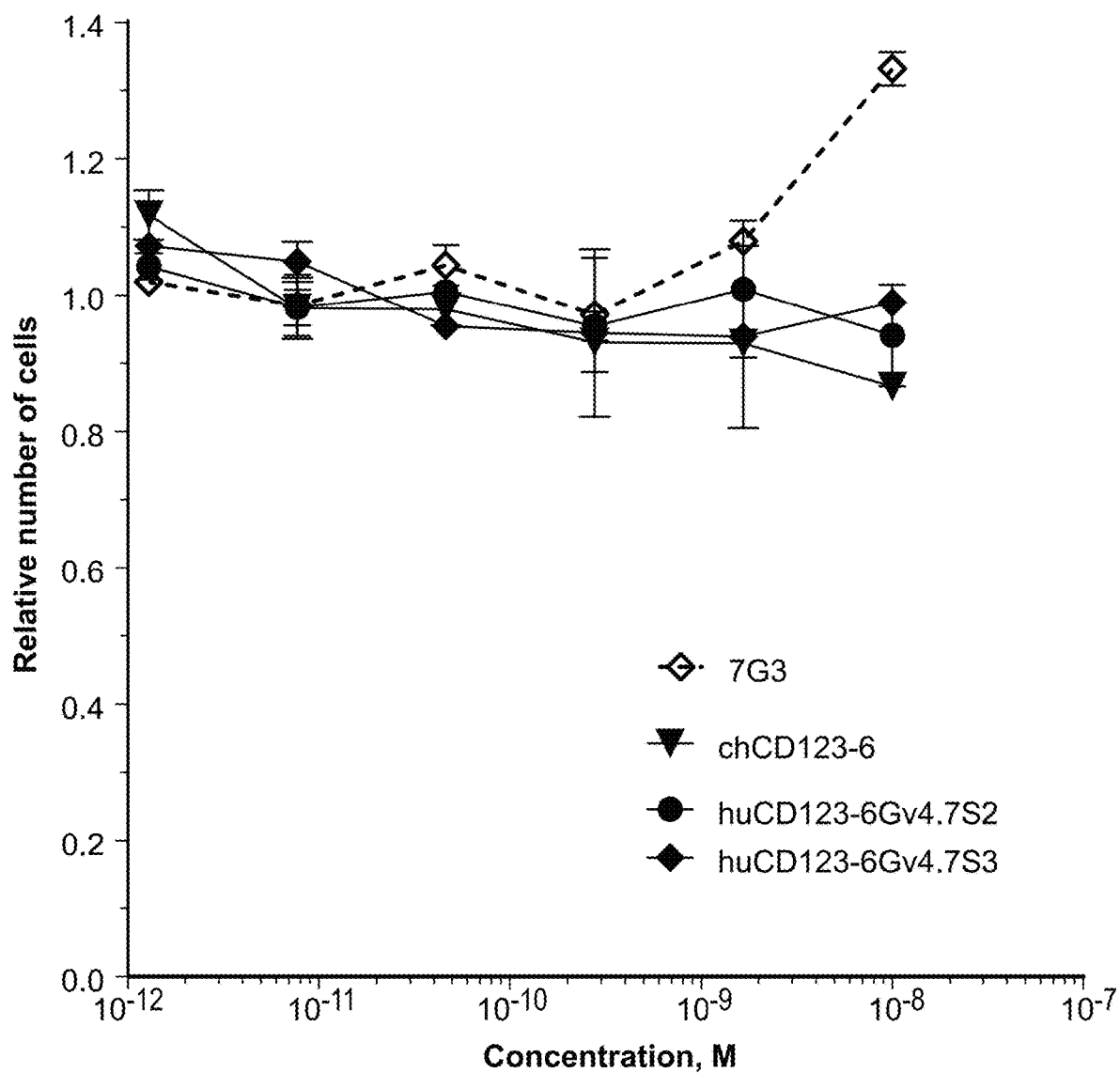

The inhibition of TF-1 cell proliferation by huCD123-6Gv4.7S2, huCD123-6Gv4.7S3, chCD123-6, and 7G3 was IL-3 dependent, as these antibodies had no inhibitory effect when the cells were grown in the presence of another growth factor GM-CSF (FIG. 8B).

Therefore, huCD123-6Gv4.7 retains the functional activity of its murine and chimeric counterparts, and is significantly more active than the 7G3 antibody in inhibiting IL-3 dependent proliferation.

Example 8 Epitope Mapping

The CD123 antigen, IL-3 receptor chain a (IL-3Rα), is composed of 378 amino acids, containing a 306-amino acid extracellular domain involved in IL-3 binding, a 20-amino acid transmembrane domain, and a short cytoplasmic tail of 52 amino acids. The extracellular domain can be further divided into an N-terminal domain (NTD) comprising a region from the threonine at position 19 of the mature protein (e.g., post signal peptide cleavage), to the serine at position 100, and the cytokine recognition motif (CRM) composed of two discrete folding domains: domain 2 (amino acids 101-204) and domain 3 (amino acids 205-306). Epitopes for the certain anti-CD123 antibodies described herein were mapped by engineering chimeric proteins utilizing combinations of the extracellular domain of IL-3Rα and the granulocyte-macrophage colony-stimulating factor receptor a chain (GMRα), which conserves the IL-3Rα topology and shares a common β-subunit that is essential for signaling.

IL-3Rα Variants Cloning and Expression

The extracellular domain of CD123/IL-3Rα (residues 1-306) was expressed as a histidine tagged protein. The protein sequence was codon optimized and synthesized by Life Technologies and cloned in-frame with a 10-Histidine tag in the pABLT mammalian expression vector utilizing EcoRI and HindIII restrictions sites. The extracellular domain of the control GMRα protein (residue 1-325), also comprising an N-terminal domain from the serine at position 25 to the serine at position 114 of the mature protein, and an CRM domain comprising the glycine at position 115 to the valine at position 325, was similarly synthesized and cloned. Then the IL3Ra/GMRα chimeric receptor protein expression vectors were constructed by restriction digests replacing either the N-terminal domain (residues 1-100) or the CRM domain (residues 101-306) of the IL-3Rα molecule with the corresponding sequences of the GMRα molecule. IL3Rα (1-100) encodes IL3Rα residues 1-100 fused to GMRα residues 115-325, and IL3Rα (101-306) encodes GMRα residues 1-114 fused to IL3Rα residues 101-306, as illustrated in FIG. 9A.

IL3-Rα, GMRα, and the two chimeric IL-3Rα Histagged proteins, IL3-Rα (1-100) and IL3-Rα (101-306), were expressed via transient transfection of HEK 293T cells, and purified from the supernatant of the transfected cells using Ni Sepharose excel chromatography (GE healthcare) following manufacturer's instruction.

Antibody Binding to Various IL3Rα Constructs

The chimeric and humanized anti-IL3Rα antibodies were tested in enzyme-linked immunosorbent assay (ELISA) format for binding to the IL-3Rα proteins described above. Briefly, each His-tagged IL-3Rα protein purified by Ni Sepharose excel chromatography was diluted to 1 ng/mL in 50 mM sodium bicarbonate buffer pH 9.6, and 100 μL was added to each well. After a 16 hr incubation at 4° C., the plates were washed with Tris-buffered saline with 0.1% Tween-20 (TBST), then blocked with 200 μL blocking buffer (TBS with 1% BSA). Next, 100 μL of primary antibody, serially diluted in blocking buffer, was added in duplicate to the ELISA wells and incubated at room temperature for 1 hr. The plates were then washed 3 times with TBST before adding 100 μL of anti-human IgG (H+L)-HRP (Jackson ImmunoResearch) to each well. Once again the plates were incubated for 1 hr at room temperature followed by three washes with TB ST. Finally, 100 μL of TMB one component HRP microwell substrate (Surmodics) was added to each well and incubated for 5 min. The reaction was stopped by adding 100 μL stopping solution (Surmodics) and absorbances were read at 450 nm.

Figure 9B:
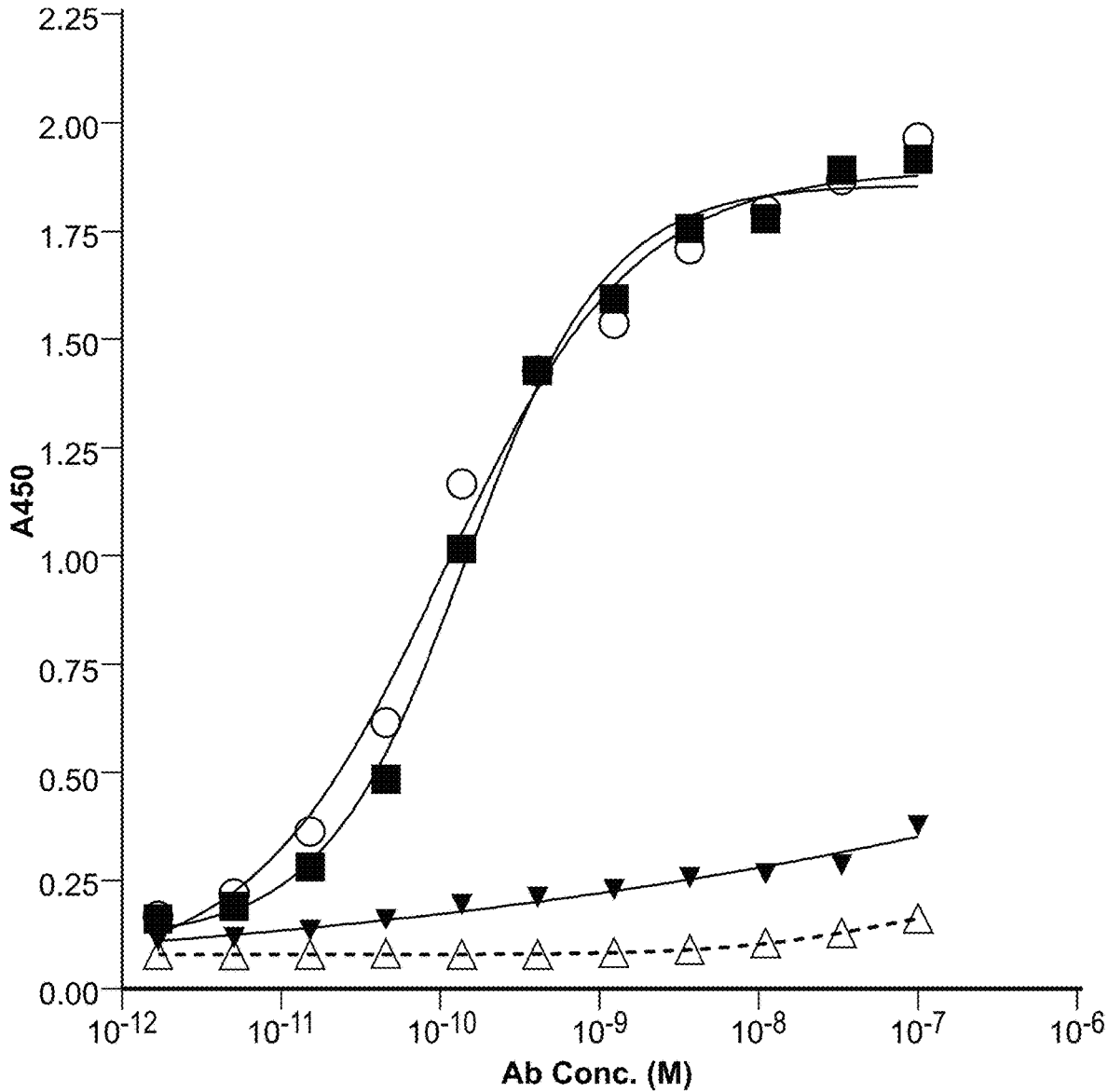
FIG. 9B shows that the CD123-6 antibody binds primarily to the CRM domain of IL-3Rα (residues 101 306).
Figure 9D:
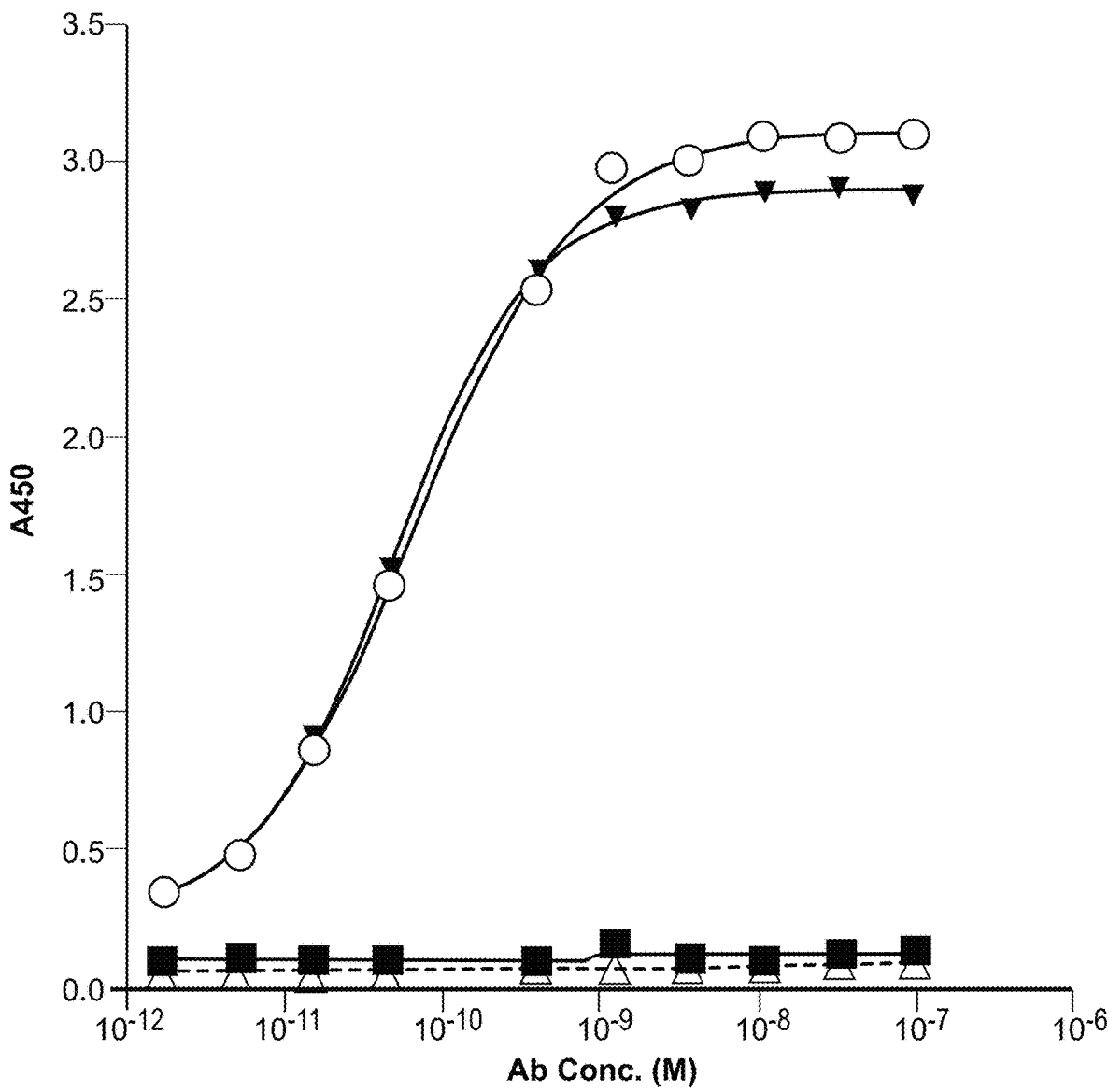
FIG. 9D shows that the CD123-14 antibody binds exclusively to the N-terminal domain of IL-3Rα (residues 1-100).
Figure 9E:
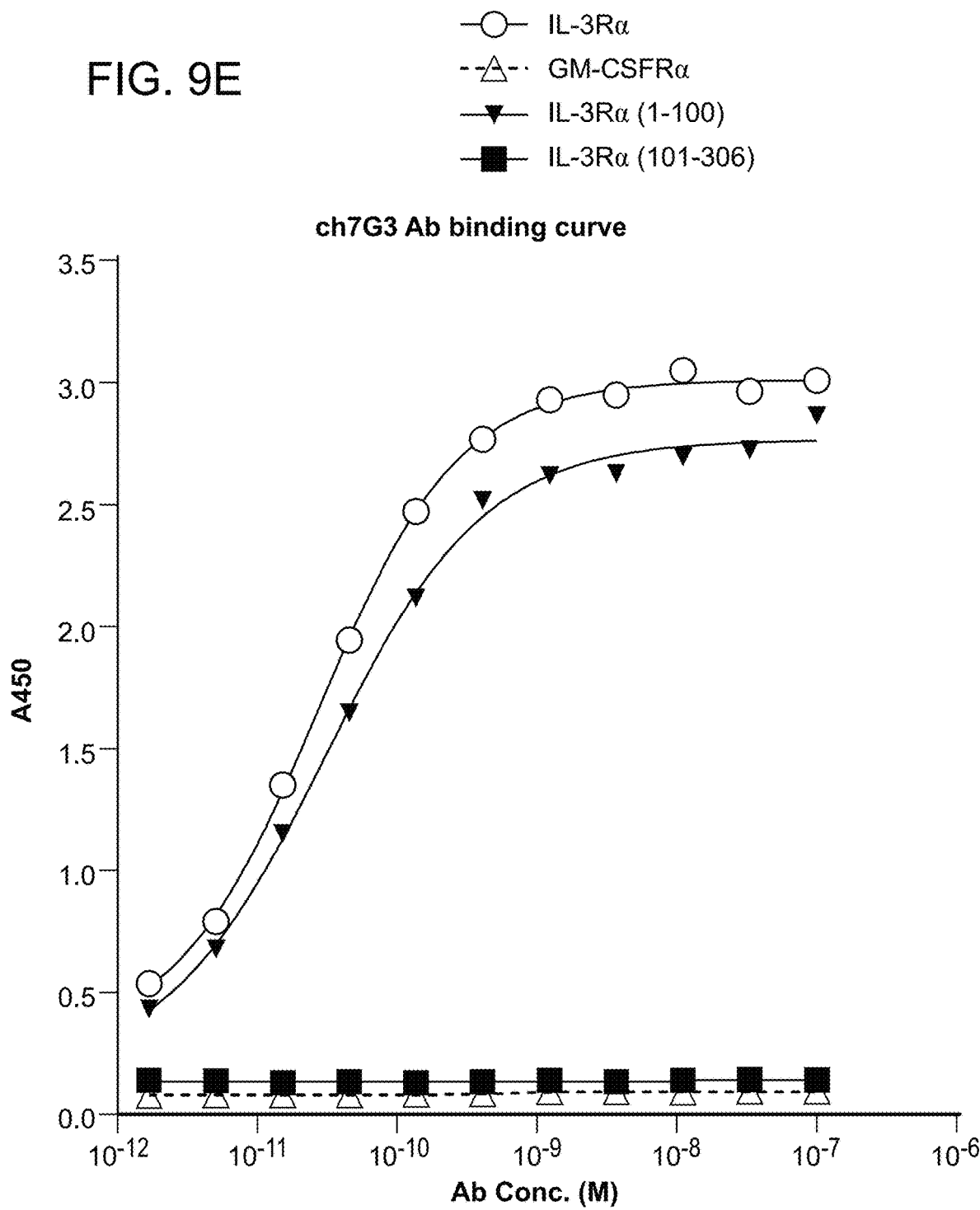
FIG. 9E shows that the 7G3 antibody binds exclusively to the N-terminal domain of IL-3Rα (residues 1-100).
Figure 9G:
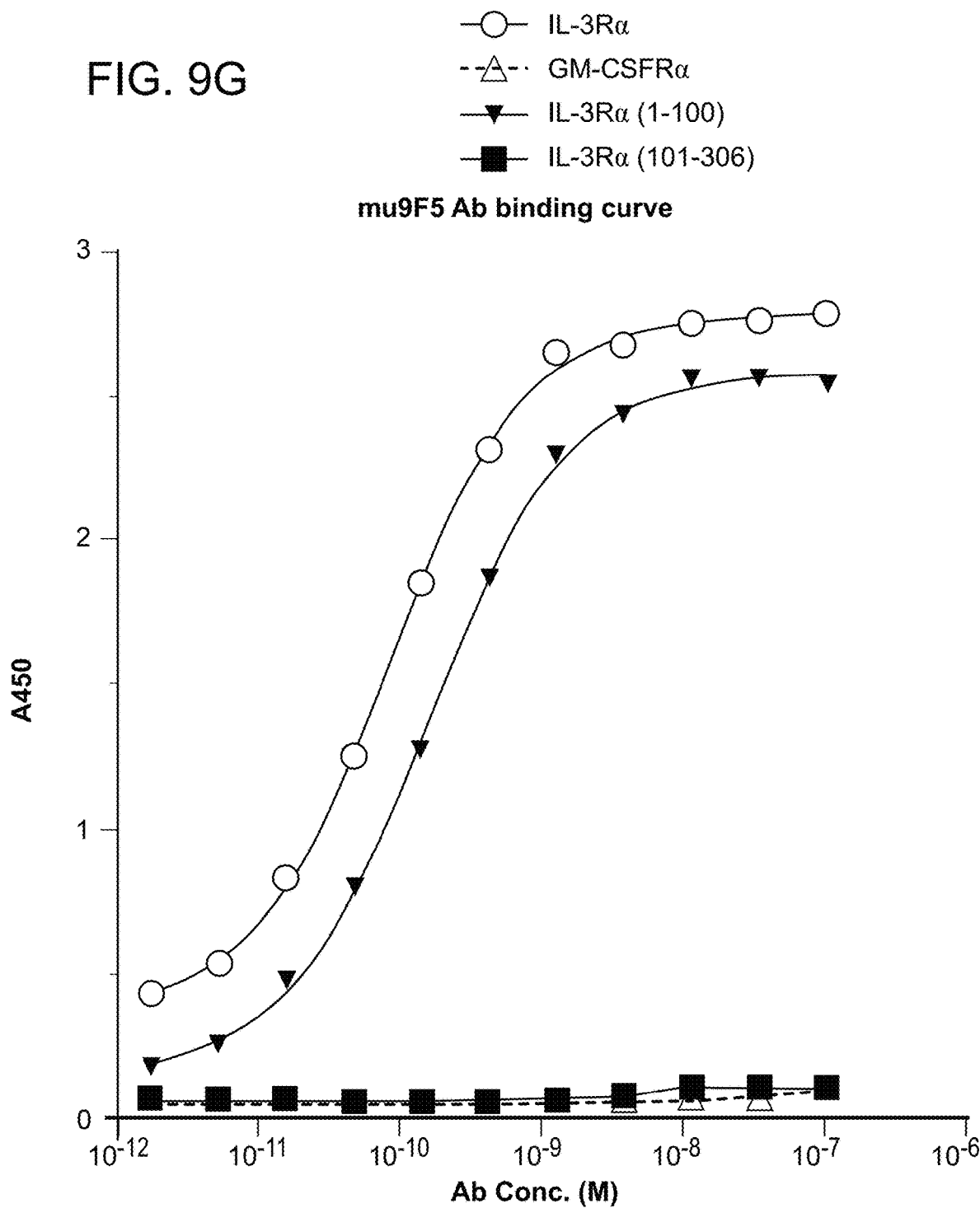
FIG. 9G shows that the 9F5 antibody binds exclusively to the N-terminal domain of IL-3Rα (residues 1-100).

Binding of the CD123 antibodies to the chimeric IL-3Rα proteins was evaluated in comparison to the wild type IL-3Rα. FIG. 9B demonstrates that the huCD123-6 antibody binds to both IL-3Rα and IL-3Rα (101-306) with similar sub-nanomolar affinities. Conversely, the huCD123-6 antibody does not bind the GMRα construct and binding is all but eliminated for the chimeric protein IL-3Rα (1-100) construct. These results indicate that huCD123-6 antibody binds primarily to the CRM domain, with perhaps only minimal contribution from the N-terminal domain of IL-3Rα. Similarly, the chCD123-3 antibody binds primarily to the IL-3Rα CRM domain, albeit with a reduced binding affinity compared to the wild type IL-3Rα (FIG. 9C). The reduction in binding affinity to chimeric receptor protein IL-3Rα (101-306) suggests a possible involvement of the N-terminal domain of the IL-3Rα in CD123-3 antibody binding. The chCD123-14 antibody however, does not recognize the chimeric receptor IL-3Rα (101-306) (FIG. 9D); rather, it binds to both IL-3Rα and IL-3Rα (1-101) with equivalent affinity. These results demonstrate that the chCD123-14 antibody binds exclusively to N-terminal domain of IL-3Rα. In comparison, the 7G3 antibody along with the two other commercially available antibodies, 6H6 and 9F5, also bind to the IL-3Rα N-terminal domain and wild-type IL-3Rα constructs, but do not recognize the CRM domain of IL3Rα (FIGS. 9E, 9F, and 9G, respectively). In summary, these data demonstrate that the epitopes of the CD123-6 and CD123-3 antibodies are located primarily within the CRM domain of the IL-3Rα, and are distinct from the 7G3 antibody epitope, which is restricted to the N-terminal domain of IL-3Rα. The CD123-14 antibody also binds an epitope confined within the N-terminal domain of IL-3Rα.

Example 9 Preparation of Lysine-Linked DM1 and IGN Conjugates of the huCD123-6 Antibody a. Preparation of huCD123Gv4.7S3-sulfo-SPDB-D1

A reaction containing 2.0 mg/mL CD123-6G4.7S3 antibody and 3.5 molar equivalents of sulfo-SPDB-D1 in situ mixture by linker in 15 mM HEPES (4-(2-hydroxyethyl)-1-piperazine ethanesulfonic acid) pH 8.5 buffer and 15% v/v DMA (N,N Dimethylacetamide) cosolvent was allowed to conjugate for 3-4 hours at 25° C. The in situ mixture was prepared by reacting 3.0 mM sulfo-SPDB linker with 3.9 mM of sulfonated compound D1 in DMA for 5 hours at 25° C. in the presence of 20 mM N,N Diisopropylethyl amine (DIPEA).

Post-reaction, the conjugate was purified and buffer exchanged into 20 mM histidine, 50 mM sodium chloride, 8.5% w/v sucrose, 0.01% Tween-20, 50 μM sodium bisulfite pH 6.2 formulation buffer using NAP desalting columns (Illustra Sephadex G-25 DNA Grade, GE Healthcare). Dialysis was performed in the same buffer for 4 hours at room temperature and then overnight at 4° C. utilizing Slide-a-Lyzer dialysis cassettes (ThermoScientific 10,000 MWCO).

The purified conjugate was found to have a final protein concentration of 1.2 mg/ml and an average of 2.9 molecules of compound D1 linked per antibody (by UV Vis using molar extinction coefficients $\varepsilon_{330\ nm}=15,484$ cm$^{-1}$M$^{-1}$ and $\varepsilon_{280\ nm}=30,115$ cm$^{-1}$M$^{-1}$ for compound D1, and $\varepsilon_{280\ nm}=207,360$ cm$^{-1}$M$^{-1}$ for huCD123-6G4.7S3 antibody); 94.3% monomer (by size exclusion chromatography); and <2% unconjugated compound D1 (UPLC Dual column, reverse-phase HPLC analysis).

b. Preparation of huCD123-6Gv4.7S3-D2

A reaction containing 2.0 mg/mL huCD123-6Gv4.7S3 antibody and 5.0 molar equivalents of compound D2 (pretreated with 5-fold excess of sodium bisulfite in 90:10 DMA:50 mM succinate pH 5.5 for 4 hours at 25° C.) in 15 mM HEPES (4-(2-hydroxyethyl)-1-piperazine ethanesulfonic acid) pH 8.5 buffer and 10% v/v DMA (N,N-Dimethylacetamide) cosolvent was incubated for 4 hours at 25° C.

Post-reaction, the conjugate was purified and buffer exchanged into 20 mM histidine, 50 mM sodium chloride, 8.5% w/v sucrose, 0.01% Tween-20, 50 μM sodium bisulfite pH 6.2 formulation buffer using NAP desalting columns (Illustra Sephadex G-25 DNA Grade, GE Healthcare). Dialysis was performed in the same buffer for 4 hours at room temperature and then overnight at 4° C. utilizing Slide-a-Lyzer dialysis cassettes (ThermoScientific 10,000 MWCO).

The purified conjugate was found to have a final protein concentration of 1.2 mg/ml and an average of 2.9 molecules of compound D2 linked per antibody (by UV Vis using molar extinction coefficients $\varepsilon_{330\ nm}=15,484$ cm$^{-1}$M$^{-1}$ and $\varepsilon_{280\ nm}=30,115$ cm$^{-1}$M$^{-1}$ for compound D2, and $\varepsilon_{280\ nm}=207,360$ cm$^{-1}$M$^{-1}$ for huCD123-6Gv4.7S3 antibody); 99.3% monomer (by size exclusion chromatography); and <2% unconjugated compound D2 (UPLC Dual column, reverse-phase HPLC analysis).

c. Preparation of huCD123-6Gv1.1-sulfo-SPDB-DGN462

NHS-sulfo-SPDB-sDGN462 was formed in situ by incubating 1.5 mM sulfo-SPDB linker, 1.95 mM sulfonated DGN462 (sDGN462) in DMA containing 10 mM DIPEA (N,N-diisopropylethylamine) for 20 min before adding 0.9 mM MPA (3-Maleimidopropionic Acid) to quench unreacted IGN thiol for 15 min at 25° C. A reaction containing 2.5 mg/mL huCD123-6Gv1.1 antibody and 7.5 molar equivalents of the resulting NHS-sulfo-SPDB-DGN462 in 15 mM HEPES (4-(2-hydroxyethyl)-1-piperazine ethanesulfonic acid) pH 8.5 buffer and 15% v/v DMA cosolvent was incubated overnight at 25° C.

Post-reaction, the conjugate was purified into 20 mM Histidine, 50 mM NaCl, 8.5% sucrose, 0.01% Tween-20, 50 μM sodium bisulfite pH 6.2 formulation buffer using NAP desalting columns (Illustra Sephadex G-25 DNA Grade, GE Healthcare). Dialysis was performed in the same buffer overnight at 4° C. utilizing Slide-a-Lyzer dialysis cassettes (ThermoScientific 10,000 MWCO).

The purified conjugate was found to have a final antibody concentration of 0.95 mg/mL and an average of 2.8 DGN462 molecules linked per antibody (by UV-Vis using molar extinction coefficients $\varepsilon_{330\ nm}=15,484$ cm$^{-1}$M$^{-1}$ and $\varepsilon_{280\ nm}=30,115$ cm$^{-1}$M$^{-1}$ for DGN462, and $\varepsilon_{280\ nm}=207,360$ cm$^{-1}$M$^{-1}$ for huCD123-6Gv1.1 antibody); 99.5% monomer (by size exclusion chromatography); and 0.6% unconjugated DGN462 (by acetone precipitation, reverse-phase HPLC analysis).

d. Preparation of huCD123-6Gv1.1-D3

A reaction containing 2.0 mg/mL huCD123-6Gv1.1 antibody and 3.5 molar equivalents D3 (pretreated with 5-fold excess of sodium bisulfite in 90:10 DMA:50 mM succinate pH 5.5 for 4 hours at 25° C.) in 15 mM HEPES (4-(2-hydroxyethyl)-1-piperazine ethanesulfonic acid) pH 8.5 buffer and 10% v/v DMA (N,N-Dimethylacetamide) cosolvent was incubated for 4 hrs at 25° C. Post-reaction, the conjugate was purified and buffer exchanged into 20 mM histidine, 50 mM sodium chloride, 8.5% w/v sucrose, 0.01% Tween-20, 50 μM sodium bisulfite pH 6.2 formulation buffer using NAP desalting columns (Illustra Sephadex G-25 DNA Grade, GE Healthcare). Dialysis was performed in the same buffer for 4 hrs at room temperature and then overnight at 4° C. utilizing Slide-a-Lyzer dialysis cassettes (ThermoScientific 10,000 MWCO).

The purified conjugate was found to have a final protein concentration of 0.9 mg/mL and an average of 3.4 D3 molecules linked per antibody (by UV-Vis using molar extinction coefficients $\varepsilon_{330\ nm}=15,484$ cm$^{-1}$M$^{-1}$ and $\varepsilon_{280\ nm}=30,115$ cm$^{-1}$M$^{-1}$ for D3, and $\varepsilon_{280\ nm}=207,360$ cm$^{-1}$M$^{-1}$ for huCD123-6Gv1.1 antibody); 96% monomer (by size exclusion chromatography); and <1% unconjugated D3 (dual column, reverse-phase HPLC analysis).

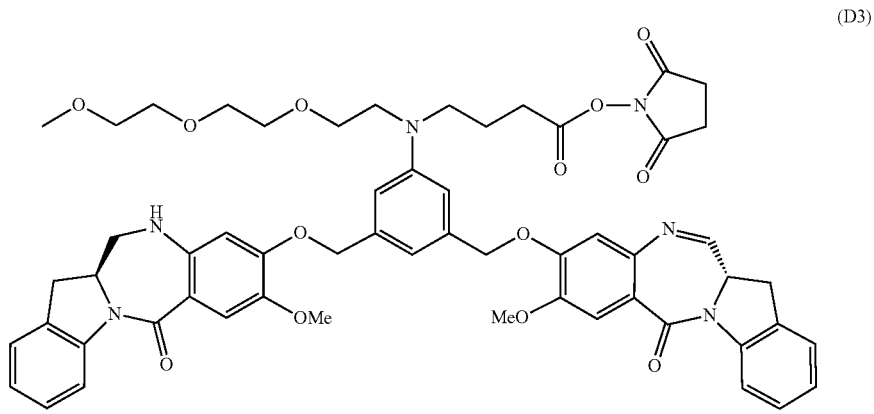 [SMILES: COCCOCCOCCN(CCCC(=O)ON1C(=O)CCC1=O)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

(D3)

e. Preparation of
huCD123-6Rv1.1-CX1-1-maytansinoid Conjugates

Humanized anti-CD123 antibody (resurfaced huCD123-6Rv1.1) was conjugated at lysine residues with maytansinoid payload via triglycyl, CX1-1 linker. A mixture containing 5 mM triglycyl, CX1-1 heterobifunctional linker (bearing N-hydroxysuccinimide and maleimide groups) and 6.5 mM DM1 maytansinoid in N,N-dimethylacetamide (DMA) containing 20 mM N,N-diisopropylethylamine (DIPEA) was incubated for about 20 min at room temperature. Unreacted DM1 was quenched with 2 mM maleimidopropionic acid (MPA) for about 20 min at room temperature before adding the reaction mixture to humanized anti-CD123 antibody (huCD123-6Rv1.1) at 4 mg/mL in 140 mM EPPS buffer, pH 8, containing about 8% DMA, at an excess of about 7.6× or 15×CX1-1-DM1 adduct over antibody. The conjugation reaction mixtures were incubated overnight at 25° C., after which the conjugates were purified and buffer exchanged into 10 mM succinate buffer, pH 5.5, containing 250 mM glycine, 0.5% sucrose, 0.01% Tween 20 using NAP desalting columns (Illustra, Sephadex G-25, GE Healthcare). Dialysis was performed in the above-described succinate buffer overnight at 4° C. utilizing Slide-a-Lyzer dialysis cassettes (Thermo Scientific; 10,000 molecular weight cut-off membrane).

The purified conjugates were found to contain an average of 4.3 and 6.7 maytansinoid molecules linked per antibody (by UV/Vis spectrometry and size-exclusion HPLC, using molar extinction coefficients of $\varepsilon_{252\,nm}$=26350 cm$^{-1}$ M$^{-1}$ and $\varepsilon_{280\,nm}$=5456 cm$^{-1}$M$^{-1}$ for DM1, and $\varepsilon_{280\,nm}$=207076 cm$^{-1}$M$^{-1}$ for huCD123 antibody), 98% monomer (by size exclusion chromatography), and a final protein concentration of 2.1 mg/mL and 1.2 mg/mL, respectively. The levels of unconjugated maytansinoid in purified conjugates were estimated by HPLC to be low (<1%). Mass spectrometry of deglycosylated conjugates indicated linked maytansinoid species.

Example 10 In Vitro Cytotoxicity Assays

The ability of antibody-drug conjugates (ADC) of huCD123-6 to kill cells that express CD123 on their cell surface was measured using in vitro cytotoxicity assays. The cell lines were cultured in culture medium as recommended by the cell supplier (ATCC or DSMZ). The cells, 2,000 to 10,000 in 100 µL of the culture medium, were added to each well of flat bottom 96-well plates. To block Fc receptors on the cell surface, the culture medium was supplemented with 100 nM chKTI antibody (an antibody of the same isotype). Conjugates were diluted into the culture medium using 3-fold dilution series and 100 µL were added per well. To determine the contribution of CD123-independent cytotoxicity, CD123 block (e.g., 100 nM of chCD123-6 antibody) was added to some wells prior to the conjugates. Control wells containing cells and the medium but lacking the conjugates, as well as wells contained medium only, were included in each assay plate. Assays were performed in triplicate for each data point. The plates were incubated at 37° C. in a humidified 6% $CO_2$ incubator for 4 to 7 days. Then the relative number of viable cells in each well was determined using the WST-8 based Cell Counting Kit-8 (Dojindo Molecular Technologies, Inc., Rockville, MD) as described in Example 4. The apparent surviving fraction of cells in each well was calculated by first correcting for the medium background absorbance, and then dividing each value by the average of the values in the control wells (non-treated cells). The surviving fraction of cells was plotted against conjugate concentration in semi-log plots.

Figure 10:
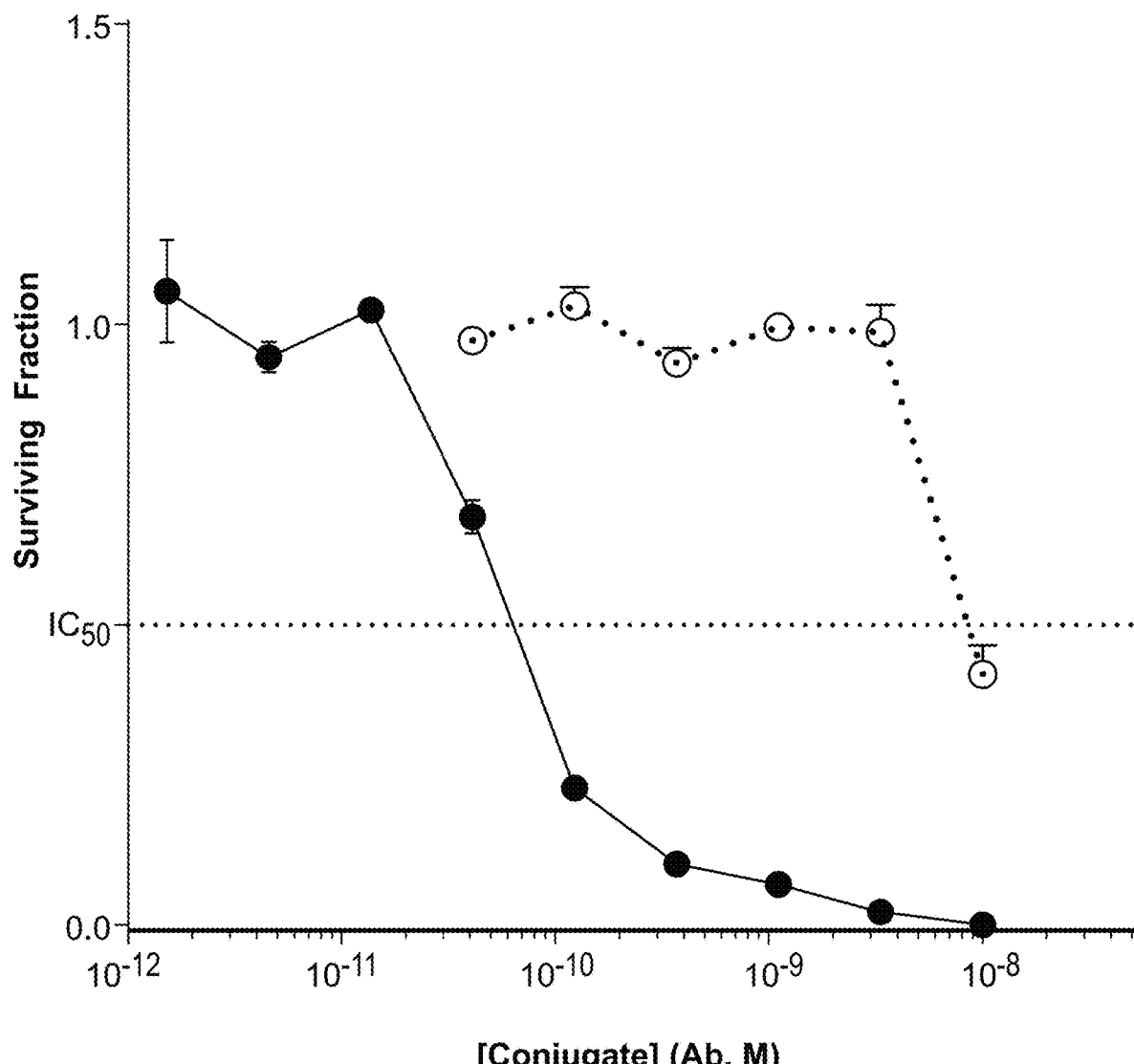
FIG. 10 demonstrates that maytansinoid DM1 conjugate of the resurfaced huCD123-6Rv1.1 antibody, huCD123-6Rv1.1-CX1-1-DM1, exhibits dose-dependent cytotoxicity on the growth factor-independent CD123-expressing AML cell line OCI-AML4. The cytotoxicity is CD123-dependent, as evidenced by the ability of excess unconjugated huCD123-6 antibody (500 nM) to block the cytotoxicity.

The results from a typical cytotoxicity assay are shown in FIG. 10. The AML cell line OCI-AML4 can proliferate without growth factors in culture medium. The cells were treated with the mytansinoid conjugate huCD123-6Rv1.1-CX1-1-DM1. The treatment resulted in dose-dependent cell killing with the $IC_{50}$ value of 0.07 nM. To assess whether the killing was due to CD123 expression, the antigen was blocked by an excess of unconjugated chCD123-6 antibody (500 nM) and potency of the conjugate was tested on the cells. The later treatment did not affect viability of the cells at the concentrations lower than 3 nM and had only moderate effect on the cell viability at 10 nM (the highest concentration tested). Thus, the huCD123-6Rv1.1-CX1-1-DM1 conjugate demonstrates high CD123-dependent cytotoxicity on OCI-AML4 cells.

Figure 11A:
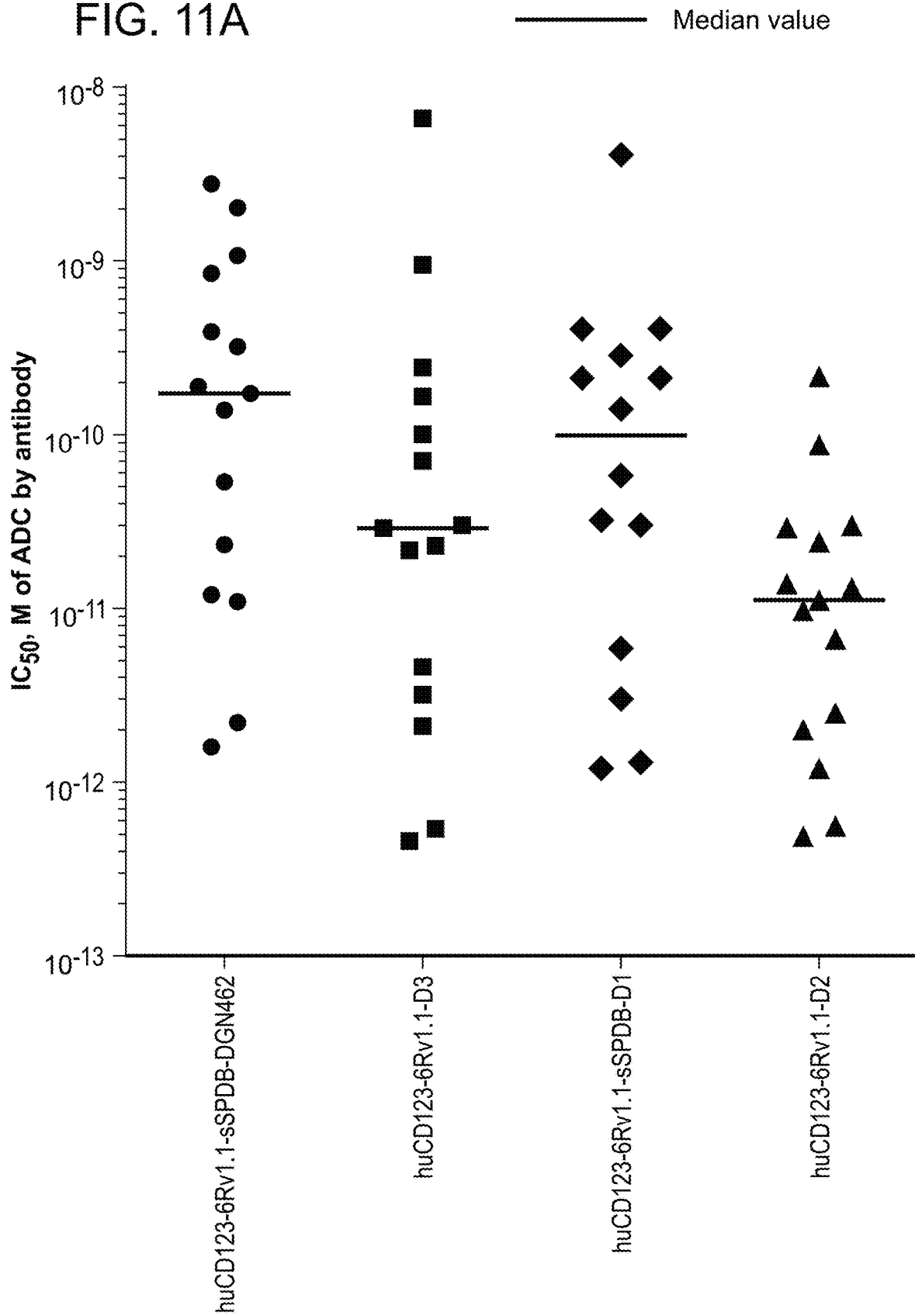
FIG. 11A shows in vitro cytotoxicity of the various resurfaced lysine-linked huCD123-6Rv1.1-IGN conjugates on multiple CD123-positive malignant cell lines of different origin.

Cytotoxicity of the conjugates of the huCD123-6 antibody linked with other cytotoxic agents (DGN462, D3, D1, and D2) via lysines was also tested in vitro. Fifteen CD123-positive cell lines of different origin (AML, B-ALL, CML and NHL) were used in the study (table immediately below). The majority of the cell lines were derived from patients carrying a malignancy with at least one negative prognostic factor (e.g., overexpression of P-glycoprotein, overexpression of EVI1, p53 alterations, DNMT3A mutation, FLT3 internal tandem duplication). The conjugates demonstrated high potency on these cell lines with $IC_{50}$ values ranging from sub-pM to low nM (table immediately below, FIG. 11A).

In vitro cytotoxicity of the various lysine-linked huCD123-6-IGN conjugates on CD123-positive cell lines of different origin

| Cell line name | Origin | Negative prognostic factor | $IC_{50}$, M | | | |
|---|---|---|---|---|---|---|
| | | | DGN462 ADC | D3 ADC | D2 ADC | D1 ADC |
| THP1 | AML | p53 deletion | 1.9E−10 | 3.0E−11 | 6.7E−12 | 5.8E−11 |
| SHI-1 | AML | p53 gene alterations | 1.7E−10 | 2.9E−11 | 1.3E−11 | 3.2E−11 |
| KO52 | AML | p53 mutant, Pgp overexpression | 3.9E−10 | 2.4E−10 | 1.4E−11 | 4.1E−10 |
| KASUMI-3 | AML | EVI1 and Pgp overexpression | 2.8E−09 | 2.3E−11 | 9.8E−12 | 1.4E−10 |
| KG-1 | AML | p53 mutant, Pgp overexpression | 8.5E−10 | 6.6E−09 | 2.2E−10 | 4.1E−09 |
| OCI-AML2 | AML | DNMT3A mutation | 1.4E−10 | 1.0E−10 | 8.8E−11 | 2.1E−10 |
| HNT-34 | AML | MECOM (EVI1) overexpression | 2.3E−11 | 3.2E−12 | 2.0E−12 | 5.9E−12 |

-continued

In vitro cytotoxicity of the various lysine-linked huCD123-6-IGN conjugates on CD123-positive cell lines of different origin

| Cell line name | Origin | Negative prognostic factor | IC$_{50}$, M | | | |
|---|---|---|---|---|---|---|
| | | | DGN462 ADC | D3 ADC | D2 ADC | D1 ADC |
| MV4-11 | AML | FLT3 internal tadem duplication | 1.6E−12 | 5.4E−13 | 5.6E−13 | 1.3E−12 |
| MOLM-13 | AML | FLT3 internal tadem duplication | 2.2E−12 | 4.6E−13 | 4.9E−13 | 1.2E−12 |
| EOL-1 | AML | | 9.0E−12 | 3.3E−12 | 2.5E−12 | 4.7E−12 |
| MOLM-1 | CML | EVI1 and Pgp overexpression | 1.1E−09 | 7.1E−11 | 2.9E−11 | 2.1E−10 |
| KOPN8 | B-ALL | | 5.3E−11 | 2.2E−11 | 1.1E−11 | 3.0E−11 |
| JM-1 | B-ALL | | 3.2E−10 | 1.7E−10 | 2.4E−11 | 4.1E−10 |
| KCL-22 | CML | | 2.0E−09 | 9.5E−10 | 3.0E−11 | 2.9E−10 |
| Granta519 | NHL | | 1.2E−11 | 2.1E−12 | 1.2E−12 | |

The above data seems to suggest that the B-ALL cell lines (KOPN8 and JM-1) are very sensitive to the IGN compounds. To further validate this finding, cytotoxicity of the conjugates of the huCD123-6Gv4.7 antibody linked with D1 or D2, via lysines or cysteines, was tested using the same B-ALL cell lines, KOPN8 and JM-1, plus an additional B-ALL cell line "380 cells." Negative controls using conjugates with an antibody that does not bind to these B-ALL cell lines—KTI—were included in the assays. The results in FIG. 11B confirmed the above finding.

The above table also shows that the huCD123-IGN compounds are highly active against the various AML cell lines. Representative data using Lys- and Cys-linked IGN compounds are shown in FIG. 11C. Consistent with the data shown in FIG. 11C, additional data (shown in the table below and FIG. 21) on cytotoxicity of the Cys-linked conjugate (huCD123-6Gv4.7-CysMab-D5) demonstrate that the conjugate is highly potent against various CD123-positive AML cell lines, including those with poor prognostic factors.

| Cell line | Poor prognostic factor | huCD123-CysMab-D$_5$ IC$_{50}$ pMol | Fold-specificity IC$_{50}$ control ADC/IC$_{50}$ huCD123-CysMab-D5 |
|---|---|---|---|
| CD123 negative cell lines | | | |
| Namalwa | | 10000 | 1 |
| K562 | | 8000 | 1 |
| CD123 positive AML cell lines | | | |
| SKM-1 | P53 | 7 | 57 |
| KO52 | | 20 | 100 |
| EOL-1 | | 2 | 1000 |
| UCSD-AML1 | EVI OX | 1 | 400 |
| KG-1 | P53, MDR1 | 60 | 95 |
| THP-1 | P53 | 30 | 167 |
| SHI-1 | P53 | 6 | >3.333 |
| MOLM-1 | MDR1 and EVI1 OX | 120 | >167 |
| Molm-13 | FLT/ITD | 0.5 | 2000 |
| MV4-11 | FLT/ITD | 1 | 2000 |
| KASUMI-3 | P53 and MDR1 | 3 | 100 |
| HNT-34 | EVI1 OX | 1 | 1100 |

Figure 11D:
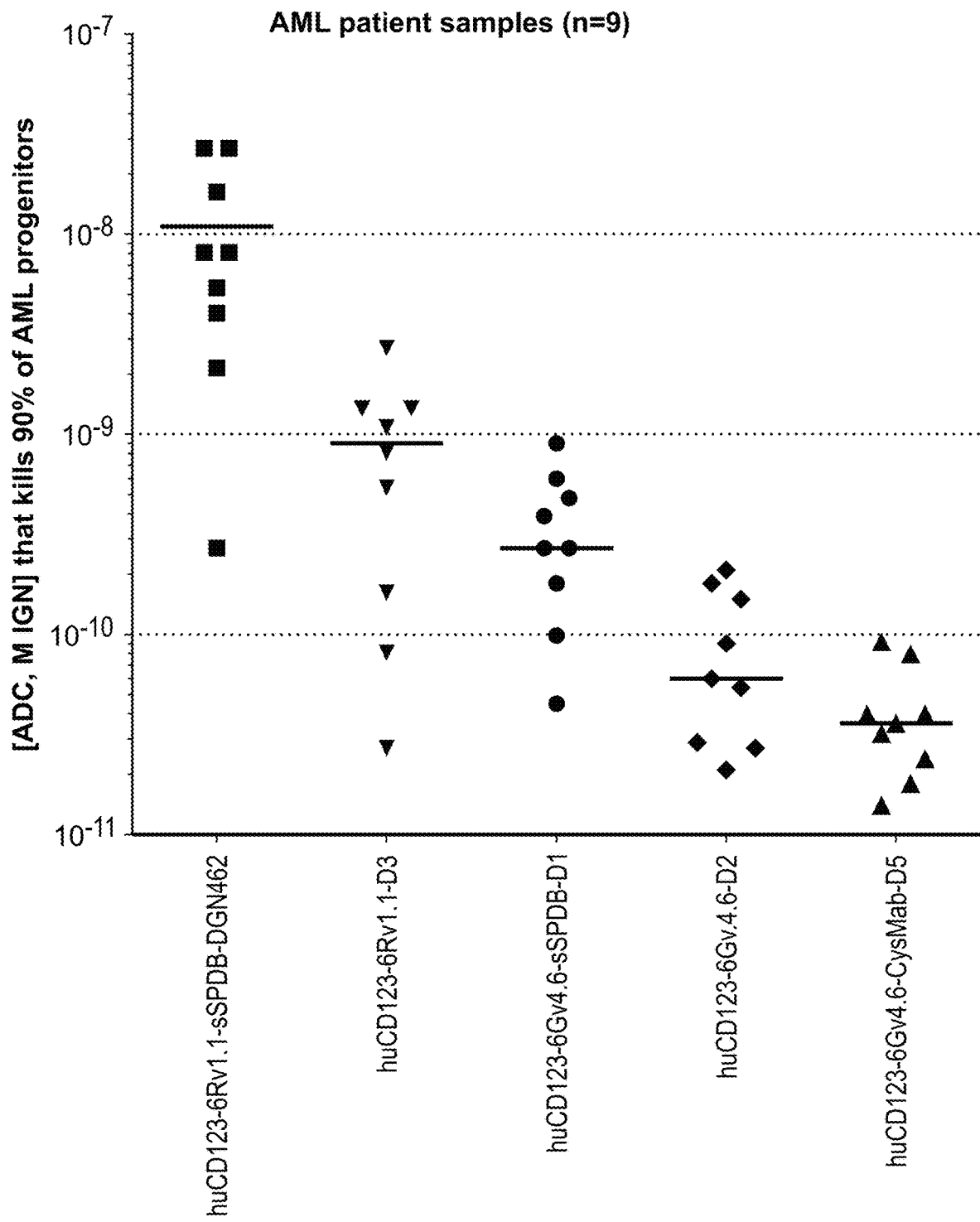
FIG. 11D shows that nearly all of the various Lys- or Cys-linked CD123-IGN conjugates of the invention kill 90% of the AML progenitor cells from 9 AML patient samples at nM or sub-nM concentrations.

Interestingly, preliminary data suggests that Cys-linked D5 conjugate appears to be particularly potent on AML progenitor cells, even when compared to potent conjugates of Lys-linked D2 or Lys-linked D1. See FIG. 11D, in which 9 AML patient samples were used to test the potency of the various IGN conjugates of the invention.

Figure 18:
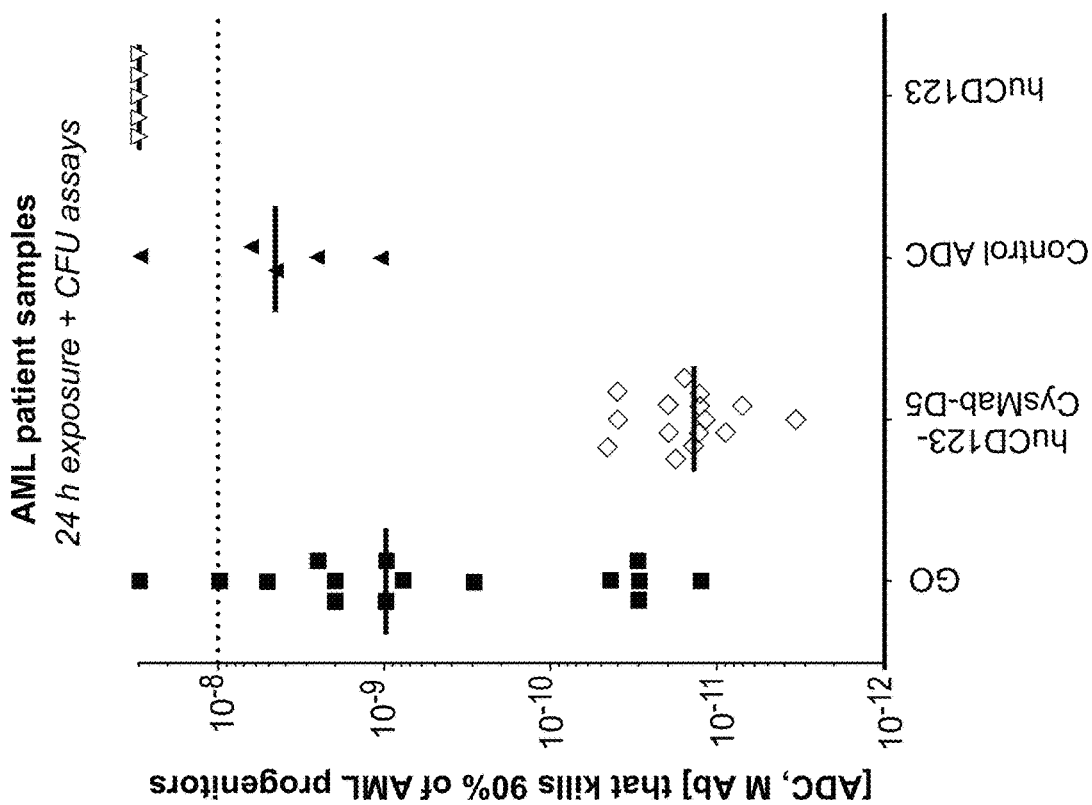
FIG. 18 shows that the Cys-linked huCD123-6Gv4.7-CysMab-D5 conjugate has higher activity than gemtuzumab ozogamicin (GO) (also known as Mylotarg) in unselected AML patient samples.

Additional in vitro cytotoxicity studies show that the Cys-linked D5 conjugate has 74 fold higher activity than Mylotarg in unselected AML patient samples. See FIG. 18.

Figure 11E:
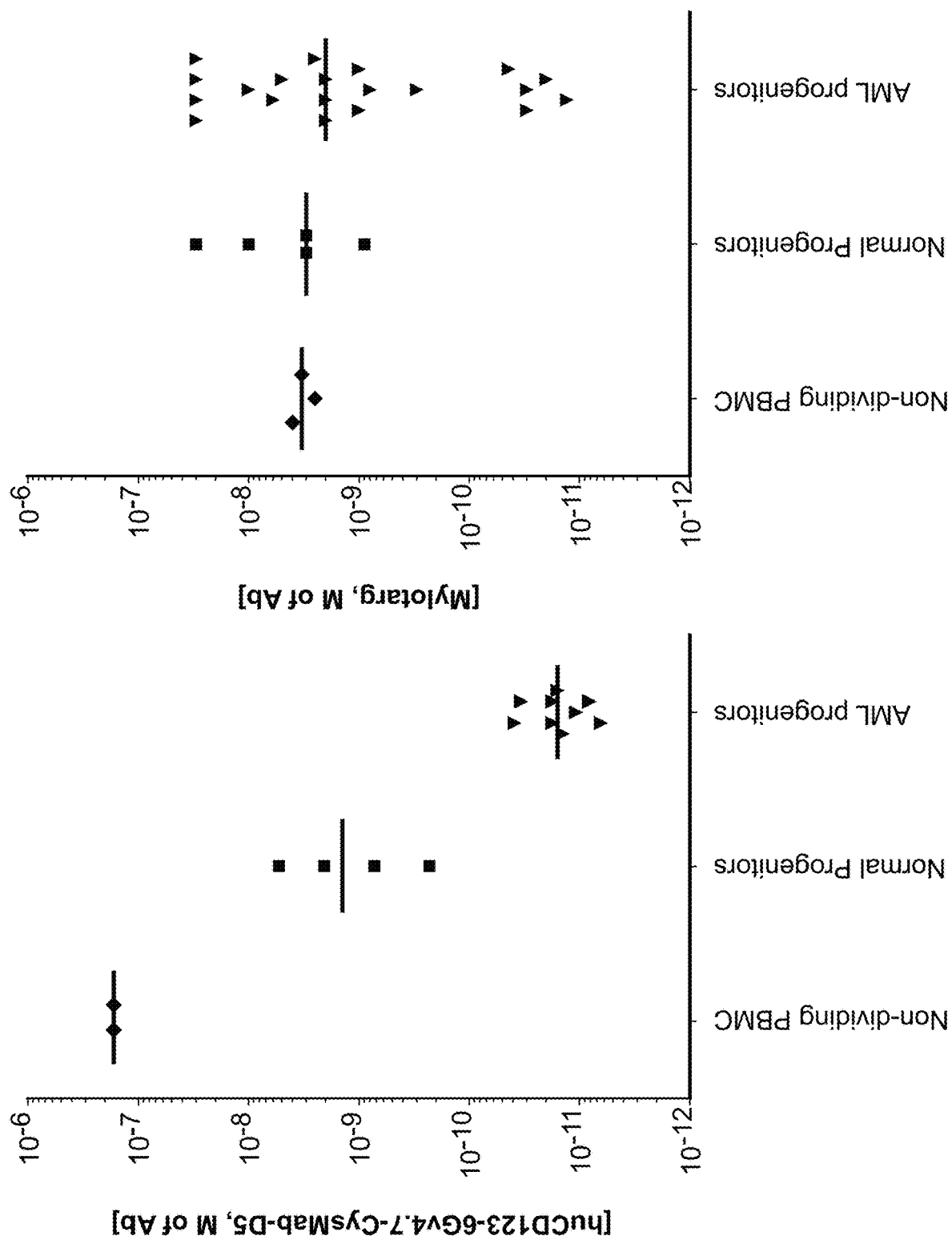
FIG. 11E shows that the Cys-linked huCD123-6Gv4.7-CysMab-D5 conjugate kills normal blood cells at concentrations that are >100-fold higher than those needed to kill AML progenitors. In comparison, Mylotarg does not exhibit such preferential killing effect.
Figure 19:
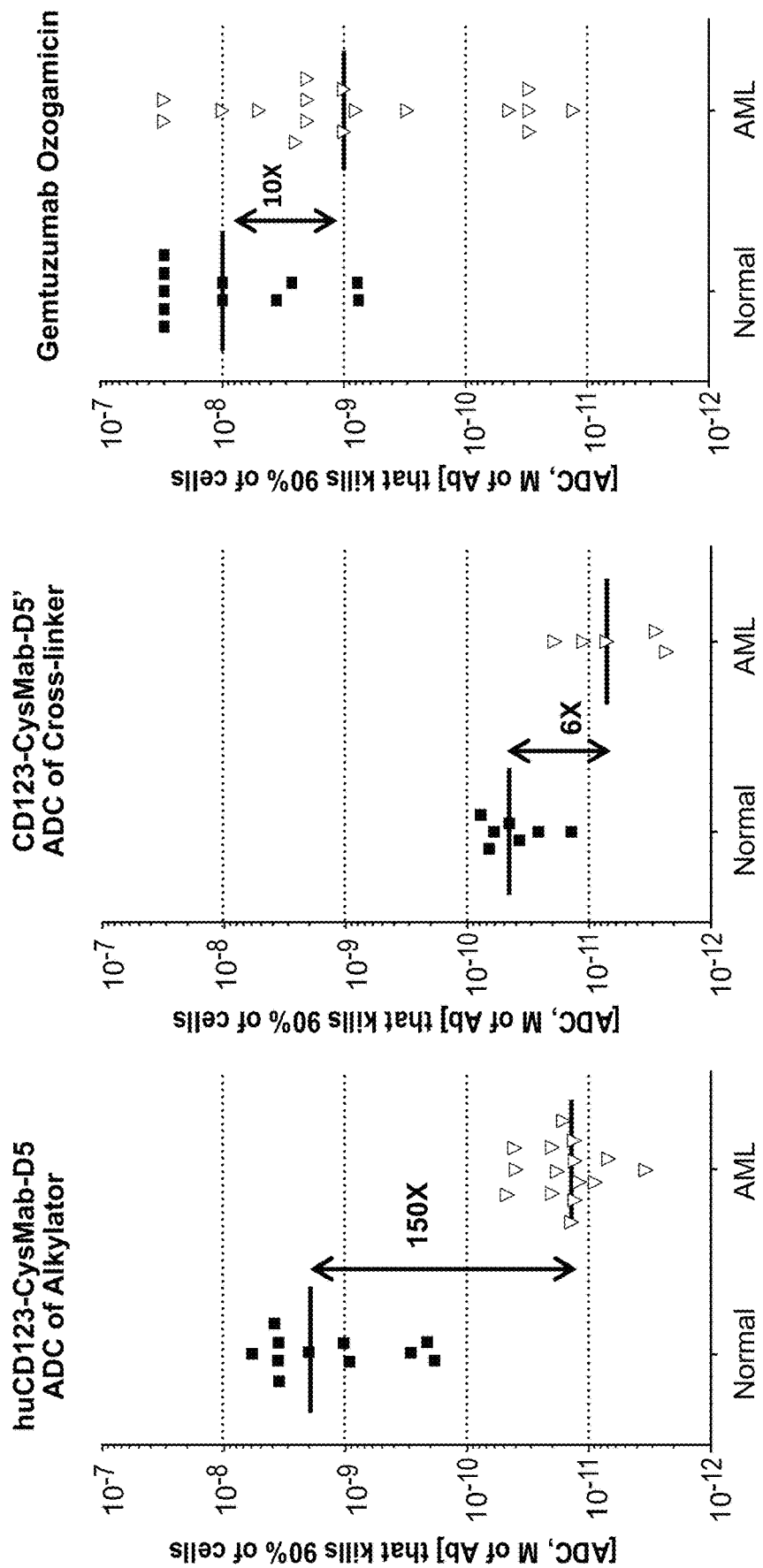
FIG. 19 shows that the Cys-linked huCD123-6Gv4.7-CysMab-D5 conjugate kills normal progenitor cells at concentrations that are >100-fold higher than those needed to kill AML progenitors. In comparison, Mylotarg and huCD123-6G4.7-CysMab-D5' (ADC of DNA cross-linker D5') do not exhibit such preferential killing effect.

In addition, FIG. 11E and FIG. 19 show that the Cys-linked huCD123 D5 conjugate kills normal blood cells at concentrations that are >100-fold higher than those needed to kill AML progenitors. In comparison, Mylotarg (gemtuzumab ozogamicin) does not exhibit such preferential killing effect, with only 10 fold difference in cytotoxicity between normal progenitor cells and AML progenitor cells. In FIG. 19, additional AML patient samples were tested. In addition, the huCD123 conjugate of D5', a DNA cross-linker, was also tested and it only exhibits 6 fold difference in cytotoxicity between normal progenitor cells and AML progenitor cells (see FIG. 19).

Example 11 In Vitro Potency of Lysine-Linked IGN Conjugates on Primary AML Patient Samples The ability of the various lysine-linked huCD123-6-IGN conjugates to kill primary AML cells was measured using colony forming unit (CFU) assays. Frozen Peripheral Blood Mononuclear Cells (PBMC) and Bone Marrow Mononuclear Cells (BMMC) from patients with AML were purchased from Conversant Biologics Inc. (Huntsville, AL) and AllCells, LLC (Alameda, CA). The cells were thawed as recommended by the suppliers, washed and resuspended in the RPMI culture medium (RPMI-1640, 10% fetal bovine serum, 50 ng/mL SCF and 50 ng/mL FLT3L). To block Fc receptors on the cell surface, the culture medium was supplemented with 100 nM chKTI antibody (an antibody of the same isotype). The cells, 200,000 in 150 μL of the culture medium, were added to each well of flat bottom 96-well plates. Conjugates were diluted into the medium using 10-fold dilution series and 50 μL were added per well. Control wells contained cells and the medium but lacked the conjugates. The plates were incubated at 37° C. in a humidified 6% CO$_2$ incubator for 18 hours. Then the cells were transferred to tubes containing 2.2 mL of METHOCULT™ H4534 without EPO (StemCell Technologies, Vancouver, BC), mixed, and the mixtures were transferred to 6-well plates. The plates were incubated at 37° C. in a humidified 6% CO$_2$ incubator until colonies formed (usually 10 to 16 days) and were counted. Percent inhibition of colony formation was determined by comparing the counts in the conjugate-treated samples by that in the non-treated control. The percent colony inhibition was plotted against the conjugate concentration and the conjugate concentration that inhibits 90% of the colony formation ($IC_{90}$) was determined from the curves.

Figure 12A:
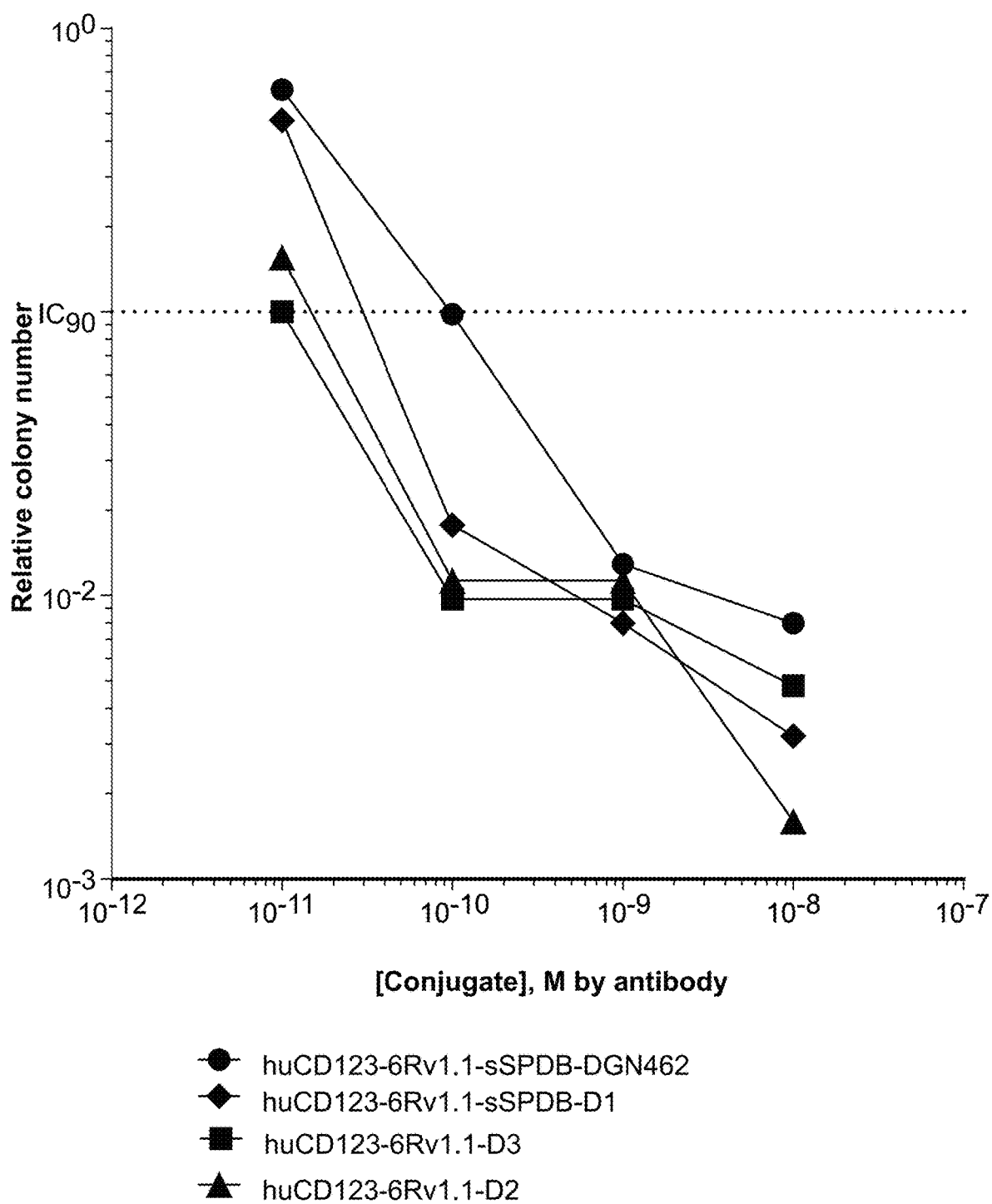
FIGS. 12A and 12B show in vitro cytotoxicity of the various lysine-linked huCD123-6Rv1.1-IGN conjugates on primary cells from AML patients. The result from a typical CFU assay for one primary patient sample is presented in FIG. 12A.
Figure 12B:
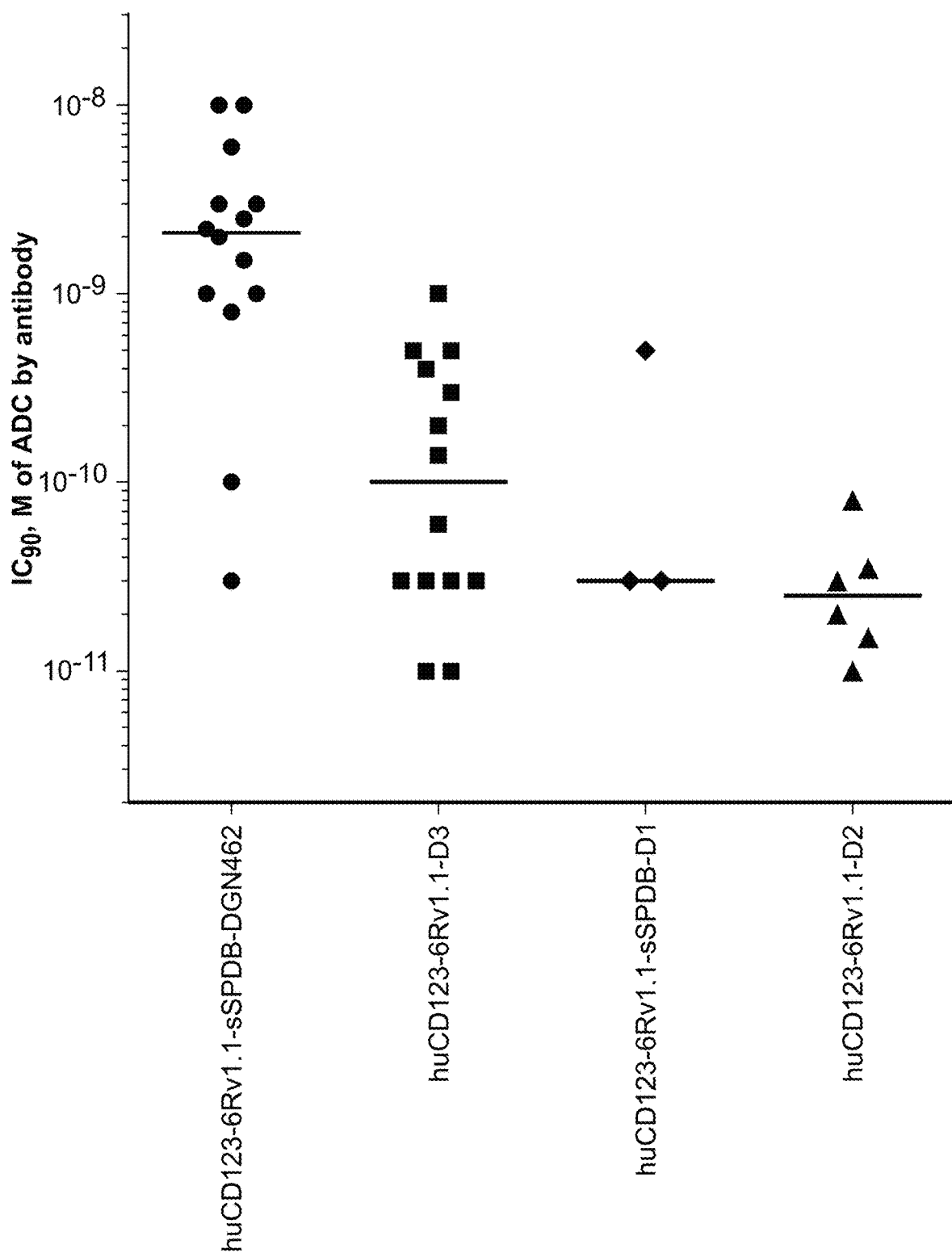

The result from a typical CFU assay for one primary patient sample is presented in FIG. 12A. The huCD123-6-IGN conjugates demonstrated a dose-dependent cytotoxicity with the $IC_{90}$ values of 0.1 nM, 0.01 nM, 0.03 nM, and 0.012 nM for huCD123-6Gv1.1-sSPDB-DGN462, huCD123-6Gv1.1-D3, huCD123-6Gv1.1-sSPDB-D1 and huCD123-6Gv1.1-D2, respectively. FIG. 12B shows the $IC_{90}$ values for all AML patient samples treated with the conjugates. The median $IC_{90}$ values for each conjugate are presented as solid lines and equal to 2 nM, 0.1 nM, 0.03 nM, and 0.02 nM for huCD123-6Gv1.1-sSPDB-DGN462, huCD123-6Gv1.1-D3, huCD123-6Gv1.1-sSPDB-D1, and huCD123-6Gv1.1-D2, respectively. Thus, the lysine-linked huCD123-6-IGN conjugates demonstrated high potency on samples from AML patients.

Example 12 Preparation of Ser Site-Specific Conjugates of the huCD123-6 Antibody a) N-Terminal Antibody Conjugation—a Two-Step Approach huCD123-6Gv4.6/7S3 antibody (having huCD123-6Gv4 LCVR (SEQ ID NO: 37, including an engineered N-terminal Ser) and HCVR Gv6/7 (SEQ ID NO: 34)) ([1], in Scheme 1 as shown in FIG. 15; 3 mg/mL in PBS, pH7.4) was treated with 5 mM aqueous sodium periodate (50 equivalents, 25° C., 30 minutes). The mixture was then buffer exchanged through a NAP desalting column (Illustra Sephadex G-25 DNA Grade, GE Healthcare) into sodium acetate buffer, pH5.0.

The resulting solution was treated with 4-Aminophenethyl alcohol (100 mM in DMA [N,N-Dimethylacetamide]) to 10% v/v cosolvent. Heterobifunctional Linker1 ([3] in Scheme 1; 5 equivalents) was subsequently introduced, and the reaction vessel was sealed and incubated at 37° C. for 24 hours.

The mixture was then buffer exchanged through a NAP desalting column (Illustra Sephadex G-25 DNA Grade, GE Healthcare) into HEPES (4-(2-hydroxyethyl)-1-piperazine ethanesulfonic acid), pH8.5 buffer. The solution was then adjusted with DMA (N,N-Dimethylacetamide) cosolvent (10% v/v), and treated with sulfonated DGN462 (sDGN462) ([5], Scheme 1; free thiol; 5 equivalents), at 25° C. for 6 hours.

The resulting conjugate was buffer exchanged into 250 mM Glycine, 10 mM Histidine, 1% sucrose, 0.01% Tween-20, 50 µM sodium bisulfate formulation buffer at pH 6.2 using a NAP filtration column (Illustra Sephadex G-25 DNA Grade, GE Healthcare). Dialysis was performed in the same buffer for 4 hours at 25° C. utilizing Slide-a-Lyzer dialysis cassettes (ThermoScientific 10,000 MWCO).

The purified conjugate ([6], Scheme 1) was found to have a homogenous average of two DGN462 molecules linked per antibody (via Q-ToF Mass Spectrometry), >98% monomer (via Size Exclusion Chromatography), <2% free drug (via acetone precipitated reverse-phase HPLC analysis), and a final protein concentration of 0.18 mg/mL (via UV-Vis using molar extinction coefficients $\varepsilon_{280}$=213320 $M^{-1}$ $cm^{-1}$ for the huCD123-6Gv4.6/7S3 antibody).

b) N-Terminal Antibody Conjugation—IGN Direct Link

The engineered N-terminal Ser-containing huCD123-6Gv4.7S2 antibody, engineered with an N-terminal serine on the heavy chain (huCD123-6Gv4.7S2, which comprises heavy chain sequence SEQ ID NO: 53 in which Xaa is Val, and light chain sequence SEQ ID NO: 51) ([1] in Scheme 2, FIG. 16; 3 mg/mL in PBS, pH7.4) was treated with 5 mM aqueous sodium periodate (50 molar equivalents) at 25° C. for 30 minutes. The mixture was then buffer exchanged through a NAP desalting column (Illustra Sephadex G-25 DNA Grade, GE Healthcare) into sodium acetate buffer, pH5.0.

The resulting solution was treated with p-phenylenediamine (100 mM in DMA [N,N-Dimethylacetamide]) to 10% v/v cosolvent. Then, an in situ sulfonated-D8 (or sD8) ([3], Scheme 2; 5 molar equivalents) was subsequently introduced, and the reaction vessel was sealed and incubated at 37° C. for 24 hours.

The mixture was then buffer exchanged through a NAP desalting column (Illustra Sephadex G-25 DNA Grade, GE Healthcare) into 250 mM Glycine, 10 mM Histidine, 1% sucrose buffer at pH 6.2. Dialysis was performed in the same buffer for 4 hours at 25° C., utilizing Slide-a-Lyzer dialysis cassettes (ThermoScientific 10,000 MWCO).

The purified conjugate ([4], Scheme 2) was found to have a homogenous average of two D8 molecules linked per antibody (via Q-ToF Mass Spectrometry), >96% monomer (via Size Exclusion Chromatography), <3% free drug (via HISEP reverse-phase HPLC analysis), and a final protein concentration of 1.4 mg/mL (via UV-Vis using molar extinction coefficients $\varepsilon_{280}$=213320 $M^{-1}$ $cm^{-1}$ for the huCD123-6Gv4.7S2 antibody).

The in situ sulfonated-D8 (or sD8) described above was prepared according to the following procedure: The D8 reagent, as a lyophilized, white solid, was dissolved in DMA (N,N-Dimethylacetamide) to a 10-20 mM stock concentration solution. Fresh sodium bisulfite (500 mM solution in water, 5 molar equivalents) was added and the resulting solution reacted for 4-6 hours at 25° C. before a 15 hour hold step at 4° C. A further aliquot of fresh sodium bisulfite (500 mM solution in water, 2 molar equivalents) was introduced and allowed to react for 4 hours at 25° C. before storage at −80° C. until further use.

c) N-Terminal Antibody Conjugation—Two-Step Protocol for CD123-6Gv4.7

The huCD123-6Gv4.7S3 antibody (see above) engineered with an N-terminal serine on the light chain (huCD123-6Gv4.7S3) ([1] in Scheme 3, FIG. 17; 3 mg/mL in PBS, pH7.4) was treated with 5 mM aqueous sodium periodate (50 molar equivalents) at 25° C. for 30 minutes. The mixture was then buffer exchanged through a NAP desalting column (Illustra Sephadex G-25 DNA Grade, GE Healthcare) into sodium acetate buffer, pH5.0.

The resulting solution was treated with 4-Aminophenethyl alcohol (100 mM in DMA [N,N-Dimethylacetamide]) to 10% v/v cosolvent. Heterobifunctional Linker1 ([3], Scheme 3; 5 molar equivalents) was subsequently introduced, and the reaction vessel was sealed and incubated at 37° C. for 24 hours.

The mixture was then buffer exchanged through a NAP desalting column (Illustra Sephadex G-25 DNA Grade, GE Healthcare) into HEPES (4-(2-hydroxyethyl)-1-piperazine ethanesulfonic acid) pH8.5 buffer. The solution was then adjusted with DMA (N,N-Dimethylacetamide) cosolvent (10% v/v), and treated with sulfonated-D1 (or sD1) ([5], Scheme 3; free thiol; 5 molar equivalents) at 25° C. for 6 hours.

The resulting conjugate was buffer exchanged into 250 mM Glycine, 10 mM Histidine, 1% sucrose, 0.01% Tween-20, 50 μM sodium bisulfite formulation buffer at pH 6.2, using a NAP filtration column (Illustra Sephadex G-25 DNA Grade, GE Healthcare). Dialysis was performed in the same buffer for 4 hours at 25° C., utilizing Slide-a-Lyzer dialysis cassettes (ThermoScientific 10,000 MWCO).

The purified conjugate ([6], Scheme 3) was found to have an average of 2.0 molecules of D1 linked per antibody (via Q-ToF Mass Spectrometry), >96% monomer (via Size Exclusion Chromatography), <3% free drug (via acetone precipitated reverse-phase HPLC analysis), and a final protein concentration of 0.4 mg/mL (via UV-Vis using molar extinction coefficients $\varepsilon_{280}=213320$ $M^{-1}$ $cm^{-1}$ for the huCD123-6Gv4.7S3 antibody).

Example 13 In Vitro Cytotoxicity of Site-Specific Conjugates of the huCD123-6 Antibody The ability of site-specific conjugates of huCD123-6 with the various IGN compounds (huCD123-6Gv4.6-CysMab-D5 and huCD123-6Rv1.1S2-SeriMab-D8) to kill cells that express CD123 on their cell surface was compared to that of the lysine-linked conjugates containing the matching antibody and the payload (huCD123-6Gv4.6-D2 and huCD123-6Rv1.1-D2) using in vitro cytotoxicity assays. The cytotoxicity assays were carried out and analyzed as described in Example 10.

The huCD123-6Gv4.6-CysMab-D5 conjugate (in which the huCD123-6Gv4.6-CysMab has an Ig heavy chain sequence of SEQ ID NO: 54, and a light chain sequence of SEQ ID NO: 51) was at least as active as the lysine-linked huCD123-6Gv4.6-D2 conjugate (in which the huCD123-6Gv4.6 antibody has an Ig heavy chain sequence of SEQ ID NO: 50, and a light chain sequence of SEQ ID NO: 51) on multiple cell lines. Several examples of the cytotoxicity assay using the AML cell line EOL-1, the B-ALL cell line KOPN-8 and the CML cell line MOLM-1 are shown in FIGS. 13A-13C, respectively. Both conjugates killed the cells in a dose-dependent manner with the $IC_{50}$ values of approximately 0.002 nM, 0.005 nM, and 0.02 nM for EOL-1 cells, KOPN-8 cells and MOLM-1 cells, respectively. The killing was CD123-dependent as the conjugates were at least 100 fold less toxic to the cells when the CD123 antigen was blocked by the unconjugated chCD123-6 antibody.

Figure 14B:
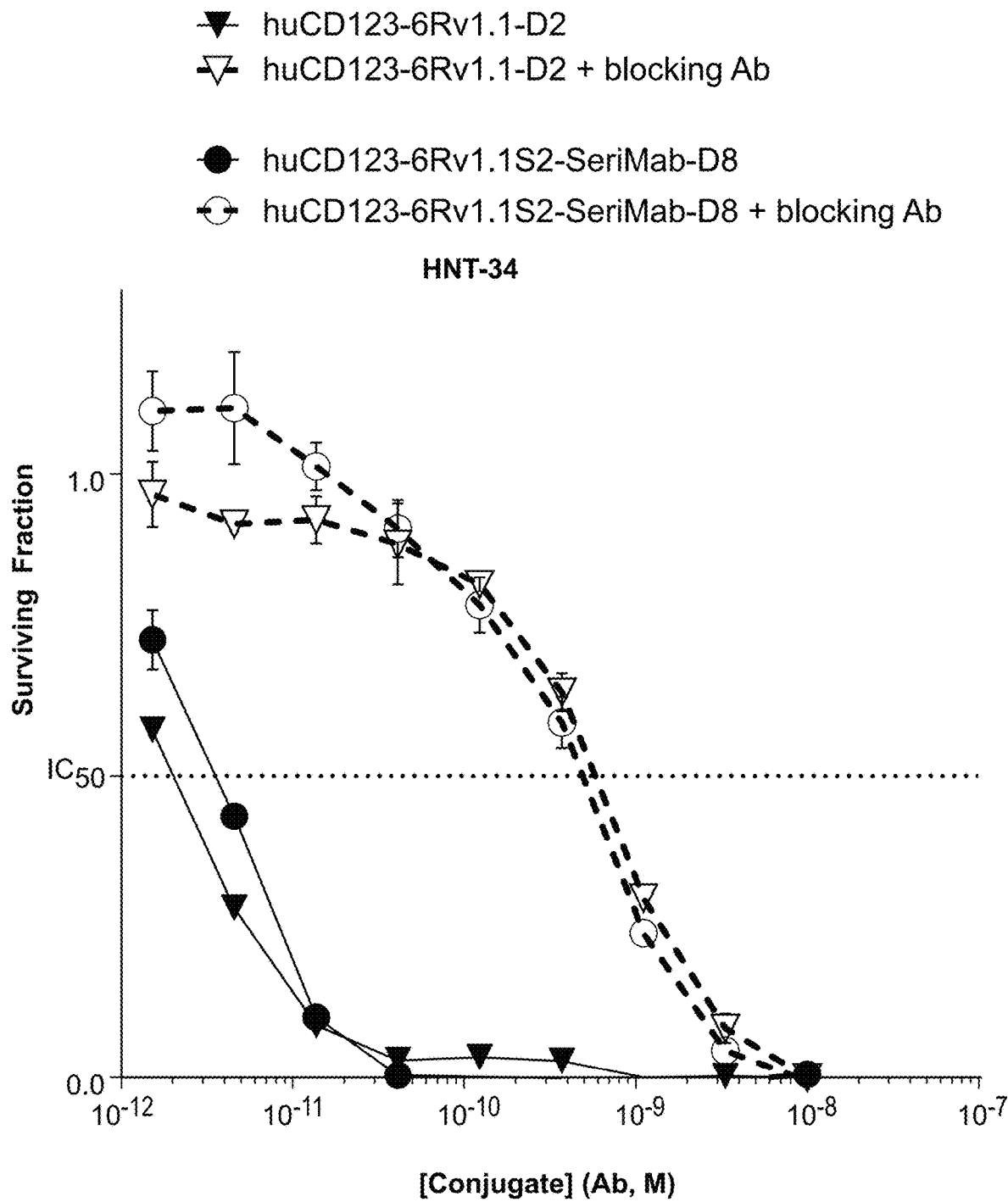

The huCD123-6Rv1.152-SeriMab-D8 conjugate (in which the resurfaced huCD123-6Rv 1.1 S2 antibody has an Ig heavy chain sequence of SEQ ID NO: 60 except that the N-terminal residue is Ser, and a light chain sequence of SEQ ID NO: 61) maintained target (CD123) binding, and was at least as active as the lysine-linked huCD123-6Rv1.1-D2 conjugate (in which the resurfaced huCD123-6Rv1.1 antibody has an Ig heavy chain sequence of SEQ ID NO: 60, and a light chain sequence of SEQ ID NO: 61) on multiple cell lines. Several examples of the cytotoxicity assay using the AML cell lines SHI-1 and HNT-34, as well as the CML cell line MOLM-1 are shown in FIGS. 14A-14C, respectively. Both conjugates killed the cells in a dose-dependent manner with the $IC_{50}$ values of approximately 0.01 nM, 0.002 nM, and 0.03 nM for SHI-1 cells, HNT-34 cells, and MOLM-1 cells, respectively. The killing was CD123-dependent as the conjugates were at least 100 fold less toxic to the cells when the CD123 antigen was blocked by the unconjugated huCD123-6 antibody.

In another experiment, it was found that Ser-linked DGN462 compound with huCD123 antibody has 3-fold higher antigen-specific potency than lysine linked version with higher DAR (data not shown).

Example 14 In Vivo Efficacy Studies Using the CD123-IGN Conjugates in the MV4-11 AML Subcutaneous Mice Model Subcutaneously implanted tumor cells represent a convenient means to test novel potential anti-cancer drugs in vivo. A large variety of human and murine cell lines derived from both solid tumors and leukemias, covering a wide range of tumor genotypes and phenotypes, have been adapted to grow in a murine host, and thus allow testing of a subject therapeutic agent in the appropriate tumor model.

A subcutaneous acute myeloid leukemia model (AML), as outlined in the protocol below, is used to test the efficacy of the subject CD123 antibody drug conjugates (ADCs) for their ability to decrease tumor burden in vivo. Specifically, female SCID mice are each inoculated subcutaneously in the right flank with about $1\times10^7$ MV4-11 cells, a human AML cell line. On day 14 post-inoculation, mice are randomly divided into groups based on tumor volume, and treated with 400 mg/kg of human IgG by intraperitoneal injection to block Fc receptors on MV4-11 cells. The subject anti-D123 ADCs or non-targeting antibody controls (chKTI-lysine linked-D1, chKTI-lysine linked D2, and huKTI-CysMab linked D2 in which the huKTI antibody has an engineered Cys at a position corresponding to the $5^{th}$ to the last residue of SEQ ID NO: 54) are administered intravenously once, on day 15 post-inoculation, at a dose of 1 or 3 μg/kg. Mice are treated with 100 mg/kg of human IgG again on day 20 post-inoculation. Animals are monitored daily, and tumor volume is measured twice weekly. The treatment groups and control groups are listed below with the respective doses.

| Group | Treatment | Dose (μg/kg) (Actual dose (μg/kg)) | Route and schedule |
|---|---|---|---|
| 1 | Vehicle | — | i.v., × 1 |
| 2 | huCD123-sSPDB-D1 | 1 (0.78) | i.v., × 1 |
| 3 | huCD123-lysine linked-D2 | 1 (0.89) | i.v., × 1 |
| 4 | huCD123-CysMab-D5 | 1 (0.91) | i.v., × 1 |
| 5 | huCD123-sSPDB-D1 | 3 (2.35) | i.v., × 1 |
| 6 | huCD123-lysine linked-D2 | 3 (2.69) | i.v., × 1 |
| 7 | huCD123-CysMab-D5 | 3 (2.88) | i.v., × 1 |
| 8 | chKTI-sSPDB-D1 | 3 | i.v., × 1 |
| 9 | chKTI-lysine linked-D2 | 3 | i.v., × 1 |
| 10 | huKTI-CysMab-D5 | 1 (0.91) | i.v., × 1 |
| 11 | huKTI-CysMab-D5 | 3 (2.88) | i.v., × 1 |

The huCD123 antibody used in the study is the humanized huCD123-6Gv4.7 antibody, which is linked to D1 or D2 through Lys linkage, or through engineered Cys-linkage as described herein above. The Lys-linked chimeric KTi antibody-based IGN conjugates and the Cys-linked human KTi antibody-based IGN conjugates are also included as controls. The latter KTi CysMab antibody has an engineered Cys in the heavy chain CH3 domain at a position corresponding to the $5^{th}$ to the last residue of SEQ ID NO: 54.

Figure 20:
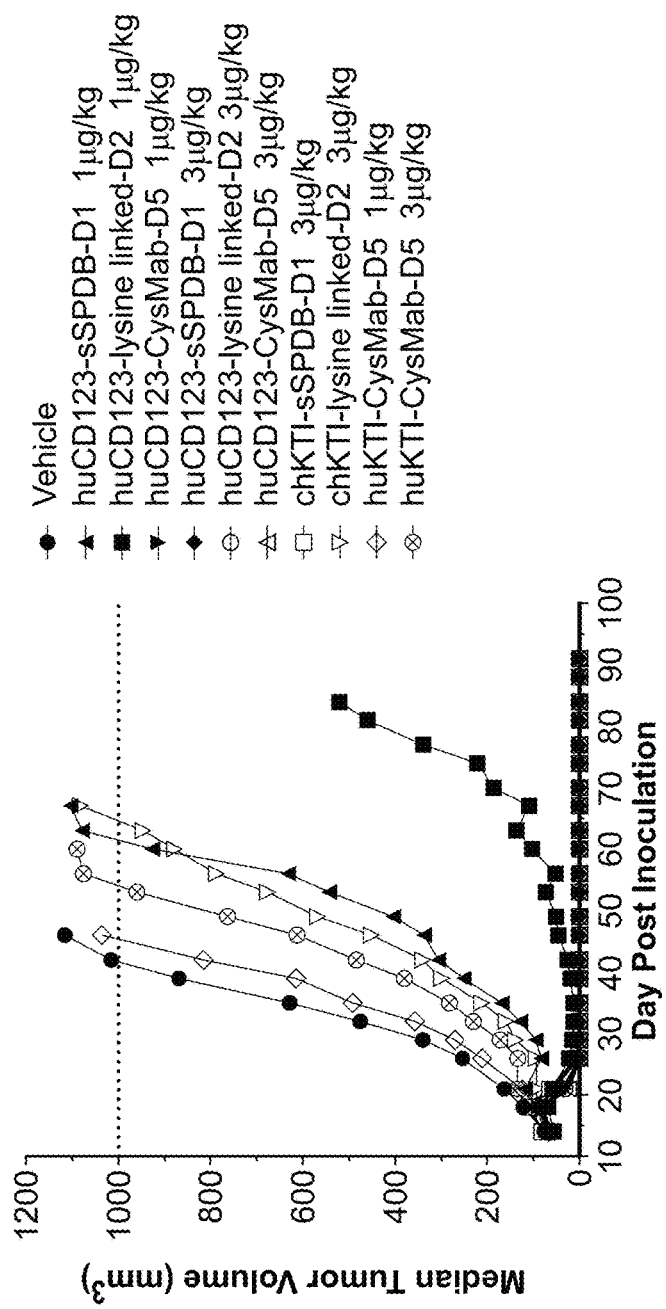
FIG. 20 shows in vivo efficacy of CD123-IGN conjugates in the MV4-11 AML subcutaneous mice model.

Preliminary data shows that the Lys- and Cys-linked IGN compounds are highly active against the MV4-11 xenograft tumors in the in vivo mouse model (see, FIG. 20).

Example 15. Preparation of Cys Site-Specific Conjugates of the huCD123-6 Antibody huCD123-6Gv1.1 S2-CysMab-D7 huCD123-6Gv1.1S2-CysMab is a CDR grafted humanized antibody with LCVR sequences of SEQ ID NO: 33 and HC sequence of SEQ ID NO: 48 (except that the first residue is Ser), and including an engineered Cys corresponding to the $5^{th}$ to the last residue of SEQ ID NO: 54 or 56.

This huCD123 antibody bearing two unpaired cysteine residues in the reduced state was prepared using standard procedures. To a solution of this intermediate in phosphate buffered saline (PBS), 5 mM N,N,N',N'-ethylenediaminetetracetic acid (EDTA) pH 6.0 was added N,N-dimethylacetamide (DMA), propylene glycol, and 10 molar equivalents of D7 as a stock solution in DMA to give a reaction mixture with a final solvent composition of 2% v/v DMA and 38% v/v propylene glycol in PBS 5 mM EDTA pH 6.0. The reaction was allowed to proceed for 24 hours at 25° C.

The conjugate was purified into 20 mM histidine, 50 mM sodium chloride, 8.5% sucrose, 0.01% Tween-20, 50 µM sodium bisulfite pH 6.2 formulation buffer using Sephadex G25 desalting columns, concentrated by ultrafiltration through a membrane with 10 kDa molecular weight cutoff, and filtered through a 0.22 µm syringe filter. The conjugate was then dialyzed against the same buffer using a membrane with 10 kDa molecular weight cutoff.

The conjugate was found to have 2 mol D7/mol antibody by UV-Vis; 97.2% monomer by SEC; and 1.9% unconjugated D7 by SEC/reverse-phase HPLC. LC-MS of the deglycosylated conjugate is not shown.

huCD123-6Gv4.7-CysMab-D5 huCD123-6Gv4.7-CysMab is a CDR grafted humanized antibody with LCVR sequences of SEQ ID NO: 34 (in which Xaa is Val) and HCVR sequence of SEQ ID NO: 35, and including an engineered Cys corresponding to the $5^{th}$ to the last residue of SEQ ID NO: 54 or 56.

This huCD123 antibody bearing two unpaired cysteine residues in the reduced state was prepared using standard procedures. To a solution of this intermediate in phosphate buffered saline (PBS), 5 mM N,N,N',N'-ethylenediaminetetracetic acid (EDTA) pH 6.0 was added N,N-dimethylacetamide (DMA), propylene glycol, and 10 molar equivalents of D5 as a stock solution in DMA to give a reaction mixture with a final solvent composition of 2% v/v DMA and 38% v/v propylene glycol in PBS 5 mM EDTA pH 6.0. The reaction was allowed to proceed for 24 hours at 25° C.

The conjugate was purified into 20 mM histidine, 50 mM sodium chloride, 8.5% sucrose, 0.01% Tween-20, 50 µM sodium bisulfite pH 6.2 formulation buffer using Sephadex G25 desalting columns, concentrated by ultrafiltration through a membrane with 10 kDa molecular weight cutoff, and filtered through a 0.22 µm syringe filter. The conjugate was then dialyzed against the same buffer using a membrane with 10 kDa molecular weight cutoff.

The conjugate was found to have 2 mol D5/mol antibody by UV-Vis and 94.8% monomer by SEC. LC-MS of the deglycosylated conjugate is not shown.

huCD123-6Gv4.7-CysMab-D4

The above huCD123 antibody bearing two unpaired cysteine residues in the reduced state was prepared using standard procedures. To a solution of this intermediate in phosphate buffered saline (PBS), 5 mM N,N,N',N'-ethylenediaminetetracetic acid (EDTA) pH 6.0 was added N,N-dimethylacetamide (DMA), propylene glycol, and 5 molar equivalents of D4 as a stock solution in DMA to give a reaction mixture with a final solvent composition of 2% v/v DMA and 38% v/v propylene glycol in PBS 5 mM EDTA pH 6.0. The reaction was allowed to proceed for 6 hours at 25° C.

The conjugate was purified into 20 mM histidine, 50 mM sodium chloride, 8.5% sucrose, 0.01% Tween-20, 50 µM sodium bisulfite pH 6.2 formulation buffer using Sephadex G25 desalting columns, concentrated by ultrafiltration through a membrane with 10 kDa molecular weight cutoff, and filtered through a 0.22 µm syringe filter. The conjugate was then dialyzed against the same buffer using a membrane with 10 kDa molecular weight cutoff.

The conjugate was found to have 1.8 mol D4/mol antibody by UV-Vis and 97.4% monomer by SEC. LC-MS of the deglycosylated conjugate is not shown.

Example 16. Synthesis of Compound D1

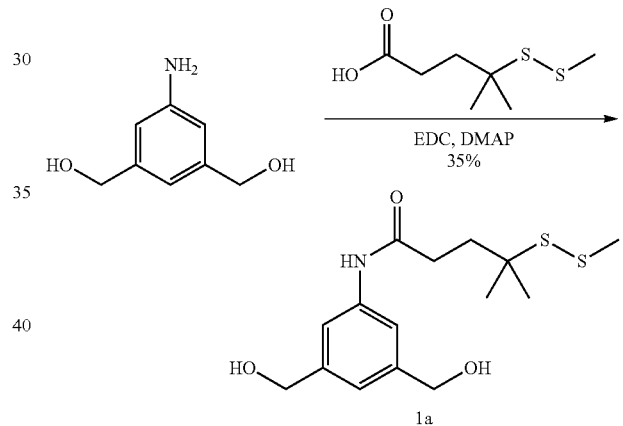

Compound 1a:

To a stirred solution of (5-amino-1,3-phenylene)dimethanol (1.01 g, 6.59 mmol) in anhydrous dimethylformamide (16.48 mL) and anhydrous tetrahydrofuran (16.48 ml) was added 4-methyl-4-(methyldisulfanyl)pentanoic acid (1.281 g, 6.59 mmol), N-(3-dimethylaminopropyl)-N'-ethylcarbodiimide hydrochloride (2.53 g, 13.19 mmol), and 4-dimethylaminopyridine (0.081 g, 0.659 mmol). The resulting mixture was stirred for 18 hours at room temperature. The reaction was quenched with saturated ammonium chloride solution and extracted with ethyl acetate (3×50 mL). The organic extracts were washed with water and brine, then dried over anhydrous sodium sulfate. The solution was filtered and concentrated in vacuo and the resulting residue was purified by silica gel chromatography (Ethyl acetate/Hexanes) to obtain compound 1a as a white solid (0.70 g, 32% yield). $^1$H NMR (400 MHz, DMSO-d6: δ 9.90 (s, 1H), 7.43 (s, 2H), 6.93 (s, 1H), 5.16 (t, 2H, J=5.7 Hz), 4.44 (d, 4H, J=5.7 Hz), 2.43 (s, 3H), 2.41-2.38 (m, 2H), 1.92-1.88 (m, 2H), 1.29 (s, 6H). MS (m/z), found 330.0 (M+1)$^+$.

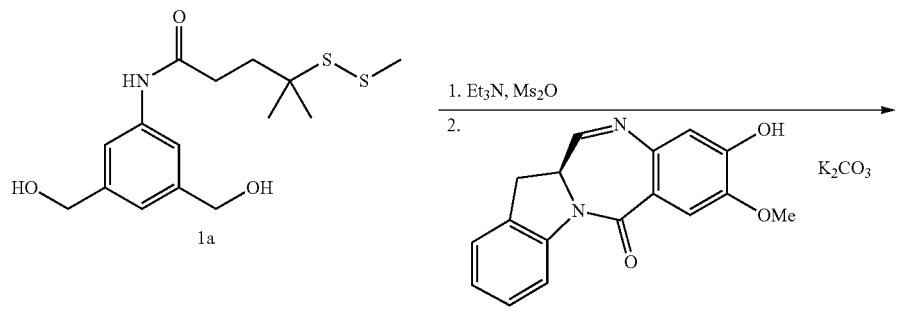

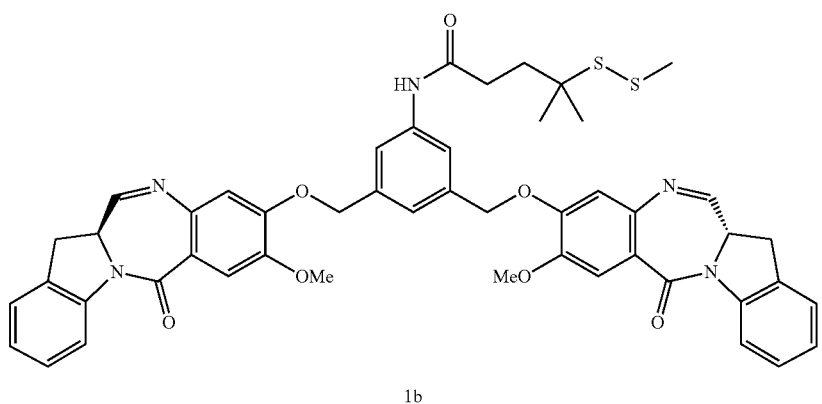

Compound 1b:

To a cooled (−10° C.) solution of compound 1a (219 mg, 0.665 mmol) in anhydrous dichloromethane (6.65 mL) was added triethylamine (463 µl, 3.32 mmol) followed by dropwise addition of methanesulfonic anhydride (298 mg, 1.662 mmol). The mixture stirred at −10° C. for 2 hours, then the mixture was quenched with ice water and extracted with cold ethyl acetate (2×30 mL). The organic extracts were washed with ice water, dried with anhydrous sodium sulfate, filtered and concentrated under reduced pressure to obtain the crude dimesylate.

The crude dimesylate (227 mg, 0.467 mmol) and IGN (or indolinobenzodiazepine) monomer A (303 mg, 1.028 mmol) were dissolved in anhydrous DMF (3.11 mL). Potassium carbonate (161 mg, 1.169 mmol) was added and the mixture stirred for 18 hours at room temperature. Deionized water was added and the resulting precipitate was filtered and rinsed with water. The solid was re-dissolved in dichloromethane and washed with water. The organic layer was dried with anhydrous magnesium sulfate, filtered, and concentrated. The crude residue was purified by silica gel chromatography (Methanol/Dichloromethane) to give compound 1b (227 mg, 36% yield). MS m/z found 882.5 $(M+1)^+$.

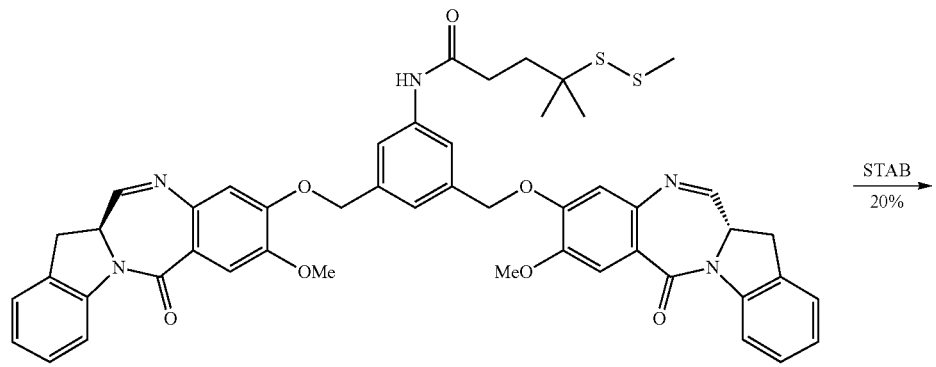

-continued

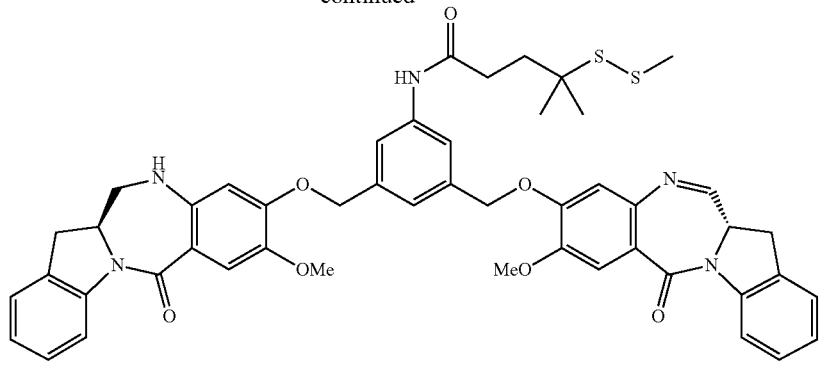

1c

Compound 1c:

To a suspension of compound 1b (227 mg, 0.167 mmol) in anhydrous 1,2-dichloroethane (3.346 mL) was added sodium triacetoxyborohydride (37.3 mg, 0.167 mmol). The mixture was stirred at room temp for one hour upon which it was quenched with saturated ammonium chloride solution. The mixture was extracted with dichloromethane and washed with brine. The organic layer was dried with anhydrous magnesium sulfate, filtered and concentrated. The crude residue was purified by RP-HPLC (C18, Water/Acetonitrile). Fractions containing desired product were extracted with dichloromethane, dried with anhydrous magnesium sulfate, filtered and concentrated to give compound 1c (35 mg, 19% yield). MS (m/z), found 884.3 (M+1)$^+$.

Compound 1d:

To a solution of compound 1c (18 mg, 0.017 mmol) in acetonitrile (921 μL) and methanol (658 μL) was added tris(2-carboxyethyl)phosphine hydrochloride (17.51 mg, 0.060 mmol) (neutralized with saturated sodium bicarbonate solution (0.2 mL) in sodium phosphate buffer (132 μL, 0.75 M, pH 6.5). The mixture was stirred at room temperature for 3.5 hours, then diluted with dichloromethane and deionized water. The organic layer was separated, washed with brine, dried with anhydrous sodium sulfate, filtered and concentrated under reduced pressure to obtain the crude thiol. MS (m/z), found 838.3 (M+1)$^+$.

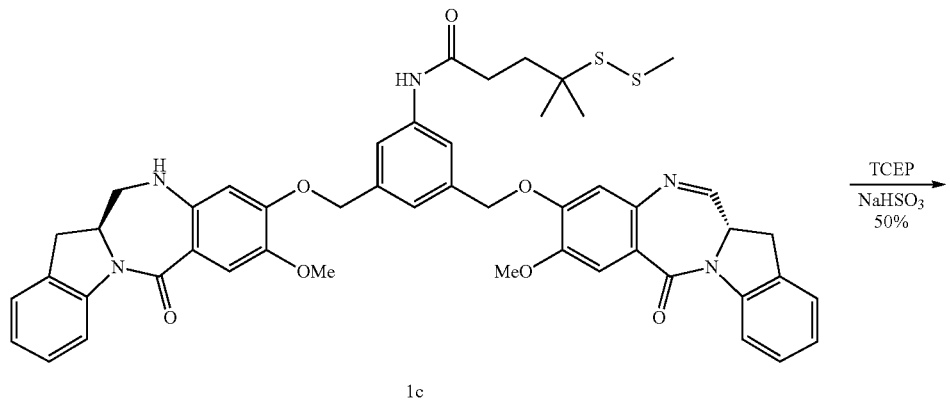

1c $$\xrightarrow[\text{NaHSO}_3]{\text{TCEP}} 50\%$$

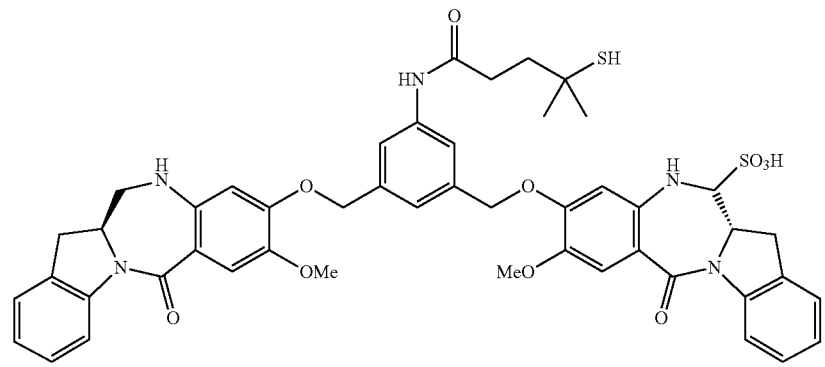

1d

The crude thiol (15.5 mg, 0.018 mmol) was dissolved in 2-propanol (1.23 mL). Deionized water (617 µL) and sodium bisulfite (5.77 mg, 0.055 mmol) were added and the mixture stirred for five hours at room temperature. The reaction was frozen in an acetone/dry ice bath, lyophilized, and purified by RP-HPLC (C18, deionized water/acetonitrile). Fractions containing desired product were frozen and lyophilized to give compound (12S,12aS)-9-((3-(4-mercapto-4-methylpentanamido)-5-((((R)-8-methoxy-6-oxo-11,12,12a,13-tetrahydro-6H-benzo[5,6][1,4]diazepino[1,2-a]indol-9-yl)oxy)methyl)benzyl)oxy)-8-methoxy-6-oxo-11,12,12a,13-tetrahydro-6H-benzo[5,6][1,4]diazepino[1,2-a]indole-12-sulfonic acid (compound sulfonated-D1 (sD1)) (6.6 mg, 39% yield). MS (m/z), found 918.2 (M−1)⁻.

Example 17. Synthesis of 2,5-dioxopyrrolidin-1-yl 6-(((S)-1-(((S)-1-((3-((((S)-8-methoxy-6-oxo-11,12,12a,13-tetrahydro-6H-benzo[5,6][1,4]diazepino[1,2-a]indol-9-yl)oxy)methyl)-5-((((R)-8-methoxy-6-oxo-12a,13-dihydro-6H-benzo[5,6][1,4]diazepino[1,2-a]indol-9-yl)oxy)methyl) phenyl)amino)-1-oxopropan-2-yl)amino)-1-oxopropan-2-yl)amino)-6-oxohexanoate, Compound D2

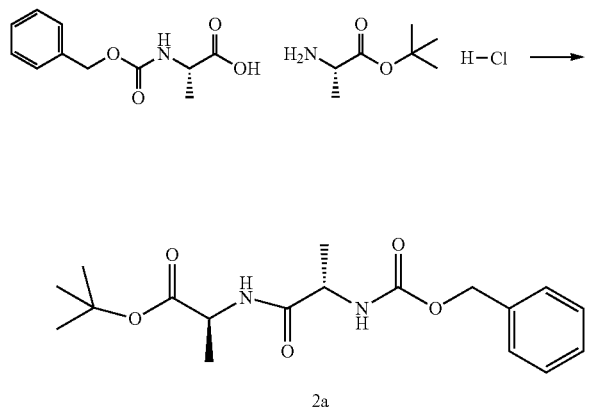

Step 1: (S)-2-(((benzyloxy)carbonyl)amino)propanoic acid (5 g, 22.40 mmol) and (S)-tert-butyl 2-aminopropanoate hydrochloride (4.48 g, 24.64 mmol) were dissolved in anhydrous DMF (44.8 mL). EDC·HCl (4.72 g, 24.64 mmol), HOBt (3.43 g, 22.40 mmol), and DIPEA (9.75 mL, 56.0 mmol) were added. The reaction stirred under argon, at room temperature, overnight. The reaction mixture was diluted with dichloromethane and then washed with saturated ammonium chloride, saturated sodium bicarbonate, water, and brine. The organic layer was dried over sodium sulfate and concentrated. The crude oil was purified via silica gel chromatography (Hexanes/Ethyl Acetate) to yield compound 2a (6.7 g, 85% yield). $^1$H NMR (400 MHz, CDCl$_3$): δ 7.38-7.31 (m, 5H), 6.53-6.42 (m, 1H), 5.42-5.33 (m, 1H), 5.14 (s, 2H), 4.48-4.41 (m, 1H), 4.32-4.20 (m, 1H), 1.49 (s, 9H), 1.42 (d, 3H, J=6.8 Hz), 1.38 (d, 3H, J=7.2 Hz).

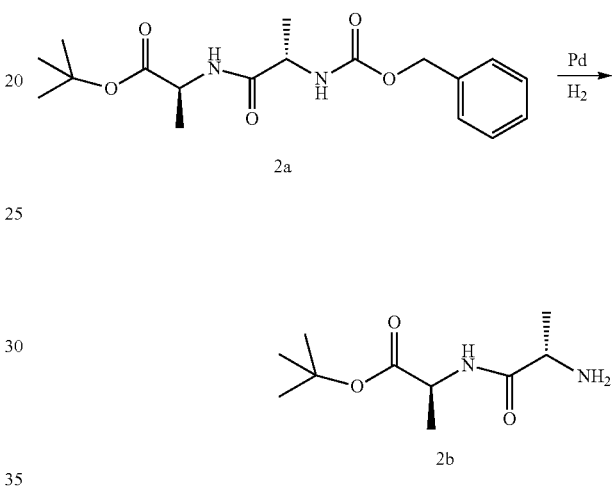

Step 2: Compound 2a (6.7 g, 19.12 mmol) was dissolved in methanol (60.7 mL) and water (3.03 mL). The solution was purged with argon for five minutes. Palladium on carbon (wet, 10%) (1.017 g, 0.956 mmol) was added slowly. The reaction was stirred overnight under an atmosphere of hydrogen. The solution was filtered through Celite, rinsed with methanol and concentrated. It was azeotroped with methanol and acetonitrile and the resulting oil was placed directly on the high vacuum to give compound 2b (4.02 g, 97% yield) which was used directly in the next step. $^1$H NMR (400 MHz, CDCl$_3$): δ 7.78-7.63 (m, 1H), 4.49-4.42 (m, 1H), 3.55-3.50 (m, 1H), 1.73 (s, 2H), 1.48 (s, 9H), 1.39 (d, 3H, J=7.2 Hz), 1.36 (d, 3H, J=6.8 Hz).

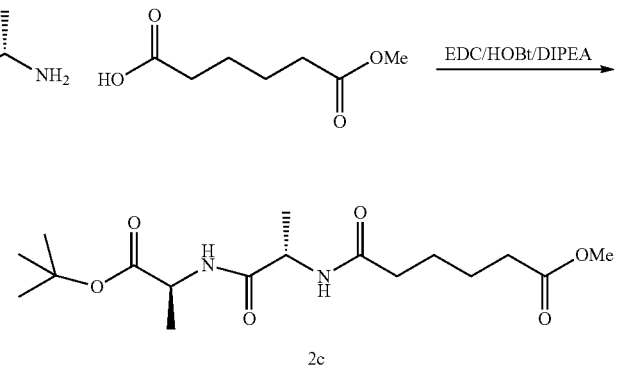

Step 3: Compound 2b (4.02 g, 18.59 mmol) and mono methyladipate (3.03 mL, 20.45 mmol) were dissolved in anhydrous DMF (62.0 mL). EDC·HCl (3.92 g, 20.45 mmol), HOBt (2.85 g, 18.59 mmol) and DIPEA (6.49 mL, 37.2 mmol) were added. The mixture was stirred overnight at room temperature. The reaction was diluted with dichloromethane/methanol (150 mL, 5:1) and washed with saturated ammonium chloride, saturated sodium bicarbonate, and brine. It was dried over sodium sulfate, filtered and stripped. The compound was azeotroped with acetonitrile (5×), then pumped on the high vacuum at 35° C. to give compound 2c (6.66 g, 100% yield). The crude material was taken onto next step without purification. $^1$H NMR (400 MHz, CDCl$_3$): δ 6.75 (d, 1H, J=6.8 Hz), 6.44 (d, 1H, J=6.8 Hz), 4.52-4.44 (m, 1H), 4.43-4.36 (m, 1H), 3.65 (s, 3H), 2.35-2.29 (m, 2H), 2.25-2.18 (m, 2H), 1.71-1.60 (m, 4H), 1.45 (s, 9H), 1.36 (t, 6H, J=6.0 Hz).

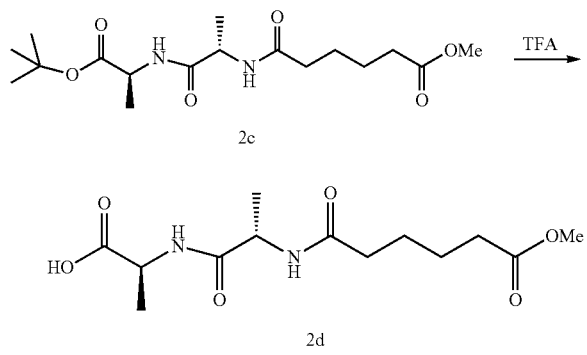

Step 4: Compound 2c (5.91 g, 16.5 mmol) was stirred in TFA (28.6 mL, 372 mmol) and deionized water (1.5 mL) at room temperature for three hours. The reaction mixture was concentrated with acetonitrile and placed on high vacuum to give crude compound 2d as a sticky solid (5.88 g, 100% yield). $^1$H NMR (400 MHz, CDCl$_3$): δ 7.21 (d, 1H, J=6.8 Hz), 6.81 (d, 1H, J=7.6 Hz), 4.69-4.60 (m, 1H), 4.59-4.51 (m, 1H), 3.69 (s, 3H), 2.40-2.33 (m, 2H), 2.31-2.24 (m, 2H), 1.72-1.63 (m, 4H), 1.51-1.45 (m, 3H), 1.42-1.37 (m, 3H).

Step 5: Compound 2d (5.6 g, 18.52 mmol) was dissolved in anhydrous dichloromethane (118 mL) and anhydrous methanol (58.8 mL). (5-amino-1,3-phenylene)dimethanol (2.70 g, 17.64 mmol) and EEDQ (8.72 g, 35.3 mmol) were added and the reaction was stirred at room temperature, overnight. The solvent was stripped and ethyl acetate was added. The resulting slurry was filtered, washed with ethyl acetate and dried under vacuum/N2 to give compound 2e (2.79 g, 36% yield). $^1$H NMR (400 MHz, DMSO-d6): δ 9.82 (s, 1H), 8.05, (d, 1H, J=9.2 Hz), 8.01 (d, 1H, J=7.2 Hz), 7.46 (s, 2H), 6.95 (3, 1H), 5.21-5.12 (m, 2H), 4.47-4.42 (m, 4H), 4.40-4.33 (m, 1H), 4.33-4.24 (m, 1H), 3.58 (s, 3H), 2.33-2.26 (m, 2H), 2.16-2.09 (m, 2H), 1.54-1.46 (m, 4H), 1.30 (d, 3H, J=7.2 Hz), 1.22 (d, 3H, J=4.4 Hz).

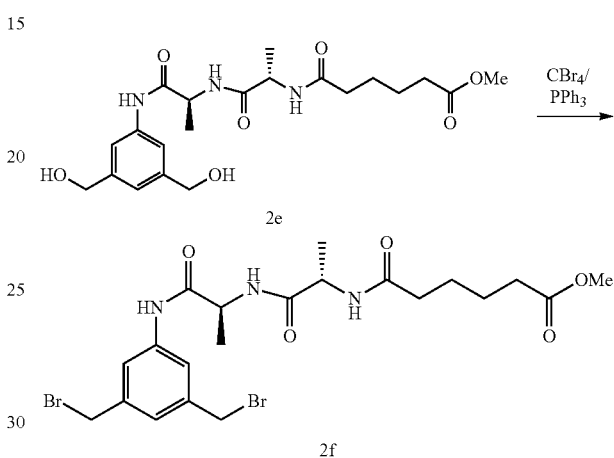

Step 6: Compound 2e (0.52 g, 1.189 mmol) and carbon tetrabromide (1.183 g, 3.57 mmol) were dissolved in anhydrous DMF (11.89 mL). Triphenylphosphine (0.935 g, 3.57 mmol) was added and the reaction stirred under argon for four hours. The reaction mixture was diluted with DCM/MeOH (10:1) and washed with water and brine, dried over sodium sulfate, filtered, and concentrated. The crude material was purified by silica gel chromatography (DCM/MeOH) to give compound 2f (262 mg, 39% yield). $^1$H NMR (400 MHz, DMSO-d6): δ 10.01 (s, 1H), 8.11 (d, 1H, J=6.8 Hz), 8.03 (d, 1H, J=6.8 Hz), 7.67 (s, 2H), 7.21 (s, 1H), 4.70-4.64 (m, 4H), 4.40-4.32 (m, 1H), 4.31-4.23 (m, 1H), 3.58 (s, 3H), 2.34-2.26 (m, 2H), 2.18-2.10 (m, 2H), 1.55-1.45 (m, 4H), 1.31 (d, 3H, J=7.2 Hz), 1.21 (d, 3H, J=7.2 Hz).

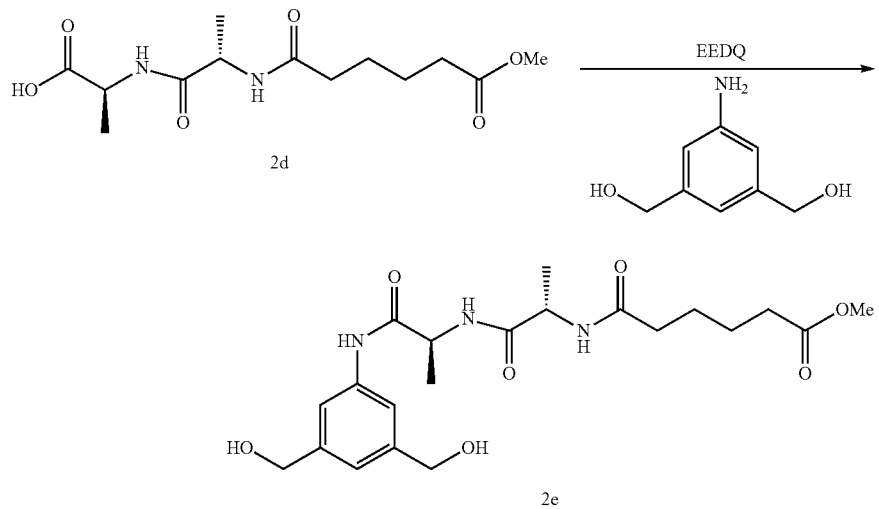

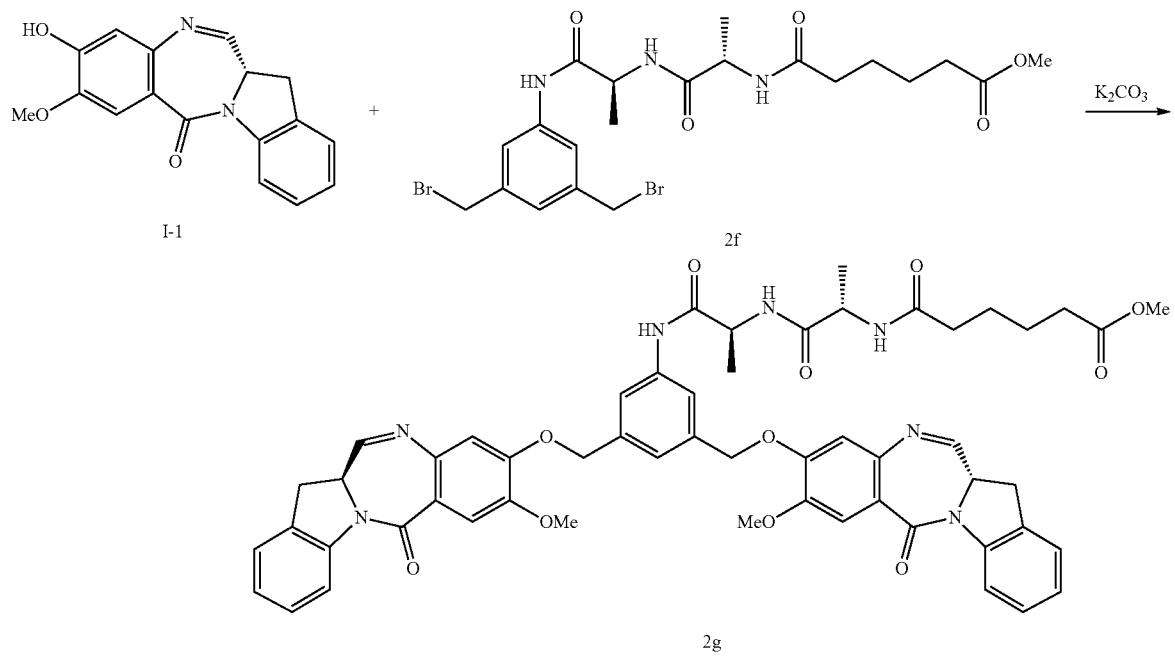

Step 7: Dibromide compound 2f and IGN monomer compound I-1 were dissolved in DMF. Potassium carbonate was added and was stirred at rt overnight. Water was added to the reaction mixture to precipitate the product. The slurry was stirred at rt for 5 min and was then filtered and dried under vacuum/N2 for 1 h. The crude material was purified by silica gel chromatography (dichloromethane/methanol) to give compound 2g (336 mg, 74% yield). LCMS=5.91 min (15 min method). MS (m/z): 990.6 (M+1)+.

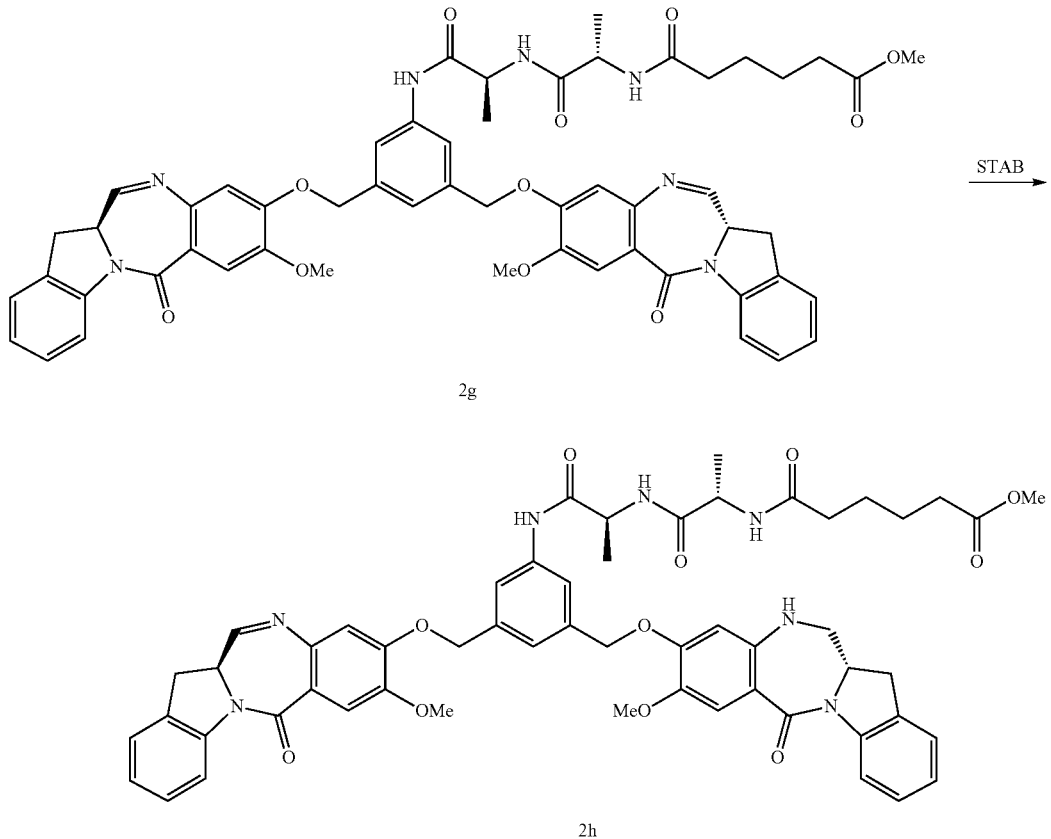

Step 8: Diimine compound 2g was dissolved in 1,2-dichloroethane. NaBH(OAc)$_3$ was added to the reaction mixture and was stirred at rt for 1 h. The reaction was diluted with CH$_2$Cl$_2$ and was quenched with sat'd aq NH$_4$Cl solution. The layers were separated and was washed with brine, dried over Na$_2$SO$_4$ and concentrated. The crude material was purified via RPHPLC (C18 column, Acetonitrile/Water) to give compound 2h (85.5 mg, 25% yield). LCMS=6.64 min (15 min method). MS (m/z): 992.6 (M+1)$^+$.

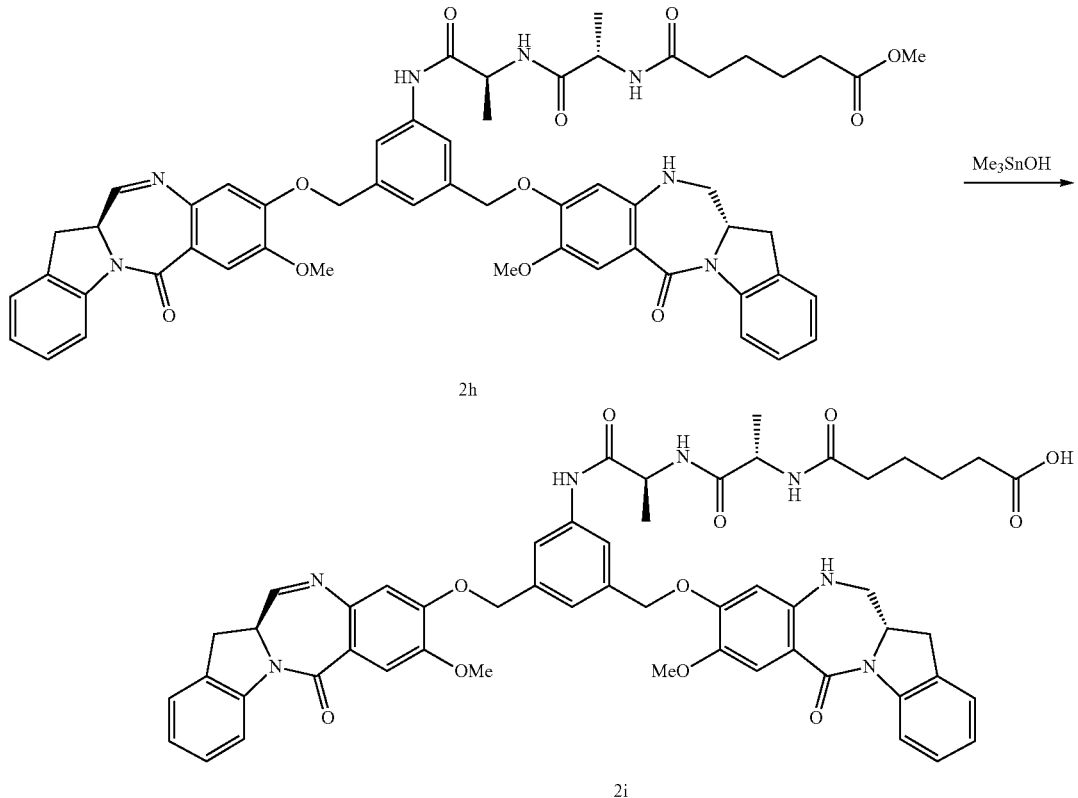

2h

2i

Step 9: Methylester compound 2h was dissolved in 1,2-dichloroethane. Trimethylstannanol was added to the reaction mixture and was heated at 80° C. overnight. The reaction mixture was cooled to rt and was diluted with water. The aqueous layer was acidified to pH ~4 with 1 M HCl. The mixture was extracted with CH$_2$Cl$_2$/MeOH (10:1, 3×20 mL). The combined organic layers were washed with brine and was dried over Na$_2$SO$_4$ and concentrated. The crude material was passed through a silica plug to give compound 2i (48.8 mg, 80% yield). LCMS=5.89 min (15 min method). MS (m/z): 978.6 (M+1)$^+$.

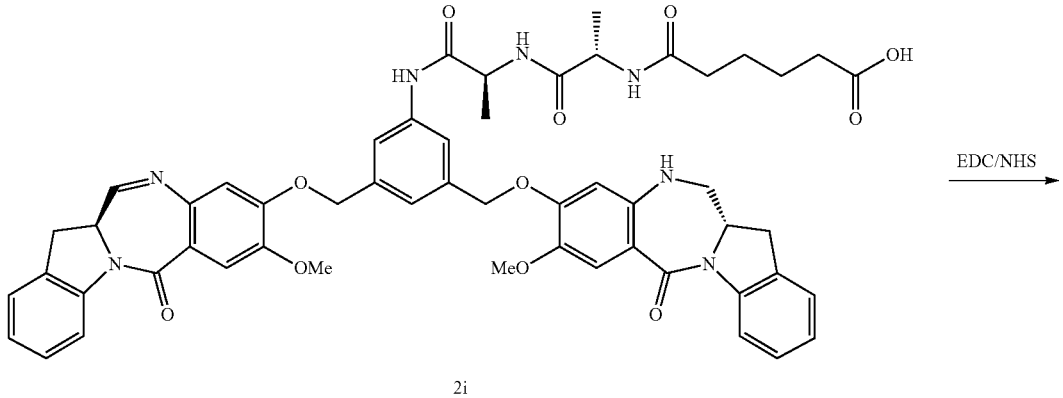

2i

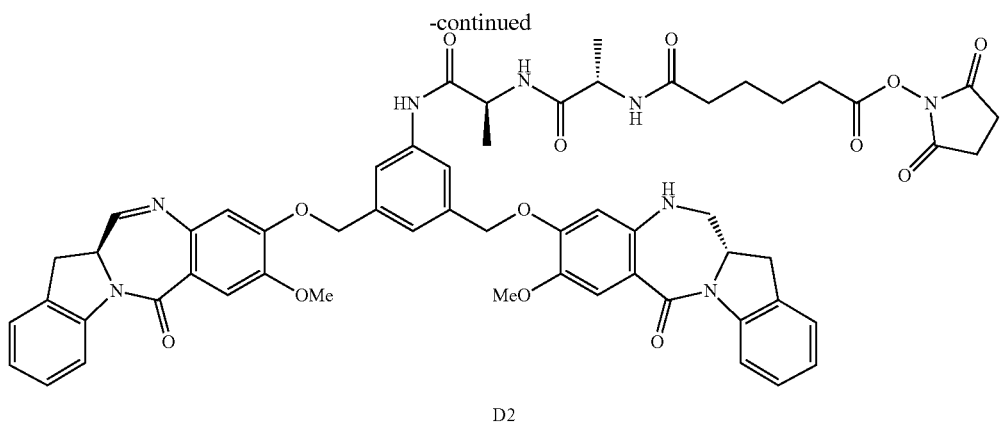

D2

Step 10: EDC·HCl was added to a stirred solution of acid compound 2i and N-hydroxysuccinamidein $CH_2Cl_2$ at rt. The reaction mixture was stirred for 2 h. The reaction mixture was diluted with $CH_2Cl_2$ and was washed with water (1×15 mL) and brine (1×15 mL). The organic layer was dried over $Na_2SO_4$, filtered and concentrated. The crude material was purified via RPHPLC ($C_{18}$ column, Acetonitrile/Water) to give 2,5-dioxopyrrolidin-1-yl 6-(((S)-1-(((S)-1-((3-((((S)-8-methoxy-6-oxo-11,12,12a,13-tetrahydro-6H-benzo[5,6][1,4]diazepino[1,2-a]indol-9-yl)oxy)methyl)-5-((((R)-8-methoxy-6-oxo-12a,13-dihydro-6H-benzo[5,6][1,4]diazepino[1,2-a]indol-9-yl)oxy)methyl) phenyl)amino)-1-oxopropan-2-yl)amino)-1-oxopropan-2-yl)amino)-6-oxohexanoate, compound D2 (8.2 mg, 30% yield). LCMS=6.64 min (15 min method). MS (m/z): 1075.4 $(M+1)^+$.

Example 18. Synthesis of N-(2-(2,5-dioxo-2,5-dihydro-1H-pyrrol-1-yl)ethyl)-11-(3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)-13,13-dimethyl-2,5,8-trioxa-14,15-dithia-11-azanonadecan-19-amide, Compound D6

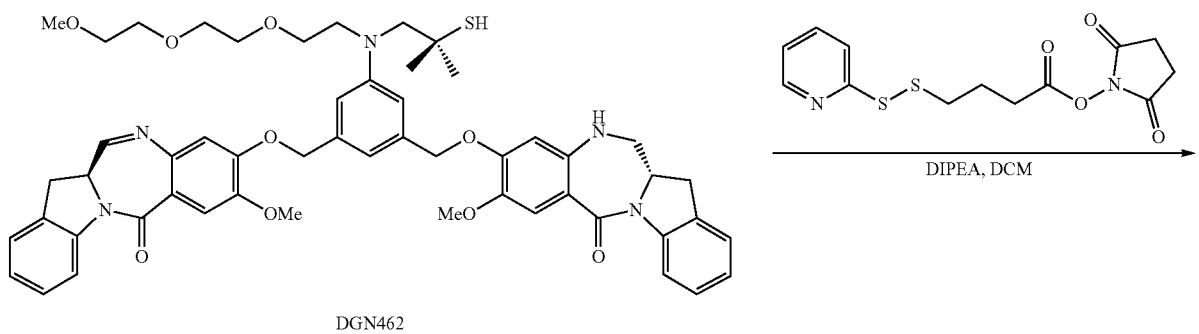

DGN462

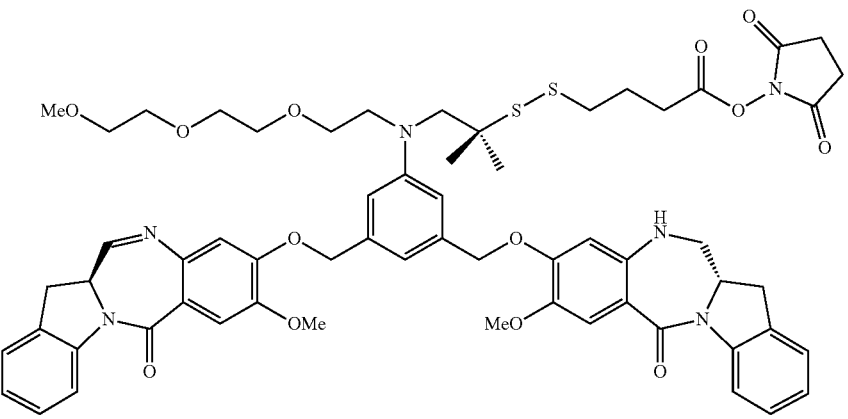

6a

Step 1: To a solution of the free thiol DGN462 (40 mg, 0.042 mmol) and NHS 4-(2-pyridyldithio)butanate (35 mg, 80% purity, 0.085 mmol) in anhydrous dichloromethane (0.5 mL) was added anhydrous diisopropylethylamine (0.015 mL, 0.085 mmol) and was stirred at room temperature for 16 hours. The reaction mixture was quenched with saturated ammonium chloride and diluted with dichloromethane. The obtained mixture was separated in a separatory funnel. The organic layer was washed with brine, dried over anhydrous sodium sulfate, filtered and stripped under reduced pressure. The residue was purified by semi-preparative reverse phase HPLC (C18 column, $CH_3CN/H_2O$). The fractions that contained pure product were combined, frozen and lyophilized to give the desired NHS ester, compound 6a (29.7 mg, 60% yield). LCMS=9.1 min (15 min method). MS (m/z): 1157.3 $(M+1)^+$.

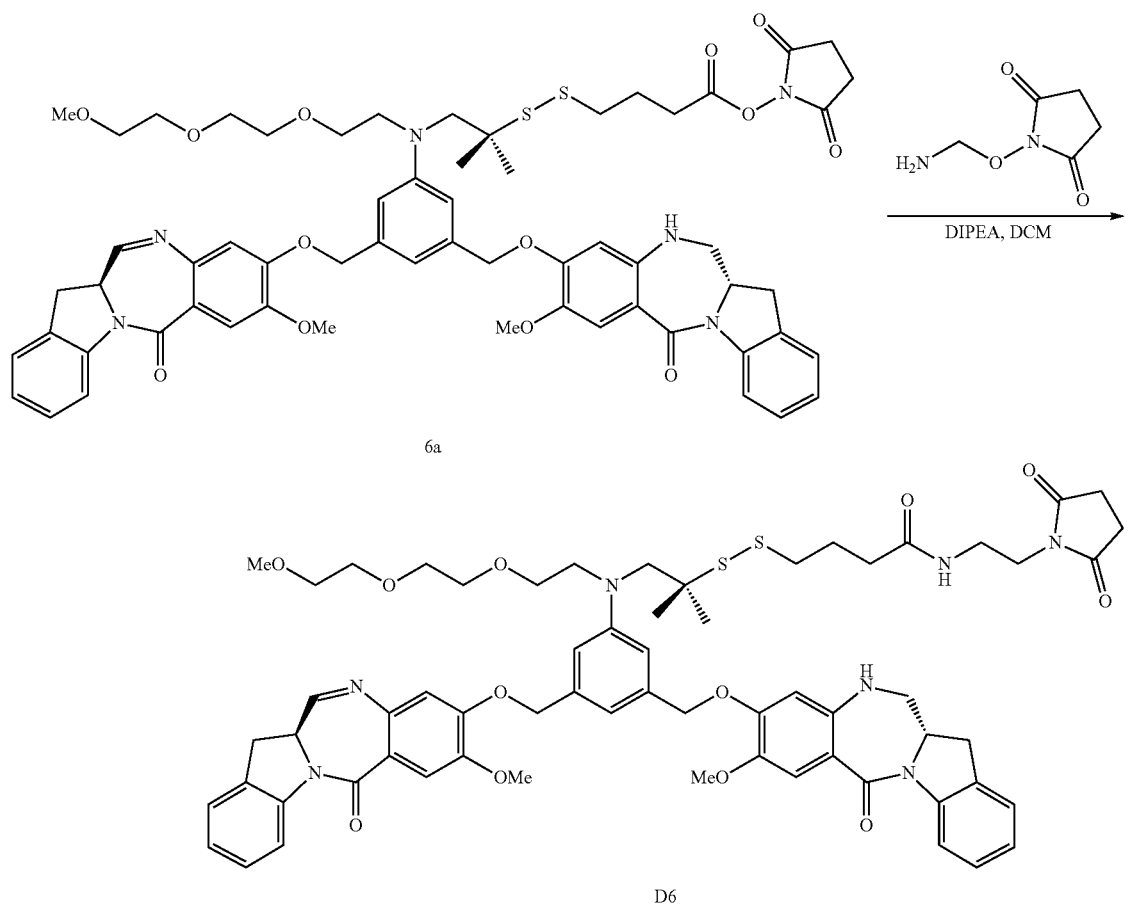

6a

D6

Step 2: To a solution of the NHS ester, compound 6a (12.3 mg, 0.011 mmol) and N-(2-aminoethyl)maleimide hydrochloride (2.0 mg, 0.011 mmol) in anhydrous dichloromethane (0.3 mL) was added DIPEA (0.0022 mL, 0.013 mmol). The mixture was stirred at room temperature for 3 hours then it was stripped under reduced pressure. The residue was purified by semi-preparative reverse phase HPLC (C18 column, $CH_3CN/H_2O$). The fractions that contained pure product were combined, frozen and lyophilized to give the desired maleimide, compound D6 (10 mg, 80% yield). LCMS=8.3 min (15 min method). MS (m/z): 1181.8 $(M+1)^+$.

Example 19. Synthesis of N1-(2-(2,5-dioxo-2,5-dihydro-1H-pyrrol-1-yl)ethyl)-N6-((S)-1-(((S)-1-((3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)amino)-1-oxopropan-2-yl)amino)-1-oxopropan-2-yl)adipamide, compound D5

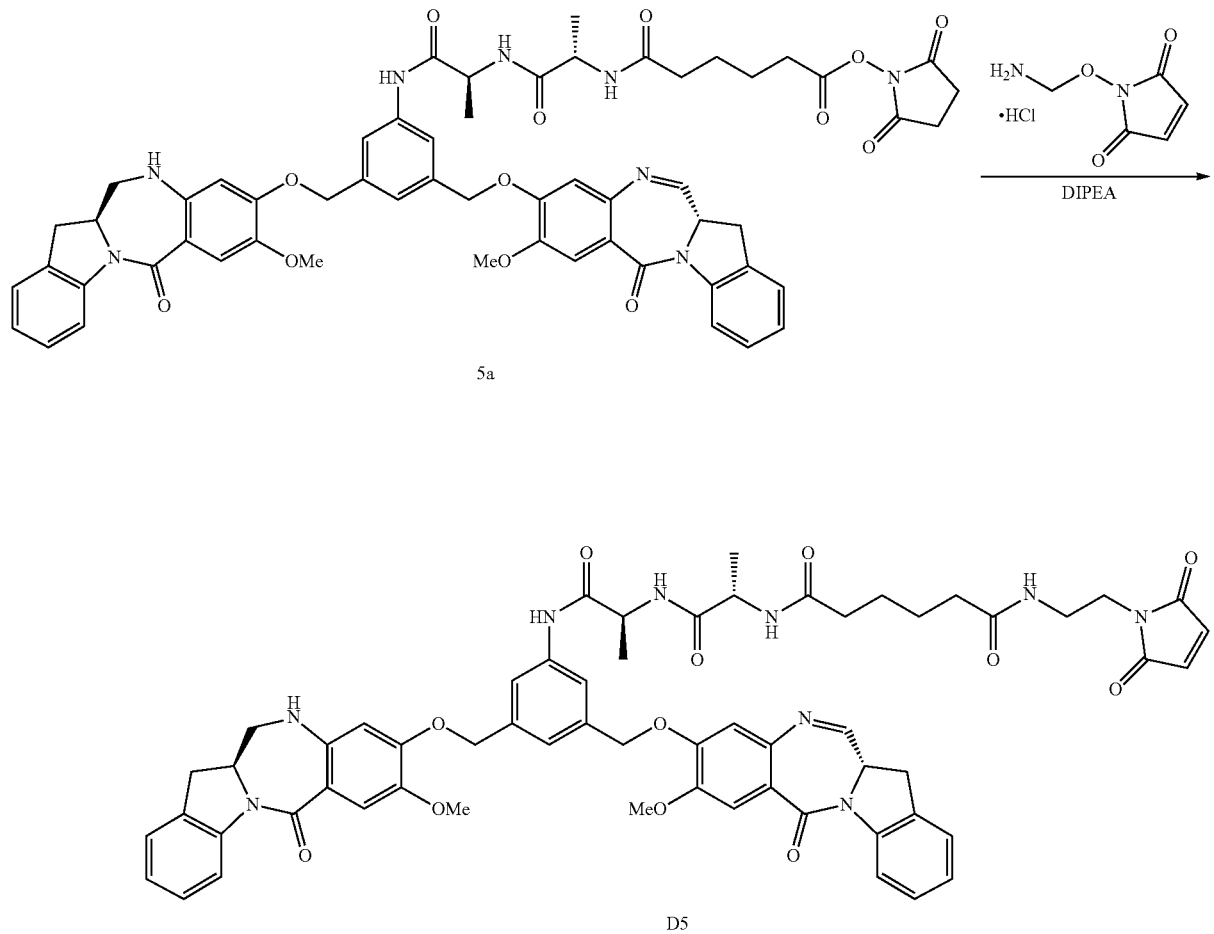

NHS ester, compound 5a (8.2 mg, 7.6 µmol) and 1-(2-aminoethyl)-1H-pyrrole-2,5-dione hydrochloride (2.2 mg, 0.011 mmol) were dissolved in anhydrous dichloromethane (305 µL) at room temperature. DIPEA (2.66 µL, 0.015 mmol) was added and the reaction and was stirred for 3.5 hours. The reaction mixture was concentrated and was purified by RPHPLC (C18 column, $CH_3CN/H_2O$, gradient, 35% to 55%). The desired product fractions were frozen and lyophilized to give maleimide, compound D5 as a solid white powder (5.3 mg, 58% yield). LCMS=5.11 min (8 min method). MS (m/z): 1100.6 $(M+1)^+$.

Example 20. Synthesis of 1-((2-(2,5-dioxo-2,5-dihydro-1H-pyrrol-1-yl)ethyl)amino)-4-((5-((3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)amino)-2-methyl-5-oxopentan-2-yl)disulfanyl)-1-oxobutane-2-sulfonic acid, Compound D4

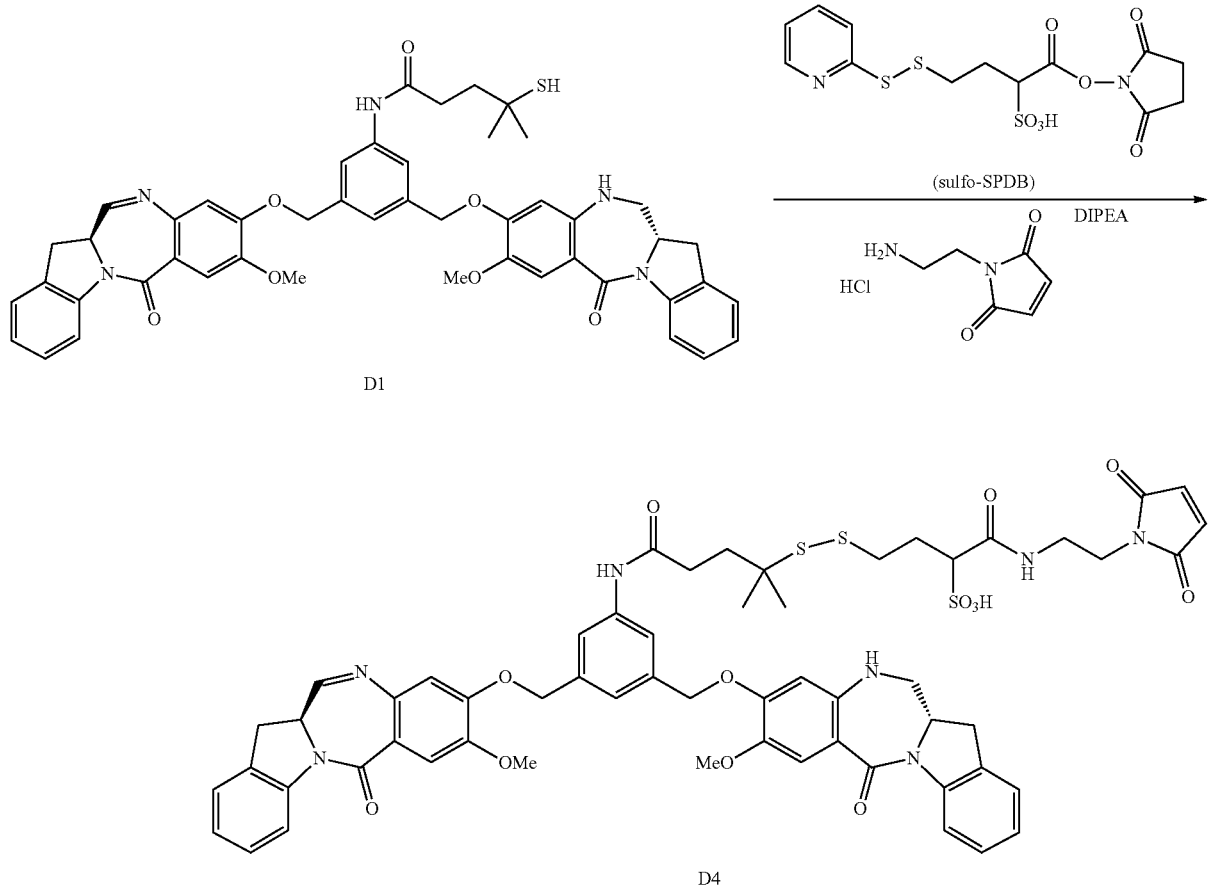

To a suspension of the free thiol, D1 (88 mg, 0.105 mmol) and 1-((2,5-dioxopyrrolidin-1-yl)oxy)-1-oxo-4-(pyridin-2-yldisulfanyl)butane-2-sulfonic acid (sulfo-SPDB) (64.0 mg, 0.158 mmol) in anhydrous dichloromethane (2.10 mL) was added DIPEA (55.0 µL, 0.315 mmol) under nitrogen at room temperature. The mixture stirred for 16 hours and then 1-(2-aminoethyl)-1H-pyrrole-2,5-dione hydrochloride (55.6 mg, 0.315 mmol), anhydrous dichloromethane (1.0 mL) and DIPEA (0.055 mL, 0.315 mmol) were added. The mixture stirred for an additional 5 hours at room temperature upon which the reaction was concentrated in vacuo. The resulting residue was purified by RP-HPLC (C18, CH$_3$CN/H$_2$O). Fractions containing desired product were frozen and lyophilized to give maleimide, D4 (20 mg, 16% yield) as a white solid. LCMS=4.92 min (8 min method). MS (m/z): 1158.6 (M+1)$^+$.

Example 21. Synthesis of N-(2-(2,5-dioxo-2,5-di-hydro-1H-pyrrol-1-yl)ethyl)-11-(3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)-2,5,8-trioxa-11-azapentadecan-15-amide, compound D7

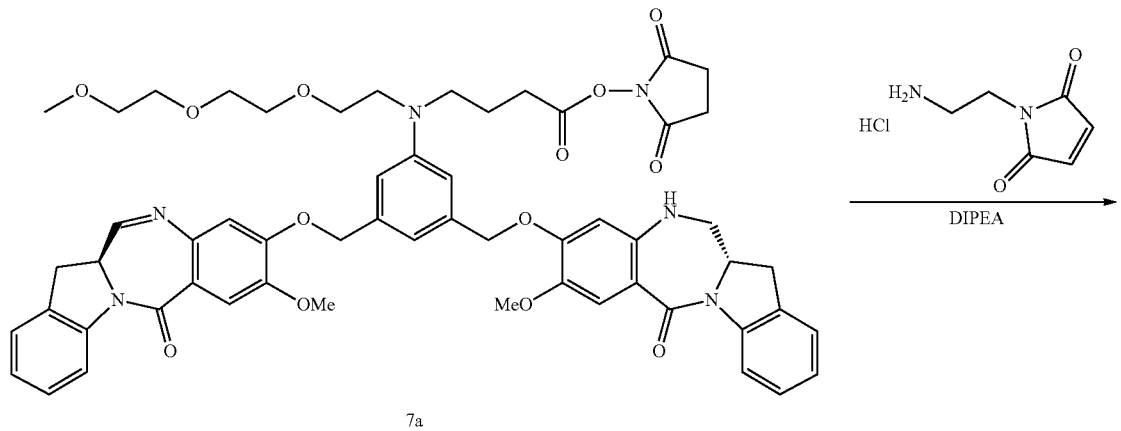

To a solution of NHS ester, 7a (5 mg, 4.82 μmol) and 1-(2-aminoethyl)-1H-pyrrole-2,5-dione hydrochloride (1.7 mg, 9.64 μmol) in anhydrous dichloromethane (200 μL) was added DIPEA (1.512 μL, 8.68 μmol) under nitrogen. The mixture was stirred at room temperature for 4 hours and then concentrated in vacuo. The resulting residue was purified by RP-HPLC (C18, CH$_3$CN/H$_2$O). Fractions containing desired product were frozen and lyophilized to give maleimide, compound D7 (3.5 mg, 68% yield). LCMS=4.61 min (15 min method). MS (m/z): 1062.8 (M+1)$^+$.

Example 22. Synthesis of Compound D8

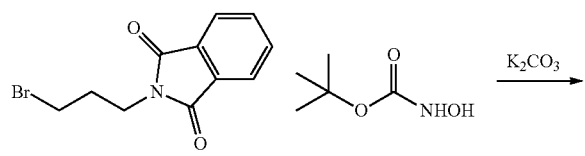

Step 1: Tert-butyl hydroxycarbamate (1.490 g, 11.19 mmol) was dissolved in anhydrous DMF (22.38 mL). 2-(3-bromopropyl)isoindoline-1,3-dione (3 g, 11.19 mmol) and potassium carbonate (3.09 g, 22.38 mmol) were added and the reaction stirred overnight at room temperature. It was diluted with cold water and extracted with EtOAc. The organic was washed with brine, dried over sodium sulfate and the crude residue was purified by silica gel flash chromatography (EtOAc/Hex, gradient, 0% to 45%) to obtain compound 8a as sticky solid (2.41 g, 67% yield). LCMS=4.99 min (8 min method). $^1$H NMR (400 MHz, CDCl$_3$): δ 7.86-7.83 (m, 2H), 7.73-7.77 (m, 2H), 7.28 (bs, 1H), 3.92 (t, 2H, J=6.0 Hz), 3.82 (t, 2H, 6.9 Hz), 2.05-1.98 (m, 2H), 1.47 (s, 9H).

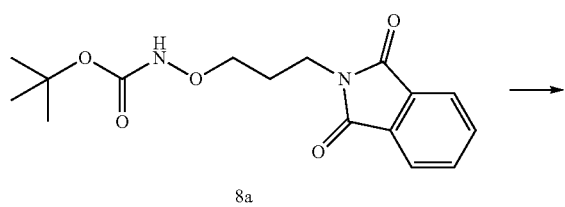

8a

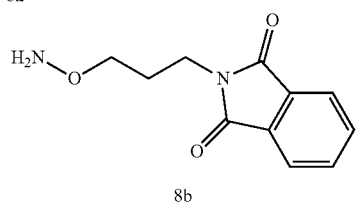

8b

Step 2: Compound 8a (2.41 g, 7.52 mmol) was dissolved in anhydrous DCM (18.81 mL) and cooled to 0° C. in an ice bath. A freshly mixed solution of DCM (9.40 ml) and TFA (9.40 ml) was added and the ice bath was removed. The reaction stirred at room temperature for 1 hour and was diluted with DCM and washed with saturated sodium bicarb. The organic layer was washed with brine, dried, filtered and concentrated to give compound 8b (1.32 g, 80% yield). The crude material was used without further purification. $^1$H NMR (400 MHz, CDCl$_3$): δ 7.85-7.82 (m, 2H), 7.72-7.69 (m, 2H), 3.78 (t, 2H, J=7.0 Hz), 3.72 (t, 2H, 6.0 Hz), 1.99-1.93 (m, 2H).

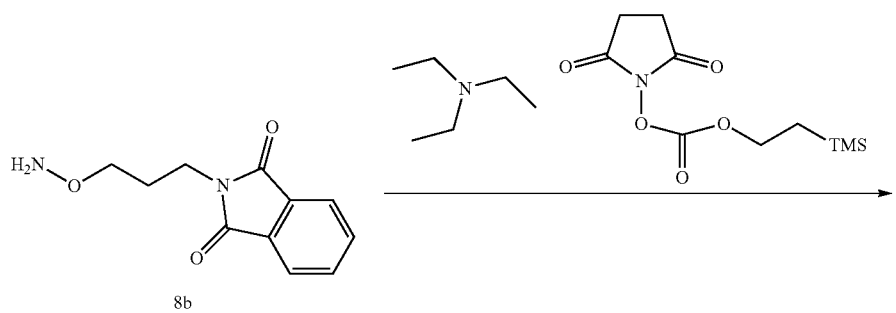

8b

8c

Step 3: Compound 8b (100 mg, 0.454 mmol) was dissolved in anhydrous DCM (4.5 mL) TEA (127 μl, 0.908 mmol) and 2,5-dioxopyrrolidin-1-yl (2-(trimethylsilyl)ethyl) carbonate (177 mg, 0.681 mmol) were added and the reaction stirred at room temperature overnight. The reaction was diluted with DCM, washed with brine, dried, filtered, and evaporated. The crude residue was purified by silica gel flash chromatography (EtOAc/Hex, gradient, 0% to 40%) to obtain compound 8c (148 mg, 89% yield). LCMS=5.91 min (8 min method). $^1$H NMR (400 MHz, CDCl$_3$): δ 7.86-7.83 (m, 2H), 7.73-7.69 (m, 2H), 7.39 (bs, 1H), 4.26-4.20 (m, 2H), 3.94 (t, 2H, J=6.0 Hz), 3.83 (t, 2H, 6.9 Hz), 2.06-1.98 (m, 2H), 1.05-0.98 (m, 2H), 0.04 (s, 9H).

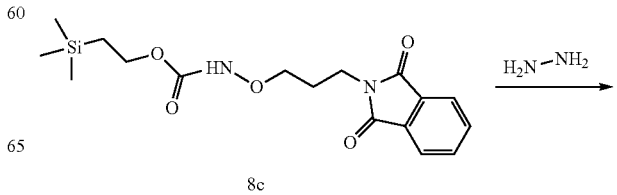

8c

-continued

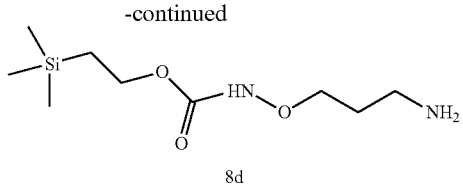

8d

Step 4: Compound 8c (148 mg, 0.406 mmol) was dissolved in Ethanol (2.7 mL) and stirred until completely soluble. Hydrazine (63.7 µl, 2.030 mmol) was added and the reaction stirred at room temperature until rapid formation of a white precipitate at 1 hour. The reaction was filtered through celite and rinsed with additional ethanol. The filtrate was evaporated and purified by silica gel flash chromatography (A=MeOH, B=EtOAc gradient, 100% to 10%). Product fractions were detected by mass and evaporated to give compound 8d as a sticky solid (67.5 mg, 71% yield). $^1$H NMR (400 MHz, CDCl$_3$): δ 4.27-4.21 (m, 2H), 3.98 (t, 2H, J=5.9 Hz), 2.92-2.87 (m, 2H), 1.85-1.77 (m, 2H), 1.06-0.99 (m, 2H), 0.04 (s, 9H).

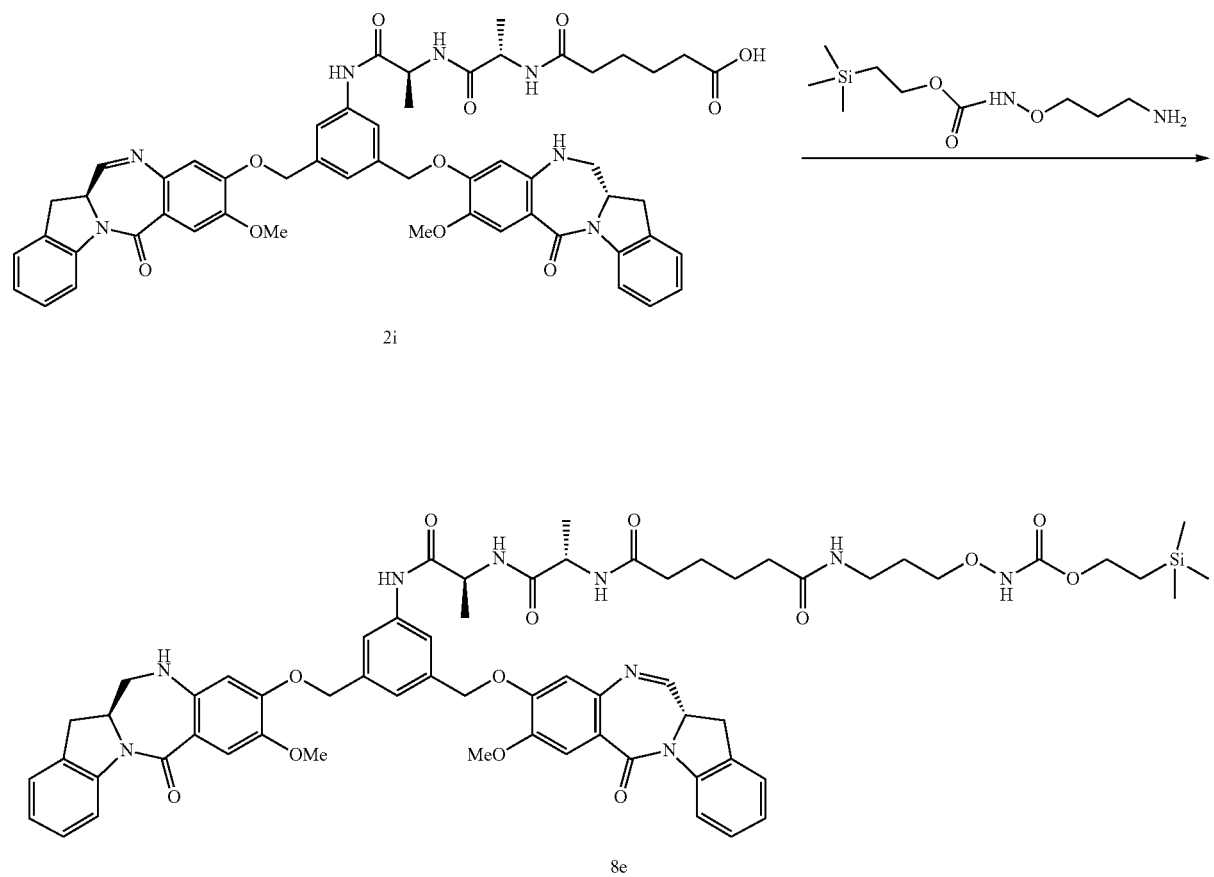

Step 5: Compound 2i (30 mg, 0.031 mmol) described above in Example 17 was suspended in anhydrous DCM (613 µl). Anhydrous DMF was added dropwise until the solution cleared. Compound 8d (21.57 mg, 0.092 mmol), EDC·HCl (29.4 mg, 0.153 mmol), and DMAP (0.749 mg, 6.13 µmol) were added and the reaction stirred at room temperature for 1 hour. It was diluted with DCM/MeOH 10:1 and then washed with water. The aqueous layer was extracted with DCM/MeOH 10:1 and the combined organic was dried and concentrated to give Compound 8e (49 mg) which was used without further purification. LCMS=5.94 min (8 min method). MS (m/z): 1194.4 (M+1)$^+$.

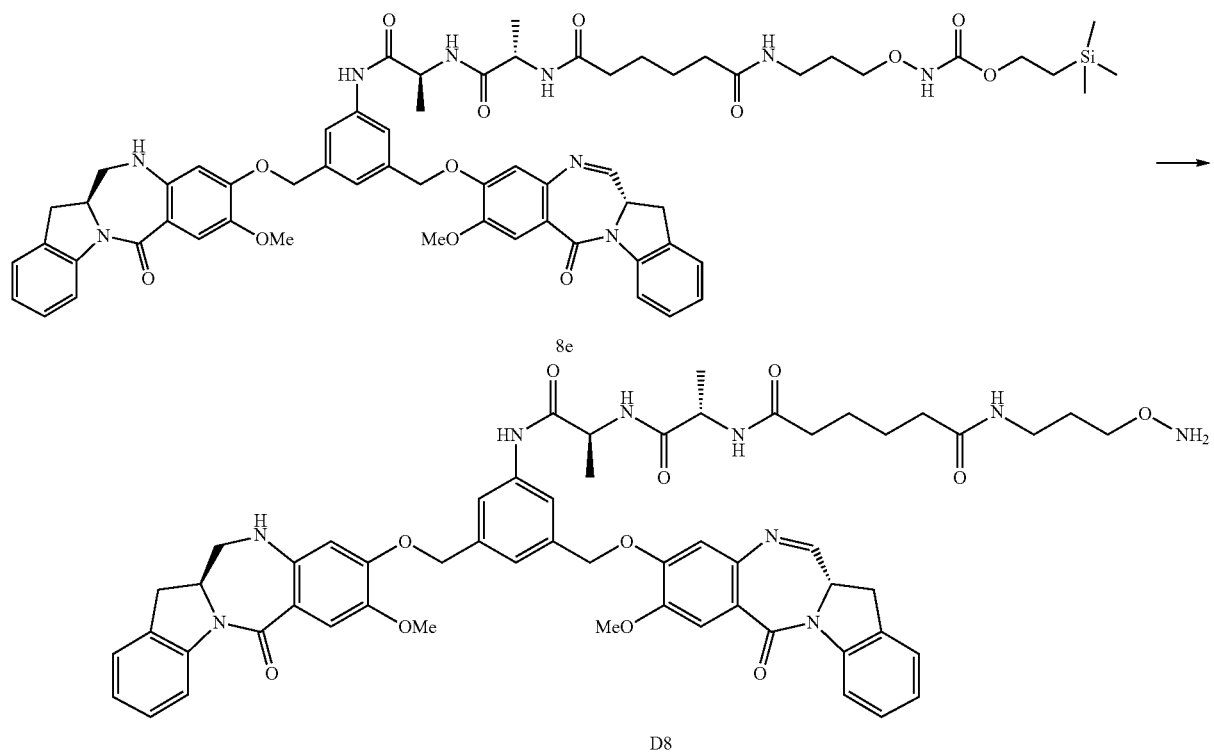

Step 6: Compound 8e (49 mg, 0.041 mmol) was dissolved in THF (820 μl) and the reaction was cooled to 0° C. in an ice bath. TBAF (205 μl, 0.205 mmol) was added and the reaction stirred for 15 minutes before the ice bath was removed. It was stirred at room temperature until completion. The reaction was cooled to 0° C., quenched with saturated ammonium chloride and extracted with DCM/ MeOH 10:1. The organic was washed with brine, dried with sodium sulfate and evaporated. The crude material was purified via RPHPLC (C18 column, Acetonitrile/Water) to give compound D8 (17.6 mg, 54% yield over 2 steps). LCMS=5.1 min (8 min method). MS (m/z): 1050.4 (M+1)$^+$.

Example 23. Synthesis of Compound D9

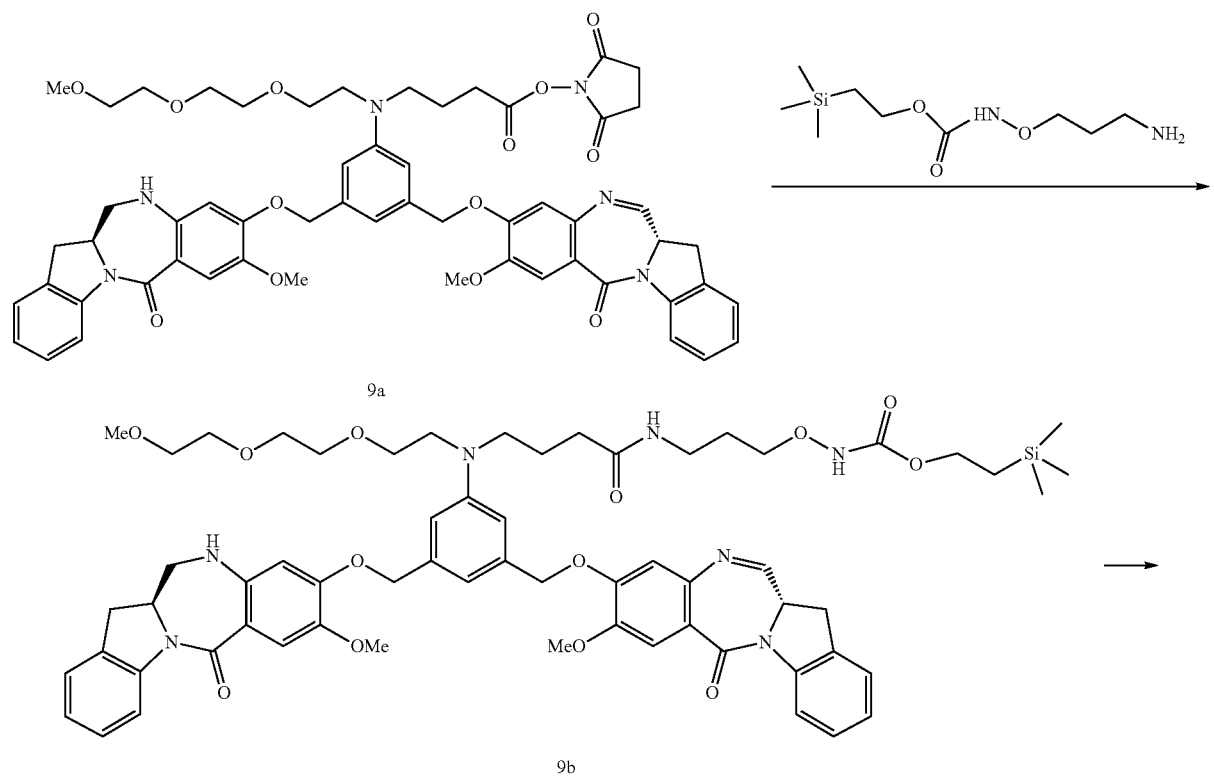

-continued

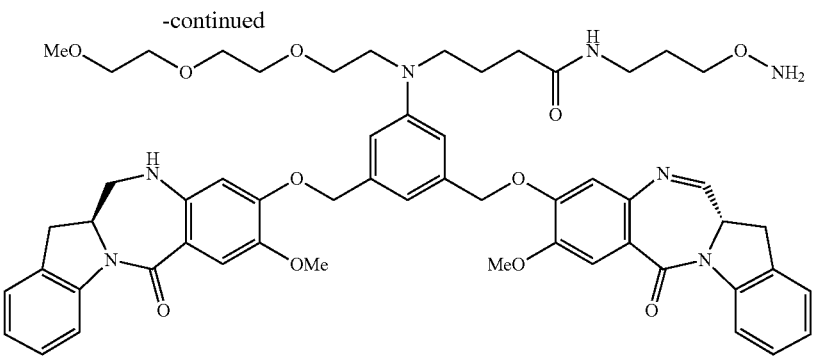

D9

Step 1: Compound 9a (17 mg, 0.016 mmol) was dissolved in DCM (328 μl). Compound 8d (5.76 mg, 0.025 mmol) and DIPEA (5.71 μl, 0.033 mmol) were added at room temperature and the reaction stirred until completion. It was diluted with 10:1 DCM:MeOH and washed with brine. The organic was dried and concentrated to give compound 9b which was used directly.

Step 2: Compound D9 was prepared similarly as compound D8 in Example 23. The crude material was purified via RPHPLC (C18 column, Acetonitrile/Water) to give compound D9 (5 mg, 31% yield over 2 steps). LCMS=5.68 min (8 min method). MS (m/z): 1012.5 (M+1)$^+$.

Example 24. In Vivo Efficacy of huCD123-CysMab-D5 in Kasumi-3-Luc-mCh-Puro Disseminated Model To test the efficacy of huCD123-CysMab-D5 for the ability to decrease disseminated tumor burden in vivo, a luciferase-expressing disseminated tumor model was used in combination with live animal imaging, as described in the protocol below.

Female NSG mice (Jackson Labs) were each injected intravenously (IV) in the tail vein with 5×10$^6$ Kasumi-3-Luc-mCh-Puro cells, a human AML cell line engineered to express luciferase and mCherry (at Molecular Imaging, Ann Arbor, MI). Luciferase expression by the Kasumi-3 cells allows tumor burden to be quantified using a live animal imager, which detects the bioluminescence signal produced by the luciferase upon exposure in vivo to the injected luciferase substrate, D-luciferin. On day 6 post-inoculation, the mice were imaged and randomized into the study groups based on bioluminescent imagining (BLI). At 24 h prior to each administration of conjugate, the mice were injected intraperitoneally (IP) with 400 mg/kg of non-targeted chKTI antibody to block Fc receptors on the Kasumi-3 AML cells, preventing non specific up-take of conjugate. On days 7 and 41 post-Kasumi-3 inoculation, the mice received single IV injections in the lateral tail vein of either vehicle, 10 μg/kg (by D5; 0.80 mg/kg by huCD123) huCD123-CysMab-D5, 3 μg/kg (by D5; 0.240 mg/kg by huCD123) huCD123-CysMab-D5 or 10 μg/kg of a non-targeted KTI-CysMab-D5 control conjugate. On days 5 and 10 post-conjugate administration, the mice received an IP injection of 100 mg/kg of non-targeted chKTI antibody to ensure continued blocking of Fc receptors on the AML tumor cells.

The mice were imaged on days 11, 13, 17, 20, 24, 27, 31, 38, 41, 45, 52, 59, 66, 73 and 80 post-Kasumi-3 inoculation. In vivo bioluminescence imaging was performed at Molecular Imaging (Ann Arbor, MI) using an IVIS 50 optical imaging (Xenogen, Alameda, CA). Animals were imaged three at a time under ~1-2% isoflurane gas anesthesia. Each mouse was injected IP with 150 mg/kg D-luciferin (luciferase substrate) and imaged in the prone, then supine positions, 10 minutes after the injection. Large to small binning of the CCD chip was used, and the exposure time was adjusted (2 seconds to 2 minutes) to obtain at least several hundred counts from the tumors that are observable in each mouse in the image and to avoid saturation of the CCD chip. Images were analyzed using Matlab R2015a. A custom script placed whole body fixed-volume ROIs on prone and supine images for each individual animal, and labeled based on animal identification. Total flux (photons/sec) was calculated and exported for all ROIs to facilitate analyses between groups. The prone and supine ROIs were summed together to estimate whole body tumor burden.

% T/C was calculated as follows=[(T, median BLI of treated group)/(C, median BLI of control group)]×100%. According to NCI standards, a T/C≤42% is the minimum level of anti-tumor activity, while a T/C value of >42% is inactive, and a T/C value of <10% is considered highly active.

% Tumor Burden Delay (% TBD) was calculated as follows: % TBD=(T−C)/C×100%, where T−C, where T is the time (in days) for the treated group and C is the time (in days) for the control group, to achieve the designated BLI signal. Adapting the same metrics applied to % ILS, we consider % TBD>25 as minimally active, % TBD>40 as active, and % TBD>50 as highly active.

The mice were weighed twice a week and were monitored for clinical signs throughout the duration of the study. Any mice reaching euthanasia criteria were euthanized. Spontaneous deaths were recorded as they were discovered. The study was ended on day 115 post-tumor cell inoculation.

Figure 22:
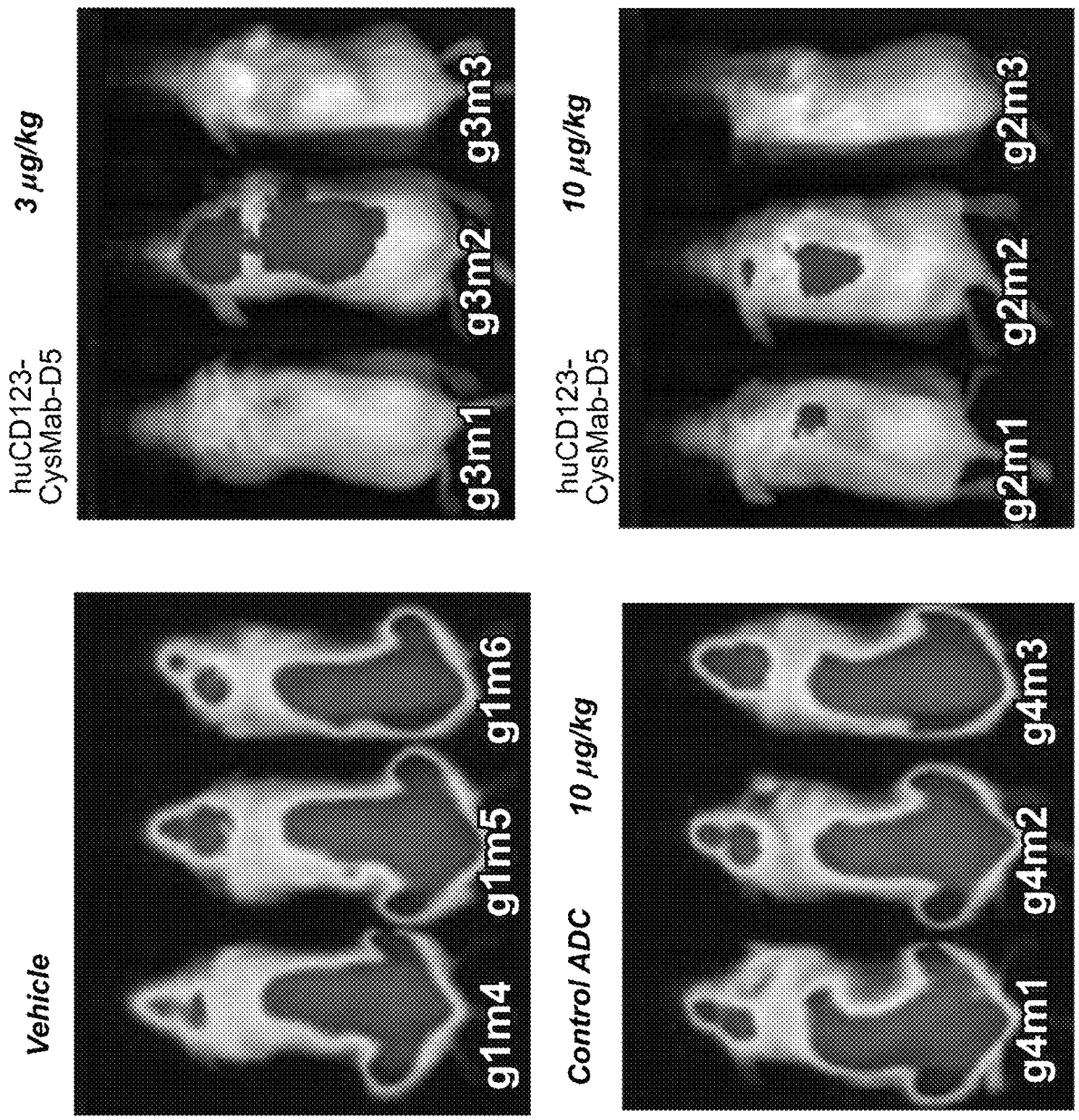
FIG. 22 shows in vivo bioluminescence imaging of mice treated with huCD123-6Gv4.7-CysMab-D5 conjugate as compared to mice treated with vehicle and control on day 26. Treatment with the conjugate significantly reduces tumor burden in mice.

Preliminary experiments show that treatment with either dose of huCD123-CysMab-D5 caused an initial regression of tumor burden over time, reaching a nadir on day 27, while tumor burden increased steadily in the vehicle- and KTI-CysMab-D5-treated groups during this period of time. See, for example, FIG. 22. The tumor growth inhibition (T/C value) calculated for these preliminary experiments showed that 10 μg/kg and 3 μg/kg of huCD123-CysMab-D5 are highly active at day 27, with % T/C values of 0.20 and 0.25, respectively. The % Tumor Burden Delay (% TBD) was also calculated, using the BLI signal at day 45 of the vehicle-treated group as the designated BLI. According to this metric, both doses of huCD123-CysMab-D5 are highly active, resulting in % TBD of >75% (10 μg/kg huCD123-

Figure 23:
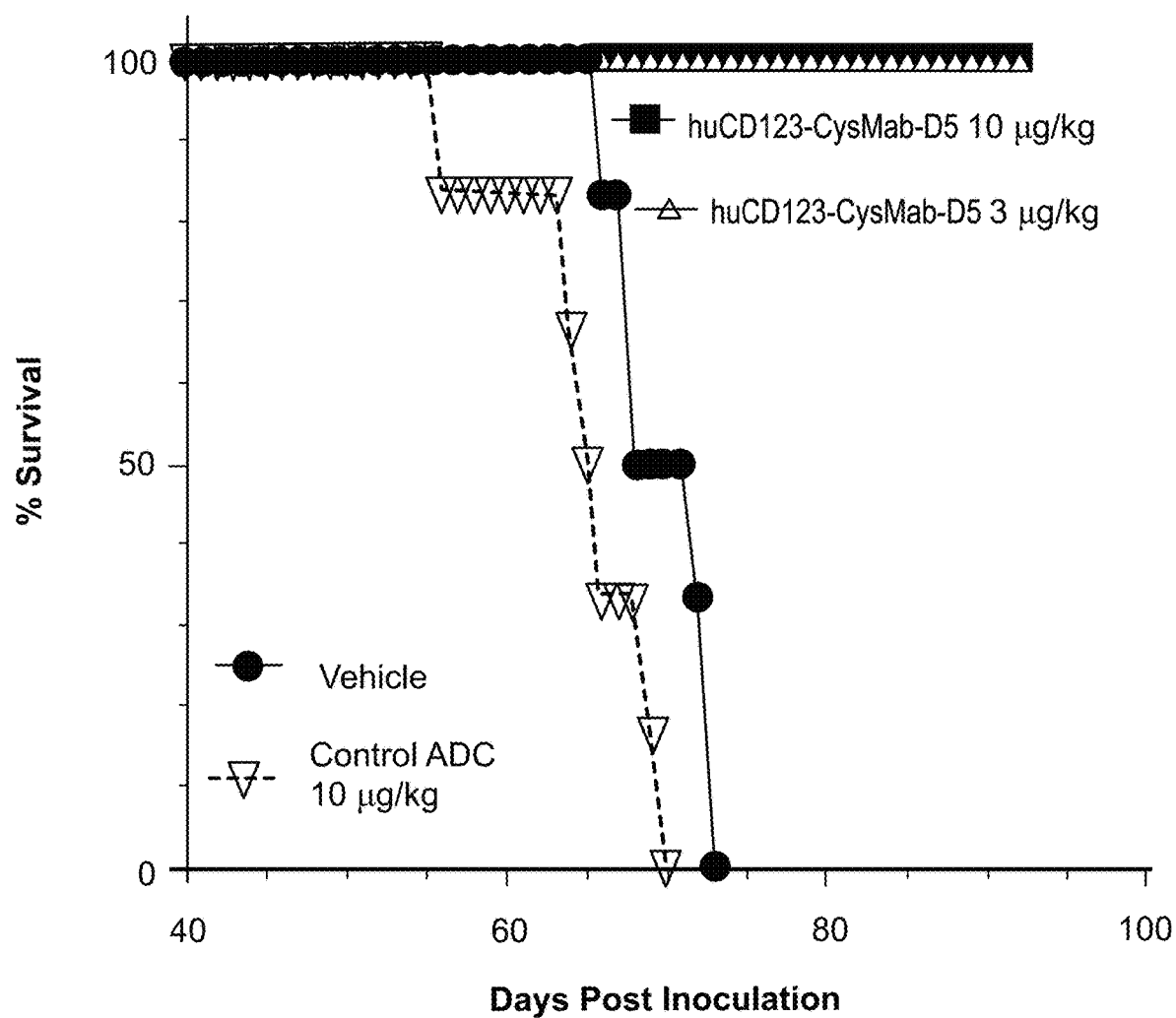
FIG. 23 shows treatment with huCD123-6Gv4.7-CysMab-D5 conjugate extended survival in 6/6 mice as compared to mice treated with vehicle and control.

CysMab-D5) and >65% (3 µg/kg huCD123-CysMab-D5), in contrast to 0% TBD seen with 10 µg/kg of the KTI-CysMab-D5 control conjugate. In addition, treatment with huCD123-CysMab-D5 at both 3 µg/kg and 10 µg/kg doses extended survival in 6/6 mice with P53 mutated and multidrug resistant AML as compared to control (see FIG. 23).

Figure 31:
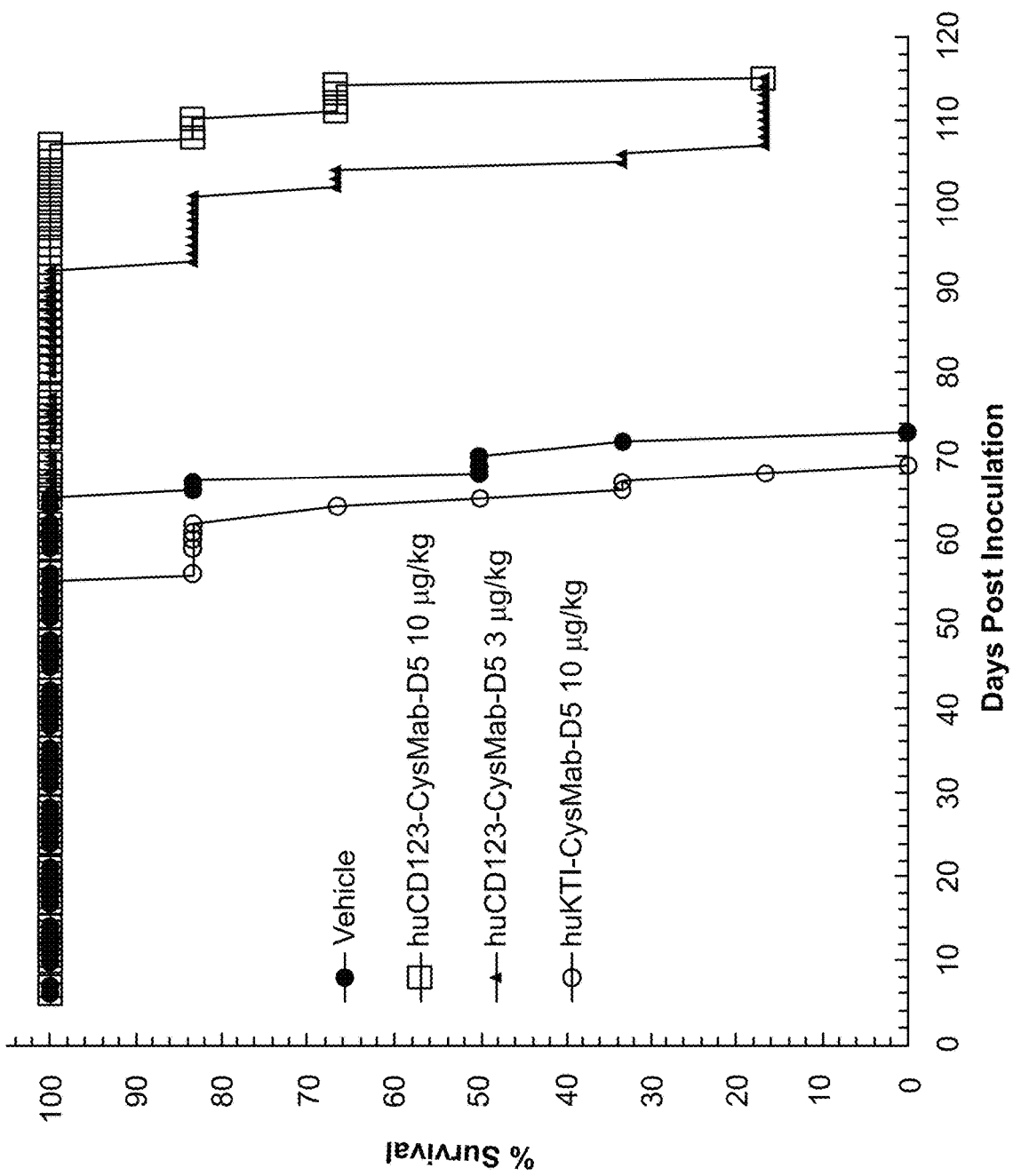
FIG. 31 shows treatment with huCD123-CysMab-D5 conjugate extended survival in mice as compared to mice treated with vehicle and control.

The survival for each of the four study groups at the end of the study is presented in FIG. 31 and is summarized in the table below. Mice treated with vehicle had a median survival of 70 days. In contrast, mice treated with 10 µg/kg (by D5, 0.80 mg/kg by huCD123) of huCD123-CysMab-D5 had a median survival of 115 days, resulting in a 64% ILS (highly active). Likewise, mice treated with 3 µg/kg (by D5, 0.240 mg/kg by huCD123) of huCD123-CysMab-D5 had a median survival time of 105 days, resulting in a 50% ILS (highly active). Mice treated with 10 µg/kg (by D5) of huKTI-CysMab-D5 non-targeted control conjugate had a median survival of 65.5 days, which generated a 0% ILS (inactive), indicating the high activity obtained with huCD123-CysMab-D5 is CD123-dependent.

| Group | Treatment | Dose (µg/kg D5) | Dose (mg/kg huCD123) | Median Survival (Days) | T-C | % ILS | Activity |
|---|---|---|---|---|---|---|---|
| 1 | Vehicle | — | — | 70 | — | — | — |
| 2 | huCD123-CysMab-D5 | 10 | 0.80 | 115 | 45 | 64 | Highly Active |
| 3 | huCD123-CysMab-D5 | 3 | 0.240 | 105 | 35 | 50 | Highly Active |
| 4 | huKTI-CysMab-D5 | 10 | 0.80 | 65.5 | 0 | 0 | Inactive |

For N=6, the media survival (days) is the mean of the days when the $3^{rd}$ and $4^{th}$ mice are lost. Using the median survival values, the % ILS (Increased Life Span) is calculated as: % ILS=(T−C)/C×100%, where T is the media survival (in days) of the treated group and C is the median survival (in days) of the control group. NCI standards for disseminated models are: ILS≥25% is minimally active, ILS>40% is active, and ILS≥50% is highly active.

Figure 24:
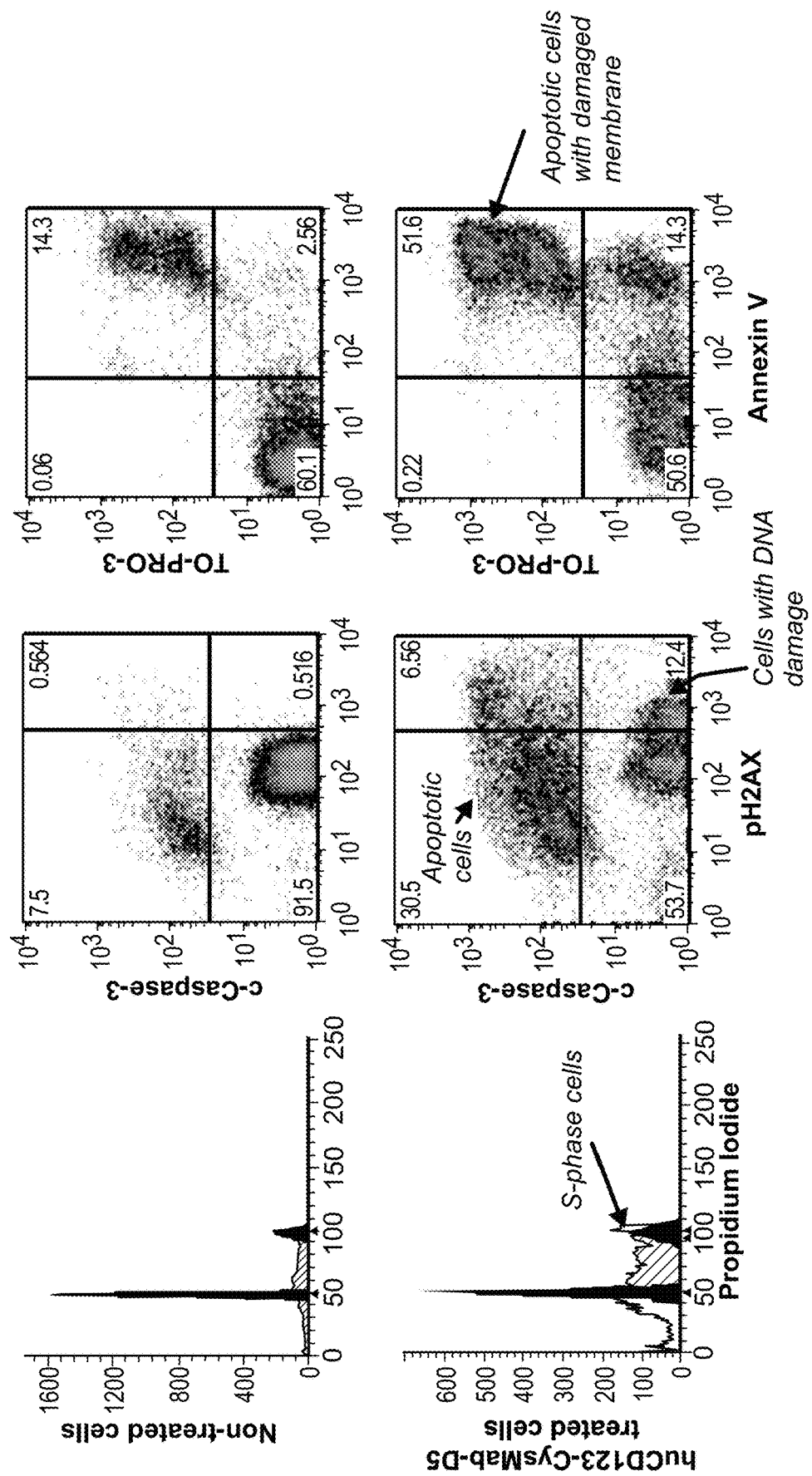
FIG. 24 shows that the incubation of MV4-11 cells with huCD123-6Gv4.7-CysMab-D5 conjugate leads to DNA damage, arrest in S-phase of the cell cycle, and apoptosis-mediated cell death.

Example 25. huCD123-CysMab-D5 Conjugate Induces DNA Damage Leading Cell Cycle Arrest in S-phase and Apoptosis-Mediated Cell Death of MV4-11 Cells To evaluate the mechanism of the huCD123-CysMab-D5-mediated cell death, CD123-expressing MV4-11 AML cells were treated with 10 nM of huCD123-CysMab-D5 for one hour, followed by an additional incubation in a conjugate-free culture medium for 48 hours at 37° C. Untreated MV4-11 cells were used as a control. The cells were harvested and stained with various reagents to quantify the number of cells in different stages of the cell cycle (propidium iodide), cells with DNA damage (pH2AX), apoptosis (Annexin-V and cleaved Caspase-3) and perforated plasma membrane (TO-PRO-3). As demonstrated in FIG. 24, incubation of MV4-11 cells with huCD123-CysMab-D5 leads to DNA damage, arrest in S-phase of the cell cycle, and apoptosis-mediated cell death.

Example 26. In Vivo Efficacy of huCD123-CysMab-D5 in Molm-13 Disseminated Model Data collection and analysis for all disseminated models: The mice were weighed twice a week and were monitored for clinical signs throughout the duration of the study. The measured end-point was survival. Animals were euthanized when hind leg paralysis was present, body weight decreased by >20% of pre-treatment weight, a visible tumor appeared, or any signs of distress were visible. Spontaneous deaths were recorded when they were discovered. For disseminated models, Tumor Growth Delay is calculated as T−C, where T is the median survival time (in days) of a treated group and C is the median survival time (in days) of the vehicle control group. The Percent Increased Life Span (% ILS) for disseminated models is calculated using the following formula: % ILS=(T−C)/C×100%. Anti-tumor activity was evaluated as per NCI standards for disseminated models: ILS≥25% is minimum active, ILS>40% is active, and ILS≥50% is highly active.

To test the efficacy of huCD123-CysMab-D5 for the ability to decrease tumor burden in vivo, a disseminated tumor model was used as described in the protocol below.

Figure 25:
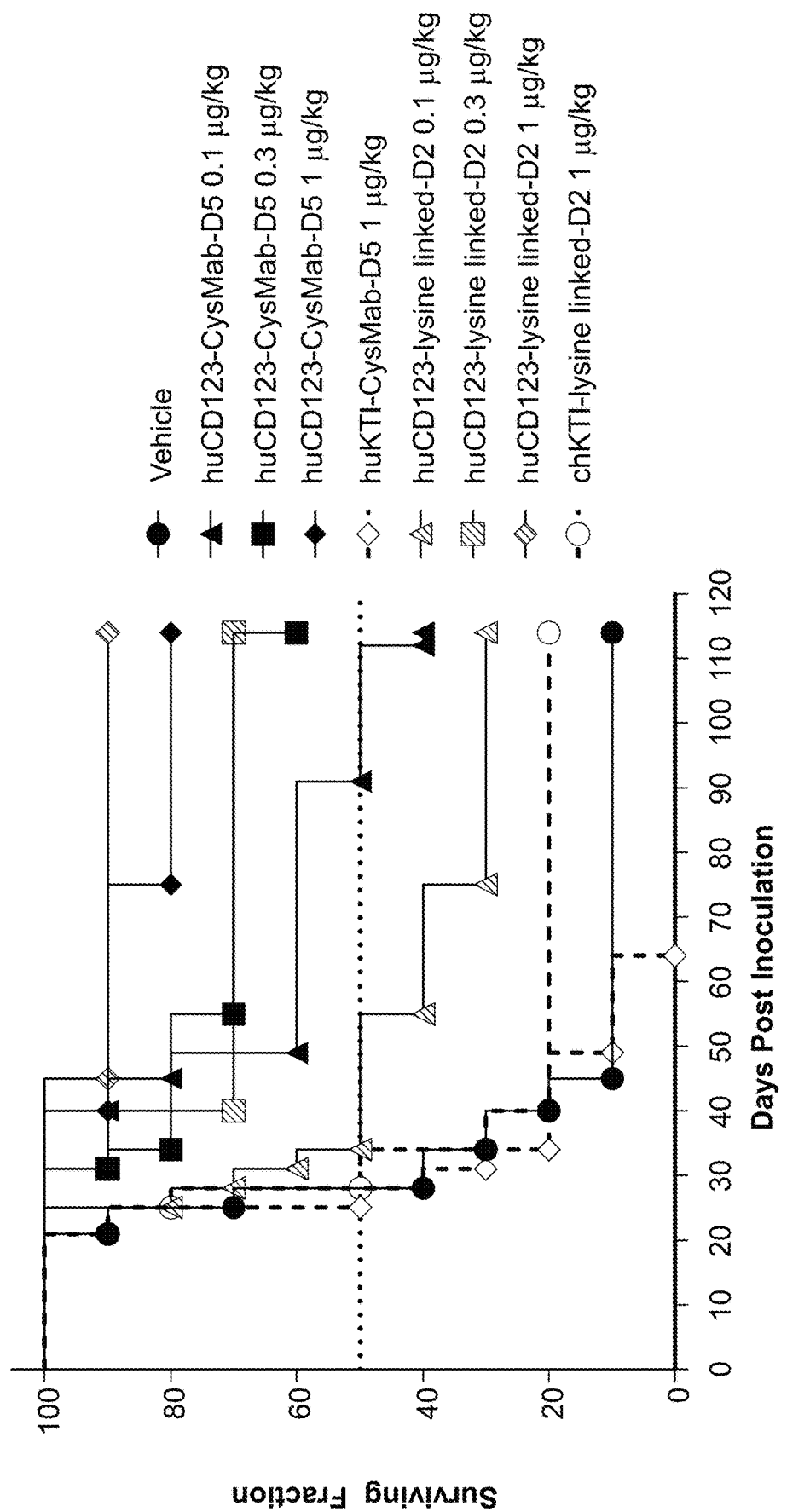
FIG. 25 shows in vivo efficacy of CD123-IGN conjugates in the Molm-13 AML disseminated model.

Female athymic nude mice were each injected intravenously in the lateral tail vein with $10 \times 10^6$ Molm-13 cells, a human AML cell line, in 100 µl of serum-free medium. On day 7 post-inoculation, mice were randomized into the study groups. At 24 h prior to conjugate administration, the mice were injected intraperitoneally with 400 mg/kg of non-targeted chKTI antibody to block Fc receptors on the Molm-13 AML cells, preventing non-specific up-take of conjugate. On day 7 post-Molm-13 inoculation, the mice received a single intravenous injection, in the lateral tail vein, of vehicle, 0.1 µg/kg (by D5; 0.008 mg/kg by huCD123) huCD123-CysMab-D5, 0.3 µg/kg (by D5; 0.024 mg/kg by huCD123) huCD123-CysMab-D5, 1 µg/kg (by D5; 0.08 mg/kg by huCD123) huCD123-CysMab-D5, 1 µg/kg (by D5; 0.08 mg/kg by huKTI) huKTI-CysMab-D5 control conjugate, 0.1 µg/kg (by D2; 0.0059 mg/kg by huCD123) huCD123-lysine linked-D2, 0.3 µg/kg (by D2; 0.018 mg/kg by huCD123) huCD123-lysine linked-D2, 1 µg/kg (by D2; 0.059 mg/kg by huCD123) huCD123-lysine linked-D2 or 1 µg/kg (by D2; 0.059 mg/kg by chKTI) chKTI-lysine linked-D2 control conjugate. On days 4 and 9 post-conjugate administration, the mice received intraperitoneal injections of 100 mg/kg of non-targeted chKTI antibody to ensure continued blocking of Fc receptors on the AML tumor cells. The results are summarized in the table below and in FIG. 25.

The huCD123-CysMab-D5 conjugate was highly active at all three doses tested, each generating a % ILS of >262.5 days. In contrast, a 1 µg/kg (by D5) dose of non-targeted huKTI-CysMab-D5 control conjugate was inactive, generating a 0% ILS. This demonstrates the CD123-dependent activity of huCD123-CysMab-D5. Similarly, huCD123-lysine linked-D2 was highly active at all three doses tested, each generating a % ILS of >59. However, a 1 µg/kg (by D2) dose of chKTI-lysine linked-D2 non-targeted control conjugate was also inactive, generating a 11% ILS, demonstrating the CD123-dependent activity of huCD123-lysine linked-D2. The one obvious difference between huCD123-CysMab-D5 and huCD123-lysine linked-D2 can be seen when comparing the % ILS obtained with the 0.1 µg/kg dose, the lowest dose tested, of each CD123-targeted conjugate. The % ILS obtained with 0.1 µg/kg of huCD123-CysMab-D5 was 262.5 days, while that obtained with 0.1 µg/kg dose of huCD123-lysine linked-D2 was 59 days, pointing to the superiority of huCD123-CysMab-D5 in this model.

| Treatment Group | Median Survival Time (Days) | Tumor Growth Delay (T-C, Days) | % ILS | Result |
|---|---|---|---|---|
| Vehicle | 28 | 0 | 0 | — |
| huCD123-CysMab-D5 (0.1 µg/kg) | 101.5 | 73.5 | 262.5 | Highly Active |
| huCD123-CysMab-D5 (0.3 µg/kg) | >101.5 | >73.5 | >262.5 | Highly Active |
| huCD123-CysMab-D5 (1 µg/kg) | >101.5 | >73.5 | >262.5 | Highly Active |
| huKTI-CysMab-D5 (1 µg/kg) | 26.5 | 0 | 0 | Inactive |
| huCD123-lysine linked-D2 (0.1 µg/kg) | 44.5 | 16.5 | 59 | Highly Active |
| huCD123-lysine linked-D2 (0.3 µg/kg) | >101.5 | >73.5 | >262.5 | Highly Active |
| huCD123-lysine linked-D2 (1 µg/kg) | >101.5 | >73.5 | >262.5 | Highly Active |
| chKTI-lysine linked-D2 (1 µg/kg) | 31 | 3 | 11 | Inactive |

Example 27. In Vivo Efficacy of huCD123-CysMab-D5 in EOL-1 Subcutaneous Models

Data collection and analysis for all subcutaneous models: The mice were weighed twice a week and were monitored for clinical signs throughout the duration of the study. Animals were euthanized when hind leg paralysis was present, body weight decreased by >20% of pre treatment weight, tumor ulceration occurred, or when any signs of distress were visible. Tumor volumes were measured one to two times weekly in three dimensions using a caliper. The tumor volume was expressed in mm$^3$ using the formula V=Length×Width×Height×½ (Tomayko and Reynolds, Cancer Chemother. Pharmacol. 24: 148-54 (1989)). Activity was assessed as described in Bissery et al., Cancer Res. 51: 4845-52 (1991). Tumor Growth Inhibition (T/C Value) was also assessed using the following formula: T/C (%)=(Median tumor volume of the treated/Median tumor volume of the control)×100%. Tumor volume was determined simultaneously for the treated (T) and the vehicle control (C) groups when tumor volume of the vehicle control reached a predetermined size (Bissery et al., Cancer Res. 51: 4845-52 (1991). The daily median tumor volume of each treated group was determined, including tumor-free mice (0 mm$^3$). According to NCI standards, a T/C≤42% is the minimum level of anti-tumor activity. A T/C<10% is considered a high anti-tumor activity level.

To test the efficacy of huCD123-CysMab-D5 for the ability to decrease tumor burden in vivo, three studies on a subcutaneous tumor model was used as described in the protocols below.

Figure 26:
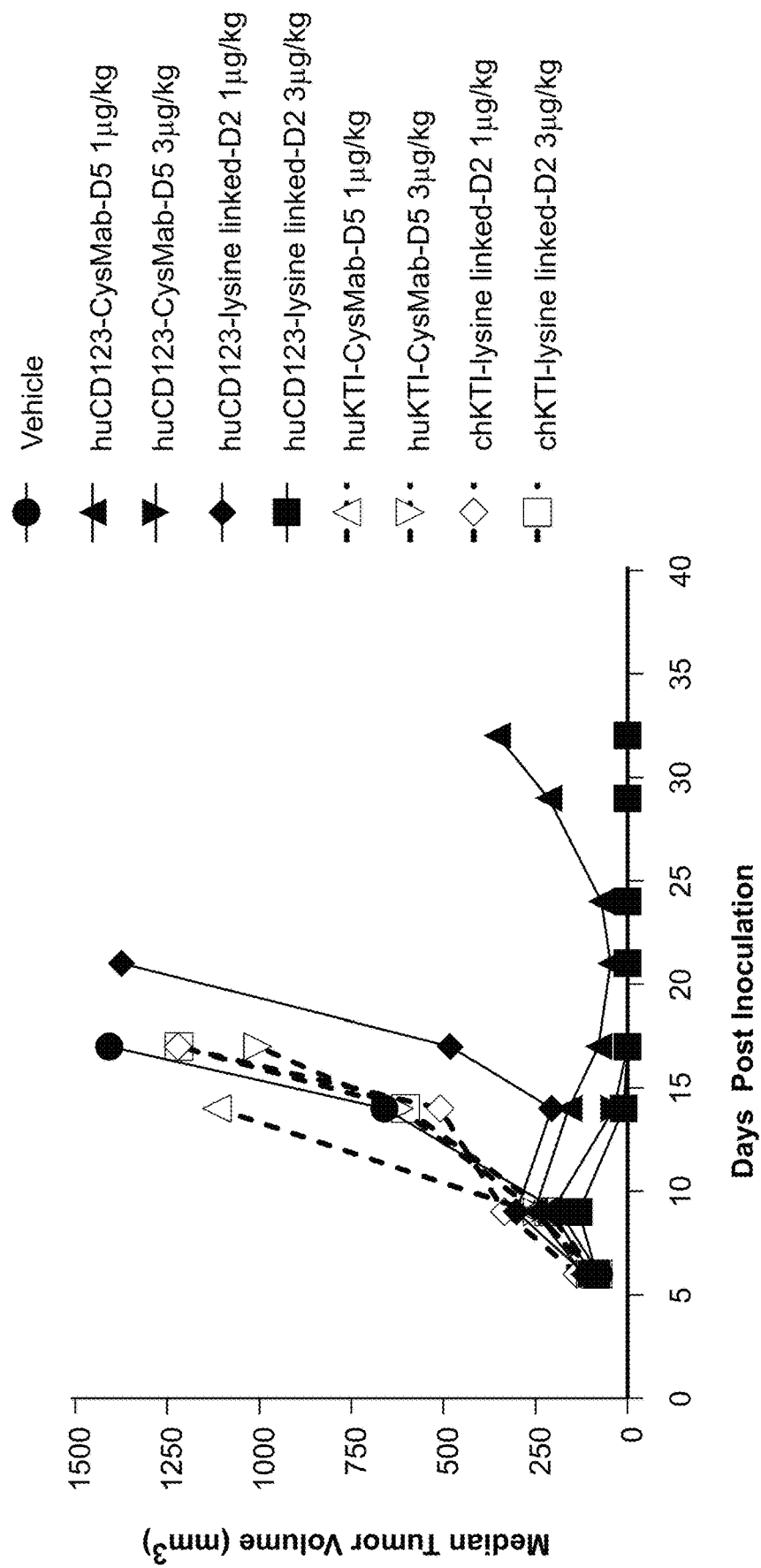
FIG. 26 shows in vivo efficacy of CD123-IGN conjugates in the EOL-1 subcutaneous model.

In a first study, Female athymic nude mice were each inoculated with 10×10$^6$ EOL-1 cells, a human AML cell line, in 100 µl serum free medium/matrigel subcutaneously in the right flank. On day 6 post-EOL-1 inoculation, mice were randomized into the study groups. At 24 h prior to conjugate administration, the mice were injected intraperitoneally with 400 mg/kg of non-targeted chKTI antibody to block Fc receptors on the EOL-1 AML cells, preventing non specific up-take of conjugate. On day 7 post-EOL-1 inoculation, the mice received a single intravenous injection, in the lateral tail vein, of vehicle, 1 µg/kg (by D5; 0.08 mg/kg by huCD123) huCD123-CysMab-D5, 3 µg/kg (by D5; 0.24 mg/kg by huCD123) huCD123-CysMab-D5, 1 µg/kg (by D2; 0.050 mg/kg by huCD123) huCD123-lysine linked-D2, 3 µg/kg (by D2, 0.151 mg/kg by huCD123) huCD123-lysine linked-D2, 1 µg/kg (by D5; 0.08 mg/kg by huKTI) huKTI-CysMab-D5 control conjugate, 3 µg/kg (by D5; 0.24 mg/kg by huKTI) huKTI-CysMab-D5 control conjugate, 1 µg/kg (by D2; 0.050 mg/kg by chKTI) chKTI-lysine linked-D2 or 3 µg/kg (by D2; 0.151 mg/kg by chKTI) chKTI-lysine linked-D2 control conjugate. On days 4 and 9 post-conjugate administration, the mice received an intraperitoneal injection of 100 mg/kg of non-targeted chKTI antibody to ensure continued blocking of Fc receptors on the AML tumor cells. The results are represented in the table below and in FIG. 26.

The 1 µg/kg (by D5) and the 3 µg/kg doses of huCD123-CysMab-D5 were active and highly active, respectively, generating 13% (3/6 CRs) and 2% T/C (5/6 CRs), respectively. In contrast, the 1 µg/kg (by D5) and the 3 µg/kg doses of huKTI-CysMab-D5 non-targeted control conjugate were inactive, with % T/C of ≥73, demonstrating that the activity of huCD123-CysMab-D5 was CD123-dependent. The 1 µg/kg (by D2) and the 3 µg/kg doses of huCD123-lysine linked-D2 were active and highly active, respectively, generating 30% (1/6 CRs) and 1% (6/6 CRs), respectively. In contrast, the 1 µg/kg (by D2) and the 3 µg/kg doses of the chKTI-lysine linked-D2 non-targeted control conjugate were both inactive, generating a 75% T/C (0/6 CRs) and an 81% T/C (0/6 CRs), respectively. This demonstrates the activity of huCD123-lysine linked-D2 was CD123-dependent. A difference between the two CD123-targeting conjugates becomes apparent when comparing 1 µg/kg (by D5) of huCD123-CysMab-D5 with 1 µg/kg (by D2) of huCD123-lysine linked-D2, in that the former results in a 13% T/C and 3/6 CRs and the latter results in a 30% T/C and only 1/6 CR, demonstrating the apparent superiority of huCD123-CysMab-D5 in this model.

| Treatment Group | % T/C (Day 15) | PR | CR | Result |
|---|---|---|---|---|
| Vehicle | — | 1/6 | 1/6 | — |
| huCD123-CysMab-D5 (1 µg/kg) | 13 | 3/6 | 3/6 | Active |
| huCD123-CysMab-D5 (3 µg/kg) | 2 | 5/6 | 5/6 | Highly Active |
| huCD123-lysine linked-D2 (1 µg/kg) | 30 | 1/6 | 1/6 | Active |
| huCD123-lysine linked-D2 (3 µg/kg) | 1 | 6/6 | 6/6 | Highly Active |
| huKTI-CysMab-D5 (1 µg/kg) | 100 | 0/6 | 0/6 | Inactive |
| huKTI-CysMab-D5 (3 µg/kg) | 73 | 1/6 | 1/6 | Inactive |
| chKTI-lysine linked-D2 (1 µg/kg) | 75 | 0/6 | 0/6 | Inactive |
| chKTI-lysine linked-D2 (3 µg/kg) | 81 | 0/6 | 0/6 | Inactive |

Figure 27:
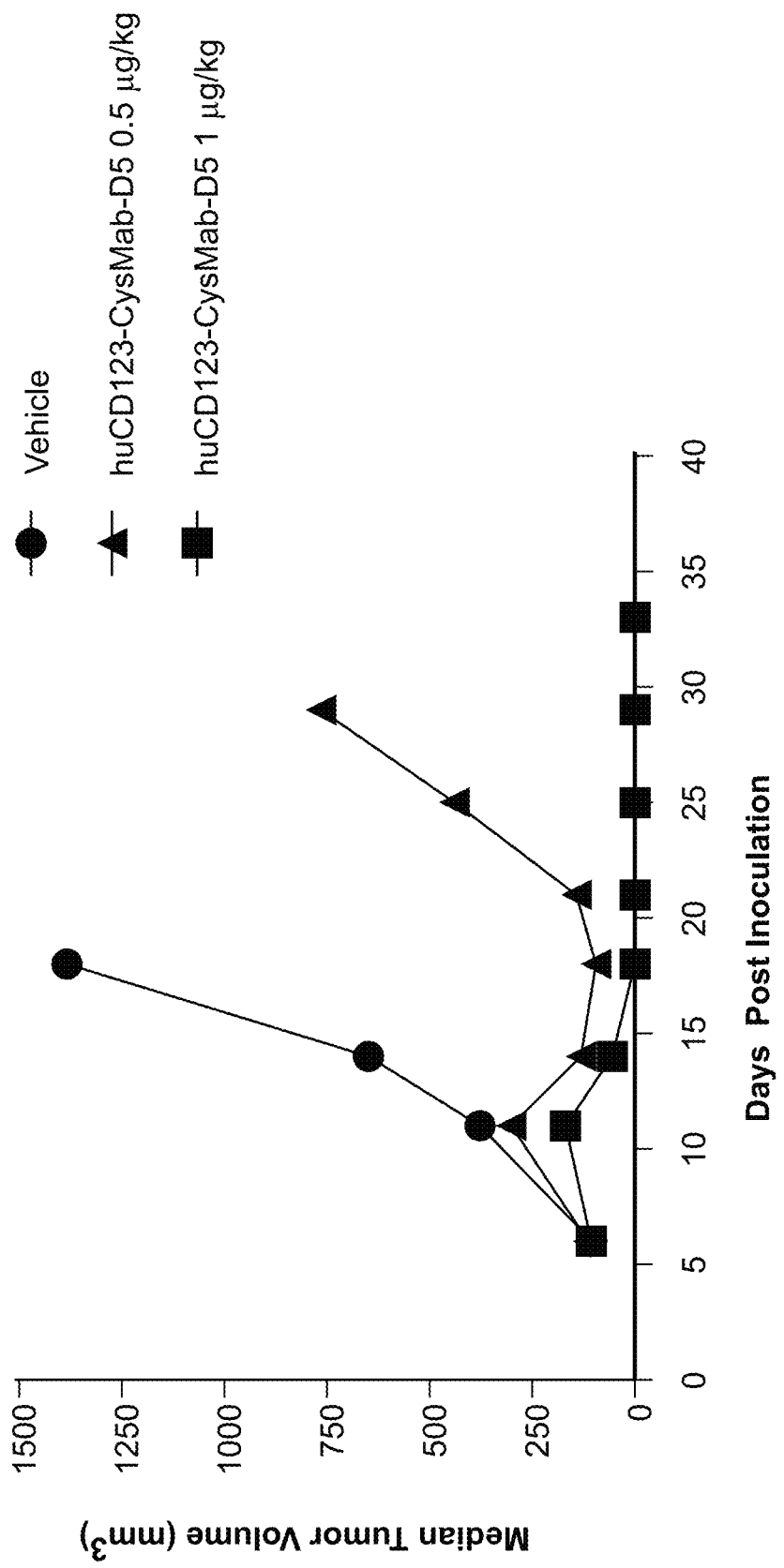
FIG. 27 shows in vivo efficacy of huCD123-CysMab-D5 conjugate at various doses in the EOL-1 subcutaneous model.

In a second study, female athymic nude mice were each inoculated with 10×10$^6$ EOL-1 cells, a human AML cell line, in 100 µl serum free medium/matrigel subcutaneously in the right flank. On day 6 post-EOL-1 inoculation, mice were randomized into the study groups. At 24 h prior to conjugate administration, the mice were injected intraperitoneally with 400 mg/kg of non-targeted chKTI antibody to block Fc receptors on the EOL-1 AML cells, preventing non specific up-take of conjugate. On day 7 post-EOL-1 inoculation, the mice received a single intravenous injection, in the lateral tail vein, of vehicle, 0.5 µg/kg (by D5; 0.04 mg/kg by huCD123) huCD123-CysMab-D5 or 1 µg/kg (by D5; 0.08 mg/kg by huCD123) huCD123-CysMab-D5. On days 4 and 9 post-conjugate administration, the mice received an intraperitoneal injection of 100 mg/kg of non-targeted chKTI antibody to ensure continued blocking of Fc receptors on the AML tumor cells. The results are represented in the table below and in FIG. 27.

The 0.5 µg/kg (by D5) dose of huCD123-CysMab-D5 was active, generating an 11% T/C and 3/6 CRs. Similarly, the 1 µg/kg dose of huCD123-CysMab-D5 was highly active, generating a 3% T/C and 6/6 CRs.

| Treatment Group | % T/C (Day 16) | PR | CR | Result |
|---|---|---|---|---|
| Vehicle | — | 0/6 | 0/6 | — |
| huCD123-CysMab-D5 (0.5 µg/kg) | 11 | 3/6 | 3/6 | Active |
| huCD123-CysMab-D5 (1 µg/kg) | 3 | 6/6 | 6/6 | Highly Active |

Figure 28:
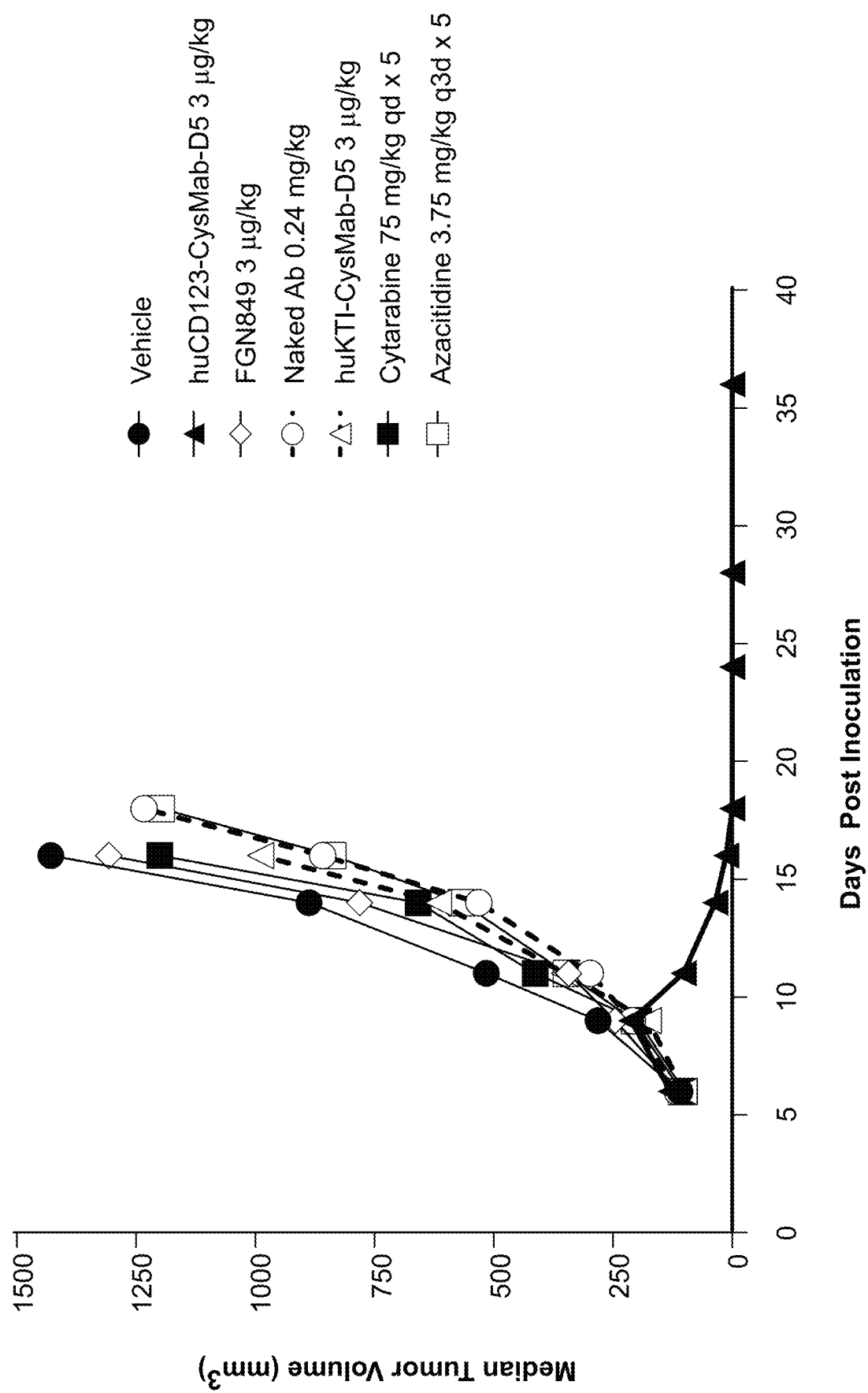
FIG. 28 shows in vivo efficacy of huCD123-CysMab-D5 conjugate compared to the corresponding free drug form of the payload (FGN849 or D5), naked antibody, control, cytarabine, and azacitidine in the EOL-1 subcatenous model.

In a third study, female athymic nude mice were each inoculated with $10 \times 10^6$ EOL-1 cells, a human AML cell line, in 100 µl serum free medium/matrigel subcutaneously in the right flank. On day 6 post-EOL-1 inoculation, mice were randomized into the study groups. At 24 h prior to conjugate administration, the mice were injected intraperitoneally with 400 mg/kg of non-targeted chKTI antibody to block Fc receptors on the EOL-1 AML cells, preventing non specific up-take of conjugate. On day 7 post-EOL-1 inoculation, mice received a single intravenous injection, in the lateral tail vein, of vehicle, 3 µg/kg (by D5; 0.24 mg/kg by huCD123) huCD123-CysMab-D5, 3 µg/kg (by D5) FGN849 (free drug form of the payload), 0.24 mg/kg unconjugated (naked) huCD123 antibody, or 3 µg/kg (by D5; 0.24 mg/kg by huKTI) huKTI-CysMab-D5 control conjugate. Mice treated with Cytarabine received a single intraperitoneal injection on days 7, 8, 9, 10 and 11 post-EOL-1 inoculation, and mice treated with Azacitidine received a single intraperitoneal injection on days 7, 10, 13, 16 and 19 post EOL-1 inoculation. On days 4 and 9 post-conjugate administration, the mice received an intraperitoneal injection of 100 mg/kg of non-targeted chKTI antibody to ensure continued blocking of Fc receptors on the AML tumor cells. The results are represented in the table below and in FIG. 28.

Out of all the articles tested, only the 3 µg/kg (by D5) dose of huCD123-CysMab-D5 demonstrated activity, generating a highly active 1% T/C and 8/8 CRs, in contrast to the 3 µg/kg (by D5) dose of huKTI-CysMab-D5 non-targeting control conjugate, which generated a 69% T/C and 0/8 CRs. A 3 µg/kg (by D5) dose of the unconjugated free drug, FGN849, was also inactive, with a 92% T/C and 0/8 CRs. Likewise, a 0.24 mg/kg dose of unconjugated ("naked") huCD123 antibody, matching the antibody dose of huCD123-CysMab-D5, was inactive, with a 60% T/C and 0/8 CRs. Cytarabine, administered at a dose of 75 mg/kg daily for 5 days, was inactive, with an 84% T/C and 0/8 CRs. Azacitidine, administered at a dose of 3.75 mg/kg once every three days for 5 doses, was inactive, with a 59% T/C and 0/8 CRs.

| Treatment Group | % T/C (Day 16) | PR | CR | Result |
|---|---|---|---|---|
| Vehicle | — | 0/8 | 0/8 | — |
| huCD123-CysMab-D5 (3 µg/kg) | 1 | 8/8 | 8/8 | Highly Active |
| FGN849 (3 µg/kg) | 92 | 0/8 | 0/8 | Inactive |
| Naked antibody (0.24 mg/kg) | 60 | 0/8 | 0/8 | Inactive |
| huKTI-CysMab-D5 (3 µg/kg) | 69 | 0/8 | 0/8 | Inactive |
| Cytarabine; 75 mg/kg, qd × 5 | 84 | 0/8 | 0/8 | Inactive |
| Azacitidine; 3.75 mg/kg, q3d × 5 | 59 | 0/8 | 0/8 | Inactive |

Example 28. In Vivo Efficacy of huCD123-CysMab-D5 and huCD123-SeriMab-sD1 in MV4-11 Disseminated Model To test the efficacy of huCD123-CysMab-D5 and huCD123-SeriMab-sD1 for the ability to decrease tumor burden in vivo, a disseminated tumor model was used as described in the protocol below.

Figure 29:
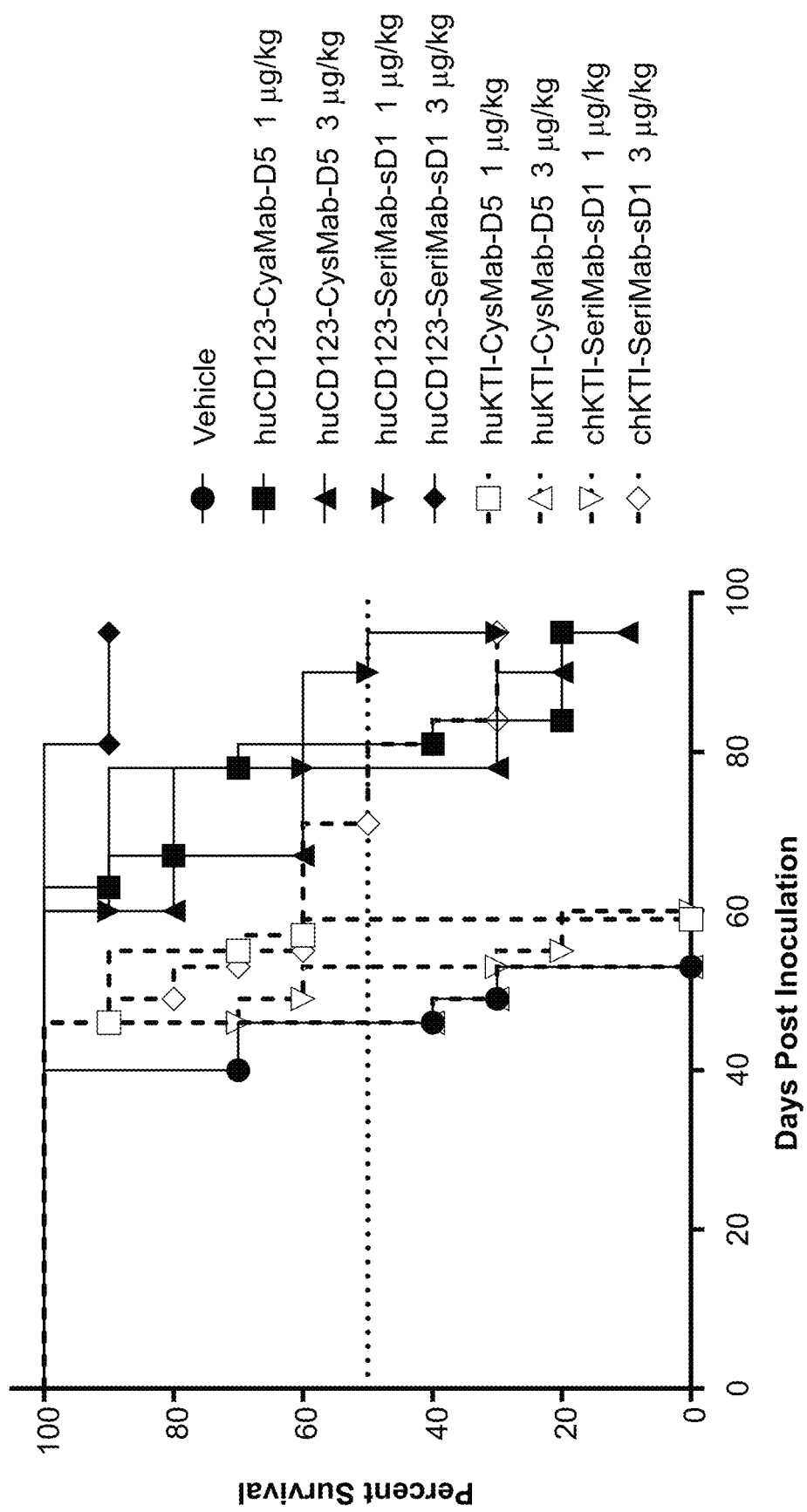
FIG. 29 shows in vivo efficacy of CD123-IGN conjugates in the MV4-11 AML disseminated model.

Female NOD SCID mice were pre-treated with 150 mg/kg cyclophosphamide to partially ablate bone marrow in order to improve the engraftment of MV4-11 cells. The cyclophosphamide (Baxter, Lot #4E011, Exp 05.2017) was reconstituted with 0.9% NaCl and was administered intraperitoneally to the mice on day −3 and day −2 prior to MV4-11 cell inoculation on day 0. Following cyclophosphamide treatment as described above, the mice were each injected intravenously in the lateral tail vein with $3 \times 10^6$ MV4-11 cells, a human AML cell line, in 100 µl of serum-free medium. On day 7 post-MV4-11 inoculation, mice were randomized into the study groups. At 24 h prior to conjugate administration, the mice were injected intraperitoneally with 400 mg/kg of non-targeted chKTI antibody to block Fc receptors on the MV4-11 AML cells, preventing non-specific up-take of conjugate. On day 7 post-MV4-11 inoculation, the mice received a single intravenous injection, in the lateral tail vein, of vehicle, 1 µg/kg (by D5; 0.08 mg/kg by huCD123) huCD123-CysMab-D5, 3 µg/kg (by D5; 0.24 mg/kg huCD123) huCD123-CysMab-D5, 1 µg/kg (by D1; 0.054 mg/kg by huCD123) huCD123-SeriMab-sD1, 3 µg/kg (by D1; 0.163 mg/kg by huCD123) huCD123-SeriMab-sD1, 1 µg/kg (by D5; 0.08 mg/kg by huKTI) huKTI-CysMab-D5 control conjugate, 3 µg/kg (by D5; 0.24 mg/kg by huKTI) huKTI-CysMab-D5 control conjugate, 1 µg/kg (by D1; 0.07 mg/kg by chKTI) chKTI-SeriMab-sD1 control conjugate or 3 µg/kg (by D1; 0.21 mg/kg by chKTI) chKTI-SeriMab-sD1 control conjugate. The results are summarized in the table below and in FIG. 29.

Both the 1 µg/kg and the 3 µg/kg (by D5) doses of huCD123-CysMab-D5 were highly active, each generating a % ILS of ≥70. In contrast, the 1 µg/kg dose (by D5) of huKTI-CysMab-D5 non-targeted control conjugate was minimally active, generating a 28% ILS. The 3 µg/kg dose of huKTI-CysMab-D5 was inactive, with a 0% ILS, demonstrating the CD123-dependent activity of huCD123-CysMab-D5. The 1 µg/kg and the 3 µg/kg (by sD1) doses of huCD123-SeriMab-sD1 were both highly active, each generating a % ILS of ≥101. However, when the activity of the non-targeted chKTI-SeriMab-sD1 control conjugates is examined, a high degree of non-specific, non-CD123-targeted activity is apparent from the 3 µg/kg dose (by sD1), which generates a 65% ILS (highly active). This indicates some of the high activity of the 3 µg/kg (by sD1) dose of CD123-targeting huCD123-SeriMab-sD1 is likely due to non-specific drug up-take mechanisms that do not involve targeting CD123. In contrast, the 1 µg/kg (by sD1) dose of chKTI-SeriMab-sD1 control conjugate is inactive, with a % ILS of 15, demonstrating that the non-specific activity of the 3 µg/kg dose of chKTI-SeriMab-sD1 is dose-dependent and that the high activity of the 1 µg/kg (by sD1) dose of huCD123-SeriMab-sD1 is indeed CD123-dependent.

| Treatment Group | Median Survival Time (Days) | Tumor Growth Delay (T-C, Days) | % ILS | Result |
|---|---|---|---|---|
| Vehicle | 46 | 0 | 0 | — |
| huCD123-CysMab-D5 (1 µg/kg) | 81 | 35 | 76 | Highly Active |
| huCD123-CysMab-D5 (3 µg/kg) | 78 | 32 | 70 | Highly Active |
| huCD123-SeriMab-sD1 (1 µg/kg) | 92.5 | 46.5 | 101 | Highly Active |
| huCD123-SeriMab-sD1 (3 µg/kg) | >92.5 | >46.5 | >101 | Highly Active |
| huKTI-CysMab-D5 (1 µg/kg) | 59 | 13 | 28 | Minimally Active |
| huKTI-CysMab-D5 (3 µg/kg) | 46 | 0 | 0 | Inactive |
| chKTI-SeriMab-sD1 (1 µg/kg) | 53 | 7 | 15 | Inactive |
| chKTI-SeriMab-sD1 (3 µg/kg) | 76 | 30 | 65 | Highly Active |

Example 29. In Vivo Efficacy of huCD123-CysMab-D5 and huCD123-SeriMab-sD1 in MV4-11 Subcutaneous Model To test the efficacy of huCD123-CysMab-D5 and huCD123-SeriMab-sD1 for the ability to decrease tumor burden in vivo, a subcutaneous tumor model was used as described in the protocol below.

Figure 30:
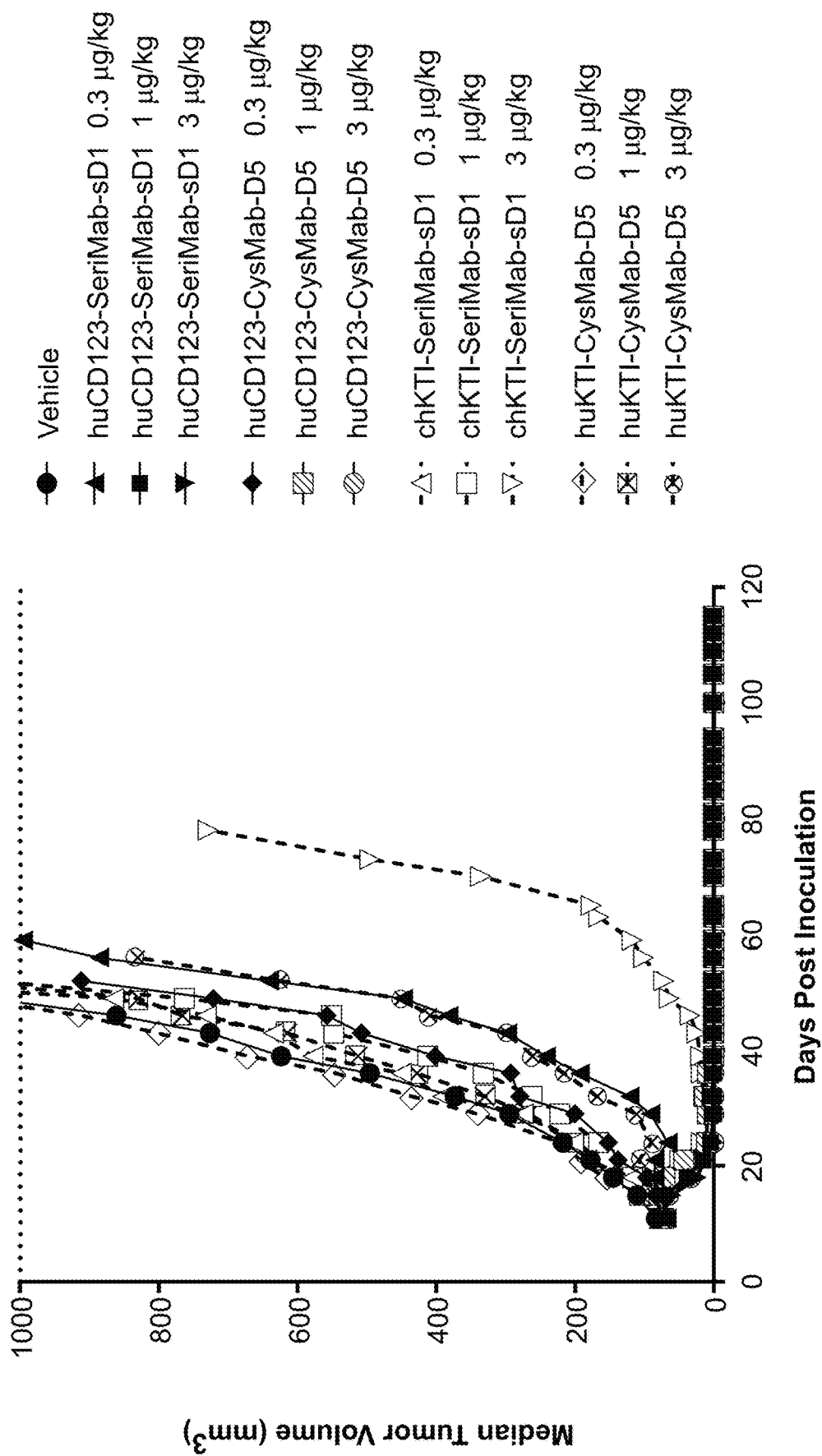
FIG. 30 shows in vivo efficacy of CD123-IGN conjugates in the MV4-11 AML subcutaneous model.

Female CB.17 SCID mice were each inoculated with 10×10$^6$ MV4-11 cells, a human AML cell line, in 100 µl serum free medium/matrigel subcutaneously in the right flank. On day 14 post-MV4-11 inoculation, mice were randomized into the study groups. At 24 h prior to conjugate administration, the mice were injected intraperitoneally with 400 mg/kg of non-targeted chKTI antibody to block Fc receptors on the MV4-11 AML cells, preventing non specific up-take of conjugate. On day 15 post-MV4-11 inoculation, the mice received a single intravenous injection, in the lateral tail vein, of vehicle, 0.3 µg/kg (by D1; 0.016 mg/kg by huCD123) huCD123-SeriMab-sD1, 1 µg/kg (by D1; 0.054 mg/kg by huCD123) huCD123-SeriMab-sD 1, 3 µg/kg (by D1; 0.16 mg/kg by huCD123) huCD123-SeriMab-sD 1, 0.3 µg/kg (by D5; 0.024 mg/kg by huCD123) huCD123-CysMab-D5, 1 µg/kg (by D5; 0.08 mg/kg by huCD123) huCD123-CysMab-D5, 3 µg/kg (by D5; 0.24 mg/kg by huCD123) huCD123-CysMab-D5, 0.3 µg/kg (by D1; 0.021 mg/kg by chKTI) chKTI-SeriMab-sD1 control conjugate, 1 µg/kg (by D1; 0.07 mg/kg by chKTI) chKTI-SeriMab-sD1 control conjugate, 3 µg/kg (by D1; 0.21 mg/kg by chKTI) chKTI-SeriMab-sD1 control conjugate, 0.3 µg/kg (by D5; 0.024 mg/kg by huKTI) huKTI-CysMab-D5 control conjugate, 1 µg/kg (by D5; 0.08 mg/kg by huKTI) huKTI-CysMab-D5 control conjugate or 3 µg/kg (by D5; 0.24 mg/kg by huKTI) huKTI-CysMab-D5 control conjugate. On day 20 post-MV4-11 inoculation, the mice injected intraperitoneally with 100 mg/kg of non-targeted chKTI antibody to ensure continued blocking of Fc receptors on the AML tumor cells. The results are represented in the table below and in FIG. 30.

The 1 µg/kg and the 3 µg/kg (by sD1) doses of huCD123-SeriMab-sD1 were both highly active, each generating a % T/C of 0 and 6/6 CRs. The lowest huCD123-SeriMab-sD1 dose tested, 0.3 µg/kg (by sD1) was inactive, with a % T/C of 43 and 0/6 CRs. However, when the activity of the non-targeted chKTI-SeriMab-sD1 control conjugates is examined, a high degree of non-specific, non-CD123-targeted activity is apparent from the 3 µg/kg dose (by sD1), which generates a 6% T/C (highly active) and 3/6 CRs. This indicates some of the high activity of the 3 µg/kg (by sD1) dose of CD123-targeting huCD123-SeriMab-sD1 is likely due to non-specific drug up-take mechanisms that do not involve targeting CD123. In contrast, both the 1 µg/kg (by sD1) and the 0.3 µg/kg doses of chKTI-SeriMab-sD1 control conjugate were inactive, generating 73% T/C and 83% T/C, respectively, demonstrating that the high non-specific activity of the 3 µg/kg dose (by sD1) of chKTI-SeriMab-sD1 is dose-dependent and that the high activity of the 1 µg/kg (by sD1) dose of huCD123-SeriMab-sD1 is indeed CD123-dependent.

The 1 µg/kg and the 3 µg/kg (by D5) doses of huCD123-CysMab-D5 were both highly active, each generating a 0% T/C, and 5/6 and 6/6 CRs, respectively. The 0.3 µg/kg (by D5) dose of huCD123-CysMab-D5, the lowest dose tested, was inactive, with a 69% T/C and 0/6 CRs. In contrast, all three doses (by D5) of the huKTI-CysMab-D5 non-targeted control conjugate were inactive, each generating ≥43% T/C and 0/6 CRs; demonstrating the CD123-dependent activity of huCD123-CysMab-D5.

| Treatment Group | % T/C (Day 49) | PR | CR | Result |
|---|---|---|---|---|
| Vehicle | — | 0/6 | 0/6 | — |
| huCD123-SeriMab-sD1 (0.3 µg/kg) | 43 | 1/6 | 0/6 | Inactive |
| huCD123-SeriMab-sD1 (1 µg/kg) | 0 | 6/6 | 6/6 | Highly Active |
| huCD123-SeriMab-sD1 (3 µg/kg) | 0 | 6/6 | 6/6 | Highly Active |
| huCD123-CysMab-D5 (0.3 µg/kg) | 69 | 0/6 | 0/6 | Inactive |
| huCD123-CysMab-D5 (1 µg/kg) | 0 | 5/6 | 5/6 | Highly Active |
| huCD123-CysMab-D5 (3 µg/kg) | 0 | 6/6 | 6/6 | Highly Active |
| chKTI-SeriMab-sD1 (0.3 µg/kg) | 83 | 0/6 | 0/6 | Inactive |
| chKTI-SeriMab-sD1 (1 µg/kg) | 73 | 0/6 | 0/6 | Inactive |
| chKTI-SeriMab-sD1 (3 µg/kg) | 6 | 5/6 | 3/6 | Highly Active |
| huKTI-CysMab-D5 (0.3 µg/kg) | 102 | 0/6 | 0/6 | Inactive |
| huKTI-CysMab-D5 (1 µg/kg) | 79 | 0/6 | 0/6 | Inactive |
| huKTI-CysMab-D5 (3 µg/kg) | 43 | 0/6 | 0/6 | Inactive |

Example 30. In Vivo Tolerability of huCD123-IGN Conjugates in Mice

To test the tolerability of huCD123-CysMab-D5 and other huCD123-IGN conjugates in vivo, a mouse model was used as described in the protocol below.

Female CD-1 mice received a single intravenous injection into the lateral tail vein of vehicle, 150 µg/kg (by D5, 12 mg/kg by huCD123) of huCD123-CysMab-D5, 125 µg/kg (by D5, 10 mg/kg by huCD123) of huCD123-CysMab-D5, 100 µg/kg (by D5, 8 mg/kg by huCD123) of huCD123-CysMab-D5, 150 µg/kg (by sD1, 14.3 mg/kg by huCD123) of huCD123-SeriMab-sD1 or 125 µg/kg (by sD 1, 11.9 by huCD123) of huCD123-SeriMab-sD 1. The huCD123 antibody does not cross-react with mouse CD123, which makes this in vivo mouse model an indicator of off-target toxicity only. The mice were observed daily for 33 days, and body weights were determined. If an animal experienced greater than 20% body weight loss or became moribund, the animal was euthanized. Other than body weight loss, no other clinical observations were made during the course of the study in any of the treatment.

Female CD-1 mice received a single intravenous injection into the lateral tail vein of vehicle, 75 μg/kg (by D2, 4.4 mg/kg by huCD123) of huCD123-lysine linked-D2, 100 μg/kg (by D2, 5.9 mg/kg by huCD123) of huCD123-lysine linked-D2 or 125 μg/kg (by D2, 7.4 mg/kg by huCD123) of huCD123-lysine linked-D2. The huCD123 antibody does not cross-react with mouse CD123, which makes this in vivo mouse model an indicator of off-target toxicity only. The mice were observed daily for 22 days, and body weights were determined. If an animal experienced greater than 20% body weight loss or became moribund, the animal was euthanized.

Figure 32:
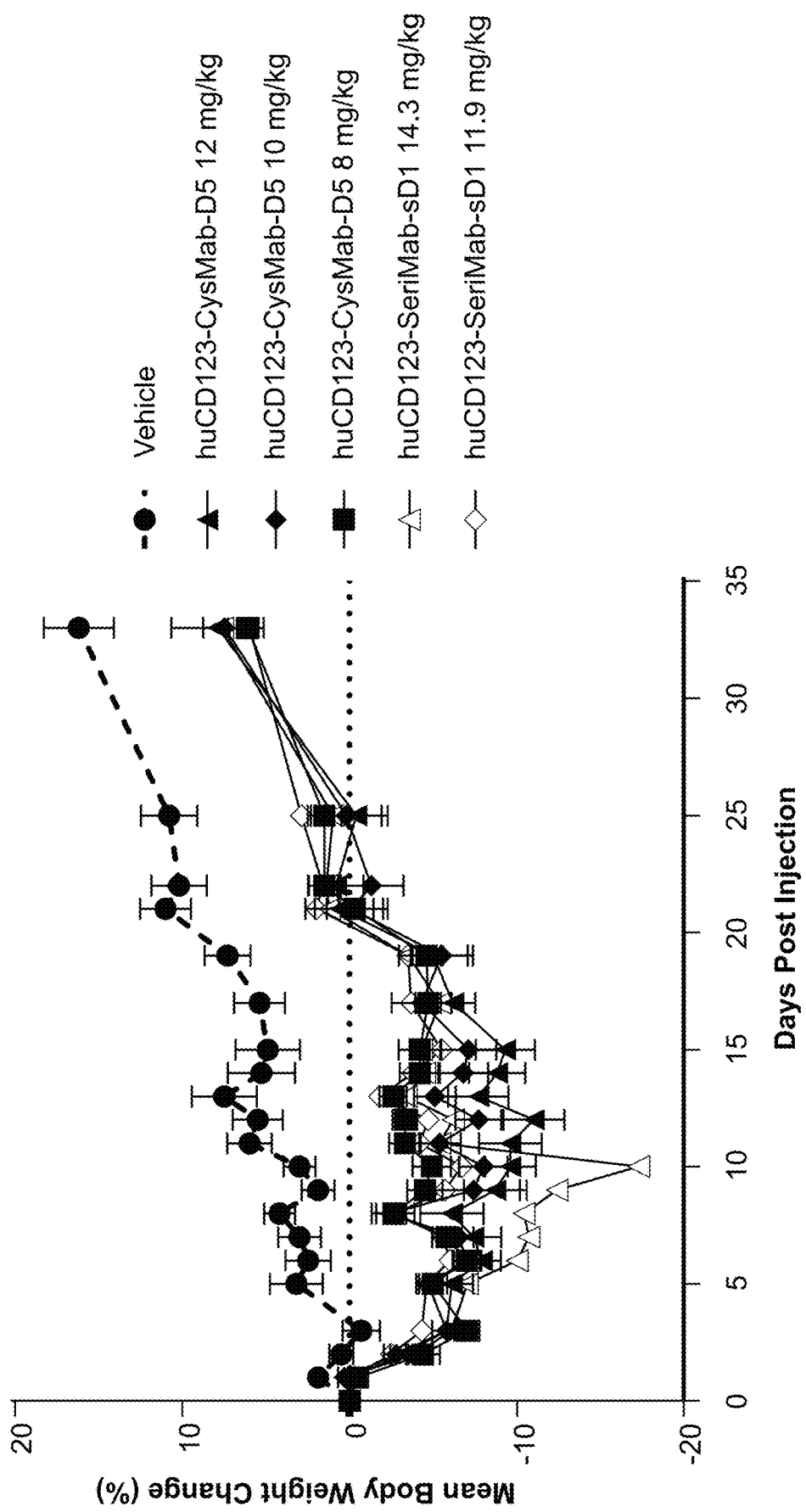
FIG. 32 shows in vivo tolerability of huCD123-CysMab-D5 and huCD123-SeriMab-sD1 conjugates in mice.
Figure 33:
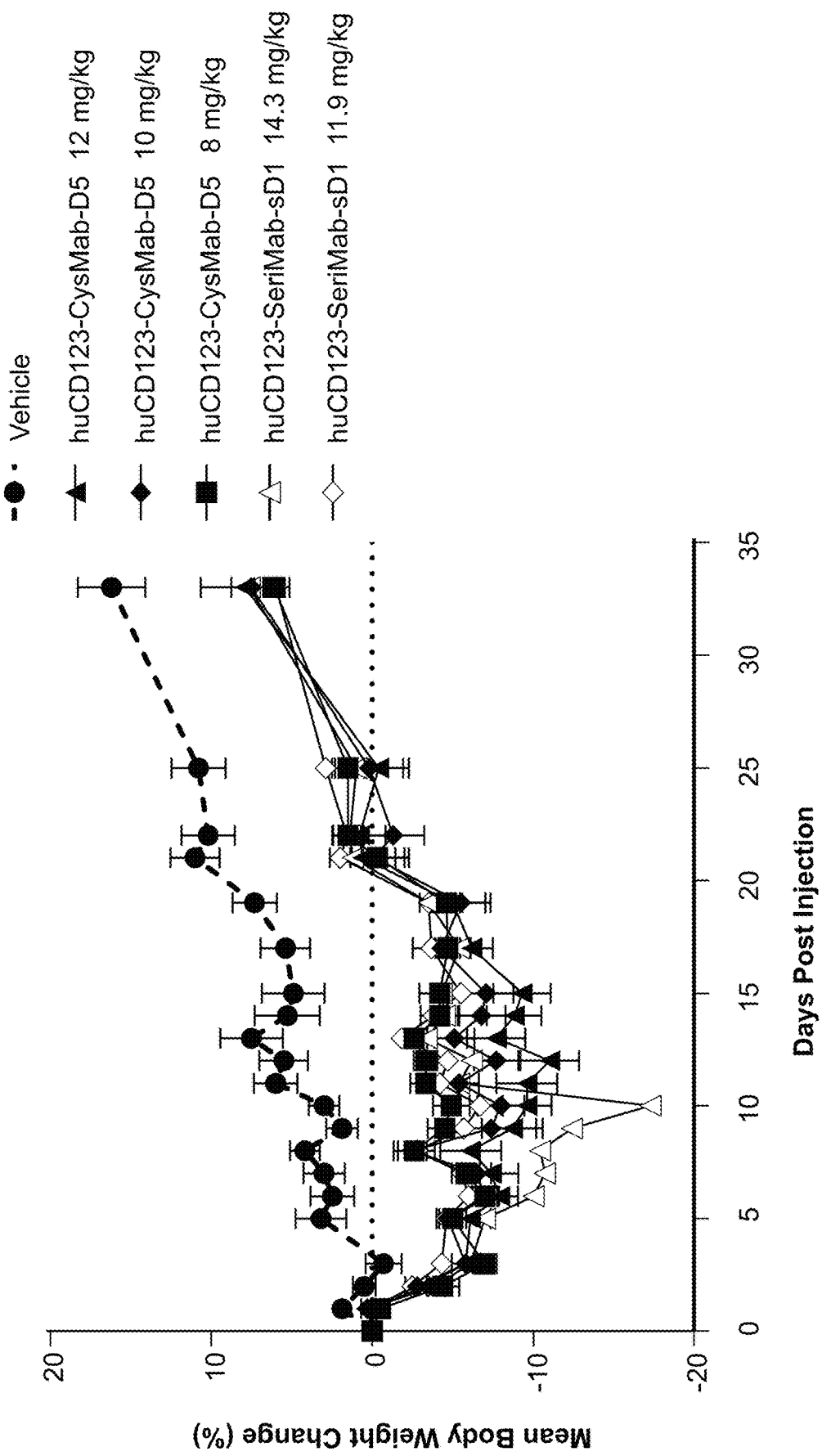
FIG. 33 shows in vivo tolerability of huCD123-lysine linked-D2 conjugate in mice.

The results are summarized in the tables below and in FIG. 32 and FIG. 33.

huCD123-CysMab-D5 was not tolerated at 150 μg/kg (by D5, 12 mg/kg by huCD123). The nadir of mean change in body weight occurred on day 12, with an 11% decrease. One out of eight mice was euthanized on day 12 due to >20% body weight loss. huCD123-CysMab-D5 was not well tolerated at 125 μg/kg (by D5, 10 mg/kg by huCD123). The nadir of mean change in body weight occurred on day 10, with an 8.6% decrease. One out of eight mice was euthanized on day 9 due to body weight loss. huCD123-CysMab-D5 was tolerated at 100 μg/kg (by D5, 8 mg/kg by huCD123). The nadir of mean change in body weight occurred on day 6, with a 7% decrease. None of the mice in this treatment group were euthanized due to body weight loss.

huCD123-SeriMab-sD1 was not tolerated at 150 μg/kg (14.3 mg/kg by huCD123). The nadir of mean change in body weight occurred on day 10, with a 17.3% decrease. Two out of eight mice were euthanized on day 10 due to body weight loss. huCD123-SeriMab-sD1 was not well tolerated at 125 μg/kg (by sD1, 11.9 mg/kg by huCD123). The nadir of mean change in body weight occurred on day 10, with a 6.7% decrease. One out of eight mice was euthanized on day 12 due to body weight loss.

huCD123-lysine linked-D2 was tolerated at 75 μg/kg (by D2, 4.4 mg/kg by huCD123). The nadir of mean change in body weight occurred on day 5, with a 6% decrease. None of the mice in this treatment group were euthanized due to body weight loss. huCD133-lysine linked-D2 was tolerated at 100 μg/kg (by D2, 5.9 mg/kg by huCD123). The nadir of mean change in body weight occurred on day 7, with an 8% decrease. None of the mice in this treatment group were euthanized due to body weight loss. huCD123-lysine linked-D2 was not tolerated at 125 μg/kg (by D2, 7.4 mg/kg by huCD123). The nadir of mean change in body weight occurred on day 9 (when N=6), with a 17% decrease. The following numbers of mice, out of the original eight, were euthanized on the days indicated, due to >20% body weight loss: one on day 8, one on day 9, two on day 10, one on day 11 and one on day 13.

| Treatment | μg/kg by drug payload | mg/kg by huCD123 | Number of mice euthanized for >20 BW loss | Body weight nadir (day) | % decrease in mean body weight at nadir |
|---|---|---|---|---|---|
| Vehicle | — | — | 0/8 | — | — |
| huCD123-CysMab-D5 | 150 | 12 | 1/8 | 12 | 11 |
| huCD123-CysMab-D5 | 125 | 10 | 1/8 | 10 | 8.6 |
| huCD123-CysMab-D5 | 100 | 8 | 0/8 | 6 | 7 |
| huCD123-SeriMab-sD1 | 150 | 14.3 | 2/8 | 10 | 17.3 |
| huCD123-SeriMab-sD1 | 125 | 11.9 | 1/8 | 10 | 6.7 |
| Vehicle | — | — | 0/8 | — | — |
| huCD123-lysine linked-D2 | 75 | 4.4 | 0/8 | 5 | 6 |
| huCD123-lysine linked-D2 | 100 | 5.9 | 0/8 | 7 | 8 |
| huCD123-lysine linked-D2 | 125 | 7.4 | 6/8 | 9 | 17 |

BW: Body weight

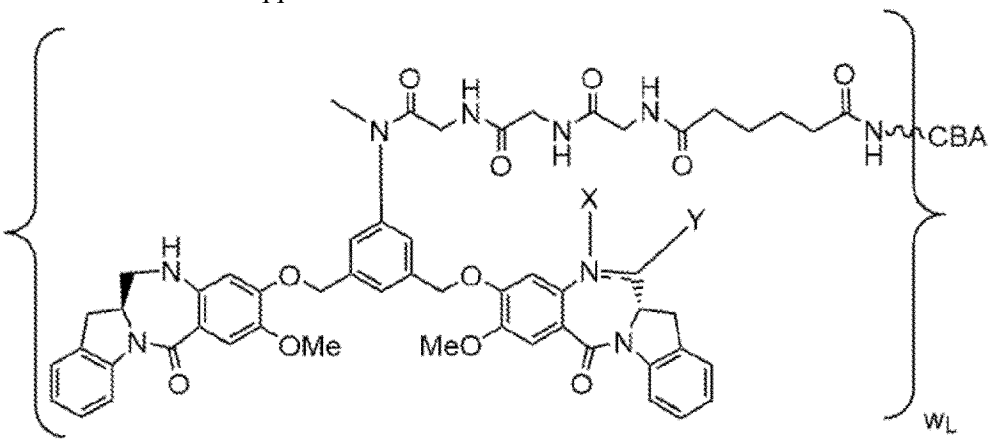

We claim:

1. An immunoconjugate having the following formula:

$$CBA-(Cy^{L1})_{w_L},$$

wherein:
$W_L$ is an integer from 1 to 20; and
$Cy^{L1}$ is represented by the following formula:

or a pharmaceutically acceptable salt thereof, wherein:

the double line == between N and C represents a single bond or a double bond, provided that when it is a double bond, X is absent and Y is —H or a ($C_1$-$C_4$) alkyl; and when it is a single bond, X is —H or an amine protecting moiety, and Y is —OH or —$SO_3$M;

wherein M is $H^+$ or a cation;

L' is represented by the following formula:

$$-NR_5-P-C(=O)-(CR_aR_b)_m-C(=O)-$$ (B1');

$R_5$ is —H or a $(C_1-C_3)$alkyl;

P is an amino acid residue or a peptide containing between 2 to 20 amino acid residues;

$R_a$ and $R_b$, for each occurrence, are each independently —H, $(C_1-C_3)$alkyl, or a charged substituent or an ionizable group Q, wherein Q is —SO$_3$M; and m is an integer from 1 to 6; and CBA is an anti-CD123 antibody or antigen-binding fragment thereof that is covalently linked through a lysine residue to $Cy^{L1}$, wherein the antibody or antigen-binding fragment thereof comprises:

a) a heavy chain variable region CDR1 having the amino acid sequence selected from the group consisting of SEQ ID NOs: 1, 5, and 12; a heavy chain variable region CDR2 having the amino acid sequence selected from the group consisting of SEQ ID NOs: 2, 3, 6-10, 13, and 14; and a heavy chain variable region CDR3 having the amino acid sequence selected from the group consisting of: SEQ ID NOs: 4, 11, 15, and 70; and b) a light chain variable region CDR1 having the amino acid sequence selected from the group consisting of: SEQ ID NOs: 16, 19, 20, 23 and 72; a light chain variable region CDR2 having the amino acid sequence selected from the group consisting of: SEQ ID NOs: 17, 21, 24 and 71; and a light chain variable region CDR3 having the amino acid sequence selected from the group consisting of: SEQ ID NOs: 18, 22, and 25;

wherein the antibody or antigen-binding fragment thereof binds an epitope within amino acids 101 to 346 of human CD123 or IL3-Rα antigen and inhibits IL3-dependent proliferation in antigen-positive TF-1 cells.

2. The immunoconjugate of claim 1, wherein the antibody or antigen-binding fragment thereof comprises:

a) an immunoglobulin heavy chain variable region comprising a CDR1 having the amino acid sequence set forth in SEQ ID NO: 5, a CDR2 having the amino acid sequence set forth in SEQ ID NO: 8, and a CDR3 having the amino acid sequence set forth in SEQ ID NO: 11; and b) an immunoglobulin light chain variable region comprising a CDR1 having the amino acid sequence set forth in SEQ ID NO: 20, a CDR2 having the amino acid sequence set forth in SEQ ID NO: 21, and a CDR3 having the amino acid sequence set forth in SEQ ID NO: 22.

3. The immunoconjugate of claim 1, wherein the antibody or antigen-binding fragment thereof comprises:

a) an immunoglobulin heavy chain variable region $(V_H)$ having the amino acid sequence set forth in SEQ ID NO: 39 or 40; and b) an immunoglobulin light chain variable region $(V_L)$ having the amino acid sequence set forth in SEQ ID NO: 41; or a) an immunoglobulin heavy chain variable region $(V_H)$ having the amino acid sequence set forth in SEQ ID NO: 34; and b) an immunoglobulin light chain variable region $(V_L)$ having the amino acid sequence set forth in SEQ ID NO: 35; wherein Xaa, the second residue from the N-terminus of SEQ ID NO: 34, is Phe or Val.

4. The immunoconjugate of claim 3 wherein the antibody or antigen-binding fragment thereof comprises the $V_H$ sequence of SEQ ID NO: 34 and the $V_L$ sequence of SEQ ID NO: 35.

5. The immunoconjuate of claim 1, wherein the antibody comprises:

a) an immunoglobulin heavy chain having the amino acid sequence set forth in SEQ ID NO: 50 and b) an immunoglobulin light chain having the amino acid sequence set forth in SEQ ID NO: 51.

6. The immunoconjugate of claim 1, wherein $R_a$ and $R_b$ are both H; and $R_5$ is H or Me.

7. The immunoconjugate of claim 1, wherein P is a peptide containing 2 to 5 amino acid residues.

8. The immunoconjugate of claim 1, wherein P is selected from Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp-Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 55), β-Ala-Leu-Ala-Leu (SEQ ID NO: 57), Gly-Phe-Leu-Gly (SEQ ID NO: 73), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala.

9. The immunoconjugate of claim 8, wherein P is Gly-Gly-Gly, Ala-Val, Ala-Ala, Ala-D-Ala, D-Ala-Ala, or D-Ala-D-Ala.

10. The immunoconjugate of claim 1, wherein the immunoconjugate is represented by the following formula:

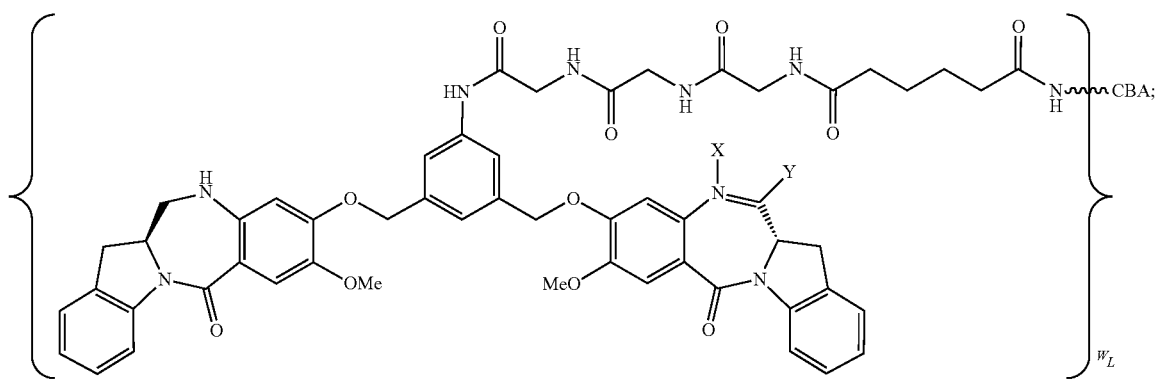

-continued
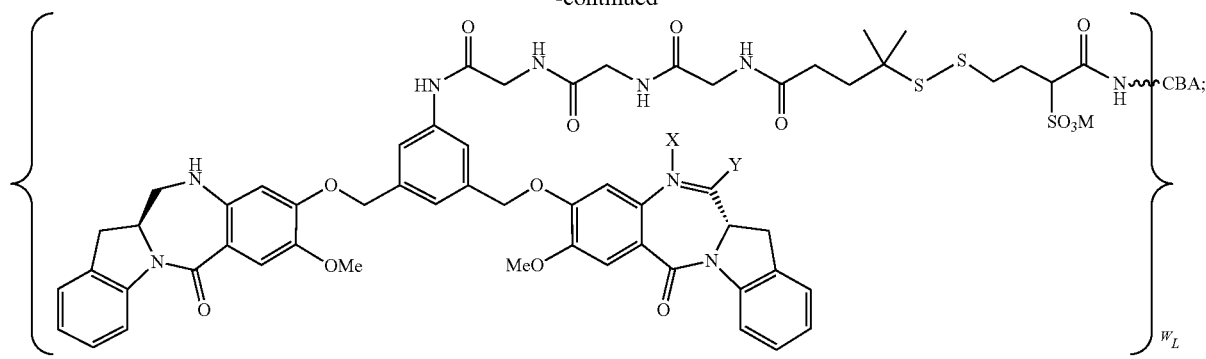
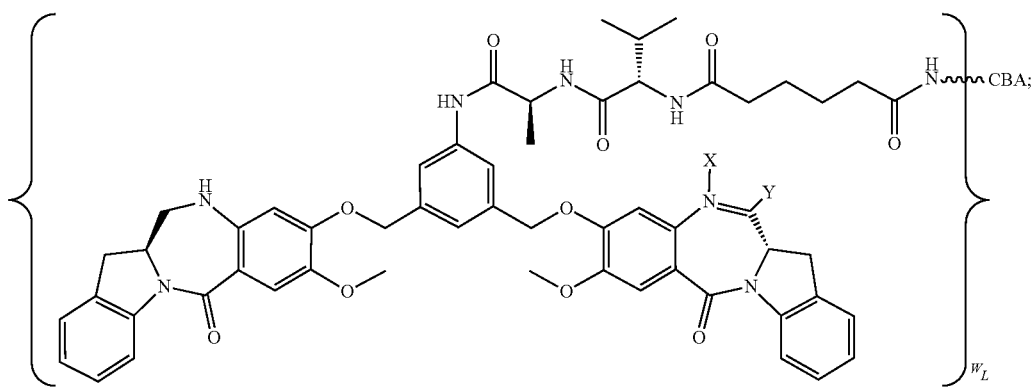
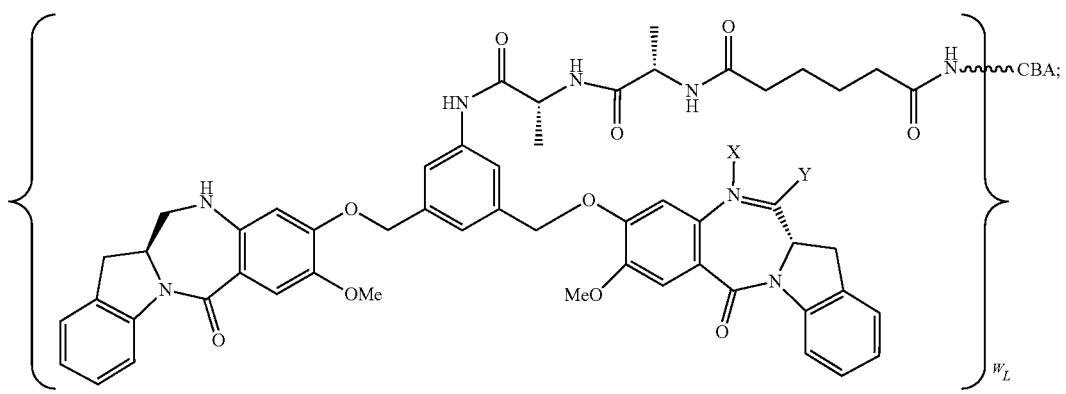
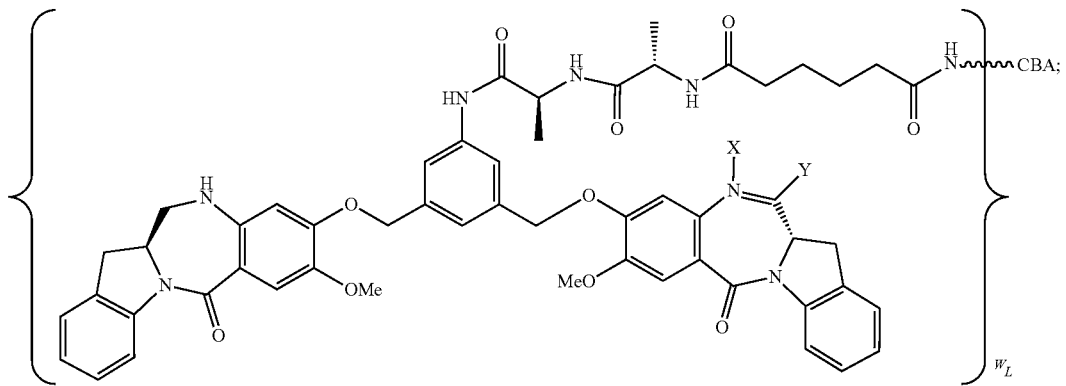

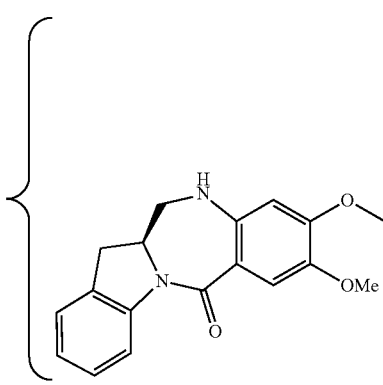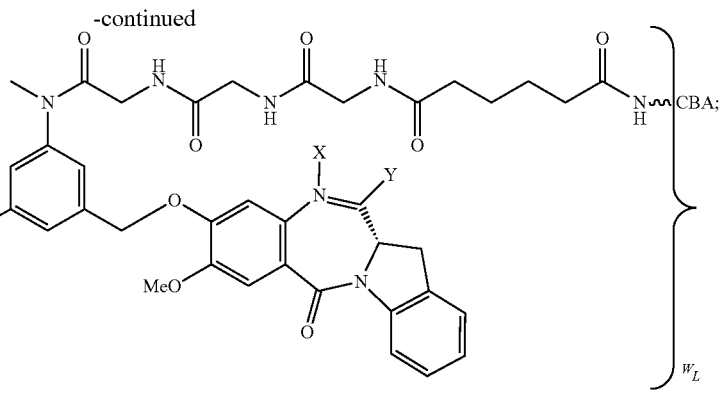

or a pharmaceutically acceptable salt thereof, wherein $W_L$ is an integer from 1 to 10; the double line ══ between N and C represents a single bond or a double bond, provided that when it is a double bond, X is absent and Y is —H; and when it is a single bond, X is —H, and Y is —OH or —SO$_3$M.

11. A pharmaceutical composition comprising the immunoconjugate of claim 1, and a pharmaceutically acceptable carrier.

* * * * *

UNITED STATES PATENT AND TRADEMARK OFFICE
CERTIFICATE OF CORRECTION

PATENT NO. : 11,897,961 B2
APPLICATION NO. : 17/711518
DATED : February 13, 2024
INVENTOR(S) : Yelena Kovtun et al.

Page 1 of 5

It is certified that error appears in the above-identified patent and that said Letters Patent is hereby corrected as shown below:

In the Claims

At Column 465, Claim number 1, Line numbers 55-65, depict the following structure:

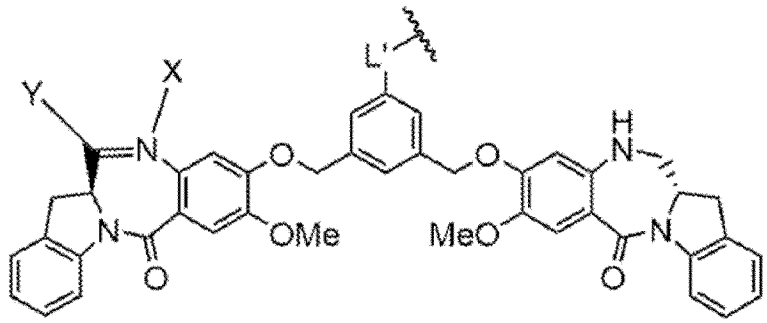

The structure should appear as:

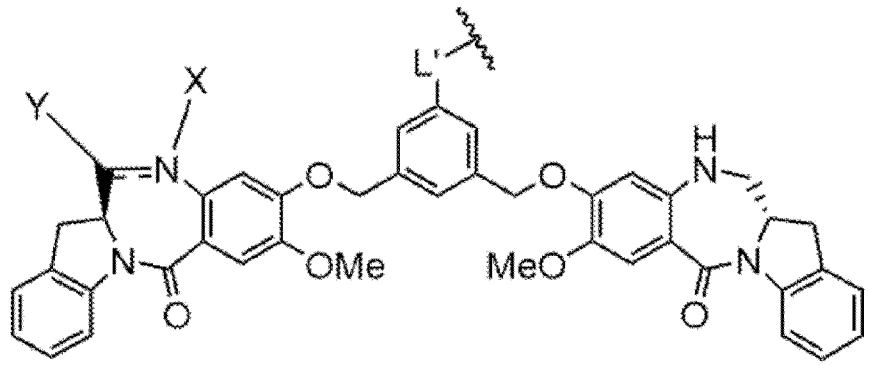

Signed and Sealed this
Seventeenth Day of September, 2024

Katherine Kelly Vidal
*Director of the United States Patent and Trademark Office*

CERTIFICATE OF CORRECTION (continued)
U.S. Pat. No. 11,897,961 B2

At Columns 467-468, Claim number 10, Line numbers 50-65, depict the following structure:

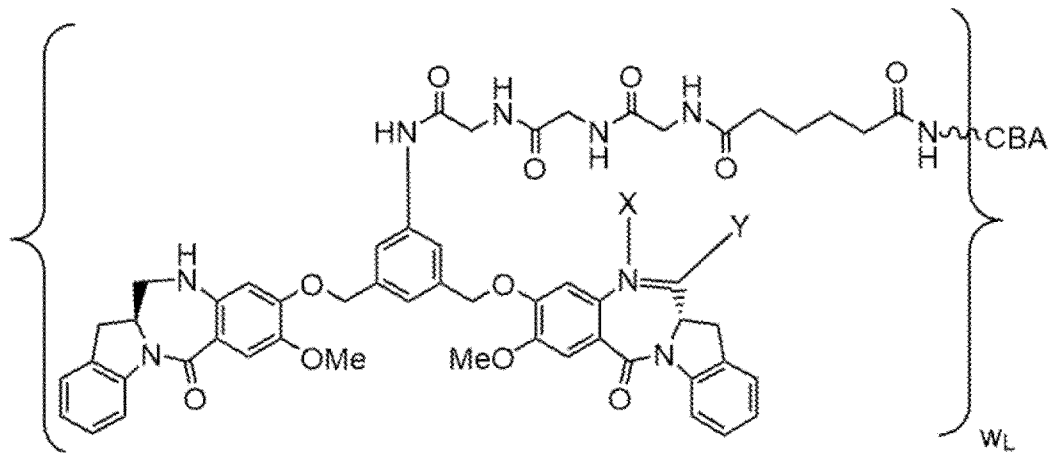

The structure should appear as:

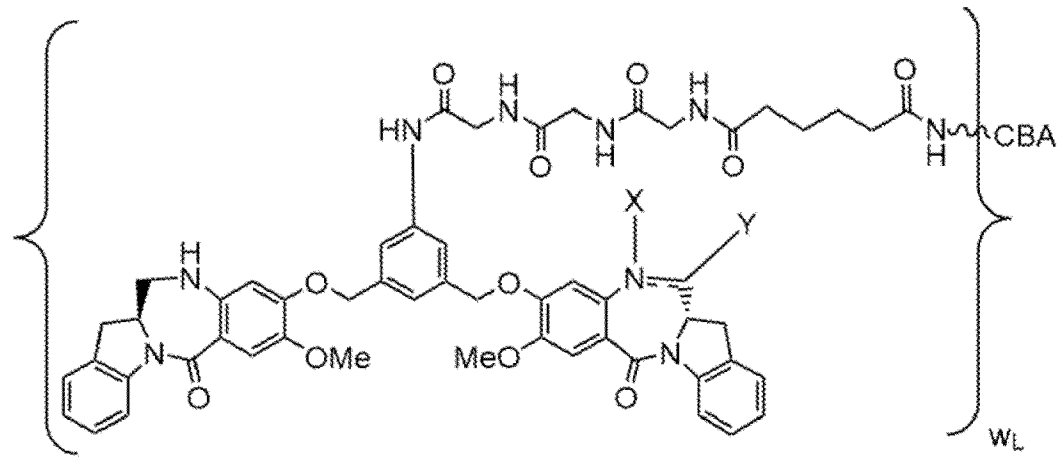

At Columns 469-470, Claim number 10, the first structure is depicted as follows:

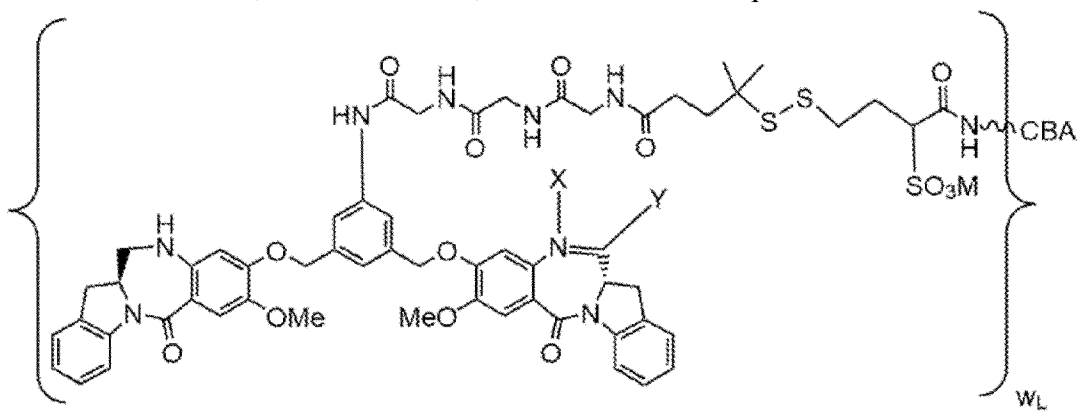

CERTIFICATE OF CORRECTION (continued)

The structure should appear as:

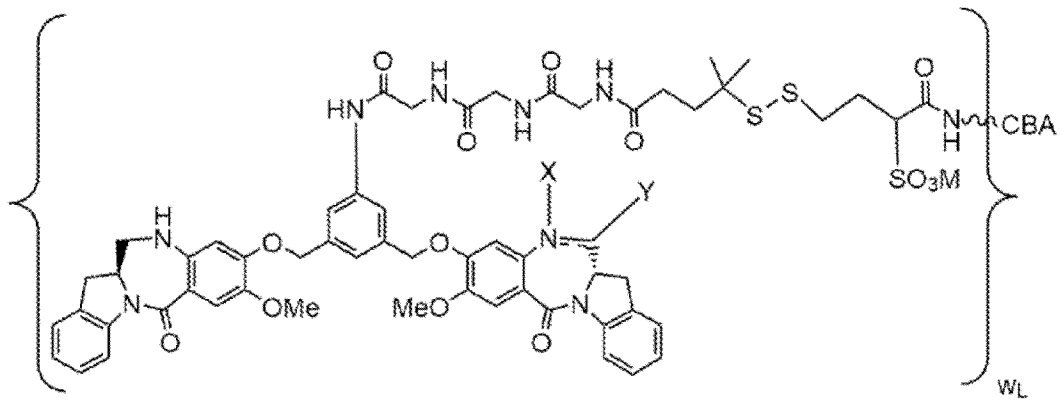

At Columns 469-470, Claim number 10, the second structure is depicted as follows:

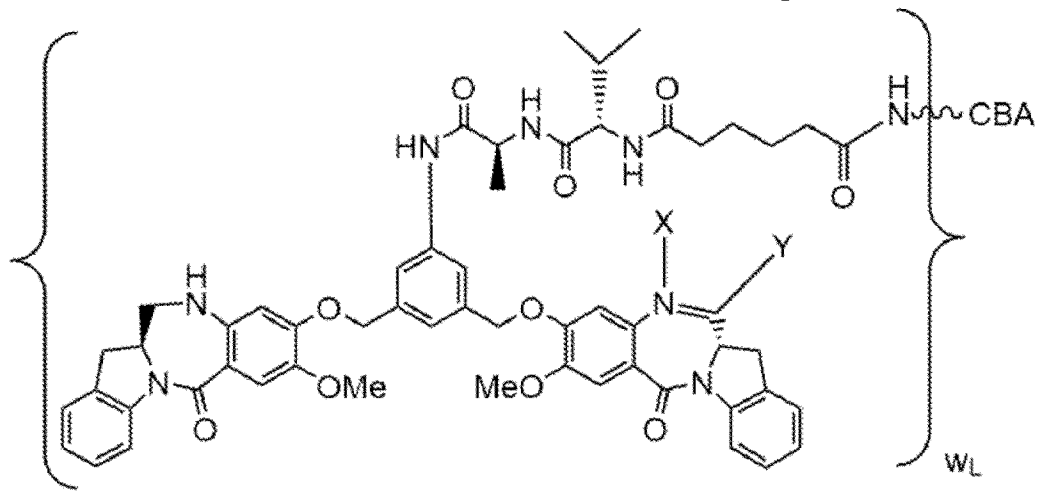

The structure should appear as:

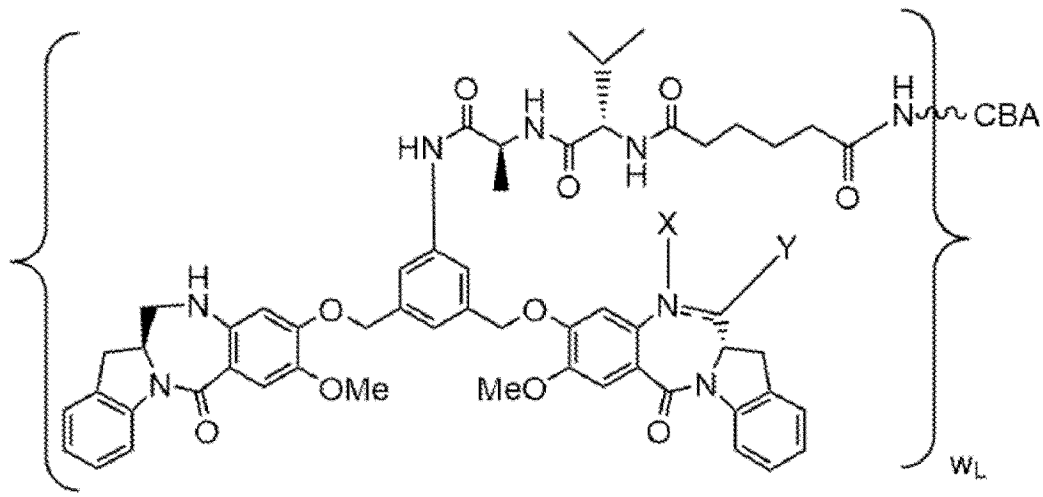

At Columns 469-470, Claim number 10, the third structure is depicted as follows:
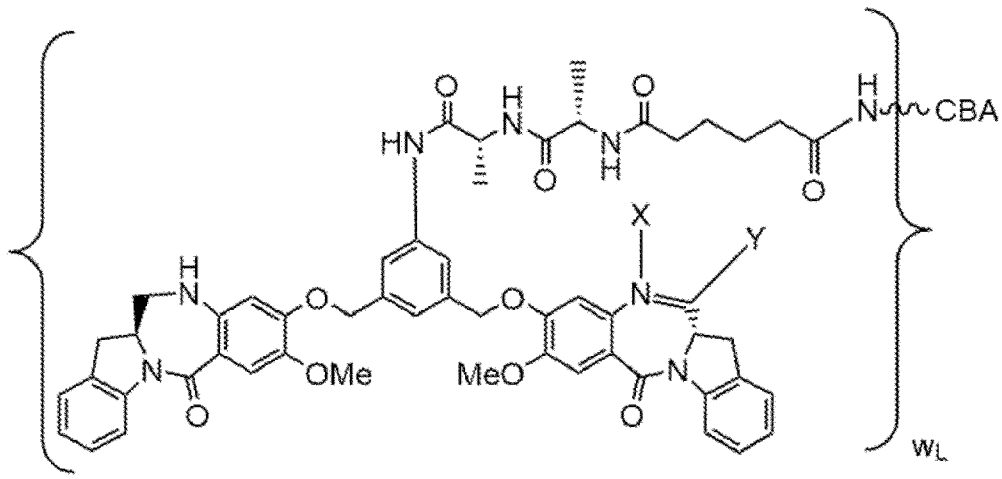
The structure should appear as:
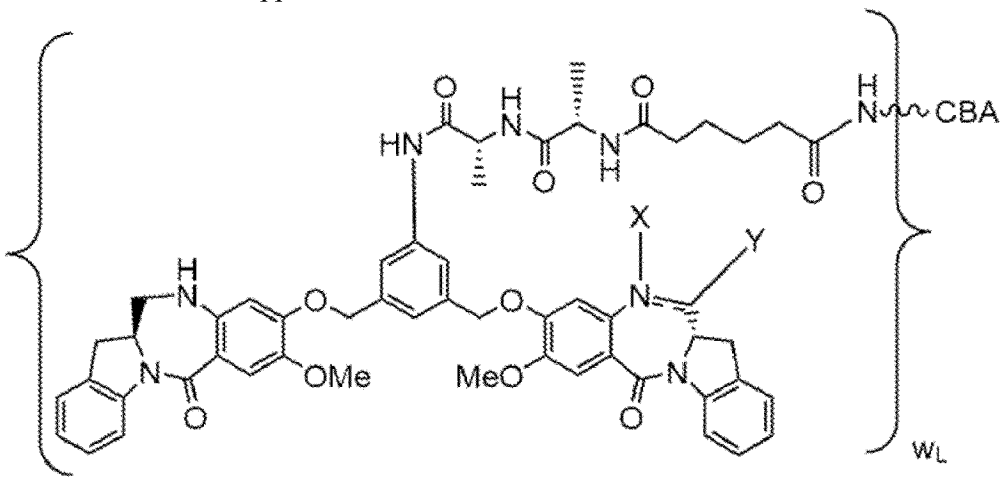
At Columns 469-470, Claim number 10, the fourth structure is depicted as follows:
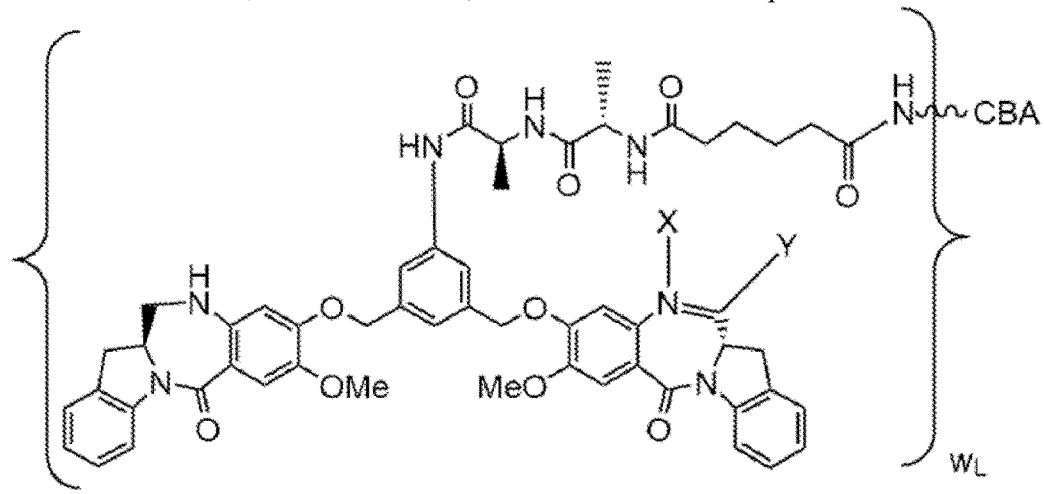
The structure should appear as:

CERTIFICATE OF CORRECTION (continued)
U.S. Pat. No. 11,897,961 B2

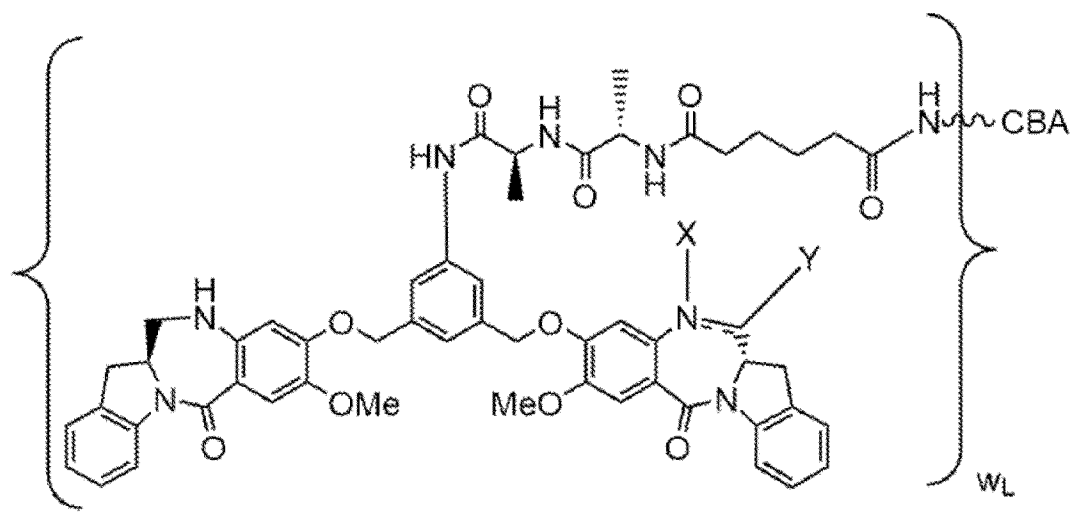

At Columns 471-472, Claim number 10, Line numbers 1-15, depict the following structure:

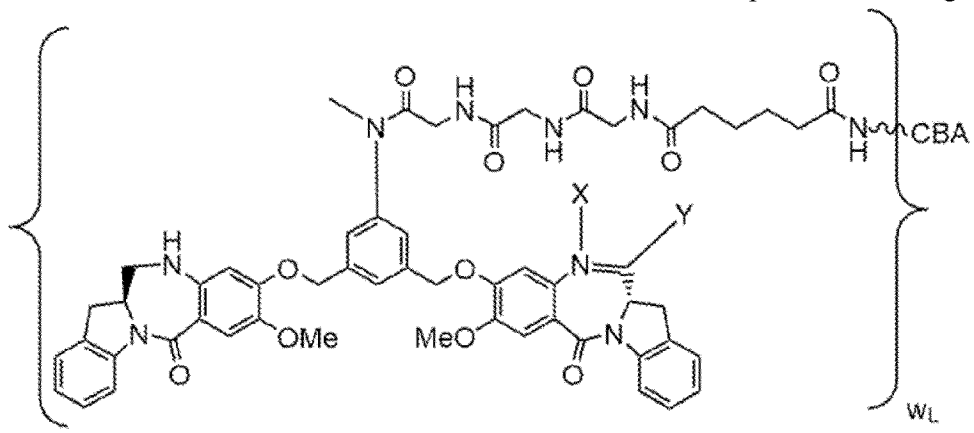

The structure should appear as:

SEQUENCE LISTING

```
<160> NUMBER OF SEQ ID NOS: 97

<210> SEQ ID NO 1
<211> LENGTH: 5
<212> TYPE: PRT
<213> ORGANISM: Artificial
<220> FEATURE:
<223> OTHER INFORMATION: Synthetic Peptide

<400> SEQUENCE: 1

Ser Tyr Val Met His
1               5

<210> SEQ ID NO 2
<211> LENGTH: 10
<212> TYPE: PRT
<213> ORGANISM: Artificial
<220> FEATURE:
<223> OTHER INFORMATION: Synthetic Peptide
```

```
<400> SEQUENCE: 2

Tyr Ile Lys Pro Tyr Lys Asp Gly Thr Lys
1               5                   10

<210> SEQ ID NO 3
<211> LENGTH: 17
<212> TYPE: PRT
<213> ORGANISM: Artificial
<220> FEATURE:
<223> OTHER INFORMATION: Synthetic Peptide

<400> SEQUENCE: 3

Tyr Ile Lys Pro Tyr Lys Asp Gly Thr Lys Tyr Asn Glu Lys Phe Lys
1               5                   10                  15

Gly

<210> SEQ ID NO 4
<211> LENGTH: 12
<212> TYPE: PRT
<213> ORGANISM: Artificial
<220> FEATURE:
<223> OTHER INFORMATION: Synthetic Peptide

<400> SEQUENCE: 4

Glu Gly Glu Asn Gly Tyr Tyr Asp Ala Met Asp Tyr
1               5                   10

<210> SEQ ID NO 5
<211> LENGTH: 5
<212> TYPE: PRT
<213> ORGANISM: Artificial
<220> FEATURE:
<223> OTHER INFORMATION: Synthetic Peptide

<400> SEQUENCE: 5

Ser Ser Ile Met His
1               5

<210> SEQ ID NO 6
<211> LENGTH: 10
<212> TYPE: PRT
<213> ORGANISM: Artificial
<220> FEATURE:
<223> OTHER INFORMATION: Synthetic Peptide

<400> SEQUENCE: 6

Tyr Ile Lys Pro Tyr Asn Asp Gly Thr Lys
1               5                   10

<210> SEQ ID NO 7
<211> LENGTH: 10
<212> TYPE: PRT
<213> ORGANISM: Artificial
<220> FEATURE:
<223> OTHER INFORMATION: Synthetic Peptide

<400> SEQUENCE: 7

Tyr Ile Arg Pro Tyr Asn Asp Gly Thr Arg
1               5                   10

<210> SEQ ID NO 8
<211> LENGTH: 17
<212> TYPE: PRT
<213> ORGANISM: Artificial
<220> FEATURE:
<223> OTHER INFORMATION: Synthetic Peptide
```

```
<400> SEQUENCE: 8

Tyr Ile Lys Pro Tyr Asn Asp Gly Thr Lys Tyr Asn Glu Lys Phe Lys
1               5                   10                  15

Gly

<210> SEQ ID NO 9
<211> LENGTH: 17
<212> TYPE: PRT
<213> ORGANISM: Artificial
<220> FEATURE:
<223> OTHER INFORMATION: Synthetic Peptide

<400> SEQUENCE: 9

Tyr Ile Arg Pro Tyr Asn Asp Gly Thr Arg Tyr Asn Gln Lys Phe Gln
1               5                   10                  15

Gly

<210> SEQ ID NO 10
<211> LENGTH: 17
<212> TYPE: PRT
<213> ORGANISM: Artificial
<220> FEATURE:
<223> OTHER INFORMATION: Synthetic Peptide

<400> SEQUENCE: 10

Tyr Ile Lys Pro Tyr Asn Asp Gly Thr Lys Tyr Asn Gln Lys Phe Gln
1               5                   10                  15

Gly

<210> SEQ ID NO 11
<211> LENGTH: 12
<212> TYPE: PRT
<213> ORGANISM: Artificial
<220> FEATURE:
<223> OTHER INFORMATION: Synthetic Peptide

<400> SEQUENCE: 11

Glu Gly Gly Asn Asp Tyr Tyr Asp Thr Met Asp Tyr
1               5                   10

<210> SEQ ID NO 12
<211> LENGTH: 5
<212> TYPE: PRT
<213> ORGANISM: Artificial
<220> FEATURE:
<223> OTHER INFORMATION: Synthetic Peptide

<400> SEQUENCE: 12

Asn Tyr Ala Met Ser
1               5

<210> SEQ ID NO 13
<211> LENGTH: 10
<212> TYPE: PRT
<213> ORGANISM: Artificial
<220> FEATURE:
<223> OTHER INFORMATION: Synthetic Peptide

<400> SEQUENCE: 13

Thr Ile Asn Ser Gly Gly Ser Phe Thr Tyr
1               5                   10
```

-continued

```
<210> SEQ ID NO 14
<211> LENGTH: 17
<212> TYPE: PRT
<213> ORGANISM: Artificial
<220> FEATURE:
<223> OTHER INFORMATION: Synthetic Peptide

<400> SEQUENCE: 14

Thr Ile Asn Ser Gly Gly Ser Phe Thr Tyr Tyr Pro Asp Ser Val Lys
1               5                   10                  15
Gly

<210> SEQ ID NO 15
<211> LENGTH: 12
<212> TYPE: PRT
<213> ORGANISM: Artificial
<220> FEATURE:
<223> OTHER INFORMATION: Synthetic Peptide

<400> SEQUENCE: 15

Gln Ser Glu Ala Tyr Tyr Gly Tyr Asp Lys Arg Thr
1               5                   10

<210> SEQ ID NO 16
<211> LENGTH: 11
<212> TYPE: PRT
<213> ORGANISM: Artificial
<220> FEATURE:
<223> OTHER INFORMATION: Synthetic Peptide

<400> SEQUENCE: 16

Lys Ala Ser Gln Asp Ile Asn Lys Tyr Ile Ala
1               5                   10

<210> SEQ ID NO 17
<211> LENGTH: 7
<212> TYPE: PRT
<213> ORGANISM: Artificial
<220> FEATURE:
<223> OTHER INFORMATION: Synthetic Peptide

<400> SEQUENCE: 17

Tyr Thr Ser Thr Leu Gln Pro
1               5

<210> SEQ ID NO 18
<211> LENGTH: 9
<212> TYPE: PRT
<213> ORGANISM: Artificial
<220> FEATURE:
<223> OTHER INFORMATION: Synthetic Peptide

<400> SEQUENCE: 18

Leu Gln Tyr Asp Asn Leu Leu Tyr Thr
1               5

<210> SEQ ID NO 19
<211> LENGTH: 11
<212> TYPE: PRT
<213> ORGANISM: Artificial
<220> FEATURE:
<223> OTHER INFORMATION: Synthetic Peptide

<400> SEQUENCE: 19

Lys Ala Ser Gln Asp Ile Asn Ser Tyr Leu Ser
1               5                   10
```

```
<210> SEQ ID NO 20
<211> LENGTH: 11
<212> TYPE: PRT
<213> ORGANISM: Artificial
<220> FEATURE:
<223> OTHER INFORMATION: Synthetic Peptide

<400> SEQUENCE: 20

Arg Ala Ser Gln Asp Ile Asn Ser Tyr Leu Ser
1               5                   10

<210> SEQ ID NO 21
<211> LENGTH: 7
<212> TYPE: PRT
<213> ORGANISM: Artificial
<220> FEATURE:
<223> OTHER INFORMATION: Synthetic Peptide

<400> SEQUENCE: 21

Arg Val Asn Arg Leu Val Asp
1               5

<210> SEQ ID NO 22
<211> LENGTH: 9
<212> TYPE: PRT
<213> ORGANISM: Artificial
<220> FEATURE:
<223> OTHER INFORMATION: Synthetic Peptide

<400> SEQUENCE: 22

Leu Gln Tyr Asp Ala Phe Pro Tyr Thr
1               5

<210> SEQ ID NO 23
<211> LENGTH: 11
<212> TYPE: PRT
<213> ORGANISM: Artificial
<220> FEATURE:
<223> OTHER INFORMATION: Synthetic Peptide

<400> SEQUENCE: 23

Arg Ala Ser Gln Ser Val Gly Thr Ser Ile His
1               5                   10

<210> SEQ ID NO 24
<211> LENGTH: 7
<212> TYPE: PRT
<213> ORGANISM: Artificial
<220> FEATURE:
<223> OTHER INFORMATION: Synthetic Peptide

<400> SEQUENCE: 24

Tyr Ala Ser Glu Ser Ile Ser
1               5

<210> SEQ ID NO 25
<211> LENGTH: 9
<212> TYPE: PRT
<213> ORGANISM: Artificial
<220> FEATURE:
<223> OTHER INFORMATION: Synthetic Peptide

<400> SEQUENCE: 25

Gln Gln Ser Lys Ser Trp Pro Leu Thr
1               5
```

<210> SEQ ID NO 26
<211> LENGTH: 121
<212> TYPE: PRT
<213> ORGANISM: Artificial
<220> FEATURE:
<223> OTHER INFORMATION: Synthetic Peptide

<400> SEQUENCE: 26

Glu Phe Gln Leu Gln Gln Ser Gly Pro Glu Val Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Met Lys Gln Lys Pro Gly Gln Gly Leu Glu Trp Ile
        35                  40                  45

Gly Tyr Ile Lys Pro Tyr Lys Asp Gly Thr Lys Tyr Asn Glu Lys Phe
    50                  55                  60

Lys Gly Lys Ala Thr Leu Ile Ser Asp Lys Pro Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Gly Glu Asn Gly Tyr Tyr Asp Ala Met Asp Tyr Trp Gly
            100                 105                 110

Gln Gly Thr Ser Val Thr Val Ser Ser
        115                 120

<210> SEQ ID NO 27
<211> LENGTH: 108
<212> TYPE: PRT
<213> ORGANISM: Artificial
<220> FEATURE:
<223> OTHER INFORMATION: Synthetic Peptide

<400> SEQUENCE: 27

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gly Gly Thr Lys Leu Glu Leu Lys Arg
            100                 105

<210> SEQ ID NO 28
<211> LENGTH: 121
<212> TYPE: PRT
<213> ORGANISM: Artificial
<220> FEATURE:
<223> OTHER INFORMATION: Synthetic Peptide

<400> SEQUENCE: 28

Glu Phe Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Thr Ser Ser
            20                  25                  30

```
Ile Met His Trp Met Lys Gln Lys Pro Gly Gln Gly Leu Glu Trp Ile
            35                  40                  45

Gly Tyr Ile Lys Pro Tyr Asn Asp Gly Thr Lys Tyr Asn Glu Lys Phe
 50                  55                  60

Lys Gly Lys Ala Thr Leu Thr Ser Asp Lys Ser Ser Thr Ala Asn
 65                  70                  75                  80

Met Glu Leu Asn Ser Leu Thr Ser Glu Asp Ser Ala Val Tyr Tyr Cys
                 85                  90                  95

Ala Arg Glu Gly Gly Asn Asp Tyr Tyr Asp Thr Met Asp Tyr Trp Gly
                100                 105                 110

Gln Gly Thr Ser Val Thr Val Ser Ser
            115                 120

<210> SEQ ID NO 29
<211> LENGTH: 108
<212> TYPE: PRT
<213> ORGANISM: Artificial
<220> FEATURE:
<223> OTHER INFORMATION: Synthetic Peptide

<400> SEQUENCE: 29

Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Ser Tyr
                 20                  25                  30

Leu Ser Trp Phe Gln Gln Lys Pro Gly Lys Ser Pro Lys Thr Leu Ile
             35                  40                  45

Tyr Arg Val Asn Arg Leu Val Asp Gly Val Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Ala Phe Pro Tyr
                 85                  90                  95

Thr Phe Gly Gly Gly Thr Lys Leu Glu Ile Lys Arg
                100                 105

<210> SEQ ID NO 30
<211> LENGTH: 125
<212> TYPE: PRT
<213> ORGANISM: Artificial
<220> FEATURE:
<223> OTHER INFORMATION: Synthetic Peptide

<400> SEQUENCE: 30

Glu Val Lys Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Asn Tyr
                 20                  25                  30

Ala Met Ser Trp Val Arg Gln Asn Ser Glu Lys Arg Leu Glu Trp Val
             35                  40                  45

Ala Thr Ile Asn Ser Gly Gly Ser Phe Thr Tyr Tyr Pro Asp Ser Val
 50                  55                  60

Lys Gly Arg Phe Thr Ile Ser Arg Asp Asn Ala Lys Asp Ser Leu Tyr
 65                  70                  75                  80

Leu Gln Met Ser Ser Leu Asn Ser Glu Asp Thr Ala Met Tyr Tyr Cys
                 85                  90                  95
```

```
Ala Arg Gln Ser Glu Ala Tyr Gly Tyr Asp Lys Arg Thr Trp Phe
                100                 105                 110

Ala Tyr Trp Gly Gln Gly Thr Leu Val Thr Val Ser Ser
        115                 120                 125

<210> SEQ ID NO 31
<211> LENGTH: 108
<212> TYPE: PRT
<213> ORGANISM: Artificial
<220> FEATURE:
<223> OTHER INFORMATION: Synthetic Peptide

<400> SEQUENCE: 31

Asp Ile Leu Leu Thr Gln Ser Pro Ala Ile Leu Ser Val Ser Pro Gly
1               5                   10                  15

Thr Arg Val Ser Phe Ser Cys Arg Ala Ser Gln Ser Val Gly Thr Ser
                20                  25                  30

Ile His Trp Tyr Gln Gln Arg Pro Asn Gly Phe Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Asn Ile Asn Ser Val Glu Ser
65                  70                  75                  80

Glu Asp Ile Ala Asp Tyr Tyr Cys Gln Gln Ser Lys Ser Trp Pro Leu
                85                  90                  95

Thr Phe Gly Ala Gly Thr Lys Leu Glu Leu Lys Arg
                100                 105

<210> SEQ ID NO 32
<211> LENGTH: 82
<212> TYPE: PRT
<213> ORGANISM: Artificial
<220> FEATURE:
<223> OTHER INFORMATION: Synthetic Peptide

<400> SEQUENCE: 32

Ala Pro Gly Gln Gly Leu Glu Trp Met Gly Tyr Ile Lys Pro Tyr Asn
1               5                   10                  15

Asp Gly Thr Lys Tyr Asn Glu Lys Phe Lys Gly Arg Val Thr Met Thr
                20                  25                  30

Arg Asp Thr Ser Thr Ser Thr Val Tyr Met Glu Leu Ser Ser Leu Arg
            35                  40                  45

Ser Glu Asp Thr Ala Val Tyr Tyr Cys Ala Arg Glu Gly Gly Asn Asp
        50                  55                  60

Tyr Tyr Asp Thr Met Asp Tyr Trp Gly Gln Gly Thr Leu Val Thr Val
65                  70                  75                  80

Ser Ser

<210> SEQ ID NO 33
<211> LENGTH: 108
<212> TYPE: PRT
<213> ORGANISM: Artificial
<220> FEATURE:
<223> OTHER INFORMATION: Synthetic Peptide

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
                20                  25                  30
```

```
Leu Ala Trp Phe Gln Gln Lys Pro Gly Lys Ala Pro Lys Ser Leu Ile
            35                  40                  45

Tyr Arg Val Asn Arg Leu Val Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Ala Phe Pro Tyr
                    85                  90                  95

Thr Phe Gly Gln Gly Thr Lys Val Glu Ile Lys Arg
                100                 105
```

<210> SEQ ID NO 34
<211> LENGTH: 121
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Phe or Val

<400> SEQUENCE: 34

```
Gln Xaa Gln Leu Val Gln Ser Gly Ala Glu Val Lys Lys Pro Gly Ala
  1               5                  10                  15

Ser Val Lys Val Ser Cys Lys Ala Ser Gly Tyr Ile Phe Thr Ser Ser
             20                  25                  30

Ile Met His Trp Val Arg Gln Ala Pro Gly Gln Gly Leu Glu Trp Ile
         35                  40                  45

Gly Tyr Ile Lys Pro Tyr Asn Asp Gly Thr Lys Tyr Asn Glu Lys Phe
 50                  55                  60

Lys Gly Arg Ala Thr Leu Thr Ser Asp Arg Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Gly Asn Asp Tyr Tyr Asp Thr Met Asp Tyr Trp Gly
                100                 105                 110

Gln Gly Thr Leu Val Thr Val Ser Ser
            115                 120
```

<210> SEQ ID NO 35
<211> LENGTH: 108
<212> TYPE: PRT
<213> ORGANISM: Artificial
<220> FEATURE:
<223> OTHER INFORMATION: Synthetic Peptide

<400> SEQUENCE: 35

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Asn Ser Tyr
             20                  25                  30

Leu Ser Trp Phe Gln Gln Lys Pro Gly Lys Ala Pro Lys Thr Leu Ile
            35                  40                  45

Tyr Arg Val Asn Arg Leu Val Asp Gly Val Pro Ser Arg Phe Ser Gly
 50                      55                  60

Ser Gly Ser Gly Asn Asp Tyr Thr Leu Thr Ile Ser Ser Leu Gln Pro
 65                  70                  75                  80
```

Glu Asp Phe Ala Thr Tyr Tyr Cys Leu Gln Tyr Asp Ala Phe Pro Tyr
            85                  90                  95

Thr Phe Gly Gln Gly Thr Lys Val Glu Ile Lys Arg
            100                 105

<210> SEQ ID NO 36
<211> LENGTH: 378
<212> TYPE: PRT
<213> ORGANISM: Artificial
<220> FEATURE:
<223> OTHER INFORMATION: Synthetic Peptide

<400> SEQUENCE: 36

Met Val Leu Leu Trp Leu Thr Leu Leu Ile Ala Leu Pro Cys Leu
1               5                   10                  15

Leu Gln Thr Lys Glu Asp Pro Asn Pro Ile Thr Asn Leu Arg Met
            20                  25                  30

Lys Ala Lys Ala Gln Gln Leu Thr Trp Asp Leu Asn Arg Asn Val Thr
            35                  40                  45

Asp Ile Glu Cys Val Lys Asp Ala Asp Tyr Ser Met Pro Ala Val Asn
        50                  55                  60

Asn Ser Tyr Cys Gln Phe Gly Ala Ile Ser Leu Cys Glu Val Thr Asn
65                  70                  75                  80

Tyr Thr Val Arg Val Ala Asn Pro Pro Phe Ser Thr Trp Ile Leu Phe
                85                  90                  95

Pro Glu Asn Ser Gly Lys Pro Trp Ala Gly Ala Glu Asn Leu Thr Cys
            100                 105                 110

Trp Ile His Asp Val Asp Phe Leu Ser Cys Ser Trp Ala Val Gly Pro
            115                 120                 125

Gly Ala Pro Ala Asp Val Gln Tyr Asp Leu Tyr Leu Asn Val Ala Asn
130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

Ile Pro Cys Thr Asp Lys Phe Val Val Phe Ser Gln Ile Glu Ile Leu
        195                 200                 205

Thr Pro Pro Asn Met Thr Ala Lys Cys Asn Lys Thr His Ser Phe Met
210                 215                 220

His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270

Arg Ala Arg Glu Arg Val Tyr Glu Phe Leu Ser Ala Trp Ser Thr Pro
        275                 280                 285

Gln Arg Phe Glu Cys Asp Gln Glu Glu Gly Ala Asn Thr Arg Ala Trp
290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335

```
Arg Ile Pro His Met Lys Asp Pro Ile Gly Asp Ser Phe Gln Asn Asp
            340                 345                 350

Lys Leu Val Val Trp Glu Ala Gly Lys Ala Gly Leu Glu Glu Cys Leu
        355                 360                 365

Val Thr Glu Val Gln Val Val Gln Lys Thr
    370                 375

<210> SEQ ID NO 37
<211> LENGTH: 108
<212> TYPE: PRT
<213> ORGANISM: Artificial
<220> FEATURE:
<223> OTHER INFORMATION: Synthetic Peptide

<400> SEQUENCE: 37

Ser Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg
            100                 105

<210> SEQ ID NO 38
<211> LENGTH: 121
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Phe or Val

<400> SEQUENCE: 38

Ser Xaa Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120
```

<210> SEQ ID NO 39
<211> LENGTH: 121
<212> TYPE: PRT
<213> ORGANISM: Artificial
<220> FEATURE:
<223> OTHER INFORMATION: Synthetic Peptide

<400> SEQUENCE: 39

Gln Val Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Ser Ser
            20                  25                  30

Ile Met His Trp Met Lys Gln Lys Pro Gly Gln Gly Leu Glu Trp Ile
        35                  40                  45

Gly Tyr Ile Arg Pro Tyr Asn Asp Gly Thr Arg Tyr Asn Gln Lys Phe
    50                  55                  60

Gln Gly Lys Ala Thr Leu Thr Ser Asp Arg Ser Ser Ser Thr Ala Asn
65                  70                  75                  80

Met Glu Leu Asn Ser Leu Thr Ser Glu Asp Ser Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Ser Val Thr Val Ser Ser
        115                 120

<210> SEQ ID NO 40
<211> LENGTH: 121
<212> TYPE: PRT
<213> ORGANISM: Artificial
<220> FEATURE:
<223> OTHER INFORMATION: Synthetic Peptide

<400> SEQUENCE: 40

Gln Phe Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Ser Ser
            20                  25                  30

Ile Met His Trp Met Lys Gln Lys Pro Gly Gln Gly Leu Glu Trp Ile
        35                  40                  45

Gly Tyr Ile Lys Pro Tyr Asn Asp Gly Thr Lys Tyr Asn Gln Lys Phe
    50                  55                  60

Gln Gly Lys Ala Thr Leu Thr Ser Asp Lys Ser Ser Ser Thr Ala Asn
65                  70                  75                  80

Met Glu Leu Asn Ser Leu Thr Ser Glu Asp Ser Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Ser Val Thr Val Ser Ser
        115                 120

<210> SEQ ID NO 41
<211> LENGTH: 108
<212> TYPE: PRT
<213> ORGANISM: Artificial
<220> FEATURE:
<223> OTHER INFORMATION: Synthetic Peptide -continued

<400> SEQUENCE: 41

Asp Ile Gln Met Thr Gln Ser Pro Ser Ser Met Ser Ala Ser Val Gly
1               5                   10                  15

Glu Arg Val Thr Ile Thr Cys Arg Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Pro
65                  70                  75                  80

Glu Asp Met Gly Ile Tyr Tyr Cys Leu Gln Tyr Asp Ala Phe Pro Tyr
                85                  90                  95

Thr Phe Gly Gln Gly Thr Lys Leu Glu Ile Lys Arg
            100                 105

<210> SEQ ID NO 42
<211> LENGTH: 445
<212> TYPE: PRT
<213> ORGANISM: Artificial
<220> FEATURE:
<223> OTHER INFORMATION: Synthetic Peptide

<400> SEQUENCE: 42

Glu Phe Gln Leu Gln Gln Ser Gly Pro Glu Val Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Met Lys Gln Lys Pro Gly Gln Gly Leu Glu Trp Ile
        35                  40                  45

Gly Tyr Ile Lys Pro Tyr Lys Asp Gly Thr Lys Tyr Asn Glu Lys Phe
    50                  55                  60

Lys Gly Lys Ala Thr Leu Ile Ser Asp Lys Pro Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Gly Glu Asn Gly Tyr Tyr Asp Ala Met Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Glu Ser Asp Leu Tyr Thr Leu Ser Ser Ser Val Thr Val Pro
            180                 185                 190

Ser Ser Pro Arg Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asn Thr Asn Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 43
<211> LENGTH: 214
<212> TYPE: PRT
<213> ORGANISM: Artificial
<220> FEATURE:
<223> OTHER INFORMATION: Synthetic Peptide

<400> SEQUENCE: 43

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gly Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

-continued

Asn Ser Trp Thr Asp Gln Asp Ser Lys Asp Ser Thr Tyr Ser Met Ser
              165                 170                 175

Ser Thr Leu Thr Leu Thr Lys Asp Glu Tyr Glu Arg His Asn Ser Tyr
        180                 185                 190

Thr Cys Glu Ala Thr His Lys Thr Ser Thr Ser Pro Ile Val Lys Ser
    195                 200                 205

Phe Asn Arg Asn Glu Cys
    210

<210> SEQ ID NO 44
<211> LENGTH: 445
<212> TYPE: PRT
<213> ORGANISM: Artificial
<220> FEATURE:
<223> OTHER INFORMATION: Synthetic Peptide

<400> SEQUENCE: 44

Glu Phe Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Thr Ser Ser
            20                  25                  30

Ile Met His Trp Met Lys Gln Lys Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Asn
65                  70                  75                  80

Met Glu Leu Asn Ser Leu Thr Ser Glu Asp Ser Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Glu Ser Asp Leu Tyr Thr Leu Ser Ser Ser Val Thr Val Pro
            180                 185                 190

Ser Ser Met Arg Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
            325                 330                 335

Thr Lys Gly Arg Pro Lys Ala Pro Gln Val Tyr Thr Ile Pro Pro Pro
        340                 345                 350

Lys Glu Gln Met Ala Lys Asp Lys Val Ser Leu Thr Cys Met Ile Thr
    355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asn Thr Asn Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
            435                 440                 445

<210> SEQ ID NO 45
<211> LENGTH: 214
<212> TYPE: PRT
<213> ORGANISM: Artificial
<220> FEATURE:
<223> OTHER INFORMATION: Synthetic Peptide

<400> SEQUENCE: 45

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Val Asn Arg Leu Val Asp Gly Val Pro Ser Arg Phe Ser Gly
50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Ala Phe Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

-continued

```
<210> SEQ ID NO 46
<211> LENGTH: 449
<212> TYPE: PRT
<213> ORGANISM: Artificial
<220> FEATURE:
<223> OTHER INFORMATION: Synthetic Peptide

<400> SEQUENCE: 46
```

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Asn Ser Glu Lys Arg Leu Glu Trp Val
        35                  40                  45

Ala Thr Ile Asn Ser Gly Gly Ser Phe Thr Tyr Tyr Pro Asp Ser Val
    50                  55                  60

Lys Gly Arg Phe Thr Ile Ser Arg Asp Asn Ala Lys Asp Ser Leu Tyr
65                  70                  75                  80

Leu Gln Met Ser Ser Leu Asn Ser Glu Asp Thr Ala Met Tyr Tyr Cys
                85                  90                  95

Ala Arg Gln Ser Glu Ala Tyr Tyr Gly Tyr Asp Lys Arg Thr Trp Phe
            100                 105                 110

Ala Tyr Trp Gly Gln Gly Thr Leu Val Thr Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Glu Ser Asp Leu Tyr Thr Leu Ser Ser Ser
            180                 185                 190

Val Thr Val Pro Ser Ser Pro Arg Pro Ser Glu Thr Val Thr Cys Asn
        195                 200                 205

Val Ala His Pro Ala Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

```
Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asn Thr Asn Gly Ser Tyr Phe Val Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
        435                 440                 445

Lys
```

```
<210> SEQ ID NO 47
<211> LENGTH: 214
<212> TYPE: PRT
<213> ORGANISM: Artificial
<220> FEATURE:
<223> OTHER INFORMATION: Synthetic Peptide

<400> SEQUENCE: 47

Asp Ile Leu Leu Thr Gln Ser Pro Ala Ile Leu Ser Val Ser Pro Gly
1               5                   10                  15

Thr Arg Val Ser Phe Ser Cys Arg Ala Ser Gln Ser Val Gly Thr Ser
            20                  25                  30

Ile His Trp Tyr Gln Gln Arg Pro Asn Gly Phe Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Asn Ile Asn Ser Val Glu Ser
65                  70                  75                  80

Glu Asp Ile Ala Asp Tyr Tyr Cys Gln Gln Ser Lys Ser Trp Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 48
<211> LENGTH: 450
<212> TYPE: PRT
<213> ORGANISM: Artificial
<220> FEATURE:
<223> OTHER INFORMATION: Synthetic Peptide
```

<400> SEQUENCE: 48

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Gly Phe Thr Ser Ser
            20                  25                  30
Ile Met His Trp Val Arg Gln Ala Pro Gly Gln Gly Leu Glu Trp Met
        35                  40                  45
Gly Tyr Ile Lys Pro Tyr Asn Asp Gly Thr Lys Tyr Asn Glu Lys Phe
    50                  55                  60
Lys Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Glu Gly Gly Asn Asp Tyr Tyr Asp Thr Met Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 49
<211> LENGTH: 214
<212> TYPE: PRT
<213> ORGANISM: Artificial
<220> FEATURE:
<223> OTHER INFORMATION: Synthetic Peptide

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ala Trp Phe Gln Gln Lys Pro Gly Lys Ala Pro Lys Ser Leu Ile
        35                  40                  45

Tyr Arg Val Asn Arg Leu Val Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 50
<211> LENGTH: 450
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Phe or Val
```

<400> SEQUENCE: 50

```
Gln Xaa Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 51
<211> LENGTH: 214
<212> TYPE: PRT
<213> ORGANISM: Artificial
<220> FEATURE:
<223> OTHER INFORMATION: Synthetic Peptide

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 52
<211> LENGTH: 1713
<212> TYPE: PRT
<213> ORGANISM: Artificial
<220> FEATURE:
<223> OTHER INFORMATION: Synthetic Peptide

<400> SEQUENCE: 52

Gly Thr Cys Ala Gly Gly Thr Cys Ala Thr Gly Gly Thr Thr Ala
1               5                   10                  15

Cys Gly Ala Ala Gly Cys Thr Gly Cys Thr Gly Ala Cys Cys Cys
            20                  25                  30

Ala Gly Gly Ala Thr Cys Cys Ala Gly Cys Cys Cys Gly Thr Gly
        35                  40                  45
```

```
Gly Gly Ala Gly Ala Gly Ala Gly Gly Gly Gly Thr Cys Thr
     50              55              60
Cys Thr Gly Ala Cys Ala Gly Cys Cys Cys Cys Ala Cys Cys
 65              70              75              80
Cys Thr Cys Cys Cys Ala Cys Thr Gly Cys Cys Ala Gly Ala Thr
                 85              90              95
Cys Cys Thr Thr Ala Thr Thr Gly Gly Gly Thr Cys Thr Gly Ala Gly
            100             105             110
Thr Thr Thr Cys Ala Gly Gly Gly Thr Gly Gly Gly Cys Cys
            115             120             125
Cys Cys Ala Gly Cys Thr Gly Gly Ala Gly Thr Thr Ala Thr Ala
     130             135             140
Ala Ala Ala Cys Ala Gly Cys Thr Cys Ala Ala Thr Cys Gly Gly
 145             150             155             160
Gly Ala Gly Thr Ala Cys Ala Ala Cys Cys Thr Thr Cys Gly Gly Thr
                 165             170             175
Thr Thr Cys Thr Cys Thr Thr Cys Gly Gly Gly Ala Ala Ala Gly
            180             185             190
Cys Thr Gly Cys Thr Thr Thr Cys Ala Gly Gly Cys Ala Cys Ala
            195             200             205
Cys Gly Gly Gly Ala Ala Gly Ala Thr Ala Thr Cys Ala Gly Ala Ala
     210             215             220
Ala Cys Ala Thr Cys Cys Thr Ala Gly Gly Ala Thr Cys Ala Gly Gly
 225             230             235             240
Ala Cys Ala Cys Cys Cys Ala Gly Ala Thr Cys Thr Thr Cys Thr
                 245             250             255
Cys Ala Ala Cys Thr Gly Gly Ala Ala Cys Cys Ala Cys Gly Ala Ala
            260             265             270
Gly Gly Cys Thr Gly Thr Thr Thr Cys Thr Thr Cys Ala Cys Ala
            275             280             285
Cys Ala Gly Thr Ala Cys Thr Thr Thr Gly Ala Thr Cys Thr Cys Cys
     290             295             300
Ala Thr Thr Thr Ala Ala Gly Cys Ala Gly Gly Cys Ala Cys Cys Thr
 305             310             315             320
Cys Thr Gly Thr Cys Cys Thr Gly Cys Gly Thr Thr Cys Cys Gly Gly
                 325             330             335
Ala Gly Cys Thr Gly Cys Gly Thr Thr Cys Cys Cys Gly Ala Thr Gly
            340             345             350
Gly Thr Cys Cys Thr Cys Cys Thr Thr Thr Gly Gly Cys Thr Cys Ala
            355             360             365
Cys Gly Cys Thr Gly Cys Thr Cys Cys Thr Gly Ala Thr Cys Gly Cys
     370             375             380
Cys Cys Thr Gly Cys Cys Thr Gly Thr Cys Thr Cys Cys Thr Gly
 385             390             395             400
Cys Ala Ala Ala Cys Gly Ala Ala Gly Ala Ala Gly Ala Thr Cys
                 405             410             415
Cys Ala Ala Ala Cys Cys Ala Cys Cys Ala Ala Thr Cys Ala Cys
            420             425             430
Gly Ala Ala Cys Cys Thr Ala Ala Ala Gly Gly Ala Thr Gly Ala Ala Ala
     435             440             445
Gly Cys Ala Ala Ala Gly Gly Cys Thr Cys Ala Gly Cys Ala Gly Thr
            450             455             460
```

Thr Gly Ala Cys Cys Thr Gly Gly Gly Ala Cys Cys Thr Thr Ala Ala
465 470 475 480

Cys Ala Gly Ala Ala Ala Thr Gly Thr Gly Ala Cys Cys Gly Ala Thr
485 490 495

Ala Thr Cys Gly Ala Gly Thr Gly Thr Gly Thr Thr Ala Ala Ala Gly
500 505 510

Ala Cys Gly Cys Cys Gly Ala Cys Thr Ala Thr Thr Cys Thr Ala Thr
515 520 525

Gly Cys Cys Gly Gly Cys Ala Gly Thr Gly Ala Ala Cys Ala Ala Thr
530 535 540

Ala Gly Cys Thr Ala Thr Thr Gly Cys Cys Ala Gly Thr Thr Thr Gly
545 550 555 560

Gly Ala Gly Cys Ala Ala Thr Thr Thr Cys Cys Thr Thr Ala Thr Gly
565 570 575

Thr Gly Ala Ala Gly Thr Gly Ala Cys Cys Ala Ala Cys Thr Ala Cys
580 585 590

Ala Cys Cys Gly Thr Cys Cys Gly Ala Gly Thr Gly Gly Cys Cys Ala
595 600 605

Ala Cys Cys Cys Ala Cys Cys Ala Thr Thr Cys Thr Cys Cys Ala Cys
610 615 620

Gly Thr Gly Gly Ala Thr Cys Cys Thr Cys Thr Thr Cys Cys Cys Thr
625 630 635 640

Gly Ala Gly Ala Ala Cys Ala Gly Thr Gly Gly Gly Ala Ala Gly Cys
645 650 655

Cys Thr Thr Gly Gly Gly Cys Ala Gly Gly Thr Gly Cys Gly Gly Ala
660 665 670

Gly Ala Ala Thr Cys Thr Gly Ala Cys Cys Thr Gly Cys Thr Gly Gly
675 680 685

Ala Thr Thr Cys Ala Thr Gly Ala Cys Gly Thr Gly Gly Ala Thr Thr
690 695 700

Thr Cys Thr Thr Gly Ala Gly Cys Thr Gly Cys Ala Gly Cys Thr Gly
705 710 715 720

Gly Gly Cys Gly Gly Thr Ala Gly Gly Cys Cys Cys Gly Gly Gly Gly
725 730 735

Gly Cys Cys Cys Cys Cys Gly Cys Gly Gly Ala Cys Gly Thr Cys Cys
740 745 750

Ala Gly Thr Ala Cys Gly Ala Cys Cys Thr Gly Thr Ala Cys Thr Thr
755 760 765

Gly Ala Ala Cys Gly Thr Thr Gly Cys Cys Ala Ala Cys Ala Gly Gly
770 775 780

Cys Gly Thr Cys Ala Ala Cys Ala Gly Thr Ala Cys Gly Ala Gly Thr
785 790 795 800

Gly Thr Cys Thr Thr Cys Ala Cys Thr Ala Cys Ala Ala Ala Ala Cys
805 810 815

Gly Gly Ala Thr Gly Cys Thr Cys Ala Gly Gly Gly Ala Ala Cys Ala
820 825 830

Cys Gly Thr Ala Thr Cys Gly Gly Gly Thr Gly Thr Cys Gly Thr Thr
835 840 845

Thr Cys Gly Ala Thr Gly Ala Cys Ala Thr Cys Thr Cys Thr Cys Gly
850 855 860

Ala Cys Thr Cys Thr Cys Cys Ala Gly Cys Gly Gly Thr Thr Cys Thr
865 870 875 880

```
Cys Ala Ala Ala Gly Thr Thr Cys Cys Ala Cys Ala Thr Cys Cys
                885                 890                 895
Thr Gly Gly Thr Gly Cys Gly Gly Gly Cys Ala Gly Gly Ala Gly
                900                 905                 910
Cys Gly Cys Ala Gly Cys Cys Thr Thr Cys Gly Gly Thr Ala Thr Cys
                915                 920                 925
Cys Cys Cys Thr Gly Cys Ala Cys Ala Gly Ala Thr Ala Ala Gly Thr
                930                 935                 940
Thr Thr Gly Thr Cys Gly Thr Cys Thr Thr Thr Thr Cys Ala Cys Ala
945                 950                 955                 960
Gly Ala Thr Thr Gly Ala Gly Ala Thr Ala Thr Ala Ala Cys Thr
                965                 970                 975
Cys Cys Ala Cys Cys Ala Ala Cys Ala Thr Gly Ala Cys Thr Gly
                980                 985                 990
Cys Ala Ala Ala Gly Thr Gly Thr Ala Ala Thr Ala Ala Gly Ala Cys
                995                 1000                1005
Ala Cys Ala Thr Thr Cys Cys Thr Thr Ala Thr Gly Cys Ala
                1010                1015               1020
Cys Thr Gly Gly Ala Ala Ala Ala Thr Gly Ala Gly Ala Ala Gly
                1025                1030               1035
Thr Cys Ala Thr Thr Cys Ala Ala Thr Cys Gly Cys Ala Ala
                1040                1045               1050
Ala Thr Thr Thr Cys Gly Cys Thr Ala Thr Gly Ala Gly Cys Thr
                1055                1060               1065
Thr Cys Ala Gly Ala Thr Ala Cys Ala Ala Ala Gly Ala Gly
                1070                1075               1080
Ala Ala Thr Gly Cys Ala Gly Cys Cys Thr Gly Thr Ala Ala Thr
                1085                1090               1095
Cys Ala Cys Ala Gly Ala Ala Cys Ala Gly Gly Thr Cys Ala Gly
                1100                1105               1110
Ala Gly Ala Cys Ala Gly Ala Ala Cys Cys Thr Cys Cys Thr Thr
                1115                1120               1125
Cys Cys Ala Gly Cys Thr Ala Cys Thr Cys Ala Ala Thr Cys Cys
                1130                1135               1140
Thr Gly Gly Ala Ala Cys Gly Thr Ala Cys Ala Cys Ala Gly Thr
                1145                1150               1155
Ala Cys Ala Ala Ala Thr Ala Ala Gly Ala Gly Cys Cys Gly
                1160                1165               1170
Gly Gly Ala Ala Ala Gly Ala Gly Thr Gly Thr Ala Thr Gly Ala
                1175                1180               1185
Ala Thr Thr Cys Thr Thr Gly Ala Gly Cys Gly Cys Cys Thr Gly
                1190                1195               1200
Gly Ala Gly Cys Ala Cys Cys Cys Cys Cys Ala Gly Cys Gly
                1205                1210               1215
Cys Thr Thr Cys Gly Ala Gly Thr Gly Cys Gly Ala Cys Cys Ala
                1220                1225               1230
Gly Gly Ala Gly Gly Ala Gly Gly Cys Gly Cys Ala Ala Ala
                1235                1240               1245
Cys Ala Cys Ala Cys Gly Thr Gly Cys Cys Thr Gly Gly Cys Gly
                1250                1255               1260
Gly Ala Cys Gly Thr Cys Gly Cys Thr Gly Cys Thr Gly Ala Thr
                1265                1270               1275
```

```
Cys Gly Cys Gly Cys Thr Gly Gly Gly Ala Cys Gly Cys Thr
    1280                1285                1290

Gly Cys Thr Gly Gly Cys Cys Thr Gly Gly Thr Cys Thr Gly
    1295                1300                1305

Thr Gly Thr Cys Thr Thr Cys Gly Thr Gly Ala Thr Cys Thr Gly
    1310                1315                1320

Cys Ala Gly Ala Ala Gly Gly Thr Ala Thr Cys Thr Gly Gly Thr
    1325                1330                1335

Gly Ala Thr Gly Cys Ala Gly Ala Gly Ala Cys Thr Cys Thr Thr
    1340                1345                1350

Thr Cys Cys Cys Gly Cys Ala Thr Cys Cys Thr Cys Ala
    1355                1360                1365

Cys Ala Thr Gly Ala Ala Ala Gly Ala Cys Cys Cys Ala Thr
    1370                1375                1380

Cys Gly Gly Thr Gly Ala Cys Ala Gly Cys Thr Thr Cys Cys Ala
    1385                1390                1395

Ala Ala Ala Cys Gly Ala Cys Ala Ala Gly Cys Thr Gly Gly Thr
    1400                1405                1410

Gly Gly Thr Cys Thr Gly Gly Gly Ala Gly Gly Cys Gly Gly Gly
    1415                1420                1425

Cys Ala Ala Ala Gly Cys Cys Gly Gly Cys Cys Thr Gly Gly Ala
    1430                1435                1440

Gly Gly Ala Gly Thr Gly Thr Cys Thr Gly Gly Thr Gly Ala Cys
    1445                1450                1455

Thr Gly Ala Ala Gly Thr Ala Cys Ala Gly Gly Thr Cys Gly Thr
    1460                1465                1470

Gly Cys Ala Gly Ala Ala Ala Ala Cys Thr Thr Gly Ala Gly Ala
    1475                1480                1485

Cys Thr Gly Gly Gly Gly Thr Cys Ala Gly Gly Cys Thr
    1490                1495                1500

Thr Gly Thr Gly Gly Gly Gly Thr Cys Thr Gly Cys Cys Thr
    1505                1510                1515

Cys Ala Ala Thr Cys Thr Cys Cys Thr Gly Gly Cys Cys Gly
    1520                1525                1530

Gly Gly Cys Cys Ala Gly Gly Cys Gly Cys Thr Gly Cys Ala
    1535                1540                1545

Cys Ala Gly Ala Cys Thr Gly Gly Cys Thr Gly Cys Thr Gly Gly
    1550                1555                1560

Ala Cys Cys Thr Gly Cys Gly Cys Ala Cys Gly Cys Ala Gly Cys
    1565                1570                1575

Cys Cys Ala Gly Gly Ala Ala Thr Gly Gly Ala Cys Ala Thr Thr
    1580                1585                1590

Cys Cys Thr Ala Ala Cys Gly Gly Thr Gly Gly Thr Gly Gly
    1595                1600                1605

Gly Cys Ala Thr Gly Gly Gly Ala Gly Ala Thr Gly Cys Cys Thr
    1610                1615                1620

Gly Thr Gly Thr Ala Ala Thr Thr Thr Cys Gly Thr Cys Cys Gly
    1625                1630                1635

Ala Ala Gly Cys Thr Gly Cys Cys Ala Gly Gly Ala Ala Gly Ala
    1640                1645                1650

Ala Gly Ala Ala Cys Ala Gly Ala Ala Cys Thr Thr Thr Gly Thr
    1655                1660                1665
```

```
Gly Thr Gly Thr Thr Thr Ala Thr Thr Thr Cys Ala Thr Gly Ala
    1670            1675                1680
Thr Ala Ala Ala Gly Thr Gly Ala Thr Thr Thr Thr Thr Thr Thr
    1685            1690                1695
Thr Thr Thr Thr Thr Thr Ala Ala Cys Cys Cys Ala Ala Ala Ala
    1700            1705                1710

<210> SEQ ID NO 53
<211> LENGTH: 450
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Phe or Val

<400> SEQUENCE: 53

Ser Xaa Gln Leu Val Gln Ser Gly Ala Glu Val Lys Lys Pro Gly Ala
1                5                  10                  15
Ser Val Lys Val Ser Cys Lys Ala Ser Gly Tyr Ile Phe Thr Ser Ser
            20                  25                  30
Ile Met His Trp Val Arg Gln Ala Pro Gly Gln Gly Leu Glu Trp Ile
        35                  40                  45
Gly Tyr Ile Lys Pro Tyr Asn Asp Gly Thr Lys Tyr Asn Glu Lys Phe
    50                  55                  60
Lys Gly Arg Ala Thr Leu Thr Ser Asp Arg Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Gly Gly Asn Asp Tyr Tyr Asp Thr Met Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly
    450

<210> SEQ ID NO 54
<211> LENGTH: 450
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Phe or Val

<400> SEQUENCE: 54

Gln Xaa Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Cys Leu Ser
            435                 440                 445

Pro Gly
    450

<210> SEQ ID NO 55
<211> LENGTH: 4
<212> TYPE: PRT
<213> ORGANISM: Artificial
<220> FEATURE:
<223> OTHER INFORMATION: Synthetic Peptide

<400> SEQUENCE: 55

Ala Leu Ala Leu
1

<210> SEQ ID NO 56
<211> LENGTH: 398
<212> TYPE: PRT
<213> ORGANISM: Artificial
<220> FEATURE:
<223> OTHER INFORMATION: Synthetic Peptide

<400> SEQUENCE: 56

Pro Tyr Asn Asp Gly Thr Lys Tyr Asn Glu Lys Phe Lys Gly Arg Ala
1               5                   10                  15

Thr Leu Thr Ser Asp Arg Ser Thr Ser Thr Ala Tyr Met Glu Leu Ser
            20                  25                  30

Ser Leu Arg Ser Glu Asp Thr Ala Val Tyr Tyr Cys Ala Arg Glu Gly
            35                  40                  45

Gly Asn Asp Tyr Tyr Asp Thr Met Asp Tyr Trp Gly Gln Gly Thr Leu
 50                  55                  60

Val Thr Val Ser Ser Ala Ser Thr Lys Gly Pro Ser Val Phe Pro Leu
 65                  70                  75                  80

Ala Pro Ser Ser Lys Ser Thr Ser Gly Gly Thr Ala Ala Leu Gly Cys
                 85                  90                  95

Leu Val Lys Asp Tyr Phe Pro Glu Pro Val Thr Val Ser Trp Asn Ser
            100                 105                 110

Gly Ala Leu Thr Ser Gly Val His Thr Phe Pro Ala Val Leu Gln Ser
        115                 120                 125

Ser Gly Leu Tyr Ser Leu Ser Ser Val Val Thr Val Pro Ser Ser Ser
    130                 135                 140

Leu Gly Thr Gln Thr Tyr Ile Cys Asn Val Asn His Lys Pro Ser Asn
145                 150                 155                 160

Thr Lys Val Asp Lys Lys Val Glu Pro Lys Ser Cys Asp Lys Thr His
                165                 170                 175

Thr Cys Pro Pro Cys Pro Ala Pro Glu Leu Leu Gly Gly Pro Ser Val
            180                 185                 190

Phe Leu Phe Pro Pro Lys Pro Lys Asp Thr Leu Met Ile Ser Arg Thr
        195                 200                 205

Pro Glu Val Thr Cys Val Val Val Asp Val Ser His Glu Asp Pro Glu
    210                 215                 220

Val Lys Phe Asn Trp Tyr Val Asp Gly Val Glu Val His Asn Ala Lys
225                 230                 235                 240

Thr Lys Pro Arg Glu Glu Gln Tyr Asn Ser Thr Tyr Arg Val Val Ser
                245                 250                 255

Val Leu Thr Val Leu His Gln Asp Trp Leu Asn Gly Lys Glu Tyr Lys
            260                 265                 270

Cys Lys Val Ser Asn Lys Ala Leu Pro Ala Pro Ile Glu Lys Thr Ile
        275                 280                 285

Ser Lys Ala Lys Gly Gln Pro Arg Glu Pro Gln Val Tyr Thr Leu Pro
    290                 295                 300

Pro Ser Arg Asp Glu Leu Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Lys Leu Thr Val Asp Lys Ser Arg
        355                 360                 365

Trp Gln Gln Gly Asn Val Phe Ser Cys Ser Val Met His Glu Ala Leu
    370                 375                 380

His Asn His Tyr Thr Gln Lys Ser Leu Cys Leu Ser Pro Gly
385                 390                 395

<210> SEQ ID NO 57
<211> LENGTH: 4
<212> TYPE: PRT
<213> ORGANISM: Artificial
<220> FEATURE:
<223> OTHER INFORMATION: Synthetic Peptide

```
<220> FEATURE:
<221> NAME/KEY: Xaa
<222> LOCATION: (1)..(1)
<223> OTHER INFORMATION: beta-Ala

<400> SEQUENCE: 57

Xaa Leu Ala Leu
1

<210> SEQ ID NO 58
<211> LENGTH: 214
<212> TYPE: PRT
<213> ORGANISM: Artificial
<220> FEATURE:
<223> OTHER INFORMATION: Synthetic Peptide

<400> SEQUENCE: 58

Ser Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 59
<211> LENGTH: 450
<212> TYPE: PRT
<213> ORGANISM: Artificial
<220> FEATURE:
<223> OTHER INFORMATION: Synthetic Peptide

<400> SEQUENCE: 59

Gln Val Gln Leu Val Gln Ser Gly Ala Glu Val Val Lys Pro Gly Ala
1               5                  10                  15

Ser Val Lys Met Ser Cys Lys Ala Ser Gly Tyr Thr Phe Thr Ser Ser
            20                  25                  30
```

-continued

```
Ile Met His Trp Met Lys Gln Lys Pro Gly Gln Gly Leu Glu Trp Ile
         35                  40                  45
Gly Tyr Ile Arg Pro Tyr Asn Asp Gly Thr Arg Tyr Asn Gln Lys Phe
 50                  55                  60
Gln Gly Lys Ala Thr Leu Thr Ser Asp Arg Ser Ser Thr Ala Asn
 65                  70                  75                  80
Met Glu Leu Asn Ser Leu Thr Ser Glu Asp Ser Ala Val Tyr Tyr Cys
                 85                  90                  95
Ala Arg Glu Gly Gly Asn Asp Tyr Tyr Asp Thr Met Asp Tyr Trp Gly
                100                 105                 110
Gln Gly Thr Ser Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Leu Gly Thr Gln Thr Tyr Ile Cys Asn Val Asn His
        195                 200                 205
Lys Pro Ser Asn Thr Lys Val Asp Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
```

-continued

His Glu Ala Leu His Asn His Tyr Thr Gln Lys Ser Leu Ser Leu Ser
435                 440                 445

Pro Gly
    450

<210> SEQ ID NO 60
<211> LENGTH: 450
<212> TYPE: PRT
<213> ORGANISM: Artificial
<220> FEATURE:
<223> OTHER INFORMATION: Synthetic Peptide

<400> SEQUENCE: 60

Gln Phe Gln Leu Val Gln Ser Gly Ala Glu Val Lys Pro Gly Ala
1               5                   10                  15

Ser Val Lys Met Ser Cys Lys Ala Ser Gly Tyr Thr Phe Thr Ser Ser
                20                  25                  30

Ile Met His Trp Met Lys Gln Lys Pro Gly Gln Gly Leu Glu Trp Ile
            35                  40                  45

Gly Tyr Ile Lys Pro Tyr Asn Asp Gly Thr Lys Tyr Asn Gln Lys Phe
    50                  55                  60

Gln Gly Lys Ala Thr Leu Thr Ser Asp Lys Ser Ser Ser Thr Ala Asn
65                  70                  75                  80

Met Glu Leu Asn Ser Leu Thr Ser Glu Asp Ser Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Ser Val Thr Val Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

```
Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450
```

<210> SEQ ID NO 61
<211> LENGTH: 214
<212> TYPE: PRT
<213> ORGANISM: Artificial
<220> FEATURE:
<223> OTHER INFORMATION: Synthetic Peptide

<400> SEQUENCE: 61

```
Asp Ile Gln Met Thr Gln Ser Pro Ser Ser Met Ser Ala Ser Val Gly
1               5                   10                  15

Glu Arg Val Thr Ile Thr Cys Arg Ala Ser Gln Asp Ile Asn Ser Tyr
            20                  25                  30

Leu Ser Trp Phe Gln Gln Lys Pro Gly Lys Ser Pro Lys Thr Leu Ile
            35                  40                  45

Tyr Arg Val Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Pro
65                  70                  75                  80

Glu Asp Met Gly Ile Tyr Tyr Cys Leu Gln Tyr Asp Ala Phe Pro Tyr
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 62
<211> LENGTH: 449
<212> TYPE: PRT
<213> ORGANISM: Artificial
<220> FEATURE:
<223> OTHER INFORMATION: Synthetic Peptide

<400> SEQUENCE: 62

```
Ala Ala Gly Cys Thr Thr Gly Cys Cys Ala Cys Cys Ala Thr Gly Gly
1               5                   10                  15

Gly Ala Thr Gly Gly Thr Cys Cys Thr Gly Cys Ala Thr Thr Ala Thr
            20                  25                  30

Cys Cys Thr Gly Thr Thr Cys Cys Thr Thr Gly Thr Ala Gly Cys Ala
        35                  40                  45

Ala Cys Thr Gly Cys Ala Ala Cys Ala Gly Gly Ala Gly Thr Cys Cys
    50                  55                  60

Ala Cys Ala Gly Cys Cys Ala Gly Gly Thr Cys Cys Ala Ala Cys Thr
65                  70                  75                  80

Gly Gly Thr Gly Cys Ala Gly Thr Cys Cys Gly Gly Gly Gly Cys Cys
                85                  90                  95

Gly Ala Gly Gly Thr Gly Ala Ala Gly Ala Ala Ala Cys Cys Ala Gly
            100                 105                 110

Gly Cys Gly Cys Ala Thr Cys Cys Gly Thr Gly Ala Ala Gly Gly Thr
        115                 120                 125

Cys Ala Gly Cys Thr Gly Thr Ala Ala Ala Gly Cys Cys Ala Gly Cys
    130                 135                 140

Gly Gly Cys Thr Ala Thr Gly Gly Thr Thr Thr Thr Ala Cys Cys Ala
145                 150                 155                 160

Gly Cys Thr Cys Ala Ala Thr Cys Ala Thr Gly Cys Ala Cys Thr Gly
                165                 170                 175

Gly Gly Thr Cys Ala Gly Gly Cys Ala Ala Gly Cys Cys Cys Cys Ala
            180                 185                 190

Gly Gly Ala Cys Ala Gly Gly Gly Thr Cys Thr Cys Gly Ala Ala Thr
        195                 200                 205

Gly Gly Ala Thr Gly Gly Gly Ala Thr Ala Cys Ala Thr Thr Ala Ala
    210                 215                 220

Gly Cys Cys Thr Thr Ala Cys Ala Ala Thr Gly Ala Thr Gly Gly Thr
225                 230                 235                 240

Ala Cys Ala Ala Ala Ala Thr Ala Thr Ala Ala Thr Gly Ala Ala Ala
                245                 250                 255

Ala Ala Thr Thr Thr Ala Ala Gly Gly Gly Thr Cys Gly Thr Gly Thr
            260                 265                 270

Thr Ala Cys Cys Ala Thr Gly Ala Cys Ala Ala Gly Gly Gly Ala Thr
        275                 280                 285

Ala Cys Ala Thr Cys Ala Ala Cys Thr Ala Gly Cys Ala Cys Thr Gly
    290                 295                 300

Thr Cys Thr Ala Thr Ala Thr Gly Gly Ala Ala Cys Thr Gly Ala Gly
305                 310                 315                 320

Cys Thr Cys Thr Cys Thr Cys Ala Gly Gly Thr Cys Cys Gly Ala Gly
                325                 330                 335

Gly Ala Thr Ala Cys Thr Gly Cys Ala Gly Thr Ala Thr Ala Thr Thr
            340                 345                 350

Ala Cys Thr Gly Cys Gly Cys Cys Cys Gly Gly Gly Ala Gly Gly Gly
        355                 360                 365
```

```
Ala Gly Gly Cys Ala Ala Cys Gly Ala Cys Thr Ala Thr Thr Ala Cys
    370                 375                 380

Gly Ala Cys Ala Cys Cys Ala Thr Gly Gly Ala Cys Thr Ala Thr Thr
385                 390                 395                 400

Gly Gly Gly Gly Gly Cys Ala Gly Gly Cys Ala Cys Ala Cys Thr
                405                 410                 415

Gly Gly Thr Thr Ala Cys Thr Gly Thr Ala Thr Cys Cys Ala Gly Cys
            420                 425                 430

Gly Cys Cys Thr Cys Thr Ala Cys Thr Ala Ala Gly Gly Cys Cys
                435                 440                 445

Cys
```

<210> SEQ ID NO 63
<211> LENGTH: 396
<212> TYPE: PRT
<213> ORGANISM: Artificial
<220> FEATURE:
<223> OTHER INFORMATION: Synthetic Peptide

<400> SEQUENCE: 63

```
Gly Ala Ala Thr Thr Cys Gly Cys Ala Cys Cys Ala Thr Gly Gly Gly
1               5                   10                  15

Gly Thr Thr Gly Gly Thr Cys Thr Thr Gly Thr Ala Thr Ala Ala Thr
                20                  25                  30

Cys Cys Thr Gly Thr Thr Cys Cys Thr Gly Gly Thr Cys Gly Cys Thr
                35                  40                  45

Ala Cys Cys Gly Cys Ala Ala Cys Ala Gly Gly Gly Thr Thr Cys
            50                  55                  60

Ala Cys Thr Cys Ala Gly Ala Cys Ala Thr Cys Ala Gly Ala Thr
65                  70                  75                  80

Gly Ala Cys Cys Cys Ala Gly Ala Thr Cys Cys Cys Thr Cys Thr
                85                  90                  95

Thr Cys Thr Cys Thr Gly Ala Gly Cys Gly Cys Thr Cys Thr Gly
                100                 105                 110

Thr Thr Gly Gly Gly Gly Ala Cys Cys Gly Gly Thr Gly Ala Cys
            115                 120                 125

Cys Ala Thr Cys Ala Cys Thr Gly Thr Cys Gly Gly Gly Cys Ala
            130                 135                 140

Thr Cys Cys Cys Ala Gly Gly Ala Cys Ala Thr Cys Ala Ala Thr
145                 150                 155                 160

Cys Thr Thr Ala Cys Cys Thr Gly Gly Cys Thr Thr Gly Gly Thr
                165                 170                 175

Cys Cys Ala Gly Cys Ala Gly Ala Ala Gly Cys Cys Cys Gly Ala
            180                 185                 190

Ala Ala Ala Gly Cys Cys Cys Thr Ala Ala Thr Cys Thr Cys Cys
                195                 200                 205

Thr Cys Ala Thr Thr Thr Ala Cys Cys Gly Gly Thr Ala Ala Ala
        210                 215                 220

Cys Cys Gly Thr Thr Thr Gly Thr Cys Thr Cys Cys Gly Gly Ala
225                 230                 235                 240

Gly Thr Gly Cys Cys Thr Thr Cys Ala Ala Gly Gly Thr Thr Ala
                245                 250                 255

Gly Thr Gly Gly Ala Thr Cys Thr Gly Gly Ala Thr Cys Ala Gly Gly
            260                 265                 270
```

```
Thr Ala Cys Ala Gly Ala Cys Thr Cys Ala Cys Thr Cys Thr Cys
            275                 280                 285
Ala Cys Cys Ala Thr Ala Ala Gly Cys Ala Gly Cys Thr Gly Cys
            290                 295                 300
Ala Ala Cys Cys Ala Gly Ala Gly Gly Ala Thr Thr Cys Gly Cys
305                 310                 315                 320
Ala Ala Cys Thr Thr Ala Cys Thr Ala Cys Thr Gly Cys Thr Gly
            325                 330                 335
Cys Ala Gly Thr Ala Thr Gly Ala Gly Cys Cys Thr Thr Cys Cys
            340                 345                 350
Cys Thr Thr Ala Cys Ala Cys Thr Thr Thr Cys Gly Gly Cys Ala
            355                 360                 365
Gly Gly Gly Gly Ala Cys Cys Ala Ala Ala Gly Thr Gly Ala Ala
            370                 375                 380
Ala Thr Ala Ala Ala Gly Cys Gly Gly Thr Ala Cys Gly
385                 390                 395

<210> SEQ ID NO 64
<211> LENGTH: 449
<212> TYPE: PRT
<213> ORGANISM: Artificial
<220> FEATURE:
<223> OTHER INFORMATION: Synthetic Peptide

<400> SEQUENCE: 64

Ala Ala Gly Cys Thr Thr Gly Cys Cys Ala Cys Cys Ala Thr Gly
1               5                   10                  15
Gly Cys Thr Gly Gly Thr Cys Cys Thr Gly Thr Ala Thr Cys Ala
            20                  25                  30
Cys Cys Thr Gly Thr Thr Cys Cys Thr Cys Gly Thr Thr Gly Cys
            35                  40                  45
Ala Cys Ala Gly Cys Ala Ala Cys Thr Gly Gly Cys Gly Thr Gly
            50                  55                  60
Ala Cys Ala Gly Cys Cys Ala Gly Thr Thr Cys Cys Ala Gly Cys
65                  70                  75                  80
Thr Gly Thr Gly Cys Ala Gly Ala Gly Thr Gly Cys Gly Cys Cys
            85                  90                  95
Gly Ala Ala Gly Thr Cys Ala Gly Ala Ala Ala Cys Cys Ala Gly
            100                 105                 110
Gly Cys Gly Cys Thr Ala Gly Thr Gly Cys Ala Ala Gly Gly Thr
            115                 120                 125
Gly Thr Cys Cys Thr Gly Thr Ala Ala Gly Gly Cys Ala Thr Cys
            130                 135                 140
Gly Gly Cys Thr Ala Cys Ala Cys Cys Thr Thr Thr Ala Cys Cys
145                 150                 155                 160
Gly Cys Thr Cys Cys Ala Thr Cys Ala Thr Gly Cys Ala Thr Gly
            165                 170                 175
Gly Gly Thr Cys Ala Gly Ala Cys Ala Gly Cys Thr Cys Cys Thr
            180                 185                 190
Gly Gly Ala Cys Ala Gly Gly Cys Cys Thr Gly Gly Ala Gly Thr
            195                 200                 205
Gly Gly Ala Thr Thr Gly Gly Gly Thr Ala Thr Ala Thr Cys Ala
            210                 215                 220
Gly Cys Cys Ala Thr Ala Cys Ala Ala Thr Gly Ala Thr Gly Gly
225                 230                 235                 240
```

```
Ala Cys Ala Ala Ala Ala Thr Ala Cys Ala Ala Thr Gly Ala Ala Ala
                245                 250                 255

Ala Gly Thr Thr Thr Ala Ala Ala Gly Gly Gly Cys Gly Ala Gly Cys
            260                 265                 270

Cys Ala Cys Thr Cys Thr Gly Ala Cys Ala Thr Cys Thr Gly Ala Thr
        275                 280                 285

Cys Gly Gly Ala Gly Thr Ala Cys Ala Ala Gly Cys Ala Cys Thr Gly
    290                 295                 300

Cys Cys Thr Ala Cys Ala Thr Gly Gly Ala Ala Thr Thr Gly Ala Gly
305                 310                 315                 320

Cys Thr Cys Ala Cys Thr Gly Cys Gly Gly Thr Cys Cys Gly Ala Ala
                325                 330                 335

Gly Ala Cys Ala Cys Thr Gly Cys Thr Gly Thr Gly Thr Ala Thr Thr
            340                 345                 350

Ala Thr Thr Gly Cys Gly Cys Thr Cys Gly Gly Gly Ala Gly Gly Gly
        355                 360                 365

Ala Gly Gly Gly Ala Ala Cys Gly Ala Cys Thr Ala Cys Thr Ala Cys
    370                 375                 380

Gly Ala Thr Ala Cys Cys Ala Thr Gly Gly Ala Cys Thr Ala Cys Thr
385                 390                 395                 400

Gly Gly Gly Gly Cys Cys Ala Gly Gly Gly Cys Ala Cys Cys Cys Thr
                405                 410                 415

Gly Gly Thr Thr Ala Cys Cys Gly Thr Cys Ala Gly Cys Ala Gly Cys
            420                 425                 430

Gly Cys Thr Thr Cys Cys Ala Cys Thr Ala Ala Gly Gly Gly Cys Cys
        435                 440                 445

Cys
```

```
<210> SEQ ID NO 65
<211> LENGTH: 396
<212> TYPE: PRT
<213> ORGANISM: Artificial
<220> FEATURE:
<223> OTHER INFORMATION: Synthetic Peptide

<400> SEQUENCE: 65

Gly Ala Ala Thr Thr Cys Gly Cys Cys Ala Cys Cys Ala Thr Gly Gly
1               5                   10                  15

Gly Thr Thr Gly Gly Thr Cys Cys Thr Gly Thr Ala Thr Cys Ala Thr
            20                  25                  30

Cys Cys Thr Cys Thr Thr Thr Cys Thr Gly Gly Thr Gly Gly Cys Ala
        35                  40                  45

Ala Cys Thr Gly Cys Ala Ala Cys Cys Gly Gly Cys Gly Thr Cys Cys
    50                  55                  60

Ala Thr Ala Gly Cys Gly Ala Cys Ala Thr Thr Cys Ala Gly Ala Thr
65                  70                  75                  80

Gly Ala Cys Ala Cys Ala Gly Thr Cys Thr Cys Cys Thr Thr Cys Thr
                85                  90                  95

Thr Cys Cys Cys Thr Gly Ala Gly Cys Gly Cys Cys Ala Gly Cys Gly
            100                 105                 110

Thr Cys Gly Gly Gly Ala Cys Cys Gly Cys Gly Thr Gly Ala Cys
        115                 120                 125

Thr Ala Thr Cys Ala Cys Ala Thr Gly Thr Cys Gly Gly Gly Cys Cys
    130                 135                 140
```

```
Thr Cys Cys Cys Ala Gly Gly Ala Cys Ala Thr Ala Ala Cys Thr
145                 150                 155                 160

Cys Thr Thr Ala Cys Cys Thr Cys Thr Cys Thr Gly Gly Thr Thr
                165                 170                 175

Cys Cys Ala Gly Cys Ala Gly Ala Ala Gly Cys Cys Thr Gly Gly
            180                 185                 190

Ala Ala Ala Gly Cys Cys Cys Ala Ala Gly Ala Cys Ala Cys
        195                 200                 205

Thr Gly Ala Thr Ala Thr Cys Ala Gly Gly Thr Ala Ala Ala
    210                 215                 220

Thr Cys Gly Thr Thr Thr Gly Gly Thr Thr Gly Ala Cys Gly Thr
225                 230                 235                 240

Gly Thr Ala Cys Cys Ala Thr Cys Ala Cys Gly Ala Thr Thr Thr
            245                 250                 255

Cys Cys Gly Gly Thr Ala Gly Thr Gly Gly Thr Cys Thr Gly Gly
            260                 265                 270

Ala Ala Ala Cys Gly Ala Thr Thr Ala Cys Ala Cys Thr Cys
        275                 280                 285

Ala Cys Ala Ala Thr Thr Ala Gly Cys Ala Gly Cys Thr Gly Cys
290                 295                 300

Ala Ala Cys Cys Ala Gly Ala Gly Gly Ala Cys Thr Thr Gly Cys
305                 310                 315                 320

Ala Ala Cys Ala Thr Ala Cys Thr Ala Thr Thr Gly Cys Cys Thr Gly
            325                 330                 335

Cys Ala Gly Thr Ala Cys Gly Ala Thr Gly Cys Thr Thr Thr Cys
            340                 345                 350

Cys Thr Thr Ala Thr Ala Cys Cys Thr Thr Cys Gly Gly Cys Ala
            355                 360                 365

Gly Gly Gly Thr Ala Cys Cys Ala Ala Gly Gly Thr Gly Gly Ala Ala
            370                 375                 380

Ala Thr Thr Ala Ala Ala Cys Gly Thr Ala Cys Gly
385                 390                 395
```

<210> SEQ ID NO 66
<211> LENGTH: 449
<212> TYPE: PRT
<213> ORGANISM: Artificial
<220> FEATURE:
<223> OTHER INFORMATION: Synthetic Peptide

<400> SEQUENCE: 66

```
Ala Ala Gly Cys Thr Thr Gly Cys Cys Ala Cys Cys Ala Thr Gly Gly
1               5                   10                  15

Gly Cys Thr Gly Gly Thr Cys Cys Thr Gly Thr Ala Thr Cys Ala Thr
                20                  25                  30

Cys Cys Thr Gly Thr Thr Cys Cys Thr Cys Gly Thr Thr Gly Cys Ala
            35                  40                  45

Ala Cys Ala Gly Cys Ala Ala Cys Thr Gly Gly Cys Gly Thr Gly Cys
        50                  55                  60

Ala Cys Ala Gly Cys Cys Ala Gly Gly Thr Cys Cys Ala Ala Cys Thr
65                  70                  75                  80

Thr Gly Thr Gly Cys Ala Gly Ala Gly Thr Gly Gly Cys Gly Cys Cys
            85                  90                  95

Gly Ala Ala Gly Thr Cys Ala Ala Gly Ala Ala Ala Cys Cys Ala Gly
        100                 105                 110
```

Gly Cys Gly Cys Thr Ala Gly Thr Gly Thr Cys Ala Ala Gly Gly Thr
            115                 120                 125

Gly Thr Cys Cys Thr Gly Thr Ala Ala Gly Gly Cys Ala Thr Cys Ala
        130                 135                 140

Gly Gly Cys Thr Ala Cys Ala Thr Cys Thr Thr Ala Cys Cys Ala
145                 150                 155                 160

Gly Cys Thr Cys Ala Thr Cys Ala Thr Gly Cys Ala Thr Thr Gly
            165                 170                 175

Gly Gly Thr Cys Ala Gly Ala Cys Ala Gly Gly Cys Thr Cys Cys Thr
            180                 185                 190

Gly Gly Ala Cys Ala Gly Gly Cys Cys Thr Gly Gly Ala Gly Thr
            195                 200                 205

Gly Gly Ala Thr Thr Gly Gly Gly Thr Ala Thr Ala Thr Cys Ala Ala
            210                 215                 220

Gly Cys Cys Ala Thr Ala Cys Ala Ala Thr Gly Ala Thr Gly Gly Gly
225                 230                 235                 240

Ala Cys Ala Ala Ala Ala Thr Ala Cys Ala Ala Thr Gly Ala Ala Ala
                245                 250                 255

Ala Gly Thr Thr Thr Ala Ala Ala Gly Gly Cys Gly Ala Gly Cys
            260                 265                 270

Cys Ala Cys Thr Cys Thr Gly Ala Cys Ala Thr Cys Thr Gly Ala Thr
            275                 280                 285

Cys Gly Gly Ala Gly Thr Ala Cys Ala Ala Gly Cys Ala Cys Thr Gly
            290                 295                 300

Cys Cys Thr Ala Cys Ala Thr Gly Gly Ala Ala Thr Thr Gly Ala Gly
305                 310                 315                 320

Cys Thr Cys Ala Cys Thr Gly Cys Gly Gly Thr Cys Gly Ala Ala
            325                 330                 335

Gly Ala Cys Ala Cys Thr Gly Cys Thr Gly Thr Gly Thr Ala Thr Thr
340 345 350

Ala Thr Thr Gly Cys Gly Cys Thr Cys Gly Gly Gly Ala Gly Gly Gly
355 360 365

Ala Gly Gly Gly Ala Ala Cys Gly Ala Cys Thr Ala Cys Thr Ala Cys
370 375 380

Gly Ala Thr Ala Cys Cys Ala Thr Gly Gly Ala Cys Thr Ala Cys Thr
385 390 395 400

Gly Gly Gly Gly Cys Cys Ala Gly Gly Gly Cys Ala Cys Cys Cys Thr
405 410 415

Gly Gly Thr Thr Ala Cys Cys Gly Thr Cys Ala Gly Cys Ala Gly Cys
420 425 430

Gly Cys Thr Thr Cys Cys Ala Cys Thr Ala Ala Gly Gly Gly Cys Cys
435 440 445

Cys

<210> SEQ ID NO 67
<211> LENGTH: 396
<212> TYPE: PRT
<213> ORGANISM: Artificial
<220> FEATURE:
<223> OTHER INFORMATION: Synthetic Peptide

```
<400> SEQUENCE: 67

Gly Ala Ala Thr Thr Cys Gly Cys Ala Cys Ala Thr Gly Gly
1               5                   10                  15

Gly Cys Thr Gly Gly Thr Cys Ala Gly Thr Ala Thr Ala Thr
                20                  25                  30

Cys Cys Thr Gly Thr Thr Thr Cys Gly Gly Thr Thr Gly Cys Ala
                35                  40                  45

Ala Cys Cys Gly Cys Ala Ala Cys Ala Gly Gly Ala Gly Thr Ala Cys
50                      55                  60

Ala Cys Thr Cys Thr Gly Ala Thr Ala Thr Cys Cys Ala Gly Ala Thr
65                      70                      75              80

Gly Ala Cys Thr Cys Ala Gly Thr Cys Thr Cys Cys Thr Cys Thr
                85                      90                      95

Thr Cys Thr Ala Thr Gly Thr Cys Thr Gly Cys Thr Cys Thr Gly
            100                     105                     110

Thr Gly Gly Gly Ala Gly Ala Gly Ala Gly Thr Cys Ala Cys
            115                     120                     125

Cys Ala Thr Cys Ala Cys Thr Gly Thr Cys Gly Cys Gly Cys Thr
            130                     135                     140

Thr Cys Cys Cys Ala Ala Gly Ala Thr Ala Thr Ala Ala Thr Ala
145                     150                     155                 160

Gly Cys Thr Ala Thr Cys Thr Gly Thr Cys Thr Thr Gly Gly Thr Thr
                165                     170                     175

Cys Cys Ala Ala Cys Ala Gly Ala Ala Ala Cys Cys Thr Gly Gly Cys
                180                     185                     190

Ala Ala Ala Thr Cys Ala Cys Cys Cys Ala Gly Ala Cys Thr Cys
                195                     200                     205

Thr Gly Ala Thr Thr Thr Ala Thr Cys Gly Gly Gly Thr Thr Ala Ala
            210                     215                     220

Cys Cys Gly Cys Cys Thr Gly Gly Thr Gly Ala Cys Gly Gly Thr
225                     230                     235                 240

Gly Thr Gly Cys Cys Thr Thr Cys Ala Cys Gly Cys Thr Cys Thr
            245                     250                     255

Cys Cys Gly Gly Cys Ala Gly Cys Gly Gly Thr Ala Gly Thr Gly
            260                     265                     270

Ala Cys Ala Ala Gly Ala Cys Thr Ala Thr Ala Cys Thr Cys Thr Gly
                275                     280                     285

Ala Cys Ala Ala Thr Thr Thr Cys Thr Thr Cys Thr Cys Thr Cys Gly
                290                     295                     300

Ala Ala Cys Cys Cys Gly Ala Gly Gly Ala Cys Ala Thr Gly Gly Gly
305                     310                     315                 320

Ala Ala Thr Cys Thr Ala Cys Thr Ala Thr Thr Gly Cys Thr Cys Gly
                325                     330                     335

Cys Ala Gly Thr Ala Thr Gly Ala Cys Gly Cys Thr Thr Thr Cys
            340                     345                     350

Cys Thr Thr Ala Thr Ala Cys Ala Thr Thr Cys Gly Gly Cys Cys Ala
            355                     360                     365

Gly Gly Gly Cys Ala Cys Ala Ala Gly Cys Thr Gly Gly Ala Ala
            370                     375                     380

Ala Thr Cys Ala Ala Ala Cys Gly Thr Ala Cys Gly
385                     390                     395
```

-continued

<210> SEQ ID NO 68
<211> LENGTH: 449
<212> TYPE: PRT
<213> ORGANISM: Artificial
<220> FEATURE:
<223> OTHER INFORMATION: Synthetic Peptide

<400> SEQUENCE: 68

```
Ala Ala Gly Cys Thr Thr Gly Cys Cys Ala Cys Cys Ala Thr Gly Gly
1               5                   10                  15

Gly Gly Thr Gly Gly Ala Gly Cys Thr Gly Cys Ala Thr Thr Ala Thr
            20                  25                  30

Thr Cys Thr Gly Thr Thr Cys Thr Thr Gly Gly Thr Cys Gly Cys Cys
        35                  40                  45

Ala Cys Cys Gly Cys Ala Ala Cys Thr Gly Gly Cys Gly Thr Cys Cys
    50                  55                  60

Ala Cys Thr Cys Thr Cys Ala Gly Gly Thr Cys Ala Gly Cys Thr
65                  70                  75                  80

Cys Gly Thr Cys Cys Ala Gly Thr Cys Thr Gly Gly Gly Cys Ala
                85                  90                  95

Gly Ala Ala Gly Thr Gly Gly Thr Cys Ala Ala Gly Cys Cys Cys Gly
            100                 105                 110

Gly Thr Gly Cys Ala Thr Cys Thr Gly Thr Gly Ala Ala Ala Thr
        115                 120                 125

Gly Thr Cys Cys Thr Gly Cys Ala Ala Ala Gly Cys Thr Ala Gly Cys
        130                 135                 140

Gly Gly Gly Thr Ala Thr Ala Cys Ala Thr Thr Cys Ala Cys Ala
145                 150                 155                 160

Cys Thr Ala Gly Thr Ala Thr Cys Ala Thr Gly Cys Ala Thr Thr Gly
                165                 170                 175

Gly Ala Thr Gly Ala Ala Ala Cys Ala Gly Ala Ala Gly Cys Cys Thr
            180                 185                 190

Gly Gly Cys Cys Ala Gly Gly Gly Thr Cys Thr Gly Gly Ala Gly Thr
        195                 200                 205

Gly Gly Ala Thr Ala Gly Gly Ala Thr Ala Thr Cys Ala Gly
        210                 215                 220

Gly Cys Cys Thr Thr Ala Cys Ala Ala Cys Gly Ala Thr Gly Gly Cys
225                 230                 235                 240

Ala Cys Thr Cys Gly Ala Thr Ala Cys Ala Ala Cys Cys Ala Ala Ala
                245                 250                 255

Ala Gly Thr Thr Cys Cys Ala Gly Gly Gly Thr Ala Ala Gly Cys
            260                 265                 270

Thr Ala Cys Ala Cys Thr Gly Ala Cys Cys Thr Cys Ala Gly Ala Cys
        275                 280                 285

Cys Gly Cys Thr Cys Ala Ala Gly Cys Ala Gly Thr Ala Cys Ala Gly
    290                 295                 300

Cys Ala Ala Ala Cys Ala Thr Gly Gly Ala Ala Cys Thr Gly Ala Ala
305                 310                 315                 320

Cys Ala Gly Thr Cys Thr Thr Ala Cys Cys Thr Cys Thr Gly Ala Gly
                325                 330                 335

Gly Ala Cys Ala Gly Thr Gly Cys Cys Gly Thr Thr Ala Cys Thr
            340                 345                 350

Ala Thr Thr Gly Cys Gly Cys Cys Ala Gly Gly Ala Gly Gly Gly
        355                 360                 365
```

```
Thr Gly Gly Cys Ala Ala Thr Gly Ala Cys Thr Cys Thr Ala Thr
    370                 375                 380

Gly Ala Thr Ala Cys Thr Ala Thr Gly Gly Ala Cys Thr Ala Cys Thr
385                 390                 395                 400

Gly Gly Gly Gly Ala Cys Ala Gly Gly Thr Ala Cys Cys Thr Cys
                405                 410                 415

Thr Gly Thr Ala Ala Cys Ala Gly Thr Thr Thr Cys Ala Ala Gly Cys
                420                 425                 430

Gly Cys Cys Ala Gly Cys Ala Cys Thr Ala Ala Gly Gly Cys Cys
            435                 440                 445

Cys

<210> SEQ ID NO 69
<211> LENGTH: 449
<212> TYPE: PRT
<213> ORGANISM: Artificial
<220> FEATURE:
<223> OTHER INFORMATION: Synthetic Peptide

<400> SEQUENCE: 69

Ala Ala Gly Cys Thr Thr Gly Cys Cys Ala Cys Cys Ala Thr Gly Gly
1               5                   10                  15

Gly Cys Thr Gly Gly Thr Cys Thr Thr Gly Thr Ala Thr Thr Ala Thr
                20                  25                  30

Thr Cys Thr Gly Thr Thr Thr Cys Thr Gly Gly Thr Thr Gly Cys Cys
                35                  40                  45

Ala Cys Cys Gly Cys Ala Ala Cys Ala Gly Gly Cys Gly Thr Thr Cys
            50                  55                  60

Ala Cys Ala Gly Thr Cys Ala Ala Thr Thr Cys Cys Ala Gly Cys Thr
65                  70                  75                  80

Gly Gly Thr Cys Cys Ala Gly Thr Cys Cys Gly Gly Cys Gly Cys Cys
                85                  90                  95

Gly Ala Gly Gly Thr Thr Gly Thr Cys Ala Ala Ala Cys Cys Thr Gly
                100                 105                 110

Gly Thr Gly Cys Cys Ala Gly Cys Gly Thr Ala Ala Gly Ala Thr Cys
                115                 120                 125

Thr Cys Cys Thr Gly Cys Ala Ala Ala Gly Cys Thr Ala Gly Cys
                130                 135                 140

Gly Gly Cys Thr Ala Thr Ala Cys Cys Thr Thr Cys Ala Cys Thr Thr
145                 150                 155                 160

Cys Thr Thr Ala Thr Thr Gly Cys Ala Cys Thr Gly
                165                 170                 175

Gly Ala Thr Gly Ala Ala Gly Cys Ala Ala Ala Gly Cys Cys Thr
                180                 185                 190

Gly Gly Ala Cys Ala Gly Gly Gly Cys Cys Thr Gly Gly Ala Ala Thr
                195                 200                 205

Gly Gly Ala Thr Cys Gly Gly Cys Thr Ala Cys Ala Thr Thr Ala Ala
                210                 215                 220

Ala Cys Cys Thr Thr Ala Thr Ala Ala Cys Gly Ala Cys Gly Gly Cys
225                 230                 235                 240

Ala Cys Ala Ala Ala Gly Thr Ala Cys Ala Ala Thr Cys Ala Gly Ala
                245                 250                 255

Ala Gly Thr Thr Cys Cys Ala Ala Gly Gly Ala Ala Ala Gly Gly Cys
                260                 265                 270
```

-continued

```
Ala Ala Cys Cys Cys Thr Gly Ala Cys Thr Cys Ala Gly Ala Cys
            275                 280                 285
Ala Ala Gly Thr Cys Thr Thr Cys Ala Thr Cys Cys Ala Cys Thr Gly
        290                 295                 300
Cys Cys Ala Ala Cys Ala Thr Gly Gly Ala Ala Cys Thr Thr Ala Ala
305                 310                 315                 320
Thr Ala Gly Thr Cys Thr Thr Ala Cys Cys Thr Cys Thr Gly Ala Gly
                325                 330                 335
Gly Ala Thr Thr Cys Cys Gly Cys Thr Gly Thr Cys Thr Ala Thr Thr
            340                 345                 350
Ala Thr Thr Gly Cys Gly Cys Thr Cys Gly Gly Gly Ala Gly Gly Gly
            355                 360                 365
Gly Gly Gly Gly Ala Ala Cys Gly Ala Cys Thr Ala Thr Thr Ala Cys
        370                 375                 380
Gly Ala Cys Ala Cys Cys Ala Thr Gly Gly Ala Ala Thr Ala Cys Thr
385                 390                 395                 400
Gly Gly Gly Gly Ala Cys Ala Gly Gly Cys Ala Cys Cys Ala
                405                 410                 415
Thr Gly Thr Thr Ala Cys Cys Gly Thr Gly Thr Cys Cys Ala Gly Cys
                420                 425                 430
Gly Cys Thr Ala Gly Cys Ala Cys Cys Ala Ala Gly Gly Gly Cys Cys
            435                 440                 445
Cys
```

<210> SEQ ID NO 70
<211> LENGTH: 16
<212> TYPE: PRT
<213> ORGANISM: Artificial
<220> FEATURE:
<223> OTHER INFORMATION: Synthetic Peptide

<400> SEQUENCE: 70

```
Gln Ser Glu Ala Tyr Tyr Gly Tyr Asp Lys Arg Thr Trp Phe Ala Tyr
1               5                   10                  15
```

<210> SEQ ID NO 71
<211> LENGTH: 7
<212> TYPE: PRT
<213> ORGANISM: Artificial
<220> FEATURE:
<223> OTHER INFORMATION: Synthetic Peptide

<400> SEQUENCE: 71

```
Arg Val Asn Arg Leu Val Ser
1               5
```

<210> SEQ ID NO 72
<211> LENGTH: 11
<212> TYPE: PRT
<213> ORGANISM: Artificial
<220> FEATURE:
<223> OTHER INFORMATION: Synthetic Peptide

<400> SEQUENCE: 72

```
Arg Ala Ser Gln Asp Ile Asn Ser Tyr Leu Ala
1               5                   10
```

<210> SEQ ID NO 73
<211> LENGTH: 4
<212> TYPE: PRT
<213> ORGANISM: Artificial

<220> FEATURE:
<223> OTHER INFORMATION: Synthetic Peptide

<400> SEQUENCE: 73

Gly Phe Leu Gly
1

<210> SEQ ID NO 74
<211> LENGTH: 61
<212> TYPE: PRT
<213> ORGANISM: Artificial
<220> FEATURE:
<223> OTHER INFORMATION: Synthetic Peptide

<400> SEQUENCE: 74

Asp Ile Gln Met Thr Gln Ser Pro Ser Ser Met Ser Ala Ser Val Gly
1               5                   10                  15

Glu Arg Val Thr Ile Thr Cys Arg Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Val Asn Arg Leu Val Asp Gly Val Pro Ser Arg
    50                  55                  60

<210> SEQ ID NO 75
<211> LENGTH: 47
<212> TYPE: PRT
<213> ORGANISM: Artificial
<220> FEATURE:
<223> OTHER INFORMATION: Synthetic Peptide

<400> SEQUENCE: 75

Phe Ser Gly Ser Gly Ser Gly Gln Asp Tyr Ser Leu Thr Ile Ser Ser
1               5                   10                  15

Leu Glu Pro Glu Asp Met Gly Ile Tyr Tyr Cys Leu Gln Tyr Asp Ala
            20                  25                  30

Phe Pro Tyr Thr Phe Gly Gln Gly Thr Lys Leu Glu Ile Lys Arg
        35                  40                  45

<210> SEQ ID NO 76
<211> LENGTH: 61
<212> TYPE: PRT
<213> ORGANISM: Artificial
<220> FEATURE:
<223> OTHER INFORMATION: Synthetic Peptide

<400> SEQUENCE: 76

Gln Val Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Ser Ser
            20                  25                  30

Ile Met His Trp Met Lys Gln Lys Pro Gly Gln Gly Leu Glu Trp Ile
        35                  40                  45

Gly Tyr Ile Arg Pro Tyr Asn Asp Gly Thr Arg Tyr Asn
    50                  55                  60

<210> SEQ ID NO 77
<211> LENGTH: 61
<212> TYPE: PRT
<213> ORGANISM: Artificial
<220> FEATURE:
<223> OTHER INFORMATION: Synethetic Peptide

```
<400> SEQUENCE: 77

Gln Val Gln Leu Val Gln Ser Gly Ala Glu Val Lys Pro Gly Ala
1               5                   10                  15

Ser Val Lys Met Ser Cys Lys Ala Ser Gly Tyr Thr Phe Thr Ser Ser
                20                  25                  30

Ile Met His Trp Met Lys Lys Pro Gly Gln Gly Leu Glu Trp Ile
                35                  40                  45

Gly Tyr Ile Lys Pro Tyr Asn Asp Gly Thr Lys Tyr Asn
    50                  55                  60

<210> SEQ ID NO 78
<211> LENGTH: 60
<212> TYPE: PRT
<213> ORGANISM: Artificial
<220> FEATURE:
<223> OTHER INFORMATION: Synthetic Peptide

<400> SEQUENCE: 78

Gln Lys Phe Gln Gly Lys Ala Thr Leu Thr Ser Asp Arg Ser Ser Ser
1               5                   10                  15

Thr Ala Asn Met Glu Leu Asn Ser Leu Thr Ser Glu Asp Ser Ala Val
                20                  25                  30

Tyr Tyr Cys Ala Arg Glu Gly Gly Asn Asp Tyr Tyr Asp Thr Met Asp
                35                  40                  45

Tyr Trp Gly Gln Gly Thr Ser Val Thr Val Ser Ser
    50                  55                  60

<210> SEQ ID NO 79
<211> LENGTH: 61
<212> TYPE: PRT
<213> ORGANISM: Artificial
<220> FEATURE:
<223> OTHER INFORMATION: Synthetic Peptide

<400> SEQUENCE: 79

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20                  25                  30

Leu Ser Trp Phe Gln Gln Lys Pro Gly Lys Ser Pro Lys Thr Leu Ile
                35                  40                  45

Tyr Arg Val Asn Arg Leu Val Asp Gly Val Pro Ser Arg
    50                  55                  60

<210> SEQ ID NO 80
<211> LENGTH: 61
<212> TYPE: PRT
<213> ORGANISM: Artificial
<220> FEATURE:
<223> OTHER INFORMATION: Synthetic Peptide

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
                20                  25                  30

Leu Ala Trp Phe Gln Gln Lys Pro Gly Lys Ala Pro Lys Ser Leu Ile
                35                  40                  45

Tyr Arg Val Asn Arg Leu Val Ser Gly Val Pro Ser Arg
    50                  55                  60
```

<210> SEQ ID NO 81
<211> LENGTH: 61
<212> TYPE: PRT
<213> ORGANISM: Artificial
<220> FEATURE:
<223> OTHER INFORMATION: Synthetic Peptide

<400> SEQUENCE: 81

```
Asp Ile Gln Met Thr Gln Ser Pro Ser Ser Leu Ser Ala Val Leu Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg
    50                  55                  60
```

<210> SEQ ID NO 82
<211> LENGTH: 61
<212> TYPE: PRT
<213> ORGANISM: Artificial
<220> FEATURE:
<223> OTHER INFORMATION: Synthetic Peptide

<400> SEQUENCE: 82

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg
    50                  55                  60
```

<210> SEQ ID NO 83
<211> LENGTH: 47
<212> TYPE: PRT
<213> ORGANISM: Artificial
<220> FEATURE:
<223> OTHER INFORMATION: Synthetic Peptide

<400> SEQUENCE: 83

```
Phe Ser Gly Ser Gly Ser Gly Gln Asp Tyr Ser Leu Thr Ile Ser Ser
1               5                   10                  15

Leu Glu Tyr Glu Asp Met Gly Ile Tyr Tyr Cys Leu Gln Tyr Asp Ala
            20                  25                  30

Phe Pro Tyr Thr Phe Gly Gly Gly Thr Lys Leu Glu Ile Lys Arg
        35                  40                  45
```

<210> SEQ ID NO 84
<211> LENGTH: 47
<212> TYPE: PRT
<213> ORGANISM: Artificial
<220> FEATURE:
<223> OTHER INFORMATION: Synthetic Peptide

<400> SEQUENCE: 84

Phe Ser Gly Ser Gly Ser Gly Thr Asp Phe Thr Leu Thr Ile Ser Ser
1               5                   10                  15

Leu Gln Pro Glu Asp Phe Ala Thr Tyr Tyr Cys Leu Gln Tyr Asp Ala
            20                  25                  30

Phe Pro Tyr Thr Phe Gly Gln Gly Thr Lys Val Glu Ile Lys Arg
        35                  40                  45

<210> SEQ ID NO 85
<211> LENGTH: 47
<212> TYPE: PRT
<213> ORGANISM: Artificial
<220> FEATURE:
<223> OTHER INFORMATION: Synthetic Peptide

<400> SEQUENCE: 85

Phe Ser Gly Ser Gly Ser Gly Thr Asp Tyr Thr Leu Thr Ile Ser Ser
1               5                   10                  15

Leu Gln Pro Glu Asp Phe Ala Thr Tyr Tyr Cys Leu Gln Tyr Asp Ala
            20                  25                  30

Phe Pro Tyr Thr Phe Gly Gln Gly Thr Lys Val Glu Ile Lys Arg
        35                  40                  45

<210> SEQ ID NO 86
<211> LENGTH: 34
<212> TYPE: PRT
<213> ORGANISM: Artificial
<220> FEATURE:
<223> OTHER INFORMATION: Synthetic Peptide

<400> SEQUENCE: 86

Phe Ser Gly Ser Gly Ser Gly Thr Asp Phe Thr Leu Thr Ile Ser Ser
1               5                   10                  15

Leu Gln Pro Glu Asp Phe Ala Thr Tyr Tyr Cys Gln Gln Tyr Asn Ser
            20                  25                  30

Tyr Pro

<210> SEQ ID NO 87
<211> LENGTH: 61
<212> TYPE: PRT
<213> ORGANISM: Artificial
<220> FEATURE:
<223> OTHER INFORMATION: Synthetic Peptide

<400> SEQUENCE: 87

Glu Phe Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Thr Ser Ser
            20                  25                  30

Ile Met His Trp Met Lys Gln Lys Pro Gly Gln Gly Leu Glu Trp Ile
        35                  40                  45

Gly Tyr Ile Lys Pro Tyr Asn Asp Gly Thr Lys Tyr Asn
    50                  55                  60

<210> SEQ ID NO 88
<211> LENGTH: 61
<212> TYPE: PRT
<213> ORGANISM: Artificial
<220> FEATURE:
<223> OTHER INFORMATION: Synthetic Peptide

```
<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Gly Phe Thr Ser Ser
            20                  25                  30

Ile Met His Trp Val Arg Gln Ala Pro Gly Gln Gly Leu Glu Trp Met
        35                  40                  45

Gly Tyr Ile Lys Pro Tyr Asn Asp Gly Thr Lys Tyr Asn
    50                  55                  60

<210> SEQ ID NO 89
<211> LENGTH: 61
<212> TYPE: PRT
<213> ORGANISM: Artificial
<220> FEATURE:
<223> OTHER INFORMATION: Synthetic Peptide

<400> SEQUENCE: 89

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn
    50                  55                  60

<210> SEQ ID NO 90
<211> LENGTH: 61
<212> TYPE: PRT
<213> ORGANISM: Artificial
<220> FEATURE:
<223> OTHER INFORMATION: Synthetic Peptide

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn
    50                  55                  60

<210> SEQ ID NO 91
<211> LENGTH: 61
<212> TYPE: PRT
<213> ORGANISM: Artificial
<220> FEATURE:
<223> OTHER INFORMATION: Synthetic Peptide

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala
    50                  55                  60
```

-continued

<210> SEQ ID NO 92
<211> LENGTH: 60
<212> TYPE: PRT
<213> ORGANISM: Artificial
<220> FEATURE:
<223> OTHER INFORMATION: Synthetic Peptide

<400> SEQUENCE: 92

```
Glu Lys Phe Lys Gly Lys Ala Thr Leu Thr Ser Asp Lys Ser Ser Ser
1               5                   10                  15

Thr Ala Asn Met Glu Leu Asn Ser Leu Thr Ser Glu Asp Ser Ala Val
            20                  25                  30

Tyr Tyr Cys Ala Arg Glu Gly Gly Asn Asp Tyr Tyr Asp Thr Met Asp
        35                  40                  45

Tyr Trp Gly Gln Gly Thr Ser Val Thr Val Ser Ser
    50                  55                  60
```

<210> SEQ ID NO 93
<211> LENGTH: 60
<212> TYPE: PRT
<213> ORGANISM: Artificial
<220> FEATURE:
<223> OTHER INFORMATION: Synthetic Peptide

<400> SEQUENCE: 93

```
Glu Lys Phe Lys Gly Arg Val Thr Met Thr Arg Asp Thr Ser Thr Ser
1               5                   10                  15

Thr Val Tyr Met Glu Leu Ser Ser Leu Arg Ser Glu Asp Thr Ala Val
            20                  25                  30

Tyr Tyr Cys Ala Arg Glu Gly Gly Asn Asp Tyr Tyr Asp Thr Met Asp
        35                  40                  45

Tyr Trp Gly Gln Gly Thr Leu Val Thr Val Ser Ser
    50                  55                  60
```

<210> SEQ ID NO 94
<211> LENGTH: 60
<212> TYPE: PRT
<213> ORGANISM: Artificial
<220> FEATURE:
<223> OTHER INFORMATION: Synthetic Peptide

<400> SEQUENCE: 94

```
Glu Lys Phe Lys Gly Arg Ala Thr Leu Thr Ser Asp Arg Ser Thr Ser
1               5                   10                  15

Thr Ala Tyr Met Glu Leu Ser Ser Leu Arg Ser Glu Asp Thr Ala Val
            20                  25                  30

Tyr Tyr Cys Ala Arg Glu Gly Gly Asn Asp Tyr Tyr Asp Thr Met Asp
        35                  40                  45

Tyr Trp Gly Gln Gly Thr Leu Val Thr Val Ser Ser
    50                  55                  60
```

<210> SEQ ID NO 95
<211> LENGTH: 60
<212> TYPE: PRT
<213> ORGANISM: Artificial
<220> FEATURE:
<223> OTHER INFORMATION: Synethetic Peptide

```
<400> SEQUENCE: 95

Glu Lys Phe Lys Gly Arg Ala Thr Leu Thr Ser Asp Arg Ser Thr Ser
1               5                   10                  15

Thr Ala Tyr Met Glu Leu Ser Ser Leu Arg Ser Glu Asp Thr Ala Val
            20                  25                  30

Tyr Tyr Cys Ala Arg Glu Gly Gly Asn Asp Tyr Tyr Asp Thr Met Asp
        35                  40                  45

Tyr Trp Gly Gln Gly Thr Leu Val Thr Val Ser Ser
    50                  55                  60

<210> SEQ ID NO 96
<211> LENGTH: 37
<212> TYPE: PRT
<213> ORGANISM: Artificial
<220> FEATURE:
<223> OTHER INFORMATION: Synthetic Peptide

<400> SEQUENCE: 96

Gln Lys Phe Gln Gly Arg Val Thr Met Thr Arg Asp Thr Ser Thr Ser
1               5                   10                  15

Thr Val Tyr Met Glu Leu Ser Ser Leu Arg Ser Glu Asp Thr Ala Val
            20                  25                  30

Tyr Tyr Cys Ala Arg
        35

<210> SEQ ID NO 97
<211> LENGTH: 60
<212> TYPE: PRT
<213> ORGANISM: Artificial
<220> FEATURE:
<223> OTHER INFORMATION: Synthetic Peptide

<400> SEQUENCE: 97

Gln Lys Phe Gln Gly Lys Ala Thr Leu Thr Ser Asp Lys Ser Ser Ser
1               5                   10                  15

Thr Ala Asn Met Glu Leu Asn Ser Leu Thr Ser Glu Asp Ser Ala Val
            20                  25                  30

Tyr Tyr Cys Ala Arg Glu Gly Gly Asn Asp Tyr Tyr Asp Thr Met Asp
        35                  40                  45

Tyr Trp Gly Gln Gly Thr Ser Val Thr Val Ser Ser
    50                  55                  60
```